United States Patent
Robillard et al.

(10) Patent No.: US 11,617,799 B2
(45) Date of Patent: Apr. 4, 2023

(54) CLEAVABLE TETRAZINE USED IN BIO-ORTHOGONAL DRUG ACTIVATION

(71) Applicants: Tagworks Pharmaceuticals B.V., Eindhoven (NL); Syncom B.V., Groningen (NL)

(72) Inventors: Marc Stefan Robillard, Eindhoven (NL); Wolter Ten Hoeve, Groningen (NL); Freek Johannes Maria Hoeben, Eindhoven (NL); Ronny Mathieu Versteegen, Eindhoven (NL); Hendricus Marie Janssen, Eindhoven (NL); Arthur Henry Antoon Marie Van Onzen, Eindhoven (NL); Raffaella Rossin, Eindhoven (NL)

(73) Assignees: TAGWORKS PHARMACEUTICALS B.V., Eindhoven (NL); SYNCOM B.V., Groningen (NL)

( * ) Notice: Subject to any disclaimer, the term of this patent is extended or adjusted under 35 U.S.C. 154(b) by 184 days.

(21) Appl. No.: 16/312,569

(22) PCT Filed: Jun. 27, 2017

(86) PCT No.: PCT/NL2017/050427
§ 371 (c)(1),
(2) Date: Dec. 21, 2018

(87) PCT Pub. No.: WO2018/004338
PCT Pub. Date: Jan. 4, 2018

(65) Prior Publication Data
US 2019/0247513 A1  Aug. 15, 2019

(30) Foreign Application Priority Data

Jun. 27, 2016 (EP) .................... 16176416

(51) Int. Cl.
| | | |
|---|---|---|
| *C07D 257/02* | (2006.01) | |
| *C07D 257/08* | (2006.01) | |
| *C07D 237/26* | (2006.01) | |
| *C07C 33/16* | (2006.01) | |
| *A61K 31/495* | (2006.01) | |
| *A61K 31/502* | (2006.01) | |
| *A61K 47/68* | (2017.01) | |
| *A61K 47/54* | (2017.01) | |
| *C07K 16/30* | (2006.01) | |
| *A61K 47/66* | (2017.01) | |
| *A61K 47/60* | (2017.01) | |
| *A61K 47/64* | (2017.01) | |
| *A61K 39/00* | (2006.01) | |

(52) U.S. Cl.
CPC ........ *A61K 47/6889* (2017.08); *A61K 47/555* (2017.08); *A61K 47/60* (2017.08); *A61K 47/6415* (2017.08); *A61K 47/66* (2017.08); *A61K 47/6817* (2017.08); *A61K 47/6897* (2017.08); *C07D 257/08* (2013.01); *C07K 16/30* (2013.01); *C07K 16/3046* (2013.01); *A61K 2039/505* (2013.01); *C07K 2317/626* (2013.01); *C07K 2317/94* (2013.01)

(58) Field of Classification Search
CPC ................ C07D 257/02; C07D 257/08; C07D 237/26; A61K 31/495; A61K 31/502; C07C 33/16
USPC .......................... 544/179, 235; 514/183, 248
See application file for complete search history.

(56) References Cited

U.S. PATENT DOCUMENTS

| | | | | |
|---|---|---|---|---|
| 9,421,274 | B2 * | 8/2016 | Robillard ............... | A61K 47/54 |
| 9,427,482 | B2 * | 8/2016 | Rossin .................... | B82Y 5/00 |
| 9,463,256 | B2 * | 10/2016 | Lub .................... | A61K 47/6889 |
| 9,913,921 | B2 * | 3/2018 | Robillard ............. | C07D 249/16 |
| 9,931,408 | B2 * | 4/2018 | Robillard ............. | C07D 237/26 |
| 10,004,810 | B2 * | 6/2018 | Robillard ............. | A61K 31/435 |
| 10,376,594 | B2 * | 8/2019 | Robillard ................ | B82Y 5/00 |
| 2015/0297741 | A1 | 10/2015 | Robillard | |

FOREIGN PATENT DOCUMENTS

WO   2010119389 A2   10/2010

OTHER PUBLICATIONS

Fu et al., "Intracellular Delivery of Functional Proteins and Native Drugs by Cell-Penetrating Poly(disulfide)s", JACS, 2015, vol. 137, No. 37, pp. 12153-12160.
Rossin et al.,"Triggered Drug Release from an Antibody-Drug Conjugate Using Fast "Click-to-Release" Chemistry in Mice", Bioconjugate Chemistry, 2016, vol. 27, No. 7, pp. 1697-1706.
Pipkorn et al., "Inverse-electron-demand Diels-Alder reaction as a highly efficient chemoselective ligation procedure: Synthesis and function of a BioShuttle for temozolomide transport into prostate cancer cells", J. Pept. Sci., 2009, vol. 15, No. 3, pp. 235-241.
International Search Report and Written Opinion for Corresponding International Application No. PCT/NL2017/050427 (20 Pages) (dated Sep. 22, 2017).

* cited by examiner

*Primary Examiner* — Brenda L Coleman
(74) *Attorney, Agent, or Firm* — Lucas & Mercanti, LLP

(57) ABSTRACT

Disclosed is an advancement in provoked chemical cleavage. Thereby the invention provides the use of a diene as a chemically cleavable group attached to a Construct, and the use of a dienophile to provoke the release of the Construct by allowing the diene to react with a dienophile capable of undergoing an inverse electron demand Diels Alder reaction with the diene. The invention includes a kit for releasing a Construct $C^A$ bound to a Trigger $T^R$, the kit having a tetrazine and a dienophile, wherein the Trigger is the tetrazine. The invention also includes the use of the formation of a pyridazine by reacting a tetrazine having a Construct $C^A$ bound thereto and a dienophile, as a chemical tool for the release, in a chemical, biological or physiological environment, of the Construct.

41 Claims, 8 Drawing Sheets

CLEAVABLE TETRAZINE USED IN BIO-ORTHOGONAL DRUG ACTIVATION

CROSS-REFERENCE TO RELATED APPLICATIONS

This application is a 371 of PCT/NL2017/050427, filed Jun. 27, 2017 which claims the benefit of European Patent Application No. 16176416.2, filed Jun. 27, 2016.

FIELD OF THE INVENTION

The invention pertains to the field of provoked chemical cleavage. Particularly, the invention pertains to providing chemical substances with a functional group capable of acting as a Trigger for release of an entity attached to said chemical group. This plays a role, e.g., in drug delivery, prodrug activation, modification of molecules under physiological conditions (e.g., in a cellular environment), in solid phase synthesis, biomolecule interactions, modification of surfaces (including cell surfaces).

BACKGROUND

The current state of the art in organic chemistry enables the preparation of highly complex molecular structures, by application of a wide toolbox of synthetic transformations. Unfortunately, the vast majority of chemical techniques is executed under strictly defined conditions, requiring toxic solvents, stoichiometric reagents, extreme temperatures, exclusion of moisture or oxygen, and with carefully designed protective group protocols. One of the most difficult challenges in synthetic chemistry remains the ability to have precise control over chemical reactivity and selectivity. These demands are amplified when it is necessary to perform selective reactions in chemically complex environments, such as those found in biology. Unfortunately, only a few chemical transformations are so mild and precise that they can be used to selectively modify biochemical structures, such as proteins or nucleic acids, which typically proceed in water and at near-ambient temperature. Moreover, such biomolecular modification must be highly chemospecific in the sense that only a single functionality of interest is selectively modified in the presence of a plethora of other functional groups. Even more challenging is to apply a chemical reaction on or in living cells or whole organisms. Selective chemical reactions that are orthogonal to the diverse functionality of biological systems are called bio-orthogonal reactions and occur between two abiotic groups with exclusive mutual reactivity. Truly bio-orthogonal reactions are not yet available as each reaction so far is orthogonal to a subset of the functionalities found in biological systems. Thus, extremely selective and high-yielding bio-orthogonal coupling chemistry reactions continue to receive interest.

Bio-orthogonal reactions are broadly useful tools with applications that span synthesis, materials science, chemical biology, diagnostics, and medicine. They are generally used in coupling reactions of small molecules, peptides, proteins, oligonucleotides, other types of polymers, glycans, nanoparticles, and on surfaces (e.g., glass slides, gold, resins). Further examples include: compound library synthesis, protein engineering, functional proteomics, activity-based protein profiling, target guided synthesis of enzyme inhibitors, chemical remodeling of cell surfaces, tracking of metabolite analogues, and imaging tagged biomolecules in live cells and animals.

Analogous to selective coupling reactions, chemoselective cleavable linkers and protecting groups have widespread application in the manipulation of conjugates and derivatives of: small molecules, polymers, and biomolecules such as peptides, proteins and DNA within the context of chemical synthesis, materials science, chemical biology, diagnostics, and medicine. [G. C. Rudolf, W. Heydenreuter, S. A. Sieber, *Curr. Opin. Chem. Biol.* 2013, 17, 110-117] For example, linker systems that allow mild cleavage under conditions ideally orthogonal to functionalities present in the biological system at hand have found application in activity-based protein profiling. Protease substrates linked to a biotin tag through a cleavable linker have been used to capture and isolate specific enzymes by the binding of the biotin tag to avidin coated resin or beads. Subsequently the captured complex can then be released under mild conditions by cleavage of the linker instead of having to break the biotin-avidin interaction. Also, chemically cleavable linkers have emerged as powerful tools in solid-phase organic synthesis, especially for the rapid production of highly diverse organic compound libraries created through combinatorial or parallel chemistry methods. Especially prominent application areas for cleavable linkers include drug delivery agents and prodrugs for pharmaceutical applications, as well as various reversible bioconjugates and sophisticated spectroscopic bioprobes for applications in the field of biological analysis.

However, chemoselective cleavable linkers and protecting groups have a limited orthogonality compared to the relatively highly bio-orthogonal coupling reactions listed above and with respect to the wide range of functionalities present in the complex environments encountered e.g. in vivo, in biological media, biomolecules, or complex materials. A wider and more uniform application scope may be achieved for chemoselective linkers and protecting groups if the aforementioned bio-orthogonal coupling reactions could be adapted to effect selective release instead of selective conjugation.

We have demonstrated that the fastest click reaction, the inverse-electron-demand Diels Alder (IEDDA) reaction, can be used for pretargeted radioimmunoimaging, treating tumor-bearing mice with trans-cyclooctene (TCO)-tagged antibody or antibody fragments, followed 1-3 days later by administration and selective conjugation of a radiolabeled tetrazine probe to the TCO tag of the tumor-bound antibody [Rossin, M. S. Robillard, *Curr. Opin. Chem. Biol.* 2014, 21, 161-169]. Based on the IEDDA conjugation we have recently developed a new release reaction, which we termed the IEDDA pyridazine elimination, a "click-to-release" approach that affords instantaneous and selective release upon conjugation [R. M. Versteegen, R. Rossin, W. ten Hoeve, H. M. Janssen, M. S. Robillard, *Angew. Chem. Int. Ed.* 2013, 52, 14112-14116]. IEDDA reactions between tetrazines (i.e. diene) and alkenes (i.e. dienophile) afford 4,5-dihydropyridazines, which usually tautomerize to 1,4- and 2,5-dihydropyridazines. We demonstrated that the 1,4-dihydropyridazine product derived from a TCO containing a carbamate-linked doxorubicin (Dox) at the allylic position and tetrazine is prone to eliminate $CO_2$ and Dox via a novel electron cascade mechanism eventually affording aromatic pyridazine. The triggered release has been demonstrated in PBS (phosphate buffered saline), serum, cell culture and in mice and holds promise for a range of applications in medicine, chemical biology, and synthetic chemistry, including triggered drug release, biomolecule uncaging and capture & release strategies.

Aforementioned technology has also been disclosed in WO2012/156919, WO2012156918A1, WO 2014/081303, and US20150297741. Herein a dienophile is used as a chemically cleavable group. The group is attached to a Construct such the release of the dienophile from the Construct can be provoked by allowing the dienophile to react with a diene. The dienophile is an eight-membered non-aromatic cyclic alkenylene group, particularly a trans-cyclooctene (TCO) group. From the viewpoint of bio-orthogonality and efficiency of release, the chemistry works well. However, the trans-cyclooctene linker deactivates slowly in circulation in vivo ($t_{1/2}$ ca 5 days) and rapidly in serum in vitro ($t_{1/2}$ ca 3 h). Also, due to steric hindrance, the reactivity of the trans-cyclooctene linker is reduced compared to a trans-cyclooctene without a drug attached adjacent to the double bond. And increasing the reactivity of the trans-cyclooctene by increasing the ring strain will lead to insufficient linker stability. In addition, there is an inverse correlation between the reactivity of the tetrazine and maximum Construct release yield of the corresponding pyridazine product. As a consequence, to achieve high release yields in vivo one must use a high dose of tetrazine (to compensate for its lower reactivity) compared with the highly reactive tetrazines typically used in vivo for bioconjugation applications.

Therefore, it is desired to provide reactants for an abiotic, bio-orthogonal reaction that are relatively stable in biological environments, that are more reactive towards each other, and that are capable of inducing increased release of a bound Construct by means of a new mechanism, thus offering a greatly versatile Construct release method.

SUMMARY OF THE INVENTION

In order to better address one or more of the aforementioned desires, and as a further advancement in provoked chemical cleavage, the invention provides, in one aspect, the use of a diene, particularly of Formula (1) defined below, as a chemically cleavable group attached to a Construct, and the use of a dienophile to provoke the release of the Construct by allowing the diene to react with a dienophile capable of undergoing an IEDDA reaction, as defined below, with the diene. Particularly, in a further aspect, the invention pertains to a kit for releasing a Construct $C^A$ bound to a Trigger $T^R$, the kit comprising a tetrazine and a dienophile, wherein the Trigger is the tetrazine. Also, in another aspect, the invention provides the use of the formation of a pyridazine by reacting a tetrazine comprising a Construct $C^A$ bound thereto and a dienophile, as a chemical tool for the release, in a chemical, biological or physiological environment, of said Construct, as defined in the claims. In a still further aspect, the invention presents a method of modifying a Drug $D^D$ compound into a Prodrug that can be triggered by an abiotic, bio-orthogonal reaction, the method comprising the steps of providing a Drug and chemically linking the Drug to a tetrazine moiety, as defined in the claims. For all of the aspects of the invention, all embodiments of the tetrazine and the dienophile as described hereinbelow, such as the tetrazine with the Construct bound thereto according to formula (1), and embodiments thereof, as defined below, are applicable.

DETAILED DESCRIPTION OF THE INVENTION

Figure 1:
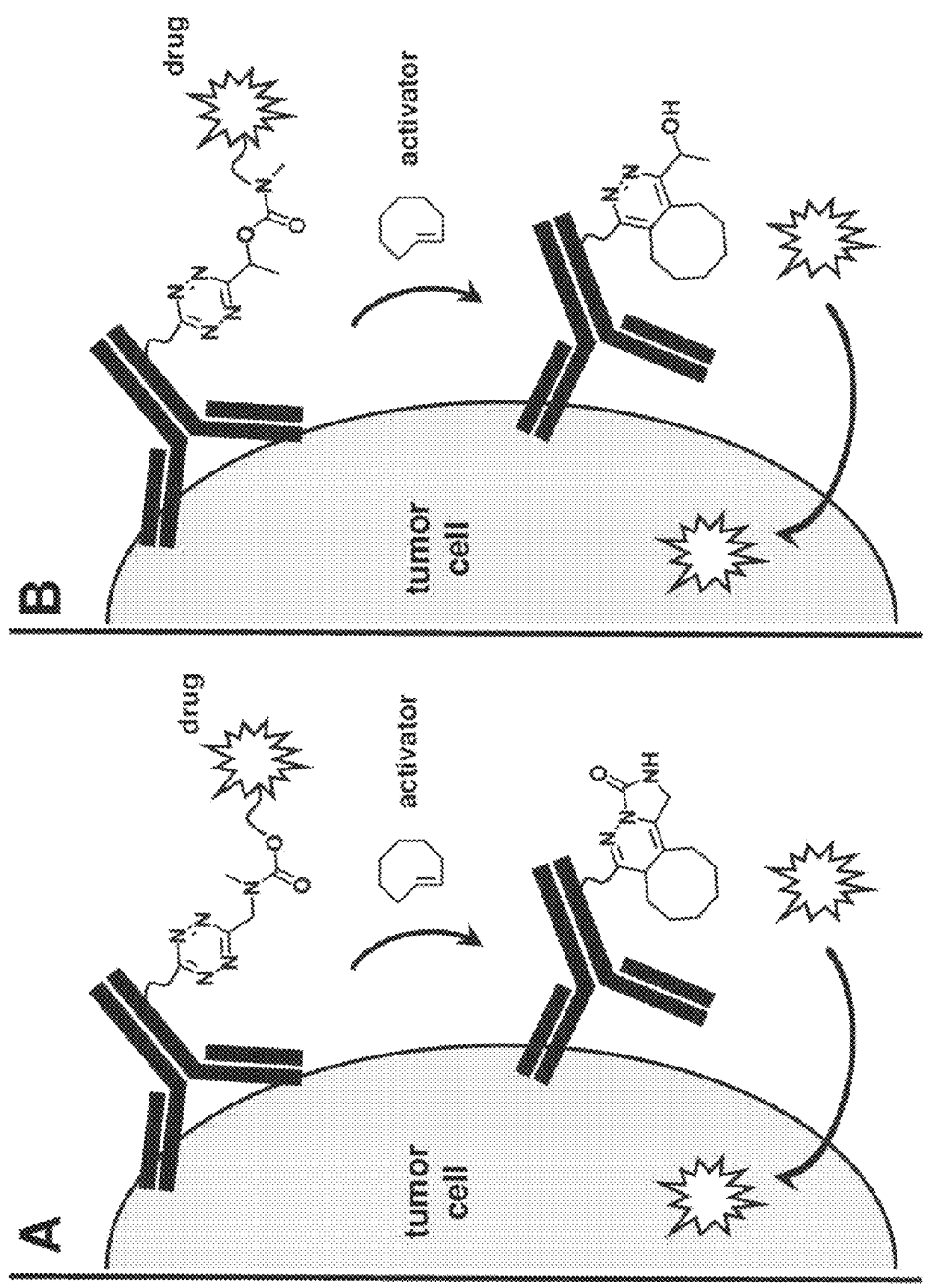
FIG. 1 depicts the general concept of ADC activation using the Triggers and Activators of the invention.

The invention provides a tool for the controlled release of a bound substance (bound to any carrier or any other chemical group) for a diverse range of applications, including but not limited to drug delivery, prodrug activation, biological and chemical sensors, chemical biology, diagnostics, and chemistry. The release can be particularly in a chemically complex environment, particularly comprising biological surroundings in vivo or in vitro, and including the synthesis and handling conditions of biomolecules, and organic chemistry and material synthesis. This includes organic solvents, aqueous solvents and media, cell lysates at ambient temperature, use in animals and humans.

The invention is based on the judicious recognition that the IEDDA reaction (as defined below) enables the controlled manipulation of a wide range of substrates in relatively complex environments, in the presence of a range of other chemical functional groups. This control can be temporal and, optionally, also spatial. The manipulation can be versatile, e.g. for a variety of purposes including but not limited to activating, deactivating, releasing, trapping, or otherwise altering a Construct attached to said chemically cleavable group.

Hereby the invention is based on the judicious choice to employ a diene, and not a dienophile, as a chemically cleavable group. Without wishing to be bound by theory, the inventors believe that the surprising feasibility of this choice can be attributed to a reaction mechanism not previously foreseen, wherein specific dihydropyridazines are key intermediates. As compared to WO2012/156919, WO2012156918A1, WO 2014/081303, and US20150297741, the initiator of the elimination reaction that occurs, as well as the leaving group, are on the same part of the dihydropyradizine, which is the part originating from the diene. In WO2012/156919, WO2012156918A1, WO 2014/081303, and US20150297741 the leaving group is on the part originating from the dienophile.

Without wishing to be bound by theory, the inventors believe that the dienes of the invention produce particular molecular structures of the IEDDA adduct (discussed below) such that a spontaneous cyclization reaction or a spontaneous cascade reaction within this IEDDA adduct occurs that leads to release of the Construct. Particularly, the inventors believe that appropriately modified IEDDA components lead to IEDDA dihydropyridazine adducts wherein the bond to the Construct on the part originating from the diene is spontaneously broken due to the presence of a NH moiety on that same part originating from the diene. Specifically, and without wishing to be bound by theory, the inventors believe that the NH moieties comprised in the various possible dihydropyridazine tautomers (such as 1,4- and/or the 2,5-dihydropyridazine tautomers) of the IEDDA adduct are nucleophilic and in some embodiments can initiate an intramolecular cyclization reaction on an electrophilic moiety that is suitably positioned on the tetrazine Trigger resulting in release of the Construct. This mechanism is termed the "Cyclization Mechanism" and an example is depicted in Scheme 1 below. Without wishing to be bound by theory, the inventors believe that in other embodiments, the NH moiety in dihydropyridazine tautomers, such as the 1,4- and/or the 2,5-dihydropyridazine tautomers, of the IEDDA adduct can initiate an intramolecular electron cascade reaction, a consecutive or concerted shift of electrons over several bonds, leading to release of the Construct that is suitably positioned on the tetrazine Trigger. This mechanism is termed the "Cascade Mechanism" and an example is depicted in Scheme 2 below. Without wishing to be bound to theory, the inventors believe that in some embodiments both mechanisms can afford release of the Construct.

Both mechanisms depicted in Scheme 1 and 2 below illustrate the general concept of using the IEDDA reaction in Construct release.

Scheme 1: Release of a Construct, here termed $C^A$, from a Trigger via the Cyclization Mechanism

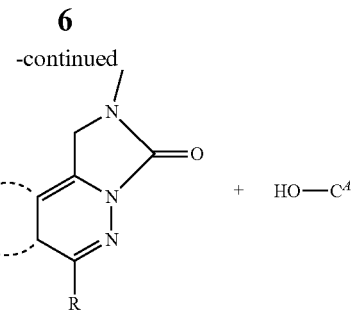

Scheme 2: Release of a Construct, here termed $C^A$, from a Trigger via the Cascade Mechanism

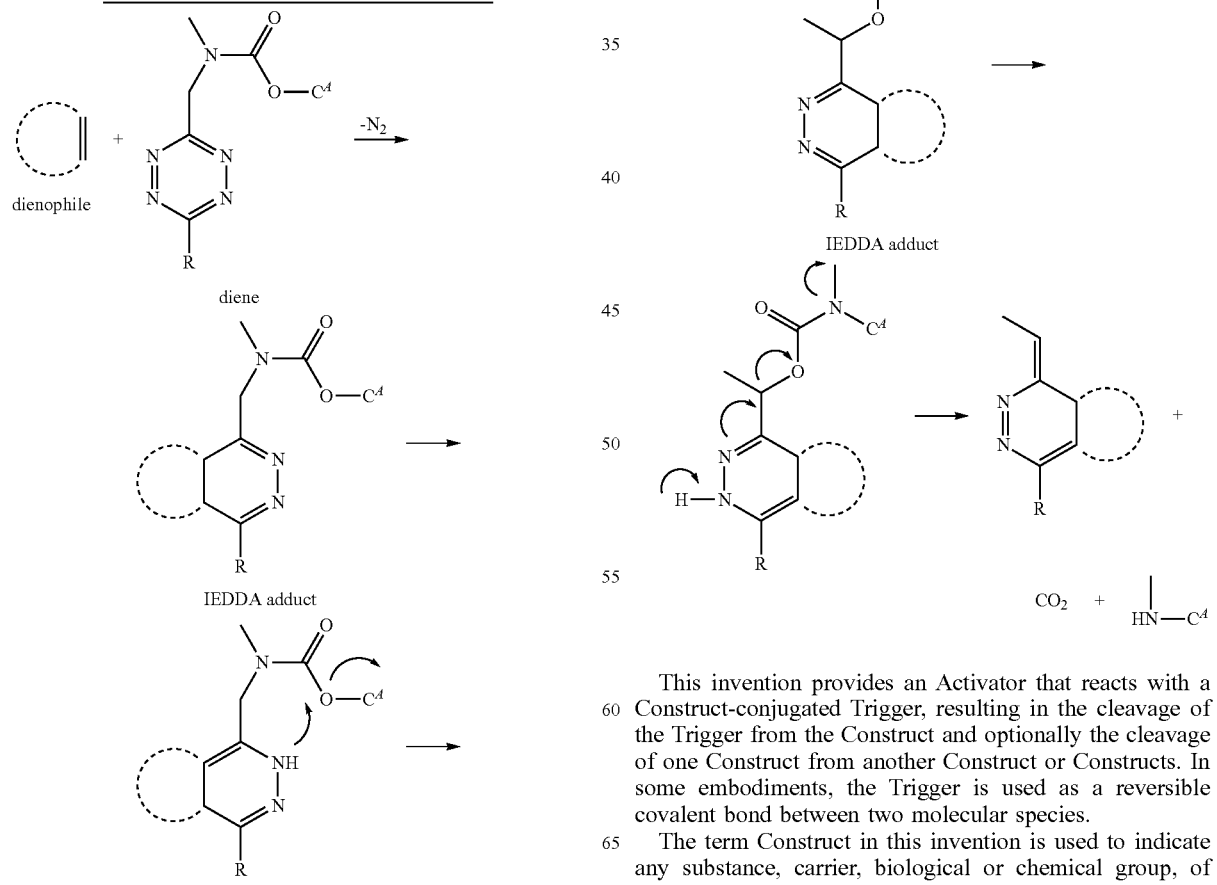

This invention provides an Activator that reacts with a Construct-conjugated Trigger, resulting in the cleavage of the Trigger from the Construct and optionally the cleavage of one Construct from another Construct or Constructs. In some embodiments, the Trigger is used as a reversible covalent bond between two molecular species.

The term Construct in this invention is used to indicate any substance, carrier, biological or chemical group, of which it is desired to have it first in a bound (or masked)

state, and being able to provoke release from that state. The Construct may be present in the form of two or more Constructs, linked via a self-immolative linker.

The established IEDDA conjugation chemistry generally involves a pair of reactants that comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a suitable dienophile, such as a trans-cyclooctene (TCO). The exceptionally fast reaction of (substituted) tetrazines, in particular electron-deficient tetrazines, with a TCO moiety results in an intermediate that rearranges to a dihydropyridazine retro Diels-Alder adduct by eliminating $N_2$ as the sole by-product. The initially formed 4,5-dihydropyridazine product may tautomerize to a 1,4- or a 2,5-dihydropyridazine product, especially in aqueous environments. Below a reaction scheme is given for a [4+2] IEDDA reaction between (3,6)-di-(2-pyridyl)-s-tetrazine diene and a trans-cyclooctene dienophile, followed by a retro Diels Alder reaction in which the product and dinitrogen is formed. The reaction product may tautomerize, and this is also shown in the scheme. Because the trans-cyclooctene derivative does not contain electron withdrawing groups as in the classical Diels Alder reaction, this type of Diels Alder reaction is distinguished from the classical one, and frequently referred to as an "inverse-electron-demand Diels Alder (IEDDA) reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "IEDDA". The product of the reaction is then the IEDDA adduct. This is illustrated in Scheme 3 below.

Scheme 3: the IEDDA conjugation reaction

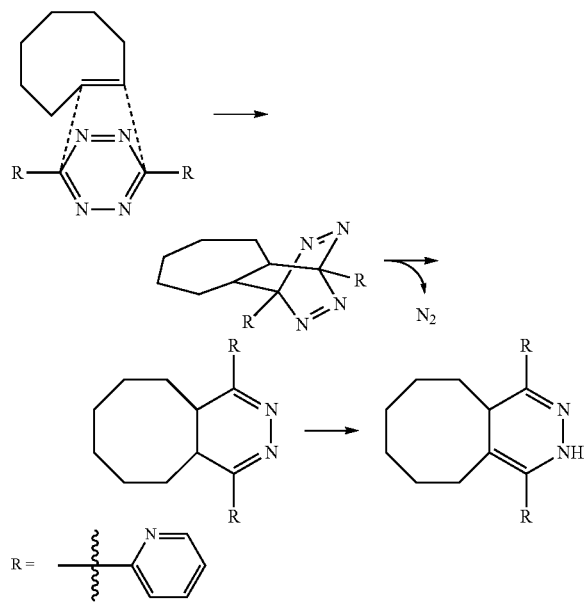

The two reactive species are abiotic and do not undergo fast metabolism or side reactions in vitro or in vivo. They are bio-orthogonal, e.g. they selectively react with each other in physiologic media. Thus, the compounds and the method of the invention can be used in a living organism. Moreover, the reactive groups are relatively small and can be introduced in biological samples or living organisms without significantly altering the size of biomolecules therein. References on the inverse electron demand Diels Alder reaction, and the behavior of the pair of reactive species include: [Thalhammer et al., Tetrahedron Lett., 1990, 31, 47, 6851-6854], [Wijnen et al., J. Org. Chem., 1996, 61, 2001-2005], [Blackman et al., J. Am. Chem. Soc., 2008, 130, 41, 13518-19], Rossin et al., Angew. Chem. Int. Ed. 2010, 49, 3375], [Devaraj et al., Angew. Chem. Int. Ed. 2009, 48, 7013], [Devaraj et al., Angew. Chem. Int. Ed., 2009, 48, 1-5].

The diene, defined in Formula (1) below, and the dienophile, also defined hereinbelow, are capable of reacting in said IEDDA reaction. The IEDDA reaction of the Trigger with the Activator leads to release of the Construct from the Trigger.

Figure 8:
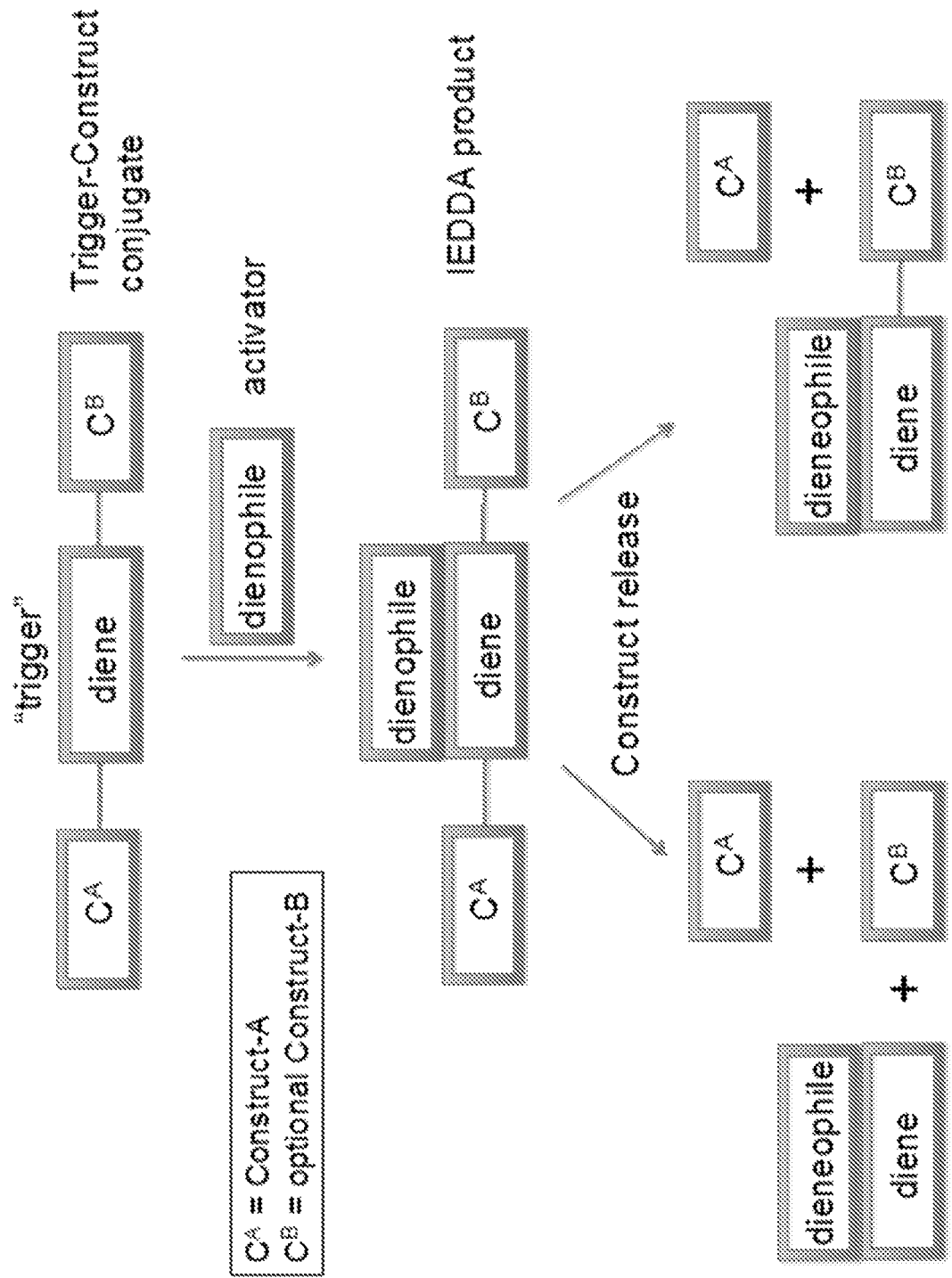
FIG. 8 depicts the general scheme of construct release of the invention as Scheme 4.

In a general sense, the invention is based on the recognition that a Construct can be released from tetrazine derivatives satisfying Formula (1) upon cycloaddition of the tetrazine with compatible dienophiles, such as trans-cyclooctene derivatives, cyclopropene derivatives, norbonene derivatives, and linear alkenes. The dienes of Formula (1) have the advantage that they react (and effectuate construct release) with substantially any dienophile. Scheme 4, FIG. 8 is a general scheme of Construct release according to this invention, wherein the Construct being released is termed Construct-A ($C^A$), and wherein another Construct, Construct-B ($C^B$) can be bound to the diene, wherein Construct-B may or may not be able to be released from the diene. Typically, only Construct A can be released from the diene.

In a broad sense, the inventors have found that—other than the attempts made on the basis of the Staudinger reaction [Van Brakel et al., Bioconjug. Chem. 2008, 19, 3, 714-718]—the selection of a tetrazine as the Trigger moiety for a masked Construct, provides a versatile tool to render Constructs into relatively stable masked or linked Constructs. The Construct release occurs through a powerful, abiotic, bio-orthogonal reaction of the diene (Trigger) with the dienophile (Activator), viz. the aforementioned IEDDA. The masked or bound Construct is a Construct-diene conjugate. Possibly the Construct A is linked to one or more additional Constructs A or B linked via a self-immolative linker. It will be understood that in Scheme 3 in the IEDDA adduct as well as in the end product after release, the indicated dienophile group and the indicated diene group are the residues of, respectively, the dienophile and diene groups after these groups have been converted in the IEDDA reaction.

It will be understood that the present invention is fundamentally different from the previously reported IEDDA-based release using the dienophile trans-cyclooctene (TCO) as the Trigger and tetrazines as the Activator [Versteegen et al., Angew. Chem. Int. Ed. 2013, 52, 14112-14116], and as described in WO2012/156919, WO2012/156918A1, WO 2014/081303, and US20150297741. E.g., the reaction mechanism is different. In accordance with the invention, the initiator of the release reaction as well as the leaving group are on the same part of the pyridazine, the part originating from the tetrazine. In the aforementioned previous disclosures, the leaving group is on the part of the pyridazine originating from the TCO. Particularly, as compared with the aforementioned previous disclosures, the present invention allows the use of dienophiles, e.g. TCOs, with increased reactivity, because the dienophile is now being used as an Activator. The requirements regarding stability of the Activator are less stringent than those for the Trigger. The Trigger typically has to withstand multiple chemical or biochemical manipulations and/or prolonged residence times in demanding conditions such as serum in vitro, intracellularly or in a living animals or humans, typically requiring stability half lives of hours to days. The Activator typically only has to be stable for a few minutes to a few hours, long enough to find and activate the Trigger. Also, without the Construct being attached adjacent to the double bond of the TCO, the TCO is much more reactive due to reduced steric hindrance, while its stability is not negatively affected. At the same time, the inventors have found that the reactivity of the tetrazine is not or much less reduced due to steric hindrance by the attached Construct. Furthermore, tetrazine-based Triggers are in general more stable than TCO-based Triggers and the stability/reactivity balance of the tetrazine as well as the release rate of the Construct can be finely tuned by the introduction of electron donating groups (EDGs) or electron-withdrawing groups (EWGs) in the tetrazine. Importantly the inventors have found that the tetrazines of this invention, i.e. the Trigger, have a similar or increased reactivity compared with the tetrazines that gave acceptable release yields when used as the Activator in the previous IEDDA-based release invention, while some tetrazines of this invention typically afford higher release yields. Lastly, the increased reactivity of the Activator facilitates the design of small, fast clearing and cell permeable Activators suitable for intracellular targets in vivo.

The invention provides, in one aspect, the use of a dienophile as an Activator for the release, in a chemical, biological, or physiological environment, of a Construct linked to a tetrazine. In connection herewith, the invention also pertains to a trans-cyclooctene, a cyclopropene, a norbonene, a acylazetine, and a linear alkene for use as an Activator for the release, in a chemical, biological, or physiological environment, of a substance linked to a tetrazine, and to a method for activating, in a chemical, biological, or physiological environment, the release of a substance linked to a tetrazine, wherein a strained or linear alkene is used as an Activator.

It will be understood that, in a broad sense, according to the invention the aforementioned IEDDA conjugation and subsequent construct release chemistry can be applied to basically any pair of molecules, groups, constructs. I.e. one of such a pair will comprise a Construct linked to a diene (the Trigger). The other one will be a complementary dienophile for use in reaction with said diene.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Certain compounds of the invention possess chiral centers and/or tautomers, and all chiral isomers, enantiomers, diasteriomers and tautomers, as well as mixtures thereof are within the scope of the invention. In several formulae, groups or substituents are indicated with reference to letters such as "A", "B", "X", "Y", and various (numbered) "R" groups. The definitions of these letters are to be read with reference to each formula, i.e. in different formulae these letters, each independently, can have different meanings unless indicated otherwise.

In several chemical formulae and texts below reference is made to "alkyl", "heteroalkyl", "aryl", "heterocycle", "heterocyclo", "carbocycle", "carbocyclo", "alkenyl", "alkynyl", "alkylene", "alkenylene", "alkynylene", "arylene", and the like. The number of carbon atoms that these groups have, excluding the carbon atoms comprised in any optional substituents as defined below, can be indicated by a designation preceding such terms (e.g. "$C_1$-$C_8$ alkyl" means that said alkyl may have from 1 to 8 carbon atoms). For the avoidance of doubt, a butyl group substituted with a —$OCH_3$ group is designated as a $C_4$ alkyl, because the carbon atom in the substituent is not included in the carbon count.

The term "alkyl" refers to a straight chain or branched, saturated or unsaturated hydrocarbon radical, derived by the removal of one hydrogen atom from a single carbon atom of the parent alkane, having 1 to 20, preferably 1 to 8 carbon atoms. Representative alkyl groups are methyl, 1-propyl, 2-propyl, 3,3-dimethyl-2-butyl. Unless specified otherwise, an alkyl group can be unsubstituted or substituted as defined below.

The term "heteroalkyl" refers to a straight chain or branched, saturated or unsaturated hydrocarbon radical, derived by the removal of one hydrogen atom from a single carbon or hetero atom of the parent alkane, having 1 to 20, preferably 1 to 8 carbon atoms, wherein 1 to 7, preferably 1 to 3 carbon atoms is replaced by a heteroatom independently selected from O, N, S, P and Si, wherein the N, S, P atoms may optionally be oxidized and the N atoms may be quaternized. The heteroatom(s) may be placed at any interior position of the alkyl group or at the position at which the alkyl group is attached to the remainder of the molecule. Up to two heteroatoms may be consecutive, such as in for example —$CH_2$—NH—$OCH_3$ and —$CH_2$—O—$Si(CH_3)_3$. In some preferred embodiments the heteroatoms are not directly bound to one another. Examples of heteroalkyls include —$CH_2CH_2$—O—$CH_3$, —$CH_2CH_2$—NH—$CH_3$, —$CH_2CH_2$—S(O)—$CH_3$—CH=CHO—$CH_3$, —$Si(CH_3)_3$. Typically a $C_1$-$C_4$ alkyl has in addition at most 2 heteroatoms. "Heteroalkyl" expressly also includes $C_1$-$C_8$ perfluoroalkyl. Unless specified otherwise, an heteroalkyl group can be unsubstituted or substituted as defined below.

The term "aryl" refers to an aromatic hydrocarbon radical, derived by the removal of one hydrogen atom from a single carbon atom of the parent aromatic ring system, having 6 to 20, preferably 6 to 12, carbon atoms. Representative aryls include but are not limited to phenyl, naphtyl, anthracenyl, and biphenyl. Unless specified otherwise, the aryl group can be unsubstituted or substituted as defined below.

The term "heterocycle" refers to a radical of an aromatic or non-aromatic ring system, derived by the removal of one hydrogen atom from a single carbon atom or heteroatom of the parent ring system, in which one or more ring atoms is a heteroatom, e.g. N, O, P, and S. The heterocycle radical has 1 to 20 carbon atoms, preferably 2 to 9 carbon atoms, more preferably 3 to 5 carbon atoms, and 1 to 6 heteroatoms, preferably 1 to 3 heteroatoms selected from N, O, P and S, wherein preferably no O—O bonds are present. One or more C, N, S, or P atoms in the heterocycle may be oxidized. A heterocycle may for example be a monocycle having 3 to 8 ring members (2 to 7 carbon atoms and 1 to 3 heteroatoms selected from N, O, P, S) or a bicycle having 7 to 10 ring members (4 to 9 carbon atoms and 1 to 3 heteroatoms selected from N, O, P, S), for example: a bicyclo [4,5], [5,5], [5,6], or [6,6] system. Unless otherwise noted, the heterocycle is attached to the remainder of the molecule through any heteroatom or carbon atom of the heterocycle that results in a stable structure. Non-limiting examples of heterocycles include benzotriazolyl, pyrrolinyl, thiazolyl, pyridyl, imidzolyl, piperidinyl, morpholinyl. Examples of heterocycles that are bound through a carbon atom of the heterocycle are 2-pyridyl, 3-pyridazinyl, 2-pyrimidinyl, 2-thiazolyl. Examples of nitrogen-bonded heterocycles are 2-pyrroline, 1-imidazolyl, 3-pyrrolinyl, 1-pyrazolyl, 1-piperidinyl. Unless specified otherwise, a heterocycle can be unsubstituted or substituted as defined below.

The term "carbocycle" refers to a radical of a saturated or unsaturated non-aromatic monocyclic or bicyclic carbocyclic ring, derived by the removal of one hydrogen atom from a single carbon atom of the parent ring system, having 3 to 12 carbon atoms, preferably having 3 to 8 carbon atoms as a monocycle and 7 to 12 carbon atoms as a bicycle. Typical monocyclic carbocycles have 3 to 6 ring atoms, still more typically 5 or 6 ring atoms. Examples of bicycles include but are not limited to [4,5], [5,5], [5,6] or [6,6] systems. Examples monocyclic carbocycles include cyclopropyl, cyclobutyl, cyclopentyl, 1-cyclopent-1-enyl, cyclohexyl, 1-cyclohex-1-enyl, cycloheptyl, cyclooctyl. Unless specified otherwise, a carbocycle can be unsubstituted or substituted as defined below.

In several other chemical formulae and texts below reference is made to "alkenyl", "alkynyl", "alkylene", "alkenylene", "alkynylene", "arylene", "heterocyclo", "carbocyclo". "Alkenyl" refers to an alkyl defined above comprising at least one carbon-carbon $sp^2$ double bond. "Alkynyl" refers to an alkyl defined above comprising at least one carbon-carbon sp triple bond. "Alkylene" refers to an alkyl defined above, wherein one of the alkyl groups' hydrogen atoms is replaced with a bond. An example is methylene (—CH$_2$—). "Alkenylene" refers to an alkyl defined above comprising at least one carbon-carbon $sp^2$ double bond, wherein one of the alkyl groups' hydrogen atoms is replaced with a bond. An example is 1,2-ethylene (—CH═CH—). "Alkynylene" refers to an alkyl defined above comprising at least one carbon-carbon sp triple bond, wherein one of the alkyl groups' hydrogen atoms is replaced with a bond. An example is acetylene. "Arylene" refers to an aryl defined above, wherein one of the aryl groups' hydrogen atoms is replaced with a bond. A "heterocyclo" refers to a heterocycle group defined above wherein one of the heterocycle groups' hydrogen atoms is replaced with a bond. A "carbocyclo" refers to a carbocycle group defined above wherein one of the carbocycle groups' hydrogen atoms is replaced with a bond.

The term "(hetero)alkyl" comprises the terms "heteroalkyl" and "alkyl".

When an (hetero)alkyl group, an aryl group, an heterocycle group, a carbocycle group, an (hetero)alkenyl group, an (hetero)alkynyl group, an (hetero)alkylene group, an (hetero)alkenylene group, an (hetero)alkynylene group, an arylene group, an heterocyclo group and a carbocyclo group is substituted, said group is substituted with one or more substituents independently selected from the group termed "Substituents 1" consisting of $C_1$-$C_8$ (hetero)alkyl, $C_6$-$C_{12}$ aryl, $C_3$-$C_8$ carbocycle, $C_2$-$C_9$ heterocycle, F, Cl, Br, I, CF$_3$, CF$_2$—R', NO, NO$_2$, N$_3$, ═O, ═S, OR', SR', CN, NC, C(═O)R', C(═S)R', OC(═O)R'', SC(═O)R'', OC(═S)R'', SC(═S)R'', S(═O)R', S(═O)$_2$R'', S(═O)$_2$OR', OS(═O)$_2$R'', PO$_3$R'$_2$, OPO$_3$R'$_2$, Si—R''$_3$, Si—OR''$_3$, B(OR')$_2$, S(═O)$_2$NR'$_2$, NR'S(═O)$_2$R'', C(═O)O—R', C(═O)S—R', C(═S)O—R', C(═S)S—R', C(═O)NR'$_2$, C(═S)NR'$_2$, C(═NR')NR'$_2$, ═NR'', ═NOR'', NR'$_2$, NR''$_3^+$, NR'C(═O)R', NR'C(═S)R', NR'C(═O)OR', NR'C(═S)OR', NR'C(═O)SR', NR'C(═S)SR', OC(═O)NR'$_2$, SC(═O)NR'$_2$, OC(═S)NR'$_2$, SC(═S)NR, NR'C(═O)NR'$_2$, NR'C(═S)NR'$_2$, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, and each R'' is independently selected from the group consisting of $C_1$-$C_8$ (hetero)alkyl, $C_6$-$C_{12}$ aryl, $C_3$-$C_8$ carbocycle, $C_2$-$C_9$ heterocycle, wherein all $C_1$-$C_8$ (hetero)alkyl, $C_6$-$C_{12}$ aryl, $C_3$-$C_8$ carbocycle, $C_2$-$C_9$ heterocycle moieties comprised in the Substituents 1 can be unsubstituted or substituted with one or more substituents independently selected from the group termed "Substituents 2" consisting of F, Cl, Br, I, CF$_3$, CF$_2$—R''', NO, NO$_2$, N$_3$, ═O, ═S, OR''', SR''', CN, NC, C(═O)R'''', C(═S)R''', OC(═O)R''', SC(═O)R''', OC(═S)R''', SC(═S)R''', S(═O)R''', S(═O)$_2$R''', S(═O)$_2$OR''', OS(═O)$_2$R''', PO$_3$R'''$_2$OPO$_3$R'''$_2$, B(OR''')$_2$, S(═O)$_2$NR'''$_2$, NR'''S(═O)$_2$R'''', C(═O)O—R''', C(═O)S—R''', C(═S)O—R''', C(═S)S—R''', C(═O)NR'''$_2$, C(═S)NR'''$_2$, C(═NR''')NR'''$_2$, ═NR'''', ═NOR'''', NR'''$_2$, NR'''$_3^+$, NR'''C(═O)R'''', NR'''C(═S)R''', NR'''C(═O)OR''', NR'''C(═S)OR''', NR'''C(═O)SR''', NR'''C(═S)SR''', OC(═O)NR'$_2$, SC(═O)NR'''$_2$, OC(═S)NR'''$_2$, SC(═S)NR'''$_2$, NR'''C(═O)NR'''$_2$, NR'''C(═S)NR'''$_2$, wherein each R''' is independently selected from the group consisting of H, unsubstituted $C_1$-$C_4$ (hetero)alkyl, unsubstituted $C_6$ aryl, and each R'''' is independently selected from the group consisting of unsubstituted $C_1$-$C_4$ (hetero)alkyl and unsubstituted $C_6$ aryl.

In some preferred embodiments, substituents selected from "Substituents 1" are $C_1$-$C_8$ (hetero)alkyl, $C_6$-$C_{12}$ aryl, $C_3$-$C_8$ carbocycle, $C_2$-$C_9$ heterocycle, F, Cl, CF$_3$, NO$_2$, N$_3$, ═O, OR', CN, C(═O)R', S(═O)$_2$R'', S(═O)$_2$OR', PO$_3$R'$_2$, S(═O)$_2$NR'$_2$, C(═O)NR'$_2$, C(═NR')NR'$_2$, NR'$_2$, NR'$_3^+$, NR'C(═O)R', NR'C(═O)OR', OC(═O)NR'$_2$, NR'C(═O)NR'$_2$, NR'C(═S)NR$_2$', wherein each R' is independently selected from the group consisting of H, $C_1$-$C_8$ (hetero)alkyl, $C_6$-$C_8$ aryl, $C_3$-$C_8$ carbocycle, $C_1$-$C_8$ heterocycle, and each R'' is independently selected from the group consisting of $C_1$-$C_8$ (hetero)alkyl, $C_6$-$C_8$ aryl, $C_3$-$C_8$ carbocycle, $C_1$-$C_8$ heterocycle, wherein all $C_1$-$C_8$ (hetero)alkyl, $C_6$-$C_{12}$ aryl, $C_3$-$C_8$ carbocycle, $C_2$-$C_9$ heterocycle moieties comprised in the Substituents 1 can be unsubstituted or substituted as described above.

In some preferred embodiments, substituents selected from "Substituents 2" are F, Cl, CF$_3$, NO$_2$, N$_3$, ═O, OR''', CN, C(═O)R''', S(═O)$_2$R''', S(═O)$_2$OR''', PO$_3$R'''$_2$, S(═O)$_2$NR'''$_2$, C(═O)NR'''$_2$, C(═NR''')NR'''$_2$, NR'''$_2$, NR''''$_{3+}$, NR'''C(═O)R''', NR'''C(═O)OR''', OC(═O)NR'''$_2$, NR'''C(═O)NR'''$_2$, NR'''C(═S)NR$_2$''', wherein each R''' is independently selected from the group consisting of H, unsubstituted $C_1$-$C_4$ (hetero)alkyl, unsubstituted $C_6$ aryl, and each R'''' is independently selected from the group consisting of unsubstituted $C_1$-$C_4$ (hetero)alkyl and unsubstituted $C_6$ aryl.

In some preferred embodiments, it is preferred that a substituted (hetero)alkyl is not substituted by a Substituent 1 being (hetero)alkyl. In some preferred embodiments, it is preferred that a substituted aryl is not substituted by a Substituent 1 being aryl. In some preferred embodiments, it is preferred that a substituted heterocycle is not substituted by a Substituent 1 being heterocycle. In some preferred embodiments, it is preferred that a substituted carbocycle is not substituted by a Substituent 1 being carbocycle.

Trigger

The Construct-Trigger conjugate comprises a Construct-A denoted as $C^A$ linked, directly or indirectly, to a Trigger moiety denoted as $T^R$, wherein the Trigger moiety is a diene. Optionally, the $T^R$ is furthermore linked, directly or indirectly, to a Construct-B denoted as $C^B$. The diene, in a broad sense, is a tetrazine, which comprises a linkage to at least $C^A$ such that the $C^A$ is released following IEDDA reaction of the tetrazine with a dienophile In this invention the diene preferably is a tetrazine that satisfies the following Formula 1:

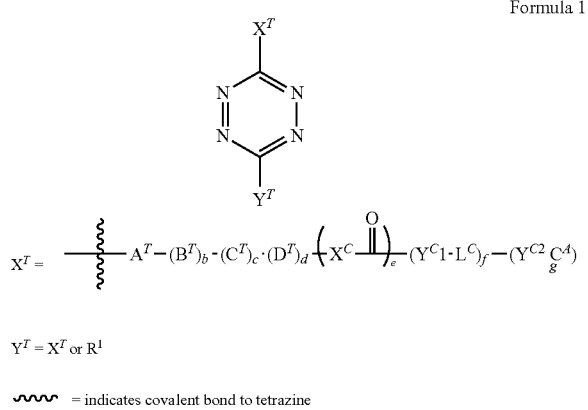

Formula 1

$Y^T = X^T$ or $R^1$

∿∿∿ = indicates covalent bond to tetrazine $A^T$, $B^T$, $C^T$, $D^T$ each independently are selected from the group consisting of $CR^2_2$, $C=O$, $C=CR^3_2$, $C=NR^6$, $C=S$, $NR^4$, O, S, $S(=O)$, or $S(=O)_2$, provided that no sets consisting of adjacent atoms are present selected from the group consisting of —O—O—, —S—N($R^4$)—, —O—S—, —O—S(=O)—, —O—S(=O)$_2$—, and —S—S—, and wherein one $R^2$ or $R^4$ group from $B^T$ and one $R^2$ or $R^4$ group from $A^T$ or $C^T$ can together be a bond, so as to form a double bond, and wherein two or more groups selected from $R^2$, $R^3$, $R^4$, $R^5$, $R^6$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; $X^C$ is O, S, $CR^5_2$ or $NR^6$; $L^C$ is a linker with f being 0 or 1; $C^A$ is Construct A; $Y^{C1}$ is O, S or a secondary amine or a tertiary amine, wherein these moieties are part of $L^C$; $Y^{C2}$ is O, S or a secondary amine or a tertiary amine, wherein these moieties are part of $C^A$; wherein f is 0 and g is 1, or wherein f is 1 and g is an integer from 1 to 9, preferably 1 to 3, more preferably 1; wherein b, c, d and e are independently 0 or 1, provided that if b is 0 then c and d are 0, and if c is 0 then d is 0, and provided that if d is 1 then b and c are 1, and that if c is 1 then b is 1, and provided that if c is 0 then e is 1; wherein when f is 1 then $Y^{C1}$ is referred to as $Y^C$, and when f is 0, then $Y^{C2}$ is referred to as $Y^C$.

Each $R^1$, $R^2$, $R^3$ and $R^5$ is independently selected from the group consisting of H, (hetero)alkyl, aryl, heterocycle, carbocycle, F, Cl, Br, I, $CF_3$, $CF_2$—R', NO, $NO_2$, $N_3$, OR', SR', CN, NC, C(=O)R', C(=S)R', OC(=O)R'', SC(=O)R'', OC(=S)R'', SC(=S)R'', S(=O)R'', S(=O)$_2$R'', S(=O)$_2$OR', OS(=O)$_2$R'', PO$_3$R'$_2$, OPO$_3$R'$_2$, Si—R''$_3$, Si—O— R''$_3$, B(OR')$_2$, S(=O)$_2$NR'$_2$, NR'S(=O)$_2$R'', C(=O)O—R', C(=O)S—R', C(=S)O—R', C(=S)S—R', C(=O)NR'$_2$, C(=S)NR'$_2$, C(=NR')NR'$_2$, NR'$_2$, NR''$_3^+$, NR'C(=O)R', NR'C(=S)R', NR'C(=O)OR', NR'C(=S)OR', NR'C(=O) SR', NR'C(=S)SR', OC(=O)NR'$_2$, SC(=O)NR'$_2$, OC(=S) NR'$_2$, SC(=S)NR'$_2$, CR'$_2$OC(=O)NR'$_2$, CR'$_2$SC(=O) NR'$_2$, CR'$_2$OC(=S)NR'$_2$, CR'$_2$SC(=S)NR'$_2$, NR'C(=O) NR'$_2$, NR'C(=S)NR'$_2$ wherein each R' is independently selected from the group consisting of H, (hetero)alkyl, aryl, carbocycle, heterocycle, and each R'' is independently selected from the group consisting of (hetero)alkyl, aryl, carbocycle, heterocycle, wherein all (hetero)alkyl, aryl, carbocycle, heterocycle moieties comprised in $R^1$, $R^2$, $R^3$ and $R^5$ can be unsubstituted or substituted, and wherein two R' or R'' groups can together form a ring.

Preferably $R^1$ is H, $C_1$-$C_8$ (hetero)alkyl, $C_6$-$C_{12}$ aryl, $C_3$-$C_8$ carbocycle, $C_2$-$C_9$ heterocycle, OR', CN, C(=O)R', C(=O)NR'$_2$, C(=NR')NR'$_2$, NR'$_2$, NR'C(=O)R', NR'C (=O)OR', OC(=O)NR'$_2$, NR'C(=O)NR'$_2$, NR'C(=S) NR'$_2$, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, and each R'' is independently selected from the group consisting of $C_1$-$C_8$ (hetero)alkyl, $C_6$-$C_{12}$ aryl, $C_3$-$C_8$ carbocycle, $C_2$-$C_9$ heterocycle; more preferably $R^1$ is H, unsubstituted $C_1$-$C_8$ (hetero) alkyl, unsubstituted $C_6$-$C_{12}$ aryl, unsubstituted $C_3$-$C_8$ carbocycle, unsubstituted $C_2$-$C_9$ heterocycle.

Preferably each $R^2$, $R^3$ and $R^5$ are each independently selected from the group consisting of H, $C_1$-$C_8$ (hetero)alkyl, $C_6$-$C_{12}$ aryl, $C_3$-$C_8$ carbocycle, $C_2$-$C_9$ heterocycle, F, $CF_3$, $NO_2$, $N_3$, OR', SR', CN, C(=O)R', S(=O)$_2$R'', S(=O)$_2$OR', PO$_3$R'$_2$, S(=O)$_2$NR'$_2$, NR'S(=O)$_2$R'', C(=O)NR'$_2$, C(=NR')NR'$_2$, NR'$_2$, NR''$_3^+$, NR'C(=O)R', NR'C(=O) NR'$_2$, NR'C(=S)NR'$_2$, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, and each R'' is independently selected from the group consisting of $C_1$-$C_8$ (hetero)alkyl, $C_6$-$C_{12}$ aryl, $C_3$-$C_8$ carbocycle, $C_2$-$C_9$ heterocycle; more preferably $R^2$, $R^3$ and $R^5$ are each independently selected from the group consisting of H, unsubstituted $C_1$-$C_8$ (hetero)alkyl, unsubstituted $C_6$-$C_{12}$ aryl, unsubstituted $C_3$-$C_8$ carbocycle, unsubstituted $C_2$-$C_9$ heterocycle, OH, S(=O)$_2$OH; even more preferably $R^2$, $R^3$ and $R^5$ are each independently selected from the group consisting of H and unsubstituted $C_1$-$C_3$ alkyl.

Each $R^4$ and $R^6$ is independently selected from the group consisting of H, (hetero)alkyl, aryl, heterocycle, carbocycle, OR', C(=O)R', C(=O)O—R', C(=O)S—R', C(=S)O— R', C(=S)S—R', C(=O)NR'$_2$, C(=S)NR'$_2$, C(=NR')NR'$_2$, NR'$_2$, preferably such that no sets consisting of adjacent atoms are present selected from the group consisting of —N—N—, —N—O—, —N—S—, —N—Si— and —N— P—, and wherein each R' is independently selected from the group consisting of (hetero)alkyl, aryl, carbocycle, heterocycle, wherein all (hetero)alkyl, aryl, carbocycle, heterocycle moieties comprised in $R^4$ and $R^6$ can be unsubstituted or substituted, and wherein two R' groups can together form a ring.

Preferably, each $R^4$ and $R^6$ is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, C(=O)R', C(=O) O—R', C(=O)NR'$_2$, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle; more preferably $R^4$ and $R^6$ are each independently selected from the group consisting of H, unsubstituted $C_1$-$C_8$ (hetero)alkyl, unsubstituted $C_6$-$C_{12}$ aryl, unsubstituted $C_3$-$C_8$ carbocycle, unsubstituted $C_2$-$C_9$ heterocycle; even more preferably $R^4$ and $R^6$ are each independently selected from the group consisting of H, unsubstituted $C_1$-$C_3$ alkyl, or together with another R group form an $C_6$-$C_{12}$ aryl, a 3- to 8-membered heterocycle, or a 3- to 8-membered annelated hetero(alkyl).

In some embodiments it is preferred that $Y^T$ is $R^1$.

In some embodiments it is preferred that $Y^T$ is $X^T$.

In some embodiments it is preferred that —C=N— and —O—N(R)— moieties are not comprised in or between $A^T$, $B^T$, $C^T$, $D^T$.

It is preferred that when e is 0 then $Y^C$ is O or S, preferably attached to an aromatic carbon atom of $L^C$ or $C^A$.

In some embodiments is preferred that at most 3 instances R groups from $R^2$, $R^3$, $R^4$, $R^5$ and $R^6$ are not H; even more preferably at most 2 R groups are not H.

In some embodiments, it is preferred that when $X^C$ is $NR^6$ that $R^6$ comprised in $X^C$ is unsubstituted $C_1$-$C_3$ alkyl.

In order to better accommodate a Trigger to function via the Cyclization mechanism there are the following preferences:

Preferably $A^T$, $B^T$, $C^T$, $D^T$ each independently are selected from the group consisting of $CR^2_2$, C=O, C=$CR^3_2$, C=$NR^6$ and $NR^4$; more preferably $A^T$, $B^T$, $C^T$, $D^T$ are $CR^2_2$. It is further preferred that if b is 0 and $X^C$ is O, S or $NR^6$ that $A^T$ is $CR^2_2$. It is further preferred that if b is 1 and c is 0 and $X^C$ is O, S or $NR^6$ that $B^T$ is $CR^2_2$. It is further preferred that if c and e are 1 and d is 0 and $X^C$ is O, S or $NR^6$ that $C^T$ is $CR^2_2$. It is further preferred that if d and e are 1 and $X^C$ is O, S or $NR^6$ that $D^T$ is $CR^2_2$.

In some embodiments it is preferred that when d and e are 1 and $X^C$ is O or S then $D^T$ is not bound to $C^T$ with a non-aromatic double bond, and that when c and e are 1 and d is 0 and Xc is O or S then $C^T$ is not bound to $B^T$ with a non-aromatic double bond, and that when b and e are 1 and c is 0 and $X^C$ is O or S then $B^T$ is not bound to $A^T$ with a non-aromatic double bond.

It is preferred that when c or d is 1 then $X^C$ is O or S.

It is preferred that when c is 0 then $Y^C$ is O or S, preferably attached to an aromatic carbon atom of $L^C$ or $C^A$.

When b is 0 and e is 1, then preferably $X^C$ is $NR^6$ and $Y^C$ is O.

When b and e are 1 and c is 0, then preferably $X^C$ is $NR^6$ and $Y^C$ is O.

When c or d is 1 and e is 1, then preferably $X^C$ is O and $Y^C$ is a secondary or tertiary amine.

When c is 0 and $X^C$ is O or S, then preferably $Y^C$ is O or S.

In a preferred embodiment, b is 0, $A^T$ is $CH_2$, and $X^C$ is $NR^6$ such that $R^6$ comprised in $X^C$ is not H.

In another preferred embodiment, b is 0, $A^T$ is $CHR^2$ with $R^2$ not being H, and $X^C$ is $NR^6$ such that $R^6$ comprised in $X^C$ is H or unsubstituted $C_1$-$C_3$ alkyl, more preferably unsubstituted $C_1$-$C_3$.

In another preferred embodiment b is 1, c is 0, $A^T$ and $B^T$ are $CH_2$, and $X^C$ is $NR^6$ such that $R^6$ comprised in $X^C$ is not H.

In order to better accommodate a Trigger to function via the Cascade mechanism there are the following preferences:

Preferably, $X^C$, if present, is O or S, and $Y^C$ is O, S, or secondary or tertiary amine.

In preferred embodiments b is 0, e is 1, $X^C$ is O and $Y^C$ is secondary or tertiary amine In a preferred embodiment, b is 0 and e is 1, $X^C$ is O, $Y^C$ is secondary or tertiary amine, $A^T$ is $CR^2_2$; more preferably $Y^C$ is a tertiary amine; more preferably $A^T$ is $CHR^2$ with $R^2$ selected from H or $C_1$-$C_3$ alkyl, preferably $C_1$-$C_3$ alkyl.

In another preferred embodiment, c is 1 and d is 0, e is 1, $A^T$ and $B^T$ are bound together through a double bond, $C^T$ is $CR^2_2$, $X^C$ is O and $Y^C$ is secondary or tertiary amine; preferably $A^T$ and $B^T$ are $CR^2_2$ wherein one $R^2$ of $A^T$ and one $R^2$ of $B^T$ together are a bond, so as to form a double bond, wherein the remaining $R^2$ groups in $A^T$, BT, $C^T$ are preferably H.

Hereinafter several embodiments are discussed, which are preferred embodiments that are general for both release mechanisms that are possible for the structures of Formula (1).

In some embodiments $R^1$ is electron-withdrawing. For example, $R^1$ may denote a substituent selected from the group consisting of $NO_2$, F, Cl, $CF_3$, CN, $CO_2R'$, C(=O)NR'$_2$, C(=O)R', $SO_2R''$, $SO_2OR'$, $SO_2NR'_2$, $PO_3R'_2$, NO, 2-pyridyl, 3-pyridyl, 4-pyridyl, 2,6-pyrimidyl, 3,5-pyrimidyl, 2,4-pyrimidyl, 2,4 imidazyl, 2,5 imidazyl, 2,3,4-triazyl, 2,3,5-triazyl, phenyl, or phenyl optionally substituted with one or more electron-withdrawing groups such as $NO_2$, F, Cl, $CF_3$, CN, $CO_2R'$, C(=O)NHR', C(=O)NR', C(=O)R', $SO_2R'$, $SO_2OR'$, $SO_2NR'_2$, $PO_3R'_2$, NO, wherein each R' is independently optionally H or each R' and each R'' is independently selected from (hetero)alkyl, aryl, carbocycle, heterocycle.

In some embodiments $R^1$ is electron-donating. Exemplary electron donating groups for $R^1$ are OR', SR', $NR'_2$, NR'C(=O)R', NR'C(=S)R', $NR'SO_2R''$ wherein each R' is independently optionally H or each R' and each R'' is independently selected from (hetero)alkyl, aryl, carbocycle, heterocycle. Examples of other electron donating groups are phenyl groups with attached to them one or more of the electron donating groups as mentioned in the list above, especially when substituted in the 2-, 4- and/or 6-position(s) of the phenyl group.

In some embodiments $R^1$ is a pyridyl or pyrimidyl moiety comprising one or more electron donating substituent selected from OR', SR', $NR'_2$, NR'C(=O)R', NH—S(=O)R' or NH—S(=O)$_2$—R'' substituents.

In some embodiments $R^1$ is (hetero)alkyl or phenyl.

Without wishing to be bound by theory, examples of $X^T$ moieties comprised in Formula (1) that are believed to afford release via the cyclization mechanism are listed below. It is preferred for the structures $X^T$-1 up to and including $X^T$-20 that $Y^C$ is O or S, preferably attached to an aromatic carbon atom of $L^C$ or $C^A$. It is preferred for the structures $X^T$-21 up to and including $X^T$-62 that $Y^C$ is a secondary or tertiary amine.

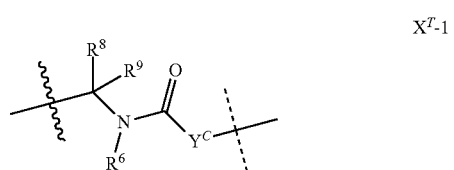

$X^T$-1

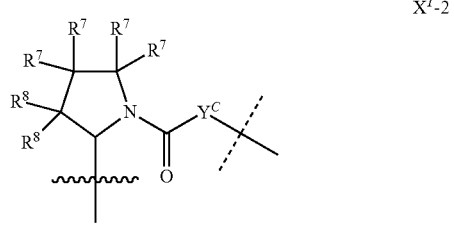

$X^T$-2

X<sup>T</sup>-3
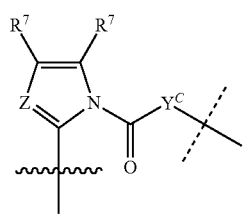
X<sup>T</sup>-4
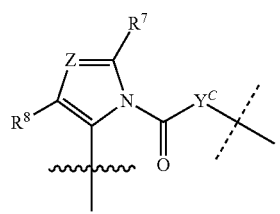
X<sup>T</sup>-5
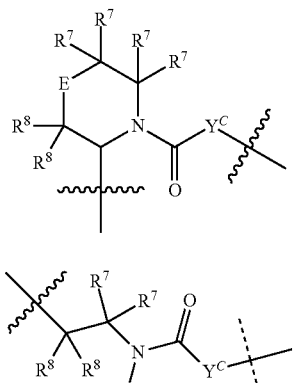
X<sup>T</sup>-6
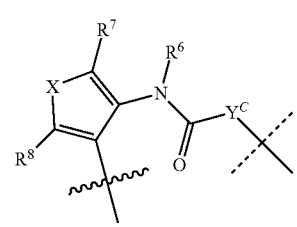
X<sup>T</sup>-7
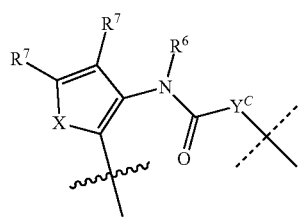
X<sup>T</sup>-8
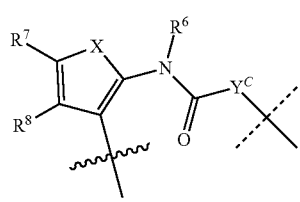
X<sup>T</sup>-9
X<sup>T</sup>-10
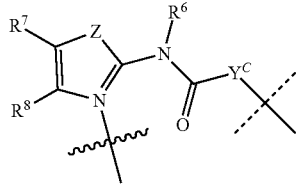
X<sup>T</sup>-11
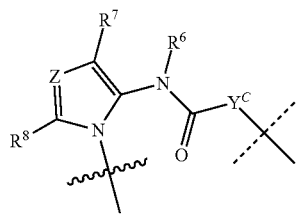
X<sup>T</sup>-12
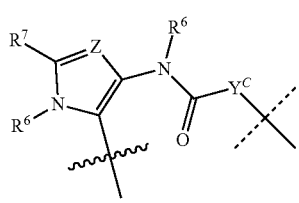
X<sup>T</sup>-13
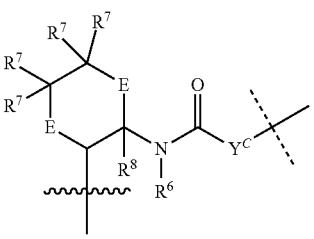
X<sup>T</sup>-14
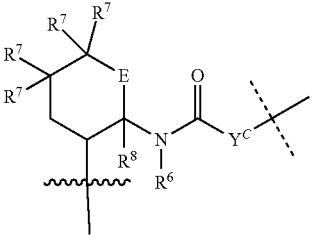
X<sup>T</sup>-15
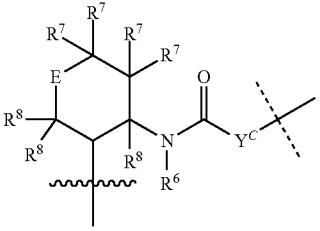
X<sup>T</sup>-16
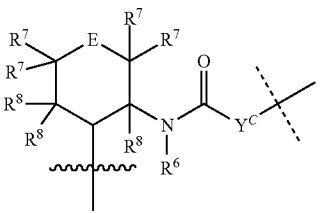

-continued
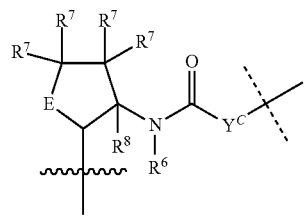
X^T-17
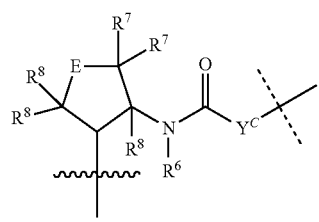
X^T-18
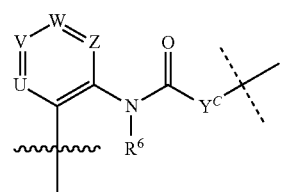
X^T-19
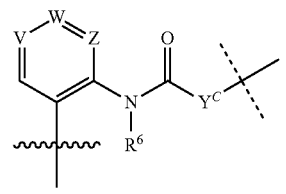
X^T-20
~~~ indicates covalent bond to tetrazine
---- indicates covalent bond to (remainder of) $L^C$ or $C^A$
U, V, W, Z = N or $R^7$
X = O or S or $NR^6$
E = O, S, $NR^6$, $CR^7_2$
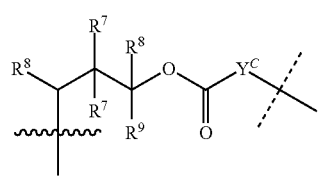
X^T-21
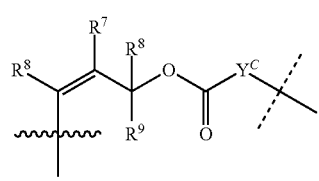
X^T-22
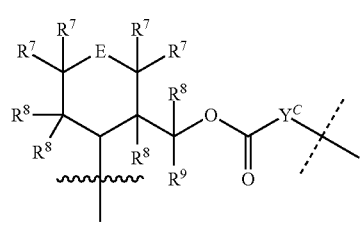
X^T-23
-continued
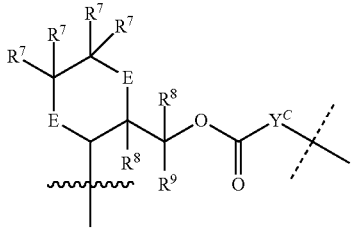
X^T-24
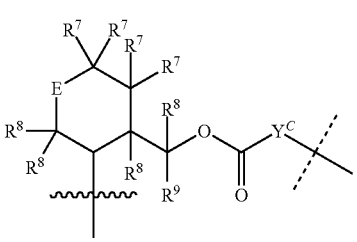
X^T-25
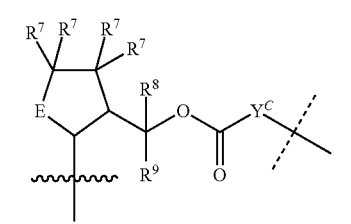
X^T-26
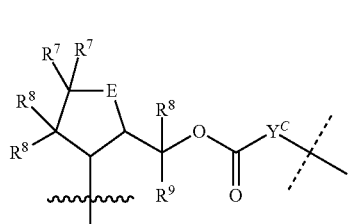
X^T-27
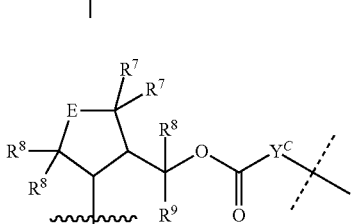
X^T-28
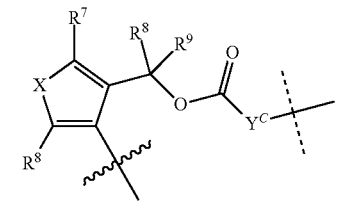
X^T-29
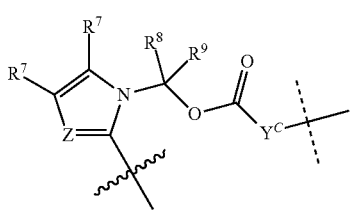
X^T-30

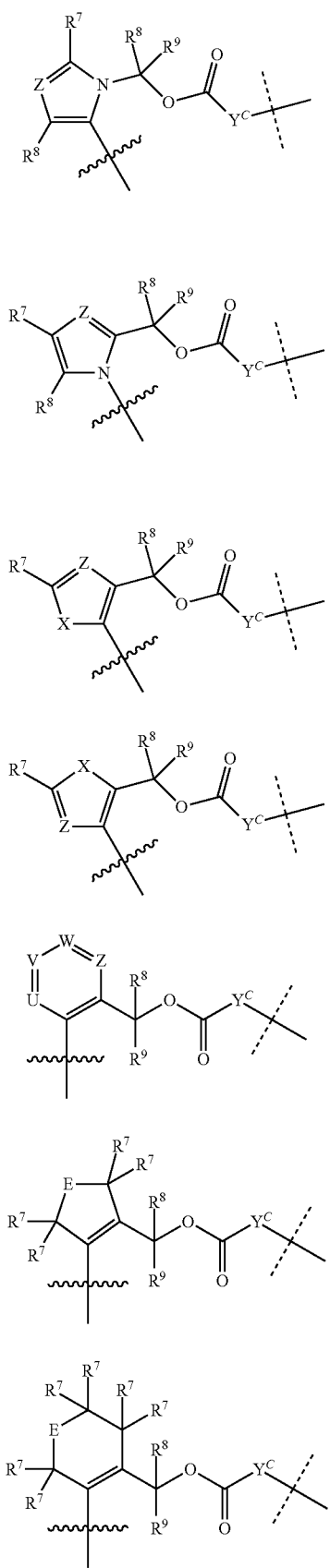
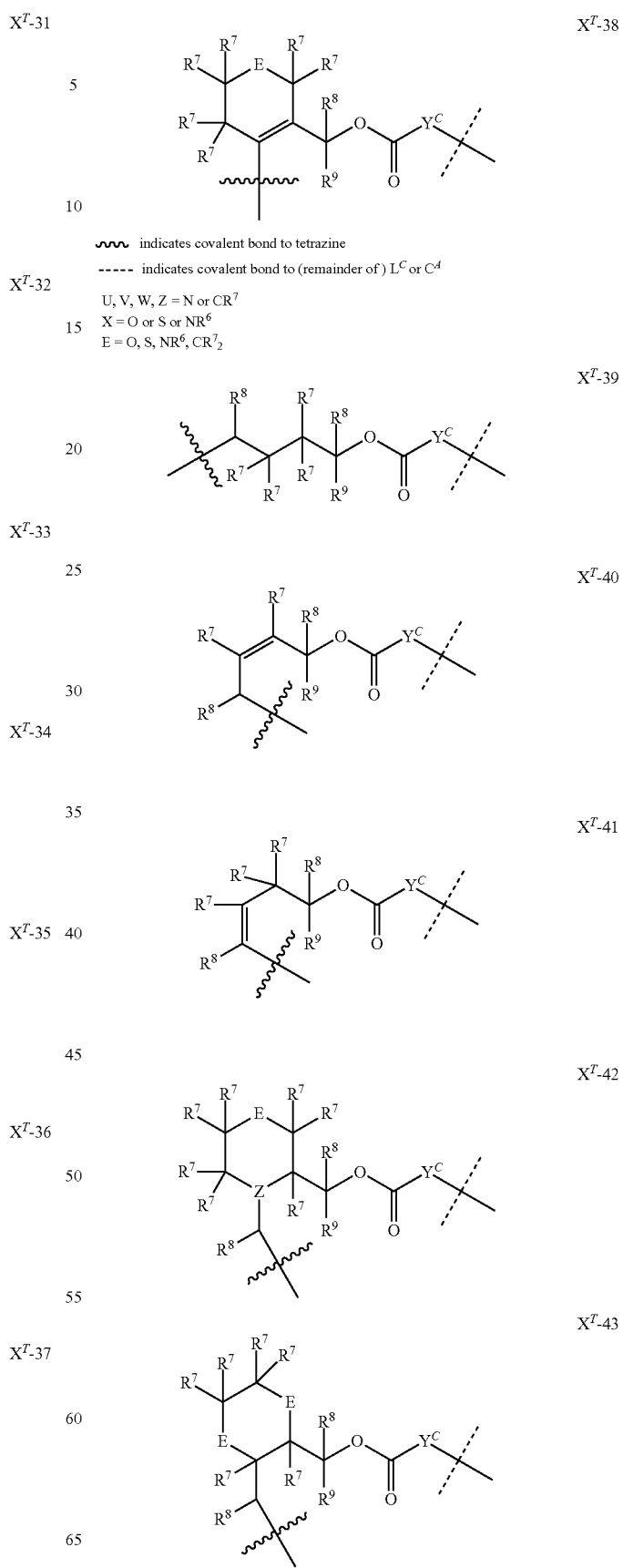
indicates covalent bond to tetrazine
----- indicates covalent bond to (remainder of) $L^C$ or $C^A$
U, V, W, Z = N or $CR^7$
X = O or S or $NR^6$
E = O, S, $NR^6$, $CR^7_2$ -continued
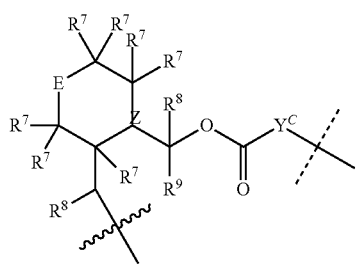 X^T-44
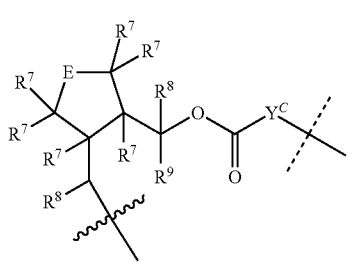 X^T-45
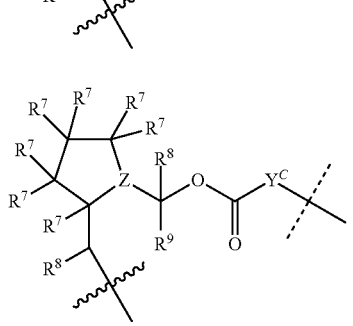 X^T-46
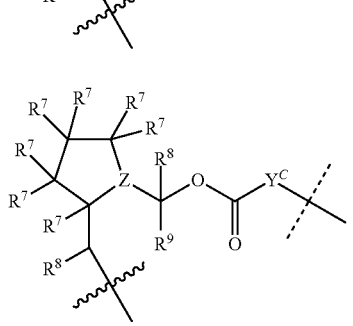 X^T-47
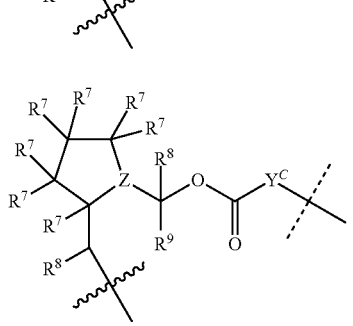 X^T-48
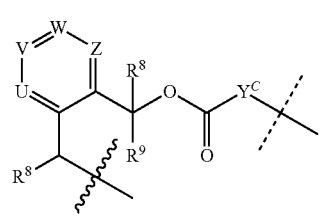 X^T-49
-continued
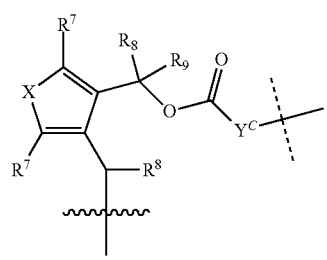 X^T-50
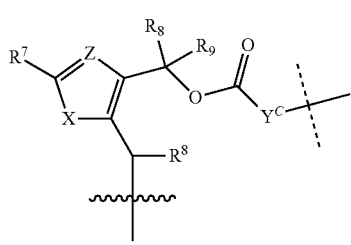 XT-51
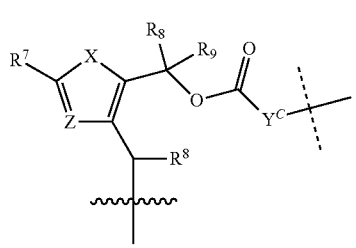 X^T-52
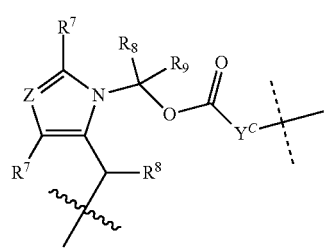 X^T-53
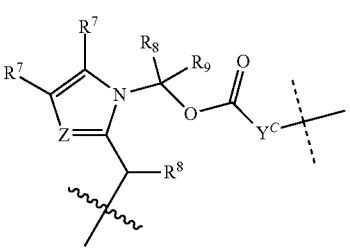 X^T-54
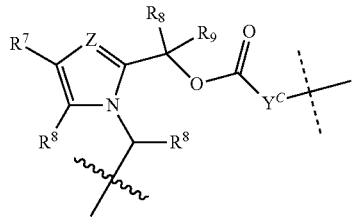 X^T-55

-continued

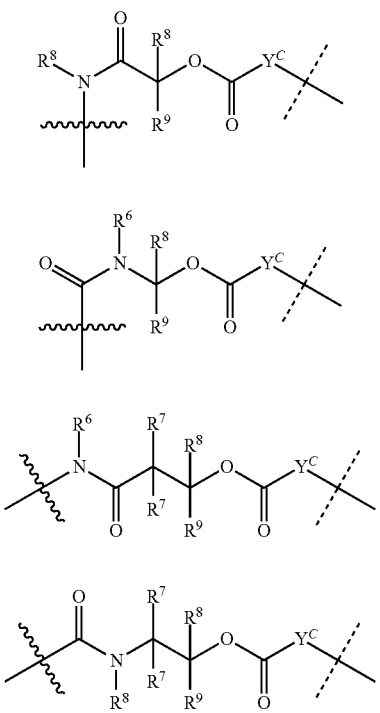

X$^T$-56

X$^T$-57

X$^T$-58

X$^T$-59

∿∿∿ indicates covalent bond to tetrazine
---- indicates covalent bond to (remainder of) L$^C$ or C$^A$ U, V, W, Z = N or CR$^7$
X = O or S or NR$^6$
E = O, S, NR$^6$, CR$^7_2$ Without wishing to be bound by theory, examples of X$^T$ moieties comprised in Formula (1) that are believed to afford release via the cascade mechanism are listed below. In addition, it is contemplated that Triggers X$^T$-29-32 (shown above) may also exhibit release via the cascade mechanism.

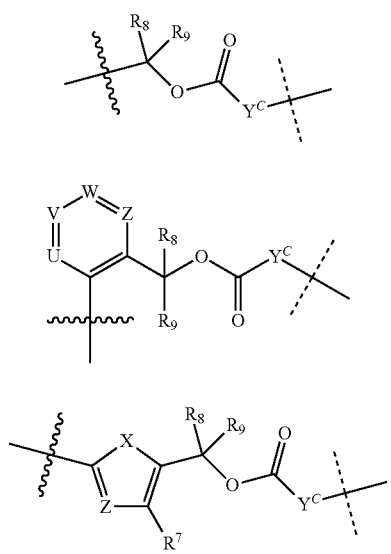

X$^T$-60

X$^T$-35

X$^T$-61

-continued

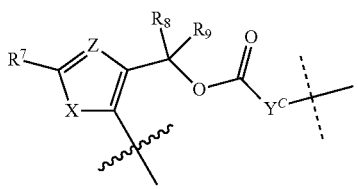

X$^T$-33

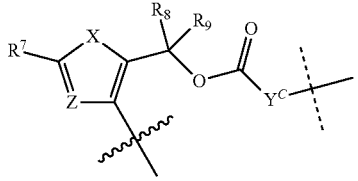

X$^T$-34

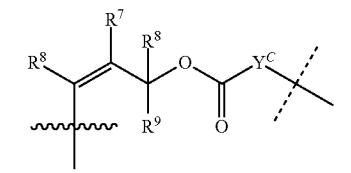

X$^T$-22

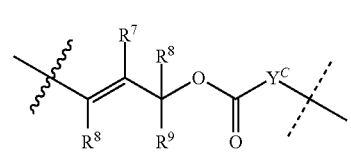

X$^T$-62

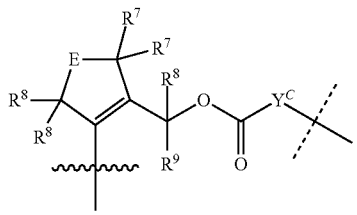

X$^T$-36

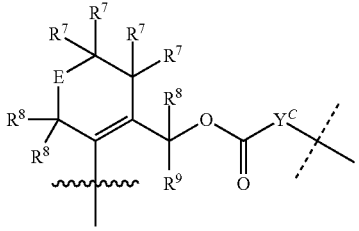

X$^T$-37

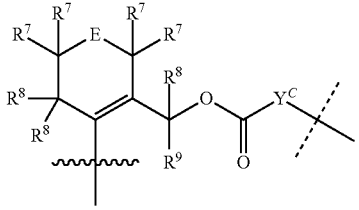

X$^T$-38

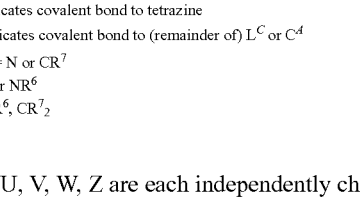

∿∿∿ indicates covalent bond to tetrazine
---- indicates covalent bond to (remainder of) L$^C$ or C$^A$ U, V, W, Z = N or CR$^7$
X = O or S or NR$^6$
E = O, S, NR$^6$, CR$^7_2$ wherein U, V, W, Z are each independently chosen from the group consisting of N and CR$^7$; X is independently chosen from the group consisting of O, S and NR$^6$; E is independently chosen from the group consisting of O, S, $NR^6$ and $CR^7_2$; with $R^7$, $R^8$ and $R^9$ each independently being selected from the group defined above for $R^1$, $R^2$, $R^3$, $R^5$, wherein two $R^6$, $R^7$, $R^8$ and/or $R^9$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle.

Preferably each $R^7$, $R^8$ and $R^9$ is independently selected from H, $C_1$-$C_8$(hetero)alkyl, $C_6$-$C_{12}$ aryl, $C_3$-$C_8$ carbocycle, $C_2$-$C_9$ heterocycle, F, $CF_3$, $NO_2$, $N_3$, OR', SR', CN, C(=O)R', S(=O)$_2$R'', S(=O)$_2$OR', $PO_3$R'$_2$, S(=O)$_2$NR'$_2$, NR'S(=O)$_2$R'', C(=O)NR'$_2$, C(=NR')NR'$_2$, NR'$_2$, NR''$_3^+$, NR'C(=O)R', NR'C(=O)NR'$_2$, NR'C(=S)NR'$_2$ wherein each R' is selected from the group consisting of H, $C_1$-$C_8$ (hetero)alkyl, $C_6$-$C_{12}$ aryl, $C_3$-$C_8$ carbocycle, $C_2$-$C_9$ heterocycle, and each R'' is independently selected from the group consisting of $C_1$-$C_8$ (hetero)alkyl, $C_6$-$C_{12}$ aryl, $C_3$-$C_8$ carbocycle, $C_2$-$C_9$ heterocycle; more preferably each $R^7$, $R^8$ and $R^9$ is independently selected from the group consisting of H, unsubstituted $C_1$-$C_8$ (hetero)alkyl, unsubstituted $C_6$-$C_{12}$ aryl, unsubstituted $C_3$-$C_8$ carbocycle, unsubstituted $C_2$-$C_9$ heterocycle, OH, S(=O)$_2$OH; even more preferably each $R^7$, $R^8$ and $R^9$ is independently selected from the group consisting of H and unsubstituted $C_1$-$C_3$ alkyl.

In some embodiments it is preferred for moieties $X^T$-1 up to and including $X^T$-20, which are believed to afford release via the cyclization mechanism, that $R^6$ is H or unsubstituted $C_1$-$C_3$ alkyl, that $R^8$ is H, and that $R^9$ is unsubstituted $C_1$-$C_3$ alkyl.

In some embodiments it is preferred for moieties $X^T$-21 up to and including $X^T$-59, which are believed to afford release via the cyclization and/or the cascade mechanism, that $R^6$ is H or unsubstituted $C_1$-$C_3$ alkyl, that $R^8$ is H, and that $R^9$ is unsubstituted $C_1$-$C_3$ alkyl, $NO_2$, $CF_3$, CN, unsubstituted $C_6$ aryl or unsubstituted $C_3$-$C_8$ heterocycle.

In some embodiments, it is preferred for moieties $X^T$-22, $X^T$-33, $X^T$-34, $X^T$-35, $X^T$-3$_6$, $X^T$-3$_7$, $X^T$-38, $X^T$-60, $X^T$-61, $X^T$-62, which are believed to afford release via the cascade mechanism, that $R^8$ is H and that $R^9$ is H, unsubstituted $C_1$-$C_3$ alkyl, unsubstituted $C_6$ aryl or unsubstituted $C_3$-$C_5$ heterocycle.

In some embodiments, it is preferred for moiety $X^T$-34, which is believed to afford release via the cascade mechanism, that $R^7$ is H or $CF_3$, that $R^8$ is H, and that $R^9$ is H or unsubstituted $C_1$-$C_3$ alkyl.

It is preferred that when $C^A$ is bound to $T^R$ or $L^C$ via an $Y^{C2}$ that is a secondary amine, i.e. an NH, this NH is a primary amine (—$NH_2$) residue from $C^A$, and when $C^A$ is bound via an $Y^{C2}$ that is a tertiary amine, i.e. N, this N is a secondary amine (—NH—) residue from $C^A$. Similarly, it is preferred that when $C^A$ is bound via an $Y^{C2}$ that is an O or S, said O or S are, respectively, a hydroxyl (—OH) residue or a sulfhydryl (—SH) residue from $C^A$.

It is further preferred that said S, N, NH, or O $Y^{C2}$-moieties comprised in $C^A$ are bound to an aliphatic or aromatic carbon of $C^A$. When e is 0 it is preferred that said S, N, NH, or O moieties comprised in $C^A$ are bound to an aromatic carbon of $C^A$. In addition, this invention contemplates that $C^A$ can be bound to $L^C$ or $T^R$ through an $Y^{C2}$ that is a nitrogen in an aromatic ring, such as in a pyrrole or an imidazole ring.

It is preferred that when $L^C$ is bound to $T^R$ via an $Y^{C1}$ that is a secondary amine, i.e. NH, this NH is a primary amine (—$NH_2$) residue from $L^C$, and when $L^C$ is bound via an $Y^{C1}$ that is a tertiary amine N, this N is a secondary amine (—NH—) residue from $L^C$. Similarly, it is preferred that when $L^C$ is bound via an $Y^{C1}$ that is an O or S, said O or S are, respectively, a hydroxyl (—OH) residue or a sulfhydryl (—SH) residue from $L^C$.

It is further preferred that said S, N, NH, or O $Y^{C1}$-moieties comprised in $L^C$ are bound to an aliphatic or aromatic carbon of $L^C$. When e is 0 it is preferred that said S, N, NH, or O moieties comprised in $L^C$ are bound to an aromatic carbon of $L^C$.

Optionally, in all of the above embodiments, one or more of $R^1$, $R^2$, $R^3$, $R^4$, $R^5$, $R^6$, $R^7$, $R^1$, $R^9$ and the self-immolative linker $L^C$, is bound to $S^P$, and/or to $C^B$ optionally via a Spacer $S^P$.

Without wishing to be bound by theory, the inventors believe that in the foregoing embodiments, the IEDDA reaction results in an intramolecular cyclization- or cascade-mediated release of the Construct $C^A$.

Linker $L^C$ $L^C$ is an optional linker, which may be self-immolative or not, or a combination thereof and which may consist of multiple units arranged linearly and/or branched and may release one or more $C^A$ moieties. It will be understood that when $L^C$ is not self-immolative $L^C$ equals a spacer $S^P$. It is preferred that $L^C$ is self-immolative.

By way of further clarification, if f is 0 the species $C^A$ directly constitutes the leaving group of the release reaction, and if f is 1, the self-immolative linker $L^C$ constitutes the leaving group of the release reaction. The position and ways of attachment of linkers $L^C$ and constructs $C^A$ are known to the skilled person, see for example [Papot et al., Anticancer Agents Med. Chem., 2008, 8, 618-637]. Nevertheless, typical but non-limiting examples of self-immolative linkers $L^C$ are benzyl-derivatives, such as those drawn below. There are two main self-immolation mechanisms: electron cascade elimination and cyclization-mediated elimination. The example below on the left functions by means of the cascade mechanism, wherein the bond to the $Y^C$ between Trigger and $L^C$, here termed $Y^{C1}$, is cleaved, and an electron pair of $Y^{C1}$, for example an electron pair of $NR^6$, shifts into the benzyl moiety resulting in an electron cascade and the formation of 4-hydroxybenzyl alcohol, $CO_2$ and the liberated $C^A$ also comprising an $Y^C$, here termed $Y^{C2}$. The example in the middle functions by means of the cyclization mechanism, wherein cleavage of the bond to the amine of $Y^{C1}$ leads to nucleophilic attack of the amine on the carbonyl, forming a 5-ring 1,3-dimethylimidazolidin-2-one and liberating the $C^A$ including $Y^{C2}$. The example on the right combines both mechanisms, this linker will degrade not only into $CO_2$ and one unit of 4-hydroxybenzyl alcohol (when $Y^{C1}$ is O), but also into one 1,3-dimethylimidazolidin-2-one unit.

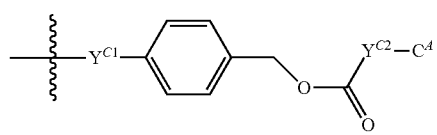

$Y^{C1}$ = O, S, $NR^6$
$Y^{C2}$ = O, S, secondary or tertiary amine;
preferably secondary or tertiary amine
∼∼∼ indicates bond to Trigger -continued

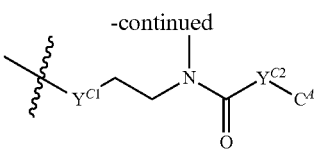

$Y^{C1}$ = NR$^6$; R$^6$ is preferably methyl
$Y^{C2}$ = O, S
⁓ indicates bond to Trigger

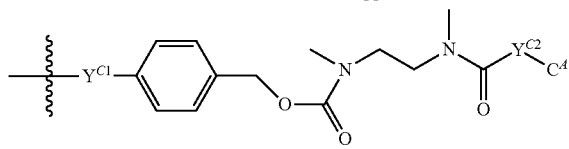

$Y^{C1}$ = O, S, NR$^6$
$Y^{C2}$ = O, S
⁓ indicates bond to Trigger

By substituting the benzyl groups of aforementioned self-immolative linkers L$^C$, it is possible to tune the rate of release of the construct C$^A$, caused by either steric and/or electronic effects on the cyclization and/or cascade release. Synthetic procedures to prepare such substituted benzyl-derivatives are known to the skilled person (see for example [Greenwald et al, J. Med. Chem., 1999, 42, 3657-3667] and [Thornthwaite et al, Polym. Chem., 2011, 2, 773-790]. Some examples of substituted benzyl-derivatives with different release rates are drawn below.

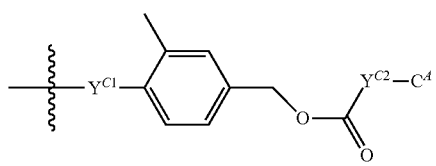

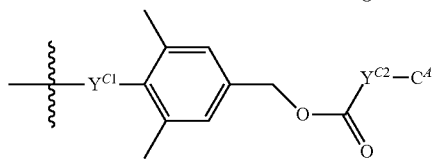

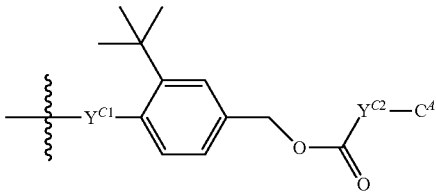

$Y^{C1}$ = O, S, NR$^6$
$Y^{C2}$ = O, S, secondary or tertiary amine; preferably secondary or tertiary amine
⁓ indicates bond to Trigger In some exemplary embodiments the L$^C$ satisfies one of the following Formulae 2a-c

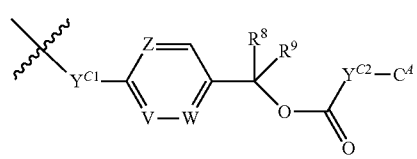

Formula 2a

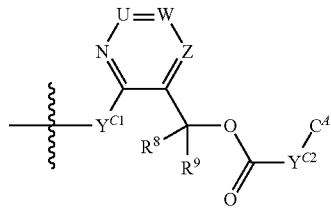

Formula 2b

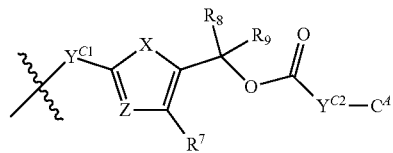

Formula 2c

⁓ indicates bond to Trigger wherein $Y^{C1}$ is O, S or NR$^6$; V, U, W, Z are each independently CR$^7$ or N; $Y^{C2}$ is O, S, secondary amine or tertiary amine, wherein these $Y^{C2}$ moieties are part of C$^A$; with R$^6$, R$^7$, R$^8$, R$^9$ as defined above. In some embodiments it is preferred that R$^6$ is H or methyl, R$^7$ is H, R$^8$ is H or methyl and R$^9$ is H. In some embodiments the R$^7$ comprised in Formula 2c is CF$_3$ and Z is N.

In other embodiments the L$^C$ satisfies the following Formula 2d

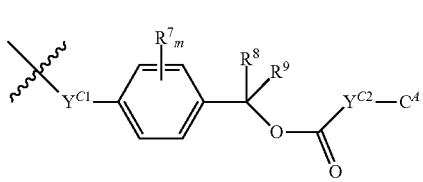

Formula 2d

⁓ indicates bond to Trigger wherein $Y^{C1}$ is O, S or NR$^6$; $Y^{C2}$ is O, S, secondary amine or tertiary amine, wherein these $Y^{C2}$ moieties are part of C$^A$; with R$^6$, R$^7$, R$^R$, R$^9$ as defined above; preferably R$^7$ is C$_1$-C$_8$ alkyl, C$_6$-C$_{12}$ aryl, C$_1$-C$_8$ O-alkyl, C$_6$-C$_{12}$O-aryl, NO$_2$, F, Cl, Br, I, CN, with m being an integer from 0 to 4; each R$^8$ and R$^9$ are independently H, C$_1$-C$_8$ alkyl, C$_6$-C$_{12}$ aryl, C$_1$-C$_8$ O— alkyl, C$_6$-C$_{12}$O-aryl, NO$_2$, F, Cl, Br, I, CN. Preferably R$^7$ is electron donating and preferably m is an integer between 0 and 2, more preferably m is 0. Preferably R$^8$ is H and R$^9$ is H or methyl.

Self-immolative linkers that undergo cyclization include but are not limited to substituted and unsubstituted aminobutyric acid amide, appropriately substituted bicyclo[2.2.1] and bicyclo[2.2.2] ring system, 2-aminophenylpropionic acid amides, and trimethyl lock-based linkers, see e.g. [Chem. Biol. 1995, 2, 223], [J. Am. Chem. Soc. 1972, 94, 5815], [J. Org. Chem. 1990, 55, 5867], the contents of which are hereby incorporated by reference.

In other embodiments such cyclization $L^C$ satisfies one of the following Formulae 3a-d.

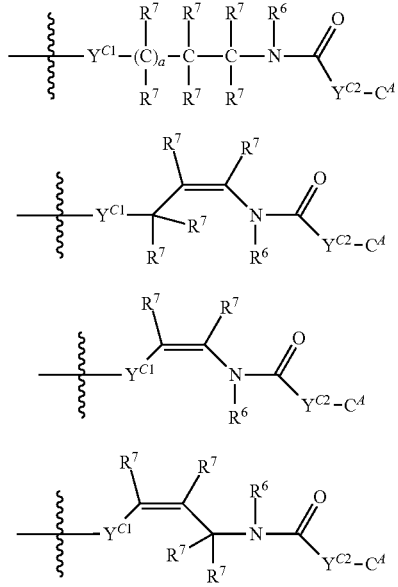

Formula 3a

Formula 3b

Formula 3c

Formula 3d $\sim\!\!\sim$ indicates bond to Trigger

Wherein $Y^{C1}$ is $NR^6$; $Y^{C2}$ is O or S, wherein these $Y^{C2}$ moieties are part of CA; a is independently 0 or 1; $R^6$ and $R^7$ are as defined above. Preferably $R^6$ and $R^7$ are H, unsubstituted $C_1$-$C_8$ alkyl, $C_6$ aryl, more preferably $R^6$ is H or methyl and $R^7$ is H.

Several non-limiting example structures of $L^C$ are shown below. In these examples $C^A$ is preferably bound to $L^C$ via an $Y^{C2}$ that is O or S, wherein 0 or S is part of $C^A$. For the avoidance of doubt, in these examples $Y^{C1}$ is not denoted as such but is embodied by the relevant NH, $NR^6$, S, O groups.


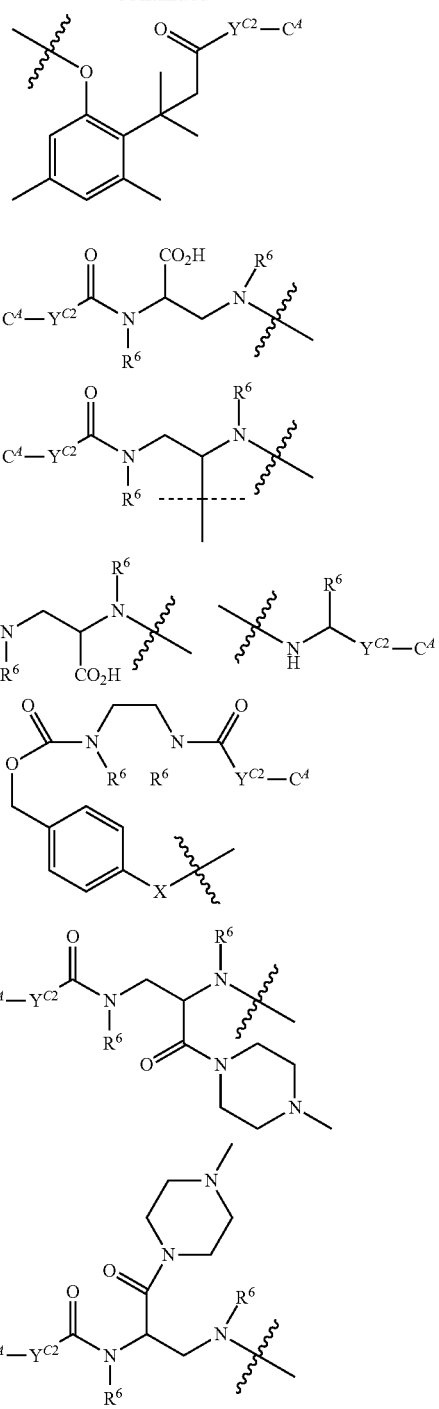

$\sim\!\!\sim$ indicates bond to Trigger
----- indicates bond to $C^B$ or $S^P$—$C^B$ or $S^P$
Preferably $Y^{C2}$ is O or S
$X = O, S, NR^6$
$R^6$ is as defined for Formula 1

Several other non-limiting example structures of $L^C$ are shown below. In these examples $C^A$ is preferably bound to $L^C$ via an $Y^{C2}$ that is a secondary or primary amine, and wherein said $Y^{C2}$ is part of $C^A$. For the avoidance of doubt, in these examples $Y^{C1}$ is not denoted as such but is embodied by the relevant NH, $NR^6$, S, O groups 33
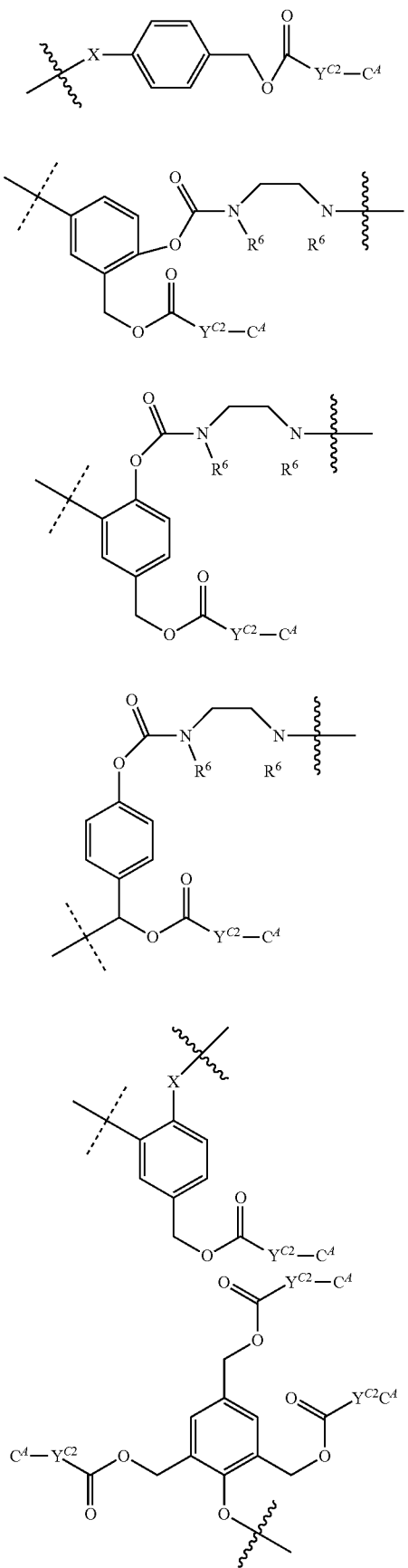
34
-continued
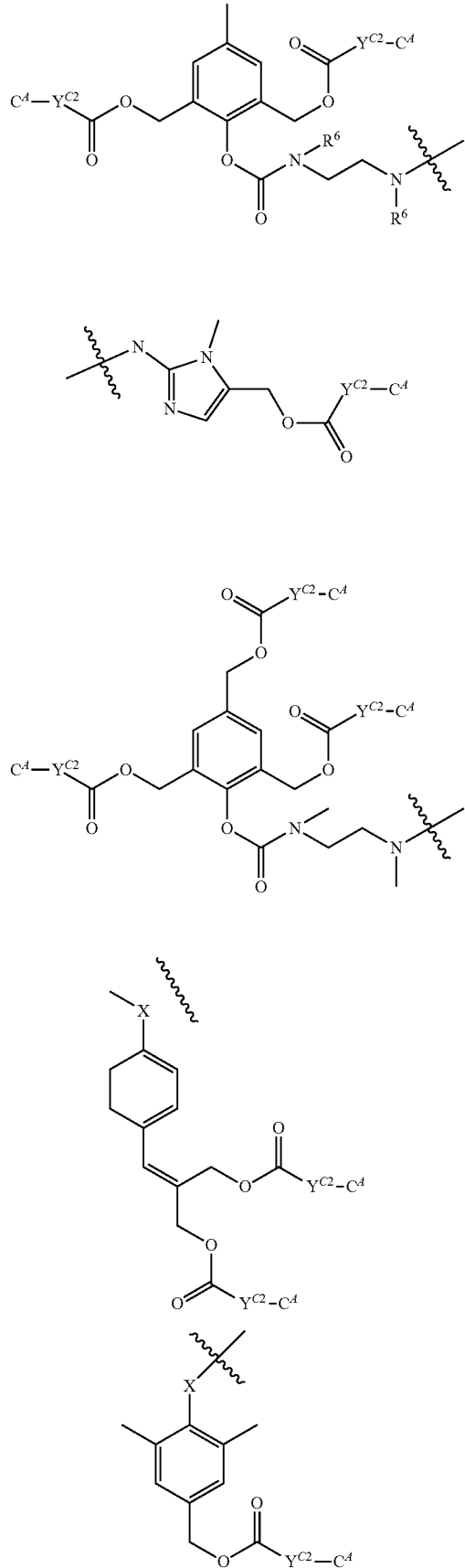

-continued

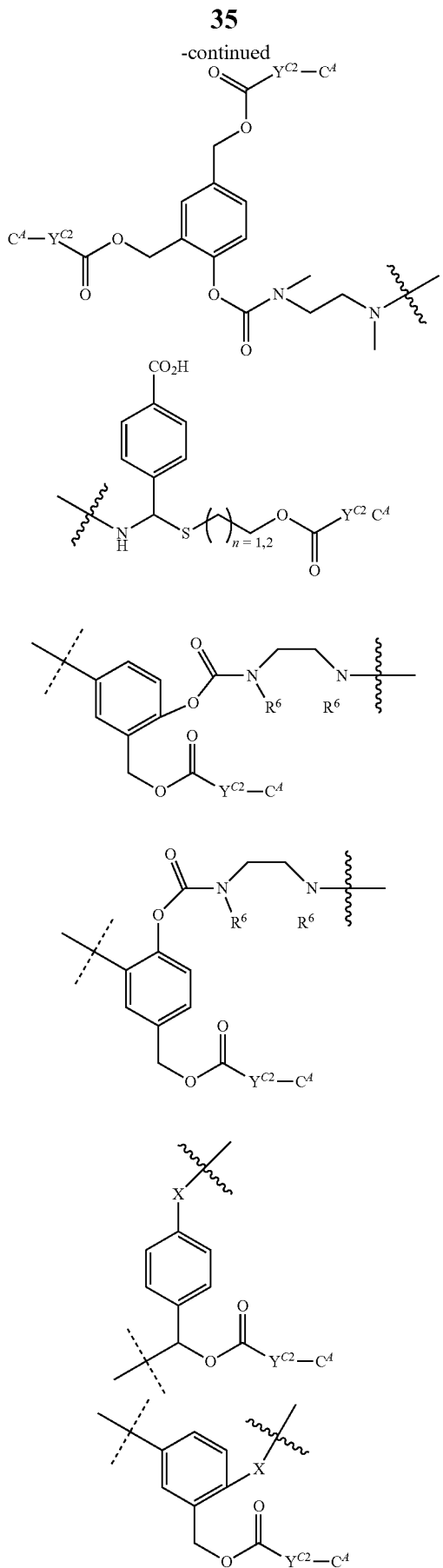

-continued

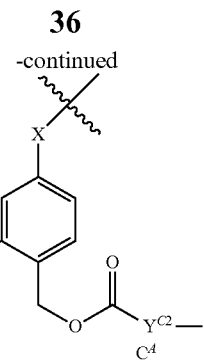

∿∿ indicates bond to Trigger

----- indicates bond to $C^B$ or $S^P$ — $C^B$ or $S^P$

Preferably $Y^{C2}$ is secondary or tertiary amine
X = O, S, $NR^6$
$R^6$ is as defined for formula 1

Further non-limiting examples of $L^C$ can be found in WO2009017394(A1), U.S. Pat. No. 7,375,078, WO2015038426A1, WO2004043493, Angew. Chem. Int. Ed. 2015, 54, 7492-7509, the contents of which are hereby incorporated by reference.

In some aspects of the invention the $L^C$ has a mass of no more than 1000 daltons, no more than 500 daltons, no more than 400 daltons, no more than 300 daltons, or from 10, 50 or 100 to 1000 daltons, from 10, 50, 100 to 400 daltons, from 10, 50, 100 to 300 daltons, from 10, 50, 100 to 200 daltons, e.g., 10-1000 daltons, such as 50-500 daltons, such as 100 to 400 daltons.

Synthesis routes to tetrazines in general are readily available to the skilled person, based on standard knowledge in the art. References to tetrazine synthesis routes include for example Lions et al, *J. Org. Chem.*, 1965, 30, 318-319; Horwitz et al, *J. Am. Chem. Soc.*, 1958, 80, 3155-3159; Hapiot et al, *New J. Chem.*, 2004, 28, 387-392, Kaim et al, *Z. Naturforsch.*, 1995, 50b, 123-127.

Activation

The Activator comprises a Bio-orthogonal Reactive Group, wherein this Bio-orthogonal Reactive Group of the Activator is a dienophile. This dienophile reacts with the other Bio-orthogonal Reactive Group, the Trigger, and that is a diene (vide supra). The dienophile of the Activator is selected so as to be capable of reacting with the diene of the Trigger by undergoing a Diels-Alder cycloaddition followed by a retro Diels-Alder reaction, giving the IEDDA adduct. This intermediate IEDDA adduct then releases the Construct or Constructs, where this Construct release can be caused by various circumstances or conditions that relate to the specific molecular structure of the IEDDA adduct. Reaction of the dienophile and the diene creates a nucleophilic site in the IEDDA adduct, and the inventors have found that this nucleophilic site can be harnessed to effectuate Construct release. Without wishing to be bound by theory, the inventors believe that the Activator provokes Construct release via a cyclization or a cascade mechanism within the IEDDA adduct, i.e. the dihydropyridazine. The cyclization mechanism and cascade mechanism can be a simple one step reaction, or they can be comprised in multiple steps that involves one or more intermediate structures. These intermediates may be stable for some time or may immediately degrade to the thermodynamic end-product or to the next intermediate structure. In any case, whether it be a simple or a multistep process, the result of the cyclization and the cascade mechanism is that the Construct gets released from the IEDDA adduct. Without wishing to be bound by theory, the design of the diene is such that the distribution of electrons within the IEDDA adduct is unfavorable, so that a rearrangement of these electrons must occur. This situation initiates the intramolecular cyclization or cascade mechanism or reaction to take place, and it therefore induces the release of the Construct or Constructs. Specifically, and without wishing to be bound by theory, the inventors believe that the NH moiety comprised in the various dihydropyridazine tautomers, such as e.g. the 1,4- and/or the 2,5-dihydropyridazine tautomers, of the IEDDA adduct are nucleophilic and in some embodiments can initiate an intramolecular cyclization reaction on an electrophilic moiety positioned on the tetrazine Trigger resulting in release of Construct A. Any of the 1,2-, 1,4-, 1,6-, 2,3-, and 2,5-dihydropyridazine tautomers contain such NH-moieties. Without wishing to be bound by theory, the inventors believe that in other embodiments, the NH moiety comprised in the various dihydropyridazine tautomers, such as e.g. the 1,4- and/or the 2,5- dihydropyridazine tautomers, of the IEDDA adduct can initiate an intramolecular electron cascade reaction, a concerted or consecutive shift of electrons over several bonds, leading to release of the Construct A. Without wishing to be bound to theory, the inventors believe that is some embodiments both mechanisms can afford release of the Construct. Occurrence of the cyclization or cascade reaction in and/or Construct release from the Trigger is not efficient or cannot take place prior to the IEDDA reaction, as the Trigger-Construct conjugate itself is relatively stable as such. The cyclization or cascade can only take place after the Activator and the Trigger-Construct conjugate have reacted and have been assembled in the IEDDA adduct. It believed that this is due to the fact that the nitrogens comprised in the aromatic tetrazine Trigger are not, or much less, nucleophilic or reactive than those in the dihydropyridazine IEDDA adduct.

The present inventors have come to the non-obvious insight, that the structure of the tetrazines of Formula (1), par excellence, are suitable to provoke the release of a Construct linked to it, as a result of the reaction involving the double bonds available in the diene and the dienophile. The features believed to enable this are (a) the nature of the IEDDA reaction, which involves a re-arrangement of double bonds, which can be put to use in provoking a cascade elimination; (b) the tendency of the IEDDA adduct to tautomerize from the 4,5-dihydropyridazine to dihydropyridazine tautomers such as the 1,4- or the 2,5-dihydropyridazine tautomer; (c) the nucleophilicity of the NH moieties comprised in e.g. the 1,4- and the 2,5-dihydropyridazine tautomers; (d) the nature of the IEDDA adduct that bears a dihydropyridazine group that is non-aromatic and that can rearrange by an cascade elimination reaction to form conjugated double bonds. Particularly, the inventors discovered that whereas the NH moieties comprised in the various dihydropyridazine tautomers may be less nucleophilic than the amines used in established self-immolative cyclization linkers [Angew. Chem. Int. Ed. 2015, 54, 7492-7509], their nucleophilicity is still sufficient to induce cyclization and cascade elimination in biological media.

It is to be emphasized that the invention is thus of a scope well beyond specific chemical structures. In a broad sense, the invention puts to use the recognition that the IEDDA reaction using a diene of Formula (1) as well as the IEDDA adduct embody a versatile platform for enabling provoked construct release in a bio-orthogonal reaction.

Reflecting this, the invention also presents the use of the inverse electron-demand Diels-Alder reaction between a trans-cyclooctene and a tetrazine as a chemical tool for the release, in a chemical, biological, or physiological environment, of a bound substance. Thereby, the inverse electron-demand Diels-Alder reaction results in the formation of a pyridazine by reacting a tetrazine comprising a Construct $C^A$ bound thereto and a dienophile. Said tetrazine with said Construct bound thereto satisfies formula (1) defined above, and particularly any embodiments thereof as described hereinbefore and hereinafter. Thus, particularly, the invention provides the use of the formation of said pyridazine as a chemical tool for the release, in a chemical, biological or physiological environment, of said Construct.

The fact that the reaction is bio-orthogonal, and that many structural options exist for the reaction pairs, will be clear to the skilled person. E.g., the IEDDA reaction is known in the art of bioconjugation, diagnostics, pre-targeted medicine. Reference is made to, e.g., WO 2010/119382, WO 2010/119389, and WO 2010/051530. Whilst the invention presents an entirely different use of the reaction, it will be understood that the various structural possibilities available for the IEDDA reaction pairs as used in e.g. pre-targeting, are also available in the field of the present invention.

Without wishing to be bound by theory, the following examples A-D illustrate how the nucleophilic dihydropyridazine in the IEDDA adduct of the invention can initiate an intramolecular cyclization, thereby releasing the Construct or Constructs. These examples feature a trans-cyclooctene as the Activator but the person skilled in art will understand that any sufficiently reactive dienophile can be used. The processes may evolve via various tautomerizations that may or may not be in equilibrium. In addition, it is contemplated that there are more possible tautomers, products and intermediates than shown in the scheme. For the avoidance of doubt, Examples A-H do not explicitly denote $Y^C$, but in Examples A-C, E-H $Y^C$ is O, leading to release of Construct-A as HO—$C^A$; in Example D $Y^C$ is NH, leading to release of Construct A as $H_2N$—$C^A$.

The release centers on the tautomerization of the 4,5 dihydropyridazine IEDDA adduct to the 1,4- or 2,5-dihydropyridazine for initiation of the cyclization and corresponding drug release. This tautomerization has been shown to effectively occur in water-free as well as in aqueous media [Adv. Heterocycl. Chem. 2001, 81, 254-303; Eur. J. Org. Chem. 1998, 2885-2896; J. Am. Chem. Soc. 2011, 133, 9646-9649]. Without wishing to be bound by theory, the invention contemplates that the 1,4-tautomer may tautomerize to the 2,5-tautomer and vice versa either directly or via formation of the 4,5-tautomer. The latter process is not shown in the schemes. The subsequent intramolecular cyclization reaction takes place due to the fact that the nucleophilic site and the electrophilic site are close proximity and produce a favorable ring structure with a low strain, typically a 5- or 6-membered ring. Additionally, the formation of the cyclic structure may also be a driving force for the intramolecular reaction to take place.

The first example A below shows the IEDDA reaction of Trigger-Construct conjugate 1, with trans-cyclooctene affording 4,5-dihydropyridazine product 2, which tautomerizes to 1,4- and 2,5-dihydropyridazines 3 and 4 (dihydropyridazine numbering depends on the specific tetrazine substituents and can therefore vary). The electron pair on the NH in 3 initiates a cyclization by reacting with the carbamate attached to the portion of the pyridazine originating from the tetrazine, resulting in formation of a favored 5-membered ring and expulsion of $C^A$. Dihydropyridazine 4 cannot release the $C^A$ via the proposed cyclization but can tautomer ize to 3 either directly or through formation of 2. While it is possible that dihydropyridazine 2, 3, and 4 oxidize to the non-releasing aromatic 6, this process is typically slower or much slower than the release process. Example B shows the same mechanism with a tetrazine that will form a 6-membered ring to initiate the release of $C^A$.

In Example C below, a symmetrical Trigger linked to two Constructs-A is used. Following IEDDA reaction to 2 and tautomerization, either tautomer 3 or 4 can release a Construct A, affording product 5. Also in this example it is possible that tautomers 2, 3, and 4 oxidize to non-releasing 6.

A

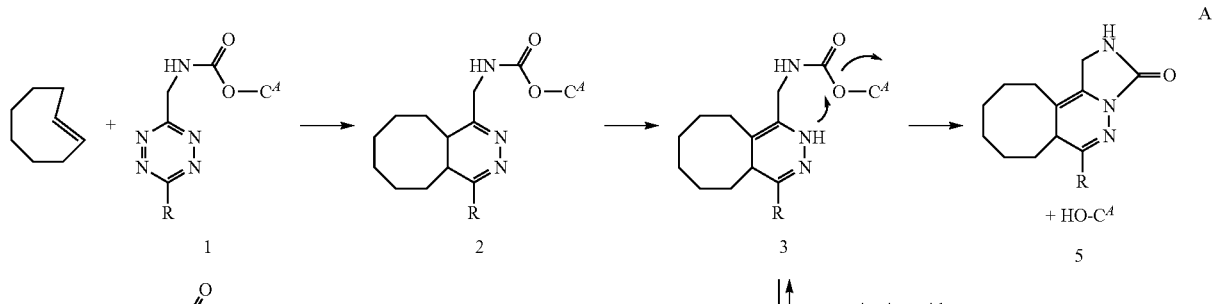

B

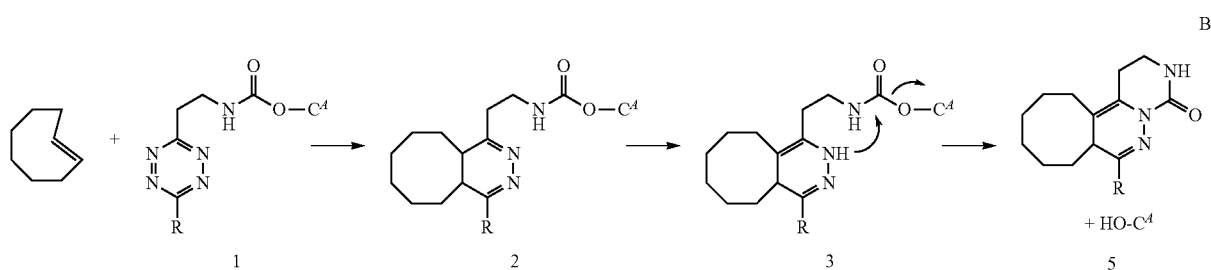

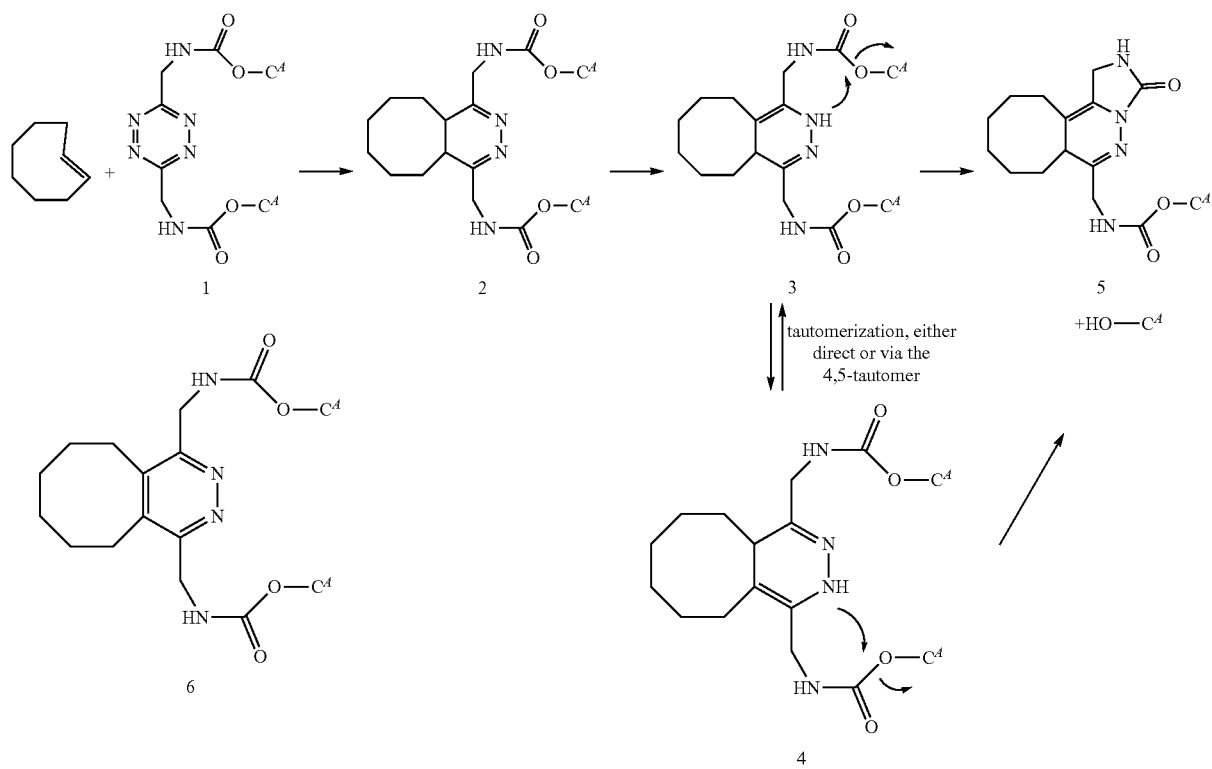

C

Example D below depicts an alternative cyclization compared with examples A-C. In this example, compound 1 has a relatively long spacer between the tetrazine and the carbamate. Upon formation of nucleophilic 3, the NH attacks the electrophilic carbon next to the carbamate resulting in release of $CO_2$ and the Construct A. Other tautomers and the oxidized pyridazine are not shown.

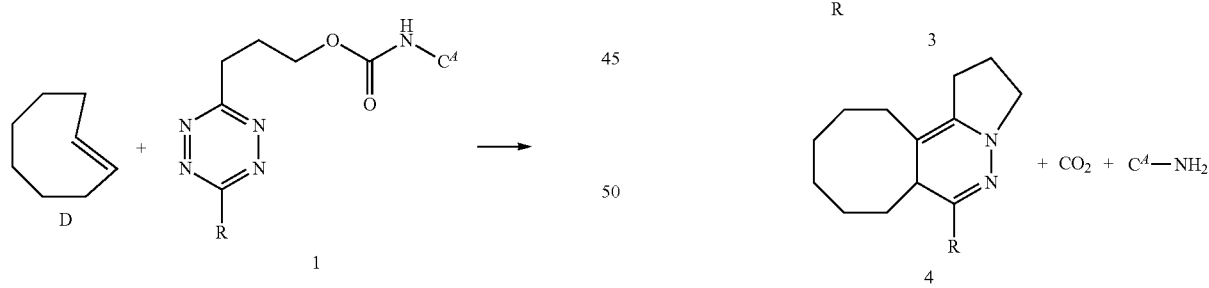

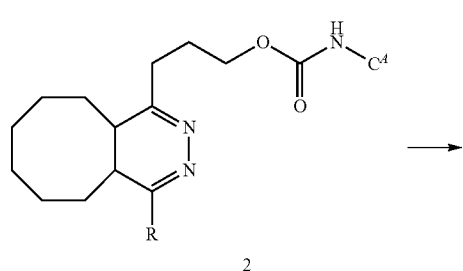

Without wishing to be bound by theory, the inventors believe that the release rate of $C^A$ from Triggers that function through the cyclization mechanism can be tuned by selecting the appropriate ring size formed upon cyclization, wherein the inventors believe that some 5-membered rings are formed faster than their corresponding 6-membered ring analogs. In addition, the nature of leaving group, i.e. $Y^C$, influences the release rate, wherein aromatic $Y^C$ is released faster than an aliphatic $Y^C$. Finally for some in vitro or chemical applications the pH can be tuned to affect the release rate, wherein it is believed that a pH increase will afford faster release and a pH decrease will afford a slower release. Likewise, the temperature is believed to affect the release in a similar manner, wherein a temperature increase will accelerate the release and a temperature decrease will slow down the release.

The following examples E-H depict the cyclization-based release from a tetrazine induced by dienophiles other than the trans-cyclooctene. As is widely known in the art, IEDDA reactions with tetrazine derivatives can occur effectively an selectively in complex environments with a wide range of dienophiles, such as strained or linear alkenes. Example E shows the activation of the Trigger-Construct by a strained alkene, a norbonene derivative. Example F shows the activation of the Trigger-Construct by a strained alkene, a cyclopropene derivative. Example G shows the activation of the Trigger-Construct by a linear alkene. Example H shows the activation of the Trigger-Construct by a strained and activated alkene, an acylazetine derivative.

E

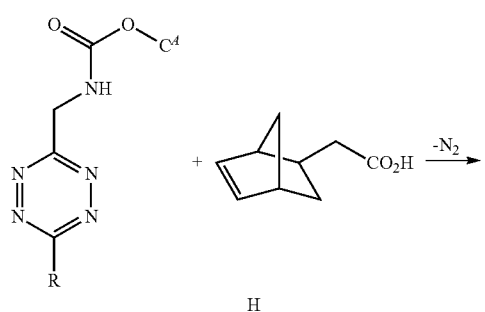

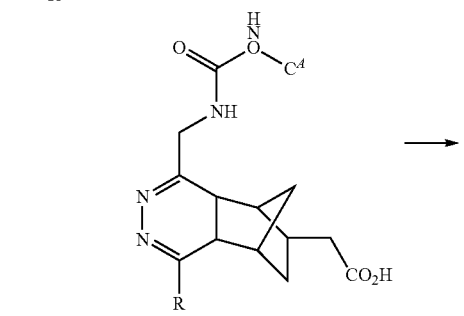

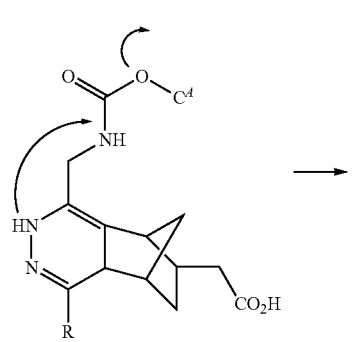

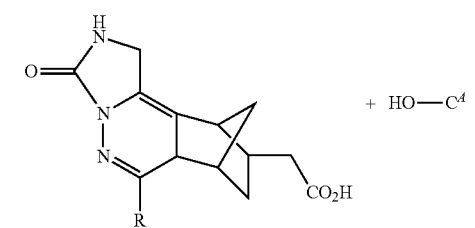

-continued

F

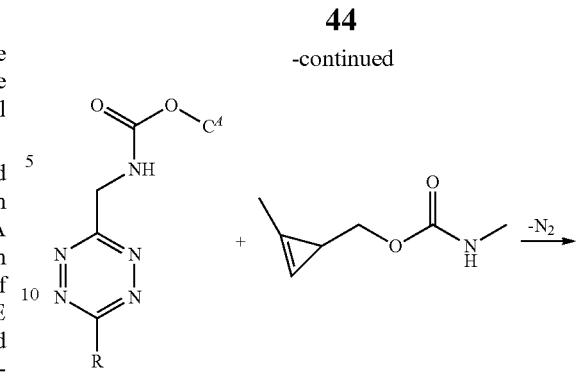

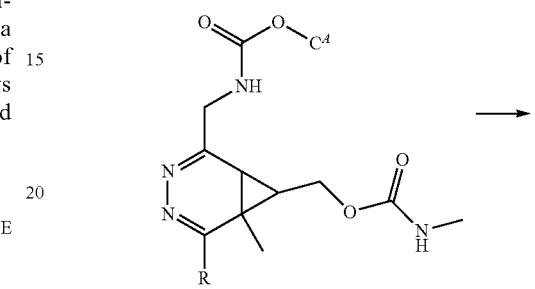

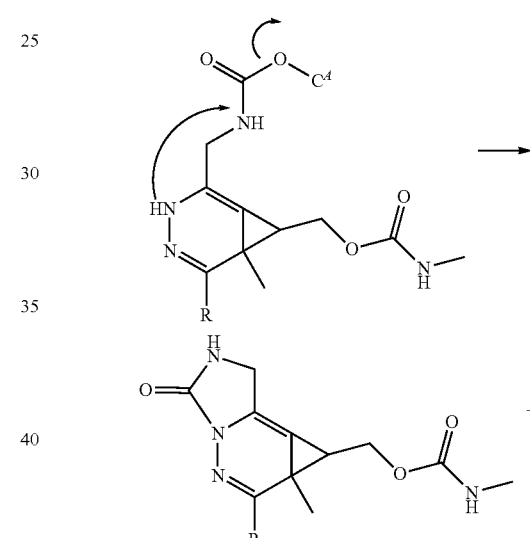

G

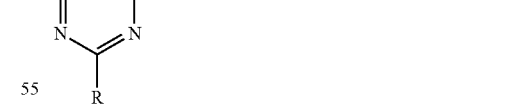
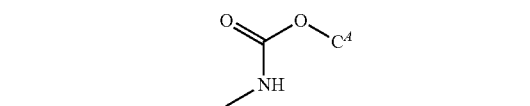
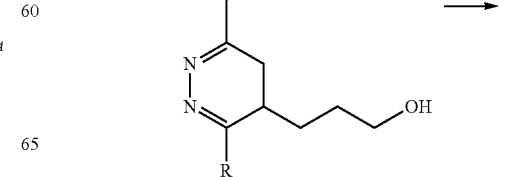

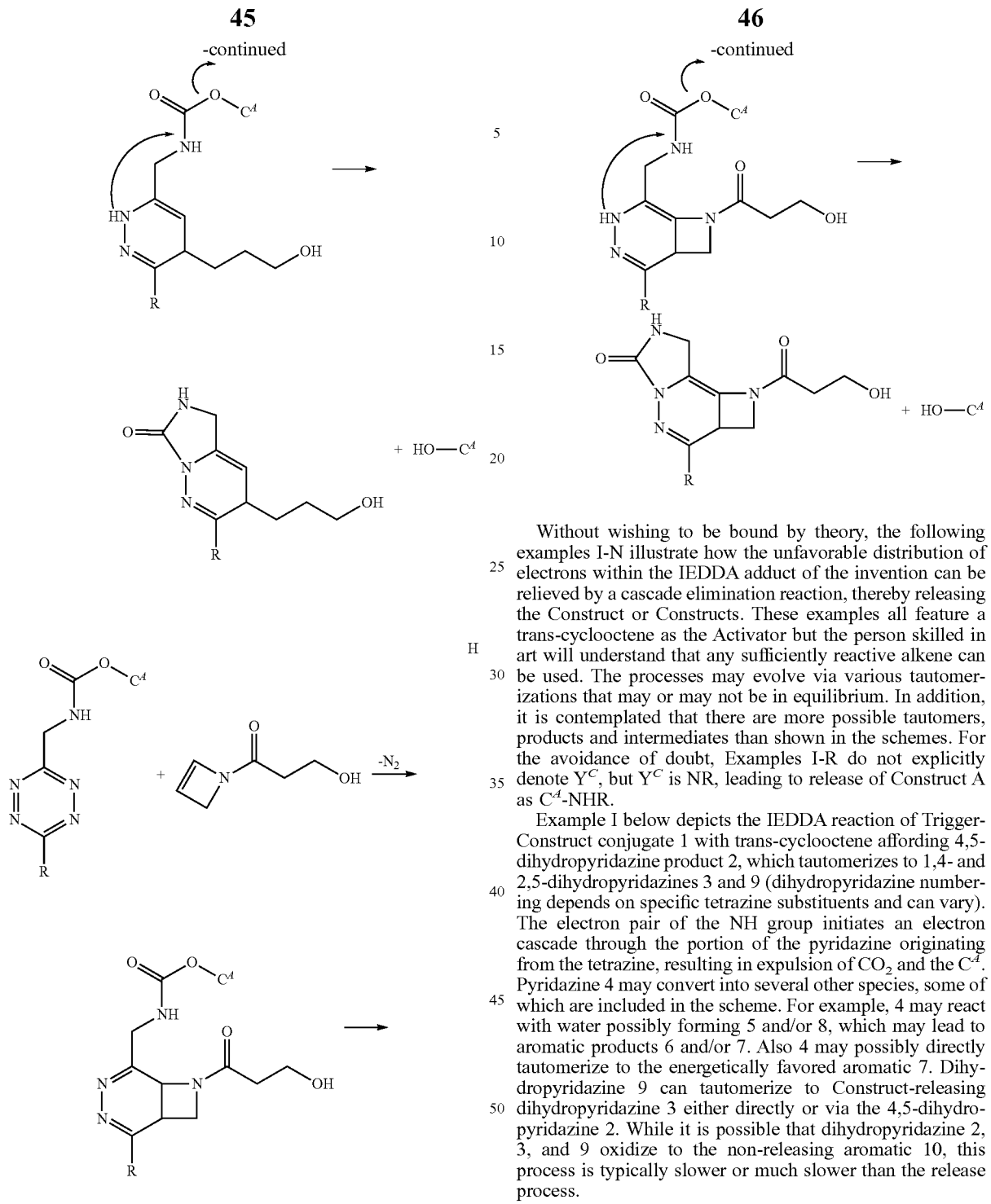

Without wishing to be bound by theory, the following examples I-N illustrate how the unfavorable distribution of electrons within the IEDDA adduct of the invention can be relieved by a cascade elimination reaction, thereby releasing the Construct or Constructs. These examples all feature a trans-cyclooctene as the Activator but the person skilled in art will understand that any sufficiently reactive alkene can be used. The processes may evolve via various tautomerizations that may or may not be in equilibrium. In addition, it is contemplated that there are more possible tautomers, products and intermediates than shown in the schemes. For the avoidance of doubt, Examples I-R do not explicitly denote $Y^C$, but $Y^C$ is NR, leading to release of Construct A as $C^A$-NHR.

Example I below depicts the IEDDA reaction of Trigger-Construct conjugate 1 with trans-cyclooctene affording 4,5-dihydropyridazine product 2, which tautomerizes to 1,4- and 2,5-dihydropyridazines 3 and 9 (dihydropyridazine numbering depends on specific tetrazine substituents and can vary). The electron pair of the NH group initiates an electron cascade through the portion of the pyridazine originating from the tetrazine, resulting in expulsion of $CO_2$ and the $C^A$. Pyridazine 4 may convert into several other species, some of which are included in the scheme. For example, 4 may react with water possibly forming 5 and/or 8, which may lead to aromatic products 6 and/or 7. Also 4 may possibly directly tautomerize to the energetically favored aromatic 7. Dihydropyridazine 9 can tautomerize to Construct-releasing dihydropyridazine 3 either directly or via the 4,5-dihydropyridazine 2. While it is possible that dihydropyridazine 2, 3, and 9 oxidize to the non-releasing aromatic 10, this process is typically slower or much slower than the release process.

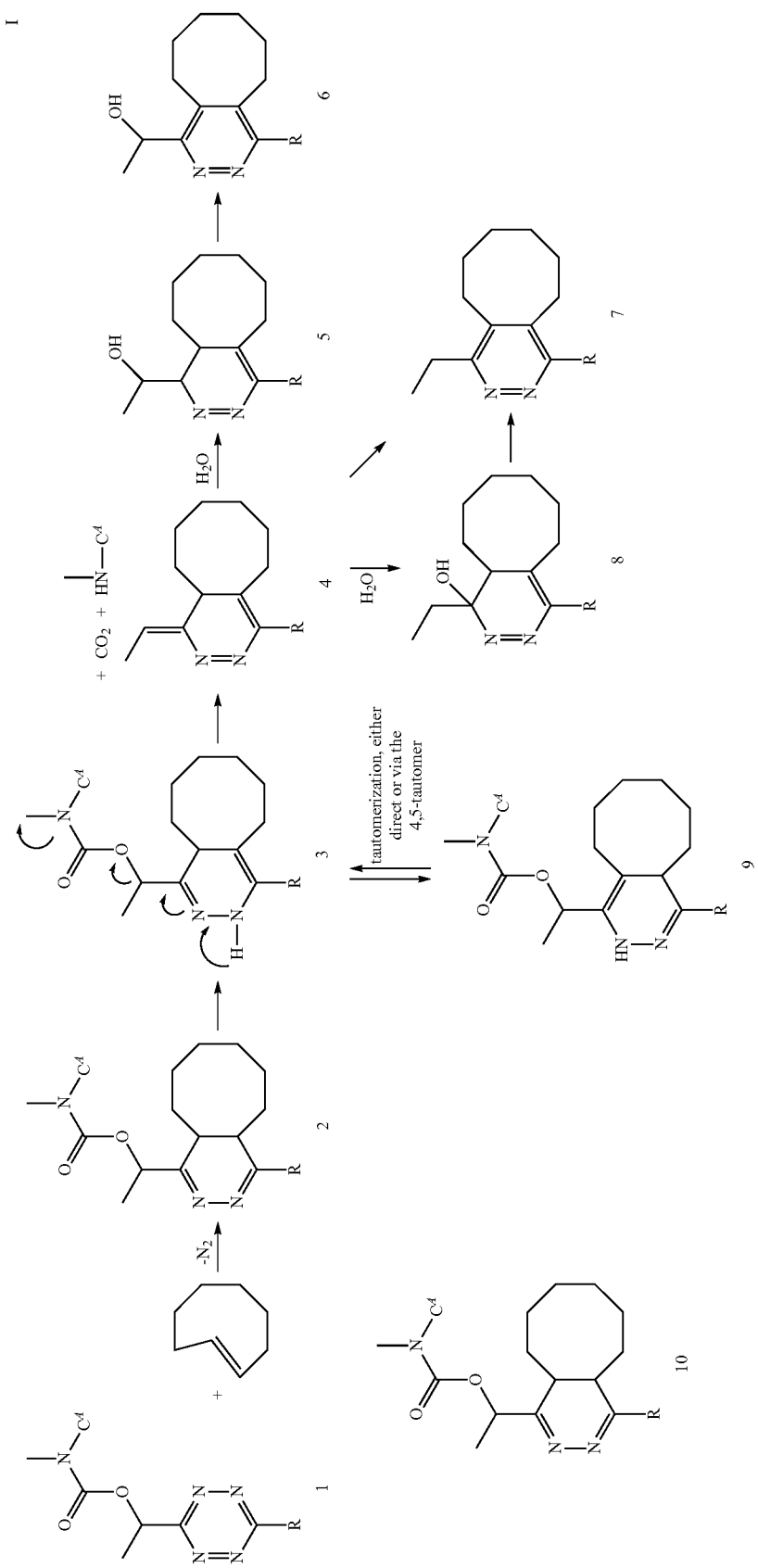

Example J below depicts the traceless release of two Constructs-A from a tetrazine Trigger. Instead of tracelessly releasing the two $C^A$ moieties, also 1 $C^A$ and 1 $C^B$ moiety can be released. The release of the first $C^A$ follows the process also shown in example I. Subsequently, compound 4 can react with water to conceivably give a variety of non-releasing products, such as 5 and 8, which can further form aromatic 6 and 9. Reaction of 4 with water can also form dihydropyridazine 7 that can tautomerize either directly or through a 4,5-dihydropyridazine to dihydropyridazine 10, which then leads to release of the second $C^A$ in the same manner as the first $C^A$. The resulting 11 can possibly form variety of products, such as 12-15. It is contemplated that at various steps in the mechanism oxidation to aromatic pyridazine can lead to non-releasing entities, such oxidation of 2, 4, and 7, as indicated in the scheme. However, typically this oxidation is slower or much slower than the release mechanism.

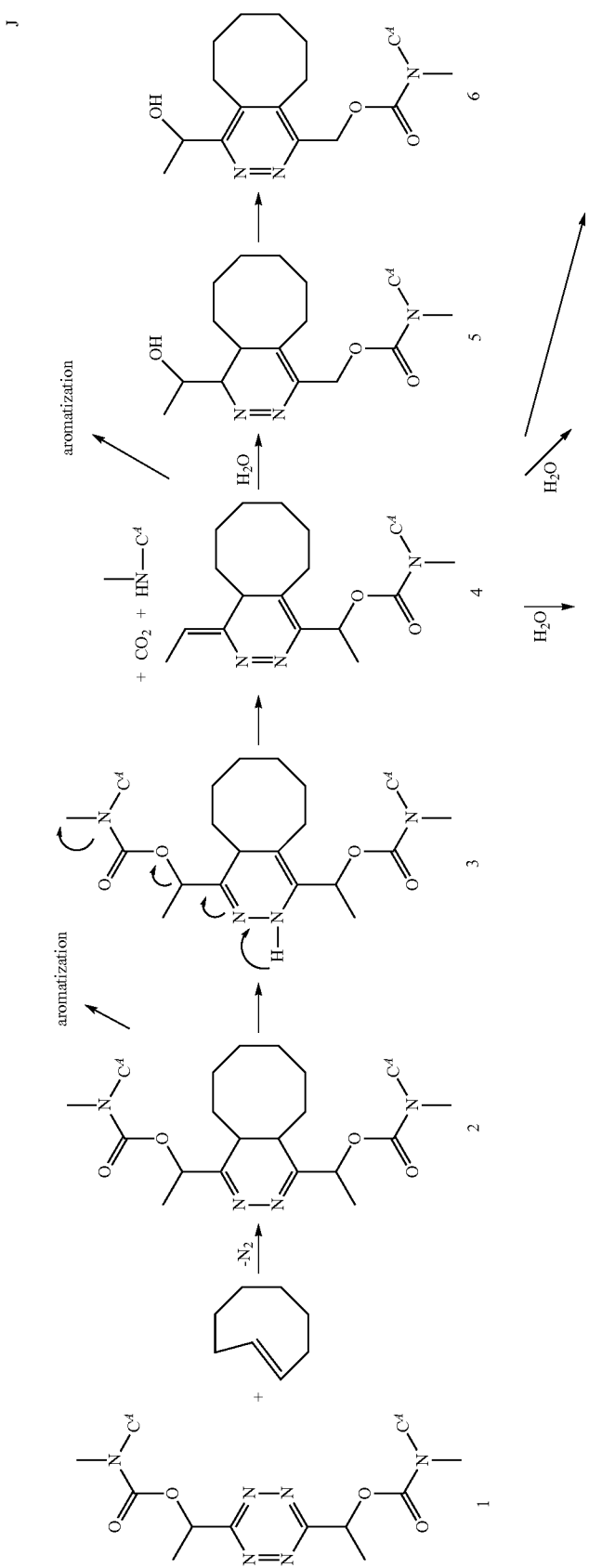

-continued
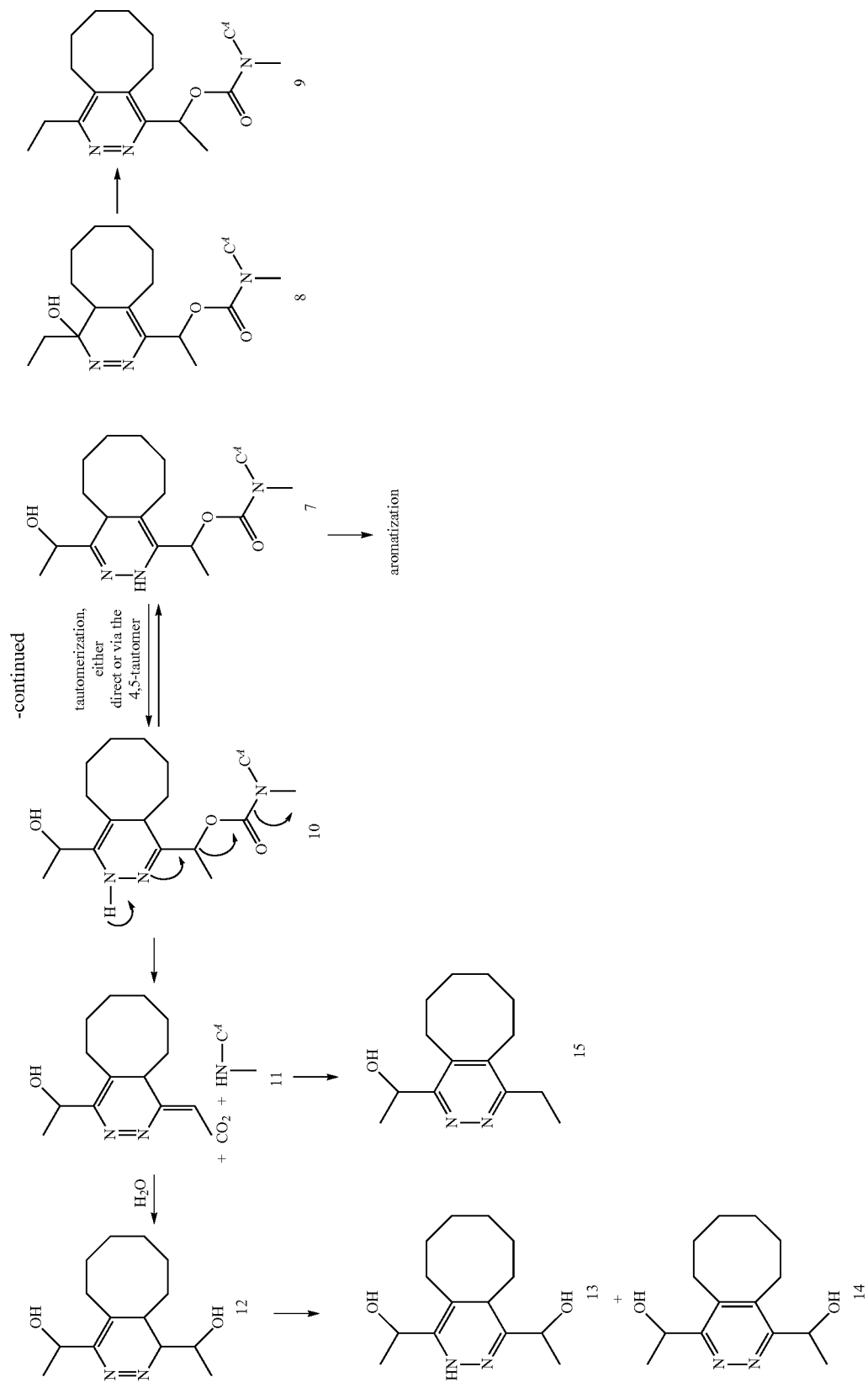

The below example K depicts alternative release mechanisms for the $C^A$-Trigger-$C^A$ of example J. Tautomerization of 4,5-dihydropyridazine 2 to 3 leads to the previously depicted cascade release initiated from the NH of the dihydropyridazine affording 4. Instead reacting with water as shown in example J, forming the 1,4-tautomer that needs to tautomerize to then release a $C^A$, in this example 4 directly releases the second $C^A$ through an electron cascade initiated from the deprotonation of the 5-H. The resulting 5 can then react with a nucleophile such as water. The inverse release sequence is also possible, wherein the first $C^A$ is released as a result of a cascade originating from the deprotonation of 4-H leading to 8, which can then release the second $C^A$ by means of a cascade starting from the NH, again affording compound 5. As mentioned previously, also here dihydropyridazines 2 and 3 can lead to non-releasing aromatic pyridazines through oxidation. Furthermore, compounds 4 and 8 may tautomerize to non-releasing aromatic derivatives (not shown). For the avoidance of doubt, the mechanism based on the cascade initiated from the deprotonation of the 5-H (or 4-H) depicted in this Example K as an alternative for example J, is also a viable alternative for or addition to the mechanisms depicted in examples I-R.

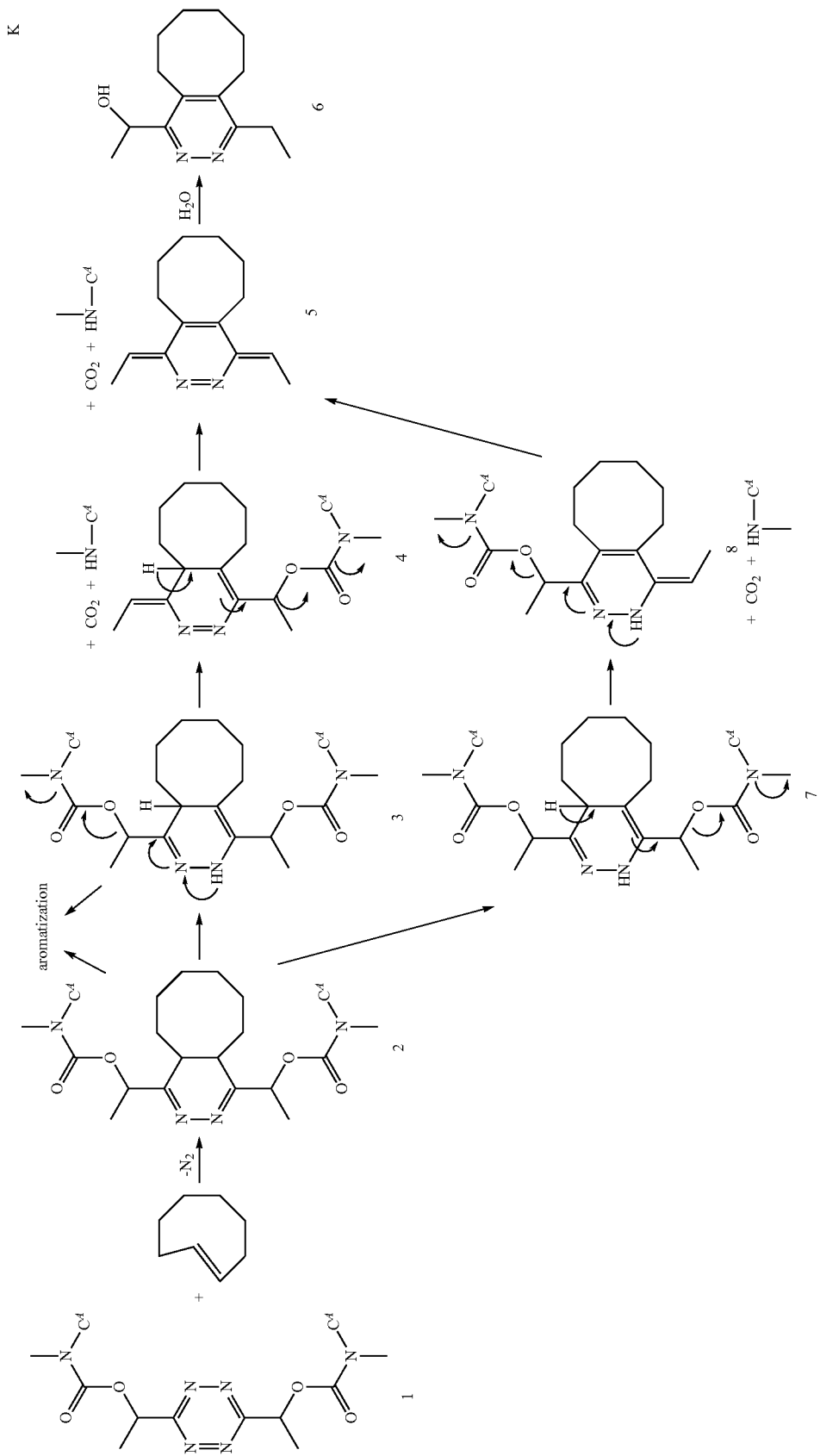

Example L below shows a Trigger comprising a double bond between tetrazine and the carbamate-linked $C^A$. In this example, formation of the 4,5-dihydropyridazine tautomer 2 leads to tautomerization to compound 3, which releases $C^A$ as a result of an electron cascade initiated by the dihydropyridazine NH. The resulting 4 can tautomerize to form the aromatic 5, or it can react with water leading to dihydropyridazine 6. Dihydropyridazine 7 can tautomerize to Construct-releasing dihydropyridazine 3 either directly or via the 4,5-dihydropyridazine 2. Also here dihydropyridazines 2 and 3 can lead to non-releasing aromatic pyridazines through oxidation.

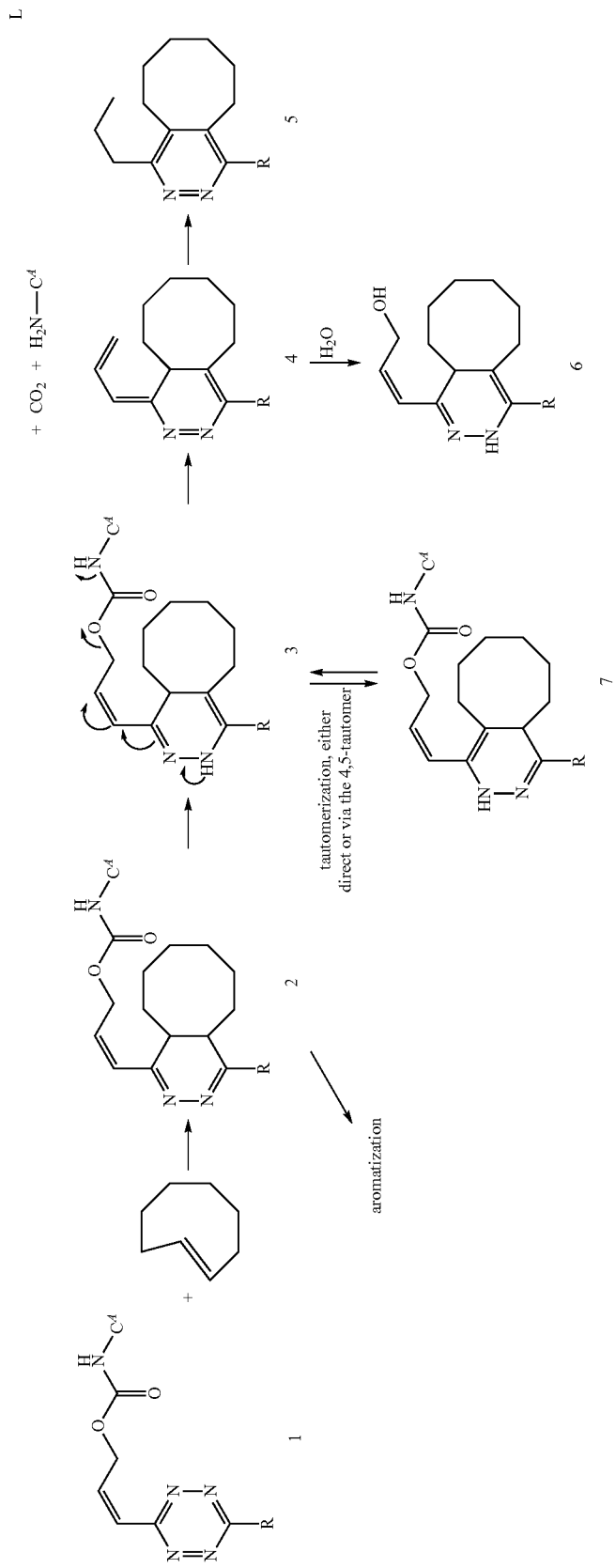

Example M below depicts the traceless release of two Constructs from a tetrazine similar to Example L. Instead of tracelessly releasing the two $C^A$ moieties, also one $C^A$ and one CD moiety can be released. The release of the $C^A$ moieties follows the process also shown in example K and L. Thus, following the release of the first $C^A$ moiety, leading to compound 5, tautomerization to 6 either directly or via a 4,5-dihydropyridazine tautomer affords the release of the second $C^A$ moiety in the same manner. For the sake of clarity several other potential products are not shown in this scheme Example N depicts the release of two $C^A$ moieties from a hybrid Trigger that combines the design of the Triggers in example I and L. Instead of tracelessly releasing the two $C^A$ moieties, also one $C^A$ and one $C^B$ moiety can be released. The release follows the same processes as shown for the other examples. For the sake of clarity several other potential products are not shown in this scheme.

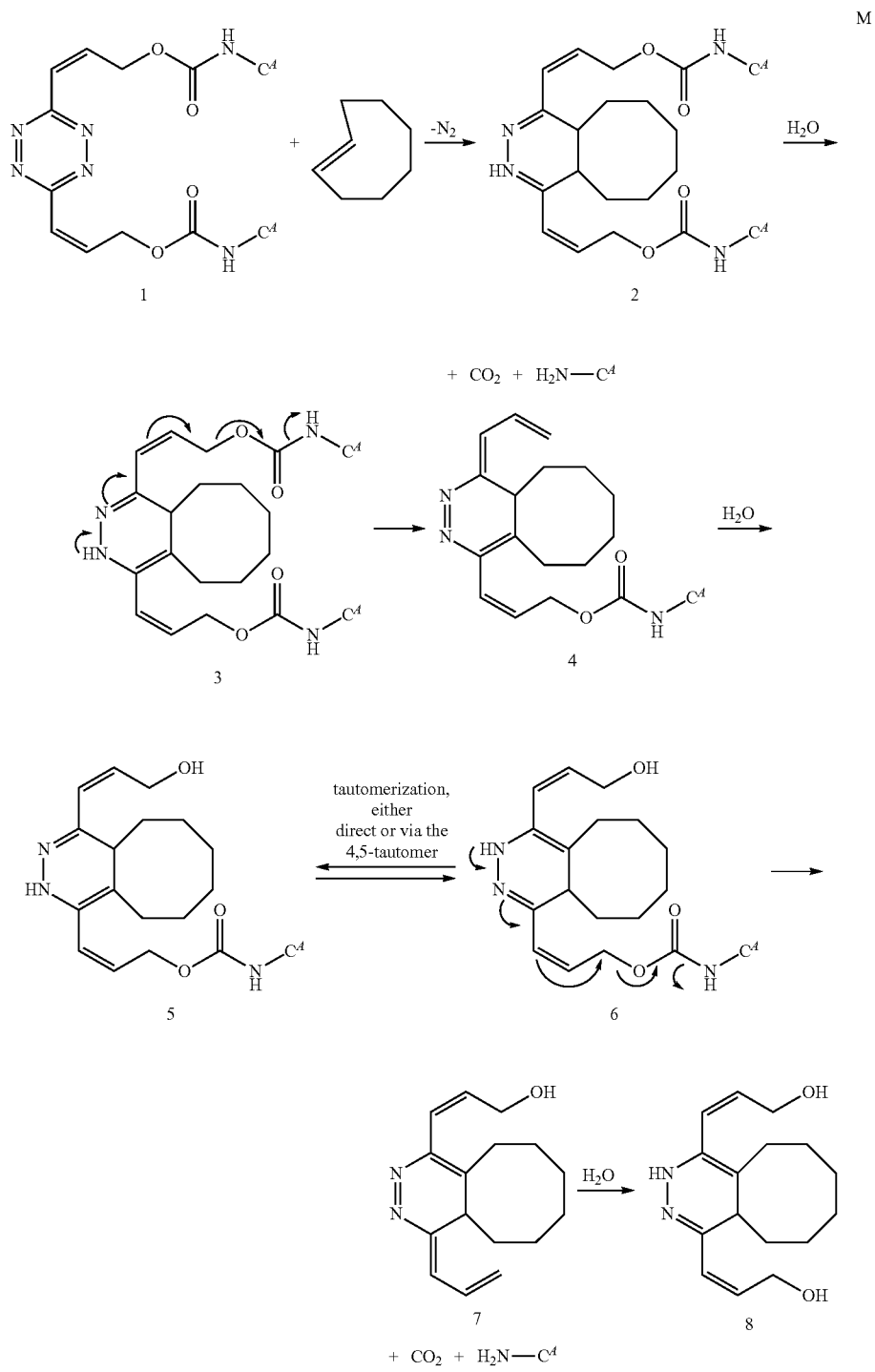

M

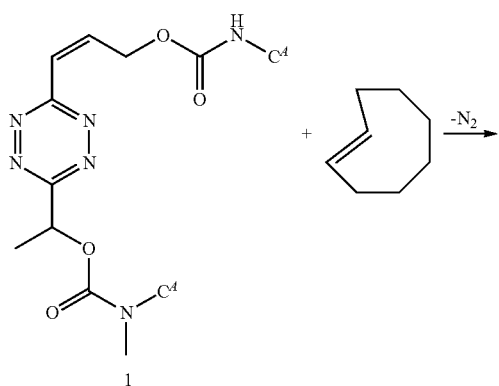

1

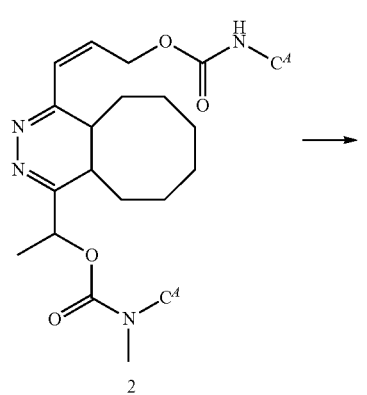

2

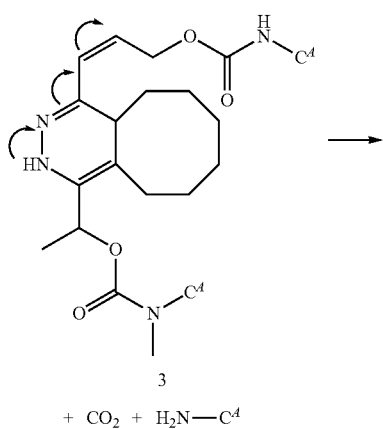

3

+ CO$_2$ + H$_2$N—C$^A$

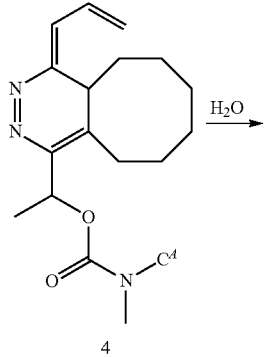

4

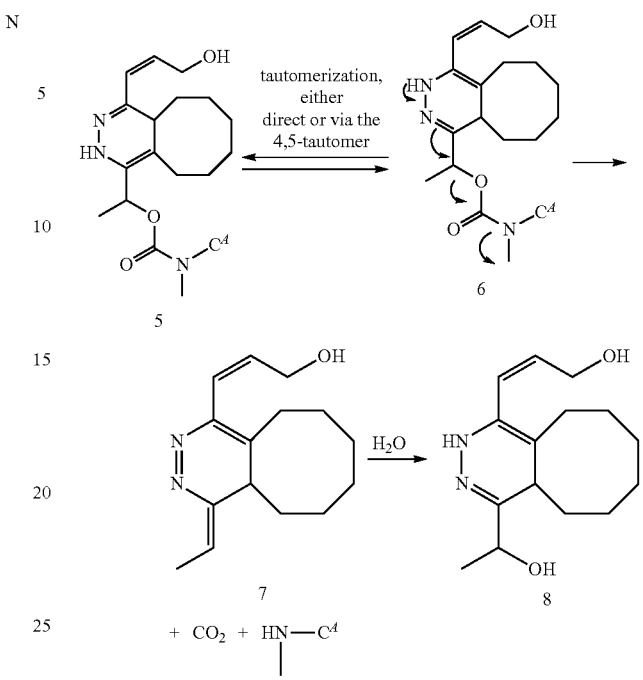

+ CO$_2$ + HN—C$^A$

The following examples O-R depict the cascade release from a tetrazine induced by dienophiles other than the trans-cyclooctene. Example O shows the activation of the Trigger-Construct by a strained alkene, a norbonene derivative. Example P shows the activation of the Trigger-Construct by a strained alkene, a cycloproponene derivative. Example Q shows the activation of the Trigger-Construct by a linear alkene. Example R shows the activation of the Trigger-Construct by a strained and activated alkene, an acylazetine derivative.

O

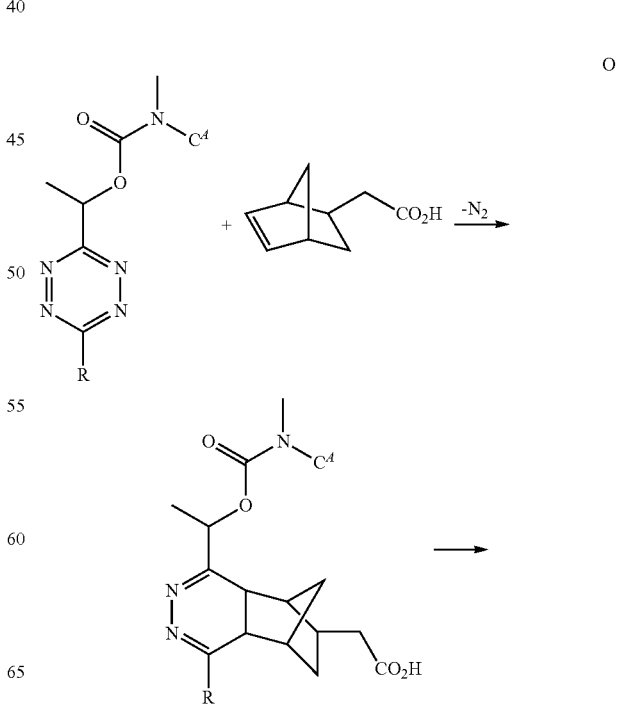

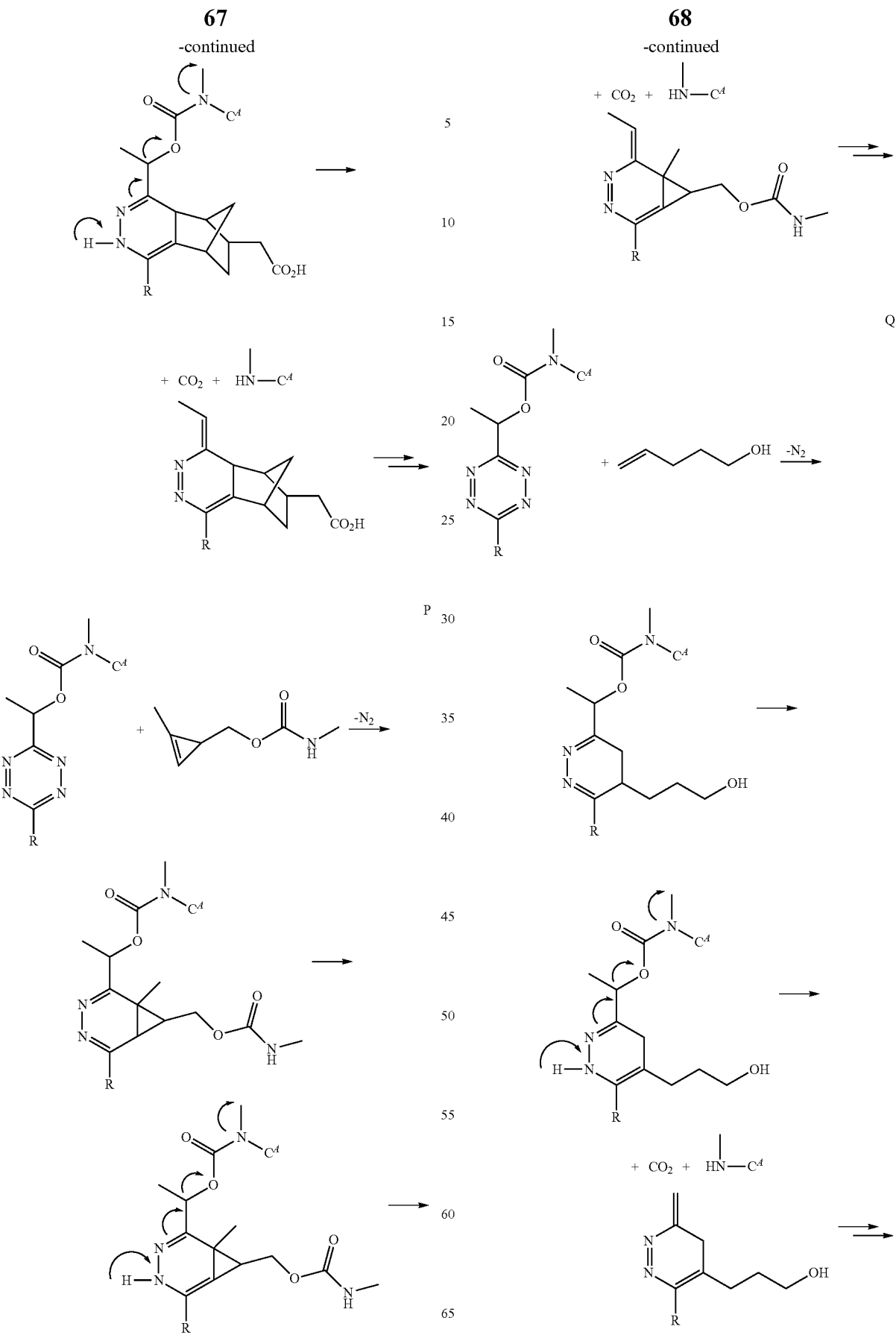

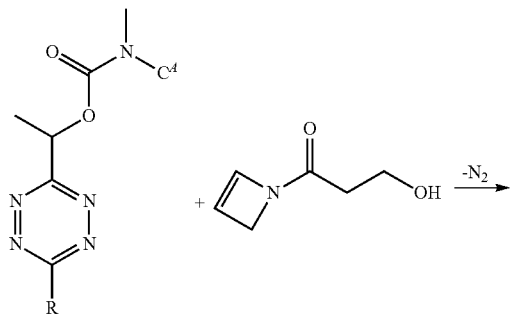

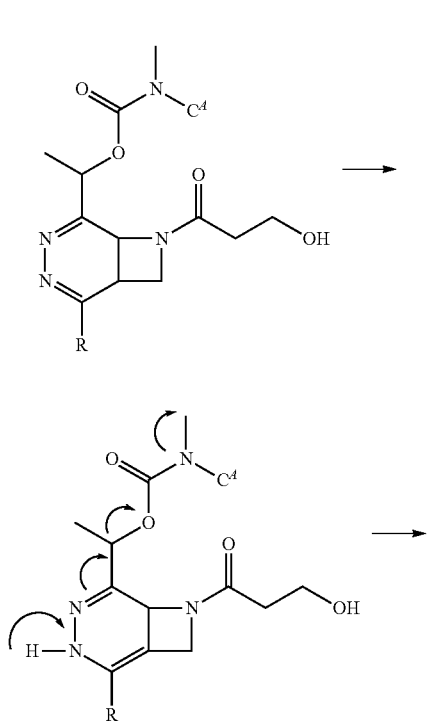

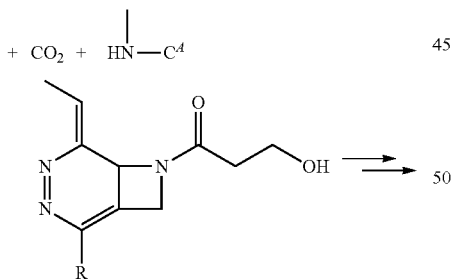

The skilled person will understand that the distribution of electrons in the EDDA adducts of the invention are generally unfavorable relative to the distribution of the electrons in the products resulting from the release of the Construct or Constructs. Thus, the formation of a species more stable than the IEDDA adduct, is the driving force for the elimination reaction. In the case of the cascade mechanism and in several embodiments of the cyclization mechanism there is formation of $CO_2$ which also a driving force of the elimination reaction In any case, and in whatever way the process is viewed, the Construct (in the examples above the construct $HO-C^A$ or $RHN-C^A$) is effectively expelled from the IEDDA adduct while it does not get expelled from the Trigger-Construct conjugate alone. In the examples A-R above, the drawn fused ring products may or may not tautomerize or isomerize to other more favorable tautomers or isomers. Also, it is conceived that other side products may be formed in addition to the drawn structures.

Exemplary Trigger believed to afford release through the cyclization and/or the cascade mechanism are shown below. For the avoidance of doubt, in these examples $Y^C$ is not denoted as such but is embodied by the relevant NH, $NR^6$, S, O groups.

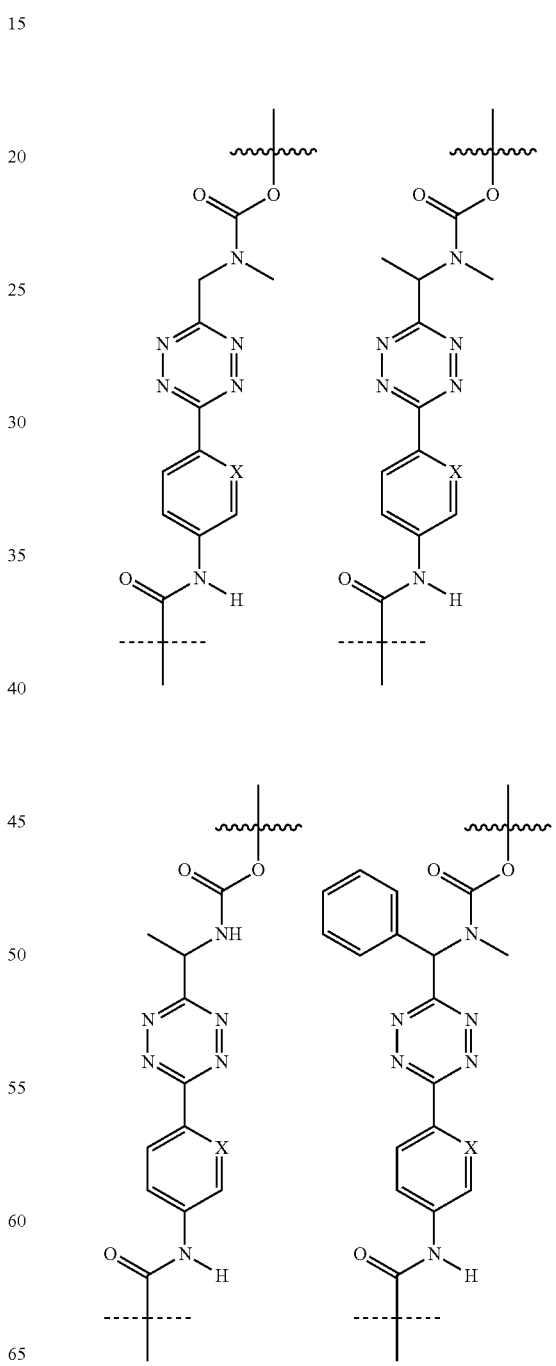

71
-continued
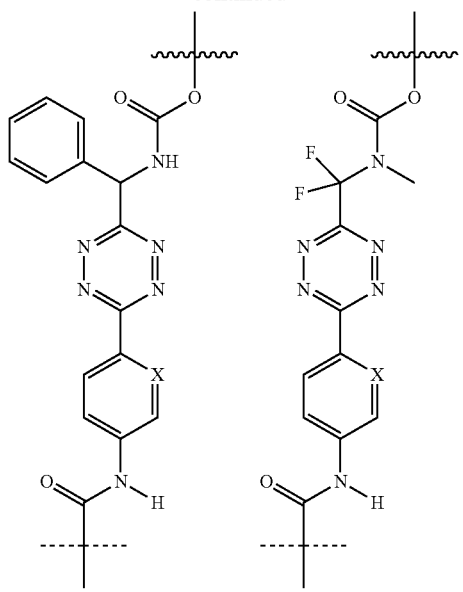
72
-continued
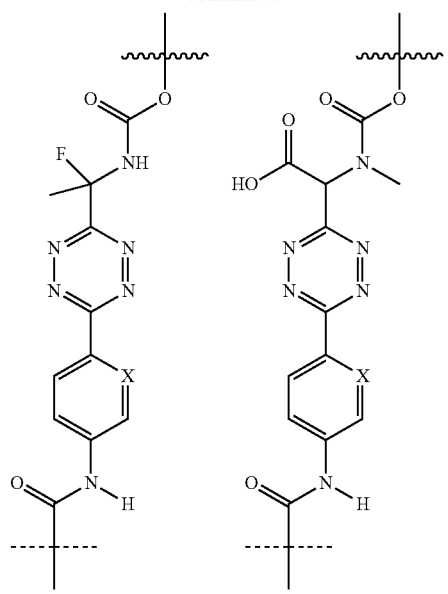
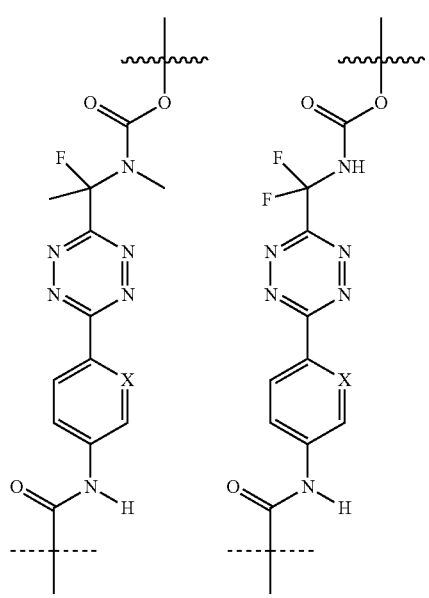

73
-continued
74
-continued
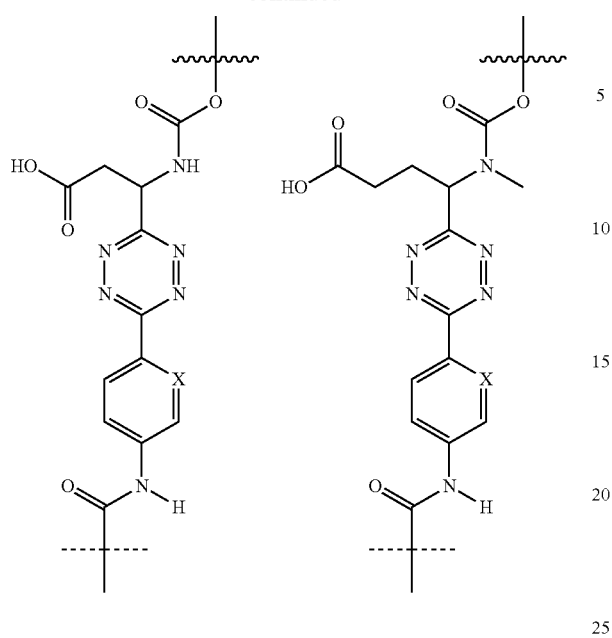
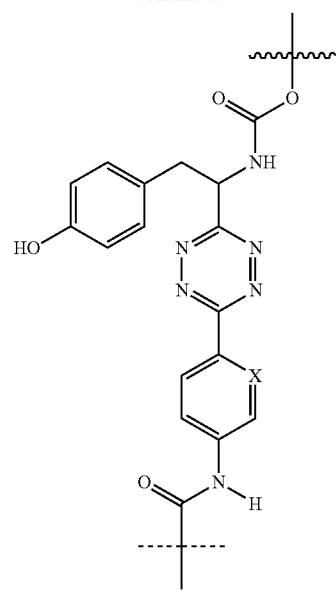
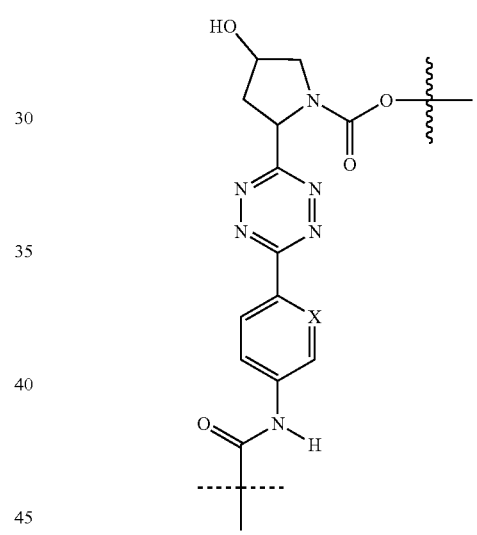
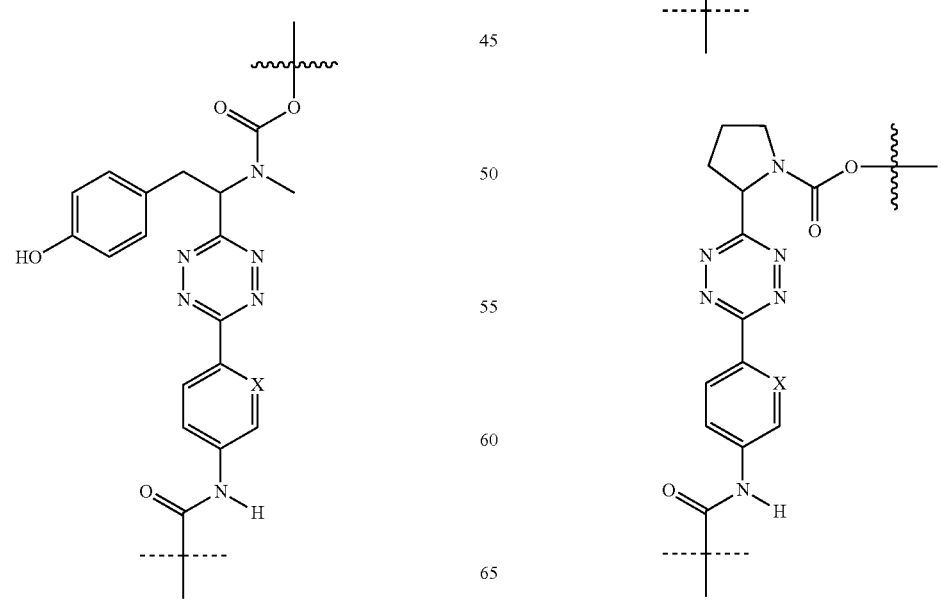

75
-continued
76
-continued
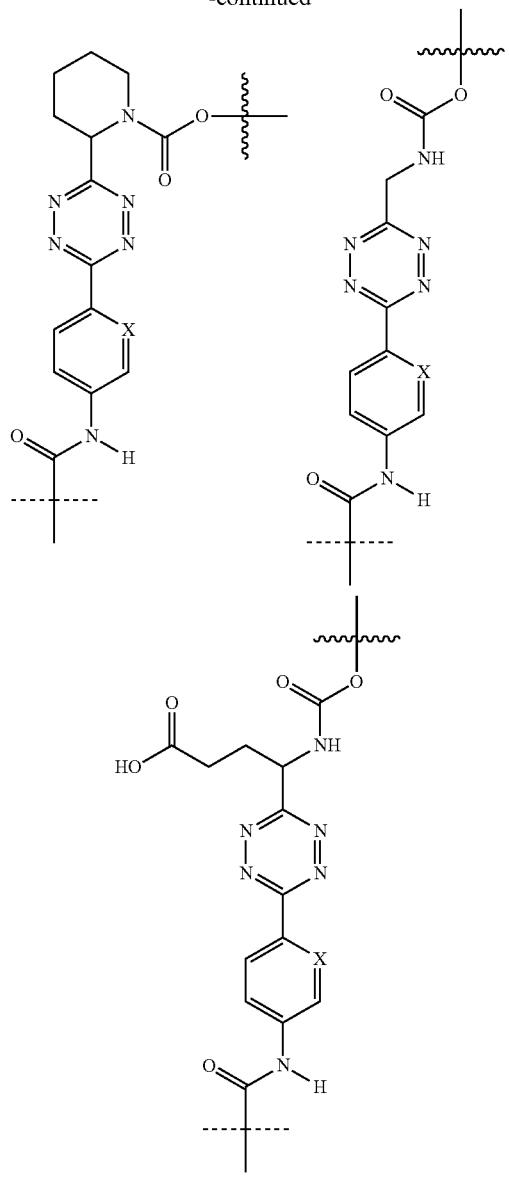
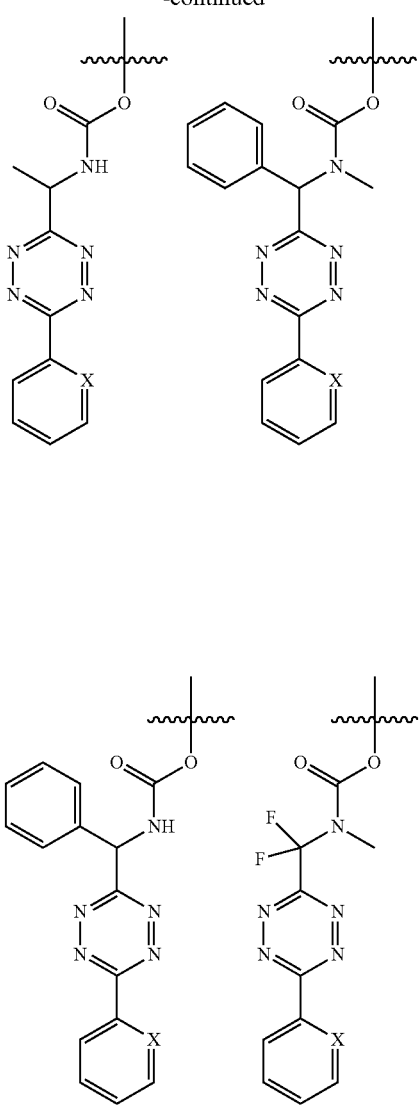
X = C or N
⁓⁓⁓ indicates bond to (remainder of) C^A, or L^C-C^A optionally comprising C^B
---- indicates bond to (remainder of) S^P, or S^P-C^B or C^B
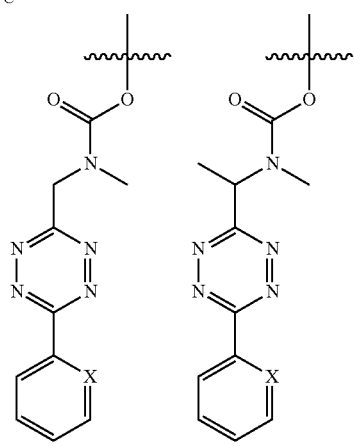
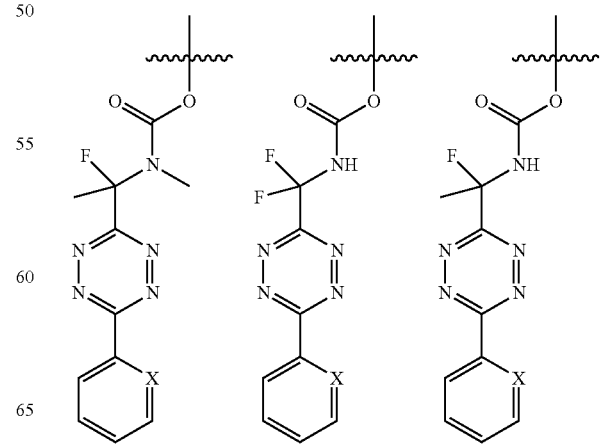

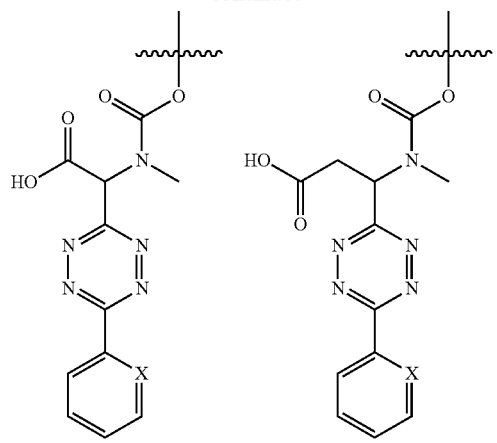
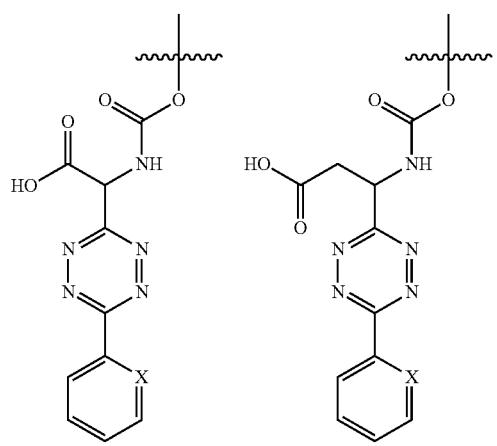
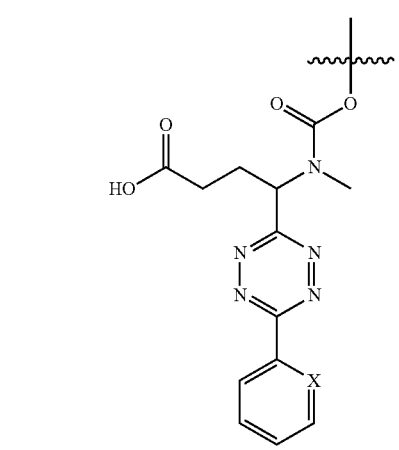
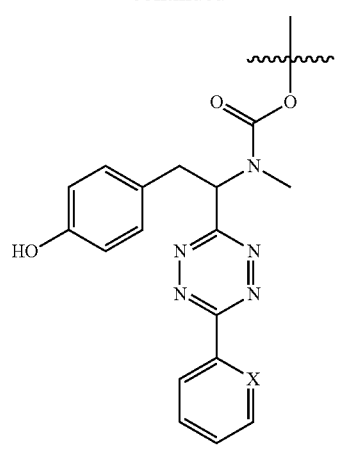
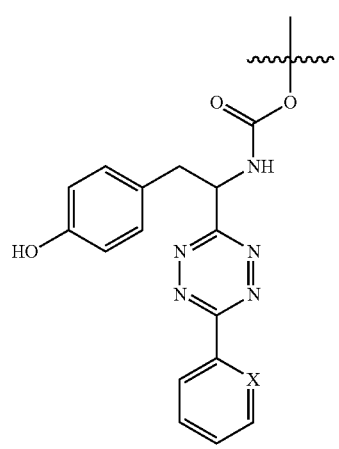
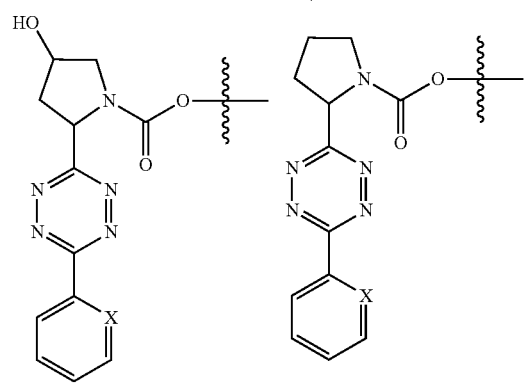
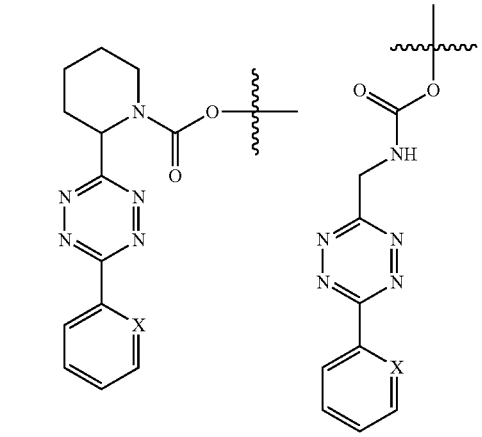

79
-continued
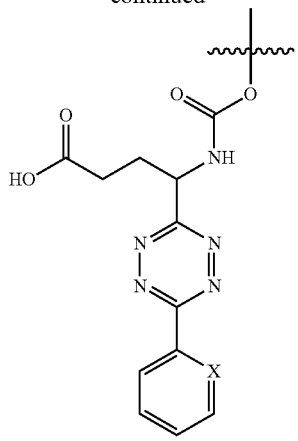
X = C or N
⸺ indicates bond to (remainder of) $C^A$, or $L^C$-$C^A$ optionally comprising $C^B$
---- indicates bond to (remainder of) $S^P$, or $S^P$-$C^B$ or $C^B$
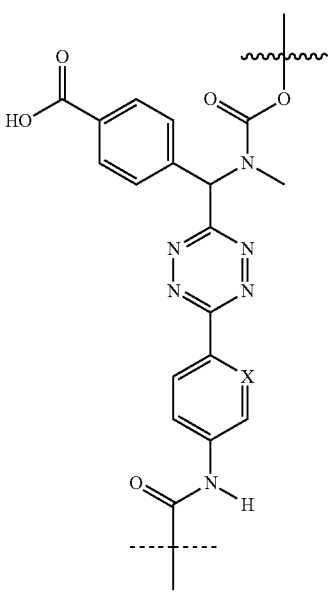
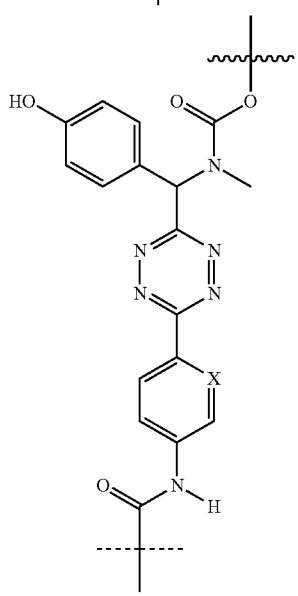
80
-continued
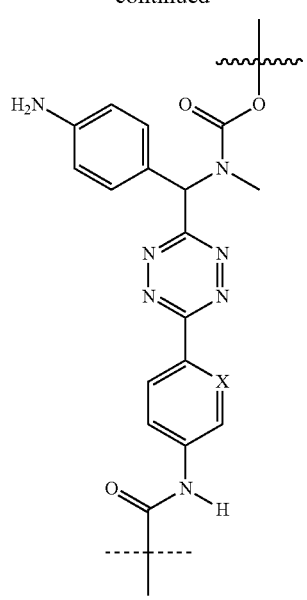
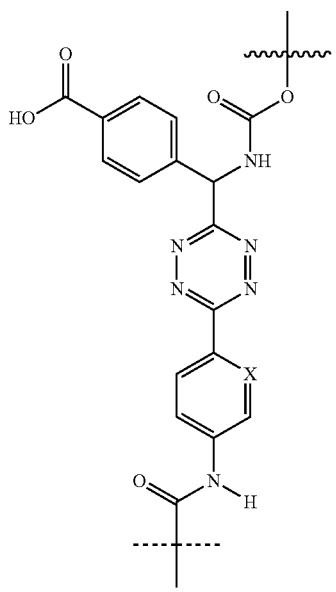

81
-continued
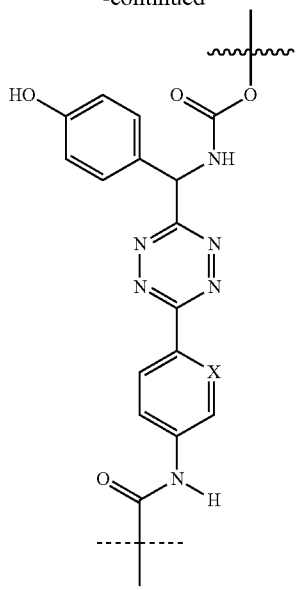
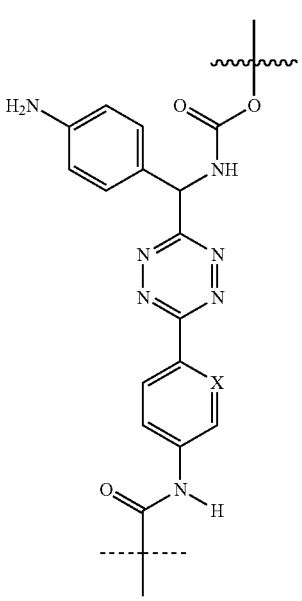
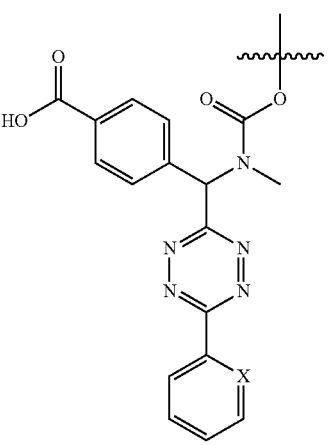
82
-continued
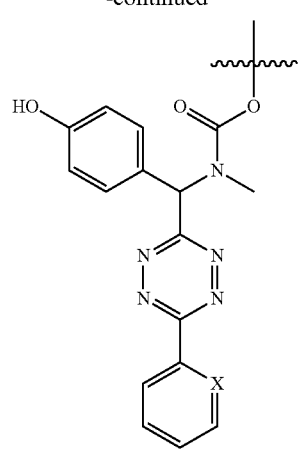
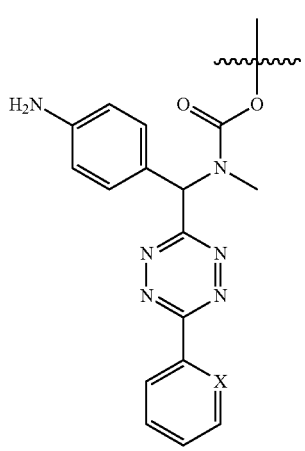
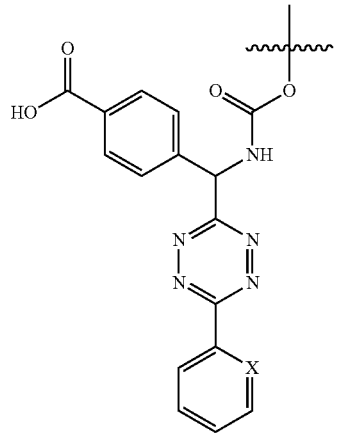

83
-continued
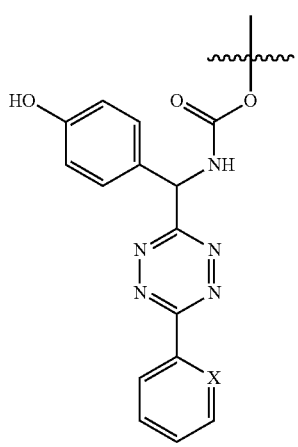
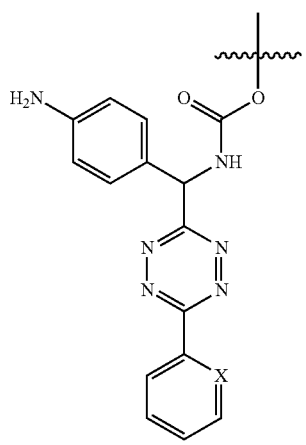
X = C or N
⁓ indicates bond to (remainder of) $C^A$, or $L^C$-$C^A$ optionally comprising $C^B$
---- indicates bond to (remainder of) $S^P$, or $S^P$-$C^B$ or $C^B$
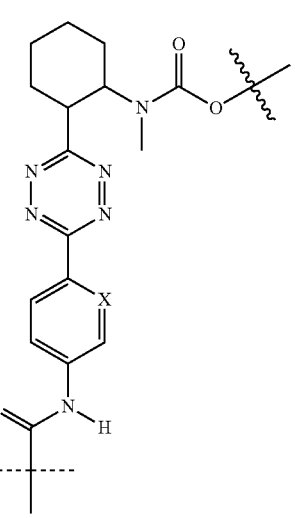
84
-continued
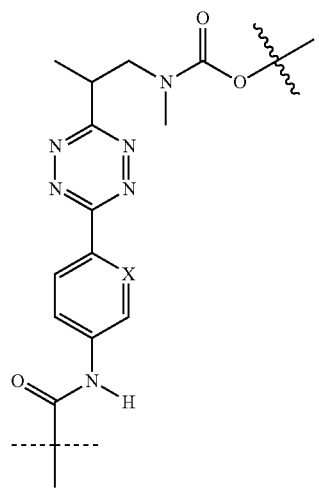
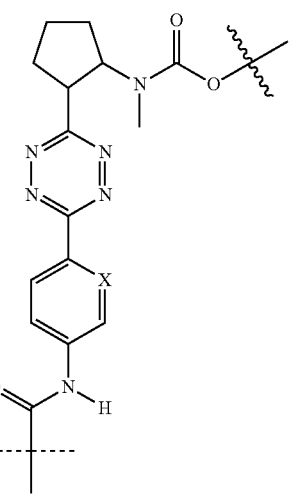
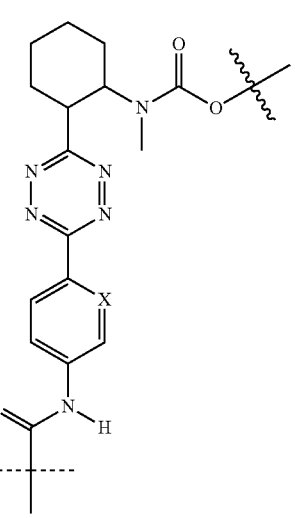

85
-continued
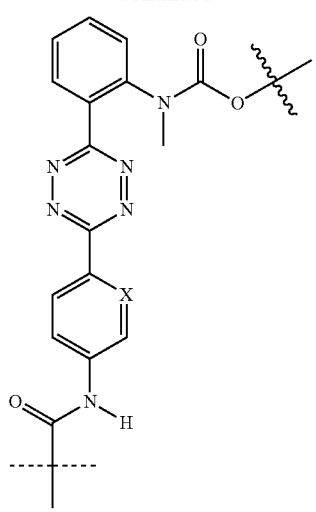
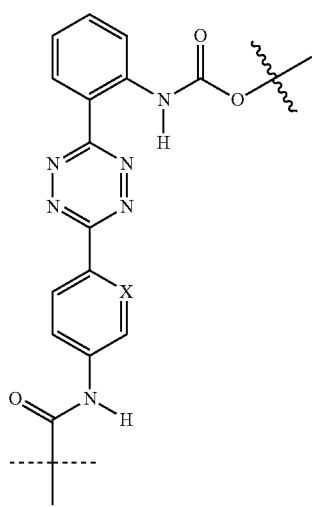
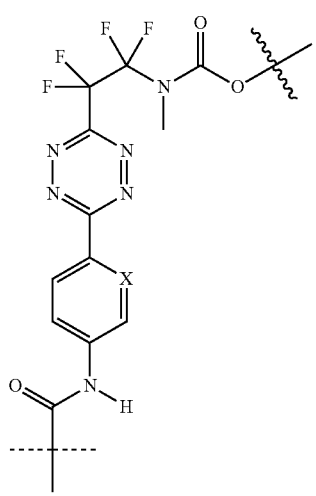
86
-continued
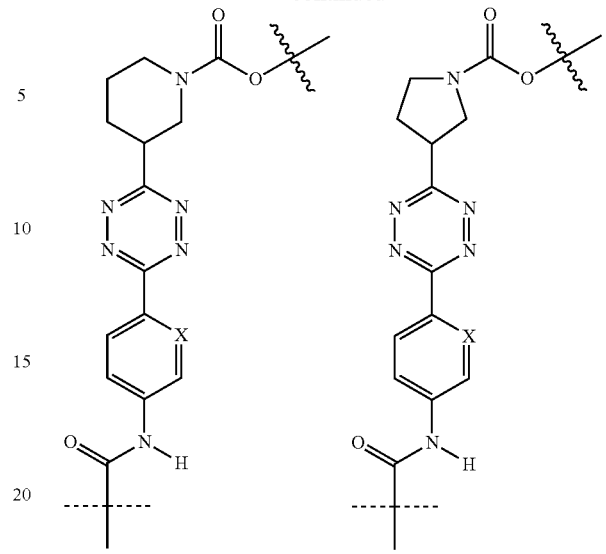
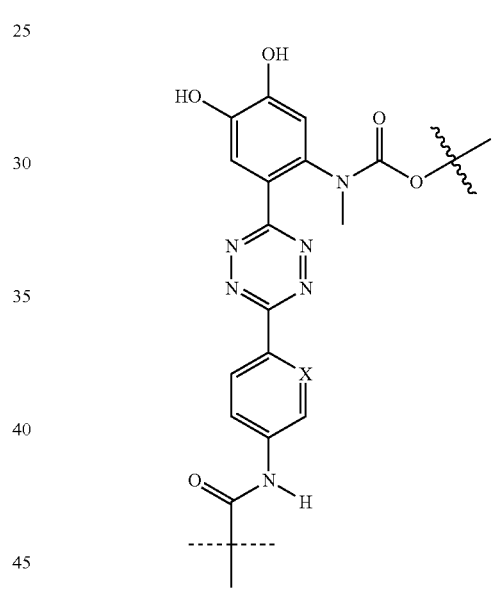
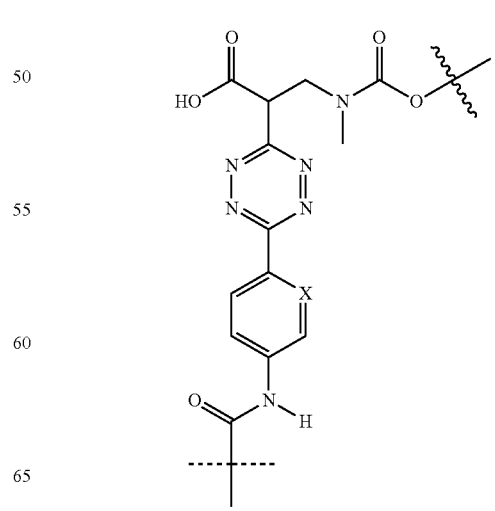

87
-continued
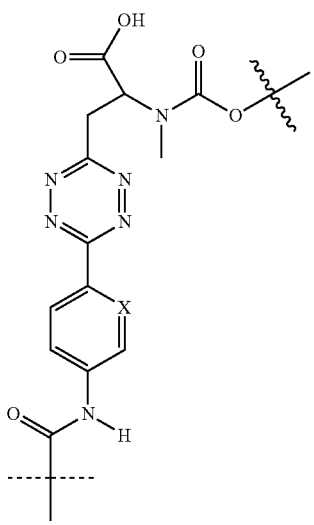
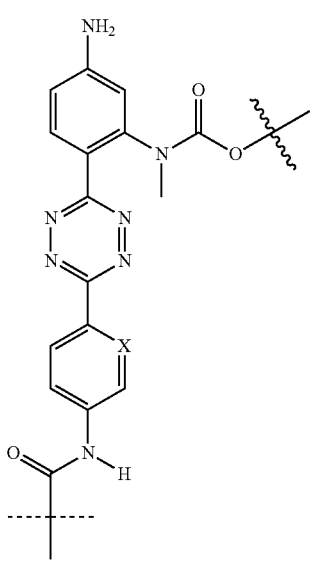
88
-continued
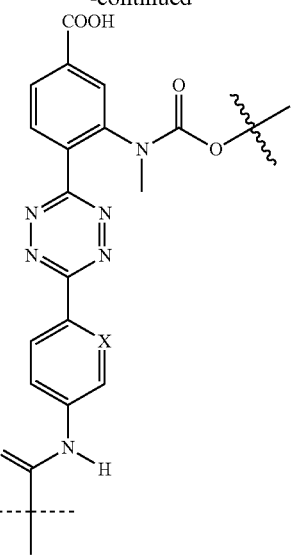
X = C or N
∿∿∿ indicates bond to (remainder of) $C^A$, or $L^C$-$C^A$ optionally comprising $C^B$
---- indicates bond to (remainder of) $S^P$, or $S^P$-$C^B$ or $C^B$
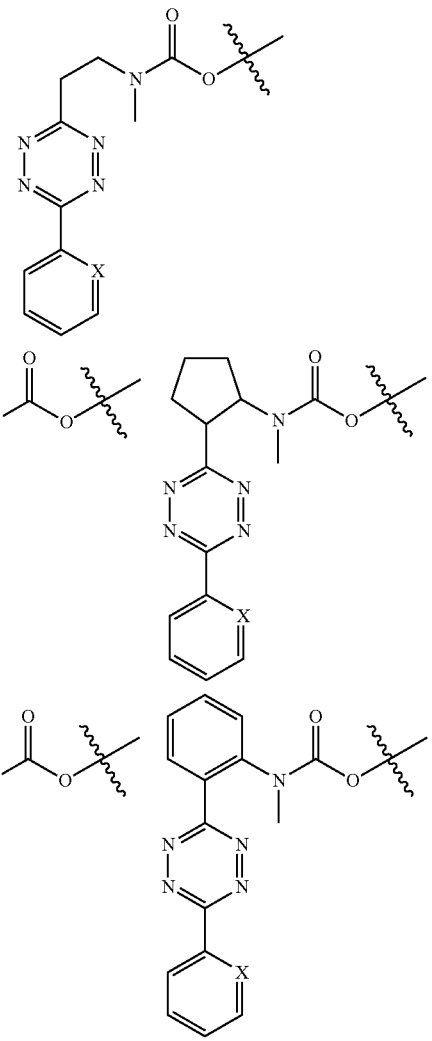

89
-continued
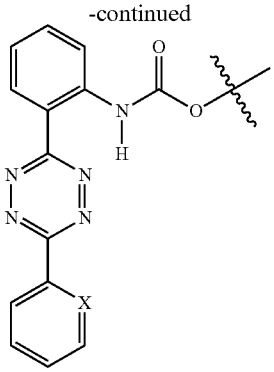
90
-continued
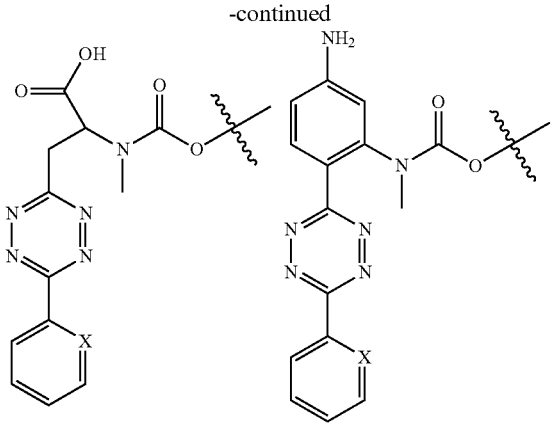
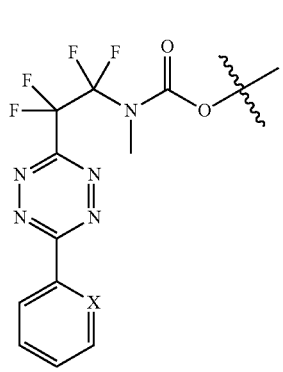
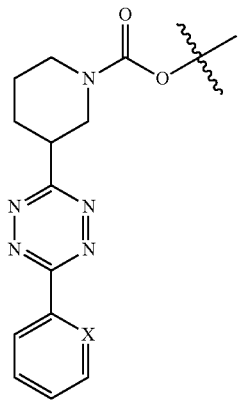
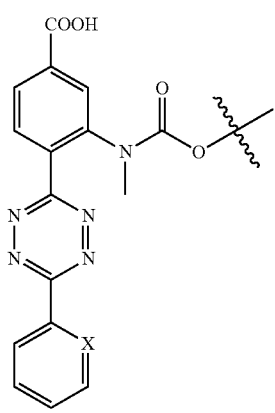
X = C or N
∿∿ indicates bond to (remainder of) C^A, or L^C-C^A optionally comprising C^B
---- indicates bond to (remainder of) S^P, or S^P-C^B or C^B
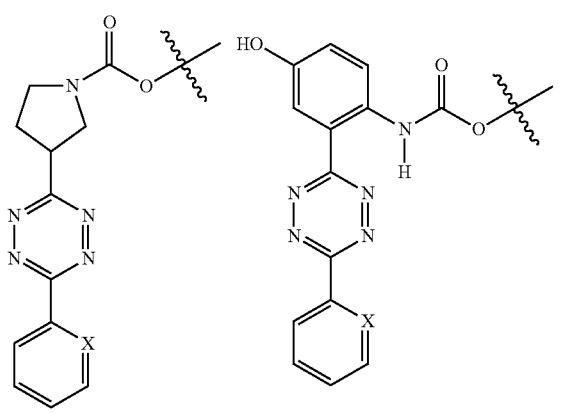
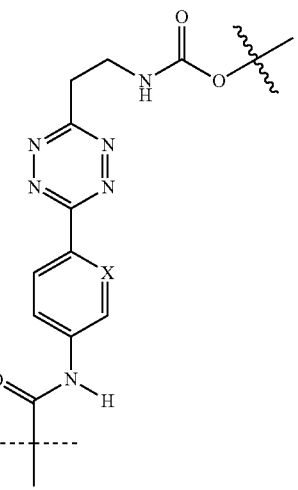

| 91 -continued | 92 -continued |
|---|---|
| 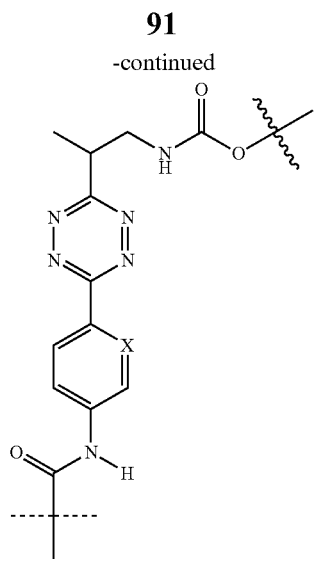 | 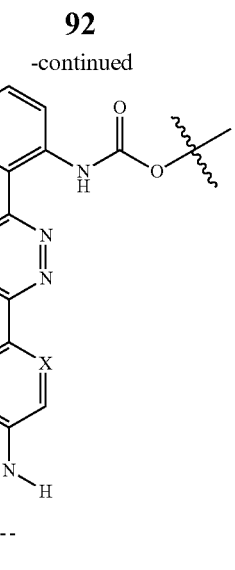 |
| 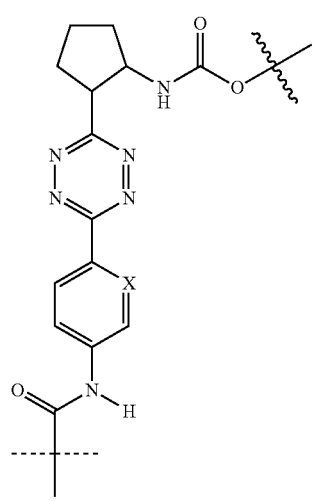 | 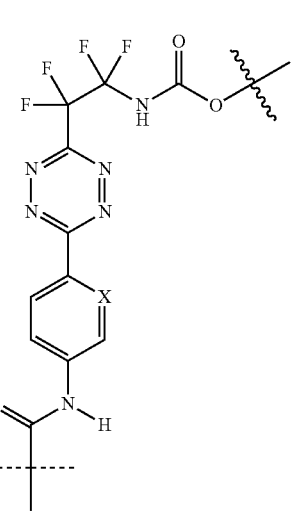 |
| 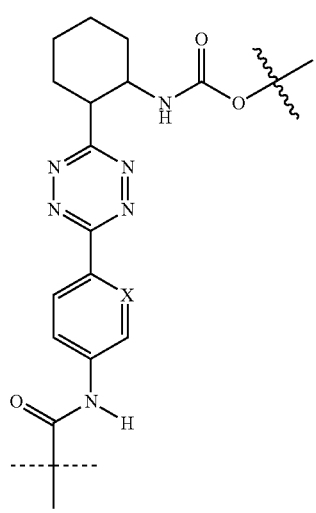 | 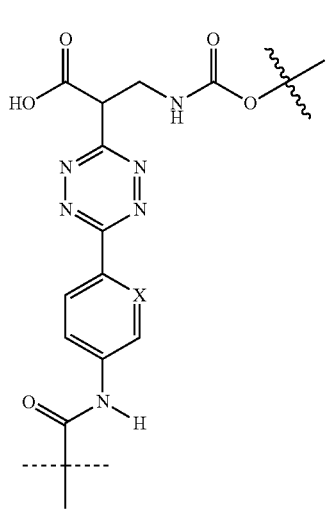 |

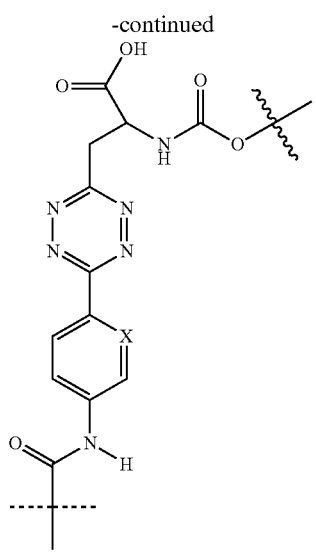
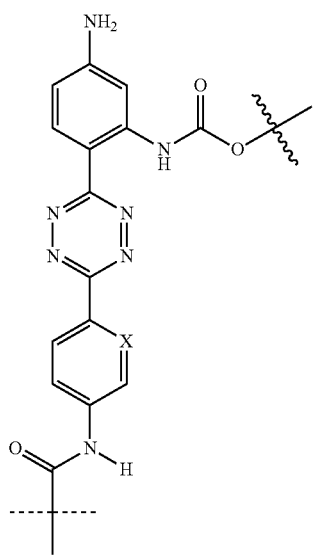
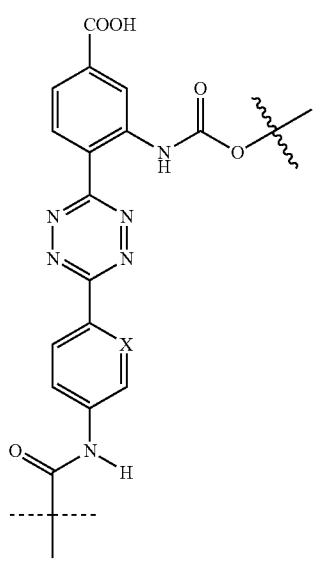
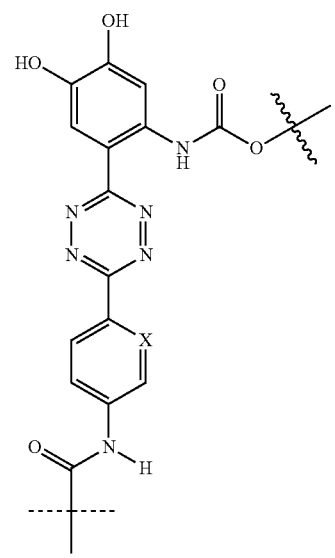
X = C or N
∿∿ indicates bond to (remainder of) $C^A$, or $L^C$-$C^A$ optionally comprising $C^B$
---- indicates bond to (remainder of) $S^P$, or $S^P$-$C^B$ or $C^B$
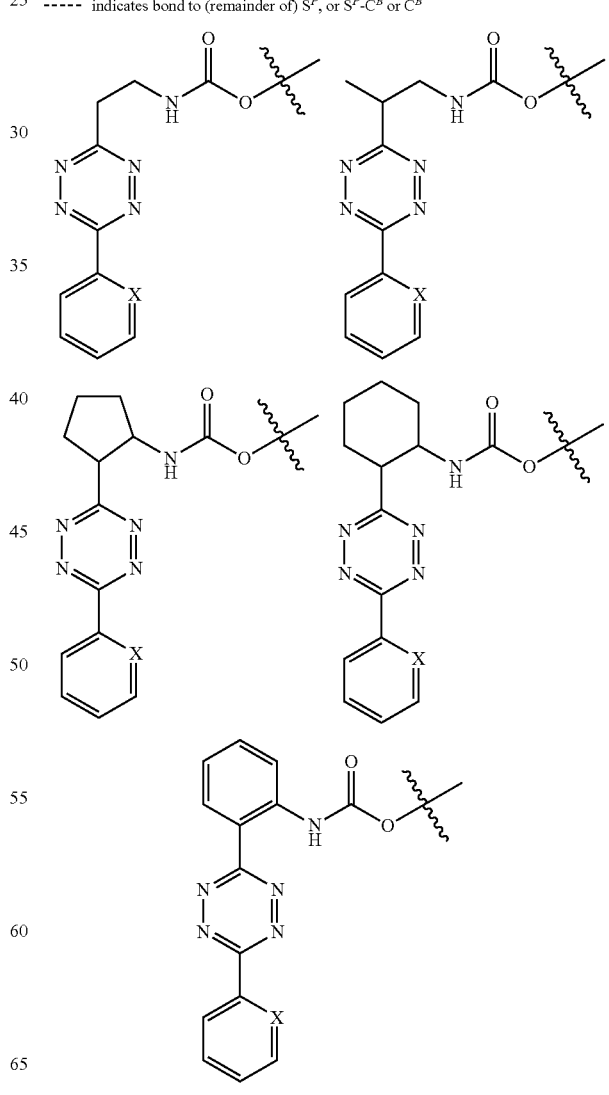

95
-continued
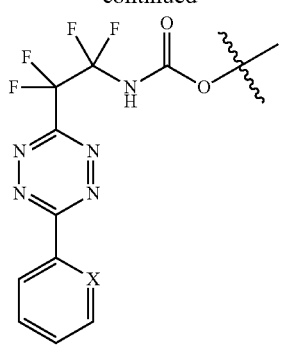
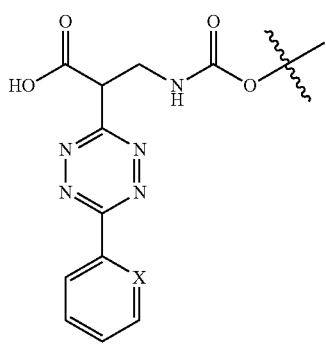
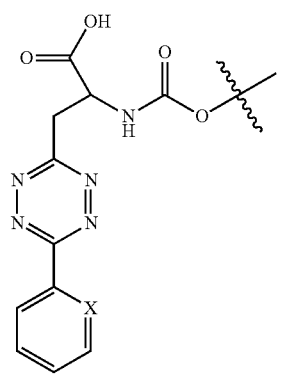
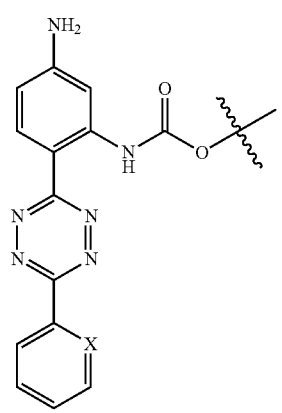
96
-continued
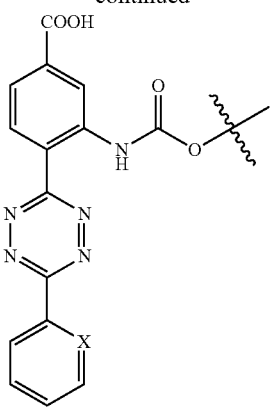
X = C or N
⌇⌇⌇ indicates bond to (remainder of) $C^A$, or $L^C$-$C^A$ optionally comprising $C^B$
----- indicates bond to (remainder of) $S^P$, or $S^P$-$C^B$ or $C^B$
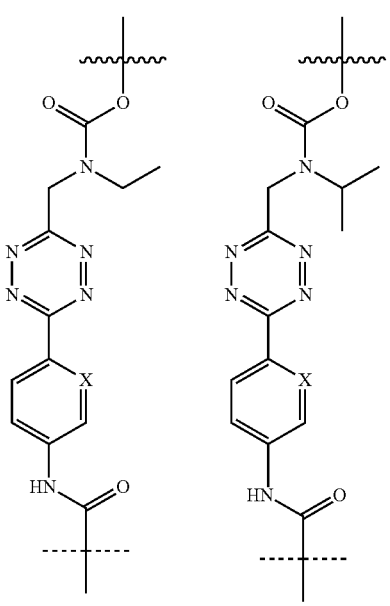

97
-continued
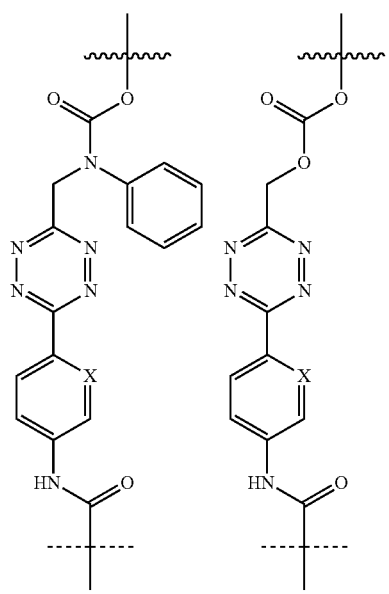
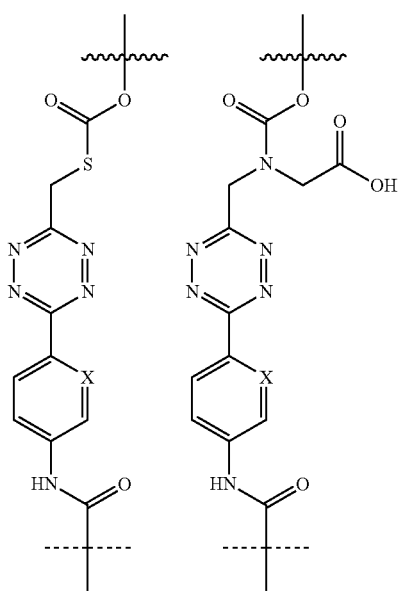
98
-continued
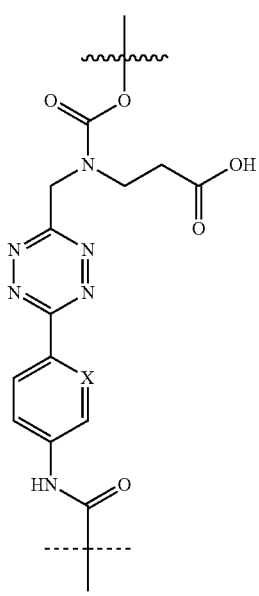
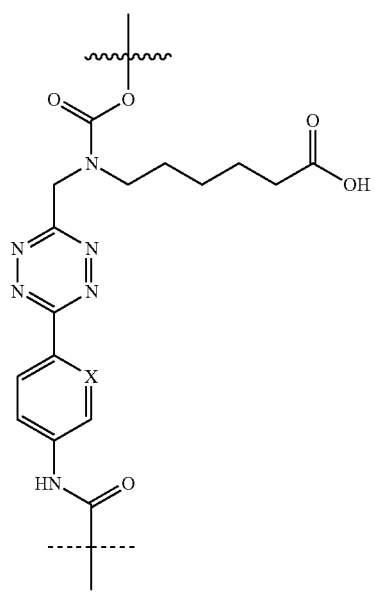

99
-continued
100
-continued
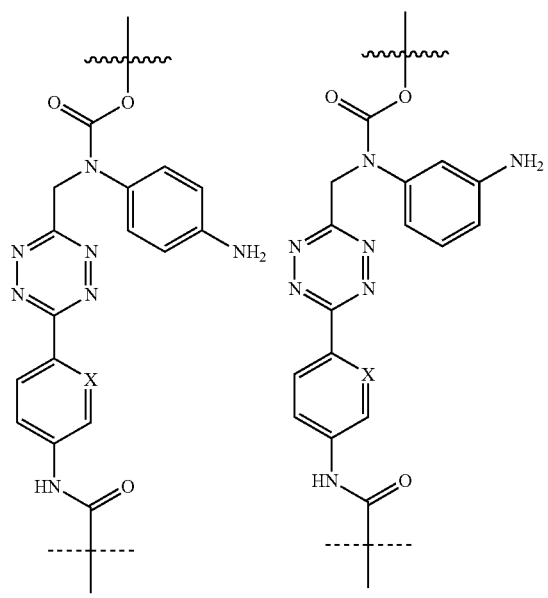
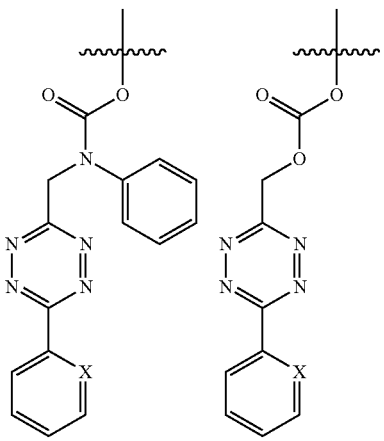
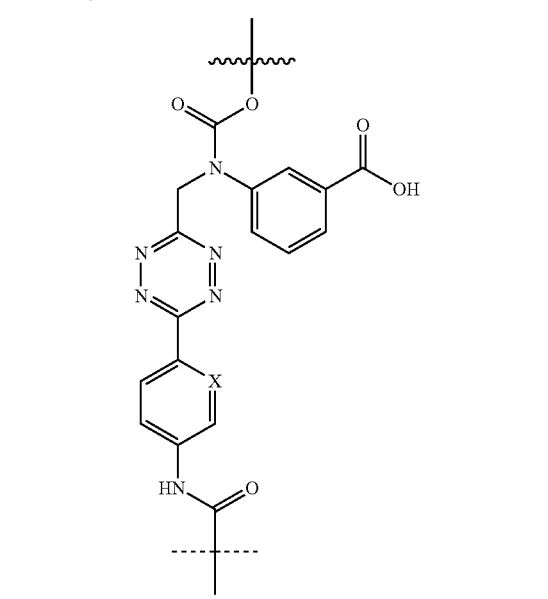
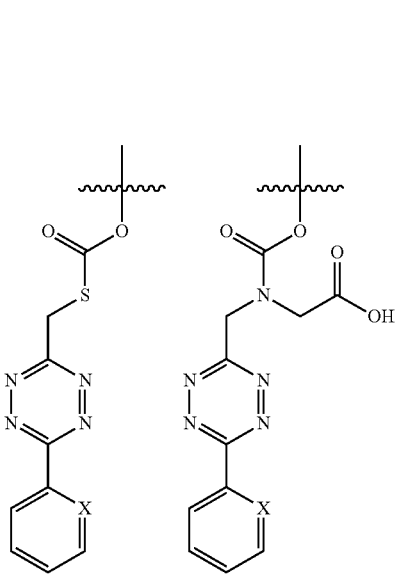
X = C or N
〰️ indicates bond to (remainder of) $C^A$, or $L^C$-$C^A$ optionally comprising $C^B$
---- indicates bond to (remainder of) $S^P$, or $S^P$-$C^B$ or $C^B$
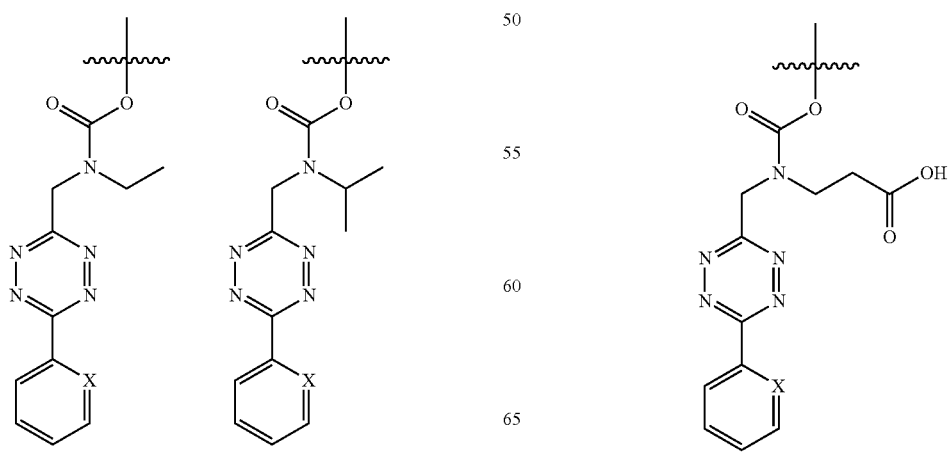

101
-continued
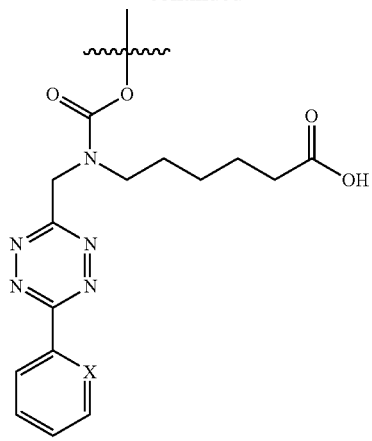
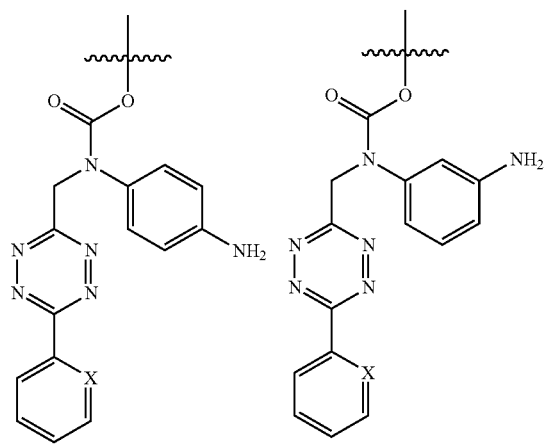
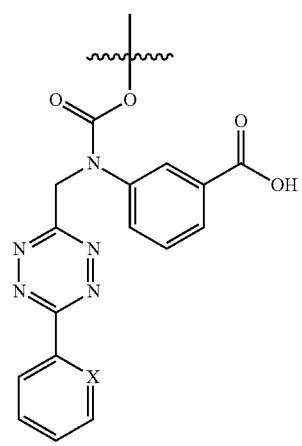
X = C or N
⁀⁀⁀ indicates bond to (remainder of) $C^A$, or $L^C$-$C^A$ optionally comprising $C^B$
- - - indicates bond to (remainder of) $S^P$, or $S^P$-$C^B$ or $C^B$
102
-continued
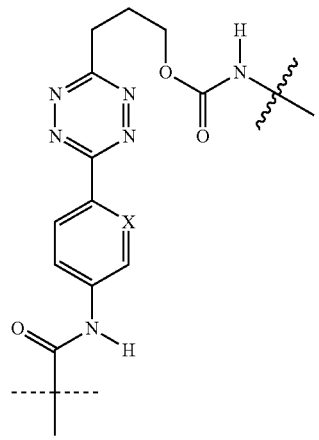
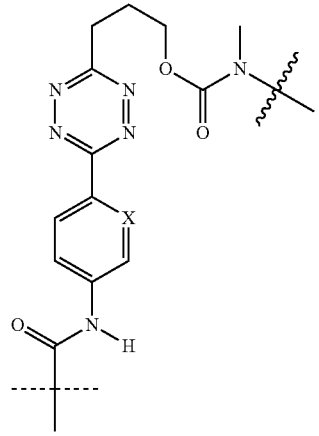
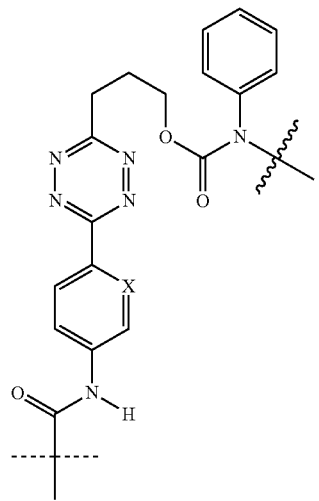

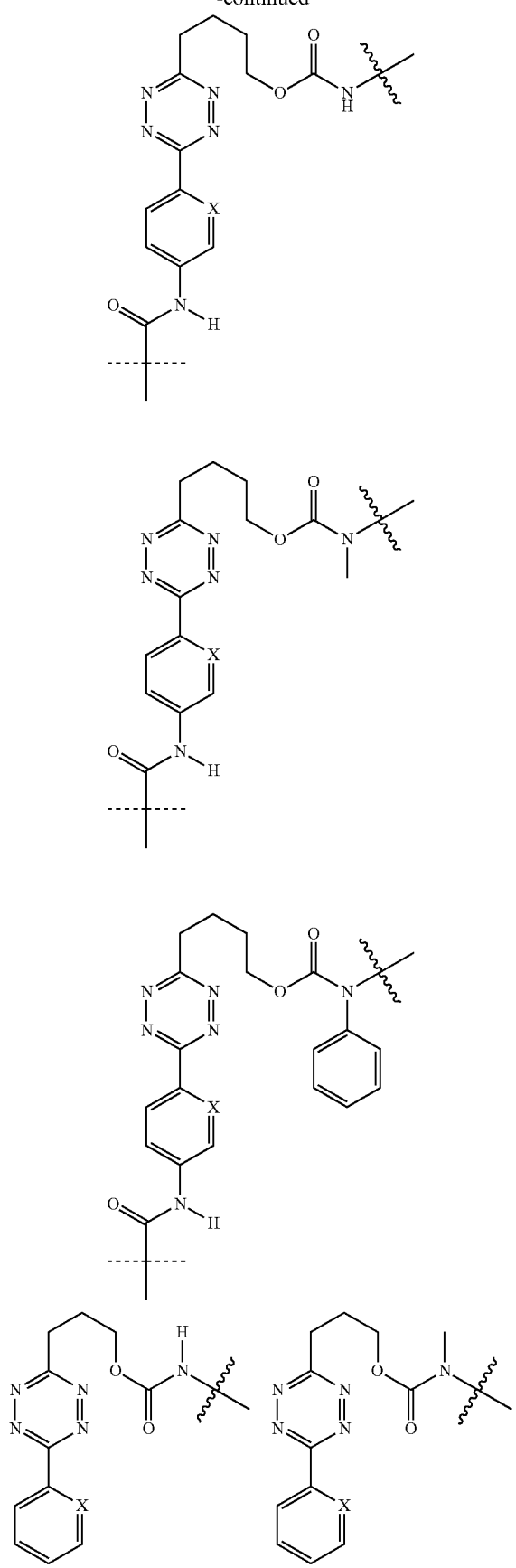
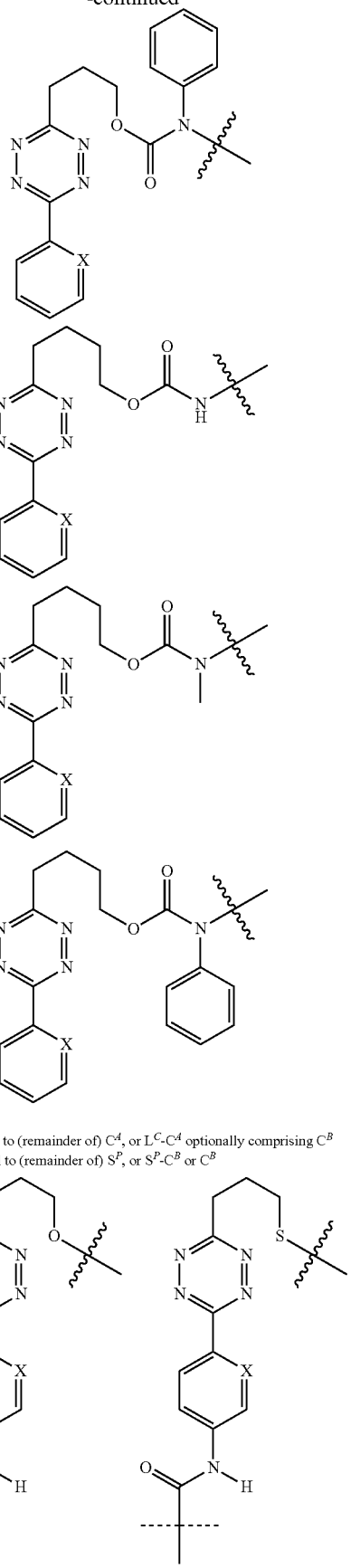
X = C or N
∿∿ indicates bond to (remainder of) $C^A$, or $L^C$-$C^A$ optionally comprising $C^B$
---- indicates bond to (remainder of) $S^P$, or $S^P$-$C^B$ or $C^B$ 105
-continued
106
-continued
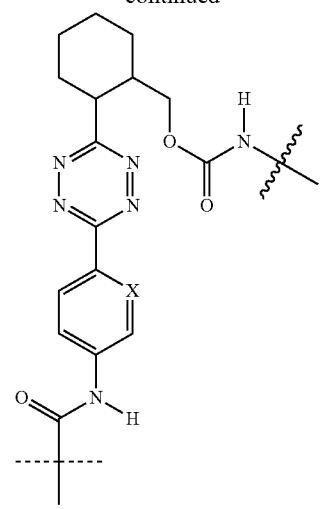
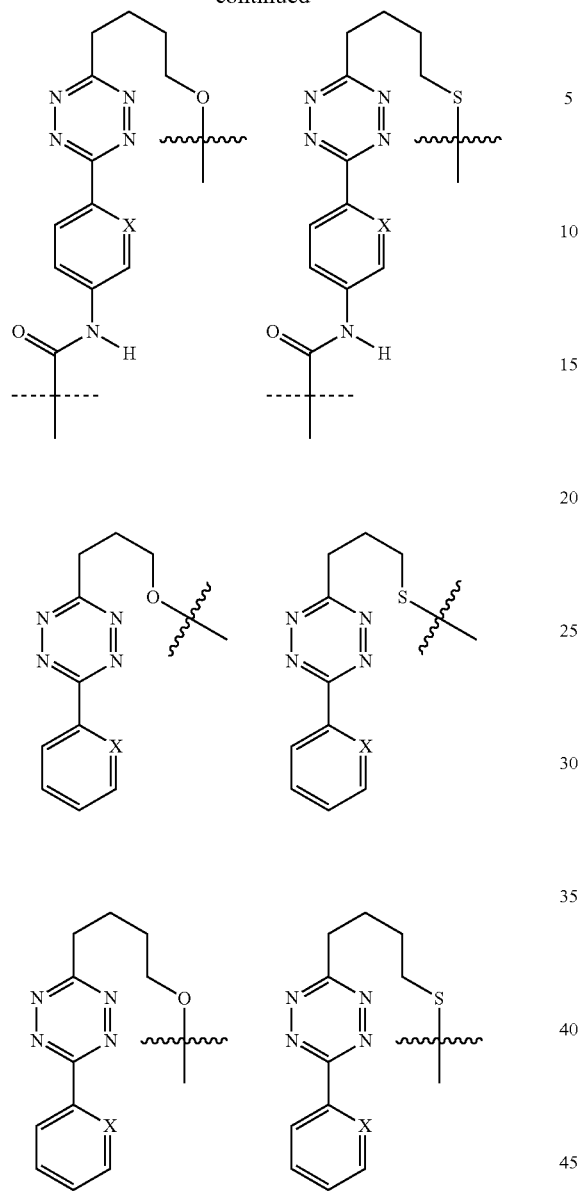
X = C or N
⌇⌇⌇ indicates bond to aromatic carbon of (remainder of) C^A, or L^C-C^A optionally comprising C^B
- - - - indicates bond to (remainder of) S^P, or S^P-C^B or C^B
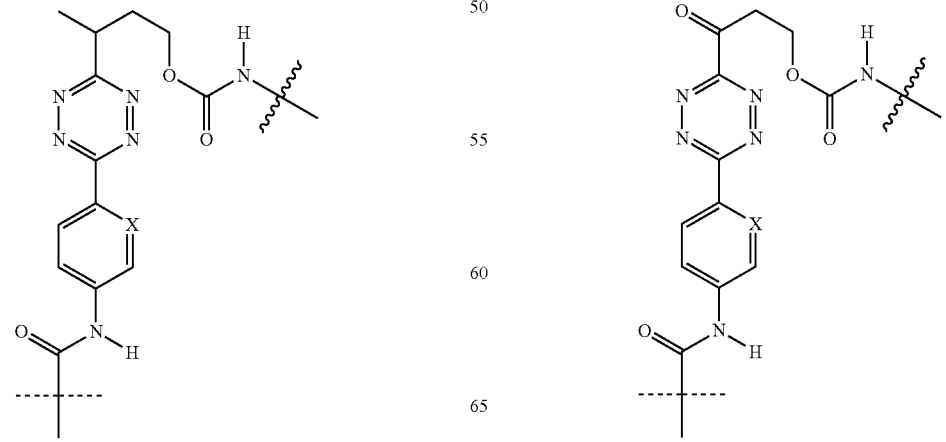

107
-continued
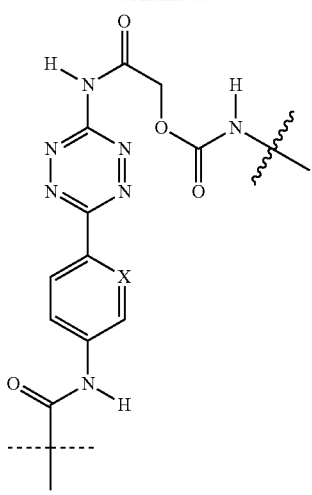
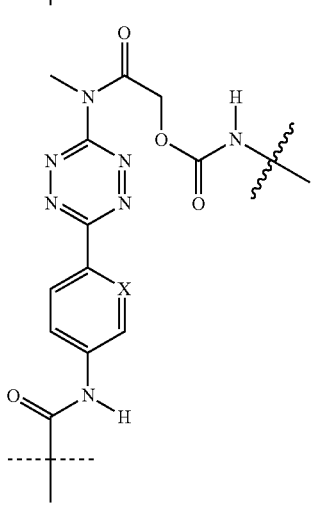
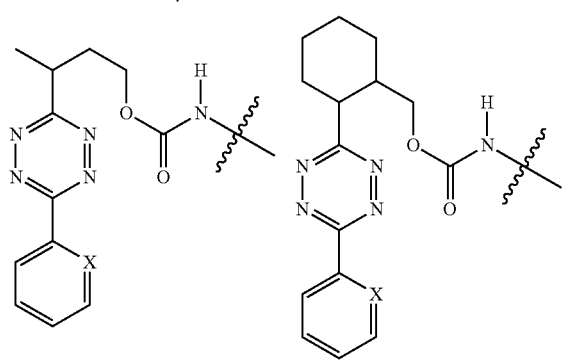
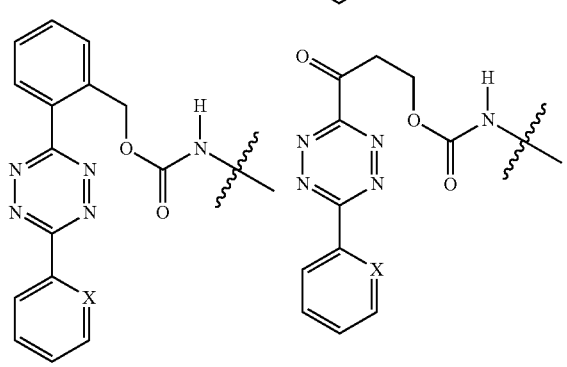
108
-continued
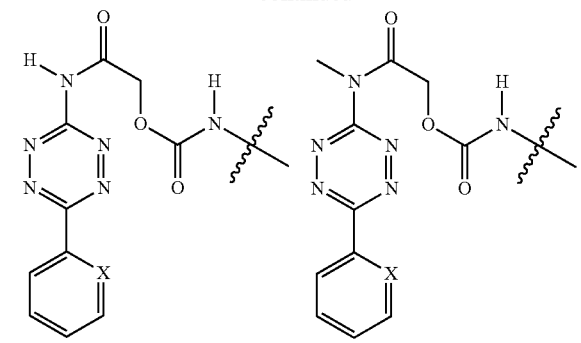
X = C or N
⁓ indicates bond to (remainder of) $C^A$, or $L^C$-$C^A$ optionally comprising $C^B$
---- indicates bond to (remainder of) $S^P$, or $S^P$-$C^B$ or $C^B$
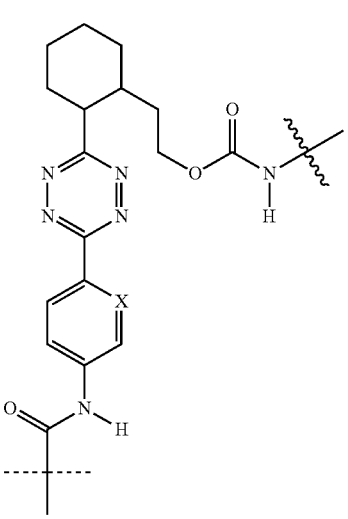
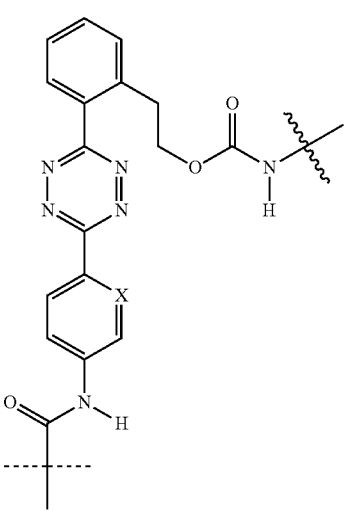

109
-continued
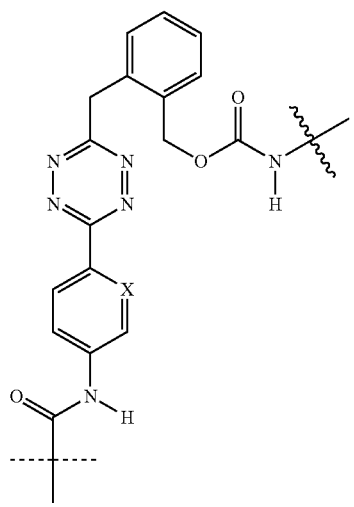
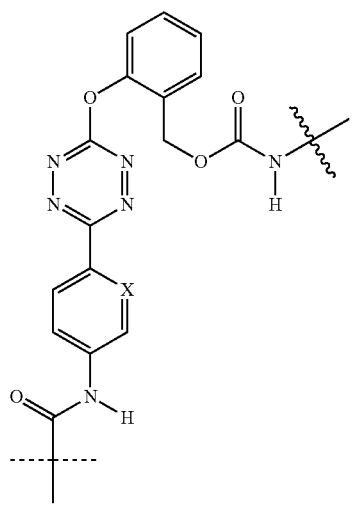
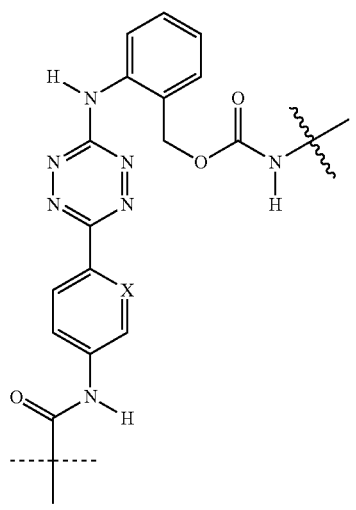
110
-continued
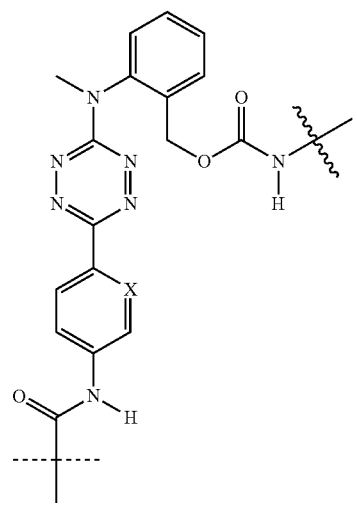
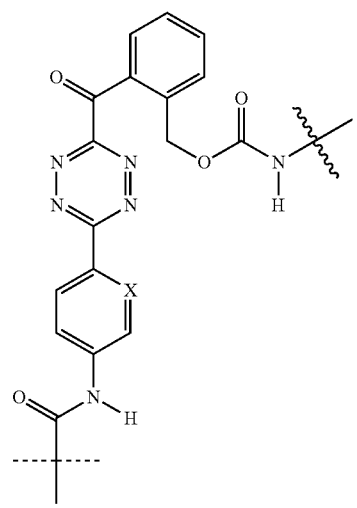
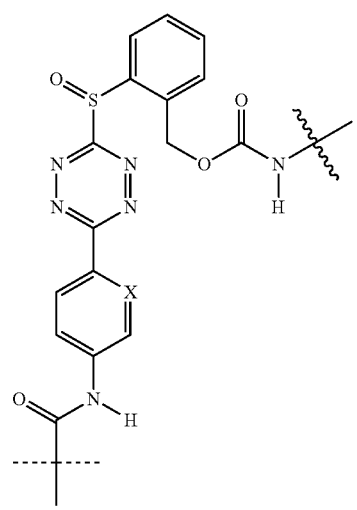

111
-continued
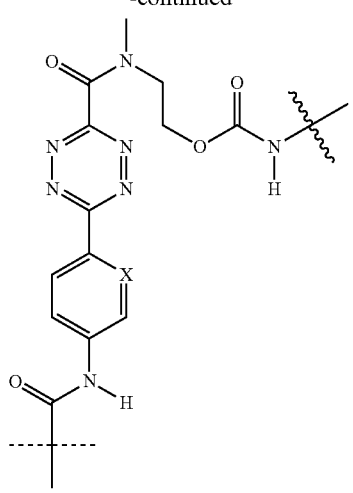
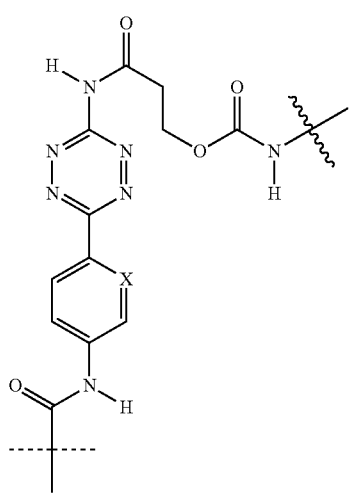
X = C or N
〜〜 indicates bond to (remainder of) $C^A$, or $L^C$-$C^A$ optionally comprising $C^B$
---- indicates bond to (remainder of) $S^P$, or $S^P$-$C^B$ or $C^B$
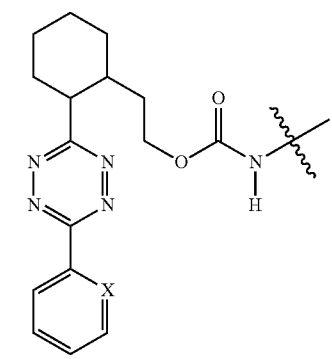
112
-continued
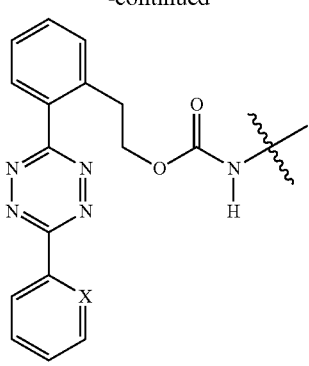
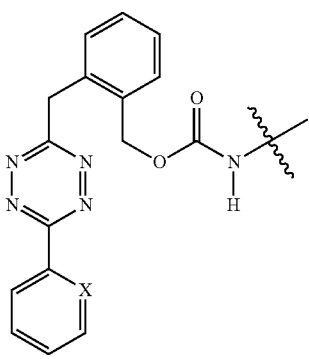
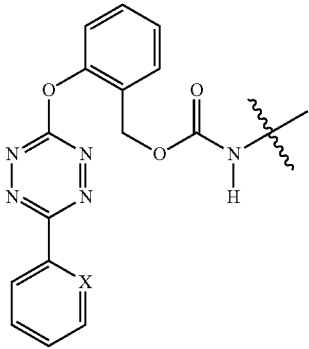
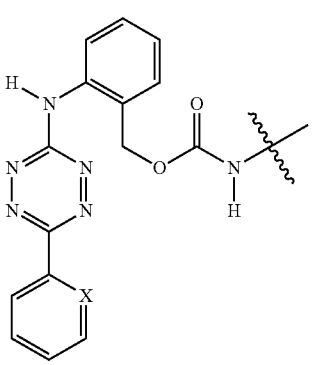

113
-continued
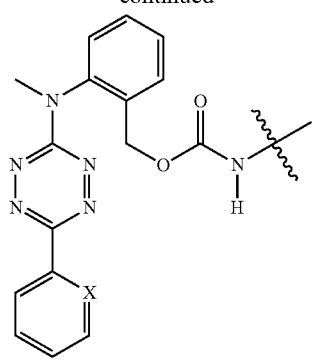
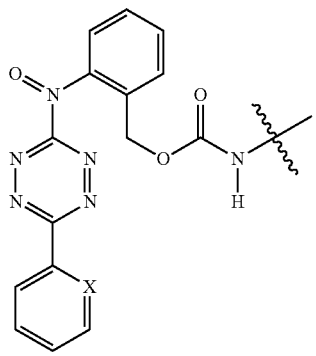
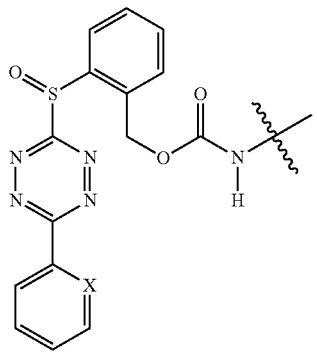
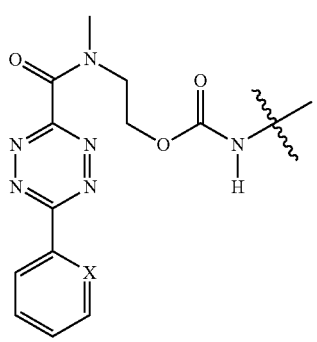
114
-continued
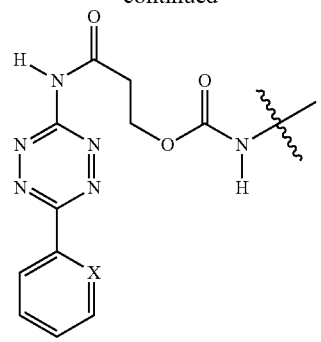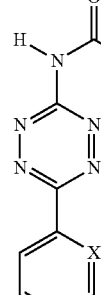
X = C or N
⌇⌇⌇ indicates bond to (remainder of) $C^A$, or $L^C$-$C^A$ optionally comprising $C^B$
---- indicates bond to (remainder of) $S^P$, or $S^P$-$C^B$ or $C^B$
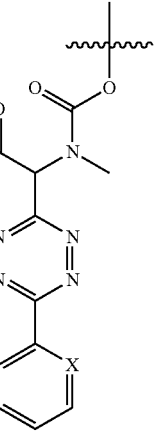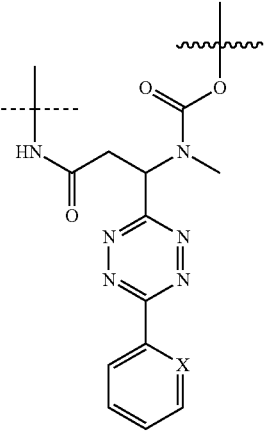
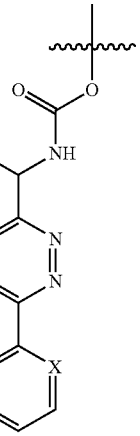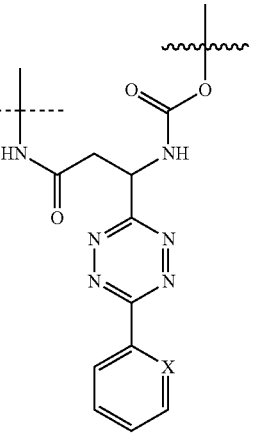

115
-continued
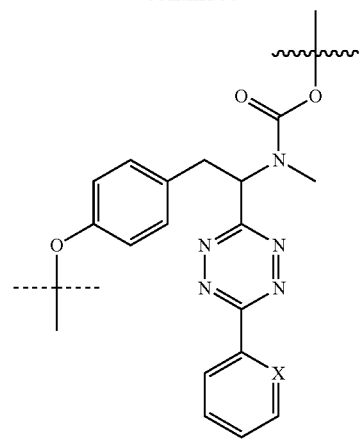
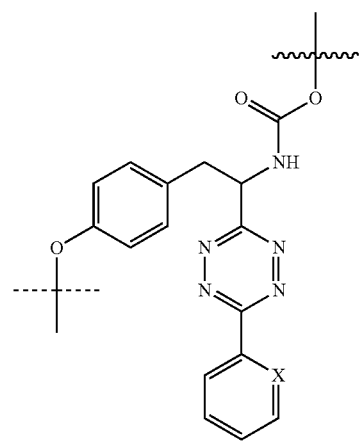
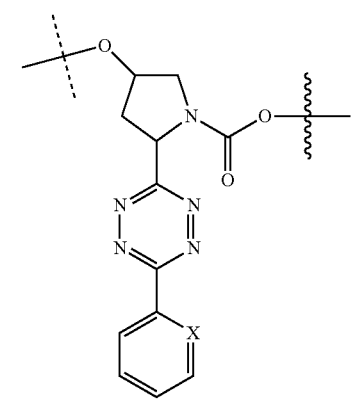
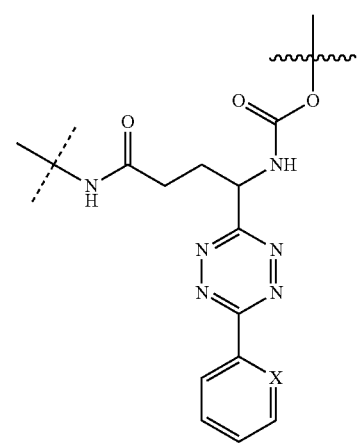
116
-continued
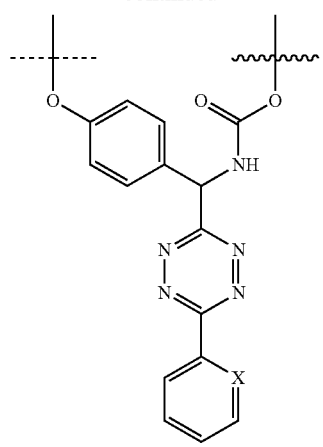
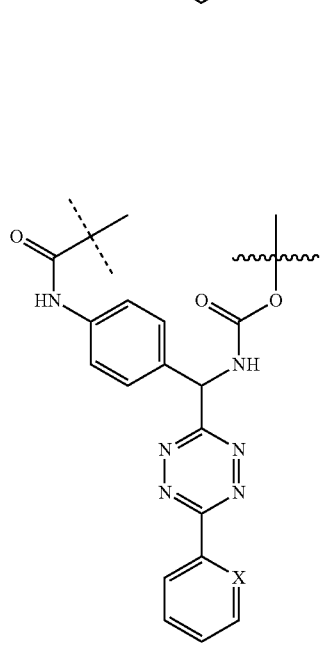
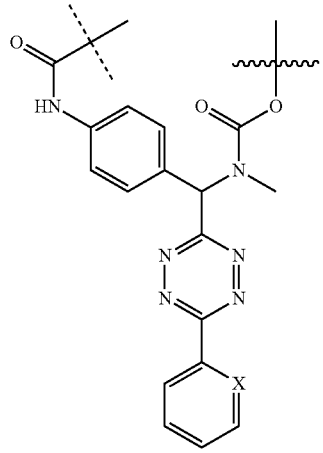

117
-continued
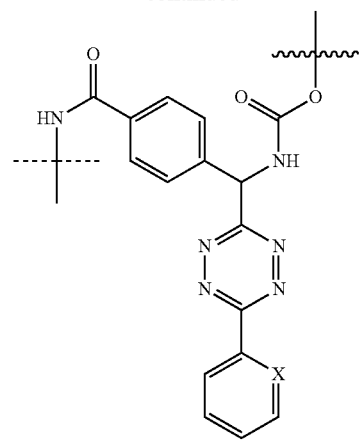
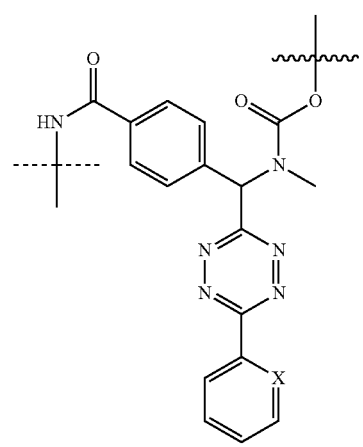
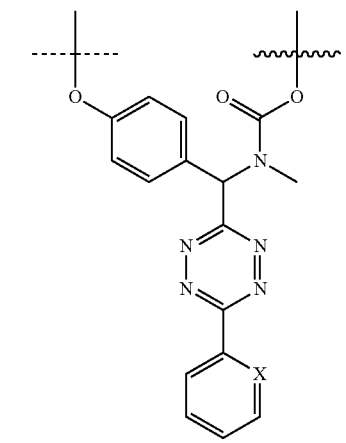
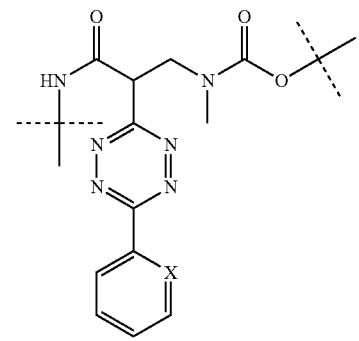
118
-continued
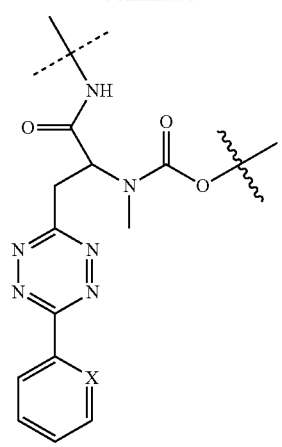
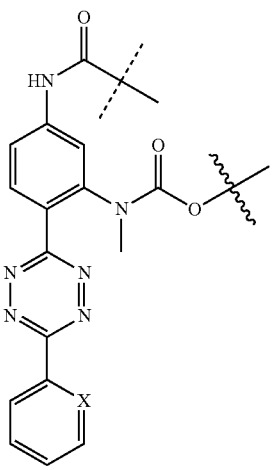
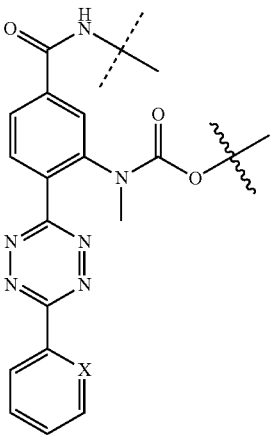
X = C or N
∿∿ indicates bond to (remainder of) $C^A$, or $L^C$-$C^A$ optionally comprising $C^B$
---- indicates bond to (remainder of) $S^P$, or $S^P$-$C^B$ or $C^B$

119
-continued
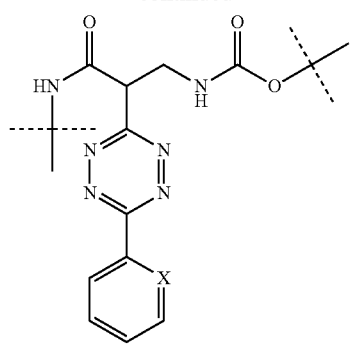
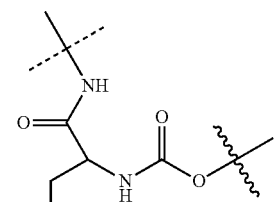
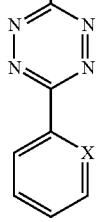
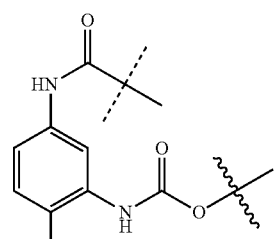
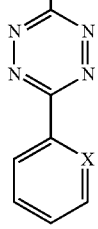
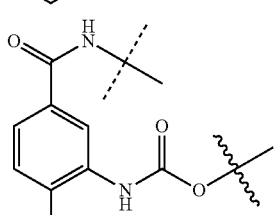
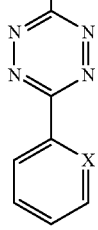
120
-continued
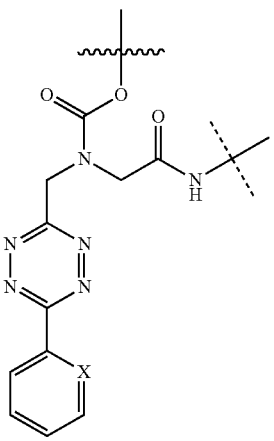
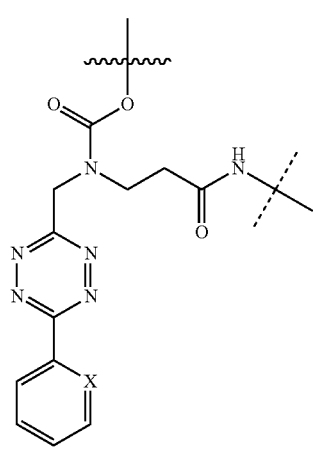
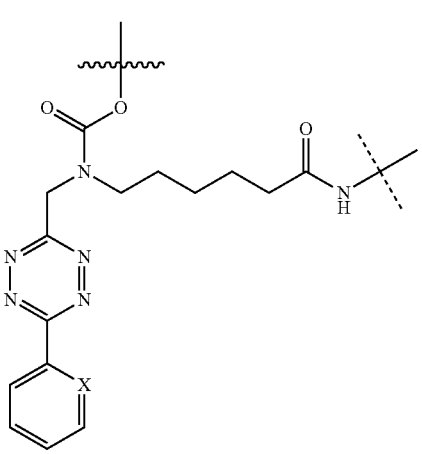

121
-continued
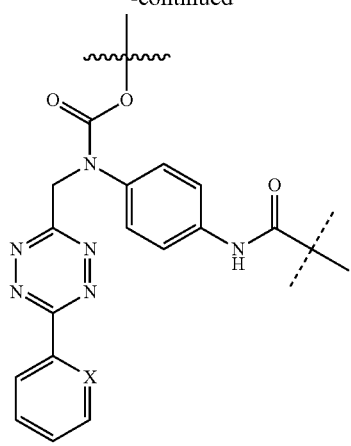
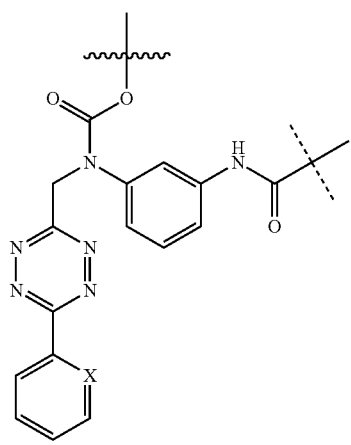
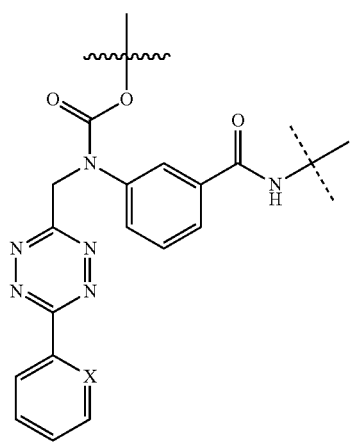
X = C or N
~~~ indicates bond to (remainder of) $C^A$, or $L^C$-$C^A$ optionally comprising $C^B$
---- indicates bond to (remainder of) $S^P$, or $S^P$-$C^B$ or $C^B$
122
-continued
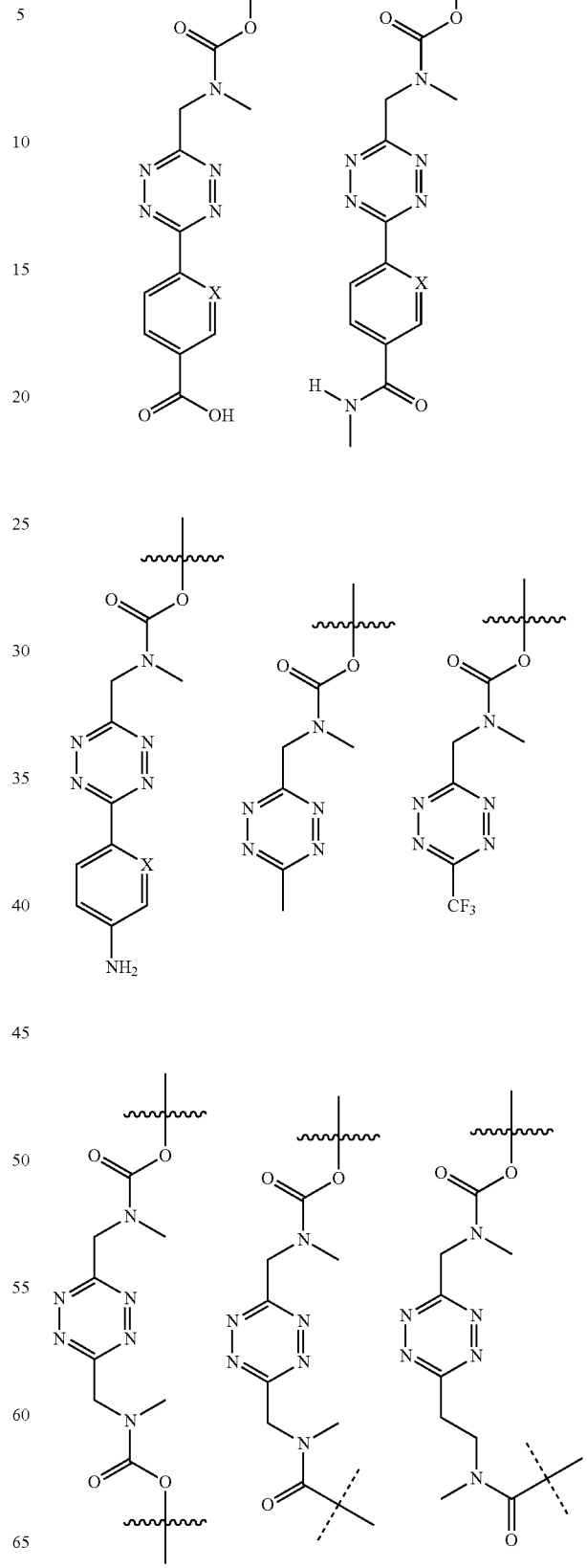

123
-continued
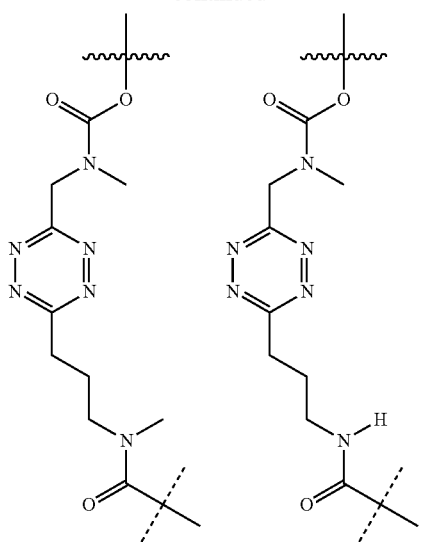
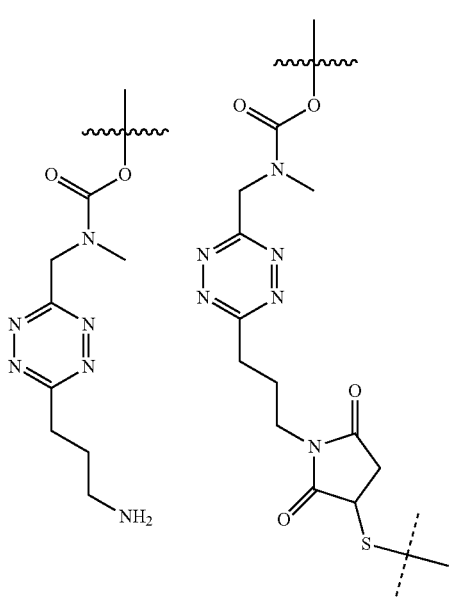
X = C or N
⁓ indicates bond to (remainder of) $C^A$, or $L^C$-$C^A$ optionally comprising $C^B$
---- indicates bond to (remainder of) $S^P$, or $S^P$-$C^B$ or $C^B$
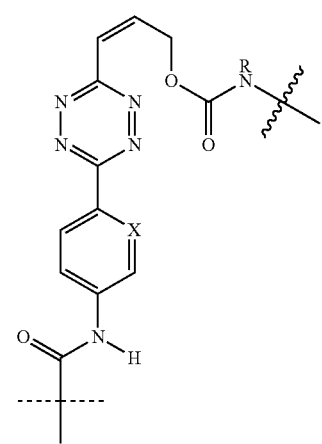
124
-continued
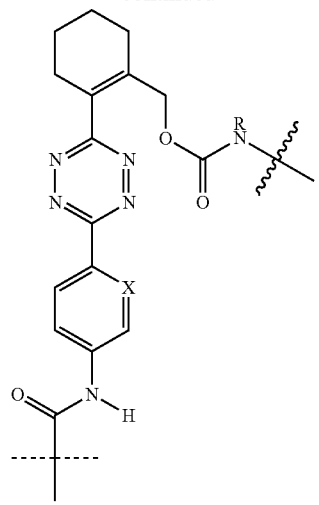
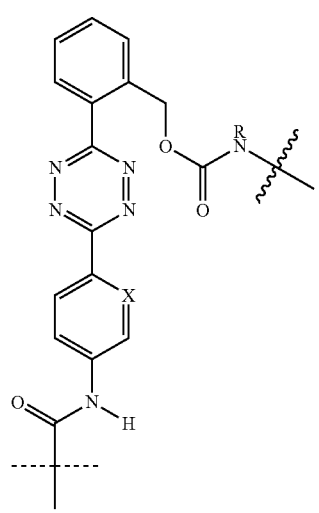
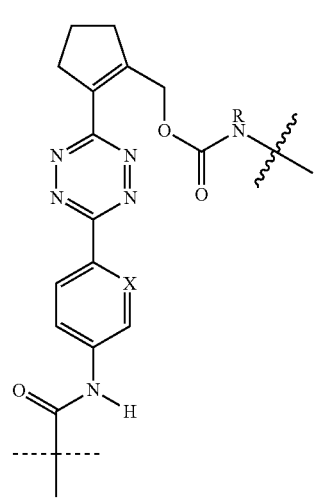

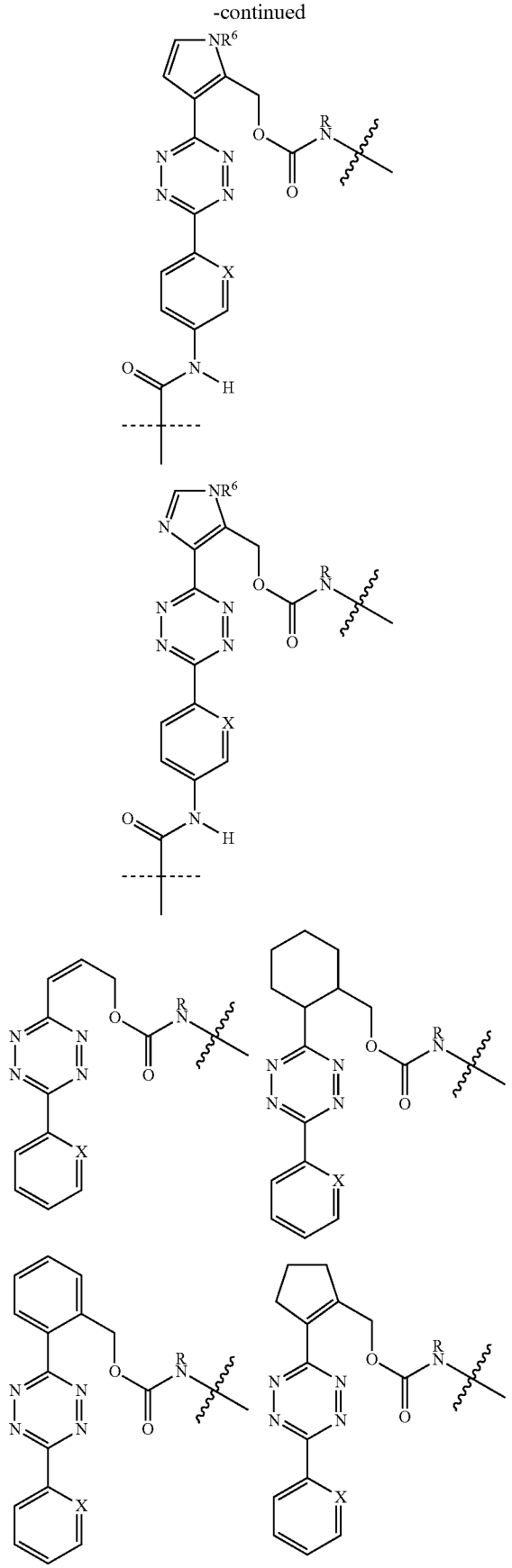
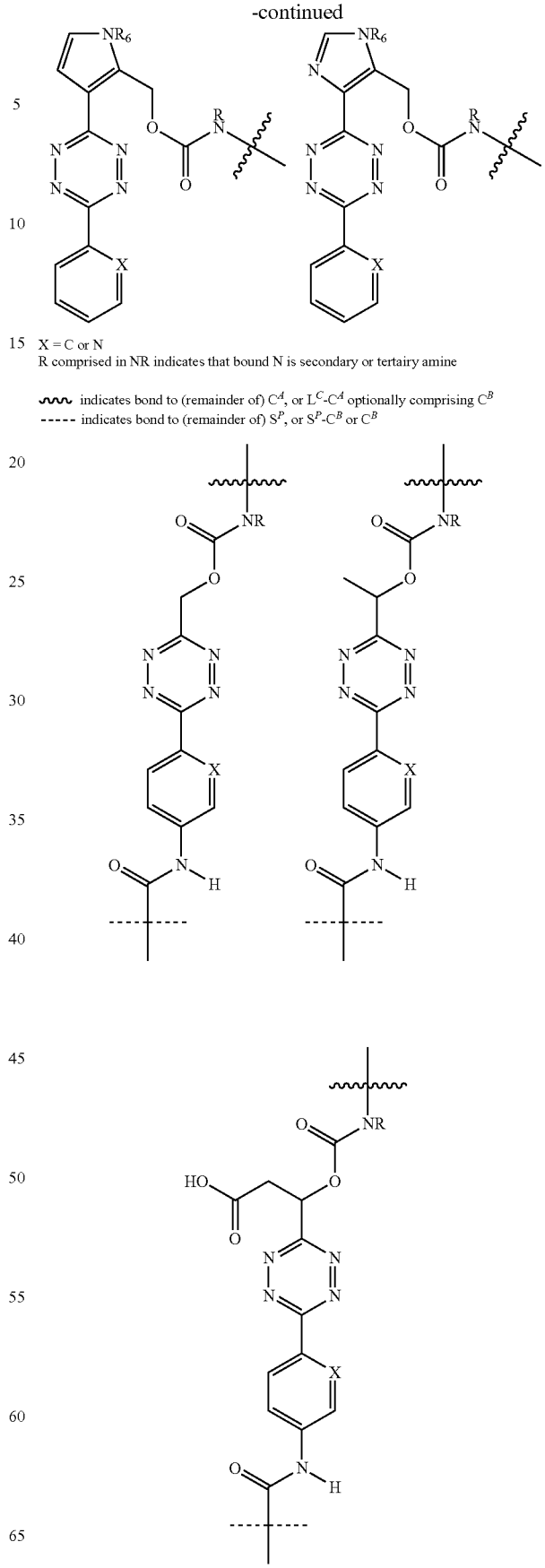
X = C or N
R comprised in NR indicates that bound N is secondary or tertairy amine
〰〰 indicates bond to (remainder of) $C^A$, or $L^C$-$C^A$ optionally comprising $C^B$
---- indicates bond to (remainder of) $S^P$, or $S^P$-$C^B$ or $C^B$ 127
-continued
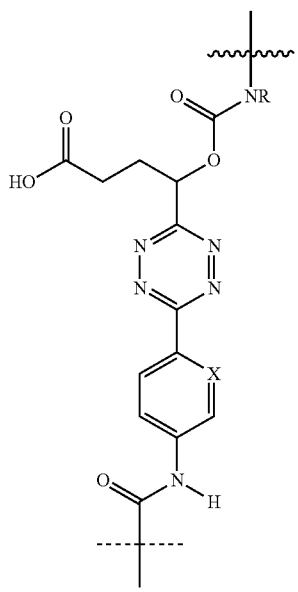
128
-continued
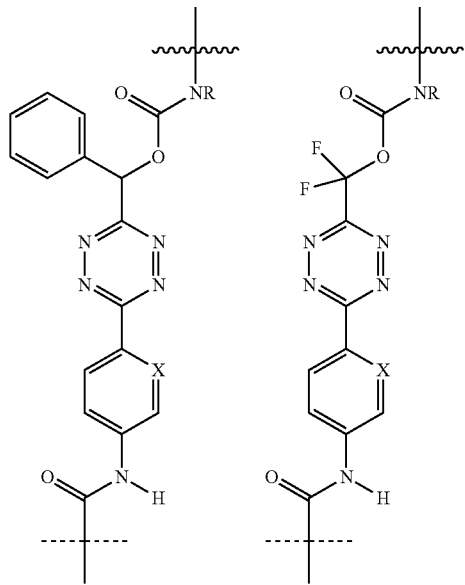
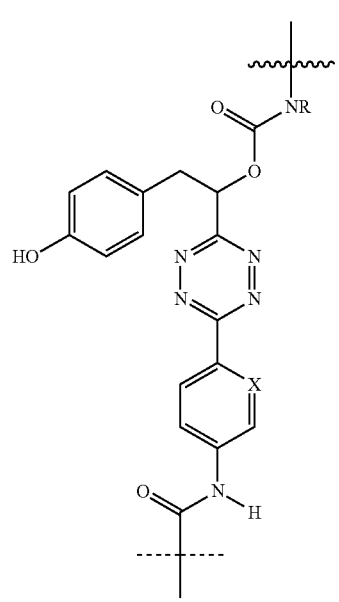
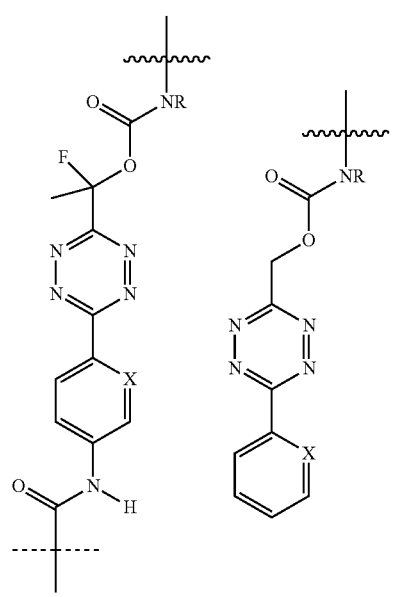
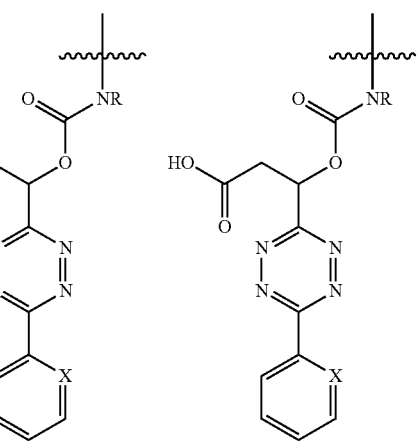

129
-continued
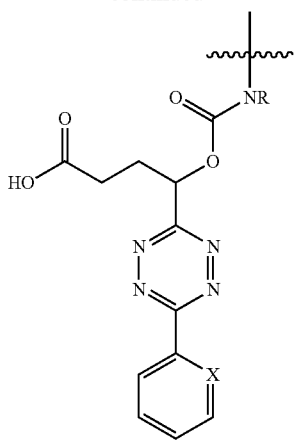
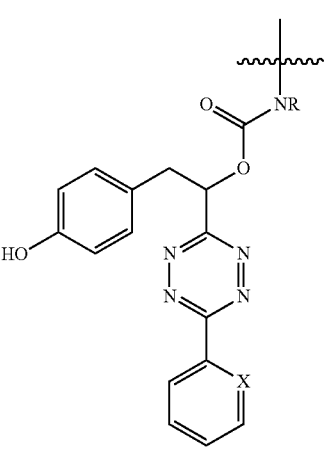
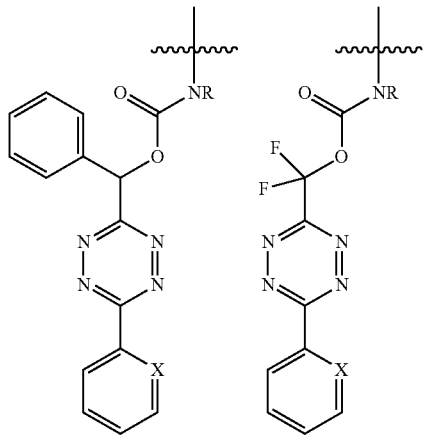
130
-continued
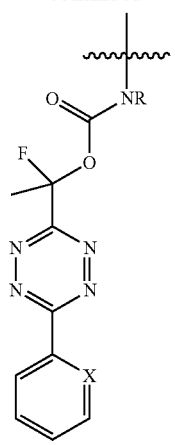
X = C or N
R comprised in NR indicates that bound N is secondary or tertairy amine
⁓⁓⁓ indicates bond to (remainder of) $C^A$, or $L^C$-$C^A$ optionally comprising $C^B$
---- indicates bond to (remainder of) $S^P$, or $S^P$-$C^B$ or $C^B$
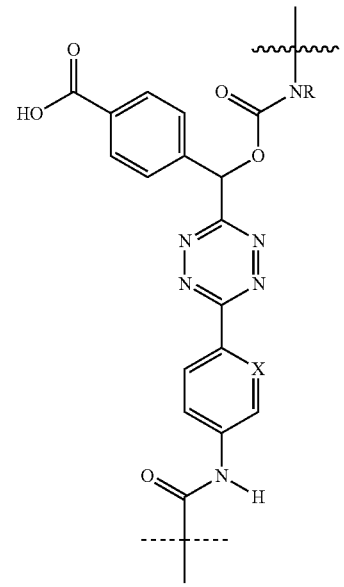
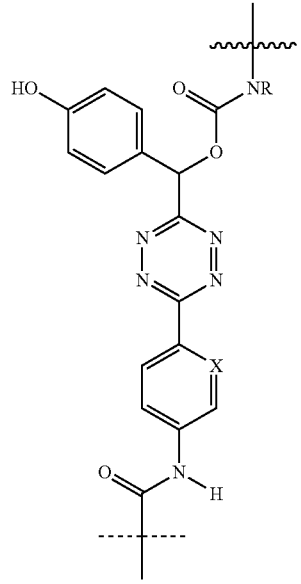

131
-continued
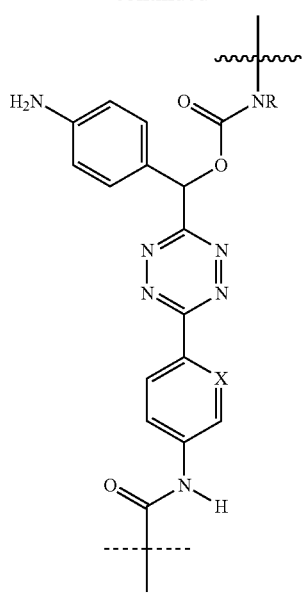
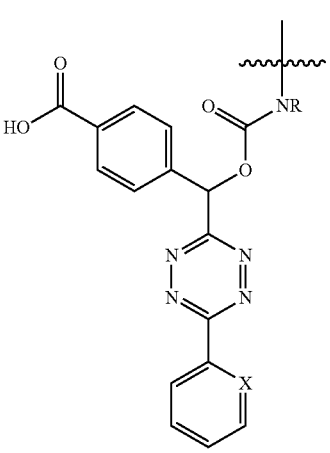
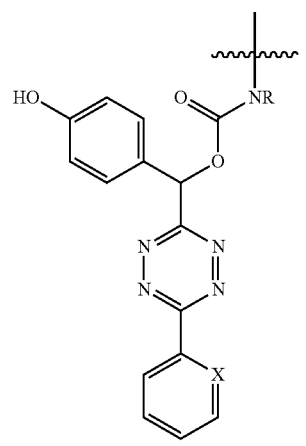
132
-continued
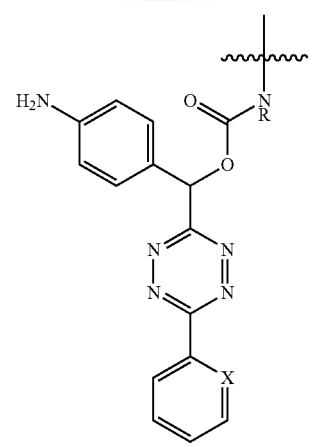
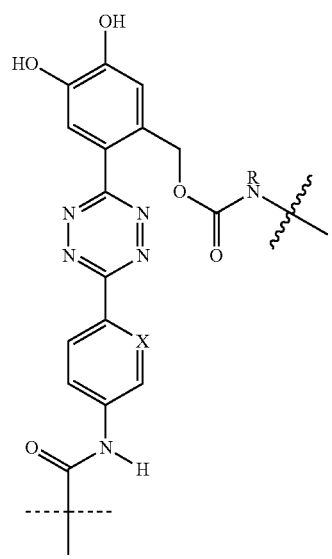
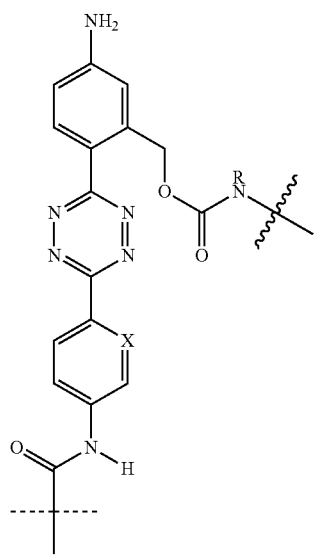

133
-continued
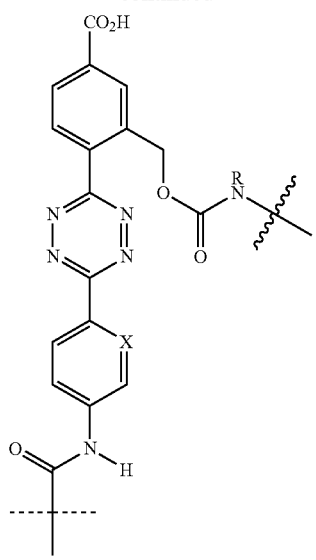
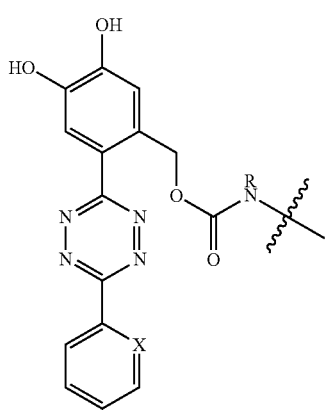
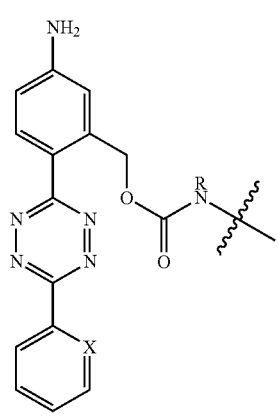
134
-continued
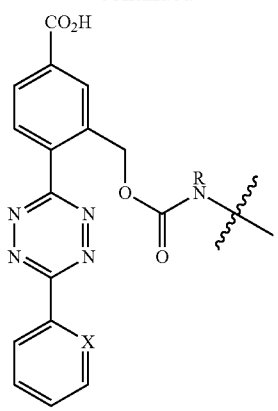
X = C or N
R comprised in NR indicates that bound N is secondary or tertairy amine
∿∿∿ indicates bond to (remainder of) $C^A$, or $L^C$-$C^A$ optionally comprising $C^B$
----- indicates bond to (remainder of) $S^P$, or $S^P$-$C^B$ or $C^B$
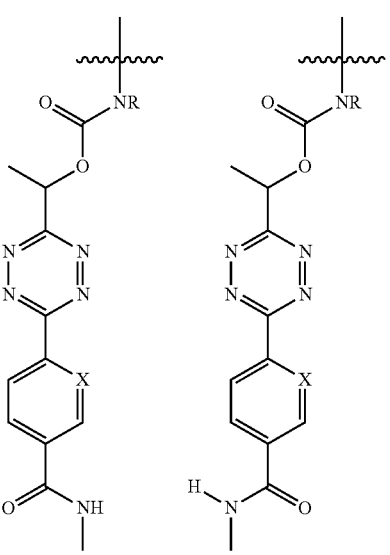
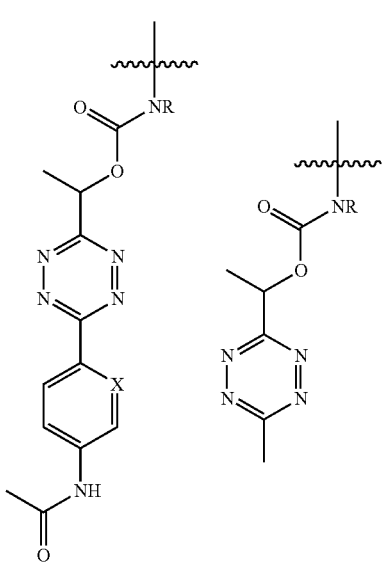

135
-continued
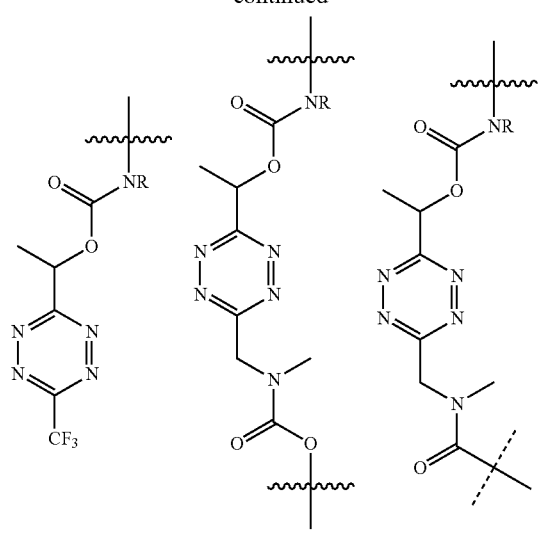
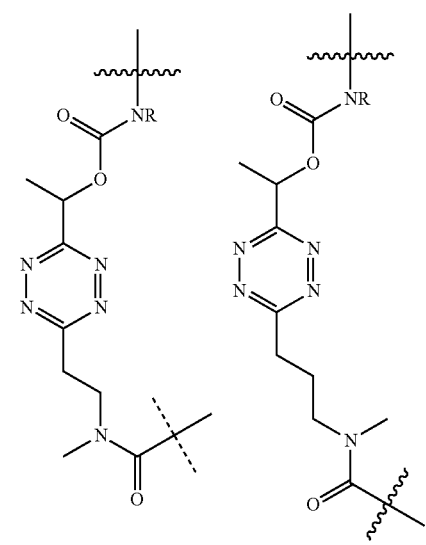
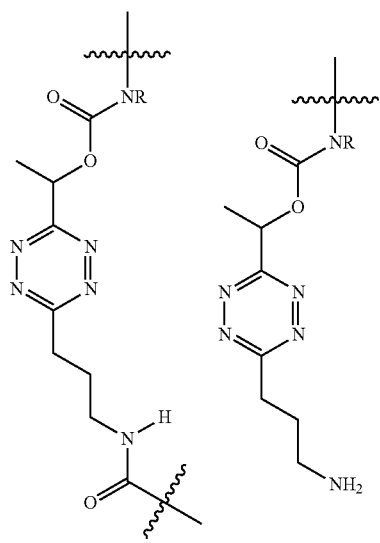
136
-continued
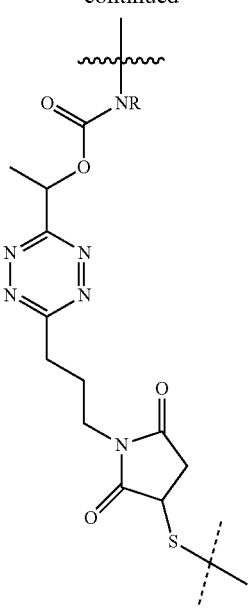
X = C or N
R comprised in NR indicates that bound N is secondary or tertairy amine
∿∿ indicates bond to (remainder of) $C^A$, or $L^C$-$C^A$ optionally comprising $C^B$
---- indicates bond to (remainder of) $S^P$, or $S^P$-$C^B$ or $C^B$
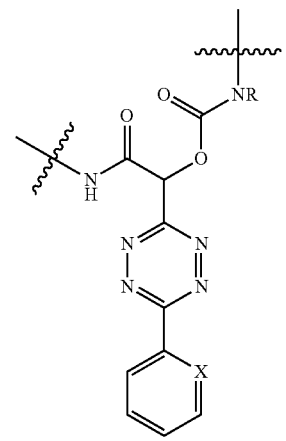
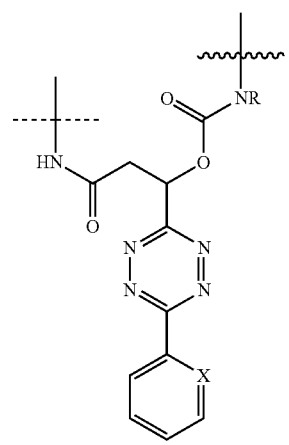

137
-continued
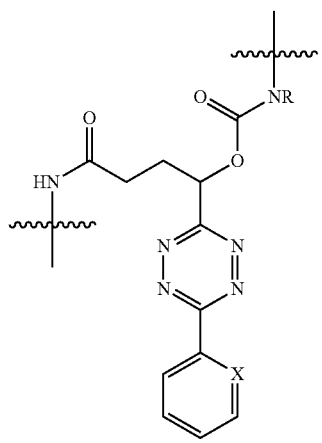
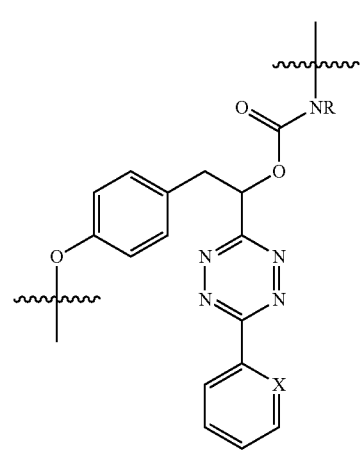
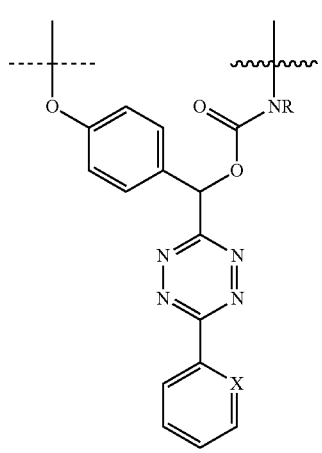
138
-continued
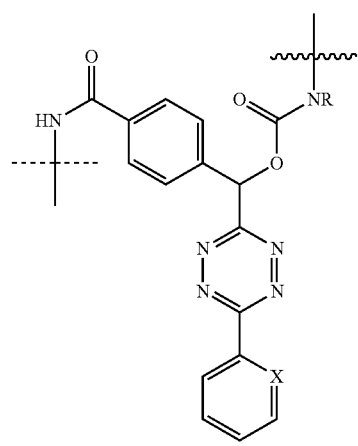
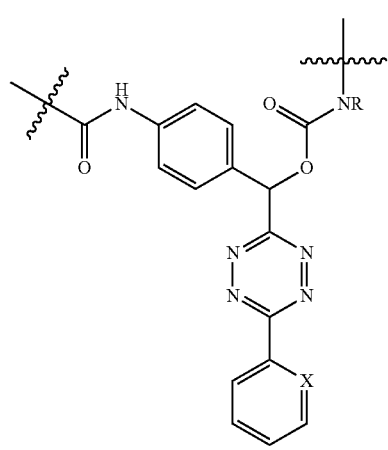
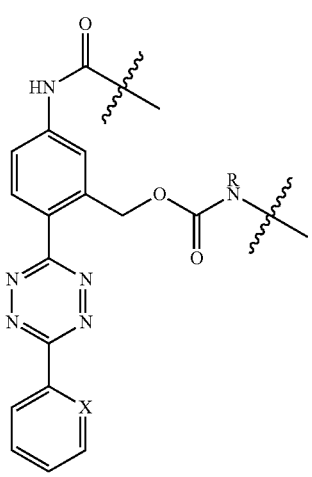

139
-continued

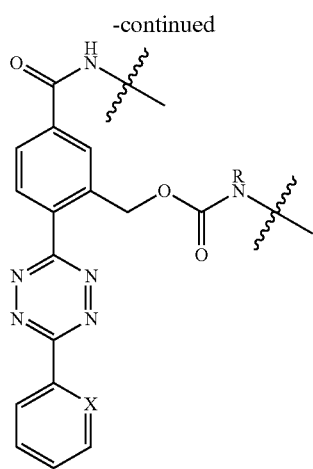

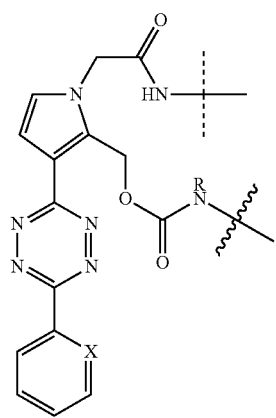

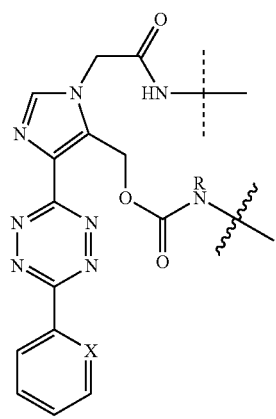

X = C or N
R comprised in NR indicates that bound N is secondary or tertairy amine ⁓⁓⁓ indicates bond to (remainder of) $C^A$, or $L^C$-$C^A$ optionally comprising $C^B$
----- indicates bond to (remainder of) $S^P$, or $S^P$-$C^B$ or $C^B$

140

A few exemplary Trigger-$L^C$ conjugates believed to afford release through the cyclization and/or the cascade mechanism are shown below:

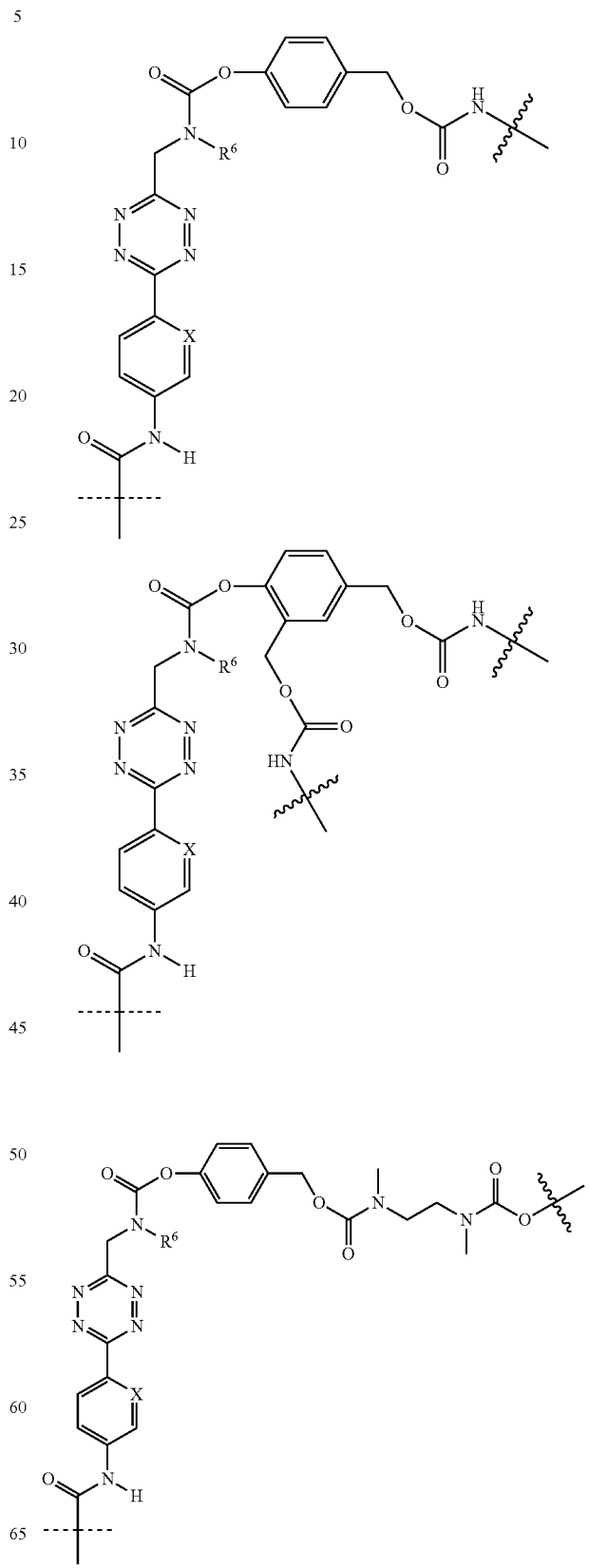

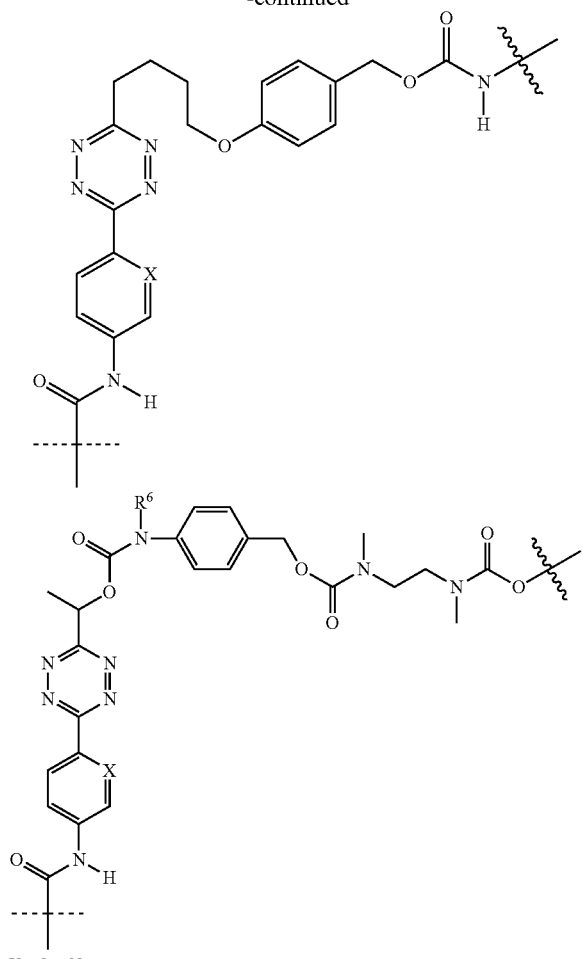

X = C or N

〜〜〜 indicates bond to (remainder of) $C^A$

- - - - indicates bond to (remainder of) $S^P$ or $S^P$-$C^B$ or $C^B$

Activator

The Activator is a dienophile. The person skilled in the art is aware of the wealth of dienophiles that are reactive in the IEDDA reaction. In preferred embodiments the dienophile comprised in the Activator is a cyclic or linear alkene. It is further preferred that the cyclic alkene is a strained alkene such as a trans-cyclooctene (TCO) derivative, a norbornene derivative, a cyclopropene derivative, an acylazetine derivative. In other preferred embodiments, the dienophile comprised in the Activator is a trans-cyclooctene derivative or analog.

Other than is the case with e.g. medicinally active substances, where the in vitro or in vivo action is often changed with minor structural changes, the present invention first and foremost requires the right chemical reactivity combined with sufficient stability for the intended application. Thus, the possible structures extend to those of which the skilled person is familiar with that these are reactive as dienophiles.

TCO-Based Activators

The dienophile Activator moiety used in the present invention comprises a trans-cyclooctene ring, the ring optionally including one or more hetero-atoms. Hereinafter this eight-membered ring moiety will be defined as a trans-cyclooctene moiety, for the sake of legibility, or abbreviated as "TCO" moiety. It will be understood that the essence resides in the possibility of the eight-membered ring to act as a dienophile. The skilled person is familiar with the fact that the dienophile activity is not necessarily dependent on the presence of all carbon atoms in the ring, since also heterocyclic monoalkenylene eight-membered rings are known to possess dienophile activity.

Thus, in general, the invention is not limited to strictly trans-cyclooctene. The person skilled in organic chemistry will be aware that other eight-membered ring-based dienophiles exist, which comprise the same endocyclic double bond as the trans-cyclooctene, but which may have one or more heteroatoms elsewhere in the ring. I.e., the invention generally pertains to eight-membered non-aromatic cyclic alkenylene moieties, preferably a cyclooctene moiety, and more preferably a trans-cyclooctene moiety.

Trans-cyclooctene or E-cyclooctene derivatives are very suitable as Activators, especially considering their high reactivity. Optionally, the trans-cyclooctene (TCO) moiety comprises at least two exocyclic bonds fixed in substantially the same plane, and/or it optionally comprises at least one substituent in the axial position, and not the equatorial position. The person skilled in organic chemistry will understand that the term "fixed in substantially the same plane" refers to bonding theory according to which bonds are normally considered to be fixed in the same plane. Typical examples of such fixations in the same plane include double bonds and strained fused rings. E.g., the at least two exocyclic bonds can be the two bonds of a double bond to an oxygen (i.e. C=O). The at least two exocyclic bonds can also be single bonds on two adjacent carbon atoms, provided that these bonds together are part of a fused ring (i.e. fused to the TCO ring) that assumes a substantially flat structure, therewith fixing said two single bonds in substantially one and the same plane. Examples of the latter include strained rings such as cyclopropyl and cyclobutyl. Without wishing to be bound by theory, the inventors believe that the presence of at least two exocyclic bonds in the same plane will result in an at least partial flattening of the TCO ring, which can lead to higher reactivity in the IEDDA reaction. A background reference providing further guidance is WO 2013/153254.

TCO moieties may consist of multiple isomers, also comprising the equatorial vs. axial positioning of substituents on the TCO. In this respect, reference is made to Whitham et al. *J. Chem. Soc.* (C), 1971, 883-896, describing the synthesis and characterization of the equatorial and axial isomers of trans-cyclo-oct-2-en-ol, identified as (1RS, 2RS) and (1SR, 2RS), respectively. In these isomers the OH substituent is either in the equatorial or axial position. Without wishing to be bound by theory, the inventors believe that the presence of an axial substituent increases the TCO ring strain resulting in higher reactivity in the IEDDA reaction. A background reference providing further guidance is WO 2012/049624.

In this invention, the TCO satisfies the following Formula (4):

Formula 4

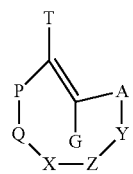

wherein A,Y,Z,X,Q,P each independently are selected from the group consisting of $CR^a_2$, $C=CR^a_2$, $C=O$, $C=S$, $C=NR^b$, S, $S=O$, $SO_2$, O, $NR^b$, and $SiR^c_2$, provided that A and P are not O or S and that $NR^b$, if present in A or P, is part of an amide moiety, with at most three of A,Y,Z,X,Q and P being selected from the group consisting of $C=CR^a_2$, $C=O$, $C=S$, and $C=NR^b$, wherein two or more R moieties together may form a ring or rings, and with the proviso that no sets consisting of adjacent atoms are present selected from the group consisting of O—O, O—$NR^b$, S—$NR^b$, O—S, O—S(O), O—$S(O)_2$, and S—S, and such that Si is only adjacent to $CR^a_2$ or O.

In an interesting embodiment, one of the bonds PQ, QX, XZ, ZY, YA is part of a fused ring or consists of $CR^a=CR^a$, such that two exocyclic bonds are fixed in the same plane; the remaining groups (A,Y,Z,X,Q, P) being independently from each other $CR^a_2$, $C=CR^a_2$, $C=O$, $C=S$, $C=NR^b$, S, SO, $SO_2$, O, $NR^b$, $SiR'_2$, provided that A and P are not O or S and that $NR^b$, if present in A or P, is part of an amide moiety, and such that at most 1 group is $C=CR^a_2$, $C=O$, $C=S$, $C=NR^h$, and no sets consisting of adjacent atoms are present selected from the group consisting of O—O, O—$NR^b$, S—$NR^b$, O—S, O—S(O), O—$S(O)_2$, and S—S, and such that Si, if present, is adjacent to $CR^a_2$ or O, and the $CR^a_2=CR^a_2$ bond, if present, is adjacent to $CR^a_2$ or $C=CR^a_2$ groups. In some embodiments it is preferred that PQ and YA are not part of an aromatic 5- or 6-membered ring, of a conjugated 7-membered ring, or of $CR^a=CR^a$. In some embodiments it is preferred that P and A are $CR^a_2$.

In a preferred embodiment, one of the bonds PQ, QX, XZ, ZY, YA is part of a fused ring or consists of $CR^a=CR^a$, such that two exocyclic bonds are fixed in the same plane; the remaining groups (A,Y,Z,X,Q, P) being $CR^a_2$.

In some embodiments fused rings are present that result in two exocyclic bonds being fixed in substantially the same plane. These are selected from fused 3-membered rings, fused 4-membered rings, fused 5-membered rings, fused bicyclic 7-membered rings, fused aromatic 5-membered rings, fused aromatic 6-membered rings, and fused planar conjugated 7-membered rings as defined below:

Fused 3-membered rings are:

Therein E and G are part of the above mentioned 8-membered ring and can be fused to PQ, QP, QX, XQ, XZ, ZX, ZY, YZ, YA, AY, provided that P and A are $CR^a$ when they are part of the fused 3-membered ring.

E-G is $CR^a$—$CR^a$, and D is $CR^a_2$, $C=O$, $C=S$, $C=NR^b$, $NR^b$, O, S; or E-G is $CR^a$—N, and D is $CR^a_2$, $C=O$, $C=S$, $C=NR^b$, $NR^bO$, or S.

Preferably E-G is $CR^a$—$CR^a$ with Ra is H; and D is $CR^a_2$. It is further preferred that Ra comprised in D is H, (hetero)alkyl, O-alkyl, aryl, O-aryl, OH or $CO_2H$.

Fused 4-membered rings are:

E-G is part of the above mentioned 8-membered ring and can be fused to PQ, QP, QX, XQ, XZ, ZX, ZY, YZ, YA, AY, provided that P and A are C or $CR^a$ when they are part of the fused 4-membered ring.

E and G each independently are $CR^a$ or N, and D and M independently from each other are $CR^a_2$, $C=O$, $C=S$, $C=NR^b$, $C=CR^a_2$, S, SO, $SO_2$, O, $NR^b$ such that no O—O or S—S groups are present; or E-D is $C=CR^a$ and G is N or $CR^a$, and M is $CR^a_2$, S, SO, $SO_2$, O or $NR^b$; or E-D is $C=N$ and G is N or $CR^a$ and M is $CR^a_2$, S, SO, $SO_2$ or O; or D-M is $CR^a=CR^a$ and E and G each independently are $CR^a$ or N; or D-M is $CR^a=N$ and E is $CR^a$ or N, and G is $CR^a$; or E is C, G is $CR^a$ or N, and D and M each independently are $CR^a_2$, S, SO, $SO_2$, O, $NR^b$, or at most one of $C=O$, $C=S$, $C=NR^b$, $C=CR^a_2$, such that no O—O or S—S groups are present; or E and G are C, and D and M independently from each other are $CR^a_2$, S, SO, $SO_2$, O or $NR^b$ such that no O—O or S—S groups are present.

Preferably E and G are $CR^a$, and D and M independently from each other are $CR^a_2$, $C=O$, $C=NR^b$, $C=CR^a_2$, S, SO, $SO_2$, O or $NR^b$ such that no O—O or S—S groups are present. It is further preferred that Ra comprised in E and G is H, and that each Ra comprised in D and M is independently selected from H, (hetero)alkyl, aryl, O-alkyl, O-aryl, OH and $CO_2H$.

Fused 5-membered rings are:

E-G is part of the above mentioned 8-membered ring and can be fused to PQ, QP, QX, XQ, XZ, ZX, ZY, YZ, YA, AY;

E and G are $CR^a$, with $R^a$ preferably being H; L and M are each independently O, S or $NR^b$; K is $CR^a_2$, $C=O$, $C=NR^b$ or $C=CR^a_2$.

Fused bicyclic 7-membered rings are:

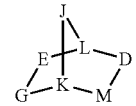

E-G is part of the above mentioned 8-membered ring and can be fused to PQ, QP, QX, XQ, XZ, ZX, ZY, YZ, YA, AY, such that P and A are C or $CR^a$, when they are part of the fused bicyclic 7-membered ring;

E and G are each independently C, $CR^a$ or N; K and L are $CR^a$; D and M form a $CR^a=CR^a$ or $CR^a=N$, or D and M independently from each other are $CR^a_2$, $C=O$, $C=S$, $C=NR^b$, $C=CR^a_2$, S, SO, $SO_2$, O or $NR^b$ such that no O—O, S—S, N—S groups are present; J is $CR^a_2$, $C=O$, $C=S$, $C=NR^b$, $C=CR^a_2$, S, SO, $SO_2$, O or $NR^b$; at most 2 N groups; or E and G are each independently C or $CR^a$; K is N and L is $CR^a$; D and M form a $CR^a=CR^a$ bond or D and M independently from each other are $CR^a_2$, $C=O$, $C=S$, $C=NR^b$, $C=CR^a_2$ or $NR^b$ such that no O—O, S—S, N—S groups are present; J is $CR^a_2$, $C=O$, $C=S$, $C=NR^b$, $C=CR''_2$, S, SO, $SO_2$, O or $NR^b$; at most 2 N groups; or E and G are each independently C or $CR^a$; K and L are N; D, M and J independently from each other are $CR^a_2$, $C=O$, $C=S$, $C=NR'$ or $C=CR^a_2$ groups;

Preferably E, G, K and L are $CR^a$; D and M are $CR^a{}_2$ or form a $CR^a$=$CR^a$; J is $CR^a{}_2$, C=O, C=S, C=$NR^b$, C=$CR^a{}_2$, S, SO, $SO_2$, O or $NR^b$. It is further preferred that $R^a$ is H, (hetero)alkyl, O-alkyl, aryl, O-aryl, OH or $CO_2H$. More preferably $R^a$ is H.

Fused aromatic 5-membered rings are

E and G are part of the above mentioned 8-membered ring and can be fused to PQ, QP, QX, XQ, XZ, ZX, ZY, YZ, YA, AY, such that P and A are C, when they are part of the fused aromatic 5-membered ring;

E and G are C; one of the groups L, K, or M are O, $NR^b$ or S and the remaining two groups are independently from each other $CR^a$ or N; or E is C and G is N and L, K and M are independently from each other $CR^a$ or N.

Fused aromatic 6-membered rings are:

E and G are part of the above-mentioned 8-membered ring and can be fused to PQ, QP, QX, XQ, XZ, ZX, ZY, YZ, YA, AY E and G are C; L, K, D and M are independently from each other $CR^a$ or N.

Fused planar conjugated 7-membered rings are

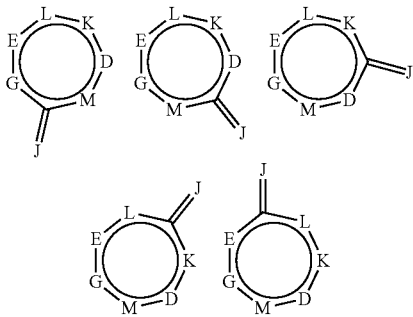

E and G are part of the above-mentioned 8-membered ring and can be fused to PQ, QP, QX, XQ, XZ, ZX, ZY, YZ, YA, AY E and G are C; L, K, D and M are $CR^a$; J is S, O, $CR^a{}_2$ or $NR^b$.

For the avoidance of doubt, this invention conceives of other fused rings in addition to those depicted in the foregoing embodiments. With reference to Formula (4), two or more R moieties together may form a ring or rings.

T, G each independently denotes H, or a substituent selected from the group consisting of alkyl, OR', NR'R', F, Cl, Br, or I, with R' being alkyl or aryl. Preferably, T and G are independently H, $CH_3$, O—$CH_3$, $N(CH_3)_2$. More preferably, T and G are H.

Each $R^a$ as above-indicated can independently be selected from the group consisting of H, (hetero)alkyl, aryl, heterocycle, carbocycle, F, Cl, Br, I, $CF_3$, $CF_2$—R', NO, $NO_2$, $N_3$, OR', SR', CN, NC, C(=O)R', C(=S)R', OC(=O)R", SC(=O)R", OC(=S)R", SC(=S)R", S(=O)R', S(=O)$_2$R", S(=O)$_2$OR', OS(=O)$_2$R", $PO_3R'_2$, $OPO_3R'_2$, Si—R"$_3$, Si—O—R"$_3$, B(OR')$_2$, S(=O)$_2$NR'$_2$, NR'S(=O)$_2$R", C(=O)O—R', C(=O)S—R', C(=S)O—R', C(=S)S—R', C(=O)NR'$_2$, C(=S)NR'$_2$, C(=NR')NR'$_2$, NR'$_2$, NR"$_3{}^+$, NR'C(=O)R', NR'C(=S)R', NR'C(=O)OR', NR'C(=S)OR', NR'C(=O)SR', NR'C(=S)SR', OC(=O)NR'$_2$, SC(=O)NR'$_2$, OC(=S)NR'$_2$, SC(=S)NR'$_2$, CR'$_2$OC(=O)NR'$_2$, CR'$_2$SC(=O)NR'$_2$, CR'$_2$OC(=S)NR'$_2$, CR'$_2$SC(=S)NR'$_2$, NR'C(=O)NR'$_2$, NR'C(=S)NR'$_2$, wherein each R' is independently selected from the group consisting of H, (hetero)alkyl, aryl, carbocycle, heterocycle, and each R" is independently selected from the group consisting of (hetero)alkyl, aryl, carbocycle, heterocycle, wherein all (hetero)alkyl, aryl, carbocycle, heterocycle moieties comprised in $R^a$ can be unsubstituted or substituted, and wherein two R' or R" groups can together form a ring.

Preferably each $R^a$ is independently selected from the group consisting of H, (hetero)alkyl, aryl, heterocycle, carbocycle, F, $CF_3$, OR', CN, C(=O)R', S(=O)$_2$R", S(=O)$_2$OR', $PO_3R'_2$, S(=O)$_2$NR'$_2$, NR'S(=O)$_2$R", C(=O)NR'$_2$, C(=NR')NR'$_2$, NR'$_2$, NR"$_3{}^+$, NR'C(=O)R', NR'C(=O)NR'$_2$, NR'C(=S)NR'$_2$, wherein each R' is independently selected from the group consisting of H, (hetero)alkyl, aryl, carbocycle, heterocycle, and each R" is independently selected from the group consisting of (hetero)alkyl, aryl, carbocycle, heterocycle; more preferably each R" is independently selected from the group consisting of H, OR', $SO_3R'$, F, $CF_3$, $CO_2H$, NR'$_2$, NR"$_3{}^+$, $C_1$-$C_8$ (hetero)alkyl, $C_6$-$C_{12}$ aryl, $C_3$-$C_8$ carbocycle, $C_2$-$C_9$ heterocycle, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, and each R" is independently selected from the group consisting of $C_1$-$C_8$ (hetero)alkyl, $C_6$-$C_{12}$ aryl, $C_3$-$C_8$ carbocycle, $C_2$-$C_9$ heterocycle; even more preferably each $R^a$ is independently selected from the group consisting H, OR', $SO_3R'$, F, $CF_3$, $CO_2H$, NR'$_2$, NR"$_3{}^+$, unsubstituted $C_1$-$C_8$(hetero)alkyl, unsubstituted $C_6$-$C_{12}$ aryl, unsubstituted $C_3$-$C_8$ carbocycle, unsubstituted $C_2$-$C_9$ heterocycle, wherein each R' is independently selected from the group consisting of H, unsubstituted $C_1$-$C_8$ (hetero)alkyl, unsubstituted $C_6$-$C_{12}$ aryl, unsubstituted $C_3$-$C_8$ carbocycle, unsubstituted $C_2$-$C_9$ heterocycle, and each R" is independently selected from the group consisting of unsubstituted $C_1$-$C_8$(hetero)alkyl, unsubstituted $C_6$-$C_{12}$ aryl, unsubstituted $C_3$-$C_8$ carbocycle, unsubstituted $C_2$-$C_9$ heterocycle.

Each $R^b$ is independently selected from the group consisting of H, (hetero)alkyl, aryl, heterocycle, carbocycle, OR', C(=O)R', C(=O)O—R', C(=O)S—R', C(=S)O—R', C(=S)S—R', C(=O)NR'$_2$, C(=S)NR'$_2$, C(=NR')NR'$_2$, NR'$_2$, preferably such that no sets consisting of adjacent atoms are present selected from the group consisting of —N—N—, —N—O—, —N—S—, —N—Si— and —N—P—, and wherein each R' is independently selected from the group consisting of H, (hetero)alkyl, aryl, carbocycle, heterocycle, wherein all (hetero)alkyl, aryl, carbocycle, heterocycle moieties comprised in $R^b$ can be unsubstituted or substituted, and wherein two R' groups can together form a ring.

Preferably, each $R^b$ is independently selected from the group consisting of H, $C_1$-$C_8$ (hetero)alkyl, $C_6$-$C_{12}$ aryl, $C_3$-$C_8$ carbocycle, $C_2$-$C_9$ heterocycle, C(=O)R', C(=O) O—R', C(=O)NR'$_2$, wherein each R' is independently selected from the group consisting of H, $C_1$-$C_8$ (hetero)alkyl, $C_6$-$C_{12}$ aryl, $C_3$-$C_8$ carbocycle, $C_2$-$C_9$ heterocycle; more preferably each $R^b$ is independently selected from the group consisting of H, unsubstituted $C_1$-$C_8$(hetero)alkyl, unsubstituted $C_6$-$C_{12}$ aryl, unsubstituted $C_3$-$C_8$ carbocycle, unsubstituted $C_2$-$C_9$ heterocycle, C(=O)R', C(=O)O—R', C(=O)NR'$_2$, wherein each R' is independently selected from the group consisting of H, unsubstituted $C_1$-$C_8$ (hetero)alkyl, unsubstituted $C_6$-$C_{12}$ aryl, unsubstituted $C_3$-$C_8$ carbocycle, unsubstituted $C_2$-$C_9$ heterocycle; even more preferably each $R^b$ is independently selected from the group consisting of H and unsubstituted $C_1$-$C_3$ alkyl.

Each $R^c$ as above indicated is independently selected from the group consisting of H, alkyl, aryl, O-alkyl, O-aryl, OH;

Two or more $R^{a,b,c}$ moieties together may form a ring; In a preferred embodiment, all the ring members of the TCO of Formula (4) are carbon atoms; preferably, A,Y,Z,X,Q and P are $CR^a_2$; such that at most three $R^a$ moieties are not hydrogen. It is more preferred that at most one $R^a$ moiety is not hydrogen. It is further preferred that at least one of the said $R^a$ moieties not being hydrogen is in the axial position.

In another preferred embodiment, the TCO of Formula (4) is a heterocyclic carbon ring, wherein one or two of Y,Z,X,Q each independently are selected from the group consisting of S, O, $NR^b$, such that no sets consisting of adjacent atoms are present selected from the group consisting of O—O, O—$NR^b$, S—$NR^b$, O—S, and S—S; the remaining groups (A,Y,Z,X,Q, P) being $CR^a_2$, such that at most three $R^a$ moieties are not hydrogen. It is more preferred that at most one $R^a$ moiety is not hydrogen. It is further preferred that at least one of the said $R^a$ moieties not being hydrogen is in the axial position.

In another preferred embodiment, one of the bonds PQ, QX, XZ, ZY, YA is an amide, the remaining groups (A,Y,Z,X,Q, P) being $CR^a_2$, with P and A preferably being $CR^a_2$, such that at most three $R^a$ moieties are not hydrogen. It is more preferred that at most one $R^a$ moiety is not hydrogen.

In all embodiments above it is preferred that if X or Z is $NR^b$ that it is part of an amide moiety.

In the foregoing dienophiles, it is preferred that the at least two exocyclic bonds fixed in the same plane are selected from the group consisting of (a) the single bonds of a fused cyclobutyl ring, (b) the hybridized bonds of a fused aromatic ring, (c) an exocyclic double bond to an oxygen, and (d) an exocyclic double bond to a carbon.

In all embodiments above one $R^{a,b,c}$ moiety may optionally be comprised in a bond to a Targeting agent $T^T$ and/or a Spacer $S^P$, defined below. Alternatively one $R^{a,b,c}$ moiety may optionally be comprised in a bond to a polymer, particle, resin, gel, surface, or a chelator for radiometals (e.g. Cu-64, Ga-68, Tc-99m, In-111, Lu-177).

The following structures are non limiting examples of suitable dienophiles:

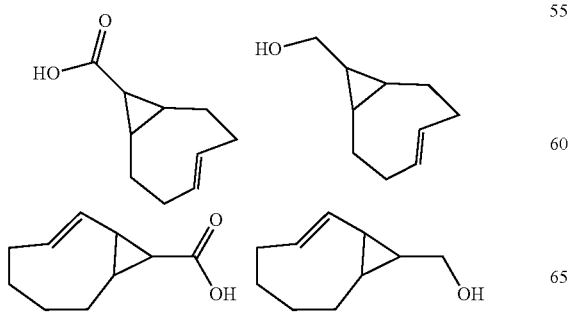

-continued

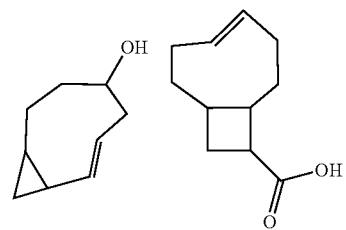

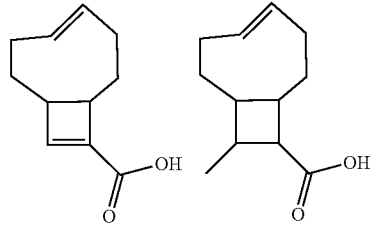

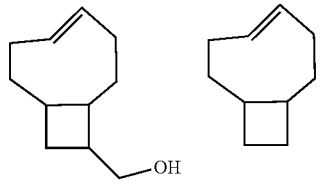

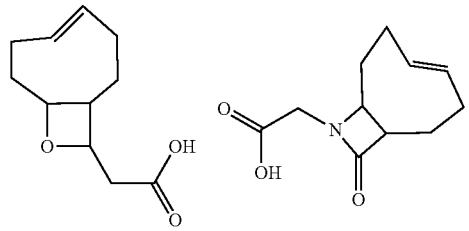

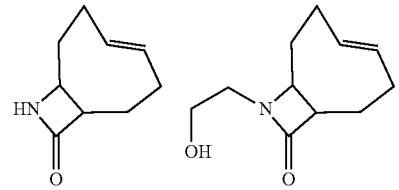

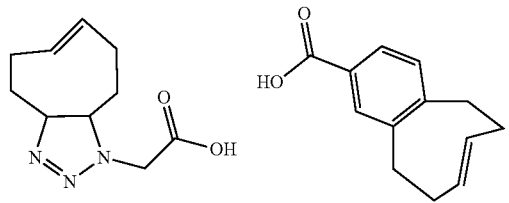

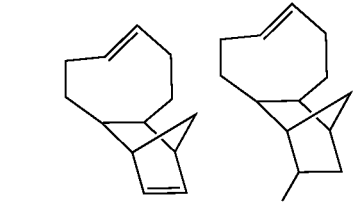

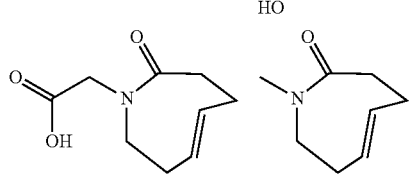

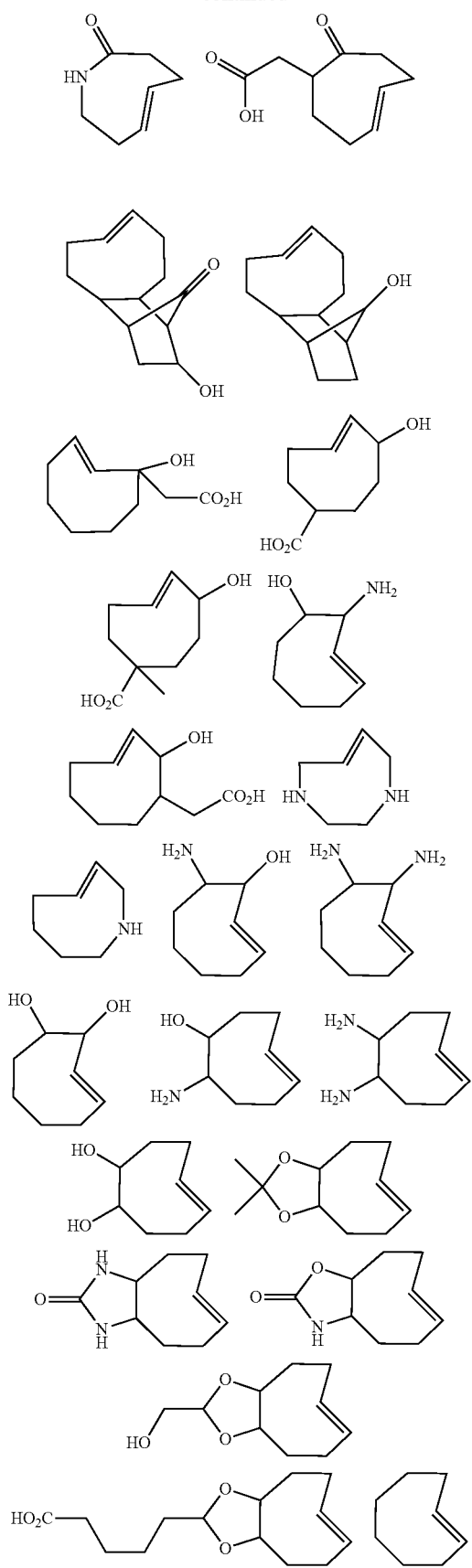
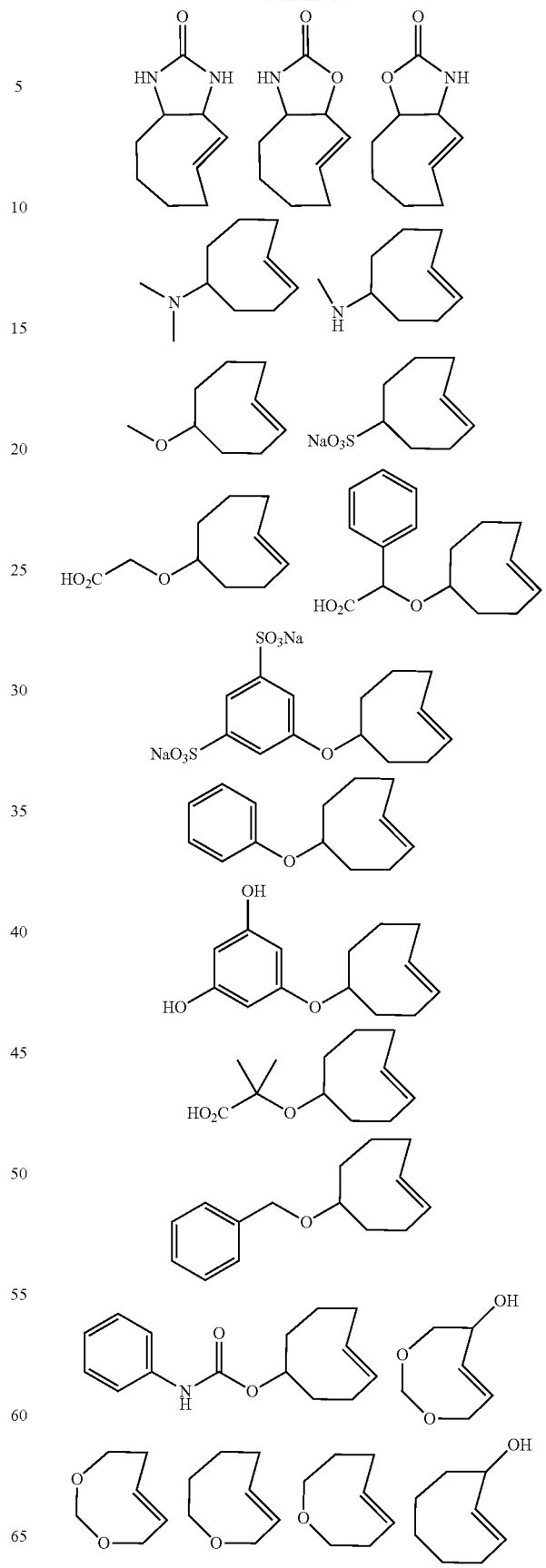

-continued

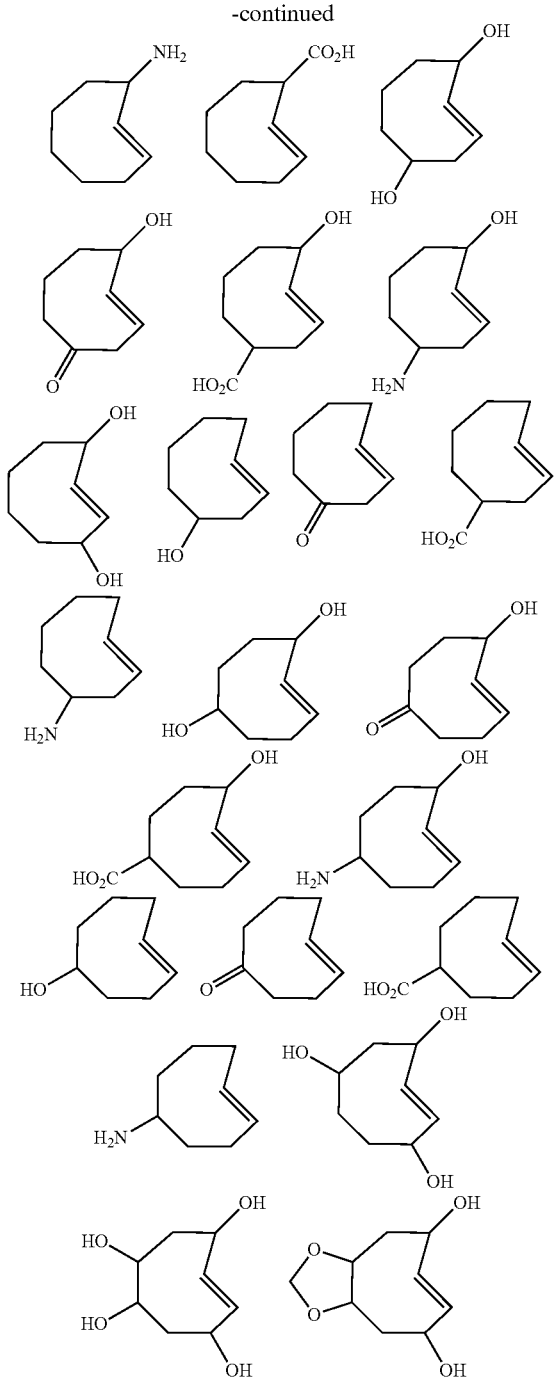

It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dieno-philes according to the present invention, also in the event that substituents would formally require the opposite nomenclature. I.e., the invention relates to cyclooctene in which carbon atoms 1 and 6 as numbered below in Formula 4b are in the E (entgegen) or trans position.

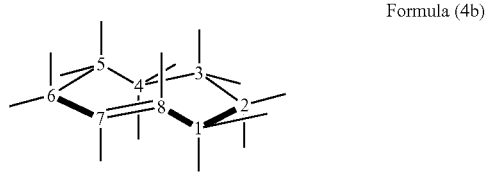

Formula (4b)

The dienophiles for use in the invention can be synthesized by the skilled person, on the basis of known synthesis routes to cyclooctenes and corresponding hetero atom(s)-containing rings. The skilled person further is aware of the wealth of cyclooctene derivatives that can be synthesized via the ring closing metathesis reaction using Grubbs catalysts. As mentioned above, the TCO possibly includes one or more heteroatoms in the ring. This is as such sufficiently accessible to the skilled person. Reference is made, e.g., to the presence of a thioether in TCO: [Cere et al. J. Org. Chem. 1980, 45, 261]. Also, e.g., an —O—SiR$_2$—O moiety in TCO: [Prevost et al. J. Am. Chem. Soc. 2009, 131, 14182]. Suitable starting compounds include the following precursors, indicated below with literature references. Where a cyclooctene derivative is depicted as a Z-cyclooctene it is conceived that this can be converted to the E-cyclooctene analog and that this E-cyclooctene together with those structures already drawn as the E-isomer and their derivatives can be used as Activator in this invention.

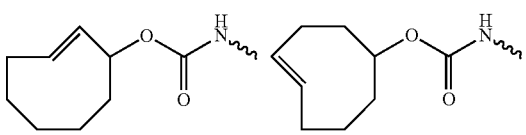

Angrew. Chem. Int. Ed. 2013, 52, 14112

Angrew. Chem. Int. Ed. 2010, 49, 3375

Angrew. Chem. Int. Ed. 2014, 53, 2245

Bioconjug. Chem. 2013, 24, 7, 1210

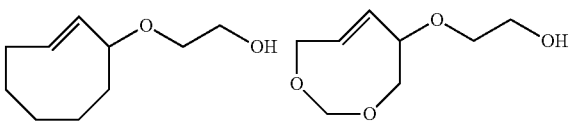

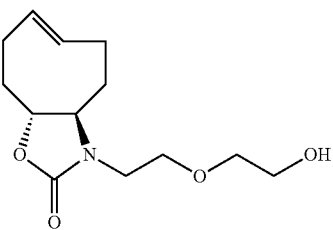

153
-continued
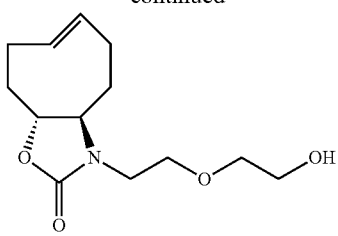
Vargas, Thesis, 2014, Univesity of Budapest
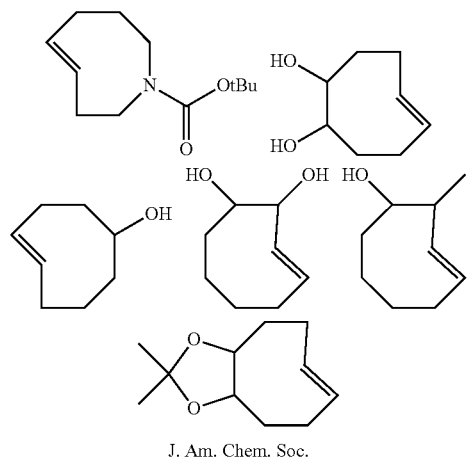
J. Am. Chem. Soc. 2008, 130, 3760
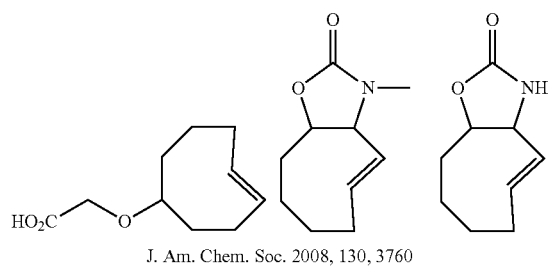
J. Am. Chem. Soc. 2008, 130, 3760
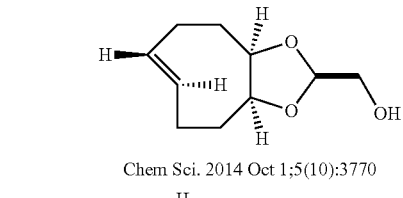
Chem Sci. 2014 Oct 1;5(10):3770
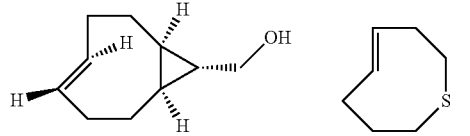
J. Am. Chem. Soc. 2011, 133, 9646    Journal of Organic Chemistry 1980, 45, 261
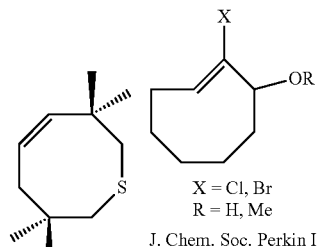
Chem. Ber. 1992, 125, 1431-1437    J. Chem. Soc. Perkin I 1975, 2422
J. Am. Chem. Soc. 1970, 92, 2566
154
-continued
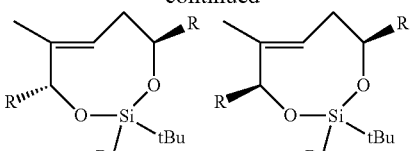
J. Am. Chem. Soc., 2009, 131, 14182
Dalton Trans 2010, 9275
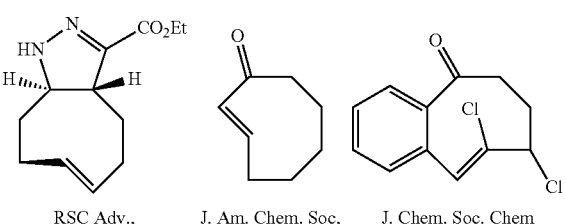
RSC Adv., 2014, 4, 52241    J. Am. Chem. Soc, 1964, 2087    J. Chem. Soc. Chem Comm 1992, 1433
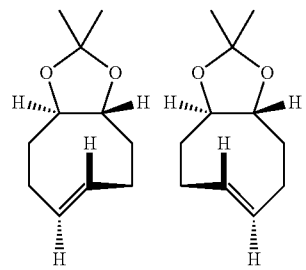
Tetrahedron: Asymmetry 15 (2004) 3123
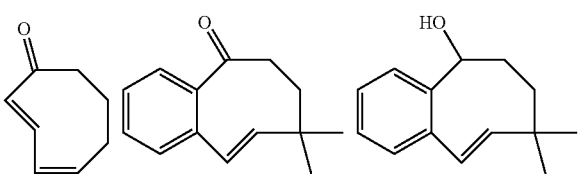
Tetrahedron Lett 1975, 49, 4327
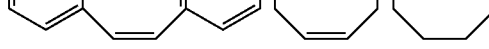
Angrew. Chem. Int. Ed. 2008, 47, 2982
Angrew. Chem. Int. Ed. 2001, 40, 820

-continued

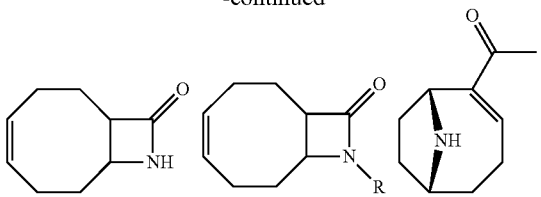

Zuniga, Thesis 2012, University of Salamanca

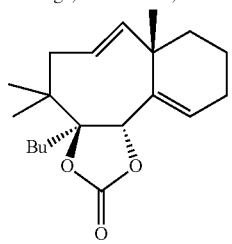 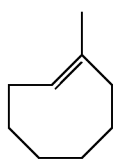

Molecules 2010, 15, 4242-4260    J. Am. Chem. Soc 1992, 114, 3044

∿∿ = rest of molecule

Other Dienophiles

Other dienophiles that are suitable Activators include linear alkenes, organic isonitriles, cyclopropene derivatives, norbornene derivatives, acylazetine derivatives. Several non-limiting examples including literature references regarding their use in a reactions with tetrazines are listed below.

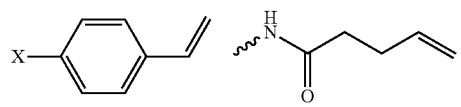

X = MeO, Me, H
J. Org. Chem. 1996, 61, 2001

Angrew. Chem. Int. Ed. 2013, 52, 4265

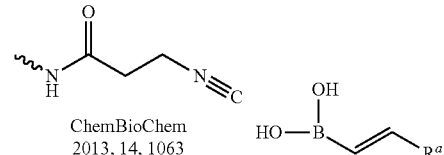

ChemBioChem 2013, 14, 1063

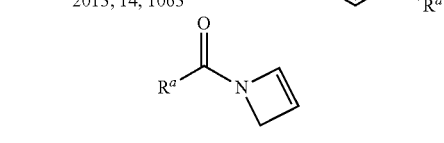

Org. Lett. 2014, 16, 2744

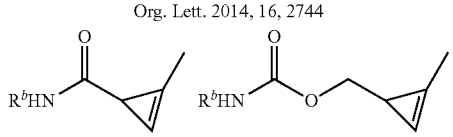

Angrew Chem Int Ed 2012; 5, 7476

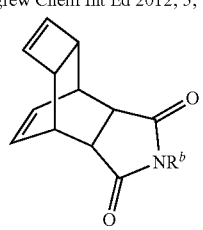

Int. J. Med. Sci. 2010, 7, 19

-continued

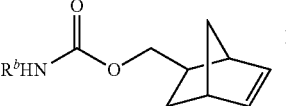

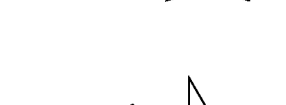

J. Am. Chem Soc. 2010 132, 8846
Angrew. Chem. Int. Ed. 2012, 51, 4166

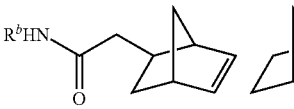

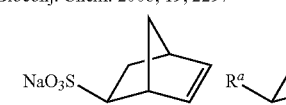

Bioconj. Chem. 2008, 19, 2297

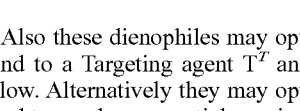

$R^a$ and $R^b$ as defined in Formula 4 for trans-cyclooctenes

Also these dienophiles may optionally be comprised in a bond to a Targeting agent $T^T$ and/or a Spacer $S^P$, defined below. Alternatively they may optionally be comprised in a bond to a polymer, particle, resin, gel, surface, or a chelator for radiometals (e.g. Cu-64, Ga68, Tc-99m, In-111, Lu-177).

Further Considerations Regarding the Activator

In some embodiments, the Trigger-Construct conjugate is comprised in a Prodrug and applied in living systems. In the context of this invention a Prodrug can be a Drug (i.e. Construct A) bound to a Trigger, directly or through a Linker, wherein either the Trigger or the Linker is bound to a Targeting agent (defined herein below). In other embodiments a Prodrug is a Drug (i.e. Construct A or B) bound to a Trigger, directly or through a Linker, wherein either the Trigger or the Linker is bound to a Masking Moiety (defined herein below). In both embodiments the Drug is activated following IEDDA reaction between the Prodrug and the Activator.

In preferred embodiments, the Activator is a TCO and has useful and beneficial pharmacological and pharmacokinetic properties, implying that the Activator is non-toxic or at least sufficiently low in toxicity, produces metabolites that are also sufficiently low in toxicity, is sufficiently soluble in the applicable chemical, biological, or physiological solutions, can be applied in aqueous or other formulations that are routinely used in pharmaceutics, and has the right log D value where this value reflects the hydrophilic/hydrophobic balance of the Activator molecule at physiological pH. Log D values of Activators can be tuned by adding or removing polar or apolar groups in their designs.

The Activator according to the invention has an appropriate reactivity towards the Trigger-Construct conjugate, and this can be regulated by tuning the strain in the dienophile and by tuning the electron-density in the diene and the dienophile.

In some embodiments, the Activator has a good bioavailability, implying that it is available inside the (human)

body for executing its intended purpose: effectively reaching the Trigger-Construct conjugate, e.g. a Prodrug (as defined in the following sections), at the Primary Target. Accordingly, in some embodiments the Activator does not stick significantly to blood components or to tissue that is non-targeted. Alternatively, the Activator may be designed to bind to albumin proteins that are present in the blood, to increase the blood circulation time, increasing reaction time with the Trigger. The blood circulation time of the Activator can also be increased by increasing the molecular weight of the Activator, e.g. by attaching polyethylene glycol (PEG) groups, defined below as Spacer $S^P$, to the Activator ('pegylation'). Alternatively, the PKPD of the Activator may be modulated by conjugating the Activator to another moiety such as a polymer, protein, (short) peptide, carbohydrate, defined below as Spacer $S^P$ and/or Targeting agent $T^T$, to achieve spatial control over the activation. Alternatively, the PKPD of the Activator may be modulated by incorporating it into or onto a liposome, polymersome, micelle, particles, and the like, e.g. to achieve improved pharmacokinetics and target uptake.

The Activator according to the invention may be multimeric, so that multiple dienophile moieties may be attached to a molecular scaffold such as Spacer $S^P$, defined herein, particularly to e.g. multifunctional molecules, carbohydrates, polymers, dendrimers, proteins or peptides, where these scaffolds or Spacers are preferably water soluble. Examples of scaffolds or Spacers $S^P$ that can be used are (multifunctional) polyethylene glycols, poly (propylene imine) (PPI) dendrimers, PAMAM dendrimers, glycol based dendrimers, particles, heparin derivatives, hyaluronic acid derivatives or serum albumin proteins such as HSA. Furthermore, especially for in vitro applications, outlined herein below, the Activator may be conjugated to surfaces, gels, resins, especially solid phase synthesis resins, such as polystyrene, Janda gel and the like.

With respect to application in a cellular environment, such as in vivo, depending on the position of the Trigger-Construct (e.g. inside the cell or outside the cell) the Activator is designed to be able to effectively reach this Trigger-Construct. Therefore, the Activator can for example be tailored by varying its log D value, its reactivity or its charge.

Alternatively, Activators may optionally comprise a membrane translocation moiety (e.g. adamantine, poly-lysine/arginine, TAT, human lactoferrin) to reach an intracellular Prodrug. Exemplary references regarding such moieties include: Trends in Biochemical Sciences, 2015., 40, 12, 749; J. Am. Chem. Soc. 2015, 137, 12153-12160; Pharmaceutical Research, 2007, 24, 11, 1977.

According to the invention, a mixture of different Activators can be applied. This may be relevant for regulation of the release profile of the Construct.

The Activator that according to the invention will cause and regulate drug activation at the Primary Target, in case of applications in Prodrug activation, as explained further below, may additionally be modified with moieties giving extra function(s) to the Activator, either for in-vitro and/or for in-vivo studies or applications. For example, the Activator may be modified with dye moieties or fluorescent moieties, see e.g. [Hilderbrand et al., Bioconjug. Chem., 2008, 19, 2297-2299] for 3-(4-benzylamino)-1,2,4,5-tetrazine that is amidated with the near-infrared (NIR) fluorophore VT680), or they may be functionalized with imaging probes, where these probes may be useful in imaging modalities, such as the nuclear imaging techniques PET or SPECT. In this way, the Activator will not only initiate drug activation, but can also be localized inside the (human) body, and can thus be used to localize the Prodrug inside the (human) body. Consequently, the position and amount of drug release can be monitored. For example, the Activator can be modified with DOTA, DTPA, NOTA, desferal, HYNIC chelates, where these chelates are ideally suited for complexation with radiometals for nuclear imaging. In other examples, the Activator may be linked to $^{123}$I or $^{18}$F moieties, which are well established for use in SPECT or PET imaging, respectively. Furthermore, when used in combination with e.g. beta-emitting isotopes, such as Lu-177, or Y-90, Prodrug activation can be combined with localized radiotherapy in a pretargeted format.

Construct-Trigger

A Construct-Trigger comprises a conjugate of the Construct or Constructs $C^A$ and the Trigger $T^R$. Optionally the Trigger is further linked to Construct or Constructs $C^B$.

The general formula of the Construct-Trigger is shown below in Formula (5a) and (5b). For the avoidance of doubt, as $Y^C$ is part of $L^C$ and $C^A$, $Y^C$ is not separately denoted in Formula (5a) and (5b).

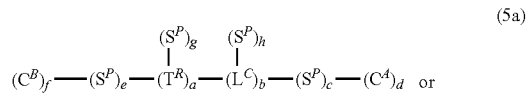

(5a)

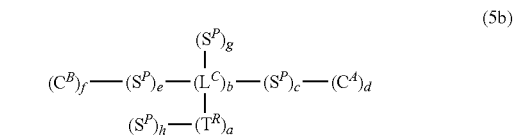

(5b)

$C^A$ is Construct A, $C^B$ is Construct B, $S^P$ is Spacer; $T^R$ is Trigger, and $L^C$ is Linker.

$b,c,e,f,g,h \geq 0; a,d \geq 1.$  Formula (5a):

$c,e,f,g,h \geq 0; a,b,d \geq 1.$  Formula (5b):

In the Trigger-Construct conjugate, the Construct $C^A$ and the Trigger $T^R$—the tetrazine derivative—can be directly linked to each other. They can also be bound to each other via a self-immolative linker $L^C$, which may consist of multiple (self-immolative, or non immolative) units. With reference to Formula 5a and 5b, when $L^C$ contains a non immolative unit, this unit equals a Spacer and $c \geq 1$. It will be understood that the invention encompasses any conceivable manner in which the diene Trigger is attached to the one or more Construct $C^A$. The same holds for the attachment of one or more Construct $C^B$ to the Trigger or the linker $L^C$. The same holds for the optional attachment of one or more Spacer $S^P$ to the Trigger or the linker $L^C$. Methods of affecting conjugation, e.g. through reactive amino acids such as lysine or cysteine in the case of proteins, are known to the skilled person. Exemplary conjugation methods are outlined in the section on Conjugation herein below.

It will be understood that the Construct $C^A$ is linked to the tetrazine in such a way that the Construct $C^A$ is eventually capable of being released after formation of the IEDDA adduct. Generally, this means that the bond between the Construct $C^A$ and the tetrazine, or in the event of a self-immolative Linker $L^C$, the bond between the Linker and the tetrazine and between the Construct $C^A$ and the Linker, should be cleavable. Predominantly, the Construct $C^A$ and the optional Linker is linked via a hetero-atom, preferably via O, N, NH, or S. The cleavable bond is preferably selected from the group consisting of carbamate, thiocarbamate, carbonate, ester, amide, thioester bonds.

It will be understood that Formula (1) describes the Trigger and describes how the Trigger is attached to $C^A$, $C^B$, $L^C$, $S^P$, but that species $C^A$, $C^B$, $L^C$, $S^P$, are not part of the Trigger and should be viewed as separate entities, as can be seen in e.g. Scheme 4 (FIG. 8) and Formula 5.

Spacers $S^P$

Spacers $S^P$ may consist of one or multiple Spacer Units $S^U$ arranged linearly and/or branched and may be connected to one or more $C^B$ moieties and/or one or more $L^C$ or $T^R$ moieties. The Spacer may be used to connect $C^B$ to one $T^R$ (Example A below; with reference to Formula 5a and 5b: f, e, a=1) or more $T^R$ (Example B and C below; with reference to Formula 5a and 5b: f, e=1, a≥1), but it can also be used to modulate the properties, e.g. pharmacokinetic properties, of the $C^B$-$T^R$-$C^A$ conjugate (Example D below; with reference to Formula 5a and 5b: one or more of c,e,g,h≥1). Thus a Spacer does not necessarily connect two entities together, it may also be bound to only one component, e.g. the $T^R$ or $L^C$. Alternatively, the Spacer may comprise a Spacer Unit linking $C^B$ to $T^R$ and in addition may comprise another Spacer Unit that is only bound to the Spacer and serves to modulate the properties of the conjugate (Example F below; with reference to Formula 5a and 5b: e≥1). The Spacer may also consist of two different types of $S^U$ constructs, e.g. a PEG linked to a peptide, or a PEG linked to an alkylene moiety (Example E below; with reference to Formula 5a and 5b: e≥1). For the sake of clarity, Example B depicts a $S^U$ that is branched by using a multivalent branched Su. Example C depicts a $S^U$ that is branched by using a linear Su polymer, such as a peptide, whose side chain residues serve as conjugation groups.

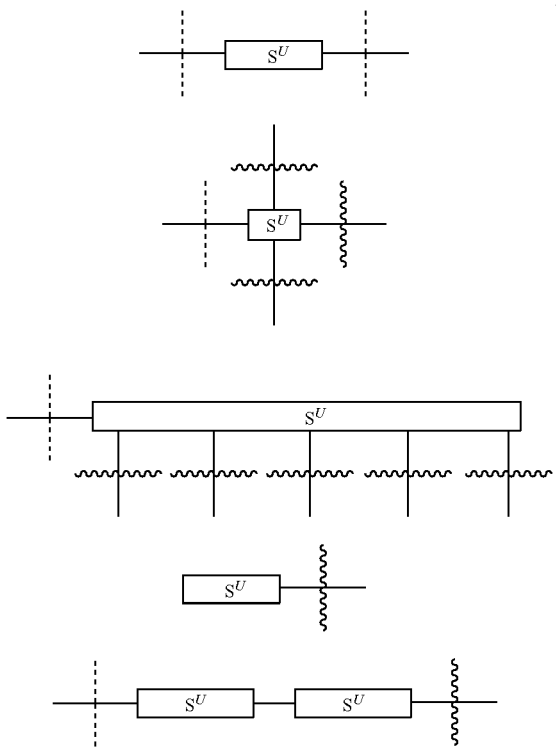

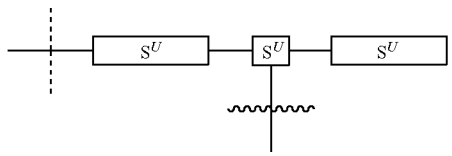

∼∼∼ indicates bond to $T^R$ or $L^C$ or (remainder of) $S^P$

---- indicates bond to (remainder of) $C^B$

The Spacer may be bound to the Activator in similar designs such as depicted in above examples A-F.

The Spacer Units include but are not limited to amino acids, nucleosides, nucleotides, and biopolymer fragments, such as oligo- or polypeptides, oligo- or polypeptoids, or oligo- or polylactides, or oligo- or poly-carbohydrates, varying from 2 to 200, particularly 2 to 113, preferably 2 to 50, more preferably 2 to 24 and more preferably 2 to 12 repeating units. Exemplary preferred biopolymer $S^U$ are peptides.

Yet other examples are alkyl, alkylene, alkenyl, alkenylene, alkynyl, alkynylene, cycloalkyl, cycloalkylene, cycloalkenyl, cycloalkenylene, cycloalkynyl, cycloalkynylene, aryl, arylene, alkylaryl, alkylarylene, arylalkyl, arylalkylene, arylalkenyl, arylalkenylene, arylalkynyl, arylalkynylene, polyethyleneamino, polyamine, which may be substituted or unsubstituted, linear or branched, may contain further cyclic moieties and/or heteroatoms, preferably O, N, and S, more preferably O; wherein in some embodiments these example $S^U$ comprise at most 50 carbon atoms, more preferably at most 25 carbon atoms, more preferably at most 10 carbon atoms. In some embodiments the $S^U$ is independently selected from the group $Q^1$ consisting of $(CH_2)_r$, $(C_3$-$C_8$ carbocyclo), O—$(CH_2)_r$, arylene, $(CH_2)_r$-arylene, arylene-$(CH_2)_r$, $(CH_2)_r$—$(C_3$-$C_8$ carbocyclo), $(C_3$-$C_8$ carbocyclo)-$(CH_2)_r$, $(C_3$-$C_8$ heterocyclo, $(CH_2)_r$—$(C_3$-$C_8$ heterocyclo), $(C_3$-$C_8$ heterocyclo)-$(CH_2)_r$, —$(CH_2)_r$C(O)NR$^4$ $(CH_2)_r$, $(CH_2CH_2O)_r$, $(CH_2CH_2O)_rCH_2$, $(CH_2)_rC(O)NR^4$ $(CH_2CH_2O)_r$, $(CH_2)_rC(O)NR^4(CH_2CH_2O)_rCH_2$, $(CH_2CH_2O)_r$ C(O)NR$^4$(CH$_2$CH$_2$O)$_r$, $(CH_2CH_2O)_r$ C(O) NR$^4$(CH$_2$CH$_2$O)$_r$CH$_2$, $(CH_2CH_2O)_r$C(O)NR$^4$CH$_2$; wherein r is independently an integer from 1-10, and R$^4$ is as defined in Formula (1).

Other examples of Spacer Units $S^U$ are linear or branched polyalkylene glycols such as polyethylene glycol (PEG) or polypropylene glycol (PPG) chains varying from 2 to 200, particularly 2 to 113, preferably 2 to 50, more preferably 2 to 24 and more preferably 2 to 12 repeating units. It is preferred that when polyalkylene glycols such as PEG and PPG polymers are only bound via one end of the polymer chain, that the other end is terminated with —OCH$_3$, —OCH$_2$CH$_3$, OCH$_2$CH$_2$CO$_2$H.

Other polymeric Spacer Units are polymers and copolymers such as poly(N-(2-hydroxypropyl)methacrylamide) (HPMA), polylactic acid (PLA), polylactic-glycolic acid (PLGA), polyglutamic acid (PG), dextran, polyvinylpyrrolidone (PVP), poly(1-hydroxymethylethylene hydroxymethyl-formal (PHF). Other exemplary polymers are polysaccharides, glycopolysaccharides, glycolipids, polyglycoside, polyacetals, polyketals, polyamides, polyethers, polyesters. Examples of naturally occurring polysaccharides that can be used as SU are cellulose, amylose, dextran, dextrin, levan, fucoidan, carraginan, inulin, pectin, amylopectin, glycogen, lixenan, agarose, hyaluronan, chondroitinsulfate, dermatansulfate, keratansulfate, alginic acid and heparin. In yet other exemplary embodiments, the polymeric $S^U$ comprises a copolymer of a polyacetal/polyketal and a hydrophilic polymer selected from the group consisting of polyacrylates, polyvinyl polymers, polyesters, polyorthoesters, polyamides, oligopeptides, polypeptides and derivatives thereof. Exemplary preferred polymeric $S^U$ are PEG, HPMA, PLA, PLGA, PVP, PHF, dextran, oligopeptides, and polypeptides.

In some aspects of the invention polymers used in a $S^U$ have a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa.

Other exemplary $S^U$ are dendrimers, such as poly(propylene imine) (PPI) dendrimers, PAMAM dendrimers, and glycol based dendrimers.

The $S^U$ of the invention expressly include but are not limited to conjugates prepared with commercially available cross-linker reagents such as BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB, DTME, BMB, BMDB, BMH, BMOE, BM(PEO)$_3$ and BM(PEO)$_4$.

To construct a branching Spacer one may use a $S^U$ based on one or several natural or non-natural amino acids, amino alcohol, aminoaldehyde, or polyamine residues or combinations thereof that collectively provide the required functionality for branching. For example serine has three functional groups, i.e. acid, amino and hydroxyl groups and may be viewed as a combined amino acid an aminoalcohol residue for purpose of acting as a branching SU. Other exemplary amino acids are lysine and tyrosine.

In some embodiments, the Spacer consist of one Spacer Unit, therefore in those cases $S^P$ equals $S^U$. In other embodiments the Spacer consist of two, three or four Spacer Units.

In some aspects of the $S^P$ has a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa. In some aspects of the invention, the $S^P$ has a mass of no more than 5000 daltons, no more than 4000 daltons, no more than 3000 daltons, no more than 2000 daltons, no more than 1000 daltons, no more than 800 daltons, no more than 500 daltons, no more than 300 daltons, no more than 200 daltons. In some aspects the $S^P$ has a mass from 100 daltons, from 200 daltons, from 300 daltons to 5000 daltons. In some aspects of the $S^P$ has a mass from 30, 50, or 100 daltons to 1000 daltons, from about 30, 50, or 100 daltons to 500 daltons.

Conjugation

Spacers and ways of linking them to for example an $C^A$, $C^B$, $T^R$, $L^C$ or an Activator, as well as methods of linking $C^B$ to $T^R$ or $L^C$, are well known in the art. In addition, methods to site specifically conjugate unto a protein $C^B$, for example through genetic incorporation of an artificial amino acid followed by bioorthogonal conjugation with that amino acid, are well known in the art. For example reference is made to the following references, the contents of which are hereby incorporated by reference: PCT patent applications WO2015095755A1, WO2015195925A1, WO2015057066A1; and to the reviews Int. J. Mol. Sci. 2016, 17, 194; mAbs 2014, 6, 1, 34-45; mAbs 2014, 6, 1, 46-53; Bioconjug. Chem. 2015, 26, 176-192; Eur. Polym. J. 2013, 49, 2906-2918; Prog. Polym. Sci. 2007, 32, 933-961; ChemMedChem 2011, 6, 963-974; Chem. Rev. 2015, 115, 2174-2195; Pharm. Res., 2015, DOI 10.1007/s11095-015-1657-7; J. Med. Chem. 2011, 54, 10, 3606-23.

For example, to achieve conjugation among $C^B$, $S^P$, $T^R$ or $L^C$, or between a $S^P$ or a $T^T$ (defined below) and an Activator, use can be made of conjugation moieties $M^C$, wherein the moieties $M^C$ are part of the $C^B$, $C^A$, $S^P$, $T^R$, $L^C$, $T^T$, $M^M$ (defined below) and the Activator. For example, conjugation moieties $M^C$ can be used for the conjugation of the Spacer $S^P$, Trigger $T^R$ or Linker $L^C$ to Construct B. The conjugation moieties can also be comprised in $S^P$ and $T^R$ to conjugate them to one another. Likewise the conjugation moieties can be comprised in $S^P$ or TT and the Activator to conjugate them to one another. As such, in some embodiments, the conjugation moieties $M^C$ can equal an R group as defined for Formulae 1-4. A person skilled in the art will understand that there are many ways to achieve covalent attachment of $S^P$, $T^R$, $L^C$ and $C^B$ to one another, and likewise attachment of Activator to $T^T$ or $S^P$, including C—C bond formation reactions, C—O bond formation reactions, C—N bond formation reactions, C—S bond formation reactions, S—S bond formation reactions, and the like. Typical conjugation bonds include but are not limited to amides, carbamates, esters, ethers, thioethers, urea. For the avoidance of doubt, the Conjugation moieties $M^C$ are not explicitly depicted in Formulae 1-4, 5a-b, 6a-d, 7a-d, 8a-c but it shall be understood that these Conjugation moieties $M^C$ are comprised in these Formulae because the $M^C$ moieties are comprised in $C^B$, $C^A$, $S^P$, $T^R$, $L^C$, $T^T$, $M^M$.

Typical $M^C$ groups that can be used or introduced and used in e.g. $C^B$, $S^P$, $T^R$, $L^C$ $T^T$, $M^M$, $C^A$ and the Activator, include but are not limited to azido groups, keto groups, aldehyde groups, alkynyl groups such as (hetero)cycloalkynyl group and terminal alkynyl groups, thiols, hydroxy groups, halogens, sulfonyloxy groups, N-maleimide groups, halogenated acetamido groups, mercaptoacetamido groups, sulfonylated hydroxyacetamido groups, amino groups such as primary amines or secondary amines, aminooxy groups, hydrazyl groups, carboxylic acids and their activated esters such as N-hydroxysuccinimide ester and para-nitrophenyl ester, vinyl pyridine, disulfide, pyridyl disulfide, isocyanate, isothiocyanate, sulfonyloxy, mercaptoacetamide, anhydrides, acid chlorides, sulfonyl chlorides, nitrone and nitrile oxide derivatives.

Typical groups that can be introduced and/or used as a $M^C$ in protein-based $C^B$ such as antibodies, include but are not limited to azido groups, aldehyde groups, keto groups, amino groups, alkynyl groups, disulfides, thiols, halogen groups, sulfonyloxy groups, halogenated acetamido groups, mercaptoacetamido groups, sulfonylated hydroxyacetamido groups.

Preferred moieties used to react and bind with an azido group are alkynyl groups, preferably terminal alkynyl groups and (hetero)cycloalkynyl groups.

Preferred moieties used to react and bind with a keto or aldehyde group are amines, aminooxy groups, e.g. —O—NH$_2$, and hydrazinyl groups, e.g. —N(H)NH$_2$—.

Preferred moieties used to react and bind with an alkynyl derivative include but are not limited to azide, nitrone and nitrile oxide derivatives.

Groups reactive with a thiol moiety include but are not limited to maleimide, iodoacetamide, bromoacetamide, vinyl pyridine, disulfide, pyridyl disulfide, isocyanate, isothiocyanate, sulfonyloxy, mercaptoacetamide, a terminal alkene.

Groups reactive towards amines include but are not limited to activated esters, e.g. NHS esters or 4-nitrophenyl esters, anhydrides, acid chlorides, sulfonyl chlorides, isocyanates and isothiocyanates.

In some aspects the $M^C$ is an electrophilic group that is capable of interacting with a reactive nucleophilic group present on another $M^C$ to provide a covalent bond. Nucleophilic groups include but are not limited to sulfhydryl, hydroxyl, and amino functional groups. Useful electrophilic groups include but are not limited to maleimide groups, haloacetamide groups and NHS esters.

In other aspect the $M^C$ is a nucleophilic group reactive towards an electrophilic group on another $M^C$. Useful electrophilic groups include but are not limited to aldehyde and ketone carbonyl groups. Useful corresponding nucleophilic groups include but are not limited to hydrazide, hydroxylamine, amino, hydrazine, thiosemicarbazone, hydrazine carboxylate and arylhydrazide.

In some embodiments a sulfur atom of a $M^C$ is bound to a succinimide ring system of another $M^C$ by reaction of a thiol functional group with a maleimide moiety. In other embodiments a thiol functional group reacts with an alpha haloacetamide moiety to provide a sulfur-bonded conjugate by nucleophilic displacement of its halogen substituent.

The following scheme depicts non-limiting examples of conjugates of $C^B$ with $S^P$ and/or $T^R$ and/or $L^C$.

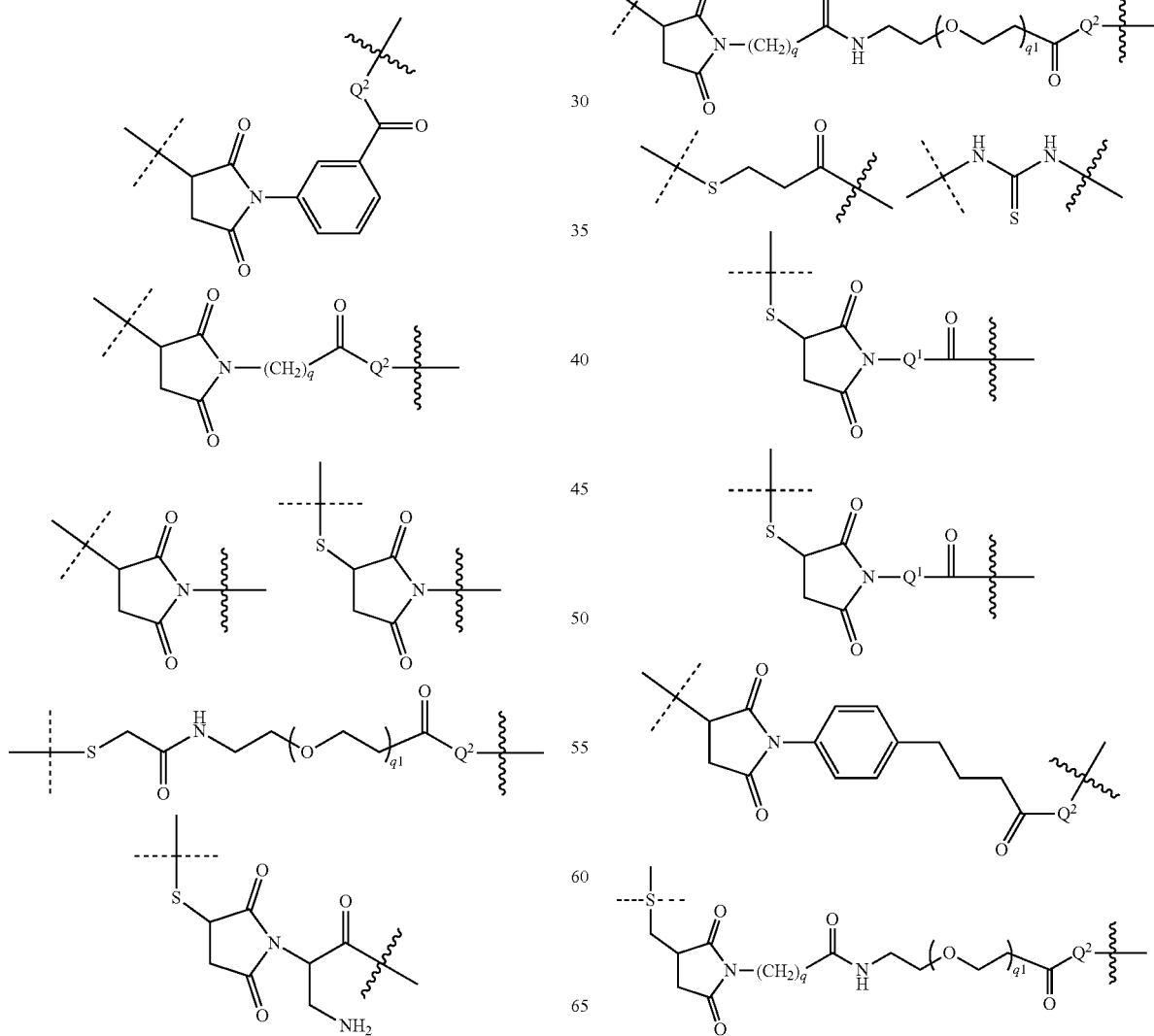

-continued

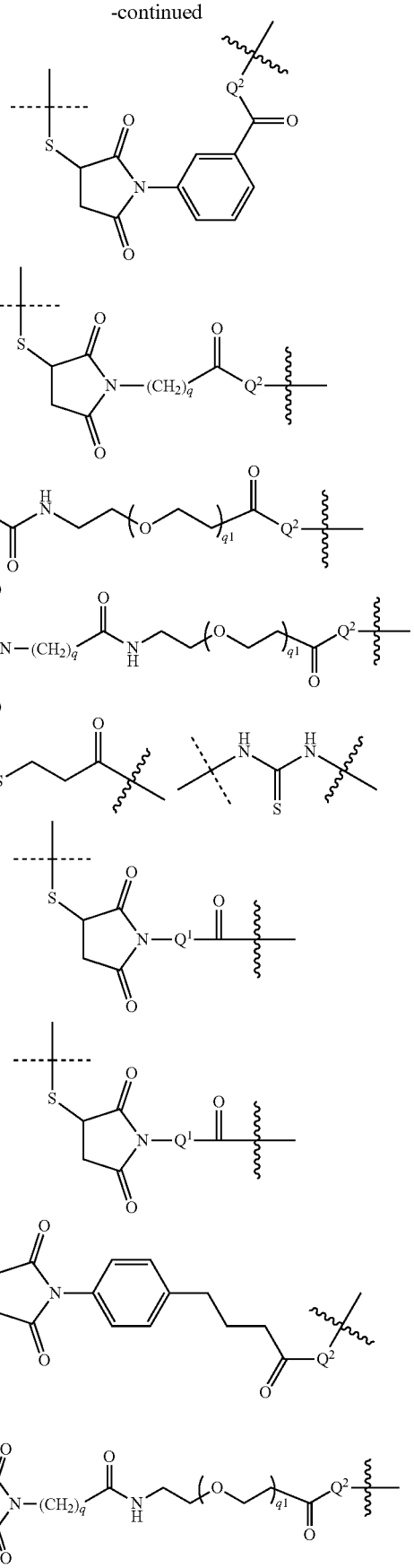

165
-continued
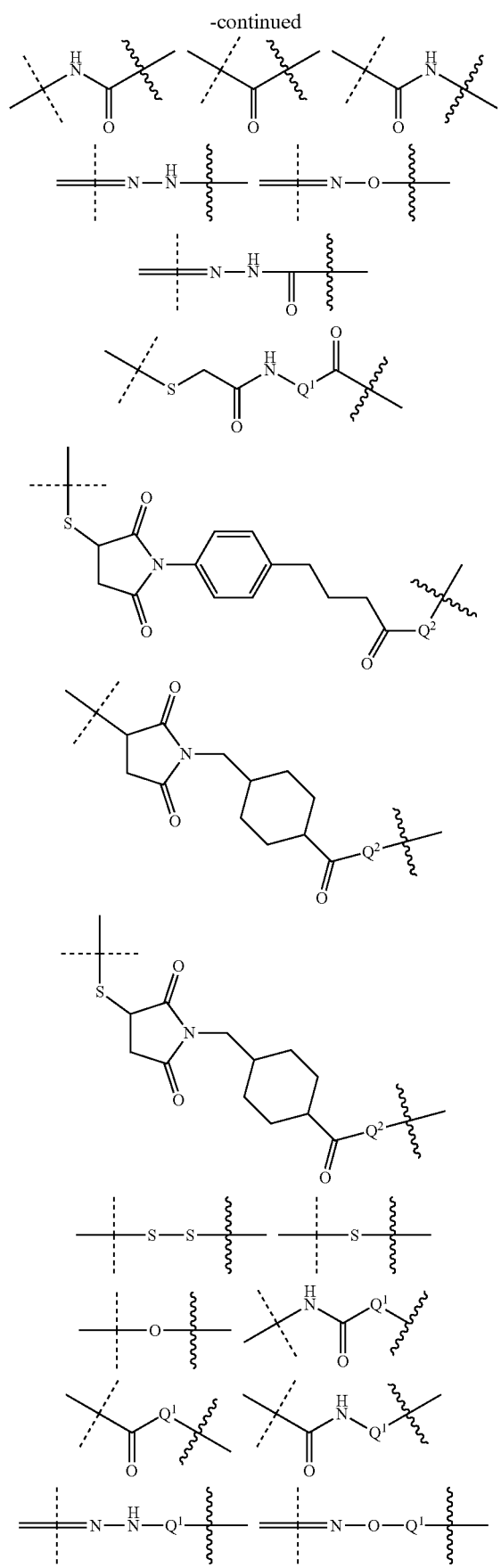
166
-continued
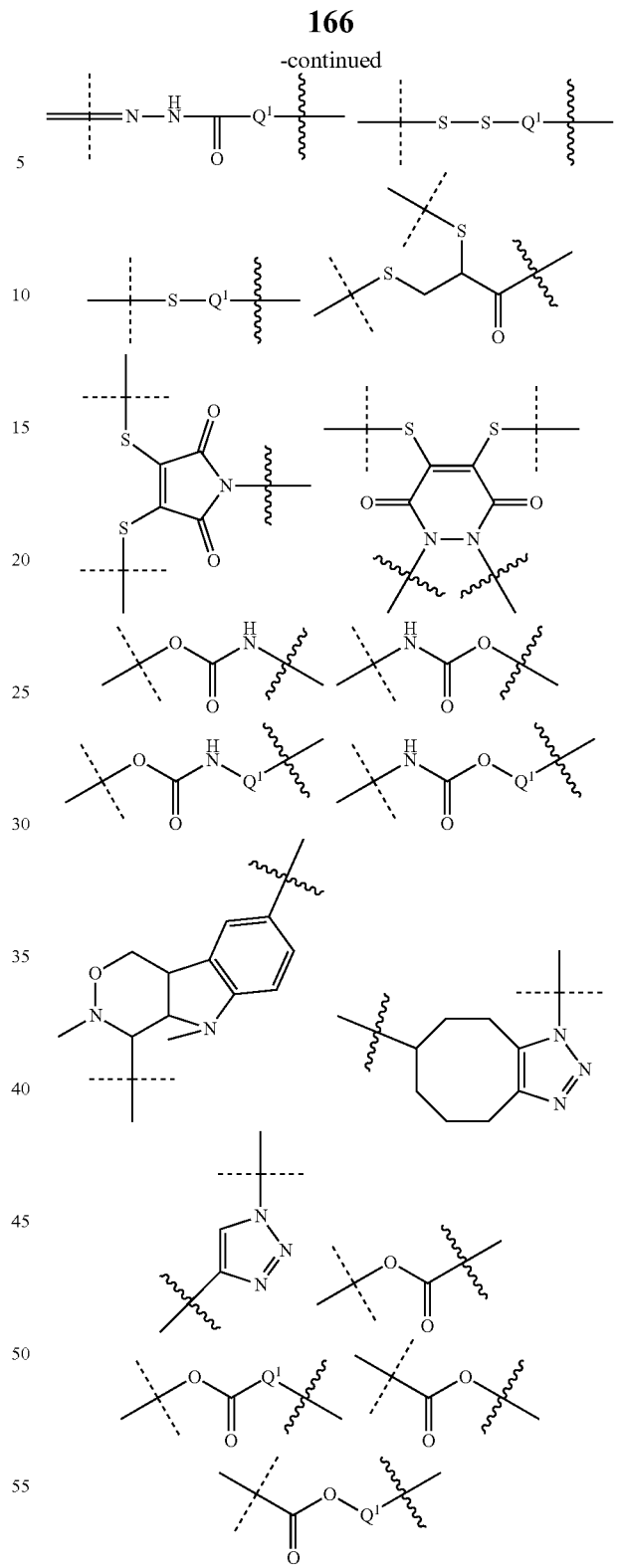
∿∿ indicates bond to (remainder of) $S^P$, $T^R$ or $L^C$
---- indicates bond to (remainder of) $C^B$
Wherein each Q are as defined above; wherein each $Q^2$ is independently NH or O and each q is independently an integer from 1 to 10, preferably 1 to 5, and q1 is independently an integer from 1 to 50, preferably 1 to 24, more preferably 1-12.

The following scheme depicts examples of branching Spacers.
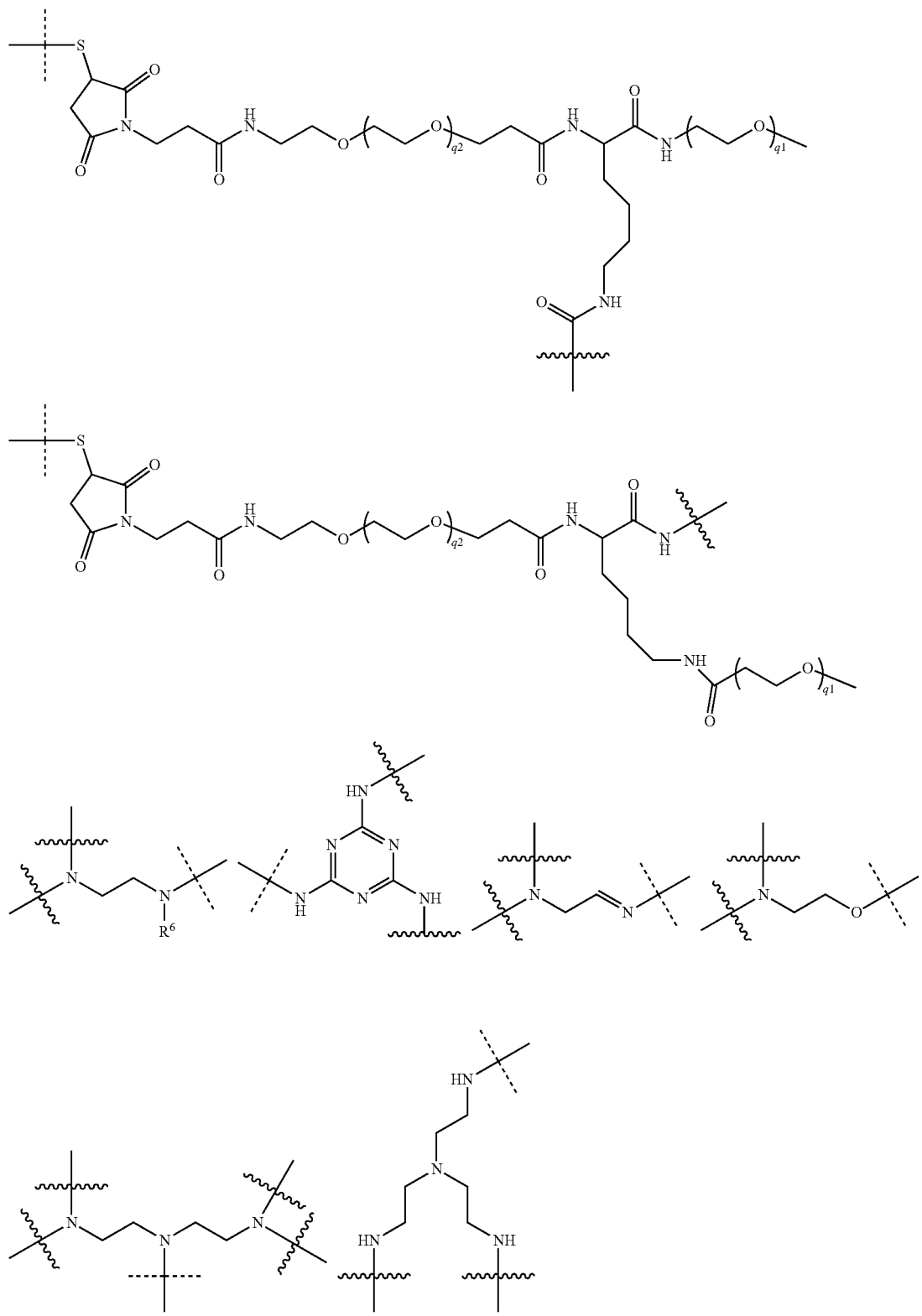
ᔕᔕᔕ indicates bond to (remainder of) $S^P$, $T^R$ or $L^C$
---- indicates bond to (remainder of) $C^B$ wherein q2 is independently an integer from 1 to 50; in some embodiments q2 preferably is 1 to 24; in other embodiments q2 preferably is 1-12; in yet other embodiments q2 preferably is 1 to 6. Wherein q1 is independently an integer from 1 to 50, preferably 1 to 24, more preferably 1-12.

Examples of Spacers comprising a $M^C$ for conjugation to $C^B$ are shown in the following scheme.

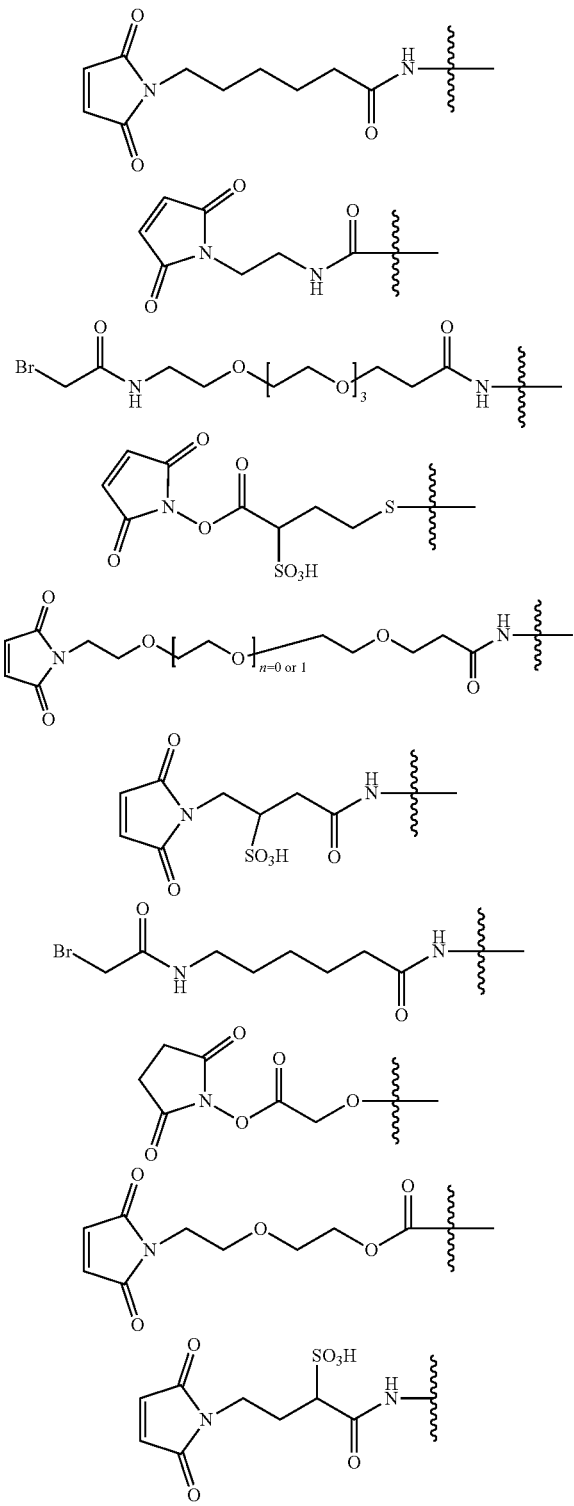

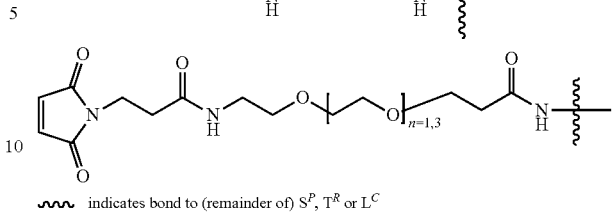

ᨏᨏᨏ indicates bond to (remainder of) $S^P$, $T^R$ or $L^C$

Use of Tetrazine as a Carrier

The invention also pertains to the use of a tetrazine satisfying Formula (1) as a carrier for a therapeutic compound. The tetrazine is to be read as a tetrazine in a broad sense, as discussed above. A therapeutic compound is a drug or other compound or moiety intended to have therapeutic application. The use of tetrazine as a carrier according to this aspect of the invention does not relate to the therapeutic activity of the therapeutic compound. In fact, also if the therapeutic compound is a drug substance intended to be developed as a drug, many of which will fail in practice, the application of tetrazine as a carrier still is useful in testing the drug. In this sense, the tetrazine in its capacity of a carrier is to be regarded in the same manner as a pharmaceutical excipient, serving as a carrier when introducing a drug into a subject.

The use of a tetrazine as a carrier has the benefit that it enables the administration, to a subject, of a drug carried by a moiety that is open to a bio-orthogonal reaction, with a dienophile, particularly a trans-cyclooctene. This provides a powerful tool not only to affect the fate of the drug carried into the body, but also to follow its fate (e.g. by allowing a labeled dienophile to react with it), or to change its fate (e.g. by allowing pK modifying agents to bind with it). This is all based on the possibility to let a dienophile react with the tetrazine in the above-discussed IEDDA reaction. The carrier is preferably reacted with an Activator as discussed herein, so as to provoke the release of the therapeutic compound from the tetrazine, as amply discussed herein.

Targeting

In some embodiments, the kits and method of the invention are very suitable for use in targeted therapy, e.g. Prodrug therapy. A "Primary Target" as used in the present invention relates to a target for a targeting agent for therapy. For example, a Primary Target can be any molecule, which is present in an organism, tissue or cell. Targets include cell surface targets, e.g. receptors, glycoproteins, glycans, carbohydrates; structural proteins, e.g. amyloid plaques; abundant extracellular targets such as in stroma, extracellular matrix targets such as growth factors, and proteases; intracellular targets, e.g. surfaces of Golgi bodies, surfaces of mitochondria, RNA, DNA, enzymes, components of cell signaling pathways; and/or foreign bodies, e.g. pathogens such as viruses, bacteria, fungi, yeast or parts thereof. Examples of Primary Targets include compounds such as proteins of which the presence or expression level is correlated with a certain tissue or cell type or of which the expression level is up-regulated or down-regulated in a certain disorder. According to a particular embodiment of the present invention, the Primary Target is a protein such as a (internalizing or non-internalizing) receptor.

According to the present invention, the Primary Target can be selected from any suitable targets within the human or animal body or on a pathogen or parasite, examples include but are not limited to a group comprising cellular components such as cell membranes and cell walls, receptors such as cell membrane receptors, intracellular structures such as Golgi bodies or mitochondria, enzymes, receptors, DNA, RNA, viruses or viral particles, macrophages, tumor-associated macrophages, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-)angiogenesis marker, gastrin receptor, dopaminergic system, serotonergic system, GABAergic system, adrenergic system, cholinergic system, opioid receptors, GPIIb/IIIa receptor and other thrombus related receptors, fibrin, calcitonin receptor, tuftsin receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase, integrin receptor, fibronectin targets, AOC3, ALK, AXL, C242, CA-125, CCL11, CCR5, CD2, CD3, CD4, CD5, CD15, CA15-3, CD18, CD19, CA19-9, CD20, CD21, CD22, CD23, CD25, CD28, CD30, CD31, CD33, CD37, CD38, CD40, CD41, CD44v6, CD45, CD51, CD52, CD54, CD56, CD62E, CD62P, CD62L, CD70, CD72, CD74, CD79-B, CD80, CD105, CD125, CD138, CD141, CD147, CD152, CD154, CD174, CD227, CD326, CD340, VEGF/EGF and VEGF/EGF receptors, VEGF-A, VEGFR2, VEGFR1, TAG72, CEA, MUC1, MUC16, GPNMB, PSMA, Cripto, Tenascin C, Melanocortin-1 receptor, G250, HLA DR, ED-B, TMEFF2, EphB2, EphB4, EphA2, FAP, Mesothelin, GD2, GD3, CAIX, 5T4, clumping factor, CTLA-4, CXCR2, FGFR1, FGFR2, FGFR3, FGFR4, HER2, NaPi2b, NOTCH1, NOTCH2, NOTCH3, NOTCH4, ErbB2, ErbB3, EpCAM, FLT3, HGF, HER2, HER3, HM124, ICAM, ICOS-L, IGF-1 receptor, TRPVI, CFTR, gdNMB, CA9, c-KIT, c-MET, ACE, APP, adrenergic receptor beta2, Claudine 3, RON, ROR1, PD-L1, PD-L2, B7-H3, B7-H4, IL-2 receptor, IL-4 receptor, IL-13 receptor, integrins, IFN-alpha, IFN-gamma, IgE, IGF-1 receptor, IL-1, IL-4, IL-5, IL-6, IL-12, IL-13, IL-22, IL-23, interferon receptor, ITGB2 (CD18), LFA-1 (CD11a), L-selectin, P-selectin, E-selectin, mucin, myostatin, NCA-90, NGF, PDGFR alpha, prostatic carcinoma cells, *Pseudomonas aeruginosa*, rabies, RANKL, respiratory syncytial virus, Rhesus factor, SLAMF7, sphingosine-1-phosphate, TGF-1, TGFbeta2, TGFbeta, TNFalpha, TRAIL-R1, TRAIL-R2, CTAA16.88, vimentin, matrix metalloproteinases (MMP) such as MMP2, MMP9, MMP14, LDL receptor, endoglins, polysialic acids and their corresponding lectins.

An example of fibronectin targets are the alternatively spliced extra-domain-A (ED-A) and extra-domain-B (ED-B) of fibronectin. Non-limiting examples of targets in stroma can be found in V. Hofmeister, D. Schrama, J. C. Becker, *Cancer Immun. Immunother.* 2008, 57, 1, the contents of which are hereby incorporated by reference.

Targeting Agents $T^T$

A Targeting Agent, $T^T$, binds to a Primary Target. In order to allow specific targeting of the above-listed Primary Targets, the Targeting Agent $T^T$ can comprise compounds including but not limited to antibodies, antibody derivatives, antibody fragments, antibody (fragment) fusions (e.g. bi-specific and tri-specific mAb fragments or derivatives), proteins, peptides, e.g. octreotide and derivatives, VIP, MSH, LHRH, chemotactic peptides, bombesin, elastin, peptide mimetics, carbohydrates, monosaccharides, polysaccharides, oligonucleotides, aptamers, viruses, whole cells, phage, drugs, polymers, liposomes, chemotherapeutic agents, receptor agonists and antagonists, cytokines, hormones, steroids, toxins. Examples of organic compounds envisaged within the context of the present invention are, or are derived from, estrogens, e.g. estradiol, androgens, progestins, corticosteroids, methotrexate, folic acid, and cholesterol.

According to a particular embodiment of the present invention, the Primary Target is a receptor and a Targeting Agent is employed, which is capable of specific binding to the Primary Target. Suitable Targeting Agents include but are not limited to, the ligand of such a receptor or a part thereof which still binds to the receptor, e.g. a receptor binding peptide in the case of receptor binding protein ligands. Other examples of Targeting Agents of protein nature include insulin, transferrin, fibrinogen-gamma fragment, thrombospondin, claudin, apolipoprotein E, Affibody molecules such as for example ABY-025, Ankyrin repeat proteins, ankyrin-like repeat proteins, interferons, e.g. alpha, beta, and gamma interferon, interleukins, lymphokines, colony stimulating factors and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin. Alternative examples of targeting agents include DNA, RNA, PNA and LNA which are e.g. complementary to the Primary Target.

Examples of peptides as targeting agents include LHRH receptor targeting peptides, EC-1 peptide, RGD peptides, HER2-targeting peptides, PSMA targeting peptides, somatostatin-targeting peptides, bombesin. Other examples of targeting agents include lipocalins, such as anticalins. One particular embodiment uses Affibodies™ and multimers and derivatives.

In one embodiment antibodies are used as the $T^T$. While antibodies or immunoglobulins derived from IgG antibodies are particularly well-suited for use in this invention, immunoglobulins from any of the classes or subclasses may be selected, e.g. IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, recombinant antibodies, anti-idiotype antibodies, multispecific antibodies, antibody fragments, such as, Fv, VHH, Fab, F(ab)$_2$, Fab', Fab'-SH, F(ab')$_2$, single chain variable fragment antibodies (scFv), tandem/bis-scFv, Fc, pFc', scFv-Fc, disulfide Fv (dsFv), bispecific antibodies (bc-scFv) such as BiTE antibodies, trispecific antibody derivatives such as tribodies, camelid antibodies, minibodies, nanobodies, resurfaced antibodies, humanized antibodies, fully human antibodies, single domain antibodies (sdAb, also known as Nanobody™), chimeric antibodies, chimeric antibodies comprising at least one human constant region, dual-affinity antibodies such as dual-affinity retargeting proteins (DART™) and multimers and derivatives thereof, such as divalent or multivalent single-chain variable fragments (e.g. di-scFvs, tri-scFvs) including but not limited to minibodies, diabodies, triabodies, tribodies, tetrabodies, and the like, and multivalent antibodies. Reference is made to [Trends in Biotechnology 2015, 33, 2, 65], [Trends Biotechnol. 2012, 30, 575-582], and [Canc. Gen. Prot. 2013 10, 1-18], and [Bio-Drugs 2014, 28, 331-343], the contents of which are hereby incorporated by reference. "Antibody fragment" refers to at least a portion of the variable region of the immunoglobulin that binds to its target, i.e. the antigen-binding region.

Other embodiments use antibody mimetics as $T^T$, such as but not limited to Affimers, Anticalins, Avimers, Alphabodies, Affibodies, DARPins, and multimers and derivatives thereof; reference is made to [Trends in Biotechnology 2015, 33, 2, 65], the contents of which is hereby incorporated by reference. For the avoidance of doubt, in the context of this invention the term "antibody" is meant to encompass all of the antibody variations, fragments, derivatives, fusions, analogs and mimetics outlined in this paragraph, unless specified otherwise.

In a preferred embodiment the $T^T$ is selected from antibodies and antibody derivatives such as antibody fragments, fragment fusions, proteins, peptides, peptide mimetics.

In another preferred embodiment the $T^T$ is selected from antibody fragments, fragment fusions, and other antibody derivatives that do not contain a Fc domain.

In another embodiment the TT is a polymer and accumulates at the Primary Target by virtue of the EPR effect. Typical polymers used in this embodiment include but are not limited to polyethyleneglycol (PEG), poly(N-(2-hydroxypropyl)methacrylamide) (HPMA), polylactic acid (PLA), polylactic-glycolic acid (PLGA), polyglutamic acid (PG), polyvinylpyrrolidone (PVP), poly(1-hydroxymethylethylene hydroxymethyl-formal (PHF). Other examples are copolymers of a polyacetal/polyketal and a hydrophilic polymer selected from the group consisting of polyacrylates, polyvinyl polymers, polyesters, polyorthoesters, polyamides, oligopeptides, polypeptides and derivatives thereof. Other examples are oligopeptides, polypeptides, glycopolysaccharides, and polysaccharides such as dextran and hyaluronan, In addition reference is made to [G. Pasut, F. M. Veronese, Prog. Polym. Sci. 2007, 32, 933-961].

According to a further particular embodiment of the invention, the Primary Target and Targeting Agent are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting Primary Targets with tissue-, cell- or disease-specific expression. For example, the CC49 antibody targets TAG72, the expression of which is limited in normal tissues, but receptors are overexpressed in various solid tumor cell types.

In one embodiment the Targeting Agent specifically binds or complexes with a cell surface molecule, such as a cell surface receptor or antigen, for a given cell population. Following specific binding or complexing of the $T^T$ with the receptor, the cell is permissive for uptake of the Prodrug, which then internalizes into the cell. The subsequently administered Activator will then enter the cell and activate the Prodrug, releasing the Drug inside the cell. In another embodiment the Targeting Agent specifically binds or complexes with a cell surface molecule, such as a cell surface receptor or antigen, for a given cell population. Following specific binding or complexing of the TT with the receptor, the cell is not permissive for uptake of the Prodrug. The subsequently administered Activator will then activate the Prodrug on the outside of the cell, after which the released Drug will enter the cell.

As used herein, a $T^T$ that "specifically binds or complexes with" or "targets" a cell surface molecule, an extracellular matrix target, or another target, preferentially associates with the target via intermolecular forces. For example, the ligand can preferentially associate with the target with a dissociation constant ($K_d$ or $K_D$) of less than about 50 nM, less than about 5 nM, or less than about 500 pM.

In another embodiment the targeting agent $T^T$ localizes in the target tissue by means of the EPR effect. An exemplary $T^T$ for use in with the EPR effect is a polymer.

It is preferred that when a $T^T$ is comprised in an embodiment of the invention, it equals $C^A$.

Administration of a Prodrug

When administering the Prodrug (as further defined in the sections below) and the Activator to a living system, such as an animal or human, in preferred embodiments the Prodrug is administered first, and it will take a certain time period before the Prodrug has reached the Primary Target. This time period may differ from one application to the other and may be minutes, days or weeks. After the time period of choice has elapsed, the Activator is administered, will find and react with the Prodrug and will thus activate the Prodrug and/or afford Drug release at the Primary Target. In some preferred embodiments, the time interval between the administration of the Prodrug and the Activator is between 10 minutes and 4 weeks. In some preferred embodiments, the time interval between the administration of the Prodrug and the Activator is between 1 hour and 2 weeks, preferably between 1 and 168 hours, more preferably between 1 and 120 hours, even more preferably between 1 and 96 hours, most preferably between 3 and 72 hours.

The compositions of the invention can be administered via different routes including but not limited to intravenous or subcutaneous injection, intraperitoneal, local injection, oral administration, rectal administration and inhalation. Formulations suitable for these different types of administrations are known to the skilled person. Prodrugs or Activators according to the invention can be administered together with a pharmaceutically acceptable carrier. A suitable pharmaceutical carrier as used herein relates to a carrier suitable for medical or veterinary purposes, not being toxic or otherwise unacceptable. Such carriers are well known in the art and include for example saline, buffered saline, dextrose, water, glycerol, ethanol, and combinations thereof. The formulation should suit the mode of administration.

It will be understood that the chemical entities administered, viz. the Prodrug and the Activator, can be in a modified form that does not alter the chemical functionality of said chemical entity, such as salts, hydrates, or solvates thereof.

After administration of the Prodrug, and before the administration of the Activator, it is preferred to remove excess Prodrug by means of a Clearing Agent in cases when Prodrug activation in circulation is undesired and when natural Prodrug clearance is insufficient. A Clearing Agent is an agent, compound, or moiety that is administered to a subject for the purpose of binding to, or complexing with, an administered agent (in this case the Prodrug) of which excess is to be removed from circulation. The Clearing Agent is capable of being directed to removal from circulation. The latter is generally achieved through liver receptor-based mechanisms, although other ways of secretion from circulation exist, as are known to the skilled person. In the invention, the Clearing Agent for removing circulating Prodrug, preferably comprises a dienophile moiety, e.g. as discussed above, capable of reacting to the tetrazine moiety of the Prodrug.

In other embodiments the Activator is administered first, followed by the Prodrug, wherein the time interval between the administration of the two components ranges from 1 minute to 1 week, preferably from 10 minutes to 3 days.

In other embodiments, the Prodrug and Activator are administered at the same time. either as two separate administrations or as a co-administration.

In yet another embodiment, the Prodrug and Activator are reacted with one another prior to administration and the resulting reaction mixture is then adminstered, wherein the time interval between start of the reaction and the administration varies from 1 minute to 3 days, preferably 1 minute to 1 day, more preferably from 1 minute to 3 hours.

Application Areas

It is conceived that the invention can be used in three main application areas: 1) Cleavable Linker for Targeted Drug Conjugates in vivo (e.g. Antibody Drug Conjugates) wherein the Drug is released from a Targeting Agent; 2) Cleavable Linker or Mask in Prodrug Activation in vivo, wherein a Masking Moiety is released from the Drug, 3) Cleavable Linker or Mask for Applications in Chemistry and In Vitro. The following three sections will outline these three application areas.

Application Area 1) Cleavable Linker for Targeted Drug Conjugates In Vivo

Much effort has been devoted to drug delivery systems that effect drug release selectivity at a target site and/or at a desired moment in time. In the medical arena the use of inactive compounds such as prodrugs which are activated in a specific site in the human or animal body is well known. Also targeted delivery of inactives such as prodrugs has been studied extensively. One way is to selectively activate a (systemic) prodrug specifically by local and specific enzymatic activity. However, in many cases a target site of interest lacks a suitable overexpressed enzyme. An alternative is to transport an enzyme to target tissue via a technique called antibody-directed enzyme prodrug therapy (ADEPT). In this approach an enzyme is targeted to a tumor site by conjugation to an antibody that binds a tumor-associated antigen. After systemic administration of the conjugate, its localization at the target and clearance of unbound conjugate, a designed prodrug is administered systemically and locally activated. This method requires the catalysis of a reaction that must not be accomplished by an endogenous enzyme. Enzymes of non-mammalian origin that meet these needs are likely to be highly immunogenic, a fact that makes repeated administration impossible. Alternatively, prodrugs can be targeted to a disease site followed by disease-specific or -non-specific endogenous activation processes (e.g. pH, enzymes, thiol-containing compounds).

Targeted anticancer therapeutics are designed to reduce nonspecific toxicities and increase efficacy relative to conventional cancer chemotherapy. This approach is embodied by the powerful targeting ability of monoclonal antibodies (mAbs) to specifically deliver highly potent, conjugated small molecule therapeutics to a cancer cell. In an attempt to address the issue of toxicity, chemotherapeutic agents (drugs) have been coupled to targeting molecules such as antibodies or protein receptor ligands that bind with a high degree of specificity to tumor cell to form compounds referred to as antibody-drug conjugates (ADC) or immunoconjugates or Prodrugs. Immunoconjugates in theory should be less toxic because they direct the cytotoxic drug to tumors that express the particular cell surface antigen or receptor. This strategy has met limited success in part because cytotoxic drugs tend to be inactive or less active when conjugated to large antibodies, or protein receptor ligands. Promising advancements with immunoconjugates have seen cytotoxic drugs linked to antibodies through a linker that is cleaved at the tumor site or inside tumor cells [Senter et al, Curr. Opin. Chem. Biol. 2010, 14, 529-537]. Ideally, the mAb will specifically bind to an antigen with substantial expression on tumor cells but limited expression on normal tissues. Specificity allows the utilization of drugs that otherwise would be too toxic for clinical application. Most of the recent work in this field has centered on the use of highly potent cytotoxic agents. This requires the development of linker technologies that provide conditional stability, so that drug release occurs after tumor binding, rather than in circulation.

As a conjugate the Prodrug is inactive but upon target localization the drug is released by e.g. pH or an enzyme, which could be target specific but may also be more generic. The drug release may be achieved by an extracellular mechanism such as low pH in tumor tissue, hypoxia, certain enzymes, but in general more selective drug release can be achieved through intracellular, mostly lysosomal, release mechanisms (e.g. glutathione, proteases, catabolism) requiring the antibody conjugate to be first internalized. Specific intracellular release mechanisms (e.g. glutathione, cathepsin) usually result in the parent drug, which depending on its properties, can escape the cell and attack neighboring cells. This so called bystander effect is viewed as an important mechanism of action for a range of antibody-drug conjugates, especially in tumors with heterogeneous receptor expression, or with poor mAb penetration. Examples of cleavable linkers are: hydrazones (acid labile), peptide linkers (cathepsin B cleavable), hindered disulfide moieties (thiol cleavable). Also non-cleavable linkers can be used in mAb-drug conjugates. These constructs release their drug upon catabolism, presumably resulting in a drug molecule still attached to one amino acid. Only a subset of drugs will regain their activity as such a conjugate. Also, these aminoacid-linked drugs cannot escape the cells. Nevertheless, as the linker is stable, these constructs are generally regarded as the safest and depending on the drug and target, can be very effective.

The current Prodrug, e.g. antibody-drug conjugate, release strategies have their limitations. The extracellular drug release mechanisms are usually too unspecific (as with pH sensitive linkers) resulting in toxicity. Intracellular release depends on efficient (e.g. receptor-mediated) internalization of the mAb-drug, while several cancers lack cancer-specific and efficiently internalizing targets that are present in sufficiently high copy numbers. Intracellular release may further depend on efficient intracellular trafficking and the presence of an activating enzyme (proteases) or molecules (thiols such as glutathione) in sufficiently high amount. These parameters may vary between cancers and patients. Following intracellular release, the drug may, in certain cases, escape from the cell to target neighbouring cells. This effect is deemed advantageous in heterogeneous tumors where not every cell expresses sufficiently high amounts of target receptor. It is of further importance in tumors that are difficult to penetrate due e.g. to elevated interstitial pressure, which impedes convectional flow. This is especially a problem for large constructs like mAb (conjugates). This mechanism is also essential in cases where a binding site barrier occurs. Once a targeted agent leaves the vasculature and binds to a receptor, its movement within the tumor will be restricted. The likelihood of a mAb conjugate being restricted in the perivascular space scales up with its affinity for its target. The penetration can be improved by increasing the mAb dose, however, this approach is limited by dose limiting toxicity in e.g. the liver. Further, antigens that are shed from dying cells can be present in the tumor interstitial space where they can prevent mAb-conjugates of binding their target cell. Also, many targets are hampered by ineffective internalization, and different drugs cannot be linked to a mAb in the same way. Further, it has been proven cumbersome to design linkers to be selectively cleavable by endogenous elements in the target while stable to endogenous elements en route to the target (especially the case for slow clearing full mAbs). As a result, the optimal drug, linker, mAb, and target combination needs to be selected and optimized on a case by case basis.

It is desirable to be able to activate targeted Prodrugs selectively and predictably at the target site without being dependent on homogenous penetration and targeting, and on endogenous parameters which may vary en route to and within the target, and from indication to indication and from patient to patient. The use of a biocompatible chemical reaction that does not rely on endogenous activation mechanisms (e.g. pH, enzymes) for selective Prodrug activation would represent a powerful new tool in cancer therapy. It would expand the scope to cancer-related receptors and extracellular matrix targets that do not afford efficient internalization of the ADC and therefore cannot be addressed with the current ADC approaches. In addition, extraneous and selective activation of Prodrugs when and where required leads to enhanced control over ADC activation, intracellularly and extracellularly. Finally this approach would maximize the bystander effect, allowing more efficient Drug permeation throughout the tumor tissue.

In order to avoid the drawbacks of current prodrug activation, it has been proposed to make use of an abiotic, bio-orthogonal chemical reaction to provoke release of the Drug from the ADC. In this type of ADC, the Drug is attached to the antibody (or another type of Targeting Agent) via a Trigger, and this Trigger is not activated endogenously by e.g. an enzyme or a specific pH, but by a controlled administration of the Activator, i.e. a species that reacts with the Trigger moiety in the ADC, to induce release of the Drug from the Trigger (or vice versa, release of the Trigger from the Drug, however one may view this release process). The previously used approach applying the Staudinger Reaction for this concept [Bioconjugate Chem 2008, 19, 714-718], as well as the earlier designs to use the IEDDA for this purpose, has turned out not to work well (vide supra).

In order to better address one or more of the foregoing desires, the present invention provides a kit for the administration and activation of a Prodrug, the kit comprising a Drug, denoted as $D^D$, linked directly, or indirectly through a linker $L^C$, to a Trigger moiety $T^R$, wherein $T^R$ or $L^C$ is bound to a Targeting Agent $T^T$, and an Activator for the Trigger moiety, wherein the Trigger moiety comprises a diene and the Activator comprises a dienophile, the diene satisfying Formula (1), wherein $C^A$ is a Drug $D^D$ and $C^B$ is $T^T$.

In another aspect, the invention presents a Prodrug comprising a Drug $D^D$ compound linked, directly or indirectly, to a tetrazine moiety satisfying Formula (1).

In yet another aspect, the invention provides a method of modifying a Drug $D^D$ compound into a Prodrug that can be triggered by an abiotic, bio-orthogonal reaction, the method comprising the steps of providing a Drug and chemically linking the Drug to a tetrazine moiety satisfying Formula (1).

In a still further aspect, the invention provides a method of treatment wherein a patient suffering from a disease that can be modulated by a Drug $D^D$, is treated by administering, to said patient, a Prodrug comprising a Drug, a Trigger moiety and a Targeting agent $T^T$ after activation of which by administration of an Activator the Drug will be released, wherein the Trigger moiety comprises a structure satisfying Formula (1).

In a still further aspect, the invention is a compound comprising a tetrazine moiety, said moiety comprising a linkage to a Drug $D^D$, for use in Prodrug therapy in an animal or a human being.

In another aspect, the invention is the use of a dienophile, preferably a trans-cyclooctene as an Activator for the release, in a physiological environment, of a substance covalently linked to a compound satisfying Formula (1). In connection herewith, the invention also pertains to a dienophile, preferably a trans-cyclooctene, for use as an Activator for the release, in a physiological environment, of a substance linked to a compound satisfying Formula (1), and to a method for activating, in a physiological environment, the release of a substance linked to a compound satisfying Formula (1), wherein a trans-cyclooctene is used as an Activator.

In another aspect, the invention presents the use of the inverse electron-demand Diels-Alder reaction between a compound satisfying Formula (1) and a dienophile, preferably a trans-cyclooctene, as a chemical tool for the release, in a physiological environment, of a substance administered in a covalently bound form, wherein the substance is bound to a compound satisfying Formula (1).

A Prodrug is a conjugate of the Drug $D^D$ and the Trigger $T^R$ and thus comprises a Drug that is capable of therapeutic action after its release from the Trigger. In embodiments where the Prodrug is targeted to e.g. a Primary Target, as is the case with for example Antibody Drug Conjugates, the Prodrug comprises a Targeting agent $T^T$, which is bound to either the $T^R$ or the $L^C$.

FIG. 1 depicts a preferred embodiment of this invention. In a Panel A a Trigger is used that is believed to function via the Cyclization mechanism, in Panel B a Trigger is used that is believed to function via the Cascade mechanism. In both panels an antibody ($T^T$) conjugated to a Drug ($D^D$ being $C^A$) is administered to a cancer patient, and this Prodrug (i.e. Antibody Drug Conjugate or ADC) is allowed to circulate and bind to a Primary Target on the cancer cell. After the freely circulating ADC has sufficiently cleared from circulation, for example after 2 days post injection, the Activator, in this case a TCO, is administered and distributes systemically, allowing the reaction with the Trigger of cancer-bound Prodrug or ADC, releasing the Drug, after which the Drug can penetrate and kill neighbouring cancer cells.

The general formula of the Prodrug is shown in Formula (5a) and (5b).

For applications where Drugs are released from a Targeting Agent it is preferred that $C^B$ is a targeting agent $T^T$ and $C^A$ is a Drug $D^D$;

$$f=1; a,d \geq 1; b,c,e,g,h \geq 0. \qquad \text{Formula (5a):}$$

$$f=1; a,b,d \geq 1; c,e,g,h \geq 0. \qquad \text{Formula (5b):}$$

In preferred embodiments the $C^B$ is an antibody, which expressly includes full-length antibodies, antigen-binding fragments thereof, antibody analogs and mimetics and a fusion of antibodies, antibody derivatives, fragments, analogs and mimetics as outlined in the section on Targeting Agents $T^T$ above.

In some preferred embodiments of Formulae (5a) and (5b), the Prodrug satisfies one of the following Formulae (6a), (6b), (6c) and (6d) wherein b and e are independently 0 or 1; d is an integer ranging from 1 to 3; n and m each independently are an integer ranging from 1 to 30.

Formulae 6a-d

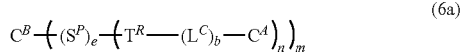
(6a)

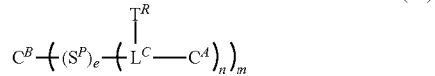
(6b)

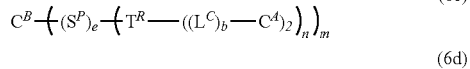
(6c)

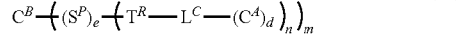
(6d)

With reference to Formulae (6a), (6b), (6c) and (6d) it is preferred that $C^B$ is an antibody or antibody derivative. In some preferred embodiments wherein the $S^P$ links the $C^B$ to one $T^R$, e is 1, n is 1 and m ranges from 1 to 10, preferably from 1 to 8, more preferably from 1 to 4. In other embodiments wherein the $S^P$ links to multiple $T^R$ moieties, e=1, n ranges from 2 to 30, preferably from 2 to 15, more preferably from 2 to 4, and m ranges from 1 to 10, preferably from 1 to 8, more preferably from 1 to 4. It is preferred that the $T^R$ comprised in Formula (6c) releases through the cascade mechanism. For the sake of clarity, in Formula (6d) one, two, or three $C^A$ moieties can be released from one $L^C$ moiety, while in (6a), (6b), (6c), one $L^C$ moiety releases one $C^A$.

According to a further particular embodiment of the invention, the Prodrug is selected so as to target and or address a disease, such as cancer, an inflammation, an autoimmune disease, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

According to one embodiment, the Prodrug and/or the Activator can be multimeric compounds, comprising a plurality of Drugs and/or bioorthogonal reactive moieties. These multimeric compounds can be polymers, dendrimers, liposomes, polymer particles, or other polymeric constructs.

It is preferred that the optional $L^C$ comprised in the Prodrug is self-immolative, affording traceless release of the Drug.

Drugs

Drugs $D^D$ that can be used in a Prodrug relevant to this invention include but are not limited to: small organic molecule drugs, steroids, lipids, proteins, aptamers, oligopeptides, oligonucleotides, oligosaccharides, as well as peptides, peptoids, amino acids, nucleotides, polynucleotides, nucleosides, DNA, RNA, toxins, glycans.

Exemplary classes of drug molecules that can be used in the practise of the present invention include but are not limited to hormones, cytotoxins, antiproliferative/antitumor agents, antiviral agents, antibiotics, cytokines, anti-inflammatory agents, antihypertensive agents, chemosensitizing and radiosensitizing agents, anti-AIDS substances, anti-viral agents, immunosuppressants, immunostimulants enzyme inhibitors, anti-Parkinson substances, neurotoxins, channel blockers, modulators of cell-extracellular matrix interactions including cell growth inhibitors and anti-adhesion molecules, inhibitors of DNA, RNA or protein synthesis, steroidal and non-steriodal anti-inflammatory agents, anti-angiogenic factors.

In some embodiments, the drug $D^D$ is a low to medium molecular weight compound (e.g. about 200 to 5000 Da, about 200 to about 1500 Da, preferably about 300 to about 1000 Da).

Exemplary drugs for use as conjugates to the Trigger and to be released upon IEDDA reaction with the Activator include but are not limited to: cytotoxic drugs, particularly those which are used for cancer therapy. Such drugs include, in general, DNA damaging agents, anti-metabolites, natural products and their analogs, enzyme inhibitors such as dihydrofolate reductase inhibitors and thymidylate synthase inhibitors, DNA binders, DNA alkylators, radiation sensitizers, DNA intercalators, DNA cleavers, microtubule stabilizing and destabilizing agents, topoisomerases inhibitors. Examples include but are not limited to platinum-based drugs, the anthracycline family of drugs, the vinca drugs, the mitomycins, the bleomycins, the cytotoxic nucleosides, taxanes, lexitropsins, the pteridine family of drugs, diynenes, the podophyllotoxins, dolastatins, maytansinoids, differentiation inducers, and taxols. Particularly useful members of those classes include, for example, auristatins, maytansines, maytansinoids, calicheamicins, dactinomycines, duocarmycins, CC1065 and its analogs, camptothecin and its analogs, SN-38 and its analogs, tubulysin M, cryptophycins, pyrrolobenzodiazepines and pyrrolobenzodiazepine dimers (PBDs), methotrexate, methopterin, dichloromethotrexate, 5-fluorouracil, DNA minor groove binders, 6-mercaptopurine, cytosine arabinoside, melphalan, leurosine, leurosideine, actinomycin, anthracyclines (doxorubicin, epirubicin, idarubicin, daunorubicin) and its analogs, mitomycin C, mitomycin A, caminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, N8-acetyl spermidine, staurosporin, colchicine, camptothecin, esperamicin, ene-diynes, and their analogues.

Other exemplary drug classes are angiogenesis inhibitors, cell cycle progression inhibitors, P13K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors, and RNA polymerase inhibitors.

Examples of auristatins include dolastatin 10, monomethyl auristatin E (MMAE), auristatin F, monomethyl auristatin F (MMAF), auristatin F hydroxypropylamide (AF HPA), auristatin F phenylene diamine (AFP), monomethyl auristatin D (MMAD), auristatin PE, auristatin EB, auristatin EFP, auristatin TP and auristatin AQ. Suitable auristatins are also described in U.S. Publication Nos. 2003/0083263, 2011/0020343, and 2011/0070248; PCT Application Publication Nos. WO09/117531, WO2005/081711, WO04/010957; WO02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,879,278; 4,816,444; and 4,486,414, the disclosures of which are incorporated herein by reference in their entirety.

Exemplary drugs include the dolastatins and analogues thereof including: dolastatin A (U.S. Pat. No. 4,486,414), dolastatin B (U.S. Pat. No. 4,486,414), dolastatin 10 (U.S. Pat. Nos. 4,486,444, 5,410,024, 5,504,191, 5,521,284, 5,530,097, 5,599,902, 5,635,483, 5,663,149, 5,665,860, 5,780,588, 6,034,065, 6,323,315), dolastatin 13 (U.S. Pat. No. 4,986,988), dolastatin 14 (U.S. Pat. No. 5,138,036), dolastatin 15 (U.S. Pat. No. 4,879,278), dolastatin 16 (U.S.

Pat. No. 6,239,104), dolastatin 17 (U.S. Pat. No. 6,239,104), and dolastatin 18 (U.S. Pat. No. 6,239,104), each patent incorporated herein by reference in their entirety.

Exemplary maytansines, maytansinoids, such as DM-1 and DM-4, or maytansinoid analogs, including maytansinol and maytansinol analogs, are described in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 6,441,163; 6,716,821 and 7,276,497. Other examples include mertansine and ansamitocin.

Pyrrolobenzodiazepines (PBDs), which expressly include dimers and analogs, include but are not limited to those described in [Denny, Exp. Opin. Ther. Patents, 10(4):459-474 (2000)], [Hartley et al., Expert Opin Investig Drugs. 2011, 20(6):733-44], Antonow et al., Chem Rev. 2011, 111(4), 2815-641.

Calicheamicins include, e.g. enediynes, esperamicin, and those described in U.S. Pat. Nos. 5,714,586 and 5,739,116

Examples of duocarmycins and analogs include CC1065, duocarmycin SA, duocarmycin A, duocarmycin B1, duocarmycin B2, duocarmycin C1, duocarmycin C2, duocarmycin D, DU-86, KW-2189, adozelesin, bizelesin, carzelesin, seco-adozelesin. Other examples include those described in, for example, U.S. Pat. Nos. 5,070,092; 5,101,092; 5,187,186; 5,475,092; 5,595,499; 5,846,545; 6,534,660; 6,548,530; 6,586,618; 6,660,742; 6,756,397; 7,049,316; 7,553,816; 8,815,226; US20150104407; 61/988,011 filed May 2, 2014 and 62/010,972 filed Jun. 11, 2014; the disclosure of each of which is incorporated herein in its entirety.

Exemplary vinca alkaloids include vincristine, vinblastine, vindesine, and navelbine, and those disclosed in U.S. Publication Nos. 2002/0103136 and 2010/0305149, and in U.S. Pat. No. 7,303,749, the disclosures of which are incorporated herein by reference in their entirety.

Exemplary epothilone compounds include epothilone A, B, C, D, E, and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO97/19086; WO98/08849; WO98/22461; WO98/25929; WO98/38192; WO99/01124; WO99/02514; WO99/03848; WO99/07692; WO99/27890; and WO99/28324; the disclosures of which are incorporated herein by reference in their entirety.

Exemplary cryptophycin compounds are described in U.S. Pat. Nos. 6,680,311 and 6,747,021; the disclosures of which are incorporated herein by reference in their entirety.

Exemplary platinum compounds include cisplatin, carboplatin, oxaliplatin, iproplatin, ormaplatin, tetraplatin.

Exemplary DNA binding or alkylating drugs include CC-1065 and its analogs, anthracyclines, calicheamicins, dactinomycines, mitromycines, pyrrolobenzodiazepines, and the like.

Exemplary microtubule stabilizing and destabilizing agents include taxane compounds, such as paclitaxel, docetaxel, tesetaxel, and carbazitaxel; maytansinoids, auristatins and analogs thereof, vinca alkaloid derivatives, epothilones and cryptophycins.

Exemplary topoisomerase inhibitors include camptothecin and camptothecin derivatives, camptothecin analogs and non-natural camptothecins, such as, for example, CPT-11, SN-38, topotecan, 9-aminocamptothecin, rubitecan, gimatecan, karenitecin, silatecan, lurtotecan, exatecan, diflometotecan, belotecan, lurtotecan and S39625. Other camptothecin compounds that can be used in the present invention include those described in, for example, J. Med. Chem., 29:2358-2363 (1986); J. Med. Chem., 23:554 (1980); J. Med Chem., 30:1774 (1987).

Angiogenesis inhibitors include, but are not limited to, MetAP2 inhibitors, VEGF inhibitors, PIGF inhibitors, VGFR inhibitors, PDGFR inhibitors, MetAP2 inhibitors. Exemplary VGFR and PDGFR inhibitors include sorafenib, sunitinib and vatalanib. Exemplary MetAP2 inhibitors include fumagillol analogs, meaning compounds that include the fumagillin core structure.

Exemplary cell cycle progression inhibitors include CDK inhibitors such as, for example, BMS-387032 and PD0332991; Rho-kinase inhibitors such as, for example, AZD7762; aurora kinase inhibitors such as, for example, AZD1152, MLN8054 and MLN8237; PLK inhibitors such as, for example, BI 2536, BI6727, GSK461364, ON-01910; and KSP inhibitors such as, for example, SB 743921, SB 715992, MK-0731, AZD8477, AZ3146 and ARRY-520.

Exemplary P13K/m-TOR/AKT signalling pathway inhibitors include phosphoinositide 3-kinase (P13K) inhibitors, GSK-3 inhibitors, ATM inhibitors, DNA-PK inhibitors and PDK-1 inhibitors.

Exemplary P13 kinases are disclosed in U.S. Pat. No. 6,608,053, and include BEZ235, BGT226, BKM120, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,944 and include GDC-0973, GSK1120212, MSC1936369B, AS703026, RO5126766 and RO4987655, PD0325901, AZD6244, AZD8330 and GDC-0973.

Exemplary B-raf inhibitors include CDC-0879, PLX-4032, and SB590885.

Exemplary B p38 MAPK inhibitors include BIRB 796, LY2228820 and SB 202190.

Exemplary receptor tyrosine kinases inhibitors include but are not limited to AEE788 (NVP-AEE 788), BIBW2992 (Afatinib), Lapatinib, Erlotinib (Tarceva), Gefitinib (Iressa), AP24534 (Ponatinib), ABT-869 (linifanib), AZD2171, CHR-258 (Dovitinib), Sunitinib (Sutent), Sorafenib (Nexavar), and Vatalinib.

Exemplary protein chaperon inhibitors include HSP90 inhibitors. Exemplary inhibitors include 17AAG derivatives, BIIB021, B11B028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCDO103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP9722, MK 4827, KU-0059436 (AZD2281), LT-673, 3-aminobenzamide, A-966492, and AZD2461.

Exemplary Wnt/Hedgehog signalling pathway inhibitors include vismodegib, cyclopamine and XAV-939.

Exemplary RNA polymerase inhibitors include amatoxins. Exemplary amatoxins include alpha-amanitins, beta amanitins, gamma amanitins, eta amanitins, amanullin, amanullic acid, amanisamide, amanon, and proamanullin.

Exemplary cytokines include IL-2, IL-7, IL-10, IL-12, IL-15, IL-21, TNF.

Other exemplary drugs include puromycins, topetecan, rhizoxin, echinomycin, combretastatin, netropsin, estramustine, cemadotin, discodermolide, eleutherobin, mitoxantrone, pyrrolobenzimidazoles (PBI), gamma-interferon, deBouganin, amanitin, irinotecan, immunotoxins, comprising e.g. ricin A, diphtheria toxin, cholera toxin.

In exemplary embodiments of the invention, the drug moiety is a mytomycin compound, a vinca alkaloid compound, taxol or an analogue, an anthracycline compound, a calicheamicin compound, a maytansinoid compound, an auristatin compound, a duocarmycin compound, SN38 or an analogue, a pyrrolobenzodiazepine compound, a tubulysin compound, a non-natural camptothecin compound, a DNA binding drug, a kinase inhibitor, a MEK inhibitor, a KSP inhibitor, a P13 kinase inhibitor, a topoisomerase inhibitor, or analogues thereof.

In one preferred embodiment the drug is a non-natural camptothecin compound, vinca alkaloid, kinase inhibitor, (e.g. P13 kinase inhibitor: GDC-0941 and PI-103), MEK inhibitor, KSP inhibitor, RNA polymerase inhibitor, PARP inhibitor, docetaxel, paclitaxel, doxorubicin, dolastatin, calicheamicins, SN38, pyrrolobenzodiazepines, DNA binding drugs, maytansinoids DM1 and DM4, auristatin MMAE, CC1065 and its analogs, camptothecin and its analogs, SN-38 and its analogs.

In another preferred embodiment the drug is selected from DNA binding drugs and microtubule agents, including pyrrolobenzodiazepines, maytansinoids, maytansines, auristatins, duocarmycins, anthracyclines, taxanes.

In another preferred embodiment the drug is selected from colchinine, vinca alkaloids, tubulysins, irinotecans, an inhibitory peptide, amanitin and deBouganin.

In another embodiment, a combination of two or more different drugs are used.

In other embodiments the released Drug $D^D$ is itself a prodrug designed to release a further drug.

Drugs optionally include a membrane translocation moiety (e.g. adamantine, poly-lysine/arginine, TAT, human lactoferrin) and/or a targeting agent (against e.g. a tumor cell receptor) optionally linked through a stable or labile linker. Exemplary references include: Trends in Biochemical Sciences, 2015., 40, 12, 749; J. Am. Chem. Soc. 2015, 137, 12153-12160; Pharmaceutical Research, 2007, 24, 11, 1977.

It will be understood that chemical modifications may also be made to the desired compound in order to make reactions of that compound more convenient for purposes of preparing conjugates of the invention. Drugs containing an amine functional group for coupling to the tetrazine include mitomycin-C, mitomycin-A, daunorubicin, doxorubicin, aminopterin, actinomycin, bleomycin, 9-amino camptothecin, N8-acetyl spermidine, 1-(2 chloroethyl)1,2-dimethanesulfonyl hydrazide, tallysomycin, cytarabine, dolastatins (including auristatins) and derivatives thereof.

Drugs containing a hydroxyl function group for coupling to the tetrazine include etoposide, camptothecin, taxol, esperamicin, 1,8-dihydroxy-bicyclo[7.3.1]trideca-4-9-diene-2,6-diyne-13-one (U.S. Pat. No. 5,198,560), podophyllotoxin, anguidine, vincristine, vinblastine, morpholine-doxorubicin, n-(5,5-diacetoxy-pentyl)doxorubicin, and derivatives thereof.

Drugs containing a sulfhydryl functional group for coupling to the tetrazine include esperamicin and 6-mecaptopurine, and derivatives thereof.

It will be understood that the drugs can optionally be attached to the tetrazine derivative through a self-immolative linker $L^C$ and which may consist of multiple (self-immolative, or non immolative) units.

It will further be understood that, in addition to the $T^T$ attached to the Trigger $T^R$ or Linker $L^C$ a targeting agent $T^T$ may optionally be attached to the Drug $D^D$, optionally via a spacer $S^P$.

Alternatively, it will be further understood that the $T^T$ may comprise one or more additional Drugs which are bound to $T^T$ by other types of linkers, e.g. cleavable by proteases, pH, thiols, or by catabolism.

The invention further contemplates that when $T^T$ is a suitably chosen antibody or antibody derivative that $T^T$ can induce antibody-dependent cellular toxicity (ADCC) or complement dependent cytotoxicity (CDC).

Several drugs may be replaced by an imagable label to measure drug targeting and release.

In the Prodrug, the Drug $D^D$ and the Trigger $T^R$—the tetrazine derivative—can be directly linked to each other. They can also be bound to each other via a self-immolative linker $L^C$ It will be understood that the invention encompasses any conceivable manner in which the diene Trigger is attached to the Drug. The same holds for the attachment of the targeting agent $T^T$ to the Prodrug. Methods of affecting conjugation to these Drugs, are known to the skilled person.

Application Area 2) Cleavable Linker or Mask in Prodrug Activation In Vivo

Another application areas that could benefit from an effective prodrug approach are the fields of protein-based therapies and immunotherapy. A major reason of failure of immunotherapy is the immunosuppressive microenvironment and tumor escape mechanisms operating in the tumor tissue. These mechanisms, for example check point inhibitors, include both cellular and soluble components and are potent enough to limit the development of durable antitumor response in patients. Prominent new directions include T-cell engaging antibody constructs (e.g., bi- or trispecific antibody fragments), which act on cancer by engaging the immune system [Trends in Biotechnology 2015, 33, 2, 65]. It has long been considered that bringing activated T-cells into direct contact with cancer cells offers a potent way of killing them [Thompson et al., Biochem. Biophys. Res. Commun. 2008, 366, 526-531]. Of the many bispecific antibodies that have been created to do this, the majority are composed of two antibody binding sites, one site targets the tumor and the other targets a T-cell [Thakur et al. Curr. Opin. Mol. Ther. 2010, 12, 3, 340-349]. However, with bispecific antibodies containing an active T-cell binding site, peripheral T-cell binding may occur. This not only prevents the conjugate from getting to the tumor but can also lead to cytokine storms and T-cell depletion. In addition, severe cytokine storms were observed for an CD28-targeted superagonist that was designed to act systemically on T-cells [N Engl J Med 2006; 355, 1018-1028]. Photoactivatable anti-T-cell antibodies, i.e. T-cell directed Prodrugs, in which the anti-T-cell activity is only restored when and where it is required (i.e. after tumor localization via the tumor binding arm), following irradiation with UV light, has been used to overcome these problems. Anti-human CD3 (T-cell targeting) antibodies could be reversibly inhibited with a photocleavable 1-(2-nitrophenyl)ethanol (NPE) Masking moiety [Thompson et al., Biochem. Biophys. Res. Commun. 366 (2008) 526-531]. However, light based activation is limited to regions in the body where light can penetrate, and is not easily amendable to treating systemic disease such as metastatic cancer.

Strongly related constructs that could benefit from a Prodrug approach are trispecific T-cell engaging antibody constructs with for example a CD3- and a CD28 T-cell engaging moiety in addition to a cancer targeting agent. Such constructs are too toxic to use as such and either the CD3 or the CD28 or both binding domains need to be masked with a Masking moiety, which can be selectively removed once the Produg has accumulated at the Primary Target.

Other proteins that could benefit from a Prodrug approach are immunotoxins. Current immunotoxins have immunogenicity issues and toxicity issues, especially towards vascular endothelial cells. Masking the targeted toxin by a Masking Moiety and removing it once the masked immunotoxin has bound to its target is expected to greatly reduce the toxicity and immunogenicity problems.

Other proteins that could benefit from a Prodrug approach are immunocytokines, which are a fusion or a conjugate between a cytokine and an antibody or antibody fragment or derivative. Reference is made to [Clinical Pharmacology: Advances and Applications 2013:5 (Suppl 1) 29-45], the contents of which are hereby incorporated by reference. Typical cytokines used in cancer therapy include IL-2, IL-7, IL-12, IL-15, IL-21, TNF [Cancer Immunol Immunother 2014, 63, 419-435]. A typical cytokine used in autoimmune diseases is the anti-inflammatory IL-10. Whereas cancer immunotherapy with cytokines in recent research was demonstrated to be effective in activating immune responses against tumor cells, one major obstacle with the use of these cytokines is their severe side effects when delivered systemically at high doses. Masking the targeted cytokine by a Masking Moiety and removing it once the masked immunocytokine has bound to its target is expected to greatly reduce the toxicity problems.

Hydrophilic polymers, such as polyethylene glycol (PEG), have been used as a masking moiety of various substrates, such as polypeptides, drugs and liposomes, in order to reduce immunogenicity of the substrate and/or to improve its blood circulation lifetime. For example, parenterally administered proteins can be immunogenic and may have a short pharmacological half-life. Proteins can also be relatively water insoluble. Consequently, it can be difficult to achieve therapeutically useful blood levels of the proteins in patients. Conjugation of PEG or other biocompatible polymers to proteins has been described as an approach to overcoming these difficulties [G. Pasut, F. M. Veronese, Prog. Polym. Sci. 32 (2007) 933-961]. Davis et al. in U.S. Pat. No. 4,179,337 disclose conjugating PEG to proteins such as enzymes and insulin to form PEG-protein conjugates having less immunogenicity yet which retain a substantial proportion of physiological activity. Veronese et al. [Appl. Biochem. Biotech., 1985, 11, 141-152] disclose activating polyethylene glycols with phenyl chloroformates to modify a ribonuclease and a superoxide dimutase. Katre et al. in U.S. Pat. Nos. 4,766,106 and 4,917,888 disclose solubilizing proteins by polymer conjugation. PEG and other polymers are conjugated to recombinant proteins to reduce immunogenicity and increase half-life. [Nitecki et al., U.S. Pat. No. 4,902,502; Enzon, Inc., PCT/US90/02133]. Garman [U.S. Pat. No. 4,935,465] describes proteins modified with a water soluble polymer joined to the protein through a reversible linking group. Cleavable PEG masking moieties have been applied, using the same (pH, thiol, enzyme) strategies as described for the ADC field, with the same drawbacks. Effective in vivo PEG cleavage strategies for protein constructs would allow spatial and temporal control over protein activity, toxicity, immunogenicity and pharmacokinetics.

As outlined above, there are protein therapeutics that are currently too unsafe to administer as such or could be made more potent and effective if the off target interactions and/or toxicity could be controlled. It is desirable to be able to activate drugs selectively and predictably at the target site without being dependent on homogenous penetration and targeting, and on endogenous parameters which may vary en route to and within the target, and from indication to indication and from patient to patient. The use of a biocompatible chemical reaction that does not rely on endogenous activation mechanisms (e.g. pH, enzymes) for selective Prodrug activation would represent a powerful new tool in therapy, for example cancer therapy. In the context of T-cell engaging anticancer antibodies, the present invention allows the systemic administration and tumor targeting of a masked inactive antibody construct (i.e. this is then the Prodrug), diminishing off-target toxicity. Upon sufficient tumor uptake and clearance from non-target areas, the tumor-bound antibody is activated by administration of the Activator, which reacts with the Trigger or Triggers on the antibody or particular antibody domain, resulting in removal of the Masking Moiety and restoration of the T-cell binding function. This results in T-cell activation and anticancer action.

In order to avoid the drawbacks of current prodrug activation, it has been proposed to make use of an abiotic, bio-orthogonal chemical reaction to provoke release of the Masking Moiety from the masked antibody. In this type of Prodrug, the Masking Moiety is attached to the antibody via a Trigger, and this Trigger is not activated endogenously by e.g. an enzyme or a specific pH, but by a controlled administration of the Activator, i.e. a species that reacts with the Trigger moiety in the Prodrug, to induce release of the Masking Moiety or the Drug from the Trigger (or vice versa, release of the Trigger from the Masking Moiety or Drug, however one may view this release process), resulting in activation of the Drug. The previously presented Staudinger approach for this concept, as well as the earlier designs to use the IEDDA for this purpose, has turned out not to work well (vide supra).

In order to better address one or more of the foregoing desires, the present invention provides a kit for the administration and activation of a Prodrug, the kit comprising a Masking Moiety, denoted as $M^M$, linked covalently, directly or indirectly, to a Trigger moiety, which in turn is linked covalently, directly or indirectly, to a Drug, denoted as $D^D$, and an Activator for the Trigger moiety, wherein the Trigger moiety comprises a diene and the Activator comprises a dienophile, the diene satisfying Formula (1).

In another aspect, the invention presents a Prodrug comprising a Masking Moiety, $M^M$, linked, directly or indirectly, to tetrazine moiety satisfying above Formula (1).

In yet another aspect, the invention provides a method of modifying a Drug, $D^D$, with a Masking Moiety $M^M$ affording a Prodrug that can be activated by an abiotic, bio-orthogonal reaction, the method comprising the steps of providing a Masking Moiety and a Drug and chemically linking the Masking Moiety and a Drug to a tetrazine moiety satisfying Formula (1).

In a still further aspect, the invention provides a method of treatment wherein a patient suffering from a disease that can be modulated by a drug, is treated by administering, to said patient, a Prodrug comprising a Trigger moiety linked to a Masking Moiety $M^M$ and a Drug $D^D$, after activation of which by administration of an Activator the Masking Moiety will be released, activating the Drug, wherein the Trigger moiety comprises a tetrazine structure satisfying Formula (1).

In a still further aspect, the invention is a compound comprising a tetrazine moiety, said moiety comprising a linkage to a Masking Moiety $M^M$, for use in prodrug therapy in an animal or a human being.

In another aspect, the invention is the use of a dienophile, preferably a trans-cyclooctene as an Activator for the release, in a physiological environment, of a substance covalently linked to a compound satisfying Formula (1). In connection herewith, the invention also pertains to a dienophile, preferably a trans-cyclooctene, for use as an Activator for the release, in a physiological environment, of a substance linked to a compound satisfying Formula (1), and to a method for activating, in a physiological environment, the release of a substance linked to a compound satisfying Formula (1), wherein a dienophile is used as an Activator.

In another aspect, the invention presents the use of the inverse electron-demand Diels-Alder reaction between a compound satisfying Formula (1) and a dienophile, preferably a trans-cyclooctene, as a chemical tool for the release, in a physiological environment, of a substance administered in a covalently bound form, wherein the substance is bound to a compound satisfying Formula (1).

For the avoidance of doubt, in the context of this invention wherein a $M^M$ is removed from an antibody (i.e. Drug) the terms "activatable antibodies" and "Prodrug" mean the same.

For the avoidance of doubt, the composition of the Prodrug outlined in this section "Application area 2" is different from the composition of the Prodrug outlined in the previous section "Application area 1", the difference residing in the use of respectively a $T^T$ or a $M^M$, as exemplified by Formulae 5a-b, 6a-d, 7a-d. A Prodrug as used in "Application area 1" comprises a $T^T$ bound to a $D^D$ via a $T^R$ and a Prodrug as used in "Application area 2" comprises a $M^M$ bound to a $D^D$ via a $T^R$.

For the avoidance of doubt, in the context of this invention wherein a $M^M$ is removed from a Drug, the Drug itself can bind to a Primary Target without the use of an additional Targeting Agent TT.

In some embodiments the activatable antibodies or Prodrugs of this invention are used in the treatment of cancer. In some embodiments the activatable antibodies or Prodrugs of this invention are used in the treatment of an autoimmune disease or inflammatory disease such as rheumatoid arthritis. In some embodiments the activatable antibodies or Prodrugs of this invention are used in the treatment of a fibrotic disease such as idiopathic pulmonary fibrosis.

Exemplary classes of Primary Targets for activatable antibodies or Prodrugs of this invention include but are not limited to cell surface receptors and secreted proteins (e.g. growth factors), soluble enzymes, structural proteins (e.g. collagen, fibronectin) and the like. In preferred embodiments the Primary Target is an extracellular target. In other embodiments, the Primary Target is an intracellular target.

In another embodiment, the drug is a bi- or trispecific antibody derivative that serves to bind to tumor cells and recruit and activate immune effector cells (e.g. T-cells, NK cells), the immune effector cell binding function of which is inactivated by being linked to a tetrazine moiety as described above. The latter, again, serving to enable bioorthogonal chemically activated drug activation.

Figure 2:
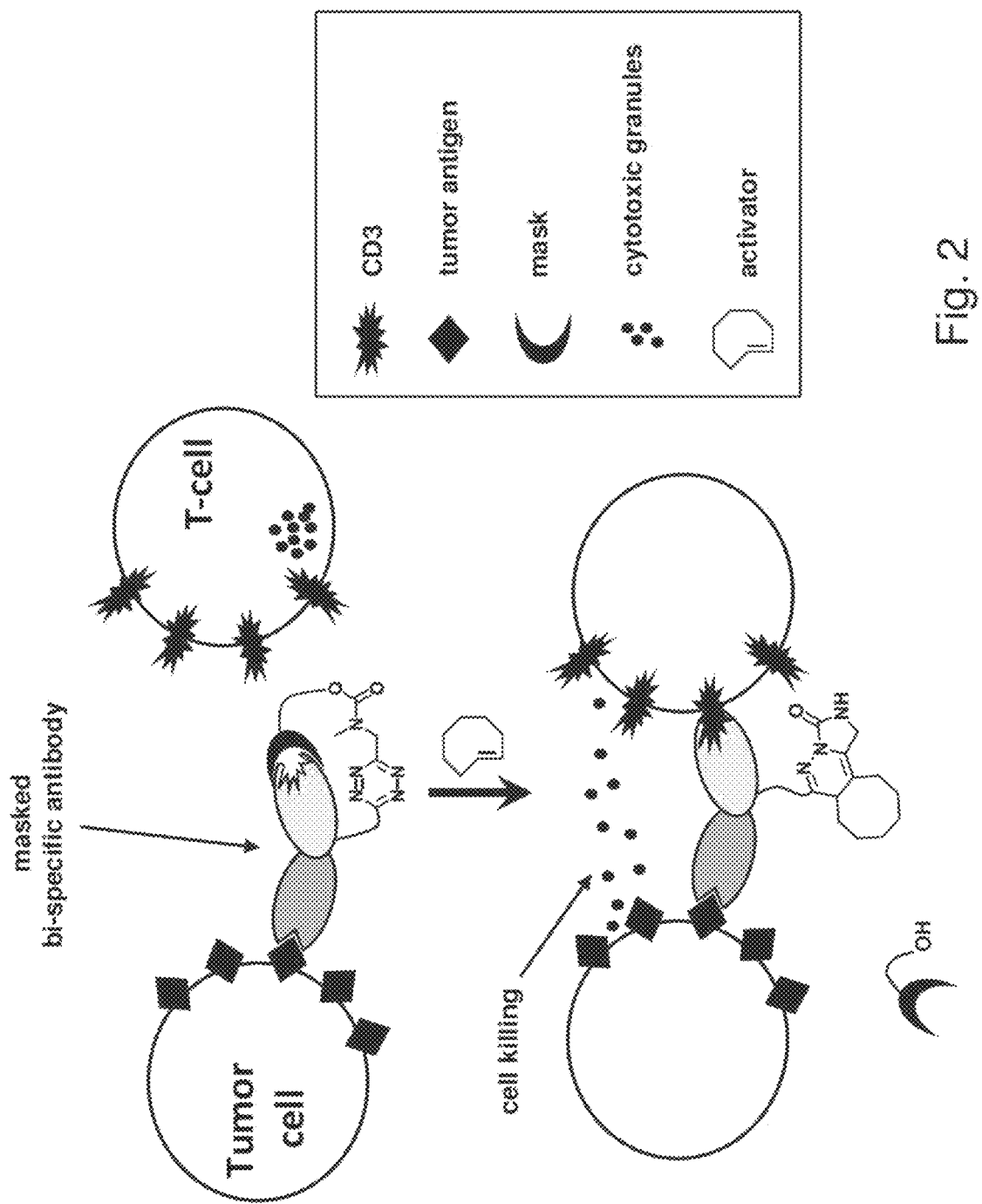
FIG. 2 depicts the general concept of Prodrug activation using the Triggers and Activator of the invention.
Figure 3:
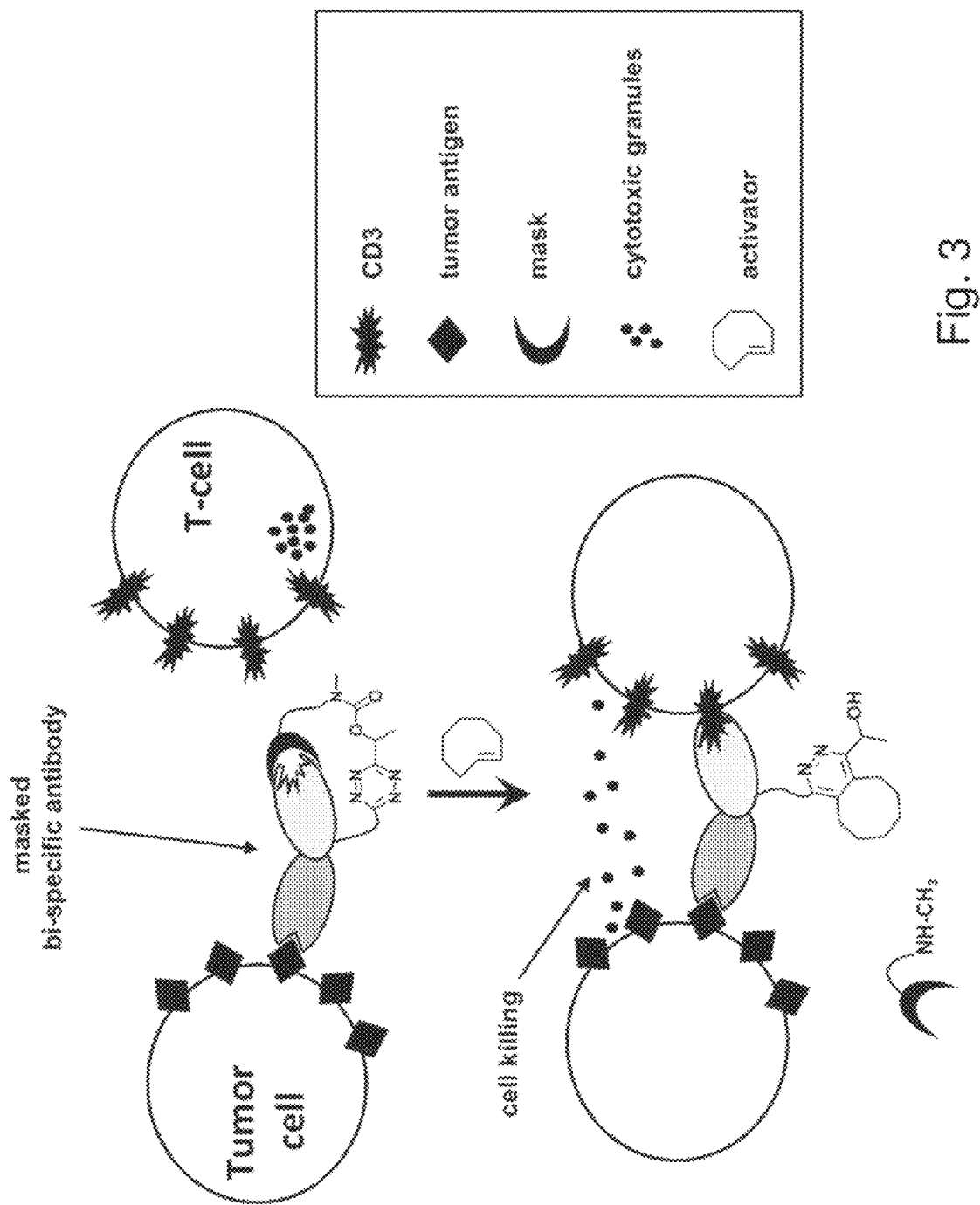
FIG. 3 depicts another general concept of Prodrug activation using the Triggers and Activator of the invention.

FIGS. 2 and 3 depict a preferred embodiment of this invention. In FIG. 2 a Trigger is used that is believed to function via the Cyclization mechanism, in FIG. 3 a Trigger is used that is believed to function via the Cascade mechanism. In both Figures a bispecific antibody drug ($D^D$) is used that targets a Primary Target on tumor cells and CD3 on T-cells. The CD3 binding antibody comprised in this bispecific antibody is masked by a Masking Moiety $M^M$ covalently linked to the antibody via a tetrazine Trigger. This Prodrug is administered to a cancer patient, and is allowed to circulate and bind to a Primary Target on the cancer cell. After the freely circulating Prodrug has sufficiently cleared from circulation, for example after 2 days post injection, the Activator, in this case a TCO, is administered and distributes systemically, allowing the reaction with the Trigger of cancer-bound Prodrug, releasing the $M^M$ from the Drug, after which the CD3 binding antibody comprised in this bispecific antibody can bind to T-cells, crosslinking the T-cell to the tumor cell, resulting in killing of the tumor cell.

For applications where masked drugs, i.e. Prodrugs, are unmasked: either $C^B$ is a Masking moiety $M^M$ and $C^A$ is Drug $D^D$ or $C^A$ is a Masking Moiety $M^M$ and $C^B$ is Drug $D^D$;

When $C^B$ is $M^M$ then the parameters in Formula (5a) are: d=1; a,f, ≥1; c,b,e,g,h≥0; and the parameters in Formula (5b) are: d=1; a,b,f, ≥1; c,e,g,h≥0

When $C^A$ is $M^M$ then the parameters in Formula (5a) are: f=1; a,d≥1; c,b,e,g,h≥0; and the parameters in Formula (5b) are: f=1; a,b,d≥1; c,e,g,h 0

When $D^D$ is $C^B$ it is preferred that $D^D$ is not attached to remainder of the Prodrug through its antigen-binding domain. Preferably $D^D$ is $C^A$.

Although it has been omitted for the sake of clarity in formula 5a-b, $D^D$ can optionally be bound to an (additional) $T^T$, optionally via $S^P$.

Masking moieties $M^M$ can for example be a protein, peptide, polymer, polyethylene glycol, carbohydrate, organic construct, or a combination thereof that further shield the bound drug $D^D$ or Prodrug. This shielding can be based on e.g. steric hindrance, but it can also be based on a non covalent interaction with the drug $D^D$. Such Masking Moiety may also be used to affect the in vivo properties (e.g. blood clearance; recognition by the immune system) of the drug $D^D$ or Prodrug.

In some embodiments the $T^R$ can itself act as a Masking Moiety, provided that CA is $D^D$. For the sake of clarity, in these embodiments the size if the $T^R$ without the attachment of a $M^M$ is sufficient to shield the Drug $D^D$ from its Primary Target.

The $M^M$ of the modified $D^D$ can reduce the $D^D$'s ability to bind its target allosterically or sterically.

In specific embodiments, the $M^M$ is a peptide and does not comprise more than 50% amino acid sequence similarity to a natural protein-based binding partner of an antibody-based $D^D$.

In some embodiments $M^M$ is a peptide between 2 and 40 amino acids in length.

In one embodiment the $M^M$ reduces the ability of the $D^D$ to bind its target such that the dissociation constant of the $D^D$ when coupled to the $M^M$ towards the target is at least 100 times greater than the dissociation constant towards the target of the $D^D$ when not coupled to the $M^M$. In another embodiment, the coupling of the $M^M$ to the $D^D$ reduces the ability of the $D^D$ to bind its target by at least 90%.

In some embodiments the $M^M$ in the masked $D^D$ reduces the ability of the $D^D$ to bind the target by at least 50%, by at least 60%, by at least 70%, by at least 75%, by at least 80%, by at least 85%, by at least 90%, by at least 95%, by at least 96%, by at least 97%, by at least 98%, by at least 99%, or by 100%, as compared to the ability of the unmasked $D^D$ to bind the target. The reduction in the ability of a $D^D$ to bind the target can be determined, for example, by using an in vitro displacement assay, such as for example described for antibody $D^D$ in WO2009/025846 and WO2010/081173.

In preferred embodiments the $D^D$ comprised in the masked $D^D$ is an antibody, which expressly includes full-length antibodies, antigen-binding fragments thereof, antibody derivatives antibody analogs, antibody mimics and fusions of antibodies or antibody derivatives.

In certain embodiments the $M^M$ is not a natural binding partner of the antibody. In some embodiments, the $M^M$ contains no or substantially no homology to any natural binding partner of the antibody. In other embodiments the $M^M$ is no more than 5%, 10%, 15%, 20%, 25%, 30%, 35%, 40%, 45%, 50%, 55%, 60%, 65%, 70%, 75%, or 80% similar to any natural binding partner of the antibody. In some embodiments the $M^M$ is no more than 5%, 10%, 15%, 20%, 25%, 30%, 35%, 40%, 45%, 50%, 55%, 60%, 65%, 70%, 75%, or 80% identical to any natural binding partner of the antibody. In some embodiments, the $M^M$ is no more than 50% identical to any natural binding partner of the antibody. In some embodiments, the $M^M$ is no more than 25% identical to any natural binding partner of the antibody. In some embodiments, the $M^M$ is no more than 20% identical to any natural binding partner of the antibody. In some embodiments, the $M^M$ is no more than 10% identical to any natural binding partner of the antibody.

In the Prodrug, the $M^M$ and the Trigger $T^R$—the tetrazine derivative—can be directly linked to each other. They can also be bound to each other via a spacer $S^P$ or a self-immolative linker $L^C$. It will be understood that the invention encompasses any conceivable manner in which the diene Trigger is attached to the $M^M$. It will be understood that $M^M$ is linked to the tetrazine in such a way that the $M^M$ is eventually capable of being released from the $D^D$ after formation of the IEDDA adduct. Generally, this means that the bond between the $D^D$ and the tetrazine, or in the event of a self-immolative linker $L^C$ the bond between the $L^C$ and the tetrazine and between the $D^D$ and the $L^C$ should be cleavable. Alternatively, this means that the bond between the $M^M$ and the tetrazine, or in the event of a self-immolative linker $L^C$ the bond between the $L^C$ and the tetrazine and between the $M^M$ and the $L^C$ should be cleavable.

In some embodiments, the antibody comprised in the masked antibody is a multi-antigen targeting antibody, comprising at least a first antibody or antigen-binding fragment or mimic thereof that binds a first Primary Target and a second antibody or antigen-binding fragment or mimic thereof that binds a second Primary Target. In some embodiments, the antibody comprised in the masked antibody is a multi-antigen targeting antibody, comprising a first antibody or antigen-binding fragment or mimic thereof that binds a first Primary Target, a second antibody or antigen-binding fragment or mimic thereof that binds a second Primary Target, and a third antibody or antigen-binding fragment or mimic thereof that binds a third Primary Target. In some embodiments, the multi-antigen targeting antibodies bind two or more different Primary Targets. In some embodiments, the multi-antigen targeting antibodies bind two or more different epitopes on the same Primary Target. In some embodiments the multi-antigen targeting antibodies bind a combination of two or more different targets and two or more different epitopes on the same Primary Target. In some embodiments the masked multi-antigen targeting antibodies comprise one $M^M$ group, or two or more $M^M$ groups.

In some embodiments of a multispecific activatable antibody, a scFv can be fused to the carboxyl terminus of the heavy chain of an IgG activatable antibody, to the carboxyl terminus of the light chain of an IgG activatable antibody, or to the carboxyl termini of both light and the heavy chain of an IgG activatable antibody. In some embodiments of a multispecific activatable antibody, a scFv can be fused to the amino terminus of the heavy chain of an IgG activatable antibody, to the amino terminus of the light chain of an IgG activatable antibody, or to the amino termini of both light and the heavy chain of an IgG activatable antibody. In some embodiments of a multispecific activatable antibody, a scFv can be fused to any combination of one or more carboxyl termini and one or more amino termini of an IgG activatable antibody. Methods of preparing multispecific antibodies are known to the person skilled in the art. In addition reference is made to [Weilde et al., Cancer Genomics & Proteomics 2013, 10, 1-18], [Weidle et al., Seminars in Oncology 2014, 41, 5, 653-660], [Jachimowicz et al., BioDrugs (2014) 28:331-343], the contents of which are hereby incorporated by reference.

In some embodiments, a $M^M$ linked to a $T^R$ is attached to and masks an antigen binding domain of the IgG. In some embodiments, a $M^M$ linked to a $T^R$ is attached to and masks an antigen binding domain of at least one scFv. In some embodiments, a MM linked to a $T^R$ is attached to and masks an antigen binding domain of the IgG and a $M^M$ linked to a $T^R$ is attached to and masks an antigen binding domain of at least one scFv.

In some embodiments, the $M^M$ has a dissociation constant, i.e., dissociation constant at an equilibrium state, $K_d$, for binding to the antibody that is greater than the $K_d$ for binding of the antibody to its Primary Target. In some embodiments, the $M^M$ has a $K_d$ for binding to the antibody that is approximately equal to the $K_d$ for binding of the antibody to its Primary Target. In some embodiments, the MM has a $K_d$ for binding to the antibody that is less than the $K_d$ for binding of the antibody to its Primary Target. In some embodiments, the $M^M$ has a $K_d$ for binding to the antibody that is no more than 2, 3, 4, 5, 10, 25, 50, 100, 250, 500, or 1,000 fold greater than the $K_d$ for binding of the antibody to its Primary Target. In some embodiments, the $M^M$ has a $K_d$ for binding to the antibody that is between 1-5, 2-5, 2-10, 5-10, 5-20, 5-50, 5-100, 10-100, 10-1,000, 20-100, 20-1,000, or 100-1,000 fold greater than the $K_d$ for binding of the antibody to its Primary Target.

In some embodiments, the $M^M$ has an affinity for binding to the antibody that is greater than the affinity of binding of the antibody to its Primary Target. In some embodiments, the $M^M$ has an affinity for binding to the antibody that is approximately equal to the affinity of binding of the antibody to its Primary Target. In some embodiments, the $M^M$ has an affinity for binding to the antibody that is less than the affinity of binding of the antibody to its Primary Target. In some embodiments, the MM has an affinity for binding to the antibody that is 2, 3, 4, 5, 10, 25, 50, 100, 250, 500, or 1,000 fold less than the affinity of binding of the antibody to its Primary Target. In some embodiments, the $M^M$ has an affinity of binding to the antibody that is between 1-5, 2-5, 2-10, 5-10, 5-20, 5-50, 5-100, 10-100, 10-1,000, 20-100, 20-1,000, or 100-1,000 fold less than the affinity of binding of the antibody to its Primary Target. In some embodiments, the $M^M$ has an affinity of binding to the antibody that is 2 to 20 fold less than the affinity of binding of the antibody to its Primary Target.

In some embodiments, a $M^M$ not covalently linked to the antibody and at equimolar concentration to the antibody does not inhibit the binding of the antibody to its Primary Target. In some embodiments, the $M^M$ does not interfere of compete with the antibody for binding to the Primary Target when the Prodrug is in a cleaved state.

In some embodiments, the antibody has a dissociation constant of about 100 nM or less for binding to its Primary Target.

In some embodiments, the antibody has a dissociation constant of about 10 nM or less for binding to its Primary Target.

In some embodiments, the antibody has a dissociation constant of about 1 nM or less for binding to its Primary Target.

In some embodiments, the coupling of the MM reduces the ability of the antibody to bind its Primary Target such that the dissociation constant ($K_d$) of the antibody when coupled to the $M^M$ towards its Primary Target is at least 20 times greater than the $K_d$ of the antibody when not coupled to the $M^M$ towards its Primary Target.

In some embodiments, the coupling of the $M^m$ reduces the ability of the antibody to bind its Primary Target such that the $K_d$ of the antibody when coupled to the $M^M$ towards its Primary Target is at least 40 times greater than the $K_d$ of the antibody when not coupled to the MM towards its Primary Target.

In some embodiments, the coupling of the $M^M$ reduces the ability of the antibody to bind its Primary Target such that the $K_d$ of the antibody when coupled to the $M^M$ towards its Primary Target is at least 100 times greater than the $K_d$ of the antibody when not coupled to the $M^M$ towards its Primary Target.

In some embodiments, the coupling of the $M^m$ reduces the ability of the antibody to bind its Primary Target such that the $K_d$ of the antibody when coupled to the $M^M$ towards its Primary Target is at least 1,000 times greater than the $K_d$ of the antibody when not coupled to the $M^M$ towards its Primary Target.

In some embodiments, the coupling of the $M^m$ reduces the ability of the antibody to bind its Primary Target such that the $K_d$ of the antibody when coupled to the $M^M$ towards its Primary Target is at least 10,000 times greater than the $K_d$ of the antibody when not coupled to the $M^M$ towards its Primary Target.

In some embodiments, for example when using a non-binding steric Mm as defined below, the coupling of the $M^M$ reduces the ability of the antibody to bind its Primary Target such that the $K_d$ of the antibody when coupled to the $M^M$ towards its Primary Target is at least 100,000 times greater than the $K_d$ of the antibody when not coupled to the $M^m$ towards its Primary Target.

In some embodiments, for example when using a non-binding steric $M^m$ as defined below, the coupling of the $M^M$ reduces the ability of the antibody to bind its Primary Target such that the $K_d$ of the antibody when coupled to the $M^M$ towards its Primary Target is at least 1,000,000 times greater than the $K_d$ of the antibody when not coupled to the $M^M$ towards its Primary Target.

In some embodiments, for example when using a non-binding steric Mm as defined below, the coupling of the $M^M$ reduces the ability of the antibody to bind its Primary Target such that the $K_d$ of the antibody when coupled to the $M^M$ towards its Primary Target is at least 10,000,000 times greater than the $K_d$ of the antibody when not coupled to the $M^m$ towards its Primary Target.

In many embodiments it may be desirable to insert one or more spacers, e.g. flexible Spacers, into the masked $D^D$ construct so as to provide for flexibility at the $M^M$-$T^R$ junction, the $T^R$-$D^D$ junction, or both. For example, the antibody or the $M^M$ may not contain a sufficient number of residues (e.g. Gly, Ser, Asp, Asn, especially Gly and Ser, particularly Gly) to provide the desired flexibility. As such the masked antibody may benefit from the introduction of a flexible Spacer $S^P$, as defined herein above, for example, one or more amino acids, PEG, PPG, or other hydrophilic polymer, or carbohydrate or oligosaccharide. Aforementioned flexible Spacer may facilitate formation and maintenance of a cyclic structure in the uncleaved masked antibody construct.

For example, in certain embodiments a Prodrug or masked $D^D$ obeys one of the following Formulae 7a-d, which are embodiments of Formulae 5a and 5b, wherein, in case of the use of peptides, the Formulae below may comprise an amino sequence in either N- to C-terminal direction or C- to N-terminal direction or both.

Formulae 7a-d $$C^B-(S^{P2})_e-T^R-(L^C)_b-(S^{P1})_c-C^A \quad (7a)$$

$$C^B-(S^{P2})_e-\underset{\underset{L^C}{|}}{T^R}-(S^{P1})_c-C^A \quad (7b)$$

$$C^B-(S^{P2})_e-(L^C)_b-T^R-(L^C)_b-(S^{P1})_c-C^A \quad (7c)$$

$$T^R-(L^C)_b-C^A \quad (7d)$$

wherein each b, c, and e are independently 0 or 1, and $S^{P1}$ and $S^{P2}$ are respectively Spacer-1 and Spacer-2 and are independently as defined for $S^P$, and wherein $C^A$ and $C^B$ are respectively $D^D$ and Mm, or wherein $C^A$ and $C^B$ are respectively $M^M$ and $D^D$.

With reference to Formulae 7a-d it is preferred that $L^C$, if present, is self-immolative. In some embodiments, it is preferred that $C^A$ is $D^D$ and $C^B$ is $M^M$ and that c is 0.

With reference to Formula 7c it is preferred that the $T^R$ releases $C^A$ and $C^B$ through the Cascade Mechanism.

With reference to Formula 7d, here $C^A$ is $D^D$ and the Trigger itself masks the $D^D$.

Suitable Spacers $S^P$, including $S^{P1}$ and $S^{P2}$, for use in a Prodrug of this invention are listed in the section Spacers herein above. In some embodiments the Spacer has at most 50 carbon atoms, more preferably at most 25 carbon atoms, more preferably at most 10 carbon atoms. Non-limiting examples of suitable Spacers are the Spacers defined as the group "$Q^1$" in the section on Spacers herein above.

In some embodiments it is preferred that the Spacer is a peptide. When $S^{P1}$ and/or $S^{P2}$ is a peptide, the peptide includes at least 1 flexible amino acid, e.g. Gly. Suitable Spacers facilitate the inhibition of the binding of the antibody to a Primary Target and are generally referred to as flexible Spacers. Suitable Spacers can be readily selected and can be of different lengths, such as from 1 amino acid (e.g. Gly) to 25 amino acids, from 1 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24 or 25 amino acids in length.

Exemplary peptide-based spacers include glycine polymers (G)n, glycine-serine polymers (including, for example, (GS)n, (GSGGS)n and (GGGS)n, where n is an integer of at least one), glycine-alanine polymers, alanine-serine polymers, and other flexible spacers known in the art. Glycine and glycine-serine polymers are relatively unstructured, and therefore may be able to serve as a neutral tether between components. Exemplary spacers include, but are not limited to GGSG, GGSGG, GGSGSG, GSGGG, GGGSG, GSSSG, and the like. The ordinary skilled artisan will recognize that design of a masked antibody can include spacers that are all or partially flexible, such that the spacer can include a flexible spacer as well as one or more portions that confer less flexible structure to provide for a desired activatable antibody structure. Aforementioned and further examples are provided in Patent applications WO2015/013671, WO2016/014974, US20150118254, US20140023664, the contents of which are hereby incorporated by reference.

Other preferred Spacers are PEG and PPG polymers, and oligopeptoids, preferably ranging from 2 to 50 repeating units, more preferably from 2 to 24 repeating units, more preferably from 2 to 12 repeating units.

In some embodiments, masked antibodies of the disclosure may in part be made biosynthetically using recombinant DNA technology and expression in eukaryotic or prokaryotic species. For example, when $C^A$ is $D^D$, the cDNAs encoding an optional $S^{P1}$ fused to the antibody chain (heavy or light) can be linked in a 5' to 3' (N- to C-terminal in the translated product) sequence to create the nucleic acid construct, which is expressed as the antibody construct following a conventional antibody expression process. Subsequently, $C^B—(S^P)_c$-$T^R$-$(L^C)_b$ (in the case of Formula 7a), $C^B—(S^{P2})_c$-$(L^C)_b$-$(T^R)$ (in the case of Formula 7b), or $C^B—(S)_e$-$(L^C)_b$-$T^R$-$(L^C)_b$ (in the case of Formula 7c), may be coupled chemically to the protein, optionally via $S^{P1}$, for example via the N-terminus. In other embodiments, $S^{P1}$ is not genetically introduced in the antibody but coupled chemically, in which case one of the following compositions are conjugated to the antibody: $C^B—(S)_e$-$T^R(L^C)_b$-$(S^{P1})_c$, $C^B—(S^{P2})_e$-$(L^C)_b$-$(T^R)$-$(S^P)_c$, $C^B—(S^P)_e$-$(L^C)_b$-$T^R$-$(L^C)_b$-$(S^{P1})_c$. For example, antibody conjugation can be done site specifically be means of the genetically engineered introduction of a cysteine or an artificial amino acid near the N-terminus of the protein. Non-limiting examples of methods for the introduction of specific residues for conjugation are site-directed mutagenesis, chemical conversion, or misincorporation of non-natural amino acids. In other cases particular interchain or intrachain disulfide bonds can be reduced followed by conjugation. Methods for site specific protein conjugation, for example by genetic incorporation of artificial amino acids, followed by selection conjugation, are known in the art and are outlined and referred to in the section on Conjugation (vide supra).

In other embodiments the $M^M$ does not bind specifically to the antibody. In these embodiments the $M^M$ is a non-binding steric $M^M$ and equals a Spacer $S^P$. In the uncleaved state, the non-binding steric $M^M$ interferes with binding of the antibody to the target. In the cleaved state the non-binding steric $M^M$ does not interfere with binding of the antibody to the target. Preferable non-binding steric $M^M$ include oligo- or polypeptides, oligo- or polypeptoids, or oligo- or polylactides, or oligo- or poly-carbohydrates, PEG, PPG, dextran, HPMA, polylactic acid (PLA), polylactic-glycolic acid (PLGA), polyglutamic acid (PG), dextran, polyvinylpyrrolidone (PVP), poly(1-hydroxymethylethylene hydroxymethyl-formal (PHF), and other hydrophilic polymers.

In some aspects of the non-binding steric $M^M$ has a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa. In some aspects of the invention, the $S^P$ has a mass of no more than 5000 daltons, no more than 4000 daltons, no more than 3000 daltons, no more than 2000 daltons, no more than 1000 daltons, no more than 800 daltons, no more than 500 daltons, no more than 300 daltons, no more than 200 daltons. In some aspects the $S^P$ has a mass from 100 daltons, from 200 daltons, from 300 daltons to 5000 daltons. In some aspects of the $S^P$ has a mass from 30, 50, or 100 daltons to 1000 daltons, from about 30, 50, or 100 daltons to 500 daltons. Preferably these non-binding steric MM have a mass of no more than 40 kDa.

The non-binding steric $M^M$ may be any biocompatible entity that is of sufficient molecular size to provide steric blockade of the antigen-combining site of the antibody when fused to a site near the antigen-combining site.

In some embodiments, the masked antibody includes a binding partner (BP) for a non-binding steric $M^M$, wherein the BP non-covalently or covalently binds to the $M^M$ when exposed thereto. The BP may be a peptide, polypeptide, small organic molecule, steroid, carbohydrate, maleimide. In some of these embodiments, the masked antibody is formulated as a composition. In some embodiments the composition also includes the non-binding steric $M^M$ as a separate component. In other embodiments the non-binding steric $M^M$ is recruited by the BP in vivo in circulation. In some examples the BP is selected from the group consisting of an albumin binding peptide, a fibrinogen binding peptide, a hemoglobin binding peptide, a transferrin binding peptide, other serum protein binding peptide, and maleimide.

Methods to design, make, develop and use masked antibodies based on protease cleavable linkers are known in the art. The design of the antibody, the location and composition of the binding $M^M$ and the non-binding $M^M$ and the location, length, nature and composition of the Spacers and Linkers $L^C$ in Formulae 7a-d can be derived from the teachings from the following patent applications: WO2015/013671, WO2016/014974, US20150118254, US20140023664, WO2013/192546, the contents of which are hereby incorporated by reference.

Non limiting examples of methods used to engineer and express antibody (derivatives) are described in US20140023664, the contents of which are hereby incorporated by reference.

Suitable formulations and administration of compounds under this invention are known in the art and are for example summarized in US20140023664, the contents of which are hereby incorporated by reference.

It will further be understood that one or more targeting agents $T^T$ may optionally be attached to the Drug $D^D$, Trigger $T^R$, Linker $L^C$ or Masking Moiety $M^M$, optionally via a spacer or spacers $S^P$.

According to a further particular embodiment of the invention, the Prodrug is selected so as to target and or address a disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

Masking moieties MM may also be used to affect the in vivo properties (e.g. blood clearance; recognition by the immune system) of the drug $D^D$ or Prodrug.

Drugs for Unmasking Approach

Drugs that can be used in a Prodrug relevant to this invention include but are not limited to: antibodies, antibody derivatives, antibody fragments, proteins, aptamers, oligopeptides, oligonucleotides, oligosaccharides, carbohydrates, as well as peptides, peptoids, steroids, toxins, hormones, viruses, whole cells, phage.

In one embodiment antibodies are used as the Drug. While antibodies or immunoglobulins derived from IgG antibodies are particularly well-suited for use in this invention, immunoglobulins from any of the classes or subclasses may be selected, e.g. IgG, IgA, IgM, IgD and IgE. Suitably, the immunoglobulins is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, recombinant antibodies, anti-idiotype antibodies, multispecific antibodies, antibody fragments, such as Fv, VHH, Fab, F(ab)$_2$, Fab', Fab'-SH, F(ab')$_2$, single chain variable fragment antibodies (scFv), tandem/bis-scFv, Fc, pFc', scFv-Fc, disulfide Fv (dsFv), bispecific antibodies (bc-scFv) such as BiTE antibodies, camelid antibodies, minibodies, nanobodies, resurfaced antibodies, humanized antibodies, fully human antibodies, single domain antibody (sdAh, also known as Nanobody™), chimeric antibodies, chimeric antibodies comprising at least one human constant region, dual-affinity antibodies such as dual-affinity retargeting proteins (DART™), and multimers and derivatives thereof, such as divalent or multivalent single-chain variable fragments (e.g. di-scFvs, tri-scFvs) including but not limited to minibodies, diabodies, triabodies, tribodies, tetrabodies, and the like, and multivalent antibodies. Reference is made to [Trends in Biotechnology 2015, 33, 2, 65], [Trends Biotechnol. 2012, 30, 575-582], and [Canc. Gen. Prot. 2013 10, 1-18], and [BioDrugs 2014, 28, 331-343], the contents of which is hereby incorporated by reference. Other embodiments use antibody mimetics as Drug, such as but not limited to Affimers, Anticalins, Avimers, Alphabodies, Affibodies, DARPins, and multimers and derivatives thereof; reference is made to [Trends in Biotechnology 2015, 33, 2, 65], the contents of which is hereby incorporated by reference. "Antibody fragment" refers to at least a portion of the variable region of the immunoglobulin that binds to its target, i.e. the antigen-binding region. Multimers may be linearly linked or may be branched and may be derived from a single vector or chemically connected, or non-covalently connected. Methods of making above listed constructs are known in the art. For the avoidance of doubt, in the context of this invention the term "antibody" is meant to encompass all of the antibody variations, fragments, derivatives, fusions, analogs and mimetics outlined in this paragraph, unless specified otherwise.

Typical drugs for which the invention is suitable include, but are not limited to: monospecific, bispecific and trispecific antibodies and antibody fragment or protein fusions, preferably bispecific and trispecific. In some embodiments the activatable antibody or derivative is formulated as part of a pro-Bispecific T Cell Engager (BITE) molecule.

Other embodiments use immunotoxins, which are a fusion or a conjugate between a toxin and an antibody. Typical toxins comprised in an immunotoxins are cholera toxin, ricin A, gelonin, saporin, bouganin, ricin, abrin, diphtheria toxin, Staphylococcal enterotoxin, *Bacillus* Cyt2Aa1 toxin, *Pseudomonas* exotoxin PE38, *Pseudomonas* exotoxin PE38KDEL, granule-associated serine protease granzyme B, human ribonucleases (RNase), or other pro-apoptotic human proteins. Other exemplary cytotoxic human proteins which may be incorporated into fusion constructs are caspase 3, caspase 6, and BH3-interacting domain death agonist (BID). Current immunotoxins have immunogenicity issues and toxicity issues, especially towards vascular endothelial cells. Masking the targeted toxin by a $M^M$ such as a PEG or peptide and removing the $M^M$ once the masked immunotoxin has bound to its target is expected to greatly reduce the toxicity and immunogenicity problems.

Other embodiments use immunocytokines, which are a fusion or a conjugate between a cytokine and an antibody. Typical cytokines used in cancer therapy include IL-2, IL-7, IL-12, IL-15, IL-21, TNF. A typical cytokine used in autoimmune diseases is the anti-inflammatory IL-10. Masking the targeted cytokine by a MM such as a PEG or peptide and removing the $M^M$ once the masked immunocytokine has bound to its target is expected to greatly reduce the toxicity problems.

In some embodiments the unmasked Drug is multispecific and binds to two or more same or different Primary Targets. In some embodiments the multispecific Drug comprises one or more (masked) antibodies (also referred to as binding moieties) that are designed to engage immune effector cells. In some embodiments the masked multispecific Prodrug comprises one or more (masked) antibodies that are designed to engage leukocytes. In some embodiments the masked multispecific Prodrug comprises one or more (masked) antibodies that are designed to engage T cells. In some embodiments the masked multispecific Prodrug comprises one or more (masked) antibodies that engage a surface antigen on a leukocyte such as on a T cell, natural killer (NK) cell, a myeloid mononuclear cell, a macrophage and/or another immune effector cell. In some embodiments the immune effector cell is a leukocyte, a T cell, a NK cell, or a mononuclear cell.

In an exemplary multispecific masked Prodrug the Prodrug comprises an antibody (i.e. binding moiety) for a cancer receptor, e.g. TAG72, a antibody for CD3 on T cells, and an antibody for CD28 on T cells, wherein either the antibody for CD3 or for CD28 or both is masked by a $M^M$. Another example is an activatable antibody that comprises an antibody for a cancer receptor, and an antibody for CD3 on T cells, wherein the antibody for CD3 is masked by a $M^M$. Another example is a Prodrug that has an antibody for a cancer receptor, and an antibody for CD28 on T cells, wherein the antibody for CD28 is masked by a MM. Another example is a Prodrug that has an antibody for a cancer receptor, and an antibody for CD16a on NK cells, wherein the antibody for CD16a is masked by a $M^M$. In yet another embodiment the unmasked Drug binds two different immune cells and optionally in addition a tumor cell. Said multispecific antibody derivatives can for example be prepared by fusing or conjugating antibodies, antibody fragments such as Fab, Fabs, scFv, camel antibody heavy chain fragments and proteins.

In some preferred embodiments the $M^M$ reduces the binding of the Drug to Primary Targets selected from CD3, CD28, PD-L1, PD-1, LAG-3, TIGIT, TIM-3, B7H4, Vista, CTLA-4 polysialic acids and corresponding lectins. In other preferred embodiments the $M^M$ masks a T-cell agonist, an NK cell agonist, an DC cell agonist.

In some embodiments of an immune effector cell engaging masked multispecific Prodrug such as a T-cell engaging multispecific activatable antibody, at least one antibody comprised in the Prodrug binds a Primary Target that is typically an antigen present on the surface of a tumor cell or other cell type associated with disease, such as, but not limited to, EGFR, erbB2, EpCAM, PD-L1, B7H3 or CD71 (transferrin receptor), and at least one other antibody comprised in the Prodrug binds Primary Target that is typically a stimulatory or inhibitory antigen present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3 or VISTA. In some embodiments it is preferred that the targeted CD3 antigen is CD38 or CD3 epsilon.

One embodiment of the disclosure is a multispecific activatable antibody that includes an antibody directed to a tumor target and another agonist antibody directed to a co-stimulatory receptor expressed on the surface of an activated T cell or NK cell, wherein the agonist antibody is masked. Examples of co-stimulatory receptors include but are not limited to CD27, CD137, GITR, HVEM, NKG2D, OX40. In this embodiment, once the Prodrug is tumor-bound and activated it would effectively crosslink and activate the T cell or NK cell expressed co-stimulatory receptors in a tumor dependent manner to enhance the activity of T cell or NK cells that are responding to any tumor antigen via their endogenous T cell or NK cell activating receptors. The activation dependent nature of these T cell or NK cell co-stimulatory receptors would focus the activity of the activated multispecific Prodrug to tumor specific T cells without activating all T cells independent of their antigen specificity.

One embodiment of the disclosure is a multispecific activatable antibody targeted to a disease characterized by T cell overstimulation, such as, but not limited to, an autoimmune disease or inflammatory disease microenvironment. Such a Prodrug includes an antibody, for example a IgG or scFv, directed to a target comprising a surface antigen expressed in a tissue targeted by a T cell in autoimmune or inflammatory disease and an antibody, for example IgG or scFv, directed to an inhibitory receptor expressed on the surface of a T cell or NK cell, wherein the T cell or NK cell inhibitory antibody is masked. Examples of inhibitory receptors include but are not limited to BTLA, CTLA-4, LAG3, PD-1, TIGIT, TIM3, and NK-expressed KIRs. Examples of a tissue antigen targeted by T cells in autoimmune disease include but are not limited to a surface antigen expressed on myelin or nerve cells in multiple sclerosis or a surface antigen expressed on pancreatic islet cells in Type 1 diabetes. In this embodiment, the Prodrug localizes at the tissue under autoimmune attack or inflammation, is activated by the Activator and co-engages the T-cell or NK cell inhibitory receptor to suppress the activity of autoreactive T cells responding to any disease tissue targeted antigens via their endogenous TCR or activating receptors.

Other non-limiting exemplary Primary Targets for the binding moieties comprised in Drugs of this invention are listed in the patent WO2015/013671, the contents of which are hereby incorporated by reference.

In another embodiment, the Drug is a masked vaccine, which can be unmasked at a desired time and/or selected location in the body, for example subcutaneously and/or in the proximity of lymph nodes. In another embodiment, the Drug is a masked antigen, e.g. a masked peptide, which optionally is present in a Major Histocompatibility Complex (MHC) and which can be unmasked at a desired time and/or selected location in the body, for example subcutaneously and/or in the proximity of lymph nodes.

The Prodrug may further comprise another linked drug, which is released upon target binding, either by proteases, pH, thiols, or by catabolism. Examples are provided in the review on Antibody-drug conjugates in [Polakis, *Pharmacol. Rev.* 2016, 68, 3-19]. Alternatively the drug is linked through a tetrazine linker, cleavable by means of the IEDDA as described in this invention. The invention further contemplates that the Prodrug can induce antibody-dependent cellular toxicity (ADCC) or complement dependent cytotoxicity (CDC) upon unmasking of one or more moieties of the Prodrug. The invention also contemplates that the Prodrug can induce antibody-dependent cellular toxicity (ADCC) or complement dependent cytotoxicity (CDC) independent of unmasking of one or more moieties of the Prodrug.

Some embodiments use as said additional drug antiproliferative/antitumor agents, antibiotics, cytokines, anti-inflammatory agents, anti-viral agents, antihypertensive agents, chemosensitizing, radiosensitizing agents, DNA damaging agents, anti-metabolites, natural products and their analogs.

It is preferred that the Drug is a protein or a antibody.

Application Area 3) Cleavable Linker or Mask for Application in Chemistry and In Vitro The invention includes in one aspect a Trigger which functions as a protective or masking group for use in organic/peptide/protein/bio-/surface/solid-phase chemistry.

Therein, with reference to formula 5a and 5b: f is preferably 0.

Selective removal of the Trigger via reaction with the Activator unmasks the construct (see examples A-D directly below). Exemplary chemical moieties that can be protected and selectively deprotected include, but are not limited to, amines, thiols, hydroxyl, aminooxy groups. Furthermore, the Activator may be conjugated to a resin, especially solid-phase synthesis resins, such as polystyrene, or to a bead. Thus circumventing the need for solution phase purification after the deprotection step.

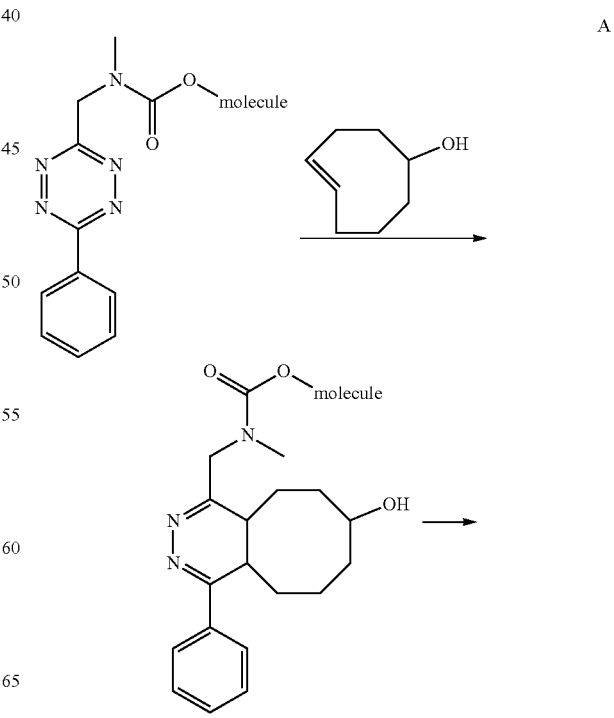

199
-continued
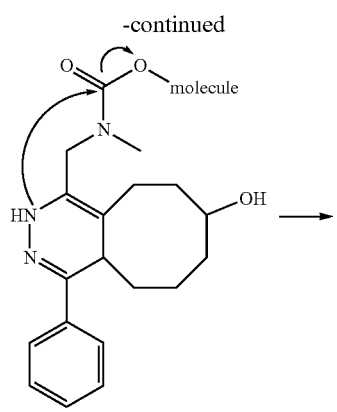
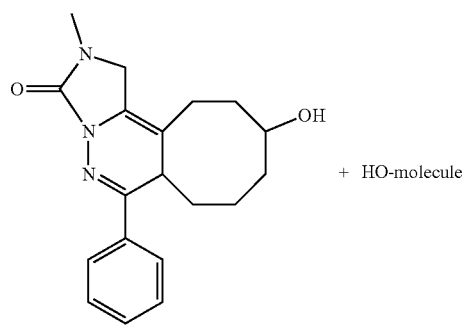
+ HO-molecule
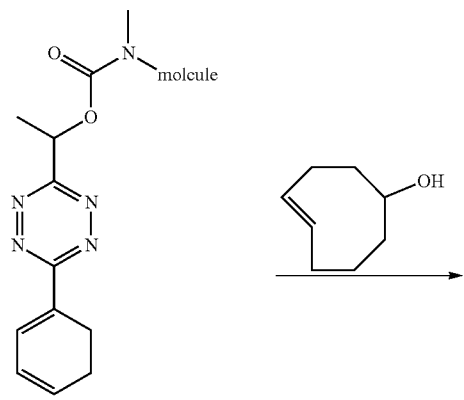
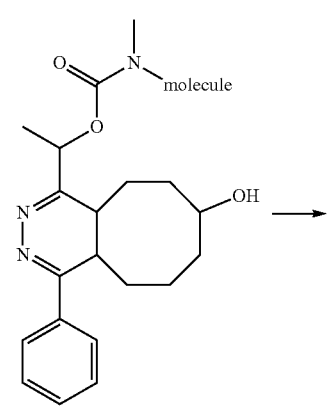
200
-continued
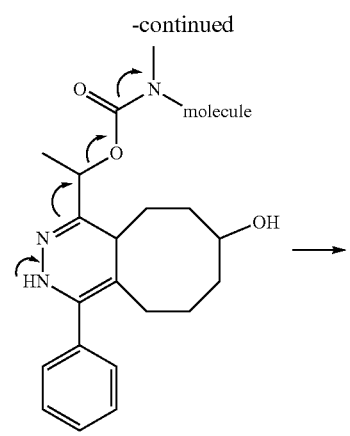
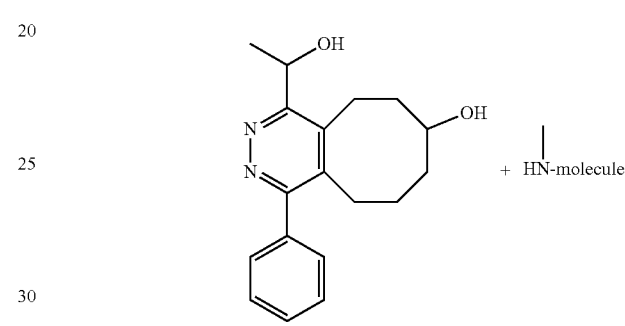
+ HN-molecule
B
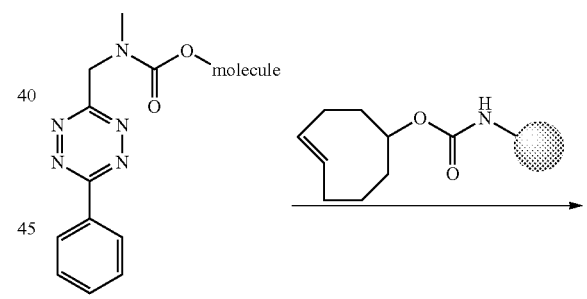
C
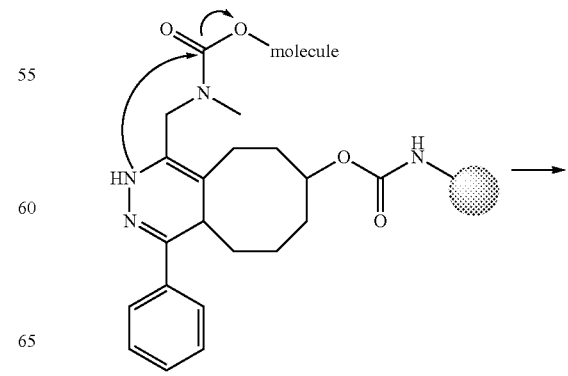

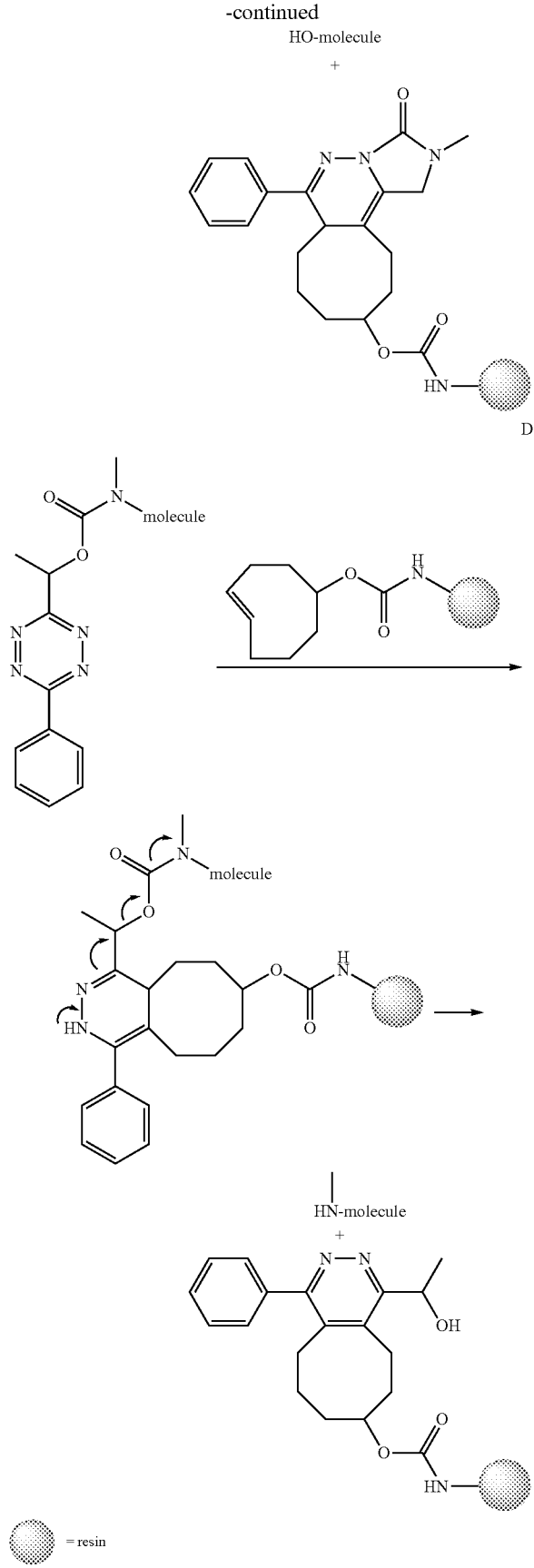

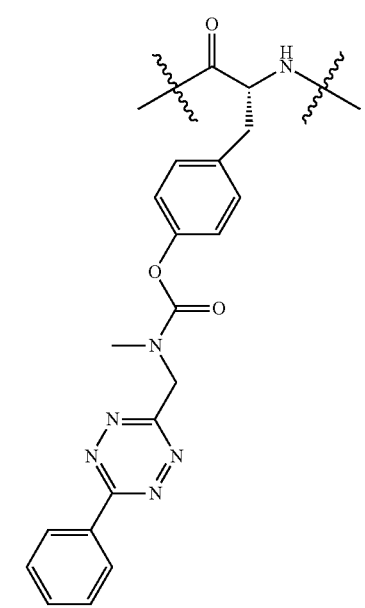

In the case of biomolecules such as proteins the Trigger can be introduced after the protein has been formed or during protein synthesis by means of genetically incorporating a Trigger-modified amino acid. There have been many studies demonstrating the incorporation of unnatural amino acids in proteins, including TCO and tetrazine (e.g. Chalker et al. Acc Chem Res, Vol. 44, No. 9, 2011, 730-741). In this way one can for example conduct bioconjugation chemistry elsewhere on the molecule, after which the tetrazine-masked amino acid can be unveiled and selectively manipulated. This so-called "Tag-and-Modify" approach thus allows for multiple and different post-translational modifications on a single protein and can be extended to controlled assembly and fragmentation of complex materials, proteins, cells, tissues. Examples of masked amino acid derivatives, which can be used in such as approach are shown below. Compound A is the amino acid tyrosine of which the hydroxyl functionality is masked by tetrazine. After release of tetrazine the hydroxyl can be used in conjugation reactions. Compound B is amino acid lysine conjugated via its e-amine moiety to a tetrazine via a self-immolative linker. Compound C is a serine conjugated to a tetrazine via a self-immolative linker.

B

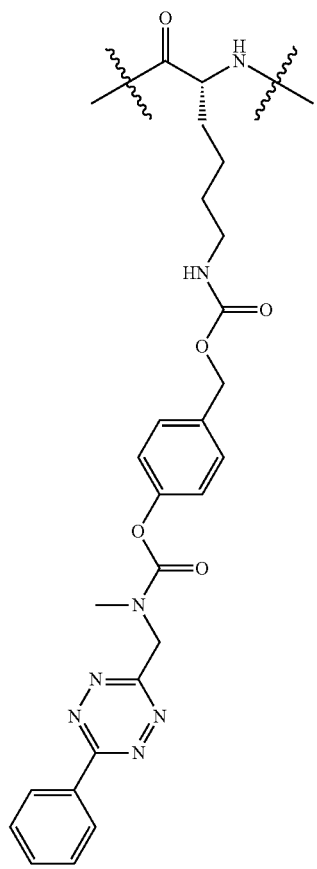

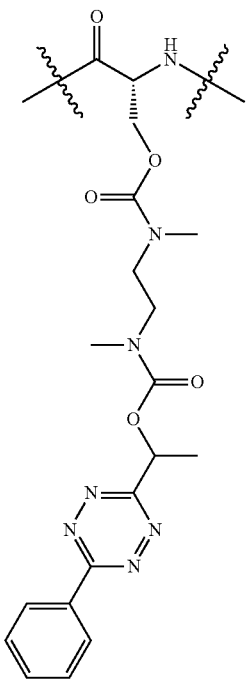

C

ᨴᨴᨴ = rest of peptide or protein

In a similar embodiment depicted below the tetrazine mask is used to stabilize protein formulations in e.g. stock solutions to prevent aggregation and precipitation. For this purpose the tetrazine is functionalized with $C^B$ being an hydrophilic moiety such as a PEG (or e.g. a carbohydrate moiety), and one or multiple tetrazine-$C^B$ groups are conjugated to the protein (being $C^A$) via e.g. tyrosine, serine or lysine residues (see examples A and B directly below). At the time of use, the protein solution is contacted with the Activator yielding the unmasked parent protein $C^A$. Also here it may be advantageous to use an Activator that is conjugated to solid phase synthesis resins or a bead, thus circumventing the need for solution phase purification after the unmasking step.

A

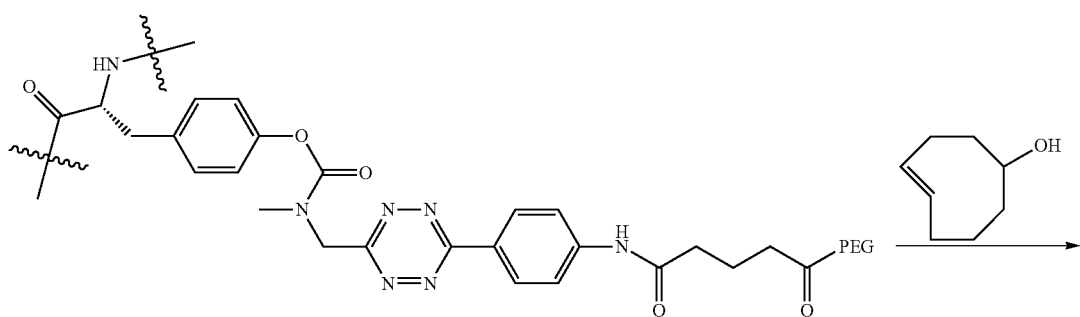

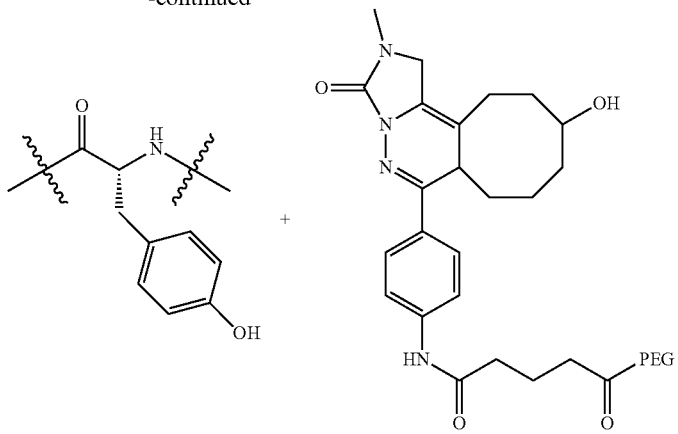

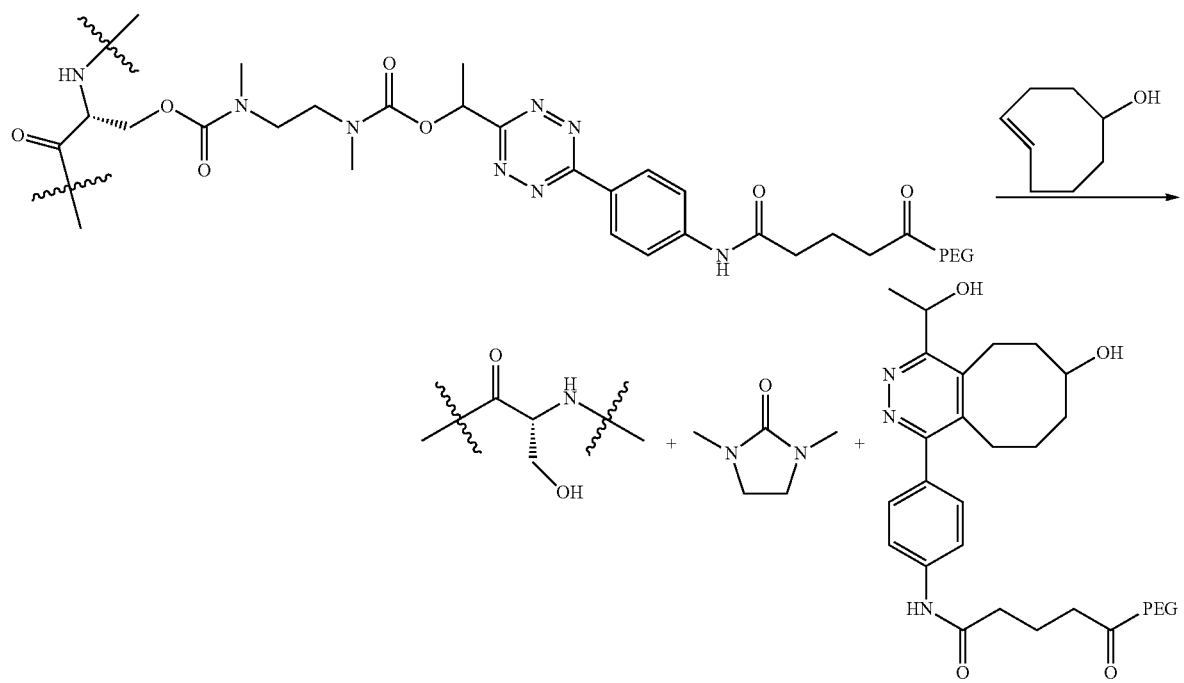

🌊🌊🌊 = rest of peptide or protein

In another embodiment the Trigger is used as a chemically cleavable mask in the patterning or etching of surfaces with application in e.g. spatially controlled cell and tissue culture, or for (e.g. protein, DNA) microarray assembly. Selective removal of the mask reveals e.g. free hydroxyl, amine or thiol moieties (comprised in $C^A$), which can be used for further modifications, such as the conjugation of cell adhering peptides in the case surfaces for cell culture. For example, the tetrazine can be used as cleavable linker between a surface or surface-coated gel and cell-interacting moieties, such as integrin binders, for use in cell culture. After cell culture on this surface or in a 3D gel the cells can be removed from the surface or the surface-coated gel by mild cleavage of the tetrazine, instead of resorting to harsh trypsinization, or physical force.

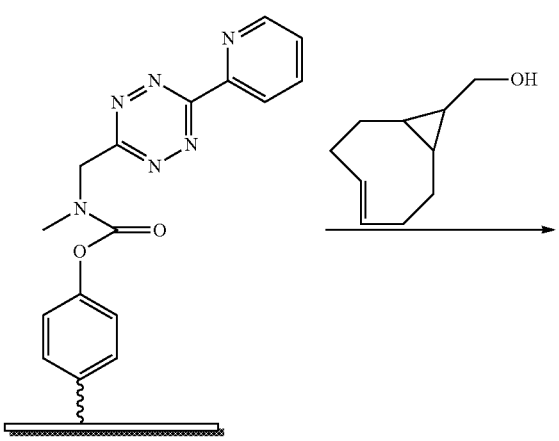

-continued

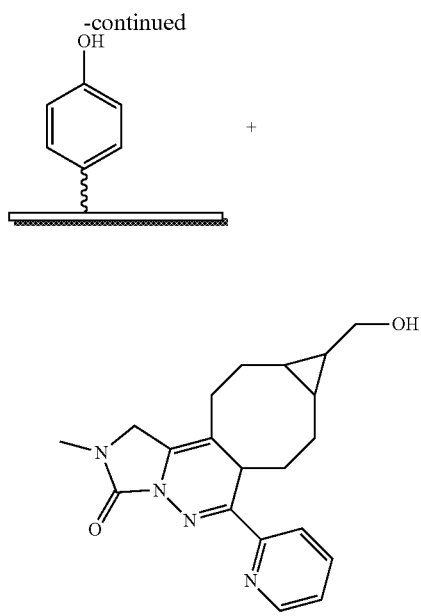

In an alternative embodiment the tetrazine mask is used to spatially and or temporally control the action of biomolecules in vitro or in vivo. For example, the action of a particular enzyme in an in vitro assay can be controlled by using an enzyme that has been deactivated through conjugation to one or more tetrazine masks, followed by contacting the enzyme with the Activator followed by release of the tetrazine mask and, affording the parent, active enzyme ($C^A$). Reference is made to [Li et al. Nat. Chem. Biol., 2014, 10, 1003-1005; Zhang et al. ACS Central Sci. 2016, 2, 5, 325-31], wherein the other, previously developed, IEDDA-based release reaction [Versteegen et al. Angew. Chem. Int. Ed. 2013, 52, 14112-14116] is used to unmask enzymes in living systems. Another example, useful in chemical biology, is the tetrazine-protection of certain amino acid residues in a protein against enzymatic action such as phosphorylation by kinase, allowing spatial and temporal control over the phosphorylation after Activator addition. Alternatively, phosphoamino acids in phosphoproteins can be masked by tetrazine to be revealed at desired time by use of the Activator, as shown in a similar approach using light activatable masks by Rothman et al (2005) J. Am. Chem. Soc, 127, 847.

In another aspect of the invention the Trigger is used as a cleavable linker in "catch and release" systems, such as those used in chemical biology. Therein, with reference to Formula 5a and 5b: f is preferably 1.

One application of these linkers is in the purification of proteins tagged with a biotinylated Activity Based Probes (ABP). Biotinylated ABPs are often used for enrichment of captured enzymes, for instance, by pull-down with streptavidin-coated beads. The main disadvantages of this approach, however, are that the conditions to liberate the captured proteins from the beads are harsh (boiling of the sample, all or not in the presence of unmodified biotin) and that, beside the target proteins, both endogenously biotinylated proteins and (denatured) streptavidin can end up in the sample. In addition the presence of the biotin complicates MS/MS analysis. Furthermore, in another application, this concept can be used to capture and release whole cells with e.g. antibodies conjugated to e.g. a bead or solid support ior example for the purpose of further analysis with FACS, requiring healthy intact cells. Several groups have developed linker systems that can be incorporated in the ABP, or alternatively in a bio-orthogonal reagent for two-step ABPP, and that can be cleaved in a chemoselective manner after affinity pull-down. Examples include the disulfide, diazobenzene, and bisaryl hydrazine cleavable linkers [Willems L. I. et al. (2011) Acc. Chem. Res. 44, 718-729]. However, these linkers have a limited bio-orthogonality. In below scheme several embodiment examples are shown of the use of the IEDDA Trigger for this application. In addition to the enhanced bio-orthogonality this method also offers the opportunity to introduce a new label or affinity tag or to preserve a synthetic handle for further modification, through the binding of the TCO Activator to the tetrazine.

Example A1 depicts the capturing of an enzyme by an ABP conjugated to biotin via a tetrazine linker. The complex is subsequently bound and isolated by streptavidin coated beads, after which the linker is cleaved by the Activator, and the enzyme, comprising the ABP linked to the IEDDA residue is released. In Example A2, the same concept is used with a reversed Trigger, leading to traceless release of the ABP-enzyme complex. Example B depicts an analogous 2 step ABP approach where the enzyme is captured by an ABP functionalized with an azide moiety. The complex is subsequently reacted with a cyclooctyne moiety, which is linked to a biotin via a tetrazine linker. It has been shown in Weissleder Angew. Chem. Int. Ed. 2011, 51, 4, 920-2 that the TCO/tetrazine pair can be used orthogonally to and in the presence of the azide-octyn pair. In Example C the cyclooctyne-tetrazine-biotin probe approach described in B) is used to capture a specific protein, which has metabolically incorporated an azide-modified aminoacid. Example D depicts the capturing of cells using magnetic beads conjugated to antibodies via the Trigger. After binding and isolation using magnetic action, the cells are detached under mild conditions by adding the Activator. Example E depicts an alternative to the general approach in Examples A-D where the tetrazine combines the function of the biotin tag with the function of releasable linker. In this example, target cells are first bound by tetrazine-modified antibodies, followed by addition of TCO-coated beads. Suitably chosen tetrazines and tetrazine-TCO pairs will give a release with a half life of >2 h and given the required reaction time of <10 minutes thus allow enough time for isolation of the bead-cell complex before the complex releases the cell automatically through release of the linker. Reference is made to [Agustin et al., Chem Commun 2016, 52, 7, 1405-8], wherein the other, previously developed, IEDDA-based release reaction [Versteegen et al. Angew. Chem. Int. Ed. 2013, 52, 14112-14116] is used to purify synthesized RNA comprising a TCO by addition of a resin-bound tetrazine, followed by capture and slow release. The tetrazine used in example F is an example of a tetrazine that gives $C^A$ release with a half life of >2 h, largely independent of the type of TCO, provided the TCO reacts with the tetrazine within ca 10 min. Features believed to enable slow release in general include the lack of a methyl substituent on carbamate linked to $C^A$ (example E vs examples A-D). Example F depicts the same embodiment as Example E but now with a Trigger that is believed to function via the Cascade Mechanism.

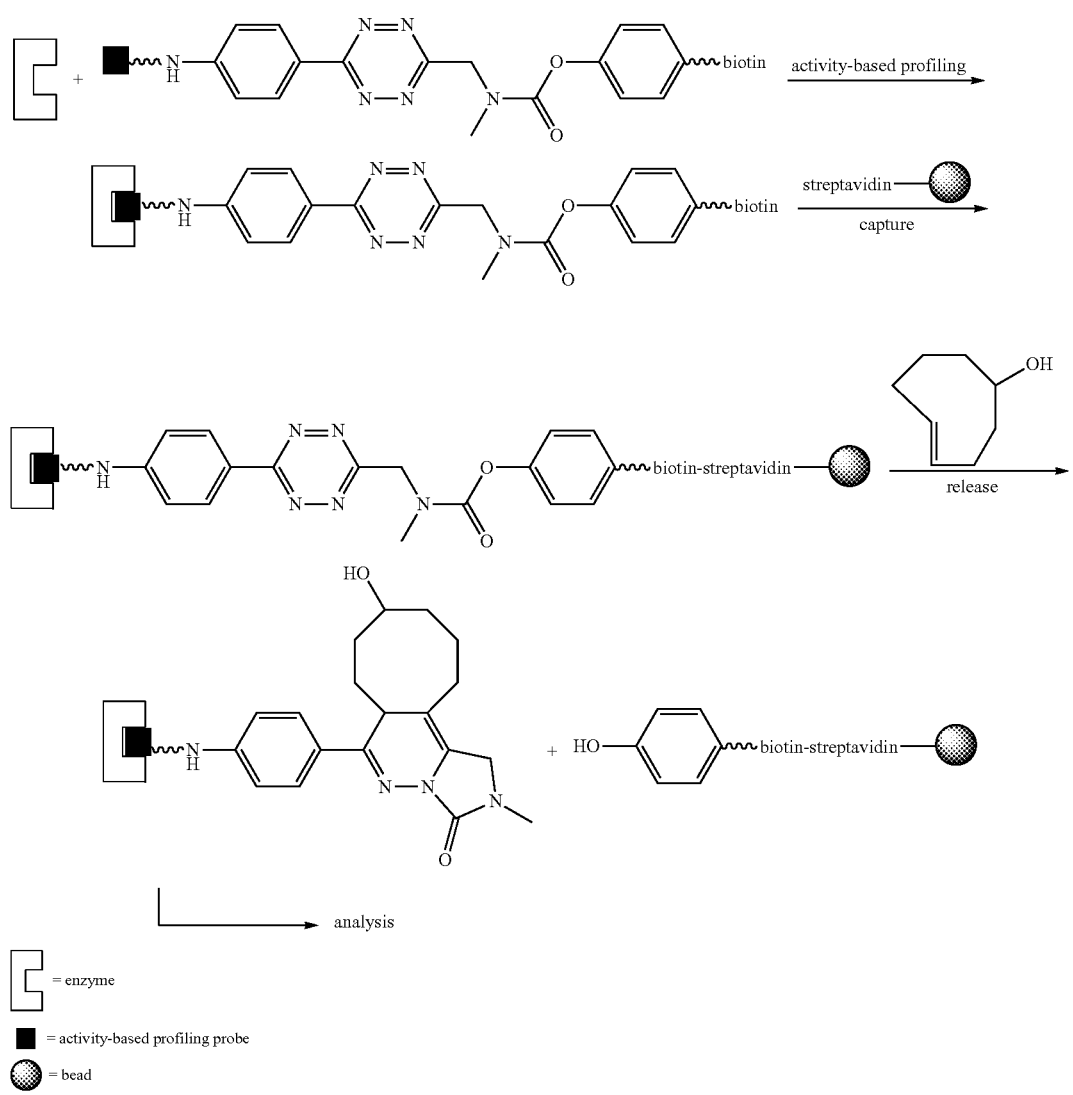
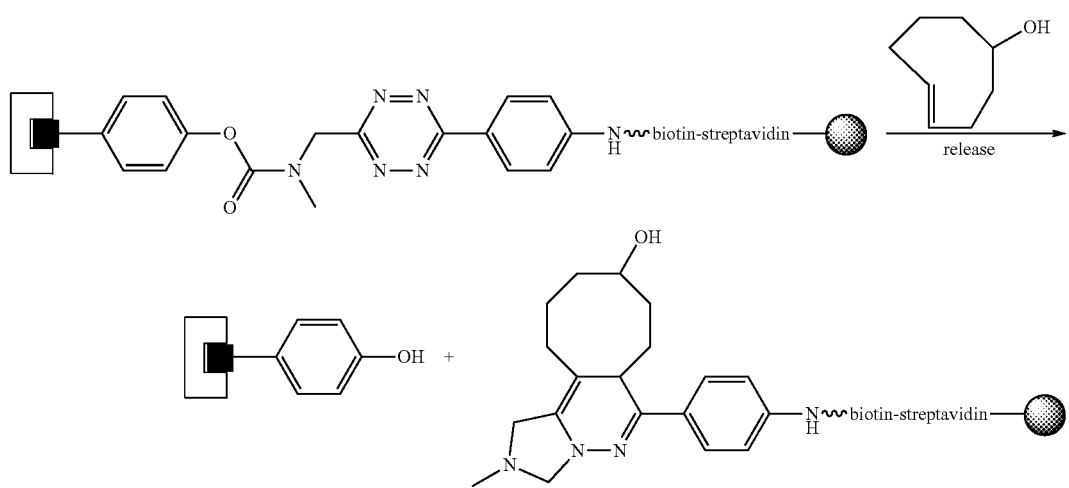
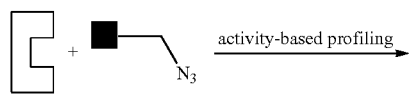

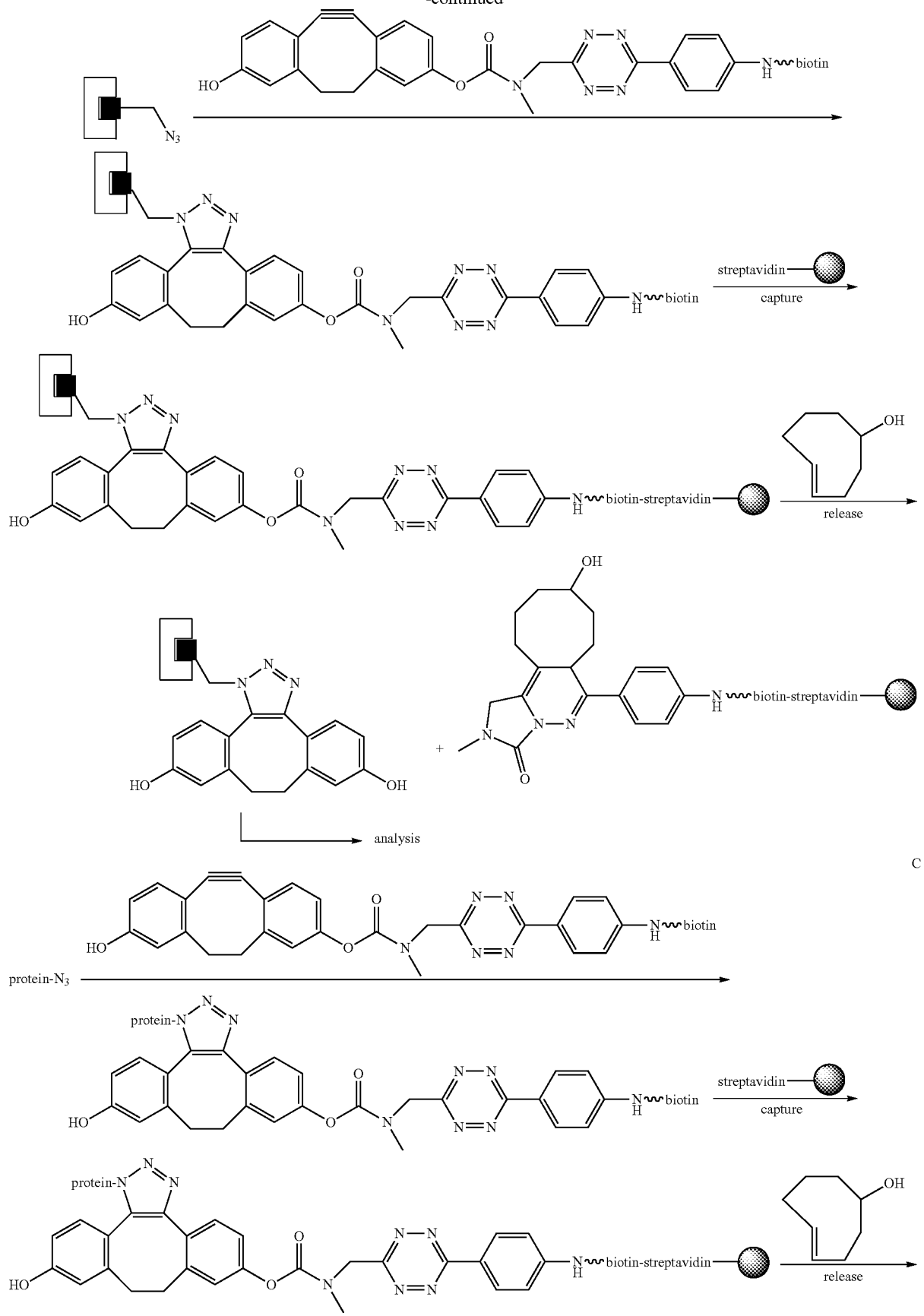

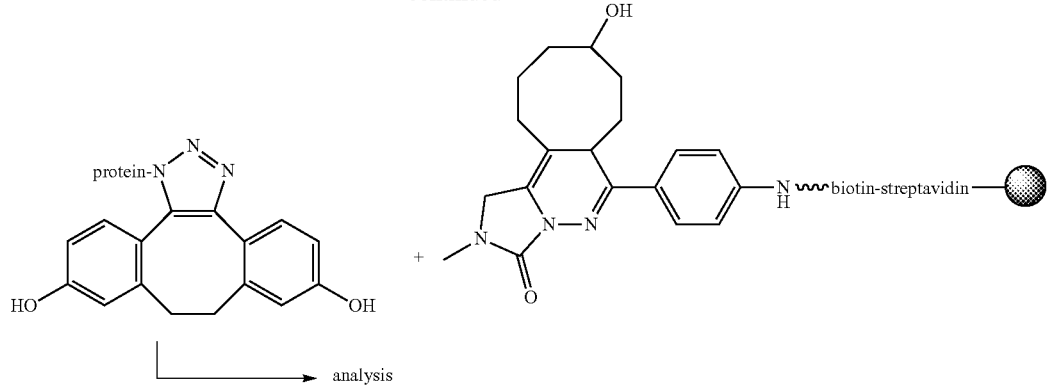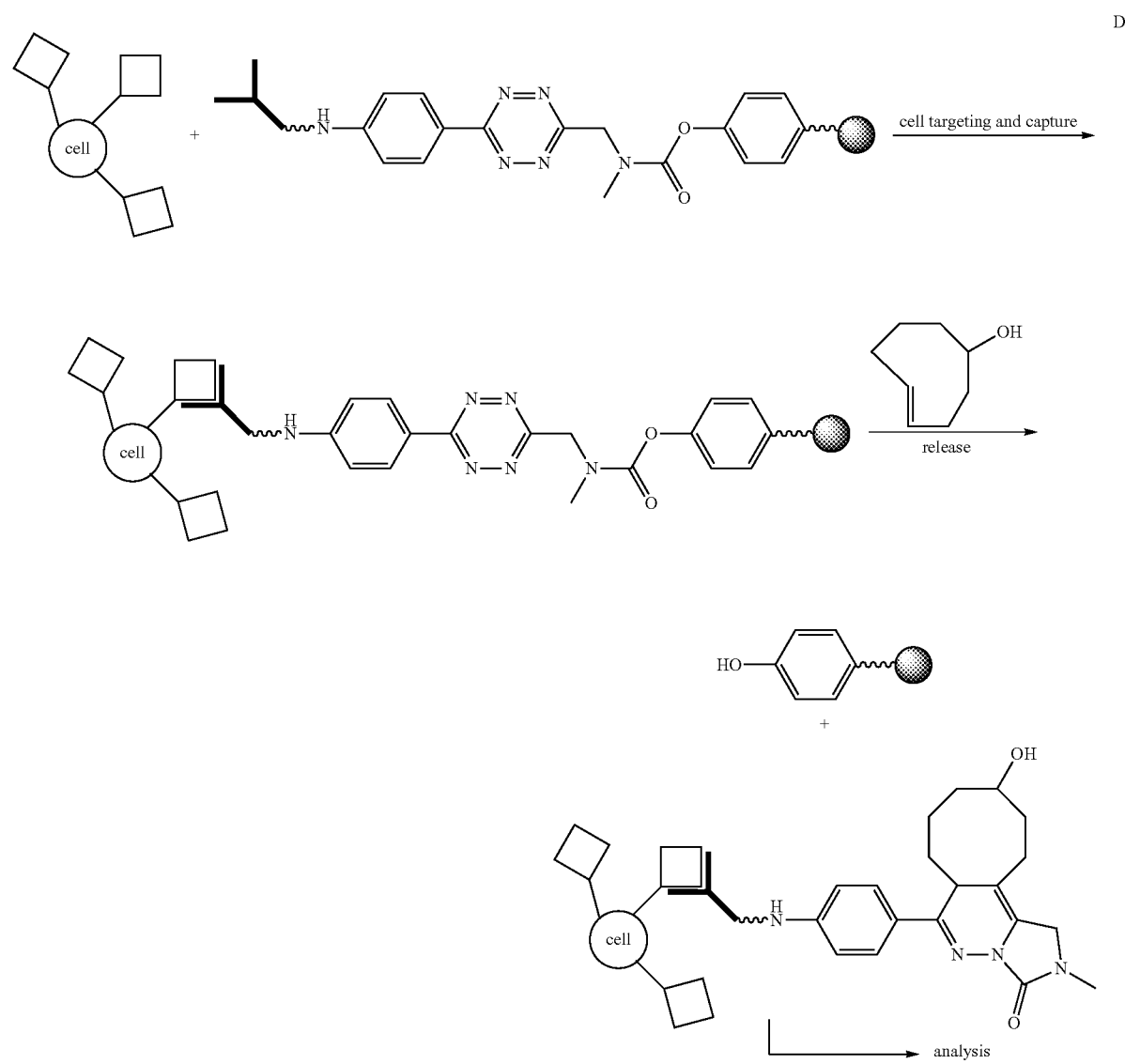

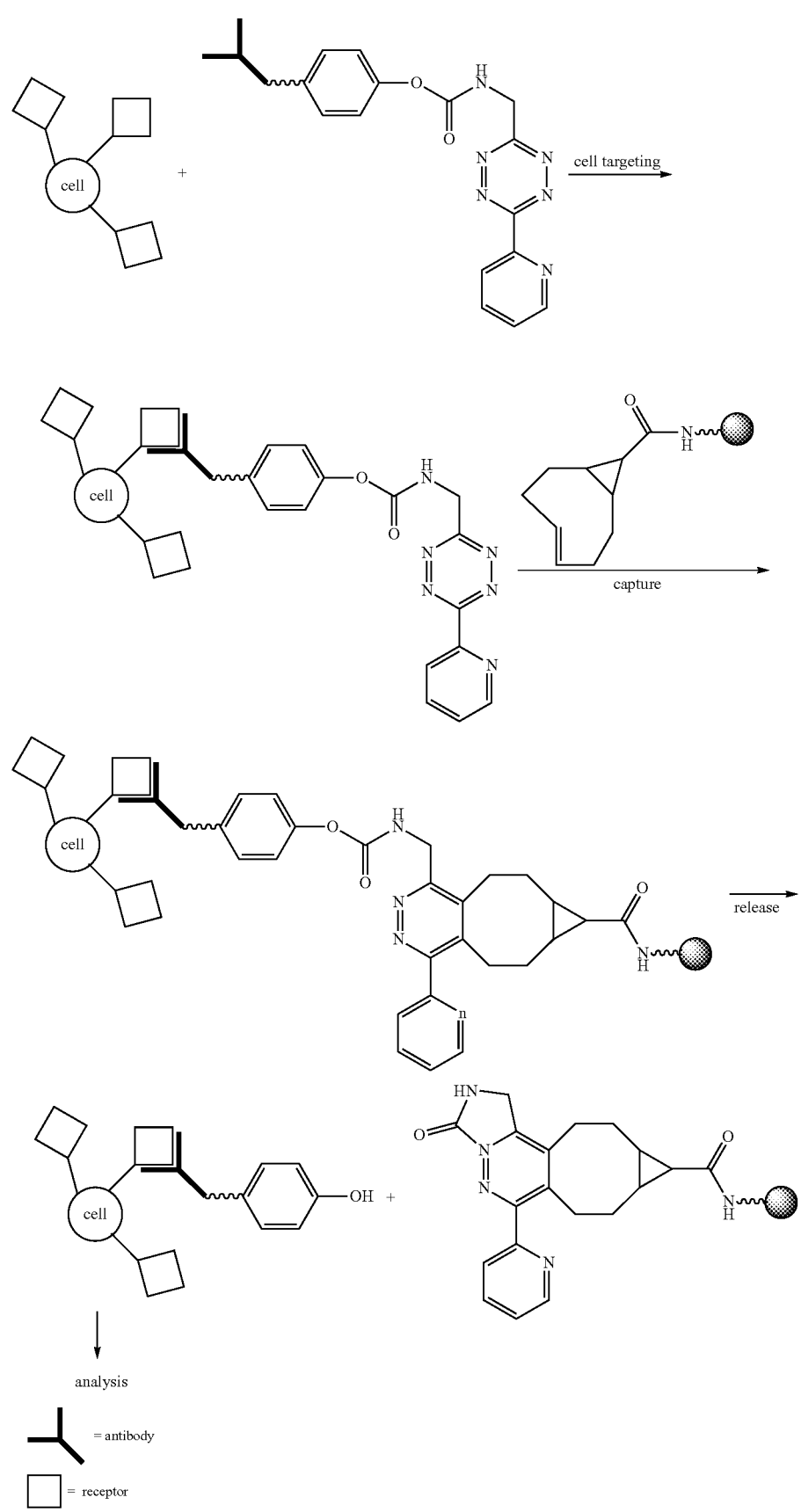

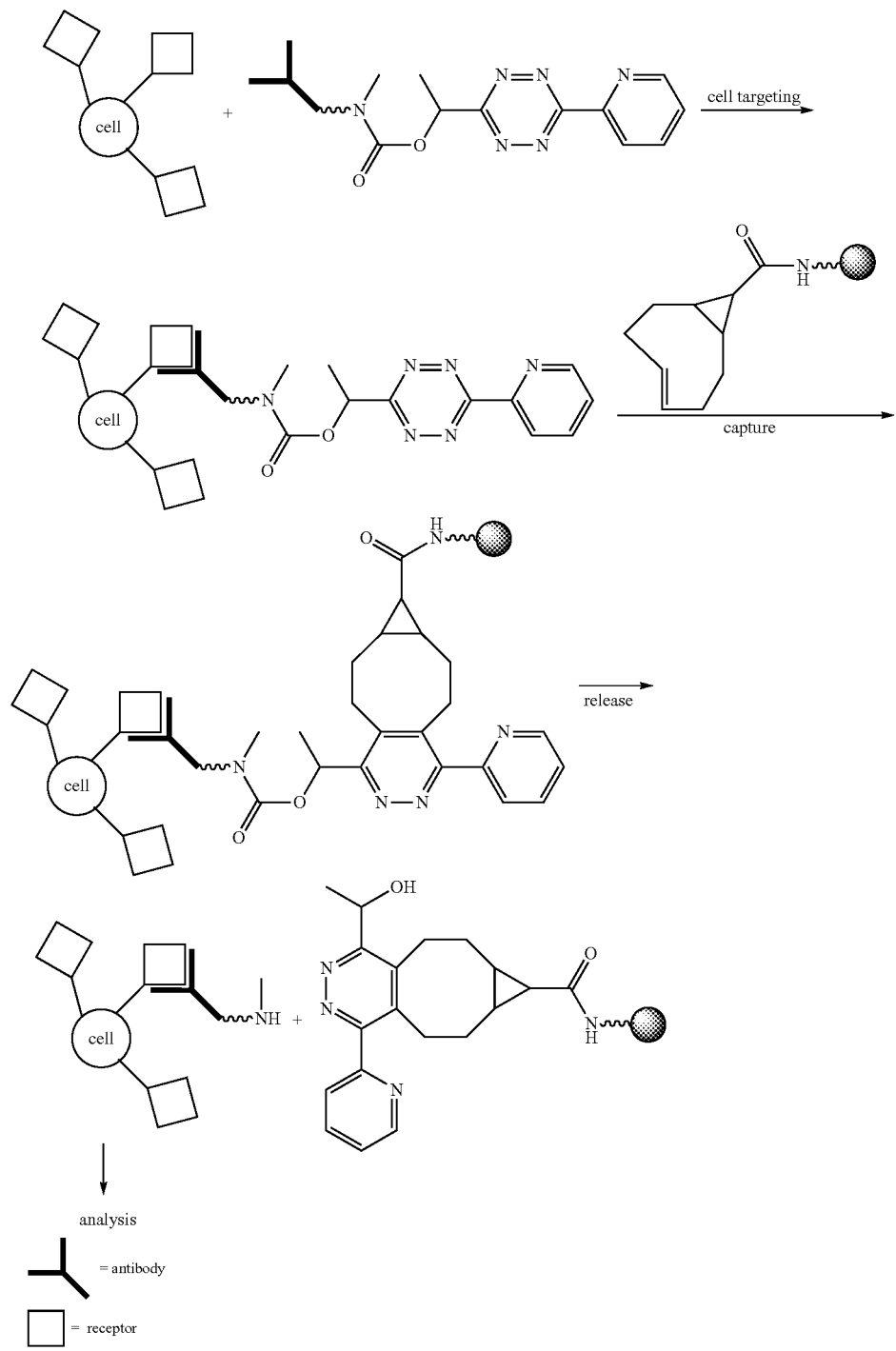

F

= antibody

= receptor

An embodiment of the invention comprises the Trigger as a chemoselective cleavable linker between a solid support and a solid support-bound substance.

Therein, with reference to Formula 5a and 5b: f is preferably 1.

In one embodiment, the Trigger is used as cleavable linker in solid phase synthesis. Solid-phase synthesis methods have been used in organic synthesis over the last decades, first for peptides, then for oligonucleotides, followed by other organic molecules. This development was accompanied by the development of various cleavable linkers for the detachment of molecules from the solid support resin. Examples include linkers that can be cleaved by acids, bases, fluoride ion, or photochemical reactions [Maruta et al. Tetrahedron Lett. 2006, 47, 2147-2150], [Shabat et al. Chem. Eur. J. 2004, 10, 2626]. An alternative bio-orthogonal approach may expand the scope of compatible functionalities. Here a solid phase synthesis resin, such as polystyrene, is functionalized with tetrazine Triggers upon which the molecule of interest, for example a peptide, is synthesized. After the synthesis is complete, the Activator is added which reacts with the Trigger releasing the product (e.g. peptide) from the resin-bound Trigger into solution (see Scheme directly below). Tetrazine moieties are sufficiently stable towards standard solid-phase peptide synthesis conditions, including piperidine and TFA treatments.

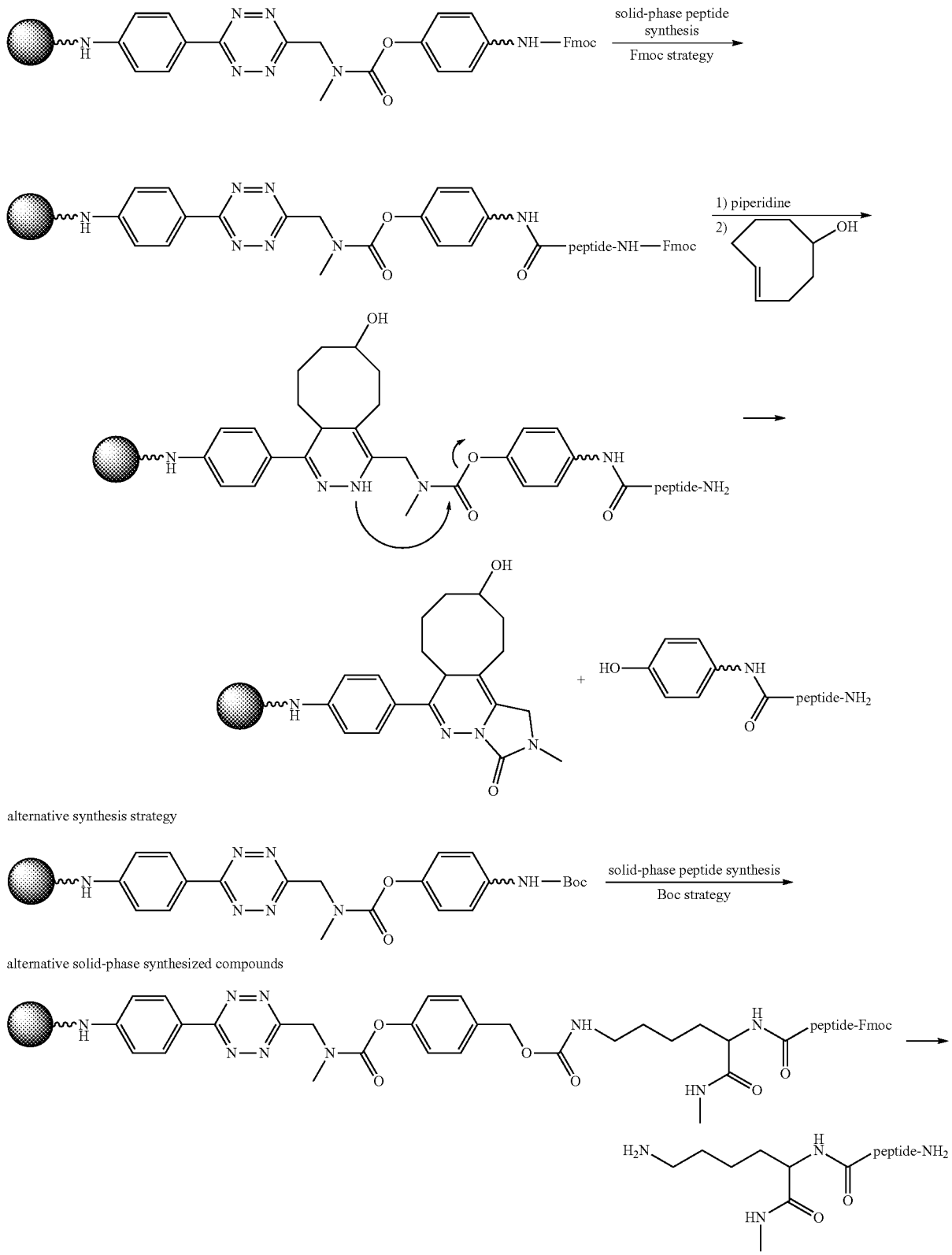

alternative synthesis strategy alternative solid-phase synthesized compounds

An alternative embodiment, shown directly below, comprises the selective release and activation of a surface-bound chemical reagent in a cartridge or a lab on a chip device.

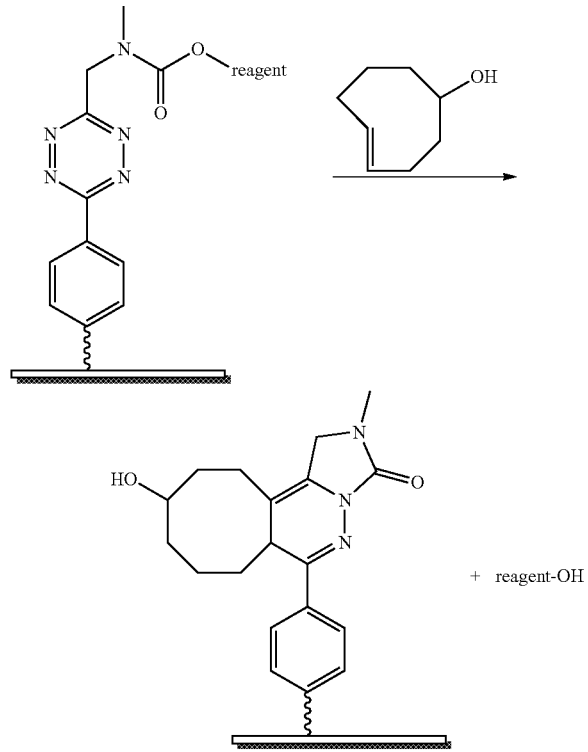

In yet another aspect the Trigger functions as a cleavable linker for reversible biomolecule crosslinking, and/or and immobilization, followed by release. Applications in chemical biology include a) the use of two proteins linked together via tetrazine, and their studying their action in e.g. a cellular environment before and after tetrazine cleavage; b) cleavage of a protein-tetrazine-targeting agent conjugate in cells to release the protein from a particular subcellular domain; c) cleavage of a protein-targeting agent-tetrazine conjugate in cells to unmask the targeting agent and target the protein to a particular subcellular domain, see [Lim Acc. Chem. Res. 2011].

In another embodiment, the $C^A$ is a masked antigen, e.g. a masked peptide comprising a peptide linked to a mask via the Trigger, which optionally is present in a Major Histocompatibility Complex (MHC), and which can be unmasked in vitro at a desired time.

In another embodiment, the $C^A$ is DNA or RNA and $C^A$ is linked via the Trigger to a transfection agent (i.e. $C^B$), designed to deliver the DNA or RNA into a cell in vivo or in vitro. Upon transfection, an activator is administered that tracelessly releases the DNA or RNA from the transfection agent.

In some preferred embodiments the conjugated Trigger obeys one of the following Formulae 8a-c, which are embodiments of Formula 5a and 5b, wherein each b, c, e, and f are independently 0 or 1, and wherein $S^{P1}$ and $S^{P2}$ are respectively Spacer-1 and Spacer-2 and are as defined for Spacer $S^P$ (vide supra), and wherein $M^{C1}$ and $M^{C2}$ are respectively Conjugation Moiety 1 and Conjugation Moiety 2 and are as defined for $M^C$ (vide supra) and wherein $M^{C1}$ and $M^{C2}$ in addition can be biotin, a DNA intercalator, or a photocrosslinker.

Formulae 8a-c

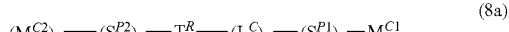

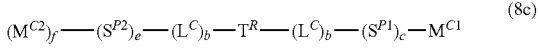

With reference to Formula 8a-c $M^{C1}$ is used to bind to a Construct A ($C^A$) as defined below, and the optional $M^{C2}$ is used to bind to Construct B ($C^B$), as defined below.

With reference to Formulae 8a-c it is preferred that $L^C$, if present, is self-immolative.

With reference to Formula 8c it is preferred that the $T^R$ releases $M^{C1}$ and $M^{C2}$ through the Cascade Mechanism.

Preferably the $M^C$ moieties is selected from biotin, DNA intercalators, photocrosslinkers, azido groups, keto groups, aldehyde groups, alkynyl groups such as (hetero)cycloalkynyl group and terminal alkynyl groups, disulfides, thiols, hydroxy groups, halogens, sulfonyloxy groups, N-maleimide groups, halogenated acetamido groups, mercaptoacetamido groups, sulfonylated hydroxyacetamido groups, primary amines, aminooxy groups, hydrazinyl groups, carboxylic acids and their activated esters such as N-hydroxysuccinimide ester and para-nitrophenyl ester, vinyl pyridine, disulfide, pyridyl disulfide, isocyanate, isothiocyanate, sulfonyloxy, mercaptoacetamide, anhydrides, acid chlorides, sulfonyl chlorides, nitrone, nitrile oxide derivatives, thiosemicarbazone, hydrazine carboxylate and arylhydrazide Suitable Spacers $S^P$, including $S^{P1}$ and $S^{P2}$, for use in a Trigger conjugate of this invention are listed in the section Spacers (vide supra). In some embodiments the Spacer has at most 50 carbon atoms, more preferably at most 25 carbon atoms, more preferably at most 10 carbon atoms. Non-limiting examples of suitable Spacers are the Spacers defined as the group "$Q^1$" in the section on Spacers herein above. Other preferred Spacers are PEG and PPG polymers, and oligopeptoids, preferably ranging from 2 to 50 repeating units, more preferably from 2 to 24 repeating units, more preferably from 2 to 12 repeating units.

In one embodiment the Trigger is used as cleavable linker in a biomolecule biotinylation agent for application in biomolecule detection, isolation and purification. Thus, use is made of biomolecule-reactive Trigger-biotin conjugates for the cleavable (reversible) attachment of biotin to peptides, proteins (for example cell surface proteins), glycoproteins, DNA and other biomolecules. The cleavable linker allows mild detachment of the bound biomolecule after affinity purifying biotinylated proteins and their binding partners using immobilized avidin or streptavidin. With reference to the scheme directly below, Probe A is useful for biotinylation of lysine residues in proteins. With R=SO$_3$Na the agent will remain charged and in the extracellular space and is especially useful for labeling cell membrane proteins. Probe B is an aminooxy-biotin reagent and probe C is a hydrazide-biotin reagent and as such B and C are useful for biotinylating glycoproteins and other molecules that have oxidizable polysaccharides groups. Compound D and E enable simple and efficient reversible biotinylation of antibodies, cysteine-containing peptides and other thiol-containing molecules. Compound F can be used to biotinylate activated esters. Compound G can be used for the biotinylation of DNA and RNA through intercalation. Compound H is a photoactivatable reagent that enables biotinylation of nucleic acids and other molecules that do not have readily available amine or sulfhydryl groups for coupling. When exposed to strong ultraviolet or visible light, the aryl azide group converts to a reactive nitrene that readily reacts to form covalent bonds with a variety of chemical groups, such as nucleic acids. Compound I is a reagent that enables proteins to be temporarily labeled at sulfhydryl sites for later photo-induced covalent attachment and transfer of biotinylation to an interacting protein, thereby tagging the previously unknown interacting protein(s) for affinity purification, detection, analysis (e.g. mass spectrometry, electrophoresis or sequencing).

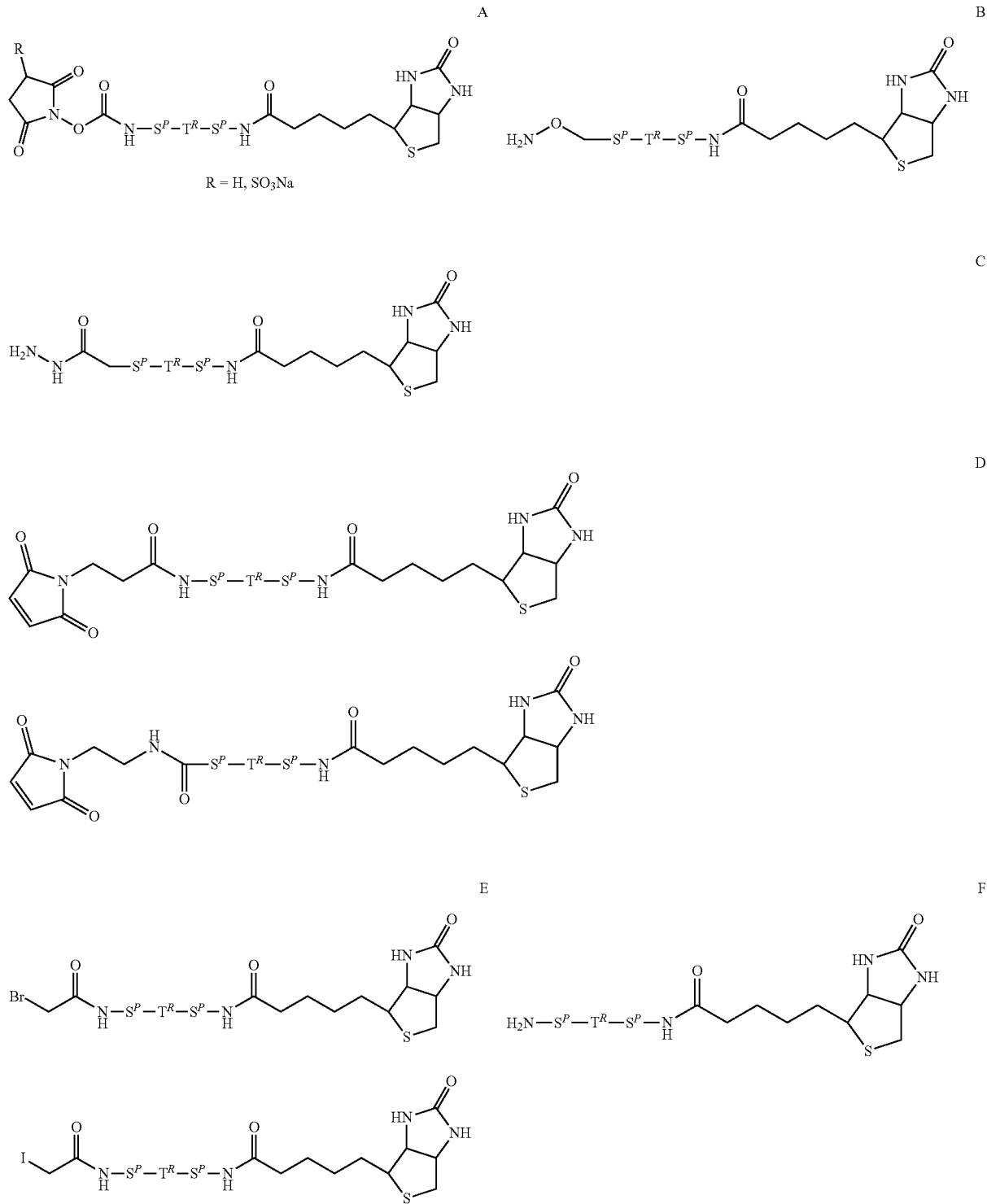

-continued
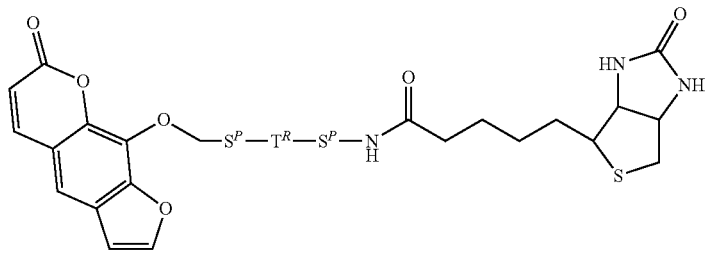
G
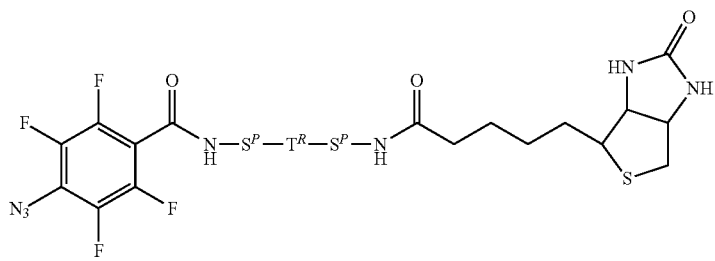
H
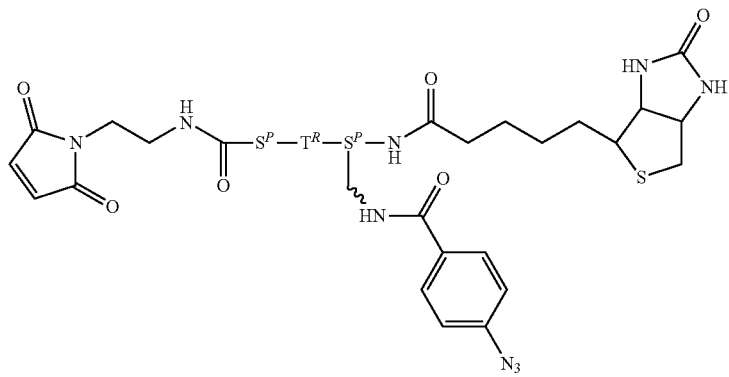
I
Examples of biotination agents believed to afford release through the cyclization mechanism are shown below:
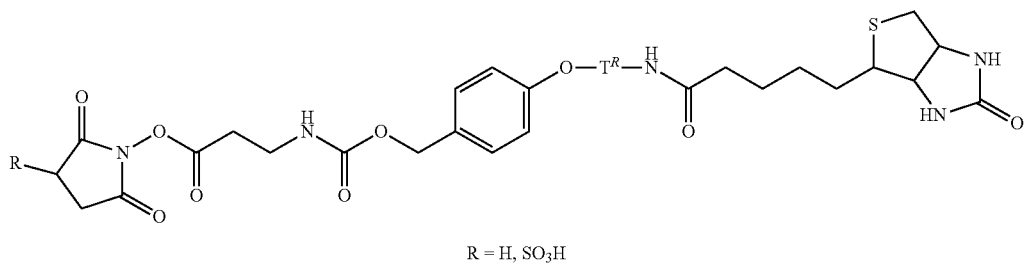
R = H, SO₃H
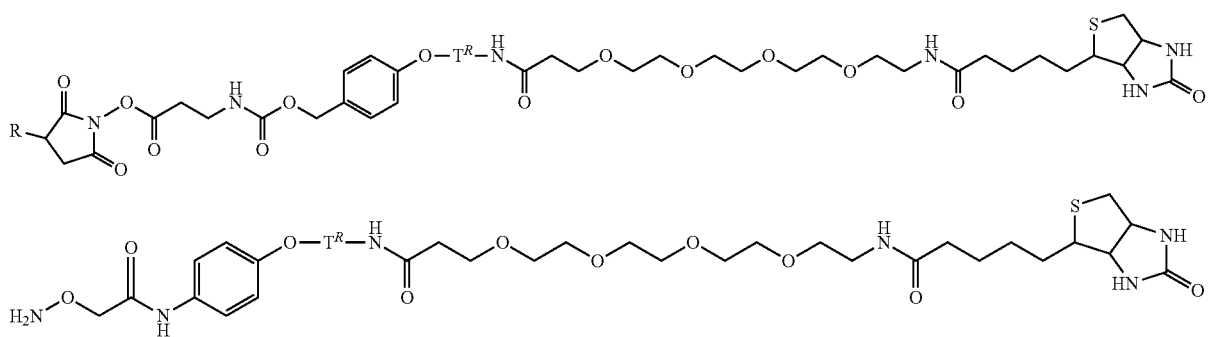

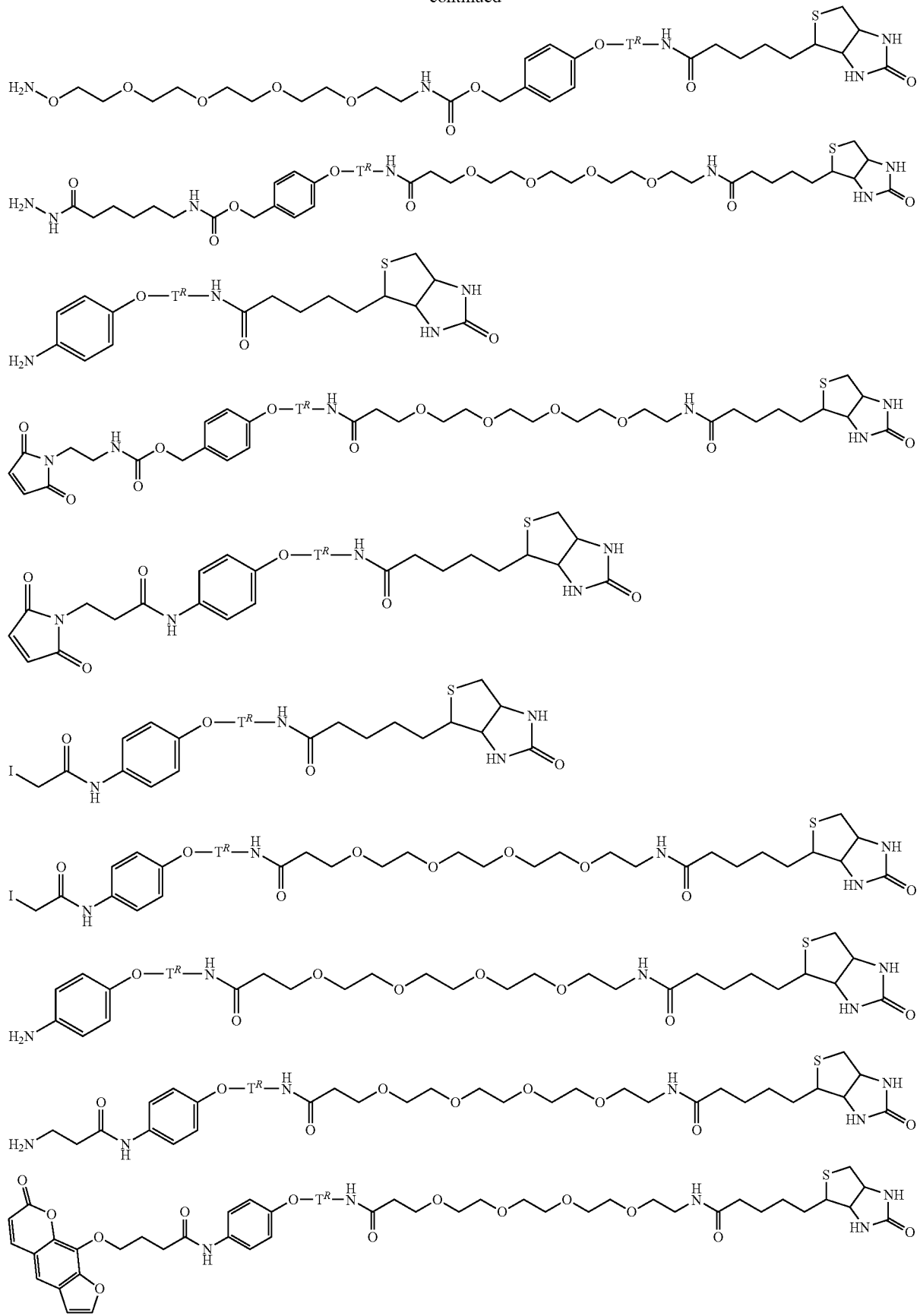

-continued
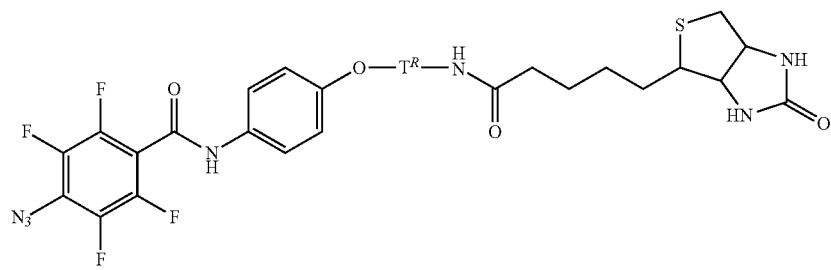
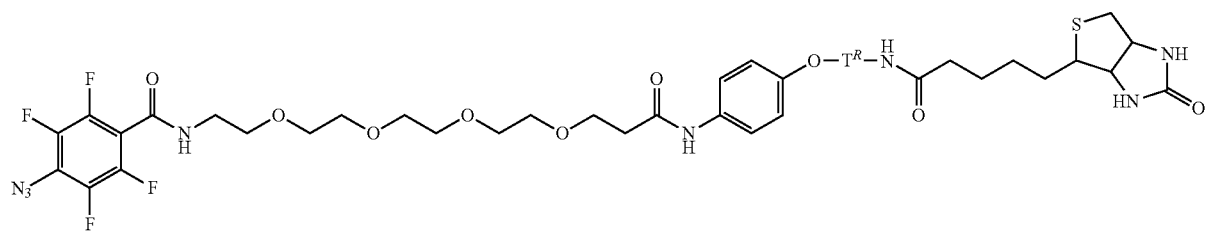
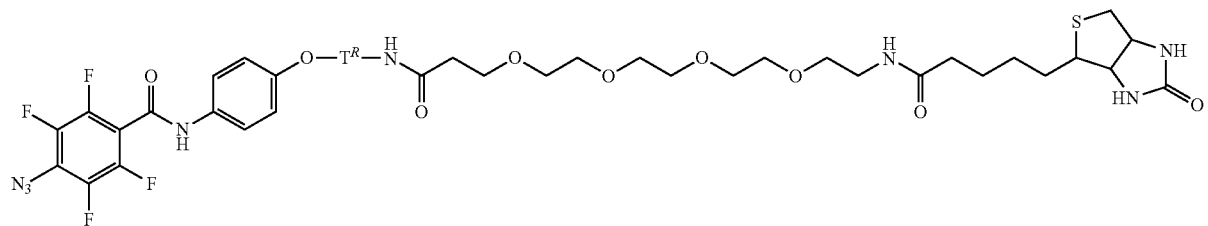
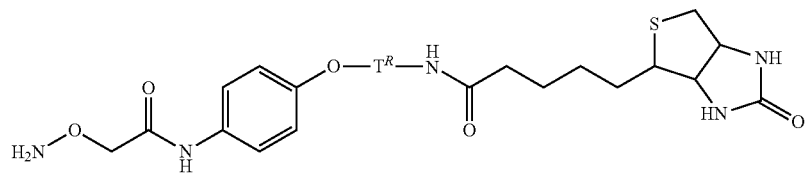
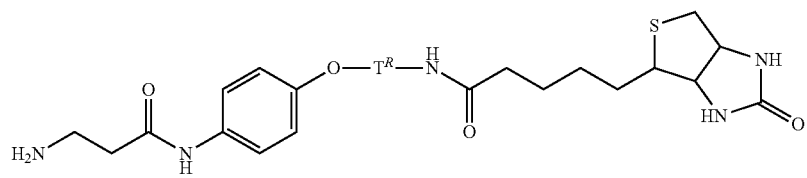
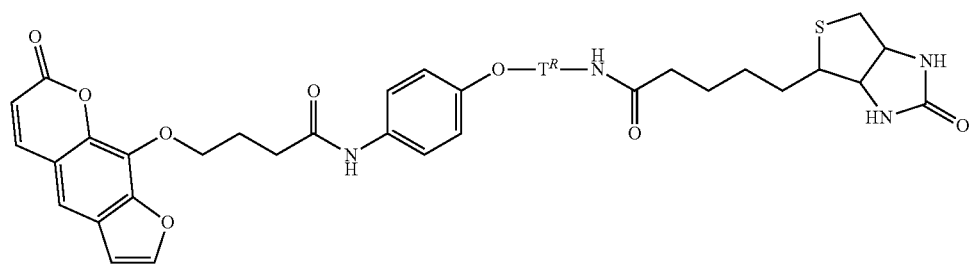
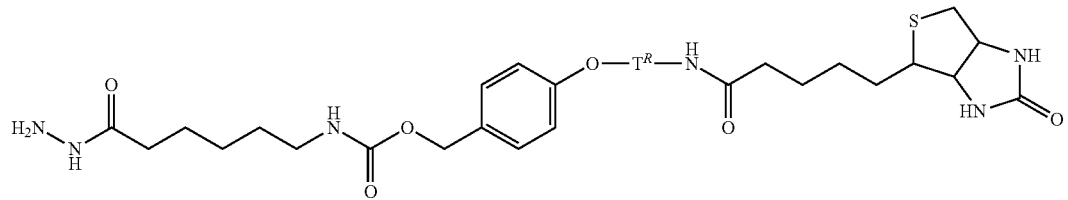

-continued
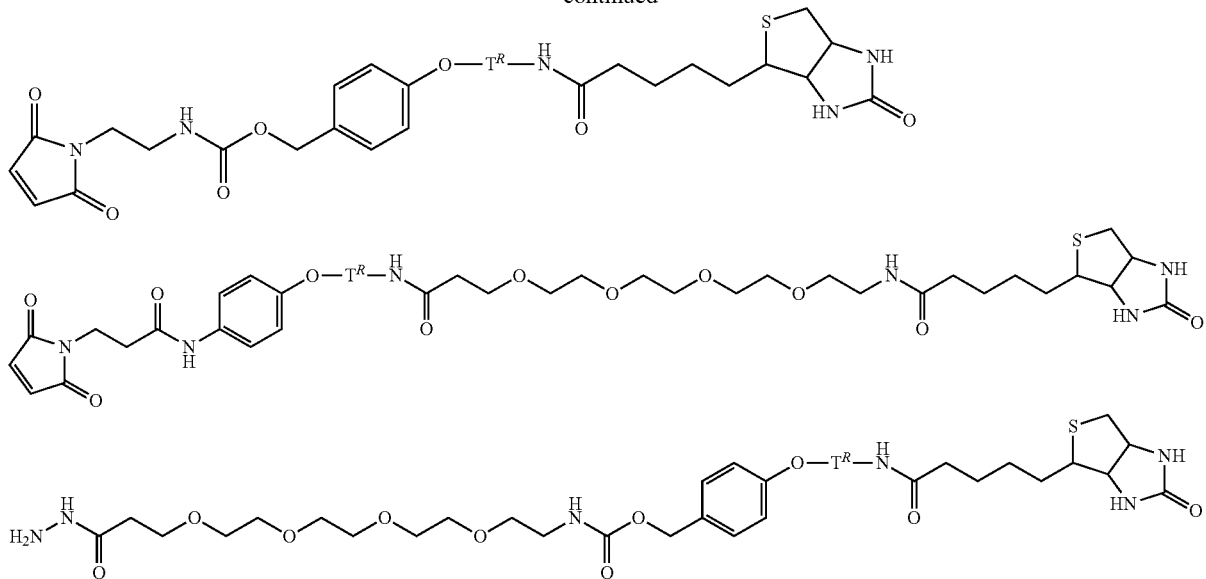
Examples of biotination agents believed to afford release through the cascade mechanism are shown below:
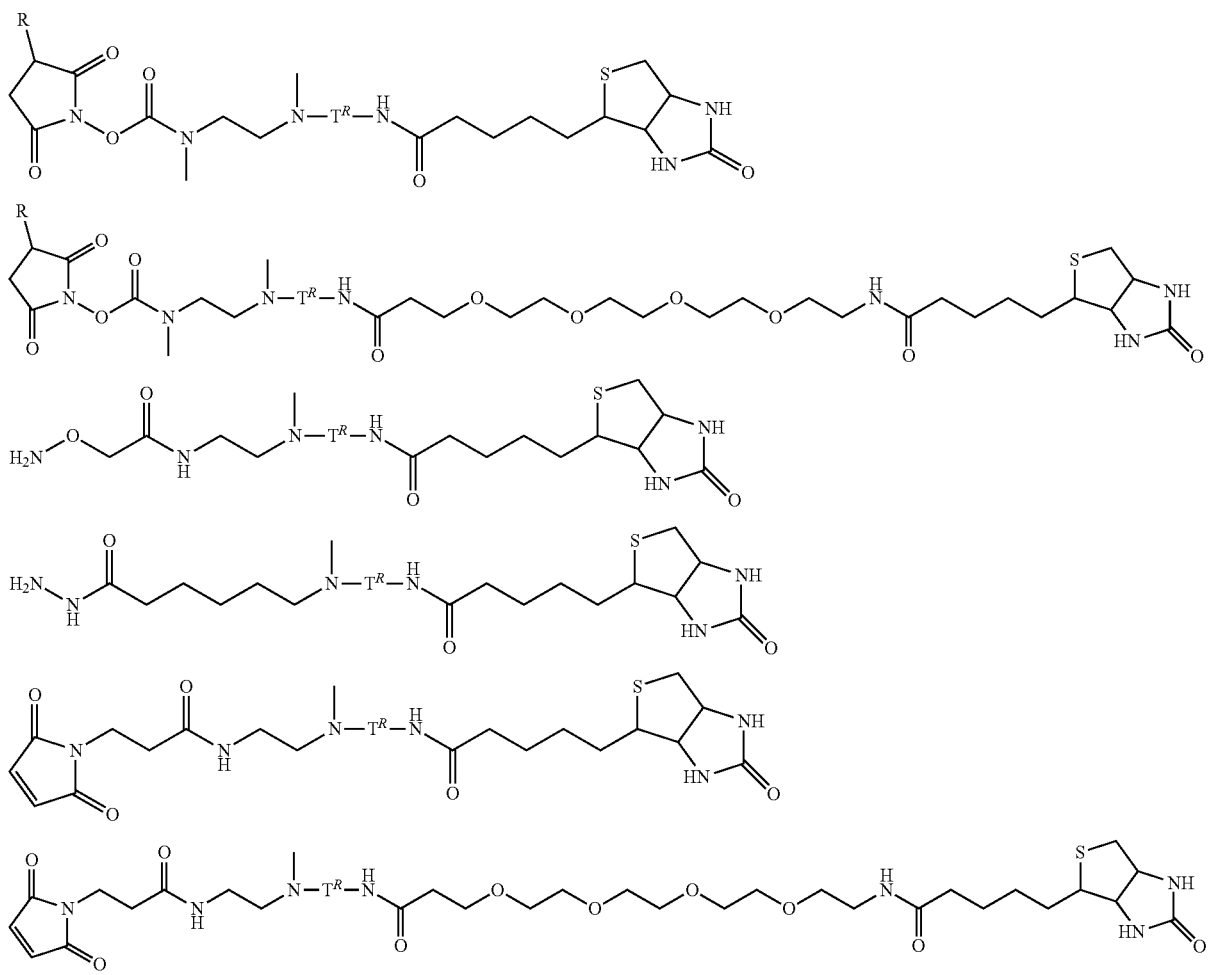

-continued
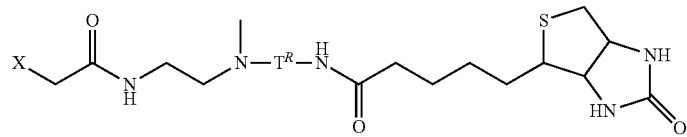
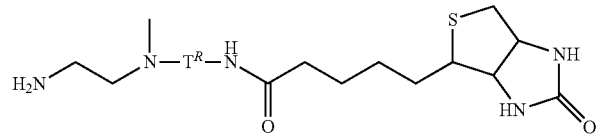
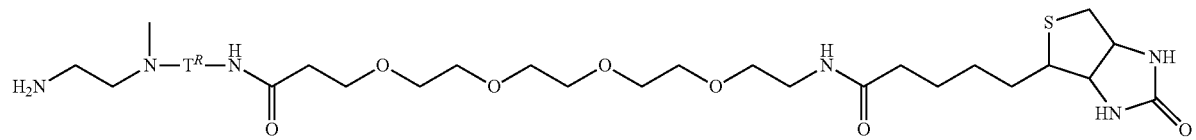
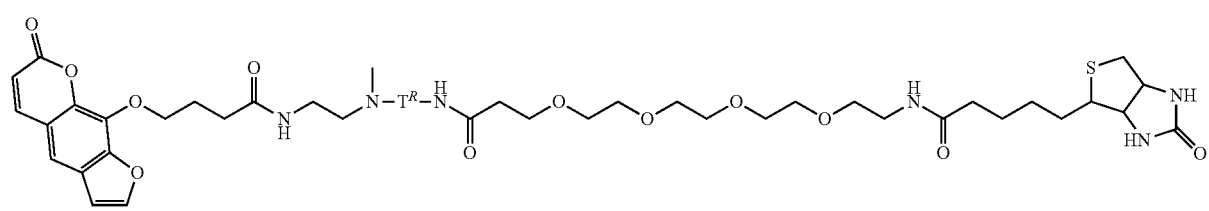
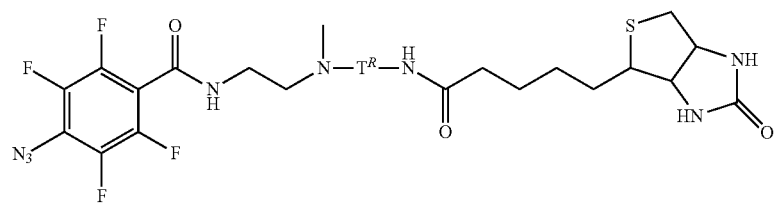
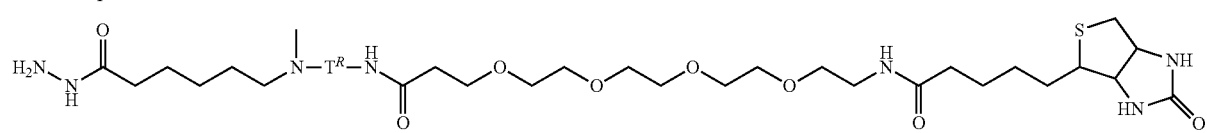
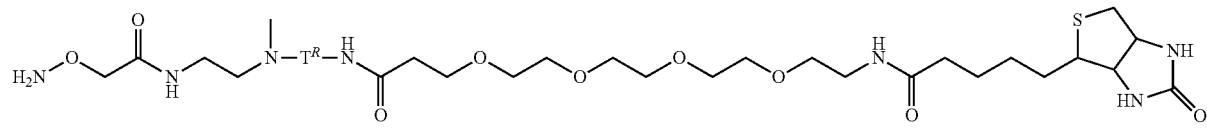
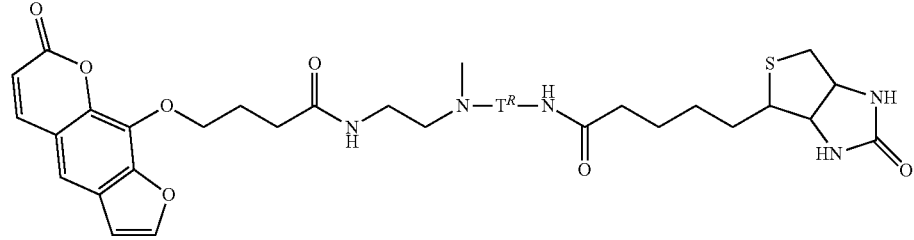
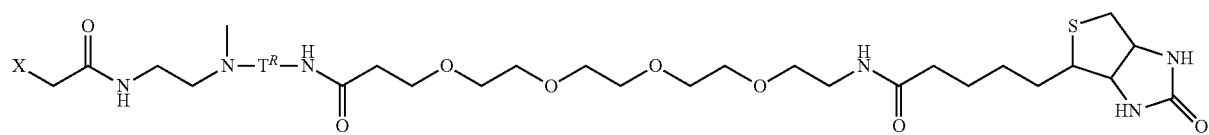
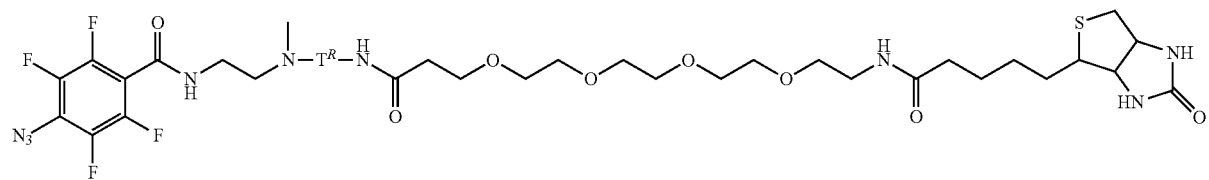

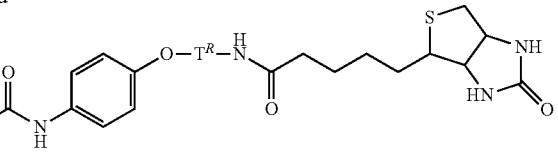

R = H, SO₃H
X = Br, I

In another embodiment the Trigger is used as cleavable linker in a crosslinker between two biomolecules for e.g. application in biomolecule detection, immobilization, isolation and purification, in particular with respect to biomolecule interactions. Examples include crosslinking of cell surface proteins prior to cell lysis and immunoprecipitation, fixing of protein interactions to allow identification of weak or transient protein interactions, fixing of tissues for immunostaining, 1-step bioconjugations, and immobilization of proteins onto e.g. amine-coated surfaces. Thus, use is made of biomolecule-reactive bifunctional crosslinkers containing a cleavable Trigger for the cleavable (reversible) attachment of biomolecules such as peptides, glycoproteins, DNA to one another. Such as linker can for example be used in a "shotgun" approach to capture interaction complexes. When using lysine reactive moieties, the reagent will crosslink any and all interacting molecules whose respective lysine residues come within the spacer length of the crosslinker. Subsequently, a particular interaction complex is detected after crosslinking and (usually) cell lysis by immunoprecipitation or by administering a specific antibody or other probe for one of the targt molecules in the complex. With reference to the scheme directly below, compounds A and B are homobifunctional lysine-reactive crosslinkers, useful for the crosslinking of for example two proteins. Compounds C are cleavable homobifunctional thiol reactive crosslinkers for covalent but reversible conjugation between e.g. proteins or peptide cysteines. Compounds D and E are cleavable heterobifunctional thiol and amine reactive crosslinkers for covalent but reversible conjugation between e.g. proteins or peptide cysteines and lysines. Compounds F are cleavable heterobifunctional thiol and aldehyde/ketone reactive crosslinkers for covalent but reversible conjugation between e.g. proteins or peptide lysines and engineered protein carbonyls or glycoproteins and other molecules that have oxidizable polysaccharides groups. Compound G and H are cleavable heterobifunctional amine-reactive photocrosslinkers, useful with molecules where no amine residue is available or accessible (even DNA, polysaccharides and other molecules). These heterobifunctional linkers enable "two-step" reactions in which "bait" proteins can be labeled, added to a cell and light-activated to crosslink at the desired time (e.g., upon cell stimulation when the interaction of interested is presumed to occur), followed by isolation and mild cleavage through the Trigger.

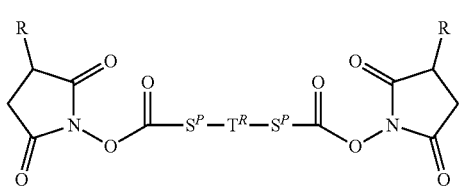

A

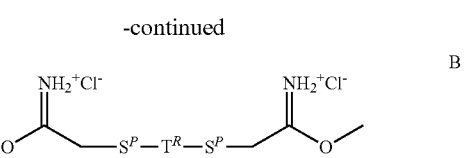

B

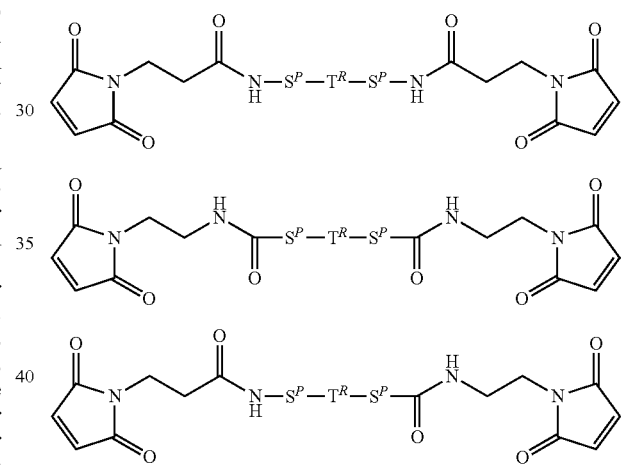

C

D

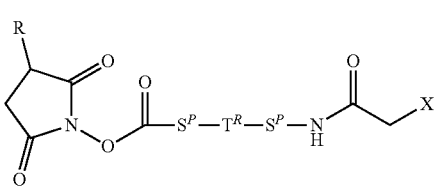

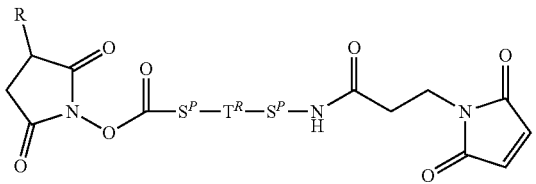

E

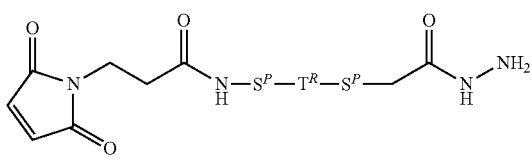
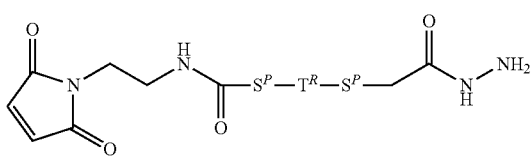
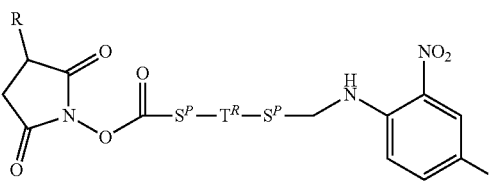
Examples of crosslinkers believed to afford release through the cyclization mechanism are shown below:
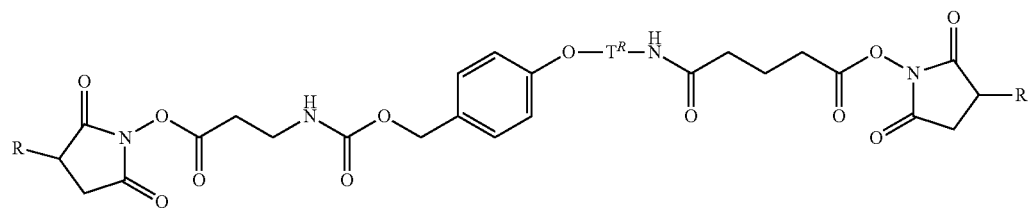
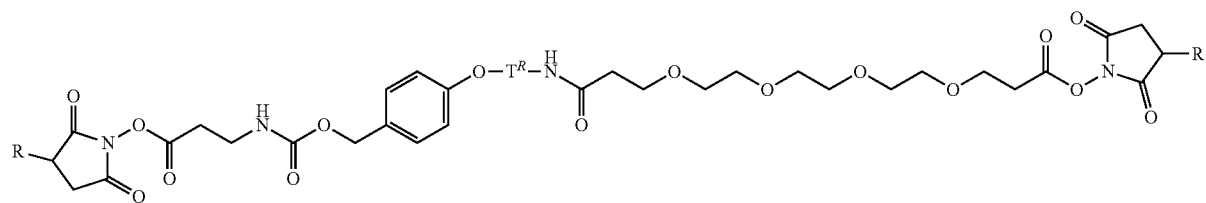
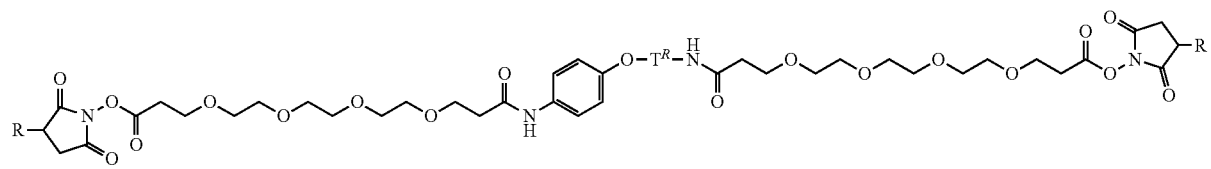
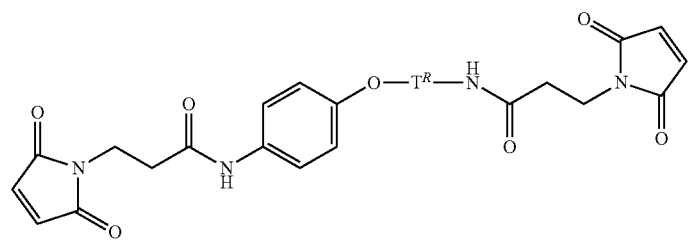
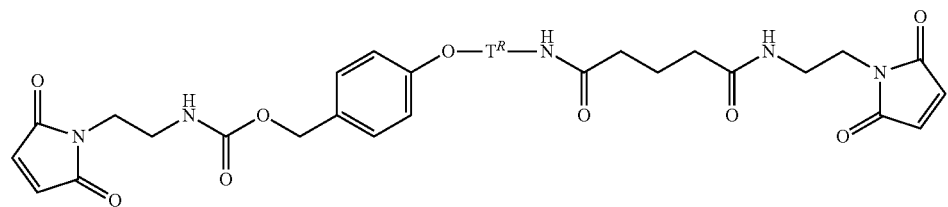

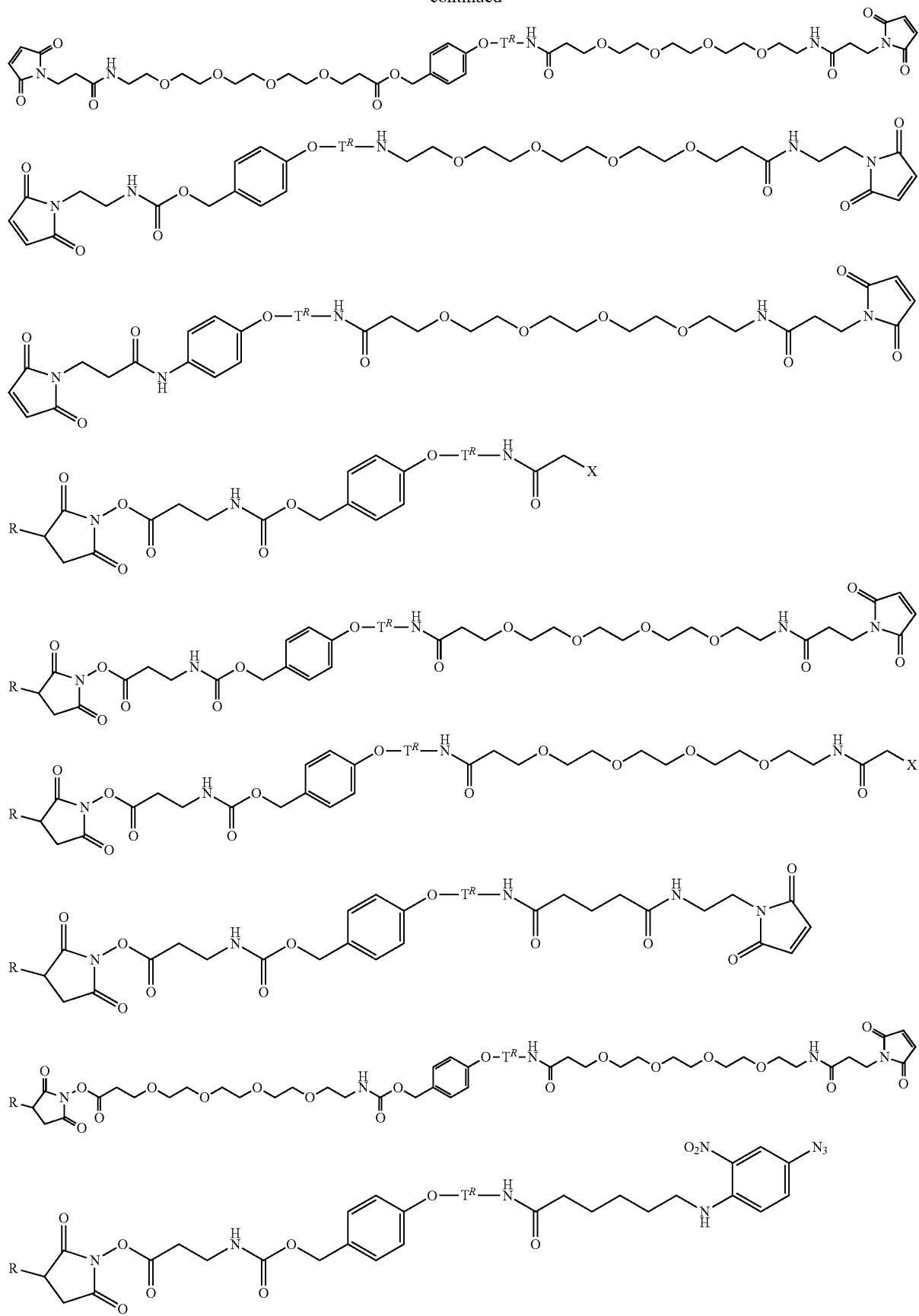

-continued
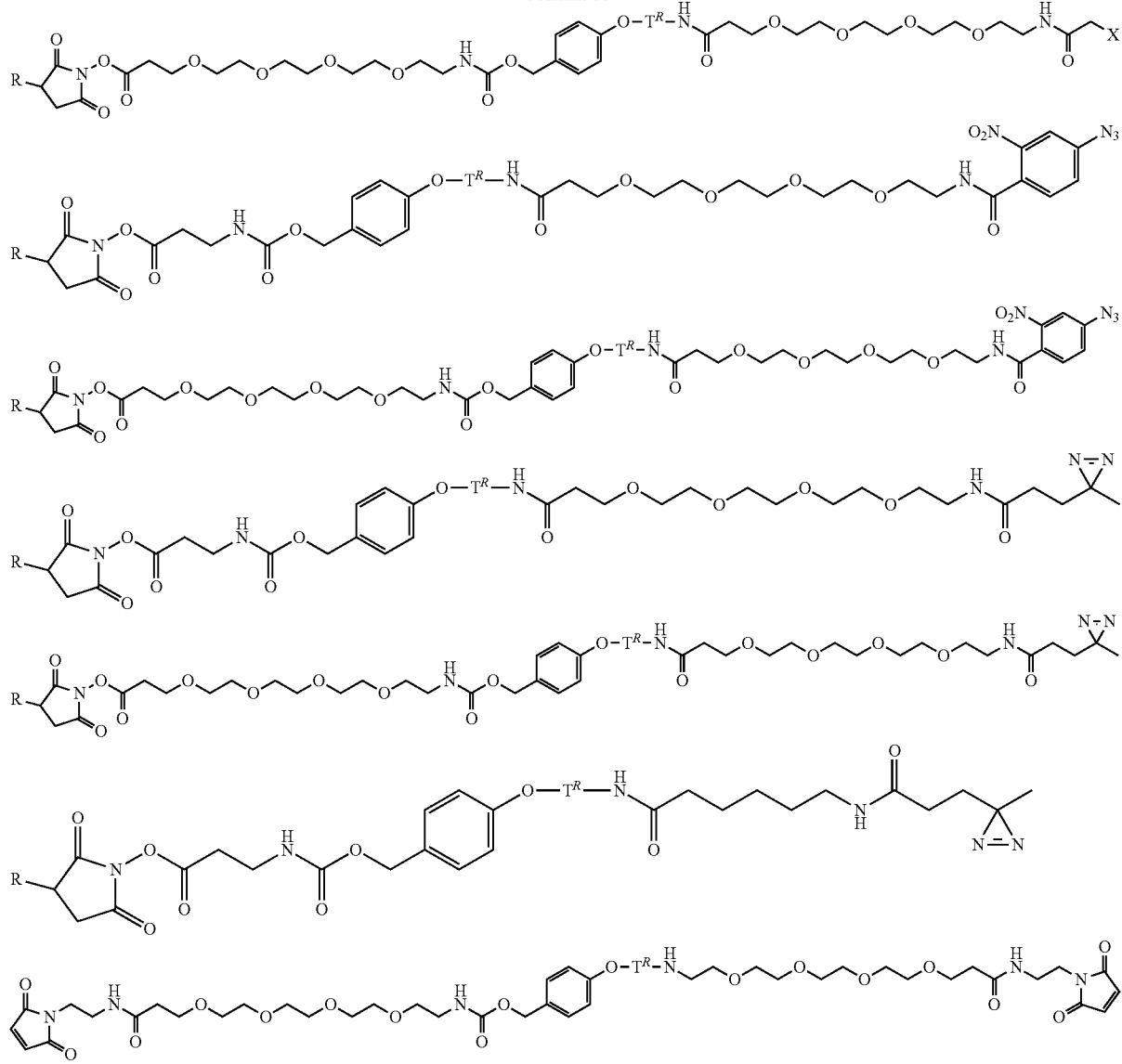
Examples of crosslinkers believed to afford release through the cascade mechanism are shown below:
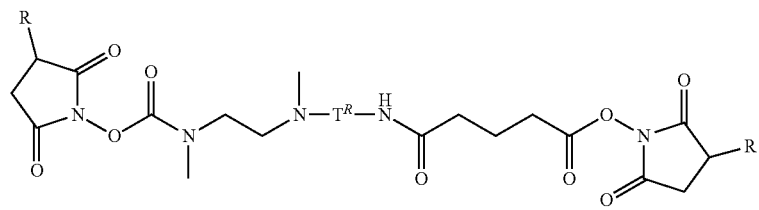
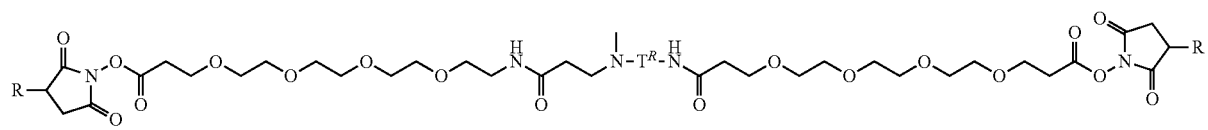

-continued
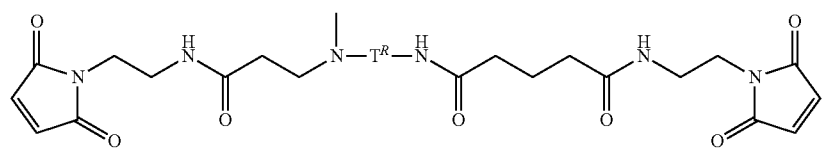
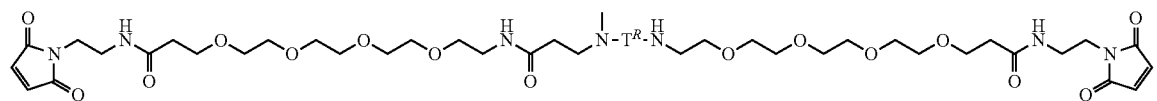
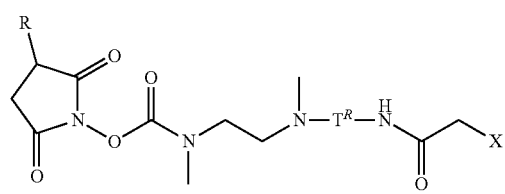
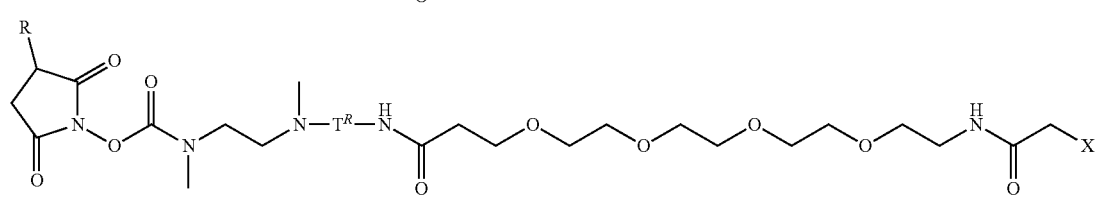
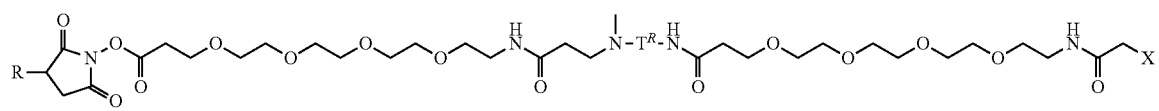
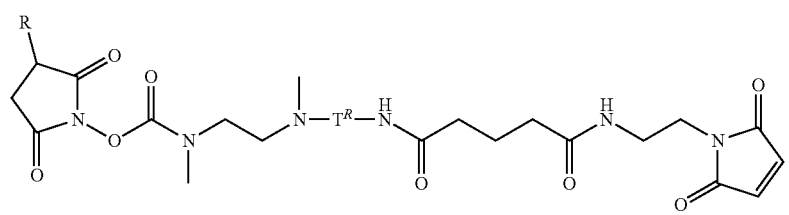
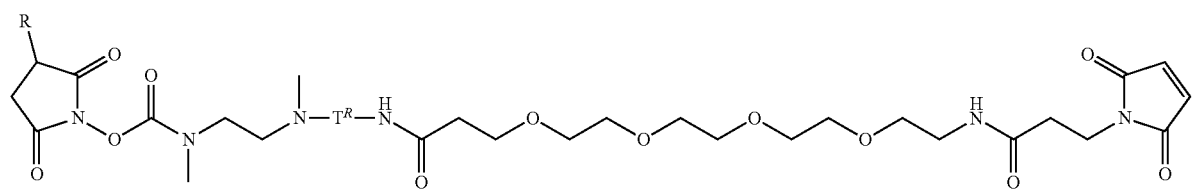
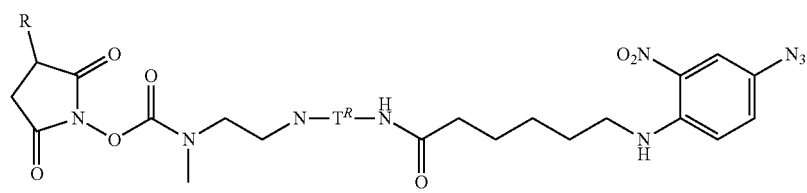
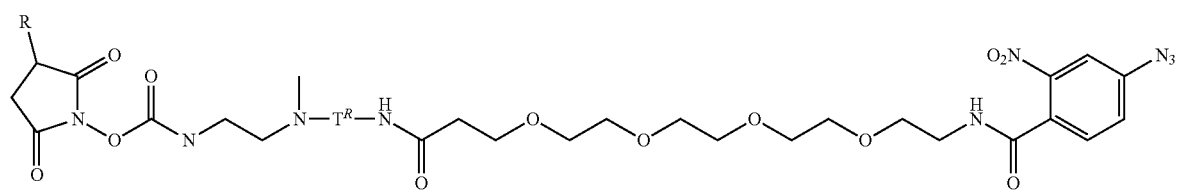
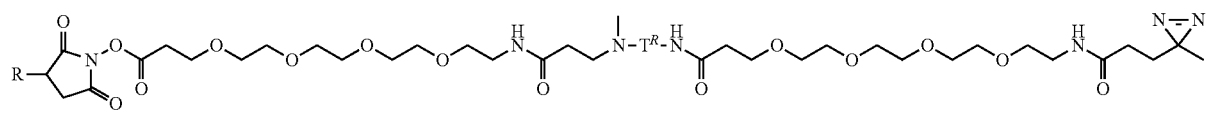

-continued

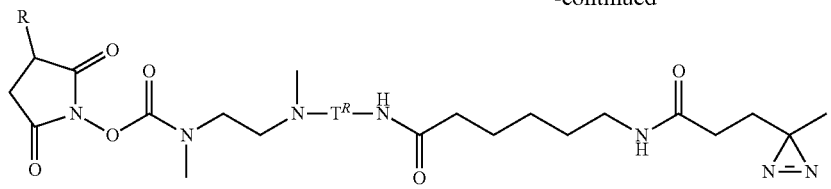

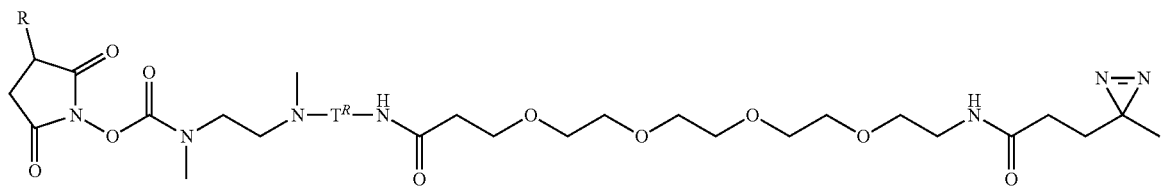

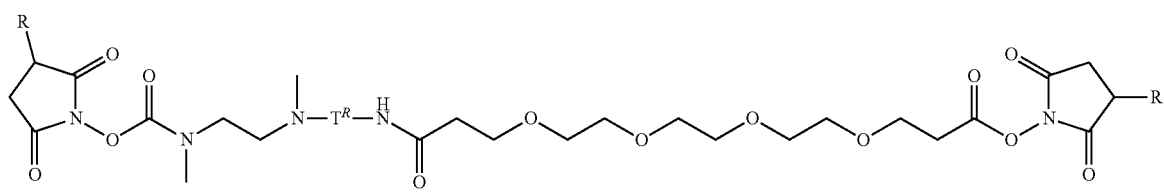

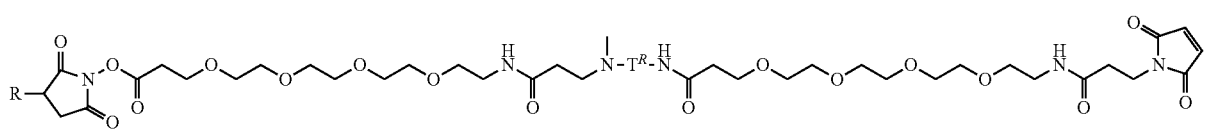

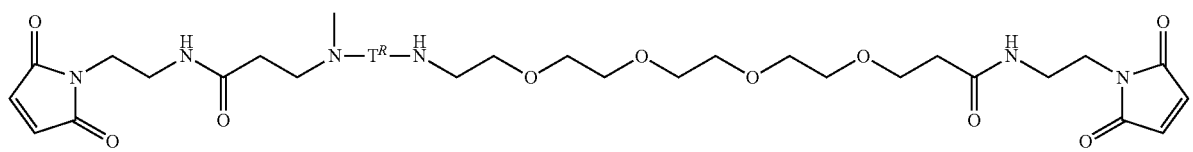

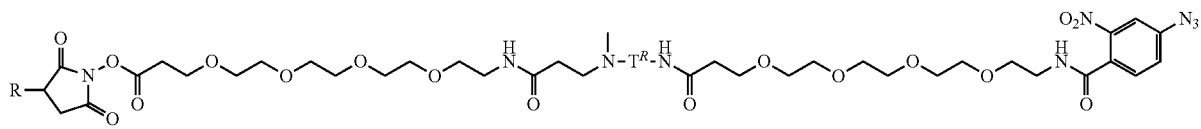

In another aspect the Trigger is used as in a radiolabeling kit, as shown in the scheme directly below. An $^{18}$F-labeled TCO is added to a peptide bound to a resin via a tetrazine Trigger. Reaction between TCO and Trigger affords liberated $^{18}$F-TCO-tetrazine-peptide while unlabeled peptide remains bound to the resin. With reference to Formula 5a and b, f is preferably 1.

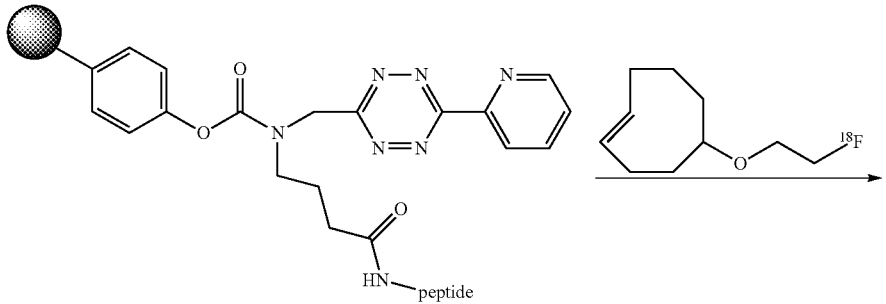

-continued

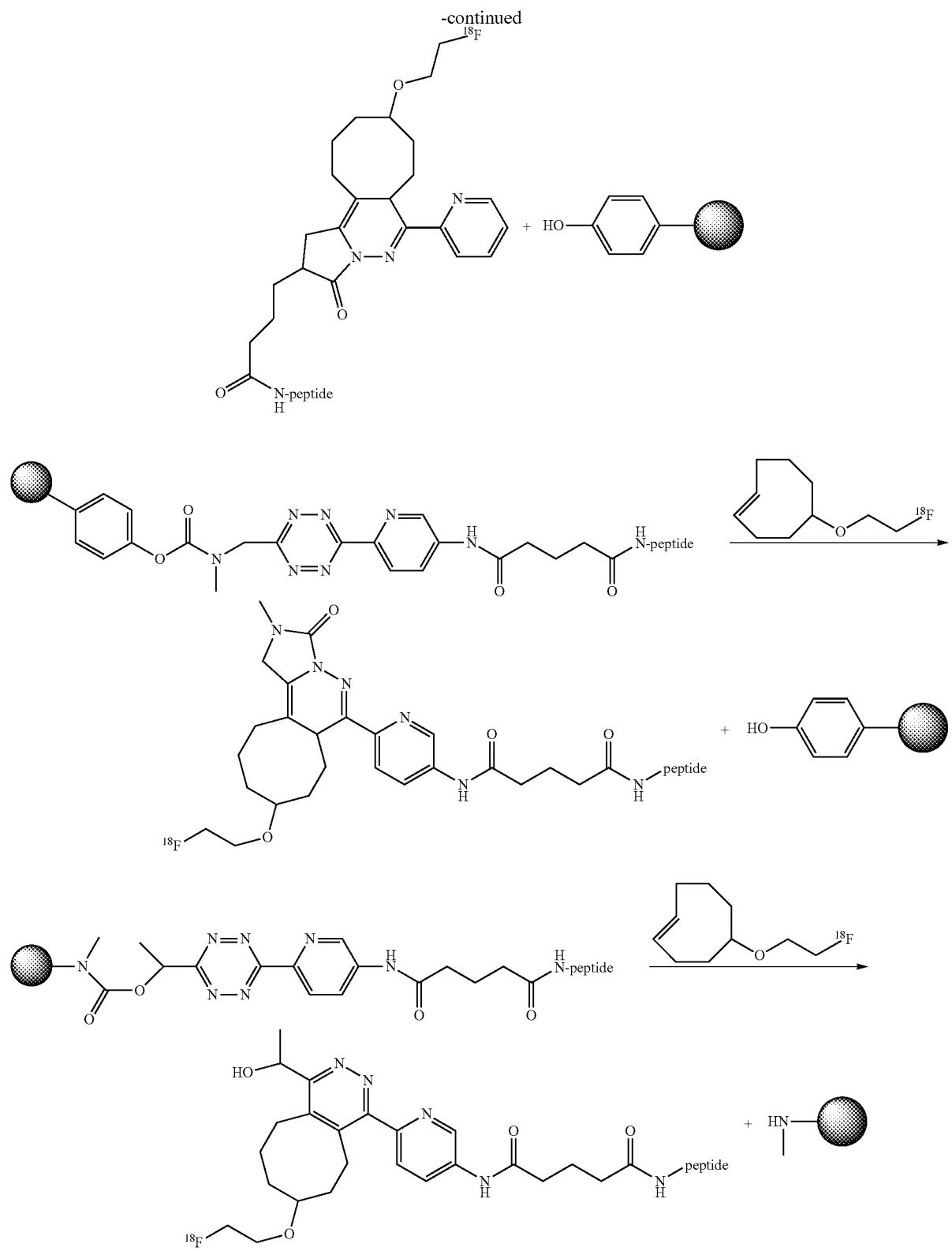

In another aspect the Trigger is used in a diagnostic kit, see directly below. With reference to Formula 5a and 5b, f is preferably 1. Immobilized (e.g. in a 96-well plate) tetrazine conjugated to one or more quenched fluorophores is contacted with a sample containing an unknown amount of TCO moieties. These TCOs have been previously incorporated in a biomolecule as amino acid residue in a metabolic engineering experiment. Reaction of the TCO with the tetrazine effects release and dequenching of the fluorophores, allowing readout via e.g. UV absorption.

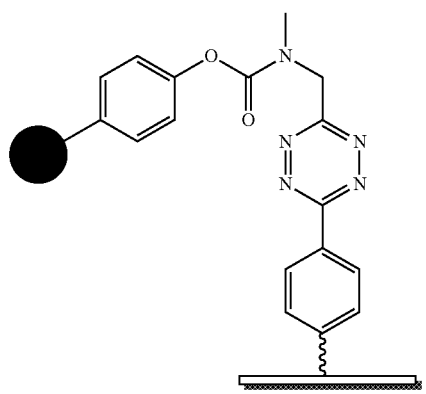
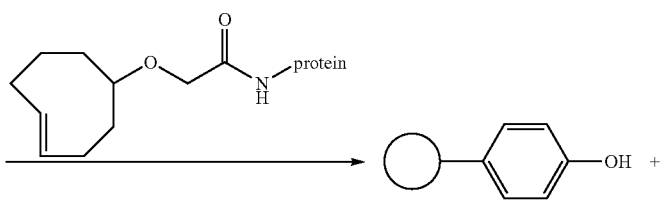
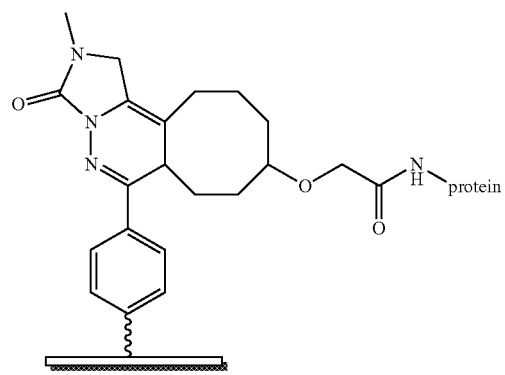

● = quenched fluorophore

○ = dequenched fluorophore

Constructs $C^A$ and $C^B$

The Constructs to be used in the present invention include but are not limited to small molecules, organic molecules, metal coordination compounds, inorganic molecules, organometallic molecules, biomolecules, drugs, polymers, resins (e.g. polystyrene, agarose) particles (e.g. beads, magnetic beads, gold, silica-based, polymer, glass, iron oxide particles, micro- and nanoparticles, such as liposomes, polymersomes), gels, surfaces (e.g. glass slides, chips, wafers, gold, metal, silica-based, polymer, plastic, resin), cells, biological tissues, pathogens (viruses, bacteria, fungi, yeast). The Constructs may for example comprise a combination of the aforementioned Constructs.

Examples of biomolecules include: carbohydrates, peptides, peptoids, lipids, proteins, enzymes, oligonucleotides, DNA, RNA, PNA, LNA, aptamers, hormones, toxins, steroids, cytokines, antibodies, antibody fragments (e.g. Fab2, Fab, scFV, diabodies, triabodies, VHH), antibody (fragment) fusions (e.g. bi-specific and tri-specific mAb fragments).

In a preferred embodiment the Construct A is a biomolecule.

In another preferred embodiment the $C^A$ is a biomolecule and $C^B$ is selected from the group of polymer, resin, particle, solid support In another preferred embodiment the $C^B$ is a biomolecule and $C^A$ is selected from the group of polymer, resin, particle, gel, surface In some embodiments, the invention relates to a kit as described above wherein the release occurs in a chemical or biological environment in vitro, and the Construct $C^A$ or $C^B$ is a polymer, resin, particle, solid support, gel, or surface.

In other embodiments, the invention relates to a kit as described above wherein the release occurs in a chemical or biological environment in vitro, and $C^A$ is or is comprised in a binding to a polymer, resin, particle, solid support, gel, or surface, and wherein $C^B$ comprises a radioisotope.

In some embodiments of the invention, $C^A$ and/or $C^B$ equals a $M^C$ and this or these $M^C$ moieties function as biomolecule binding moieties. Preferred $M^C$ moieties for use as biomolecule binding moieties include but are not limited to biotin, carboxylic acids and their activated esters such as N-hydroxysuccinimide ester and para-nitrophenyl ester, isocyanate, isothiocyanate, N-maleimide groups, bromoacetamide and iodoacetamides, azido groups, alkynyl groups such as (hetero)cycloalkynyl group and terminal alkynyl groups, aminooxy groups, hydrazinyl groups, and photoreactive groups.

In some embodiments of the invention, $C^A$ and $C^B$ equal $M^C$ and these $M^C$ moieties are bound to different locations on the same biomolecule, resulting in a cycle.

In another preferred embodiment the $C^A$ is an $M^C$ that is a biomolecule binding moiety, and $C^B$ is an $M^C$ that binds to a polymer, resin, particle or a solid support.

In another preferred embodiment the $C^B$ is an $M^C$ that is a biomolecule binding moiety and $C^A$ is an $M^C$ that binds to a polymer, resin, particle or a solid support.

In another embodiment, either $C^A$ or $C^B$ is or comprises biotin.

EXAMPLES

Example 1: Materials and Methods, General Synthetic Procedures and References Materials and Methods All reagents, chemicals, materials and solvents were obtained from commercial sources and were used as received, including nitrile starting compounds that not have been described. All solvents were of AR quality. Dry $CH_2Cl_2$, THF and DMF were dispensed from a MBRAUN MB-SPS-800 system. Moisture or oxygen-sensitive reactions were performed under an atmosphere of dry Ar. Bromoacetamide-PEG24-acid TFP ester and maleimide-PEG24-acid were obtained from Quanta BioDesign. 3,6,9,12,15,18,21,24,27,30,33-Undecaoxatetratriacontanoic acid, 37-amino-5,8,11,14,17,20,23,26,29,32,35-undecaoxa-2-azaheptatriacontanoic acid t-butyl ester and 29-amino-3,6,9,12,15,18,21,24,27-nonaoxanonacosan-1-ol were obtained from PurePEG. In the synthetic procedures, equivalents ('eq') are molar equivalents. Concentrations of reactants used in the synthetic procedures generally range from about 0.05 to about 3M, and are typically and mostly inbetween 0.1M and 1.0M. Analytical thin layer chromatography was performed on Kieselgel F-254 precoated silica plates. Column chromatography was carried out on Screening Devices B.V. flash silica gel (40-63 m mesh). $^1$H-NMR, $^{13}$C-NMR and $^{19}$F-NMR spectra were recorded on a Bruker Avance III HD (400 MHz for $^1$H-NMR, 100 MHz for $^{13}$C-NMR and 376 MHz for $^{19}$F-NMR) spectrometer at 298 K. Chemical shifts are reported in ppm downfield from TMS at room temperature. Abbreviations used for splitting patterns are s=singlet, d=doublet, t=triplet, q=quartet, qn=quintet, sept=septet, m=multiplet and br=broad. GC-MS was recorded using a Shimadzu GCMS-QP2010 plus on a Phenomenex Zebron ZB-5MS column. HPLC-PDA/MS was performed using a Shimadzu $L^C$-10 AD VP series HPLC coupled to a diode array detector (Finnigan Surveyor PDA Plus detector, Thermo Electron Corporation) and an Ion-Trap (LCQ Fleet, Thermo Scientific). HPLC-analyses were performed using a Alltech Alltima HP Cis 3p column using an injection volume of 1-4 µL, a flow rate of 0.2 mL min$^{-1}$ and typically a gradient (5% to 100% in 10 min, held at 100% for a further 3 min) of MeCN in $H_2O$ (both containing 0.1% formic acid) at 298 K. Preparative RP-HPLC (MeCN/$H_2O$ with 0.1% formic acid) was performed using a Shimadzu SCL-10A VP coupled to two Shimadzu LC-8A pumps and a Shimadzu SPD-10AV VP UV-vis detector on a Phenomenex Gemini 5µ $C_{18}$ 110 A column. HPLC-QTOF-HRMS was performed on a Waters Acquity $L^C$, that is equipped with a Sample Manager and Xevo G2 Qtof detector using Zspray lockspray ionization.

General Procedure A—Tetrazine (TZ) Synthesis

The nitrile (or combination of two different nitriles) and zinc triflate (0.05 eq to the total nitrile content) were combined. When this did not yield a clear solution this was achieved by shortly heating the mixture at 60° C. or by the addition of a minimum amount of EtOH. When a clear solution was obtained hydrazine monohydrate (5 eq to the total nitrile content) was added at once and the mixture was stirred at 60° C. for typically 16 h. The volatiles were removed in vacuo, the crude mixture containing dihydrotetrazine precursor ([2H]-TZ) was re-dissolved in THF/AcOH (1:1) and this solution was cooled on an ice-bath. $NaNO_2$ (5 eq to the total nitrile content) in water (5 to 10 mL per gram $NaNO_2$) was added dropwise (CAUTION: toxic fumes!). After stirring at room temperature for 10 min (or until a clear solution was achieved as a consequence of a delayed reaction due to a limited solubility of a reactant), water was added and the solution was extracted with $CHCl_3$ until an aqueous layer was obtained that lacked the typical TZ pink (sometimes red or purple) coloration. The organic layer was dried with $Na_2SO_4$ and the volatiles were removed in vacuo. Traces of AcOH were removed by flushing with $CHCl_3$, or by performing an additional sat. $NaHCO_3$ wash.

General Procedure B—THP Deprotection

The synthesis of THP-protected TZs was directly followed by THP-deprotection since, as a consequence of the acidic conditions, the THP group was largely removed during the oxidation process from [2H]-TZ to TZ. (Partly) THP-protected TZ was dissolved in $CHCl_3$/EtOH 2:1 and concentrated HCl was added (1 drop). The mixture was stirred at room temperature until TLC analysis indicated full conversion (generally around 1 h). The volatiles were removed in vacuo and the resulting product was flushed twice with $CHCl_3$. Note: if present, this procedure will generally remove around 5% of N-t-Boc-protecting groups.

General Procedure C—Isocyanate Coupling to TZ-Alcohol

The TZ-alcohol was dissolved in dry THF. When necessary gentle heating was applied to dissolve all starting compound. Dibutyltindilaurate (catalyst, 0.1 eq per alcohol) and isocyanate (2 eq per alcohol) were added, the mixture was stirred at 40° C. for 1 h and the solvent was removed in vacuo.

General Procedure D—TZ-Alcohol Activation and Coupling to Secondary Amine to Produce TZ-Carbamate Examples with $R^2$=H: The primary TZ-alcohol and N,N-diisopropylethylamine (1.5 eq) were dissolved in $CH_2Cl_2$ and p-nitrophenylchloroformate (1.5 eq) was added as a solid. Upon addition TLC analysis showed full conversion and the secondary amine was added (3 eq). An instantaneous color change as well as TLC analysis indicated full conversion. $CHCl_3$ was added. The organic layer was sequentially washed with 0.1 M HCl, sat. $NaHCO_3$ (until a colorless aqueous layer was obtained) and brine, dried with $Na_2SO_4$, filtrated and the filtrate was concentrated in vacuo.

Examples with $R_2$=Me: The secondary TZ-alcohol and 4-dimethylaminopyridine (1.5 eq) were dissolved in $CH_2Cl_2$ and p-nitrophenylchloroformate (1.5 eq) was added as a solution in $CH_2Cl_2$ at once (minimizing the formation of symmetrical TZ carbonate). Upon addition TLC analysis showed full conversion and the secondary amine was added (4 eq). A color change occurred gradually and the mixture was stirred at room temperature until TLC analysis indicated full conversion. $CHCl_3$ was added. The organic layer was sequentially washed with 0.1 M HCl, sat. $NaHCO_3$ (until a colorless aqueous layer was obtained) and brine, dried with $Na_2SO_4$, filtrated and the filtrate was concentrated in vacuo.

General Procedure E—N-t-Boc Deprotection tBoc-protected TZ was dissolved in $CHCl_3$/TFA (1:1) and the mixture was stirred at room temperature for 30 min to 1 h. After removal of the volatiles in vacuo the product was flushed with $CHCl_3$ (3×).

General Procedure F—Lactonitrile Activation and Coupling to Secondary Amine to Produce Carbamate Lactonitrile (racemate) was dissolved in a 1.9 M toluene solution of phosgene (2 eq) followed by the dropwise addition of N,N-diisopropylethylamine (1 eq). After stirring at room temperature for 1 h the solid was removed by filtration and the filtrate was concentrated in vacuo. The resulting oil was re-dissolved in $CHCl_3$ and the solution was washed with 0.1 M HCl (2×) and brine, dried using $Na_2SO_4$, filtrated and the filtrate was evaporated to dryness. This yielded α-cyanoethyl chloroformate as a yellow oil which was used immediately without further purification. The secondary amine (2 eq) was dissolved in toluene and, on an ice bath, a solution of the chloroformate (1 eq) in toluene was added dropwise. The mixture was stirred at room temperature for 16 h after which the white solid was removed by filtration. The solution containing the desired nitrile was evaporated to dryness and flushed with $CHCl_3$ (2×).

General Procedure G—Phenylchloroformate Coupling to TZ-Amine to Produce TZ-Carbamate The TZ-amine and N,N-diisopropylethylamine (4 eq) were dissolved in THF and phenylchloroformate (1.2 eq) was added. The mixture was stirred at room temperature until TLC analysis indicated complete conversion (typically 30 min). $CHCl_3$ was added and the organic layer was washed with 0.1 M HCl, dried with $Na_2SO_4$, filtrated and the filtrate was concentrated in vacuo.

Purification

The general procedures for the synthesis of the desired TZs and intermediates typically yield product that is not (completely) pure. The specific purification method is indicated for each compound separately. Whenever purification implied column chromatography, eluent conditions were based on the outcome of TLC analyses. Indicated percentages (%) of eluent used in column chromatography are v/v %.

Example 2: Synthesis of Tetrazine Triggers Believed to Release Via the Cascade Mechanism

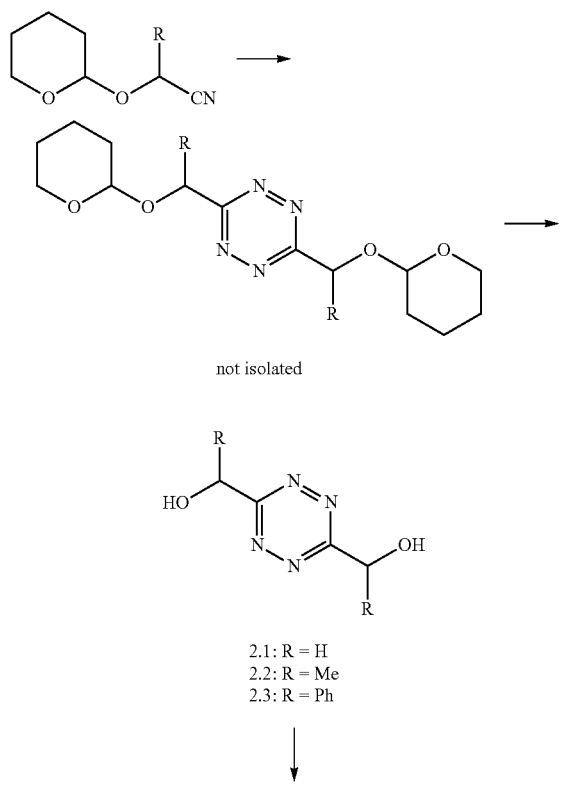

2.1: R = H
2.2: R = Me
2.3: R = Ph

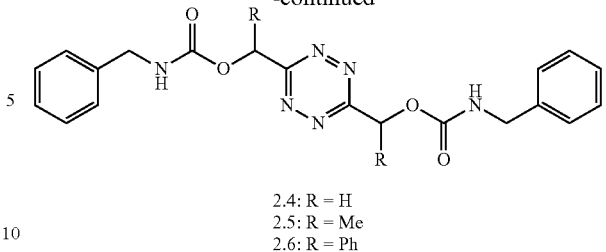

2.4: R = H
2.5: R = Me
2.6: R = Ph

The following compounds 2.1-2.3 have been prepared according to general procedures A and B.

2.1: This compound was prepared from 2-((tetrahydro-2H-pyran-2-yl)oxy)acetonitrile (Ref. 1). Column chromatography (flash $SiO_2$, 6% MeOH in $CHCl_3$) yielded pure 2.1 (49 mg, 0.34 mmol, 38% over two steps) as a pink solid. $^1$H-NMR ($CD_3OD$): δ=5.17 (s, 4H, $CH_2$). $^{13}$C-NMR ($CD_3OD$): δ=170.5, 63.5. ESI-MS: m/z Calc. for $C_4H_6N_4O_2$ 142.05; Obs. $[M+H]^+$ 143.00, $[2M+H]^+$ 245.08.

2.2: This compound was prepared from 2-((tetrahydro-2H-pyran-2-yl)oxy)propionitrile (Ref. 2). Column chromatography (flash $SiO_2$, 5% MeOH in $CHCl_3$) yielded pure 2.2 (16 mg, 91 μmol, 56% over two steps) as a pink solid. $^1$H-NMR ($CD_3OD$): δ=5.48 (q, 2H, CH), 1.80 (d, 6H, $CH_3$). $^{13}$C-NMR ($CD_3OD$): δ=173.0, 69.5, 22.3. ESI-MS: m/z Calc. for $C_6H_{10}N_4O_2$ 170.08; Obs. $[M+H]^+$ 171.00.

2.3: This compound was prepared from α-((tetrahydro-2H-pyran-2-yl)oxy)benzeneacetonitrile (Ref. 3). Column chromatography (flash $SiO_2$, 30% EtOAc in $CHCl_3$) yielded pure 2.3 (25 mg, 85 μmol, 27% over two steps) as a pink solid. $^1$H-NMR ($CD_3OD$): δ=7.54 (d, 4H, ArH), 7.35 (t, 4H, ArH), 7.28 (t, 2H, ArH), 6.33 (s, 2H, CH). $^{13}$C-NMR ($CDCl_3/CD_3OD$ 2:1): δ=170.6, 139.8, 128.7, 128.5, 126.68, 126.66, 74.35, 74.33. ESI-MS: m/z Calc. for $C_{16}H_{14}N_4O_2$ 294.11; Obs. $[M+H]^+$ 295.00.

The following compounds 2.4-2.6 have been prepared according to general procedure C using benzyl isocyanate.

2.4: This compound was prepared from 2.1. Recrystallization from $CHCl_3$ (8 mL) yielded pure 2.4 (51 mg, 0.12 mmol, 85%) as a pink solid. $^1$H-NMR (DMSO-d6): δ=8.16 (t, 2H, NH), 7.35-7.21 (m, 10H, ArH), 5.65 (s, 4H, $OCH_2$), 4.22 (d, 4H, $ArCH_2$). $^{13}$C-NMR (DMSO-d6): S=166.9, 155.9, 139.4, 128.3, 127.0, 126.9, 63.0, 43.9. ESI-MS: m/z Calc. for $C_{20}H_{20}N_6O_4$ 408.15; Obs. $[M+H]^+$ 409.17, $[2M+H]^+$817.08, $[2M+Na]^+$838.92.

2.5: This compound was prepared from 2.2. Column chromatography (flash $SiO_2$, 20% EtOAc in $CHCl_3$) and precipitation, induced by adding heptane (3 mL) to a stirred solution in $CHCl_3$ (3 mL) at 55° C., followed by cooling down, filtration, washing with pentane and drying of the solid in vacuo yielded pure 2.5 (29 mg, 66 μmol, 73%) as a pink solid. $^1$H-NMR (DMSO-d6): δ=8.12 (t, 2H, NH), 7.31 (m, 4H, ArH), 7.23 (m, 6H, ArH), 6.13 (q, 2H, CH), 4.18 (d, 4H, $ArCH_2$), 1.71 (d, 6H, $CH_3$). $^{13}$C-NMR (DMSO-d6): δ=169.7, 155.6, 139.4, 128.3, 127.0, 126.9, 126.8, 70.1, 43.8, 19.6. ESI-MS: m/z Calc. for $C_{22}H_{24}N_6O_4$ 436.19; Obs. $[M+H]^+$ 437.08, $[2M+H]^+$872.92, $[2M+Na]^+$894.75.

2.6: This compound was prepared from 2.3. Column chromatography (flash $SiO_2$) using an elution gradient of 0% to 12% EtOAc in $CHCl_3$ and, in a second chromatography step, an elution gradient of 10% to 25% acetone in heptane yielded pure 2.6 (20 mg, 36 μmol, 67%) as a pink solid. $^1$H-NMR ($CDCl_3$): δ=7.58 (d, 4H, ArH), 7.39-7.23 (m, 16H, ArH), 7.18 (2s, 2H, OCH), 5.37 (2t, 2H, NH), 4.36 (m, 4H, ArCH$_2$). $^{13}$C-NMR (CDCl$_3$): δ=169.0, 155.2, 137.9, 135.9, 129.4, 129.1, 128.9, 128.8, 127.9, 127.83, 127.79, 127.77, 127.69, 127.68, 76.3, 45.4. ESI-MS: m/z Calc. for C$_{32}$H$_{28}$N$_6$O$_4$ 560.22; Obs. [M+Na]$^+$ 583.08, [2M+H]$^+$ 1120.92, [2M+Na]$^+$1142.83.

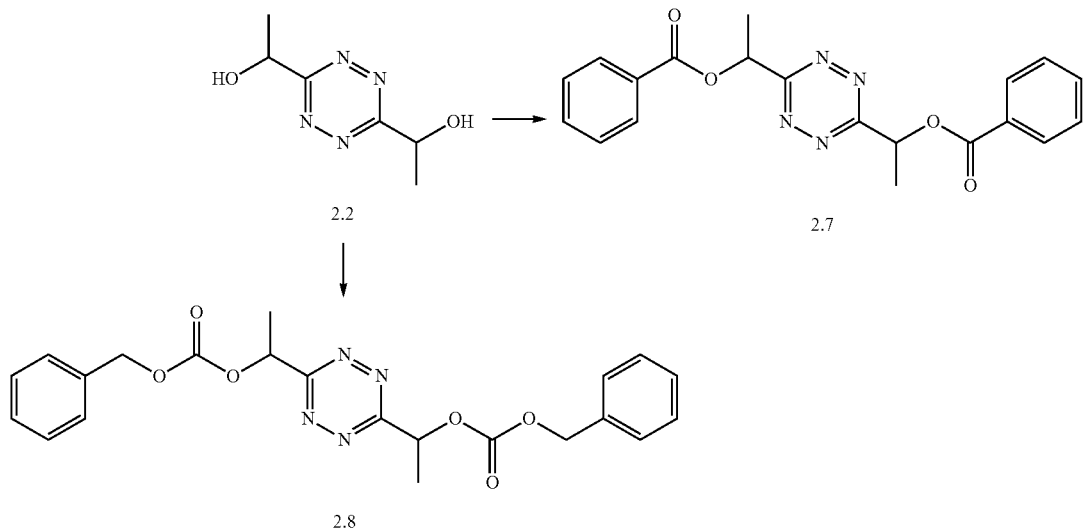

2.7: Under an Ar atmosphere, 2.2 (14 mg, 81 μmol) and 4-dimethylaminopyridine (48 mg, 0.39 mmol, 5 eq) were dissolved in CHCl$_3$/THF 1:1 (600 μL). After cooling to 0° C., benzoyl chloride (28 μL, 0.24 mmol, 3 eq) was added and the mixture was stirred at room temperature for 1 h. The solvent was removed in vacuo and column chromatography (flash SiO$_2$) using an elution gradient of 0% to 2% EtOAc in CHCl$_3$ was followed by precipitation, induced by adding heptane (6 mL) to a stirred solution in CHCl$_3$ (300 μL). Storage at −20° C. for 16 h, filtration, washing with ice-cold pentane and drying of the solid in vacuo yielded pure 2.7 (21 mg, 55 μmol, 68%) as a pink solid. $^1$H-NMR (CDCl$_3$): δ=8.11 (2d, 4H, ArH), 7.58 (2t, 2H, ArH), 7.45 (2t, 4H, ArH), 6.56 (2q, 2H, CH), 1.97 (d, 6H, CH$_3$). $^{13}$C-NMR (CDCl$_3$): δ=169.7, 166.0, 133.6, 130.09, 130.08, 129.38, 129.37, 128.6, 70.8, 19.85, 19.82. ESI-MS: m/z Calc. for C$_{20}$H$_{18}$N$_4$O$_4$ 378.13; Obs. [M+H]$^+$ 379.08, [2M+H]$^+$ 756.67, [2M+Na]$^+$778.83.

2.8: Under an Ar atmosphere, 2.2 (9.6 mg, 56 μmol) and 4-dimethylaminopyridine (34 mg, 0.28 mmol, 5 eq) were dissolved in CHCl$_3$/THF 1:1 (600 μL). After cooling to 0° C., benzyl chloroformate (40 μL, 0.26 mmol, 5 eq) was added and the mixture was stirred at room temperature for 1 h. CHCl$_3$ (40 mL) was added, the organic layer was washed with 0.1 M HCl and H$_2$O (both 20 ml), dried with Na$_2$SO$_4$, filtrated and the filtrate was concentrated in vacuo. Column chromatography (flash SiO$_2$) using an elution gradient of 0% to 2% EtOAc in CHCl$_3$ yielded pure 2.8 (19 mg, 43 μmol, 76%) as a pink oil. $^1$H-NMR (CDCl$_3$): δ=7.41-7.31 (m, 10H, ArH), 6.23 (2q, 2H, CM), 5.19 (2d, 4H, CH$_2$), 1.87 (d, 6H, CH$_3$). $^{13}$C-NMR (CDCl$_3$): δ=169.3, 154.5, 134.8, 128.81, 128.76, 128.49, 128.48, 73.62, 73.60, 70.43, 70.42, 19.64. ESI-MS: m/z Calc. for C$_{22}$H$_{22}$N$_4$O$_6$ 438.15; Obs. [M+H]$^+$ 439.17, [2M+H]$^+$876.58, [2M+Na]$^+$898.50.

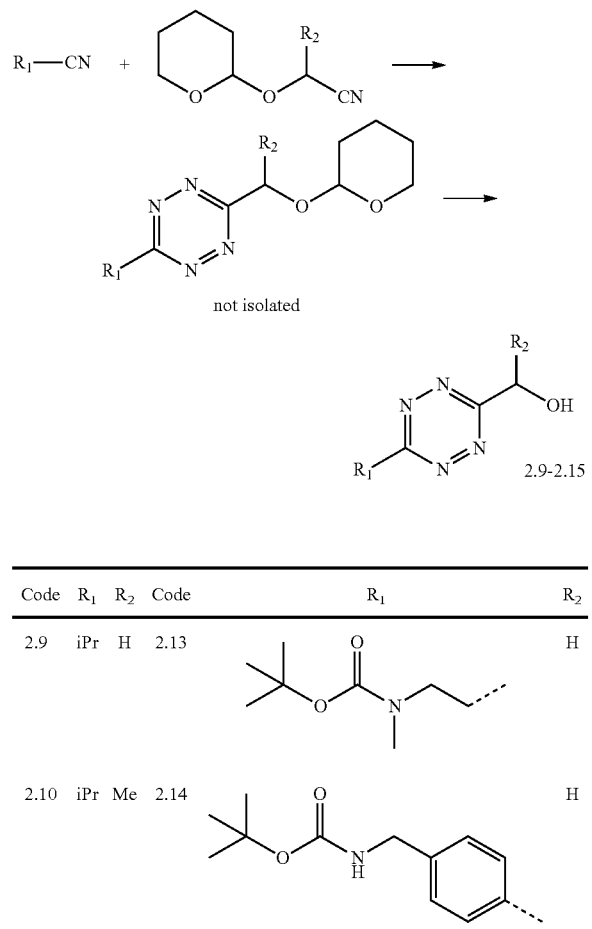

| Code | R$_1$ | R$_2$ | Code | R$_1$ | R$_2$ |
|---|---|---|---|---|---|
| 2.9 | iPr | H | 2.13 | (tert-butyl carbamate with N-methyl ethyl group) | H |
| 2.10 | iPr | Me | 2.14 | (tert-butyl carbamate with benzyl group) | H |

| Code | R₁ | R₂ | Code | R₁ | R₂ |
|---|---|---|---|---|---|
| 2.11 | Ph | H | 2.15 | 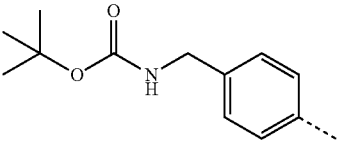 | Me |
| 2.12 | Ph | Me | | | |

The following compounds 2.9-2.15 have been prepared according to general procedures A and B.

2.9: This compound was prepared from isobutyronitrile and 2-[(tetrahydro-2H-pyran-2-yl)oxy]acetonitrile (Ref. 1) that were reacted in a 2:1 molar ratio. Column chromatography (flash SiO₂) using an elution gradient of 0% to 30% EtOAc in CHCl₃ yielded pure 2.9 (37 mg, 0.24 mmol, 15% over two steps) as a pink oil. ¹H-NMR (CDCl₃): δ=5.28 (s, 2H, CH₂), 3.70 (sept, 1H, CH), 3.11 (br, 1H, OH), 1.54 (d, 6H, CH₃). ESI-MS: m/z Calc. for C₆H₁₀N₄O 154.09; Obs. [M+H]⁺ 154.92.

2.10: This compound was prepared from isobutyronitrile and 2-[(tetrahydro-2H-pyran-2-yl)oxy]propionitrile (Ref. 2) that were reacted in a 1:1 molar ratio. Column chromatography (flash SiO₂) using an elution gradient of 0% to 16% EtOAc in CHCl₃ yielded pure 2.10 (48 mg, 0.29 mmol, 17% over two steps) as a pink solid. ¹H-NMR (CDCl₃): δ=5.42 (qn, 1H, CHO), 3.69 (sept, 1H, CH(CH₃)₂), 3.34 (d, 1H, OH), 1.78 (d, 3H, OCHCH₃), 1.55 (d, 6H, CH(CH₃)₂). ESI-MS: m/z Calc. for C₇H₁₂N₄O 168.10; Obs. [M+H]⁺ 169.00.

2.11: This compound was prepared according to Lang et al., J. Heterocycl. Chem. 1975, 12, 1143.

2.12: This compound was prepared from benzonitrile and 2-[(tetrahydro-2H-pyran-2-yl)oxy]propionitrile (Ref. 2) that were reacted in a 4:1 molar ratio. EtOH was used as a solvent. Directly after oxidation and work-up the volatiles were removed in vacuo and the mixture was stirred at 50° C. in CHCl₃ for 5 min. After cooling to room temperature, most of the relatively insoluble diphenyltetrazine byproduct was removed by filtration. Column chromatography (flash SiO₂) using an elution gradient of 0% to 10% EtOAc in CHCl₃ yielded pure 2.12 (95 mg, 0.47 mmol, 30% over two steps) as a pink solid. ¹H-NMR (CDCl₃): (5=8.62 (m, 2H, ArH), 7.69-7.58 (m, 3H, ArH), 5.49 (qn, 1H, CH), 3.39 (d, 1H, OH), 1.82 (d, 3H, CH₃). ESI-MS: m/z Calc. for C₁₀H₁₀N₄O 202.09; Obs. [M+H]⁺ 203.00.

2.13: This compound was prepared from t-butyl N-(2-cyanoethyl)-N-methylcarbamate and 2-[(tetrahydro-2H-pyran-2-yl)oxy]acetonitrile (Ref. 1) that were reacted in a 3:1 molar ratio. Column chromatography (flash SiO₂, compound adsorbed onto silica from MeOH) using an elution gradient of 10% to 50% EtOAc in CHCl₃ yielded pure 2.13 (98 mg, 0.36 mmol, 18% over two steps) as a red solid. ¹H-NMR (CDCl₃): δ=5.26 (br s, 2H, CH₂OH), 3.78 (br, 2H, NCH₂CH₂), 3.56 (t, 2H, NCH₂CH₂), 3.17 (t, 1H, OH), 2.93 (s, 3H, NCH₃), 1.32 (s, 9H, C(CH₃)₃). ESI-MS: m/z Calc. for C₁₁H₁₉N₅O₃ 269.15; Obs. [M-tboc+2H]⁺170.08, [M-tbutyl+2H]⁺213.92, [M+H]⁺ 269.83.

2.14: This compound was prepared from t-butyl N-(4-cyanobenzyl)carbamate and 2-[(tetrahydro-2H-pyran-2-yl)oxy]acetonitrile (Ref. 1) that were reacted in a 2:1 molar ratio. EtOH was used as a solvent. Directly after oxidation and work-up the volatiles were removed in vacuo and the mixture was stirred at reflux in CHCl₃ for 5 min. After cooling to room temperature, most of the relatively insoluble diphenyltetrazine derivative byproduct was removed by filtration. Column chromatography (flash SiO₂, compound adsorbed onto silica from CHCl₃/MeOH) using an elution gradient of 5% to 40% EtOAc in CHCl₃ and, in a second chromatography step (normal SiO₂), elution with 35% acetone in heptane was followed by precipitation, induced by adding heptane (8 mL) to a stirred solution in CHCl₃ (0.5 mL). Filtration, washing with pentane and drying of the solid in vacuo yielded pure 2.14 (86 mg, 0.27 mmol, 22% over two steps) as a red solid. ¹H-NMR (CDCl₃): δ=8.56 (d, 2H, ArH), 7.51 (d, 2H, ArH), 5.33 (d, 2H, CH₂OH), 5.03 (br t, 1H, NH), 4.44 (d, 2H, ArCH₂), 3.25 (br t, 1H, OH), 1.48 (s, 9H, C(CH₃)₃). ESI-MS: m/z Calc. for C₁₅H₁₉N₅O₃ 317.15; Obs. [M-tboc+2H]⁺ 218.00, [M-tbutyl+2H]⁺ 261.92.

2.15: This compound was prepared from t-butyl N-(4-cyanobenzyl)carbamate and 2-[(tetrahydro-2H-pyran-2-yl)oxy]propionitrile (Ref. 2) that were reacted in a 2:1 molar ratio. EtOH was used as a solvent. Directly after oxidation and work-up the volatiles were removed in vacuo and the mixture was stirred at reflux in CHCl₃ for 5 min. After cooling to room temperature, most of the relatively insoluble diphenyltetrazine derivative byproduct was removed by filtration. Column chromatography (flash SiO₂, compound adsorbed onto silica from CHCl₃/MeOH) using an elution gradient of 0% to 30% EtOAc in CHCl₃ was followed by precipitation, induced by adding heptane (2 mL) to a stirred solution in CHCl₃ (0.5 mL). Filtration, washing with pentane and drying of the solid in vacuo yielded pure 2.15 (50 mg, 0.15 mmol, 12% over two steps) as a pink solid. ¹H-NMR (CDCl₃): δ=8.56 (d, 2H, ArH), 7.51 (d, 2H, ArH), 5.48 (q, 1H, CH), 5.04 (br t, 1H, NH), 4.44 (d, 2H, ArCH₂), 3.49 (br, 1H, OH), 1.82 (d, 3H, CHCH₃), 1.48 (s, 9H, C(CH₃)₃). ESI-MS: m/z Calc. for C₁₆H₂₁N₅O₃ 331.16; Obs. [M-tboc+2H]⁺ 232.00, [M-tbutyl+2H]⁺ 275.92.

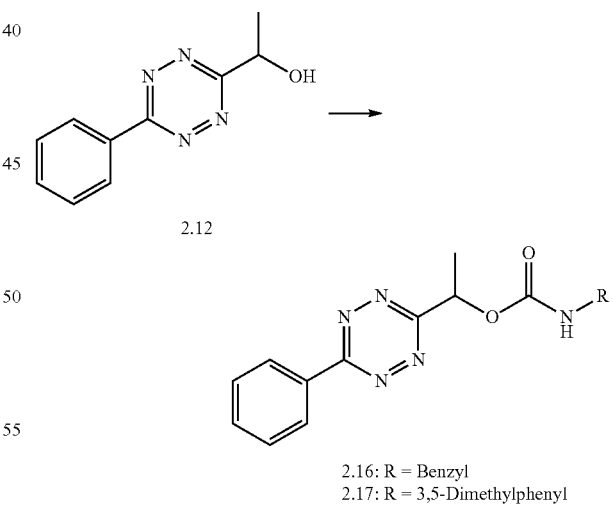

2.16: R = Benzyl
2.17: R = 3,5-Dimethylphenyl

The following compounds 2.16 and 2.17 have been prepared according to general procedure C.

2.16: This compound was prepared from 2.12 and benzyl isocyanate. Column chromatography (flash SiO₂) using an elution gradient of 0% to 3% EtOAc in CHCl₃ yielded 2.16 (5.8 mg, 17 μmol, 97%) as a pink solid. ¹H-NMR (CDCl₃): δ=8.62 (m, 2H, ArH), 7.67-7.57 (m, 3H, ArH), 7.37-7.26 (m, 5H, ArH), 6.30 (q, 1H, CH), 5.28 (br t, 1H, NH), 4.41 (m, 2H, CH$_2$), 1.86 (d, 3H, CH$_3$). ESI-MS: m/z Calc. for C$_{18}$H$_{17}$N$_5$O$_2$ 335.14; Obs. [M+H]$^+$ 336.17, [M+Na]$^+$358.25, [2M+Na]$^+$693.00.

2.17: This compound was prepared from 2.12 and 3,5-dimethylphenyl isocyanate. Column chromatography (flash SiO$_2$) using an elution gradient of 0% to 4% EtOAc in CHCl$_3$ was followed by precipitation from CHCl$_3$ (1 mL) into heptane (20 mL) and storage at −20° C. for 1 h. Filtration, washing with ice-cold pentane and drying of the solid in vacuo yielded pure 2.17 (24 mg, 69 μmol, 100%) as a pink solid. $^1$H-NMR (CDCl$_3$): δ=8.60 (m, 2H, ArH), 7.66-7.55 (m, 3H, ArH), 6.99 (s, 2H, ArH), 6.89 (br, 1H, NH), 6.70 (s, 1H, ArH), 6.34 (q, 1H, CH), 2.26 (s, 6H, ArCH$_3$), 1.90 (d, 3H, CHCH$_3$). ESI-MS: m/z Calc. for C$_{19}$H$_{19}$N$_5$O$_2$ 349.15; Obs. [M+H]$^+$ 350.08, [M+Na]$^+$372.17, [2M+H]$^+$ 698.75, [2M+Na]$^+$ 721.00.

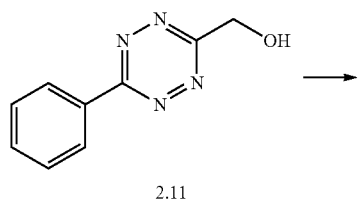

2.11

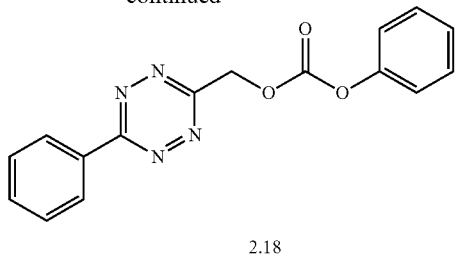

2.18

2.18: DIPEA (932 mg, 7.22 mmol) was added to a solution of 2.11 (707 mg, 3.76 mmol) in 20 mL toluene. Phenyl chloroformate (869 mg, 5.55 mmol) was added, and the mixture was stirred for 3 d. Heptane (20 mL) was added, the mixture was filtered and the solid was washed with heptane. The filtrate was purified column chromatography (flash SiO$_2$) using gradually increasing toluene % in ethyl acetate, affording 128 mg of 2.18 (0.42 mmol, 11%). $^1$H-NMR (CDCl$_3$) δ 8.64 (d, J=6.4, 2H), 7.75-7.55 (m, 3H), 7.5-7.35 (m, 2H), 7.3-7.2 (m, 3H), 5.90 (s, 2H); $^{13}$C-NMR (CDCl$_3$) δ 165.4, 164.3, 152.5, 151.0, 132.3, 131.2, 129.7, 129.5, 128.3, 126.3, 120.8, 66.4.

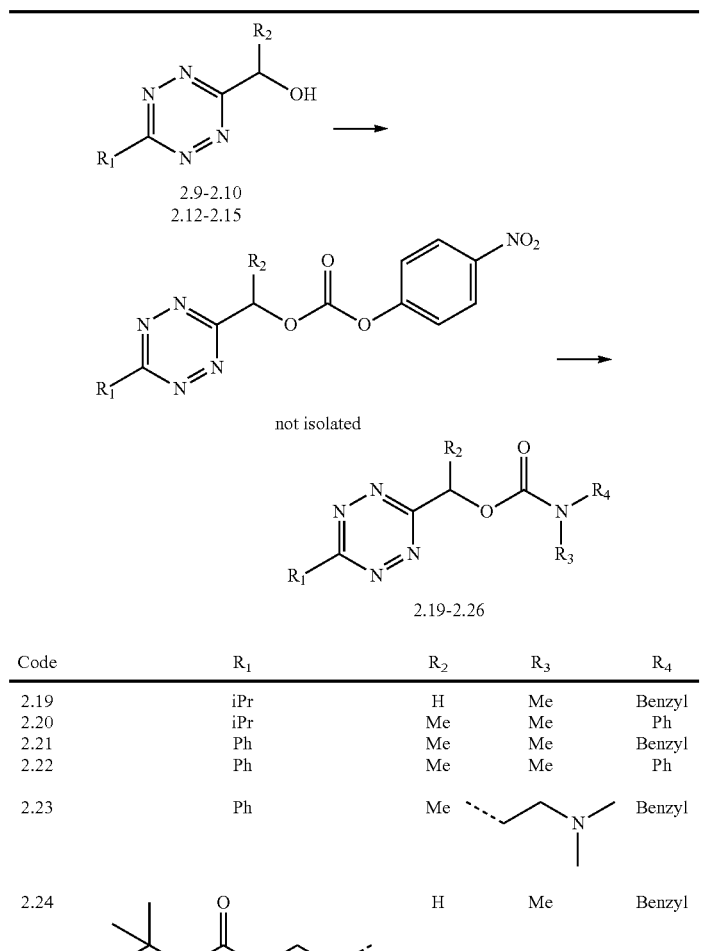

| Code | R$_1$ | R$_2$ | R$_3$ | R$_4$ |
|---|---|---|---|---|
| 2.19 | iPr | H | Me | Benzyl |
| 2.20 | iPr | Me | Me | Ph |
| 2.21 | Ph | Me | Me | Benzyl |
| 2.22 | Ph | Me | Me | Ph |
| 2.23 | Ph | Me | | Benzyl |
| 2.24 | | H | Me | Benzyl |

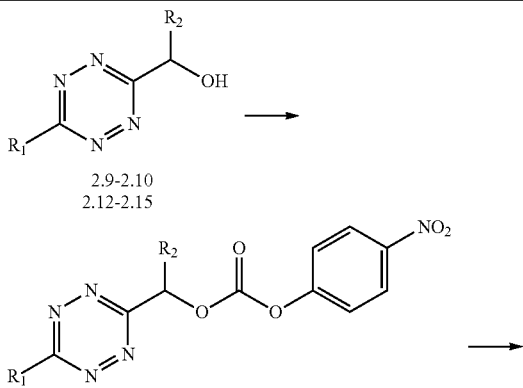

| Code | $R_1$ | $R_2$ | $R_3$ | $R_4$ |
|------|-------|-------|-------|-------|
| 2.25 | *tert*-butyl ((4-methylenephenyl)methyl)carbamate group | H | Me | Benzyl |
| 2.26 | *tert*-butyl ((4-methylenephenyl)methyl)carbamate group | Me | Me | Benzyl |

The following compounds 2.19-2.26 have been prepared according to general procedure D. All NMR spectra (except for $R_4$=Ph) indicate the presence of two carbamate rotamers.

2.19: This compound was prepared from 2.9 and N-benzylmethylamine. Column chromatography (flash $SiO_2$) using an elution gradient of 0% to 4% EtOAc in $CHCl_3$ yielded pure 2.19 (15 mg, 50 μmol, 77%) as a pink oil. $^1$H-NMR ($CDCl_3$): δ=7.39-7.26 (m, 5H, ArH), 5.76 (s, 2H, $CH_2O$), 4.60 and 4.52 (2s, 2H, $ArCH_2$), 3.67 (sept, 1H, CH), 2.96 and 2.93 (2s, 3H, $NCH_3$), 1.54 (d, 6H, $CH(CH_3)_2$). ESI-MS: m/z Calc. for $C_{15}H_{19}N_5O_2$ 301.15; Obs. [M+H]$^+$ 301.92.

2.20: This compound was prepared from 2.10 and N-methylaniline. Column chromatography (flash $SiO_2$) using an elution gradient of 0% to 4% EtOAc in $CHCl_3$ and, in a second chromatography step (normal $SiO_2$), elution with 5% acetone in heptane yielded pure 2.20 (9.0 mg, 30 μmol, 49%) as a pink oil. $^1$H-NMR ($CDCl_3$): δ=7.35 (m, 4H, ArH), 7.22 (m, 1H, ArH), 6.23 (q, 1H, CHO), 3.66 (sept, 1H, $CH(CH_3)_2$), 3.36 (br s, 3H, $NCH_3$), 1.76 (br, 3H, $OCHCH_3$), 1.54 (d, 6H, $CH(CH_3)_2$). ESI-MS: m/z Calc. for $C_{15}H_{19}N_5O_2$ 301.15; Obs. [M+H]$^+$ 301.92.

2.21: This compound was prepared from 2.12 and N-benzylmethylamine. Column chromatography (flash $SiO_2$) using an elution gradient of 0% to 2% EtOAc in $CHCl_3$ and, in a second chromatography step (normal $SiO_2$), elution with 4% acetone in heptane yielded pure 2.21 (6.0 mg, 17 μmol, 16%) as a pink oil. $^1$H-NMR ($CDCl_3$): δ=8.62 (d, 2H, ArH), 7.67-7.57 (m, 3H, ArH), 7.39-7.24 (m, 5H, ArH), 6.31 (m, 1H, CH), 4.72-4.38 (m, 2H, $ArCH_2$), 2.99 and 2.88 (2s, 3H, $NCH_3$), 1.88 (2d, 3H, $CHCH_3$). ESI-MS: m/z Calc. for $C_{19}H_{19}N_5O_2$ 349.15; Obs. [M+H]$^+$ 350.00.

2.22: This compound was prepared from 2.12 and N-methylaniline. Column chromatography (normal $SiO_2$) using elution with 4% acetone in heptane yielded pure 2.22 (10 mg, 30 μmol, 54%) as a pink oil. $^1$H-NMR ($CDCl_3$): δ=8.61 (d, 2H, ArH), 7.67-7.57 (m, 3H, ArH), 7.36 (m, 4H, ArH), 7.22 (m, 1H, ArH), 6.27 (q, 1H, CH), 3.37 (br s, 3H, $NCH_3$), 1.81 (br, 3H, $CHCH_3$). ESI-MS: m/z Calc. for $C_{18}H_{17}N_5O_2$ 335.14; Obs. [M+H]$^+$ 335.92.

2.23: This compound was prepared from 2.12 and N,N-dimethyl-N'-benzyl-1,2-ethanediamine (Ref. 4). Column chromatography (flash $SiO_2$) using an elution gradient of 1% to 4% MeOH in $CHCl_3$ and, in a second chromatography step (normal $SiO_2$), elution with 50% acetone in heptane followed by 4% MeOH in $CHCl_3$ yielded pure 2.23 (11 mg, 27 μmol, 64%) as a pink oil. $^1$H-NMR ($CDCl_3$): δ=8.62 (d, 2H, ArH, 7.67-7.57 (m, 3H, ArH), 7.38-7.24 (m, 5H, ArH), 6.31 (q, 1H, CH), 4.66 and 4.52 (2m, 2H, $ArCH_2$), 3.55-3.28 (m, 2H, $CONCH_2CH_2$), 2.58-2.40 (m, 2H, $CH_2N(CH_3)_2$), 2.26 and 2.25 (2s, 6H, $N(CH_3)_2$), 1.87 (2d, 3H, $CHCH_3$). ESI-MS: m/z Calc. for $C_{22}H_{26}N_6O_2$ 406.21; Obs. [M+H]$^+$ 407.08, [M+Na]$^+$ 429.00.

2.24: This compound was prepared from 2.13 and N-benzylmethylamine. Column chromatography (flash SiO$_2$) using an elution gradient of 2% to 25% EtOAc in CHCl$_3$ yielded pure 2.24 (17 mg, 41 μmol, 88%) as a pink oil. $^1$H-NMR (CDCl$_3$): δ=7.38-7.26 (m, 5H, ArH), 5.75 (s, 2H, CH$_2$O), 4.58 and 4.52 (2s, 2H, ArCH$_2$), 3.80 (br, 2H, NCH$_2$CH$_2$), 3.55 (t, 2H, NCH$_2$CH$_2$), 2.96-2.90 (3s, 6H, NCH$_3$), 1.34 (s, 9H, C(CH$_3$)$_3$). ESI-MS: m/z Calc. for C$_{20}$H$_{28}$N$_6$O$_4$ 416.22; Obs. [M−tboc+2H]$^+$317.00, [M+Na]$^+$ 439.00.

2.25: This compound was prepared from 2.14 and N-benzylmethylamine. Column chromatography (flash SiO$_2$) using an elution gradient of 5% to 10% EtOAc in CHCl$_3$ yielded pure 2.25 (27 mg, 58 μmol, 94%) as a pink solid. $^1$H-NMR (CDCl$_3$): δ=8.58 (d, 2H, ArH), 7.51 (d, 2H, ArH), 7.39-7.26 (m, 5H, ArH), 5.80 (s, 2H, CH$_2$O), 5.02 (br, 1H, NH), 4.60 and 4.53 (2s, 2H, CH$_2$NCH$_3$), 4.44 (d, 2H, CH$_2$NH), 2.97 and 2.94 (2s, 3H, NCH$_3$), 1.48 (s, 9H, C(CH$_3$)$_3$). ESI-MS: m/z Calc. for C$_{24}$H$_{28}$N$_6$O$_4$ 464.22; Obs. [M−tboc+2H]$^+$ 365.00, [M−tbutyl+2H]$^+$ 409.00, [M+H]$^+$ 465.00, [2M-tboc+2H]$^+$828.92, [2M+Na]$^+$950.67.

2.26: This compound was prepared from 2.15 and N-benzylmethylamine. Column chromatography (flash SiO$_2$) using an elution gradient of 5% to 10% EtOAc in CHCl$_3$ yielded pure 2.26 (23 mg, 48 μmol, 76%) as a pink solid. $^1$H-NMR (CDCl$_3$): δ=8.58 (d, 2H, ArH), 7.51 (d, 2H, ArH), 7.39-7.23 (m, 5H, ArH), 6.30 (m, 1H, CH), 4.99 (br, 1H, NH), 4.72-4.36 (m, 4H, ArCH$_2$), 2.99 and 2.87 (2s, 3H, NCH$_3$), 1.87 (2d, 3H, CHCH$_3$), 1.49 (s, 9H, C(CH$_3$)$_3$). ESI-MS: m/z Calc. for C$_{25}$H$_{30}$N$_6$O$_4$ 478.23; Obs. [M−tboc+2H]$^+$ 379.08, [M−tbutyl+2H]$^+$423.00, [M+H]$^+$ 479.00, [M+Na]$^+$ 501.08, [2M-tboc+2H]$^+$ 856.92, [2M+Na]$^+$ 978.75.

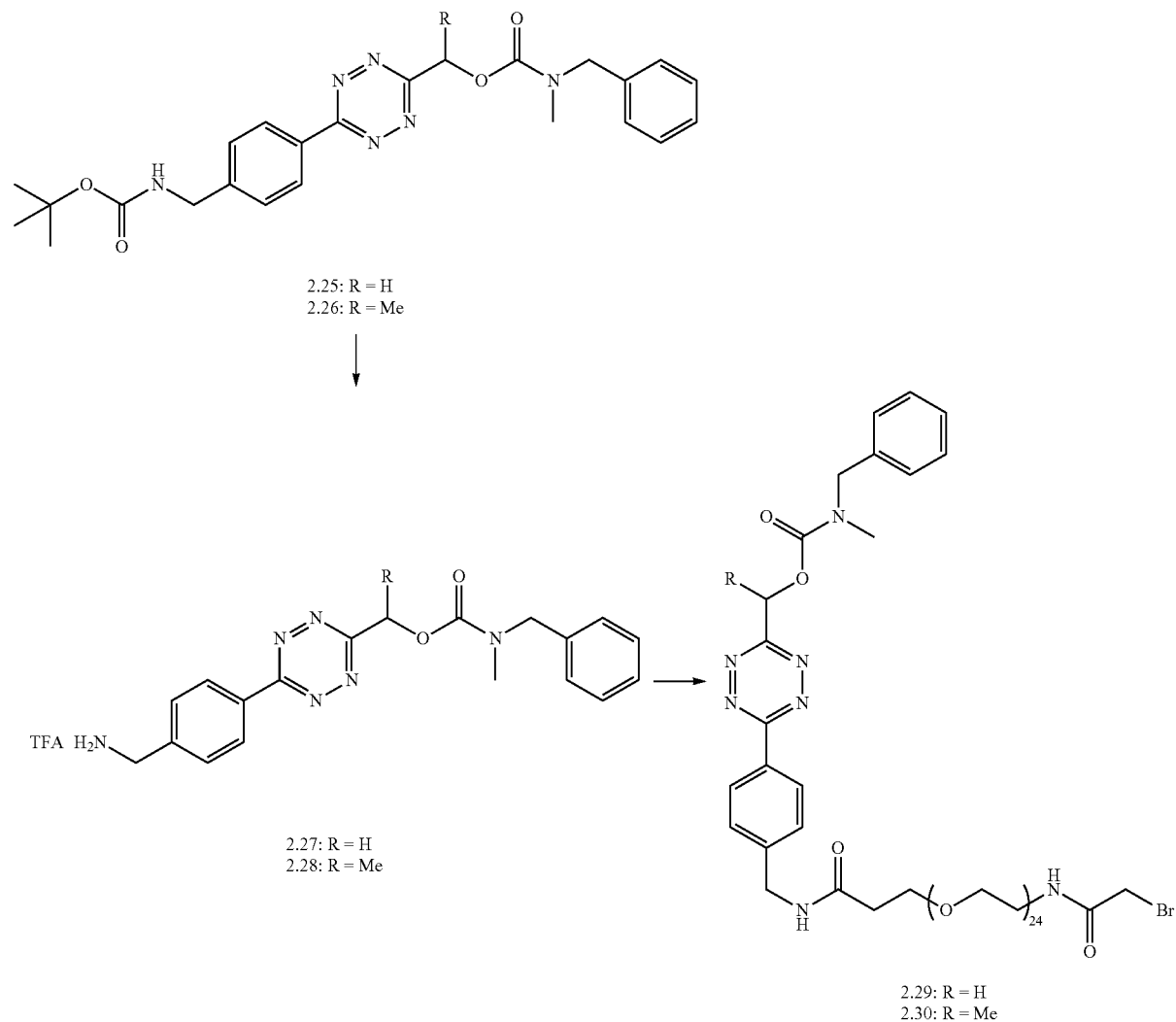

2.25: R = H
2.26: R = Me 2.27: R = H
2.28: R = Me 2.29: R = H
2.30: R = Me

The following compounds have been prepared according to general procedure E (2.27 and 2.28) followed by coupling to bromoacetamide-PEG24-acid TFP ester (2.29 and 2.30). All NMR spectra indicate the presence of two carbamate rotamers.

2.27: This compound was prepared from 2.25. Pure 2.27 (14 mg, 29 μmol, 100%) was obtained as a pink solid. $^1$H-NMR (CDCl$_3$): δ=8.41 (d, 2H, ArH), 7.49 (d, 2H, ArH), 7.34-7.18 (m, 5H, ArH), 5.71 (s, 2H, CH$_2$O), 4.54 and 4.43 (2s, 2H, CH$_2$NCH$_3$), 4.07 (br s, 2H, CH$_2$NH$_2$), 2.93 and 2.85 (2s, 3H, NCH$_3$). ESI-MS: m/z Calc. for C$_{21}$H$_{21}$F$_3$N$_6$O$_4$ 478.16; Obs. [M−TFA+H]$^+$365.00, [2M−2TFA+H]$^+$728.92, [2M−2TFA+Na]$^+$750.67.

2.28: This compound was prepared from 2.26. Pure 2.28 (12 mg, 24 µmol, 100%) was obtained as a pink solid. $^1$H-NMR (CDCl$_3$): δ=8.45 (d, 2H, ArH), 7.51 (d, 2H, ArH), 7.37-7.14 (m, 5H, ArH), 6.20 (m, 1H, CH), 4.66-4.30 (m, 2H, CH$_2$NCH$_3$), 4.14 (br s, 2H, CH$_2$NH$_2$), 2.97 and 2.81 (2s, 3H, NCH$_3$), 1.83 (2d, 3H, CHCH$_3$). ESI-MS: m/z Calc. for C$_{22}$H$_{23}$F$_3$N$_6$O$_4$ 492.17; Obs. [M−TFA+H]$^+$379.08, [2M−2TFA+H]$^+$ 756.92, [2M−2TFA+Na]$^+$ 778.67.

2.29: 2.27 (14 mg, 29 µmol) and N,N-diisopropylethylamine (17 µL, 97 µmol, 3.3 eq) were dissolved in CH$_2$Cl$_2$ (250 µL). Bromoacetamide-PEG24-acid TFP ester (41 mg, 29 µmol, 1 eq) was added, partly as a solid and as a solution in CH$_2$Cl$_2$ (150 µL), and the mixture was stirred at room temperature for 1 h. The reaction mixture was added dropwise to a stirring solution of diisopropylether (20 mL), centrifuged (5 min at 4000 rpm) and decanted. The resulting solid was washed with diethylether (20 mL) after which centrifugation and decantation were repeated. Drying of the solid in vacuo yielded pure 2.29 (32 mg, 20 µmol, 69%) as a pink solid. $^1$H-NMR (CDCl$_3$): δ=8.57 (d, 2H, ArH), 7.53 (d, 2H, ArH), 7.39-7.25 (m, 5H, ArH), 7.23 (br t, 1H, NH), 7.09 (br, 1H, NH), 5.80 (s, 2H, TZCH$_2$), 4.61 and 4.53 (2s, 2H, CH$_2$NCH$_3$), 4.58 (d, 2H, ArCH$_2$NH), 3.88 (s, 2H, CH$_2$Br), 3.83-3.43 (m, 98H, PEG OCH$_2$, OCH$_2$CH$_2$NH), 2.98 and 2.94 (2s, 3H, NCH$_3$), 2.58 (t, 2H, COCH$_2$CH$_2$). ESI-MS: m/z Calc. for C$_{72}$H$_{122}$BrN$_7$O$_{28}$ 1613.75; Obs. [M+2H]$^{2+}$ 807.67, [M+H]$^+$ 1614.25, [M+Na]$^+$ 1636.17.

2.30: This compound was synthesized from 2.28 following the procedure for 2.29 with the exception that precipitation was performed in diethylether. This yielded pure 2.30 (22 mg, 14 µmol, 56%) as a pink solid. $^1$H-NMR (CDCl$_3$): δ=8.57 (d, 2H, ArH), 7.53 (d, 2H, ArH), 7.40-7.20 (m, 6H, ArH, NH), 7.10 (br, 1H, NH), 6.29 (m, 1H, CHCH$_3$), 4.72-4.37 (m, 2H, CH$_2$NCH$_3$), 4.58 (d, 2H, ArCH$_2$NH), 3.87 (s, 2H, CH$_2$Br), 3.84-3.44 (m, 98H, PEG OCH$_2$, OCH$_2$CH$_2$NH), 2.99 and 2.87 (2s, 3H, NCH$_3$), 2.58 (t, 2H, COCH$_2$CH$_2$), 1.88 (2d, 3H, CHCH$_3$). ESI-MS: m/z Calc. for C$_{73}$H$_{124}$BrN$_7$O$_{28}$ 1627.77; Obs. [M+2H]$^{2+}$ 814.67, [M+H]$^+$ 1628.25, [M+Na]$^+$1650.25.

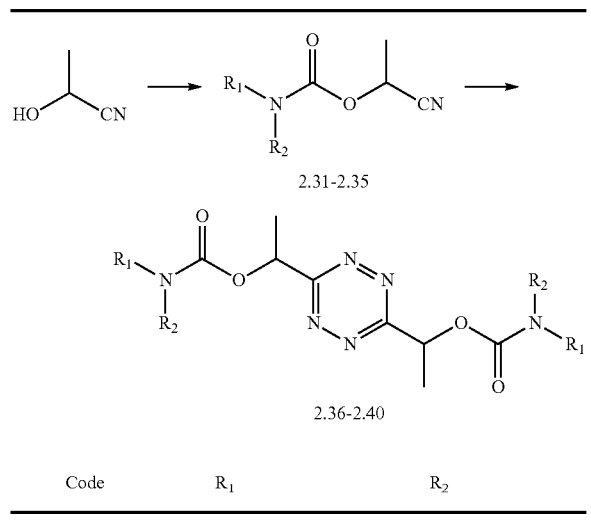

| Code | R$_1$ | R$_2$ |
|---|---|---|
| 2.31/2.36 | Benzyl | Me |
| 2.32/2.37 | Benzyl | Et |
| 2.33/2.38 | Benzyl | iPr |

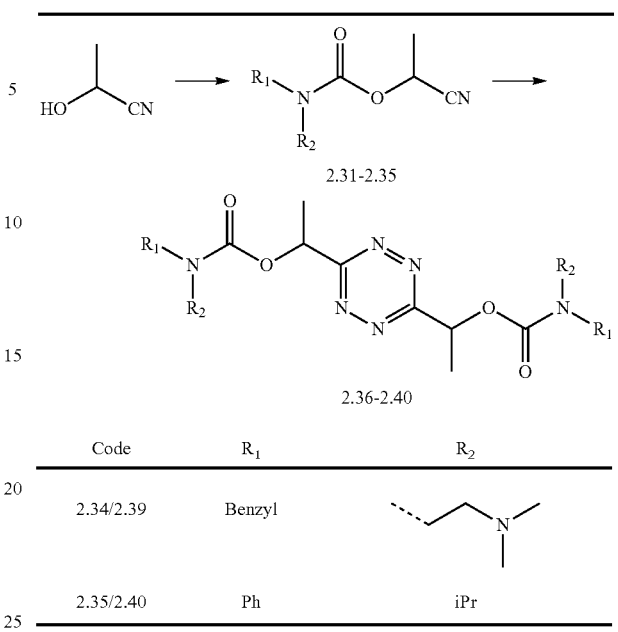

| Code | R$_1$ | R$_2$ |
|---|---|---|
| 2.34/2.39 | Benzyl | ⋯⁓N(CH$_3$)$_2$ |
| 2.35/2.40 | Ph | iPr |

The following compounds 2.31-2.35 have been prepared according to general procedure F. All NMR spectra (except for R$_1$=Ph) indicate the presence of two carbamate rotamers.

2.31: This compound was prepared from N-benzylmethylamine. Column chromatography (flash SiO$_2$) using an elution gradient of pentane/CHCl$_3$ 1:1 to CHCl$_3$ yielded pure 2.31 (0.20 g, 0.92 mmol, 56% over two steps) as a colorless oil. $^1$H-NMR (CDCl$_3$): δ=7.39-7.17 (m, 5H, ArH), 5.46 (q, 1H, CH), 4.48 (m, 2H, CH$_2$), 2.92 and 2.85 (2s, 3H, NCH$_3$), 1.69-1.62 (2d, 3H, CHCH$_3$). $^{13}$C-NMR (CDCl$_3$): δ=154.5, 154.0, 136.6, 136.5, 128.8, 128.7, 127.9, 127.7, 127.3, 118.3, 118.2, 58.7, 52.9, 52.4, 34.7, 33.6, 19.24, 19.18. GC-MS: m/z Calc. for C$_{12}$H$_{14}$N$_2$O$_2$ 218.11; Obs. [M]$^+$ 218.

2.32: This compound was prepared from N-ethylbenzylamine. Column chromatography (flash SiO$_2$) using an elution gradient of pentane/CHCl$_3$ 1:1 to CHCl$_3$ yielded pure 2.32 (0.52 g, 2.2 mmol, 50% over two steps) as a colorless oil. $^1$H-NMR (CDCl$_3$): δ=7.37-7.18 (m, 5H, ArH), 5.48 (m, 1H, CH), 4.49 (m, 2H, ArCH$_2$), 3.34 and 3.24 (2q, 2H, CH$_2$CH$_3$), 1.67 and 1.60 (2d, 3H, CHCH$_3$), 1.11 (m, 3H, CH$_2$CH$_3$). GC-MS: m/z Calc. for C$_{13}$H$_{16}$N$_2$O$_2$ 232.12; Obs. [M]$^+$232.

2.33: This compound was prepared from N-isopropylbenzylamine. Column chromatography (flash SiO$_2$) using an elution gradient of pentane/CHCl$_3$ 1:1 to CHCl$_3$ yielded pure 2.33 (0.61 g, 2.5 mmol, 58% over two steps) as a colorless oil. $^1$H-NMR (CDCl$_3$): δ=7.38-7.19 (m, 5H, ArH), 5.53 and 5.44 (2m, 1H, CHCH$_3$), 4.46 (m, 2H, CH$_2$), 4.37 and 4.14 (2m, 1H, NCH), 1.71 and 1.52 (2d, 3H, CHCH$_3$), 1.17 (m, 6H, CH(CH$_3$)$_2$). GC-MS: m/z Calc. for C$_{14}$H$_{18}$N$_2$O$_2$ 246.14; Obs. [M]$^+$246.

2.34: This compound was prepared from N,N-dimethyl-N-benzyl-1,2-ethanediamine (Ref. 4). Column chromatography (flash SiO$_2$) using an elution gradient of 10% to 40% EtOAc to 4% MeOH in CHCl$_3$ yielded pure 2.34 (0.96 g, 3.5 mmol, 64% over two steps) as a yellowish oil. $^1$H-NMR (CDCl$_3$): δ=7.38-7.18 (m, 5H, ArH), 5.46 (m, 1H, CH), 4.52 (m, 2H, ArCH$_2$), 3.38 and 3.27 (2t, 2H, CONCH$_2$CH$_2$), 2.43 and 2.35 (2t, 2H, CH$_2$N(CH$_3$)$_2$), 2.23 and 2.20 (2s, 6H, N(CH$_3$)$_2$), 1.67 and 1.61 (2d, 3H, CHCH$_3$). GC-MS: m/z Calc. for C$_{15}$H$_{21}$N$_3$O$_2$ 275.16; Obs. [M]$^+$275.

2.35: This compound was prepared from N-isopropylaniline. Column chromatography (flash SiO$_2$) using an elution gradient of heptane/CHCl$_3$ 1:1 via CHCl$_3$ to 2% EtOAc in CHCl$_3$ yielded pure 2.35 (1.15 g, 5.0 mmol, 61% over two steps) as a colorless oil. $^1$H-NMR (CDCl$_3$): δ=7.37 (m, 3H, ArH), 7.09 (d, 2H, ArH), 5.39 (br, 1H, CHCH$_3$), 4.56 (br, 1H, NCH), 1.46 (br, 3H, CHCH$_3$), 1.13 (d, 6H, CH(CH$_3$)$_2$). GC-MS: m/z Calc. for C$_{13}$H$_{16}$N$_2$O$_2$ 232.12; Obs. [M]$^+$232.

The following compounds 2.36-2.40 have been prepared according to general procedure A. EtOH was used as reaction solvent in the preparation of the [2H]-TZ precursor. All NMR spectra indicate the presence of two carbamate rotamers.

2.36: This compound was prepared from 2.31. Column chromatography (flash SiO$_2$) using an elution gradient of 5% to 15% EtOAc in CHCl$_3$ yielded pure 2.36 (50 mg, 0.11 mmol, 23%) as a pink oil. $^1$H-NMR (CDCl$_3$): δ=7.39-7.21 (m, 10H, ArH), 6.32 (m, 2H, CH), 4.72-4.38 (m, 4H, CH$_2$), 2.97 and 2.88 (2s, 6H, NCH$_3$), 1.84 (2d, 6H, CHCH$_3$). ESI-MS: m/z Calc. for C$_{24}$H$_{28}$N$_6$O$_4$ 464.22; Obs. [M+H]$^+$ 465.25, [M+Na]$^+$487.33, [2M+H]$^+$928.75, [2M+Na]$^+$ 951.08.

2.37: This compound was prepared from 2.32. Column chromatography (flash SiO$_2$) using an elution gradient of 2% to 10% EtOAc in CHCl$_3$ and, in a second chromatography step, an elution gradient of 5% to 12% acetone in heptane yielded pure 2.37 (120 mg, 0.24 mmol, 45%) as a pink oil. $^1$H-NMR (CDCl$_3$): δ=7.37-7.23 (m, 10H, ArH), 6.32 (m, 2H, CH), 4.68-4.41 (m, 4H, ArCH$_2$), 3.37 and 3.29 (2m, 4H, CH$_2$CH$_3$), 1.85 and 1.79 (2d, 6H, CHCH$_3$), 1.16 and 1.09 (2t, 6H, CH$_2$CH$_3$). ESI-MS: m/z Calc. for C$_{26}$H$_{32}$N$_6$O$_4$ 492.25; Obs. [M+H]$^+$ 493.25, [M+Na]$^+$ 515.33, [2M+H]$^+$ 984.75, [2M+Na]$^+$1007.00.

2.38: This compound was prepared from 2.33. Column chromatography (flash SiO$_2$) using an elution gradient of 2% to 10% EtOAc in CHCl$_3$ and, in a second chromatography step, 5% acetone in heptane yielded pure 2.38 (48 mg, 92 μmol, 19%) as a pink solid. $^1$H-NMR (CDCl$_3$): δ=7.37-7.17 (m, 10H, ArH), 6.33 and 6.28 (2m, 2H, CHCH$_3$), 4.64-4.22 (m, 6H, CH$_2$, NCH), 1.86 and 1.70 (2m, 6H, CHCH$_3$), 1.18 and 1.12 (2m, 12H, CH(CH$_3$)$_2$). ESI-MS: m/z Calc. for C$_{28}$H$_{36}$N$_6$O$_4$ 520.28; Obs. [M+H]$^+$ 521.33, [M+Na]$^+$ 543.42, [2M+H]$^+$ 1040.92, [2M+Na]$^+$1063.00.

2.39: This compound was prepared from 2.34. Column chromatography (flash SiO$_2$) using an elution gradient of 1% to 10% MeOH in CHCl$_3$ was followed by preparative RP-HPLC using an elution gradient of 15% to 25% MeCN in H$_2$O (both containing 0.1 v/v % formic acid). The product was extracted from the aqueous phase (which had been treated with sat. NaHCO$_3$) using CHCl$_3$. The organic layer was dried with Na$_2$SO$_4$. Filtration and removal of the solvent in vacuo yielded 2.39 (19 mg, 33 μmol, 8%) as a red oil. $^1$H-NMR (CDCl$_3$): δ=7.37-7.20 (m, 10H, ArH), 6.30 (m, 2H, CH), 4.64 and 4.52 (2m, 4H, ArCH$_2$), 3.52-3.20 (m, 4H, CONCH$_2$CH$_2$), 2.54-2.33 (m, 4H, CH$_2$N(CH$_3$)$_2$), 2.22 and 2.21 (2s, 12H, N(CH$_3$)$_2$), 1.85 and 1.80 (2d, 6H, CHCH$_3$). ESI-MS: m/z Calc. for C$_{30}$H$_{42}$N$_8$O$_4$ 578.33; Obs. [M+2H]$^{2+}$ 290.33, [M+H]$^+$ 579.42, [M+Na]$^+$601.42.

2.40: This compound was prepared from 2.35. Column chromatography (flash SiO$_2$) using an elution gradient of CHCl$_3$ to 10% EtOAc in CHCl$_3$ and, in a second chromatography step, 1% to 8% acetone in heptane was followed by precipitation, induced by adding heptane (8 mL) to a stirred solution in CHCl$_3$ (0.5 mL). Storage at room temperature for 1 h, filtration, washing with pentane and drying of the solid in vacuo yielded pure 2.40 (90 mg, 0.18 mmol, 39%) as a pink solid. $^1$H-NMR (CDCl$_3$): δ=7.36 (m, 6H, ArH), 7.20 (d, 4H, ArH), 6.21 (br, 2H, CHCH$_3$), 4.56 (br, 2H, NCH), 1.63 (br, 6H, CHCH$_3$), 1.14 (m, 12H, CH(CH$_3$)$_2$). ESI-MS: m/z Calc. for C$_{26}$H$_{32}$N$_6$O$_4$ 492.25; Obs. [M+H]$^+$ 493.17, [M+Na]$^+$515.25, [2M+Na]$^+$ 1006.67.

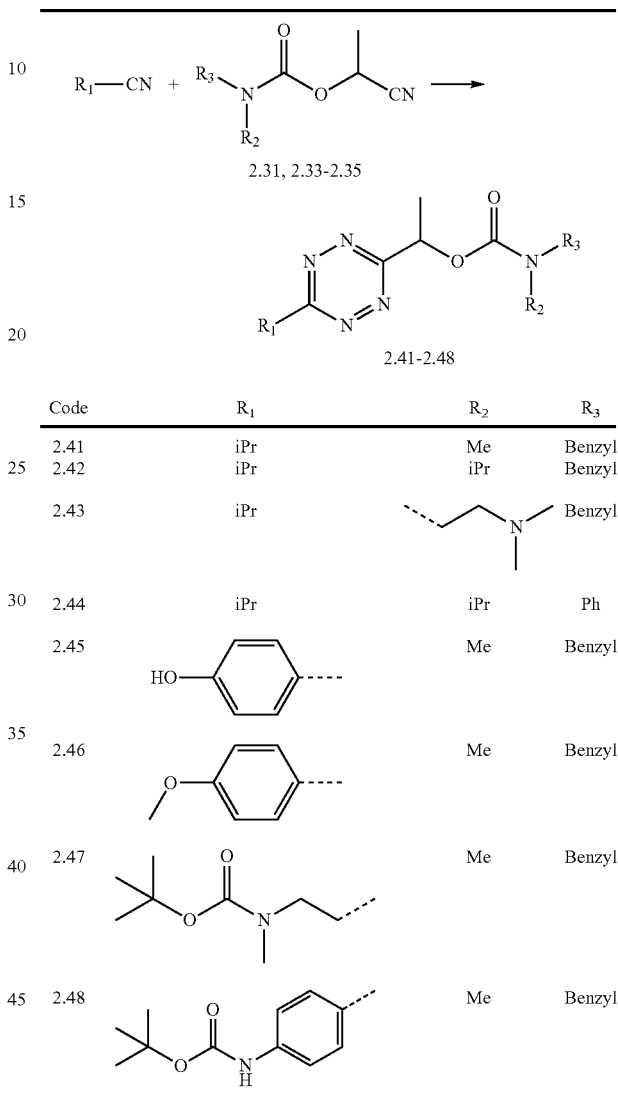

| Code | R$_1$ | R$_2$ | R$_3$ |
|---|---|---|---|
| 2.41 | iPr | Me | Benzyl |
| 2.42 | iPr | iPr | Benzyl |
| 2.43 | iPr |  | Benzyl |
| 2.44 | iPr | iPr | Ph |
| 2.45 | HO-C$_6$H$_4$- |  | Me | Benzyl |
| 2.46 | MeO-C$_6$H$_4$- | Me | Benzyl |
| 2.47 | tBuO-C(O)-N(Me)-CH$_2$CH$_2$- | Me | Benzyl |
| 2.48 | tBuO-C(O)-NH-C$_6$H$_4$- | Me | Benzyl |

The following compounds 2.41-2.48 have been prepared according to general procedure A. EtOH was used as reaction solvent in the preparation of the [2H]-TZ precursor. All NMR spectra indicate the presence of two carbamate rotamers.

2.41: This compound was prepared from isobutyronitrile and 2.31 that were reacted in a 10:1 molar ratio. Column chromatography (flash SiO$_2$) using an elution gradient of 0% to 4% EtOAc in CHCl$_3$ and, in a second chromatography step, 1% to 4% acetone in heptane yielded pure 2.41 (22 mg, 70 μmol, 7%) as a pink oil. $^1$H-NMR (CDCl$_3$): δ=7.39-7.23 (m, 5H, ArH), 6.26 (m, 1H, CHCH$_3$), 4.71-4.37 (m, 2H, CH$_2$), 3.66 (sept, 1H, CH(CH$_3$)$_2$), 2.97 and 2.87 (2s, 3H, NCH$_3$), 1.83 (2d, 3H, CHCH$_3$), 1.54 (d, 6H, CH(CH$_3$)$_2$). ESI-MS: m/z Calc. for C$_{16}$H$_{21}$N$_5$O$_2$ 315.17; Obs. [M+H]$^+$ 316.25, [M+Na]$^+$338.17, [2M+Na]$^+$653.00.

2.42: This compound was prepared from isobutyronitrile and 2.33 that were reacted in a 8:1 molar ratio. Column chromatography (flash SiO$_2$) using an elution gradient of 0% to 3% EtOAc in CHCl$_3$ and, in a second chromatography step, 1% to 2% acetone in heptane yielded pure 2.42 (22 mg, 64 µmol, 18%) as a pink oil. $^1$H-NMR (CDCl$_3$): δ=7.37-7.16 (m, 5H, ArH), 6.24 (m, 1H, CHCH$_3$), 4.64-4.23 (m, 3H, CH$_2$, NCH), 3.65 (sept, 1H, CCH(CH$_3$)$_2$), 1.86 and 1.70 (2m, 3H, CHCH$_3$), 1.54 (d, 6H, CCH(CH$_3$)$_2$), 1.19 and 1.12 (2m, 6H, NCH(CH$_3$)$_2$). ESI-MS: m/z Calc. for C$_{18}$H$_{25}$N$_5$O$_2$ 343.20; Obs. [M+H]$^+$ 344.17, [M+Na]$^+$ 366.08, [2M+Na]$^+$ 709.00.

2.43: This compound was prepared from isobutyronitrile and 2.34 that were reacted in a 10:1 molar ratio. Column chromatography (flash SiO$_2$) using an elution gradient of 1% to 5% MeOH in CHCl$_3$ and, in a second chromatography step, 15% to 40% acetone in heptane yielded pure 2.43 (35 mg, 94 µmol, 17%) as a pink oil. $^1$H-NMR (CDCl$_3$): δ=7.38-7.22 (m, 5H, ArH), 6.26 (q, 1H, CHCH$_3$), 4.64 and 4.51 (2m, 2H, ArCH$_2$), 3.66 (sept, 1H, CH(CH$_3$)$_2$), 3.52-3.23 (m, 2H, CONCH$_2$CH$_2$), 2.54-2.35 (m, 2H, CH$_2$N(CH$_3$)$_2$), 2.22 and 2.21 (2s, 6H, N(CH$_3$)$_2$), 1.85 and 1.80 (2d, 3H, CHCH$_3$), 1.54 (d, 6H, CH(CH$_3$)$_2$). ESI-MS: m/z Calc. for C$_{19}$H$_{28}$N$_6$O$_2$ 372.23; Obs. [M+H]$^+$ 373.25.

2.44: This compound was prepared from isobutyronitrile and 2.35 that were reacted in a 10:1 molar ratio. Column chromatography (flash SiO$_2$) using an elution gradient of 0% to 3% EtOAc in CHCl$_3$ and, in a second chromatography step, 1% to 2% acetone in heptane yielded pure 2.44 (44 mg, 0.13 mmol, 20%) as a pink oil. $^1$H-NMR (CDCl$_3$): δ=7.35 (m, 3H, ArH), 7.21 (d, 2H, ArH), 6.17 (m, 1H, CHCH$_3$), 4.56 (m, 1H, NCH), 3.64 (sept, 1H, CCH(CH$_3$)$_2$), 1.64 (br, 3H, CHCH$_3$), 1.53 (d, 6H, CCH(CH$_3$)$_2$), 1.14 (m, 6H, NCH(CH$_3$)$_2$). ESI-MS: m/z Calc. for C$_{17}$H$_{23}$N$_5$O$_2$ 329.19; Obs. [M+H]$^+$ 330.08, [M+Na]$^+$ 352.08, [2M+Na]$^+$ 681.00.

2.45: This compound was prepared from p-hydroxybenzonitrile and 2.31 that were reacted in a 4:1 molar ratio. DMF was added as a co-solvent due to precipitation after hydrazine monohydrate addition. After AcOH removal, the mixture was additionally washed with sat. NaHCO$_3$ (4×) and brine. Drying with Na$_2$SO$_4$, filtration and removal of the solvent in vacuo yielded crude product. Column chromatography (flash SiO$_2$) using an elution gradient of 2% to 16% EtOAc in CHCl$_3$ and, in a second chromatography step, 5% to 15% acetone in heptane yielded 2.45 (7.0 mg, 19 µmol, 1%) as a pink oil. $^1$H-NMR (CDCl$_3$): δ=8.23 (m, 2H, ArH), 7.60 (br, 1H, OH), 7.42-7.28 (m, 5H, ArH), 6.65 (m, 2H, ArH), 6.21 (m, 1H, CH), 4.80-4.46 (m, 2H, CH$_2$), 3.08 and 2.94 (2s, 3H, NCH$_3$), 1.88 (2d, 3H, CHCH$_3$). ESI-MS: m/z Calc. for C$_{19}$H$_{19}$N$_5$O$_3$ 365.15; Obs. [M+H]$^+$ 366.00, [M+Na]$^+$387.92, [2M+Na]$^+$ 752.67.

2.46: This compound was prepared from p-methoxybenzonitrile and 2.31 that were reacted in a 2:1 molar ratio. Column chromatography (flash SiO$_2$) using an elution gradient of 0% to 3% EtOAc in CHCl$_3$ and, in a second chromatography step, 2% to 5% acetone in heptane yielded pure 2.46 (15 mg, 40 µmol, 3%) as a pink oil. $^1$H-NMR (CDCl$_3$): δ=8.58 (d, 2H, ArH), 7.39-7.23 (m, 5H, ArH), 7.09 (d, 2H, ArH), 6.28 (m, 1H, CH), 4.72-4.38 (m, 2H, CH$_2$), 3.93 (s, 3H, OCH$_3$), 2.98 and 2.87 (2s, 3H, NCH$_3$), 1.87 (2d, 3H, CHCH$_3$). ESI-MS: m/z Calc. for C$_{20}$H$_{21}$N$_5$O$_3$ 379.16; Obs. [M+H]$^+$ 379.92, [M+Na]$^+$401.92, [2M+Na]$^+$780.50.

2.47: This compound was prepared from t-butyl N-(2-cyanoethyl)-N-methylcarbamate and 2.31 that were reacted in a 1:1 molar ratio. Column chromatography (flash SiO$_2$) using an elution gradient of 5% to 40% EtOAc in CHCl$_3$ and, in a second chromatography step, 5% to 10% acetone in heptane yielded pure 2.47 (16 mg, 37 µmol, 3%) as a pink oil. $^1$H-NMR (CDCl$_3$): δ=7.39-7.22 (m, 5H, ArH), 6.26 (m, 1H, CH), 4.68-4.38 (m, 2H, ArCH$_2$), 3.81 (br, 2H, NCH$_2$CH$_2$), 3.54 (t, 2H, NCH$_2$CH$_2$), 2.96 and 2.85 (2s, 3H, ArCH$_2$NCH$_3$), 2.92 (s, 3H, CH$_2$CH$_2$NCH$_3$), 1.82 (br, 3H, CHCH$_3$), 1.35 (s, 9H, C(CH$_3$)$_3$). ESI-MS: m/z Calc. for C$_{21}$H$_{30}$N$_6$O$_4$ 430.23; Obs. [M−tboc+2H]$^+$ 331.25, [M+Na]$^+$ 453.33, [2M+Na]$^+$ 882.83.

2.48: This compound was prepared from t-butyl N-(4-cyanophenyl)carbamate and 2.31 that were reacted in a 2:1 molar ratio. Prior to oxidation from [2H]-TZ to TZ, a fine orange precipitate was removed by filtering a CHCl$_3$ solution over Celite. The filtrate was concentrated and the resulting orange/red oil was then subjected to oxidation. Column chromatography (flash SiO$_2$) using an elution gradient of 0% to 8% EtOAc in CHCl$_3$ and, in a second chromatography step, 4% to 12% acetone in heptane was followed by precipitation of the impurities, induced by adding heptane (8 mL) to a stirred solution in CHCl$_3$ (0.5 mL). Storage at −20° C. for 1 h, filtration of impurities (the product dissolves and resides in the filtrate), washing with pentane and concentration of the filtrate in vacuo yielded pure 2.48 (14 mg, 30 µmol, 2%) as a pink solid. $^1$H-NMR (CDCl$_3$): δ=8.55 (d, 2H, ArH), 7.59 (d, 2H, ArH), 7.39-7.25 (m, 5H, ArH), 6.80 (br, 1H, NH), 6.29 (m, 1H, CH), 4.72-4.38 (m, 2H, CH$_2$), 2.98 and 2.88 (2s, 3H, NCH$_3$), 1.87 (2d, 3H, CHCH$_3$), 1.55 (s, 9H, C(CH$_3$)$_3$). ESI-MS: m/z Calc. for C$_{24}$H$_{28}$N$_6$O$_4$ 464.22; Obs. [M+H]$^+$ 465.00, [M+Na]$^+$ 487.00, [2M+Na]$^+$ 950.75.

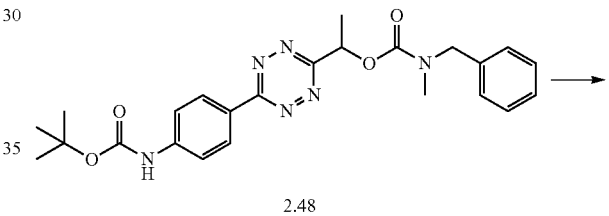

2.48

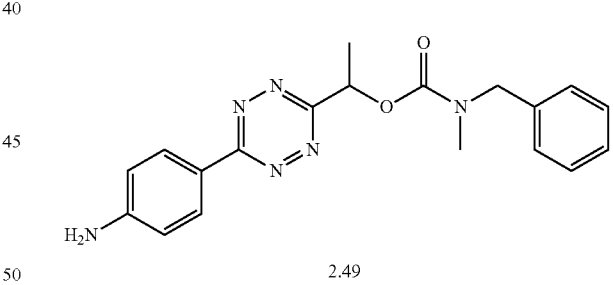

2.49

2.49: This compound was prepared from 2.48 according to general procedure E. After flushing, the compound was re-dissolved in CHCl$_3$ (50 mL) and the resulting solution was washed with sat. NaHCO$_3$ (2×20 mL), dried with Na$_2$SO$_4$ and filtrated. Concentration of the filtrate in vacuo was followed by column chromatography (flash SiO$_2$) using an elution gradient of 6% to 16% EtOAc in CHCl$_3$ yielding pure 2.49 (8.3 mg, 28 µmol, 81%) as a red oil. $^1$H-NMR (CDCl$_3$): δ=8.42 (d, 2H, ArH), 7.38-7.23 (m, 5H, ArH), 6.79 (d, 2H, ArH), 6.27 (m, 1H, CH), 4.73-4.37 (m, 2H, CH$_2$), 4.17 (br, 2H, NH$_2$), 2.97 and 2.88 (2s, 3H, NCH$_3$), 1.85 (2d, 3H, CHCH$_3$). ESI-MS: m/z Calc. for C$_{19}$H$_{20}$N$_6$O$_2$ 364.16; Obs. [M+H]$^+$ 364.92, [2M+Na]$^+$750.67.

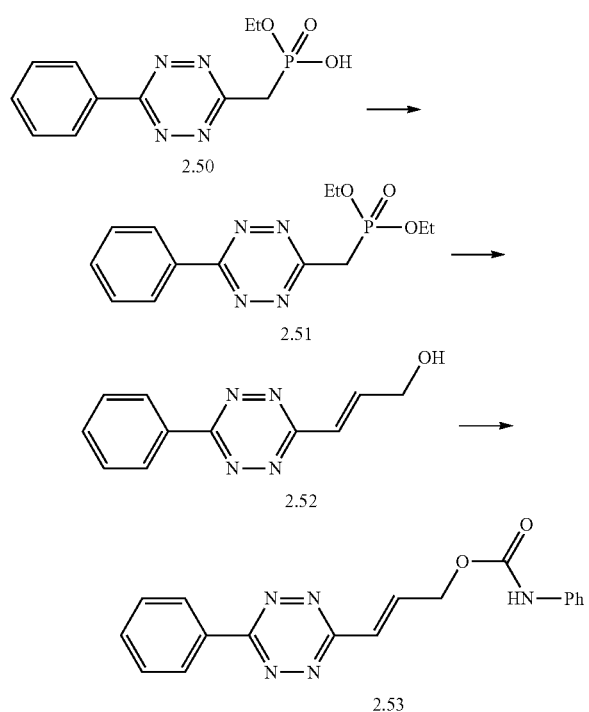

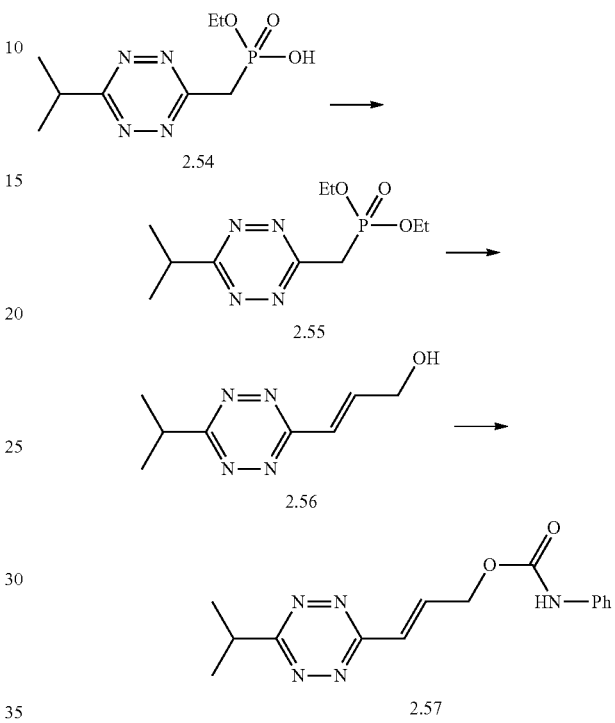

2.50: Compound 2.50 was prepared according general procedure A followed with silica chromatography of the residue using 2-5% methanol in dichloromethane. Sodium carbonate in water was added and the mixture was extracted with ethyl acetate/isopropanol (1/1). Drying and rotary evaporation gave a residue, which was dissolved in methanol. Concentrated hydrochloric acid was added, the mixture was filtered, and the filtrate was rotary evaporated. Propanol was added to the residue, the mixture was filtered, and the filtrate was rotary evaporated. Drying under high vacuum at 60° C. afforded 2.50, which was used as such in the next step.

2.51: Compound 2.50 (4.81 g) was mixed with 60 mL dichloromethane and ethanol (3.16 g, 68.7 mmol). 125 mg 4-dimethylaminopyridine was added, the mixture was cooled with ice, and DCC (7.50 g, 36.4 mmol) was added. The mixture was stirred for 2 d, then filtered, the solid being washed with dichloromethane. The filtrate was rotary evaporated, and the residue was chromatographed on silica using 5-10% methanol in dichloromethane, which afforded 2.51 (4.00 g, 12.98 mmol, 28%).

2.52: phosphonate 2.51 (3.78 g, 12.27 mmol) was dissolved in 50 mL acetonitrile. Lithium chloride (1.12 g, 26.35 mmol) was added, followed by DIPEA (4.04 g, 31.3 mmol) and glycolaldehyde dimer (830 mg, 6.91 mmol). The mixture was stirred for 7 h, then poured into a solution of 5 g ammonium chloride in 40 mL water, followed by extraction with toluene. The successive organic layers were washed with 40 mL water, then dried and rotary evaporated to give the desired product as a pink solid (400 mg, 1.87 mmol, 15%). $^1$H-NMR (CDCl$_3$) δ 8.59 (dd, J=7.8, 1.8, 2H), 7.75-7.5 (m), 7.75 (t) (4H), 7.20 (bd, J=16, 1H), 4.6 (bs, 2H). $^{13}$C-NMR (CDCl$_3$) δ 164.0, 163.6, 143.7, 132.7, 131.8, 129.4, 127.9, 122.2, 62.3. ESI-MS: m/z 215 [M+H]$^+$ 2.53: Alcohol 2.52 (50 mg, 0.233 mmol) was stirred for 4 h with 240 mg phenyl isocyanate (2.01 mmol), 10 mL dichloromethane and 2 drops triethylamine. The mixture was rotary evaporated at 60° C., and the residue was chromatographed on silica with toluene, containing a few percent of ethyl acetate. affording 25 mg 2.53 (0.075 mmol, 32%). $^1$H-NMR (CDCl$_3$) δ 8.59 (d, J=6.9, 2H), 7.7-7.55 (m, 4H), 7.5-7.05 (m, 6H), 6.8 (bs, 1H), 5.07 (dd, J=4.7, 1.8, 2H).

2.54: Compound 2.54 was prepared according to general procedure A.

2.55: Compound 2.55 was prepared in a similar way as the phenyl analogue 2.51. $^1$H-NMR (CDCl$_3$) δ 4.2 (m, 4H), 3.93 (d, J=24, 2H), 3.65 (m, J=8, 1H), 1.52 (d, J=8, 6H), 1.33 (t, J=8, 6H). $^{13}$C-NMR (CDCl$_3$) δ 164.3, 164.2, 62.9, 62.8, 34.6, 34.2, 32.7, 21.1, 16.2, 16.1. ESI-MS m/z 275 [M+H]$^+$ 2.56: The phosphonate 2.55 (365 mg, 1.33 mmol) was dissolved in 6 mL acetonitrile. Lithium chloride (212 mg, 4.99 mmol) was added, followed by DIPEA (842 mg, 6.52 mmol) and glycolaldehyde dimer (132 mg, 1.1 mmol). The mixture was stirred overnight, then poured into a mixture of 100 mL TBME and 25 mL dilute ammonium chloride solution. The layers were separated and the organic layer was washed with 25 mL water, then dried and rotary evaporated. The residue was chromatographed on silica with toluene, dichloromethane and TBME, affording 2.56 as a pink oil (0.917 mmol, 69%). $^1$H-NMR (CDCl$_3$) δ 7.62 (dt, J=16, 4.7, 1H), 7.15 (bd, J=16, 1H), 4.58 (bs, 2H), 3.62 (m, J=7.2, 1H), 1.52 (d, J=7.2, 6H). $^{13}$C-NMR (CDCl$_3$) δ 173.0, 164.0, 143.8, 121.8, 62.2, 34.1, 21.0. ESI-MS m/z 181 [M+H]$^+$ 2.57: The alcohol 2.56 (39.5 mg, 0.22 mmol) was stirred for 5 h with phenyl isocyanate (38.5 mg, 0.32 mmol, 8 mL dichloromethane and 2 drops triethylamine. The solution was poured onto a 15 g silica column. The product eluted with dichloromethane to yield 36 mg 2.57 (0.12 mmol, 55%). $^1$H-NMR (CDCl$_3$) δ 7.57 (dt, J=16, 4.7, 1H), 7.45-7.05 (m, 6H), 6.8 (m, 1H), 5.04 (dd, J=4.8, 2.4, 2H), 3.64 (m, J=7.0, 1H), 1.52 (d, J=7.0, 6H).

Example 3: Synthesis of Tetrazine Triggers Believed to Release Via the Cyclization Mechanism

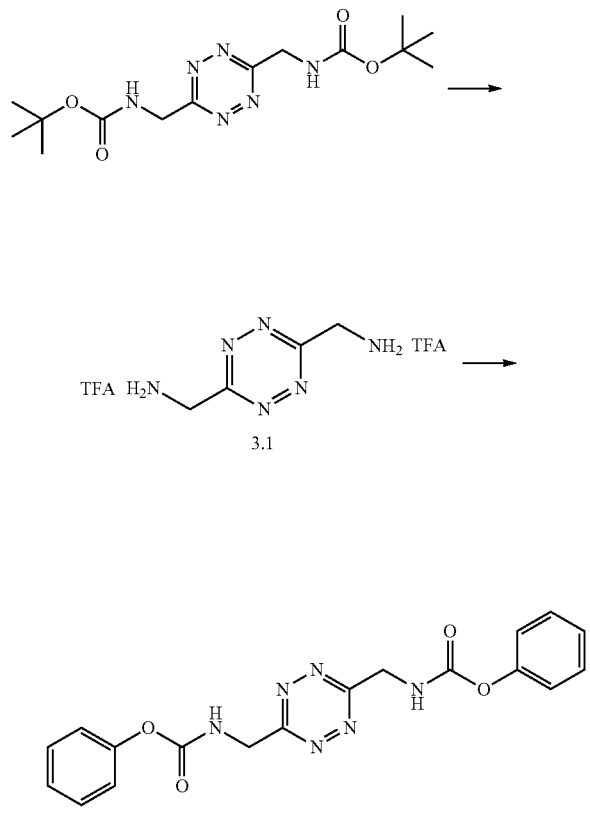

3.1

3.2

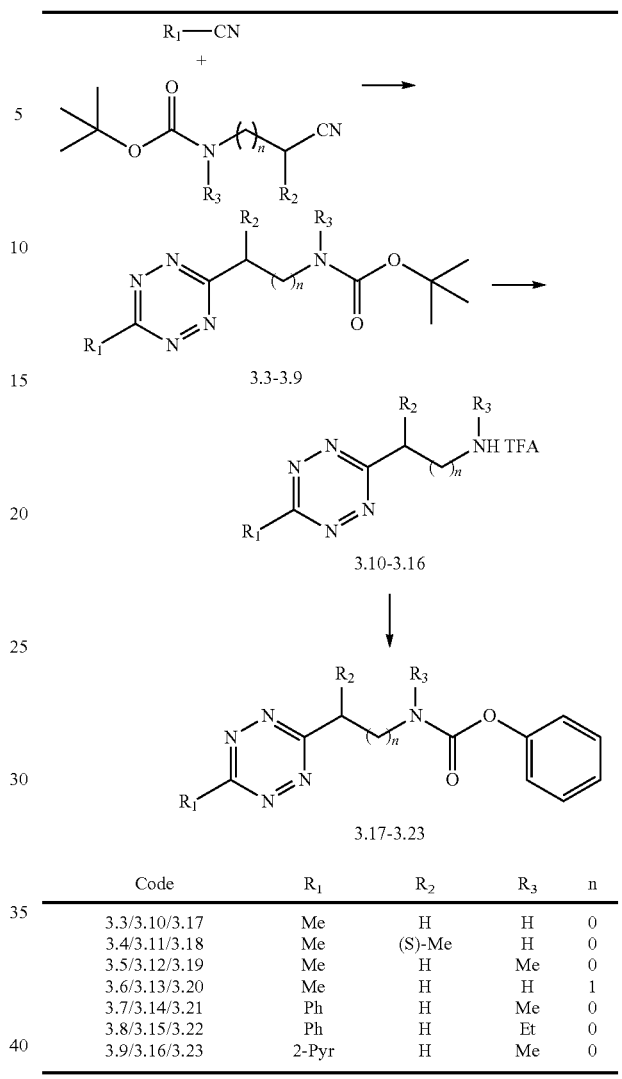

3.3-3.9

3.10-3.16

3.17-3.23

| Code | R₁ | R₂ | R₃ | n |
|---|---|---|---|---|
| 3.3/3.10/3.17 | Me | H | H | 0 |
| 3.4/3.11/3.18 | Me | (S)-Me | H | 0 |
| 3.5/3.12/3.19 | Me | H | Me | 0 |
| 3.6/3.13/3.20 | Me | H | H | 1 |
| 3.7/3.14/3.21 | Ph | H | Me | 0 |
| 3.8/3.15/3.22 | Ph | H | Et | 0 |
| 3.9/3.16/3.23 | 2-Pyr | H | Me | 0 |

3.1: This compound was prepared from di-t-butyl ((1,2,4,5-tetrazine-3,6-diyl)bis(methylene))dicarbamate (Ref. 5) according to general procedure E. Pure 3.1 (140 mg, 0.38 mmol, 100%) was obtained as a pink solid. ESI-MS: m/z Calc. for $C_8H_{10}F_6N_6O_4$ 368.07; Obs. [M−2TFA+H]⁺ 141.08.

3.2: This compound was prepared from 3.1 according to general procedure G using DMF as reaction solvent. The extraction step was omitted due to poor solubility. The product was dissolved in DMF (2 mL) and precipitated in $H_2O$ (20 mL). After filtration, washing with $H_2O$ and drying of the solid in vacuo over $P_2O_5$, the product was dissolved in DMF (2 mL) and precipitated in diethylether (20 mL). After filtration and drying of the solid in vacuo this yielded pure 3.2 (93 mg, 0.24 mmol, 64%) as a pink solid. ¹H-NMR (DMSO-d6): δ=8.68 (t, 2H, NH), 7.38 (t, 4H, ArH), 7.21 (t, 2H, ArH), 7.12 (d, 4H, ArH), 4.93 (d, 4H, CH₂). ¹³C-NMR (DMSO-d6): δ=167.6, 154.9, 150.9, 129.3, 125.1, 121.6, 43.6. ESI-MS: m/z Calc. for $C_{18}H_{16}N_6O_4$ 380.12; Obs. [M+H]⁺ 381.17, [M+Na]⁺ 403.25, [2M+H]⁺ 761.00, [2M+Na]⁺ 782.75.

The following compounds 3.3-3.9 have been prepared according to general procedure A. All NMR spectra for R₃≠H indicate the presence of two carbamate rotamers.

3.3: This compound was prepared according to a literature procedure (Ref. 5).

3.4: This compound was synthesized from acetonitrile and t-butyl N—((S)-1-cyanoethyl)carbamate that were reacted in a 2:1 molar ratio. Column chromatography (flash SiO₂) using an elution gradient of 0% to 5% EtOAc in CHCl₃ yielded pure 3.4 (200 mg, 0.84 mmol, 36%) as a pink solid. ¹H-NMR (CDCl₃): δ=5.55-5.32 (m, 2H, CH, NH), 3.07 (s, 3H, CH₃TZ), 1.67 (d, 3H, CHCH₃), 1.43 (s, 9H, C(CH₃)₃). ¹³C-NMR (CDCl₃): δ=170.2, 168.2, 155.1, 80.1, 50.0, 28.3, 21.6, 21.2. ESI-MS: m/z Calc. for $C_{10}H_{17}N_5O_2$ 239.14; Obs. [M−tboc+2H]⁺ 140.08, [M−tbutyl+2H]⁺ 184.00, [M+H]⁺ 239.92.

3.5: This compound was synthesized from acetonitrile and t-butyl N-(cyanomethyl)-N-methylcarbamate that were reacted in a 5:2 molar ratio. Column chromatography (flash SiO₂) using an elution gradient of 0% to 10% EtOAc in CHCl₃ yielded pure 3.5 (160 mg, 0.67 mmol, 33%) as a pink oil. ¹H-NMR (CDCl₃): δ=5.03 and 4.97 (2s, 2H, CH₂), 3.09 (m, 6H, CH₃TZ, NCH₃), 1.48 and 1.34 (2s, 9H, C(CH₃)₃). ¹³C-NMR (CDCl₃): δ=168.4, 168.3, 166.9, 166.6, 156.2, 155.3, 80.4, 52.0, 51.4, 35.9, 35.7, 28.4, 28.3, 21.2. ESI-MS: m/z Calc. for $C_{10}H_{17}N_5O_2$ 239.14; Obs. [M−tboc+2H]$^+$ 140.08.

3.6: This compound was synthesized from acetonitrile and t-butyl N-(2-cyanoethyl)carbamate that were reacted in a 6:1 molar ratio. Column chromatography (flash SiO$_2$) using an elution gradient of 0% to 20% EtOAc in CHCl$_3$ yielded pure 3.6 (150 mg, 0.63 mmol, 43%) as a pink oil. $^1$H-NMR (CDCl$_3$): δ=5.00 (br, 1H, NH), 3.73 (q, 2H, CH$_2$NH), 3.50 (t, 2H, TZCH$_2$), 3.05 (s, 3H, CH$_3$TZ), 1.39 (s, 9H, C(CH$_3$)$_3$). $^{13}$C-NMR (CDCl$_3$): δ=168.1, 167.7, 155.9, 79.6, 38.4, 35.5, 28.4, 21.2. ESI-MS: m/z Calc. for $C_{10}H_{17}N_5O_2$ 239.14; Obs. [M−tbutyl+2H]$^+$ 184.00.

3.7: This compound was synthesized from benzonitrile and t-butyl N-(cyanomethyl)-N-methylcarbamate that were reacted in a 9:1 molar ratio. EtOH was used as reaction solvent in the preparation of the [2H]-TZ precursor. Column chromatography (flash SiO$_2$) using an elution gradient of 0% to 10% EtOAc in CHCl$_3$ was followed by precipitation, induced by adding heptane (7 mL) to a stirred solution in CHCl$_3$ (0.5 mL). After storage at −20° C. for 16 h, filtration, washing with pentane and drying of the solid in vacuo this yielded pure 3.7 (90 mg, 0.30 mmol, 28%) as a pink solid. $^1$H-NMR (CDCl$_3$): δ=8.62 (m, 2H, ArH), 7.62 (m, 3H, ArH), 5.10 and 5.03 (2s, 2H, CH$_2$), 3.15 and 3.14 (2s, 3H, NCH$_3$), 1.50 and 1.36 (2s, 9H, C(CH$_3$)$_3$). $^{13}$C-NMR (CDCl$_3$): δ=167.0, 166.7, 165.0, 156.3, 155.3, 133.0, 132.8, 131.7, 131.6, 129.4, 128.2, 80.5, 52.1, 51.5, 36.0, 35.9, 28.4, 28.3. ESI-MS: m/z Calc. for $C_{15}H_{19}N_5O_2$ 301.15; Obs. [M−tboc+2H]$^+$ 202.25, [M−tbutyl+2H]$^+$246.08, [M+H]$^+$ 302.00.

3.8: This compound was synthesized from benzonitrile and 3.28 that were reacted in a 10:1 molar ratio. EtOH was used as reaction solvent in the preparation of the [2H]-TZ precursor. Column chromatography (flash SiO$_2$) using an elution gradient of 0% to 5% EtOAc in CHCl$_3$ and, in a second chromatography step, elution with 4% acetone in heptane yielded pure 3.8 (130 mg, 0.41 mmol, 41%) as a pink solid. $^1$H-NMR (CDCl$_3$): δ=8.62 (m, 2H, ArH), 7.62 (m, 3H, ArH), 5.07 and 5.00 (2s, 2H, TzCH$_2$), 3.57 and 3.51 (2m, 2H, NCH$_2$CH$_3$), 1.53-1.19 (m, 12H, NCH$_2$CH$_3$, C(CH$_3$)$_3$). ESI-MS: m/z Calc. for $C_{16}H_{21}N_5O_2$ 315.17; Obs. [M−tboc+2H]$^+$216.25, [M−tbutyl+2H]$^+$ 260.08, [M+Na]$^+$ 338.25.

3.9: This compound was synthesized from 2-cyanopyridine and t-butyl N-(cyanomethyl)-N-methylcarbamate that were reacted in a 10:1 molar ratio. Column chromatography (flash SiO$_2$) using an elution gradient of 0% to 25% EtOAc in CHCl$_3$ and, in a second chromatography step, an elution gradient of 20% to 30% EtOAc in CHCl$_3$ yielded pure 3.9 (110 mg, 0.36 mmol, 31%) as a pink oil. $^1$H-NMR (CDCl$_3$): δ=8.96 (m, 1H, ArH), 8.66 (t, 1H, ArH), 8.00 (m, 1H, ArH), 7.57 (m, 1H, ArH), 5.15 and 5.09 (2s, 2H, CH$_2$), 3.15 and 3.14 (2s, 3H, NCH$_3$), 1.49 and 1.36 (2s, 9H, C(CH$_3$)$_3$). $^{13}$C-NMR (CDCl$_3$): δ=167.5, 167.3, 164.3, 156.1, 155.1, 150.8, 150.0, 149.9, 137.4, 126.5, 126.4, 124.0, 80.4, 52.0, 51.5, 35.9, 35.7, 28.2, 28.1. ESI-MS: m/z Calc. for $C_{14}H_{18}N_6O_2$ 302.15; Obs. [M−tboc+2H]$^+$ 203.17, [M−ibutyl+2H]$^+$247.08, [M+H]$^+$ 303.08.

The following compounds 3.10-3.16 have been prepared according to general procedure E.

3.10: This compound was prepared according to a literature procedure (Ref. 6).

3.11: This compound was prepared from 3.4. Pure 3.11 was obtained as a pink solid (58 mg, 0.23 mmol, 100%). $^1$H-NMR (CD$_3$OD): δ=5.11 (q, 1H, CH), 3.08 (s, 3H, CH$_3$TZ), 1.84 (d, 3H, CHCH$_3$). $^{13}$C-NMR (CD$_3$OD): δ=170.6, 167.7, 163.0 (q), 118.1 (q), 50.7, 21.3, 18.8. $^{19}$F-NMR (CD$_3$OD): δ=−76.9. ESI-MS: m/z Calc. for $C_7H_{10}F_3N_5O_2$ 253.08; Obs. [M−TFA+H]$^+$140.08.

3.12: This compound was prepared from 3.5. Pure 3.12 was obtained as a pink solid (55 mg, 0.22 mmol, 100%). $^1$H-NMR (CD$_3$OD): δ=4.91 (s, 2H, CH$_2$), 3.08 (s, 3H, CH$_3$TZ), 2.96 (s, 3H, NCH$_3$). $^{13}$C-NMR (CD$_3$OD): δ=170.7, 163.8, 162.9 (q), 117.9 (q), 51.0, 34.0, 21.3. $^{19}$F-NMR (CD$_3$OD): δ=−77.0. ESI-MS: m/z Calc. for $C_7H_{10}F_3N_5O_2$ 253.08; Obs. [M−TFA+H]$^+$ 140.08.

3.13: This compound was prepared from 3.6. Pure 3.13 was obtained as a pink oil (63 mg, 0.25 mmol, 100%). $^1$H-NMR (CD$_3$OD): δ=3.74-3.59 (2m, 4H, CH$_2$CH$_2$), 3.02 (s, 3H, CH$_3$). $^{13}$C-NMR (CD$_3$OD): δ=169.5, 167.8, 162.6 (q), 117.9 (q), 38.1, 33.1, 21.1. $^{19}$F-NMR (CD$_3$OD): δ=−77.0. ESI-MS: m/z Calc. for $C_7H_{10}F_3N_5O_2$ 253.08; Obs. [M−TFA+H]$^+$140.08.

3.14: This compound was prepared from 3.7. Pure 3.14 was obtained as a pink solid (94 mg, 0.30 mmol, 100%). $^1$H-NMR (CDCl$_3$/CD$_3$OD 5:1): δ=8.60 (m, 2H, ArH), 7.66 (m, 3H, ArH), 4.90 (s, 2H, CH$_2$), 2.98 (s, 3H, CH$_3$). $^{19}$F-NMR (CDCl$_3$/CD$_3$OD 5:1): (=−76.0. ESI-MS: m/z Calc. for $C_{12}H_{12}F_3N_5O_2$ 315.09; Obs. [M−TFA+H]$^+$ 202.17.

3.15: This compound was prepared from 3.8. Pure 3.15 was obtained as a pink solid (76 mg, 0.23 mmol, 100%). $^1$H-NMR (CD$_3$OD): δ=8.58 (m, 2H, ArH), 7.65 (m, 3H, ArH), 4.44 (s, 2H, TzCH$_2$), 2.83 (q, 2H, NHCH$_2$), 1.22 (t, 3H, CH$_3$).

3.16: This compound was prepared from 3.9. Pure 3.16 was obtained as a red solid (114 mg, 0.36 mmol, 100%). $^1$H-NMR (CD$_3$OD): δ=8.90 (m, 1H, ArH), 8.76 (m, 1H, ArH), 8.19 (m, 1H, ArH), 7.77 (m, 1H, ArH), 5.05 (s, 2H, CH$_2$), 3.01 (s, 3H, CH$_3$). $^{13}$C-NMR (CD$_3$OD): δ=165.2, 165.0, 160.7 (q), 150.8, 149.9, 140.9, 129.0, 126.1, 116.9 (q), 51.2, 34.2. $^{19}$F-NMR (CD$_3$OD): δ=−77.6. ESI-MS: m/z Calc. for $C_{11}H_{11}F_3N_6O_2$ 316.09; Obs. [M−TFA+H]$^+$ 203.17.

The following compounds 3.17-3.23 have been prepared according to general procedure G. All NMR spectra for $R_3 \neq H$ indicate the presence of two carbamate rotamers.

3.17: This compound was prepared from 3.10. Column chromatography (flash SiO$_2$) using an elution gradient of 0% to 10% EtOAc in CHCl$_3$ was followed by precipitation, induced by adding diethylether (6 mL) to a stirred solution in CHCl$_3$ (0.5 mL). Storage at −20° C. for 16 h, filtration and drying of the solid in vacuo yielded pure 3.17 (71 mg, 0.29 mmol, 74%) as a pink solid. $^1$H-NMR (CDCl$_3$): δ=7.36 (t, 2H, ArH), 7.21 (t, 1H, ArH), 7.15 (d, 2H, ArH), 6.09 (br, 1H, NH), 5.11 (d, 2H, CH$_2$), 3.10 (s, 3H, CH$_3$). $^{13}$C-NMR (CDCl$_3$): δ=168.8, 166.0, 154.9, 151.0, 129.5, 125.8, 121.7, 44.0, 21.3. ESI-MS: m/z Calc. for $C_{11}H_{11}N_5O_2$ 245.09; Obs. [M+H]$^+$ 246.17.

3.18: This compound was prepared from 3.11. Column chromatography (flash SiO$_2$) using an elution gradient of 0% to 10% EtOAc in CHCl$_3$ yielded pure 3.18 (29 mg, 0.11 mmol, 94%) as a pink solid. $^1$H-NMR (CDCl$_3$): δ=7.35 (t, 2H, ArH), 7.19 (t, 1H, ArH), 7.12 (d, 2H, ArH), 6.08 (br d, 1H, NH), 5.54 (qn, 1H, CH), 3.09 (s, 3H, CH$_3$TZ), 1.78 (d, 3H, CHCH$_3$). $^{13}$C-NMR (CDCl$_3$): δ=169.7, 168.6, 154.1, 150.9, 129.4, 125.6, 121.6, 50.7, 21.7, 21.3. ESI-MS: m/z Calc. for $C_{12}H_{13}N_5C_2$ 259.11; Obs. [M+H]$^+$ 260.08.

3.19: This compound was prepared from 3.12. Column chromatography (flash SiO$_2$) using an elution gradient of 0% to 8% EtOAc in CHCl$_3$ yielded pure 3.19 (27 mg, 0.10 mmol, 87%) as a pink oil. $^1$H-NMR (CDCl$_3$): δ=7.35 (m, 2H, ArH), 7.20 (t, 1H, ArH), 7.15 and 7.05 (d, 2H, ArH), 5.23 and 5.15 (2s, 2H, CH$_2$), 3.36 and 3.22 (2s, 3H, NCH$_3$), 3.11 and 3.08 (2s, 3H, CH₃TZ). ¹³C-NMR (CDCl₃): δ=168.8, 168.6, 166.2, 155.5, 154.8, 151.4, 151.3, 129.4, 125.6, 121.8, 121.7, 52.2, 52.0, 36.4, 36.3, 21.34, 21.29. ESI-MS: m/z Calc. for C₁₂H₁₃N₅O₂ 259.11; Obs. [M+H]⁺ 260.08.

3.20: This compound was prepared from 3.13. Column chromatography (flash SiO₂) using an elution gradient of 2% to 25% EtOAc in CHCl₃ was followed by precipitation, induced by adding heptane (9 mL) to a stirred solution in hot diethylether (1 mL). Storage at −20° C. for 16 h, filtration, washing with pentane and drying of the solid in vacuo yielded pure 3.20 (17 mg, 66 μmol, 76%) as a pink solid. ¹H-NMR (CDCl₃): δ=7.34 (t, 2H, ArH), 7.18 (t, 1H, ArH), 7.08 (d, 2H, ArH), 5.62 (br t, 1H, NH), 3.90 (q, 2H, CH₂NH), 3.60 (t, 2H, TzCH₂), 3.06 (s, 3H, CH₃TZ). ¹³C-NMR (CDCl₃): δ=168.0, 154.8, 151.0, 129.4, 125.5, 121.7, 38.9, 35.1, 21.3. ESI-MS: nm/z Calc. for Cl₂H₁₃N₅O₂ 259.11; Obs. [M+H]⁺ 260.17.

3.21: This compound was prepared from 3.14. Column chromatography (flash SiO₂) using an elution gradient of 0% to 4% EtOAc in CHCl₃ and, in a second chromatography step, an elution gradient of 4% to 10% acetone in heptane yielded pure 3.21 (49 mg, 0.15 mmol, 83%) as a pink oil. ¹H-NMR (CDCl₃): δ=8.62 (m, 2H, ArH), 7.63 (m, 3H, ArH), 7.34 (m, 2H, ArH), 7.23-7.05 (m, 3H, ArH), 5.30 and 5.22 (2s, 2H, CH₂), 3.40 and 3.26 (2s, 3H, CH₃). ¹³C-NMR (CDCl₃): δ=166.1, 165.3, 165.2, 155.5, 154.7, 151.4, 151.2, 133.1, 133.0, 131.6, 131.5, 129.43, 129.39, 129.35, 128.3, 128.2, 125.6, 121.73, 121.71, 52.2, 52.0, 36.34, 36.31. ESI-MS: m/z Calc. for C₁₇H₁₅N₅O₂ 321.12; Obs. [M+H]⁺ 322.17, [2M+H]⁺ 642.92, [2M+Na]⁺ 665.00.

3.22: This compound was prepared from 3.15. Column chromatography (flash SiO₂) using an elution gradient of 0% to 4% EtOAc in CHCl₃ and, in a second chromatography step, an elution gradient of 4% to 6% acetone in heptane yielded pure 3.22 (32 mg, 95 μmol, 52%) as a pink oil. ¹H-NMR (CDCl₃): δ=8.62 (t, 2H, ArH), 7.63 (m, 3H, ArH), 7.36 (m, 2H, ArH), 7.22-7.04 (m, 3H, ArH), 5.27 and 5.19 (2s, 2H, TZCH₂), 3.77 and 3.67 (2q, 2H, CH₂CH₃), 1.39 and 1.30 (2t, 3H, CH₂CH₃). ESI-MS: m/z Calc. for C₁₈H₁₇N₅O₂ 335.14; Obs. [M+H]⁺ 336.17, [2M+H]⁺ 670.83, [2M+Na]⁺ 693.08.

3.23: This compound was prepared from 3.16. Column chromatography (flash SiO₂) using an elution gradient of 5% to 30% EtOAc in CHCl₃ and, in a second chromatography step, an elution gradient of 20% to 40% acetone in heptane yielded pure 3.23 (66 mg, 0.20 mmol, 89%) as a pink oil. ¹H-NMR (CDCl₃): δ=8.97 (t, 1H, ArH), 8.67 (m, 1H, ArH), 8.00 (m, 1H, ArH), 7.59 (m, 1H, ArH), 7.34 (m, 2H, ArH), 7.23-7.05 (m, 3H, ArH), 5.36 and 5.27 (2s, 2H, CH₂), 3.40 and 3.26 (2s, 3H, CH₃). 13C-NMR (CDCl₃): δ=166.8, 164.6, 164.4, 155.5, 154.7, 151.2, 151.1, 151.0, 150.9, 149.9, 149.8, 137.6, 137.5, 129.3, 126.7, 126.6, 125.5, 124.2, 124.1, 121.63, 121.61, 52.2, 52.0, 36.3, 36.2. ESI-MS: m/z Calc. for C₁₆H₁₄N₆O₂ 322.12; Obs. [M+H]⁺ 323.25, [2M+H]⁺645.00, [2M+Na]⁺667.08.

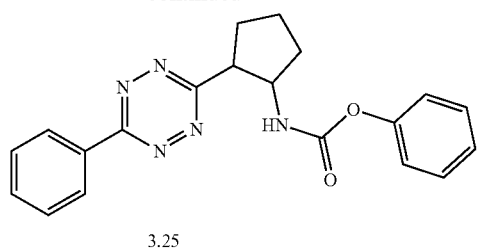

3.25

3.24 10 grams 2-aminocyclopentanecarbonitrile dissolved in 100 mL dichloromethane, cooled with ice, and di-tert-butyldicarbonate (26.4 g, 121.0 mmol) was added and the mixture was stirred overnight. Silica chromatography with heptane, toluene, and ethyl acetate mixtures followed by Kugelrohr distillation at 120-130° C./0.2 mbar yielded 12.6 g tert-butyl (2-cyanocyclopentyl)carbamate; ¹H-NMR (CDCl₃) δ 4.9 (bs, 1H), 4.1 (m, 1H), 3.2 (m, 1H), 2.1-1.3 (m) and 1.45 (s) (15H). Benzonitrile and tert-butyl (2-cyanocyclopentyl)carbamate were reacted in a 1:7 molar ratio according to general procedure A, affording tert-butyl (2-(6-phenyl-1,2,4,5-tetrazin-3-yl)cyclopentyl)carbamate 1.78 g (5.21 mmol, 30%). ¹H-NMR (CDCl₃) δ 8.6 (dd, J=1.8, 4.5, 2H), 7.6 (m, 3H), 4.8 (bm, 1H), 4.45 (bt, 0.4H), 4.25 (bt, 0.6H), 4.1 (q, J=7.8, 0.4H), 3.55 (q, J=8.6, 0.6H), 2.5-1.6 (m, 6H), 1.26 and 1.18 (2s, ca. 3/2 ratio, 9H). ¹³C-NMR (CDCl₃) δ 170.8, 169.5, 164.3, 163.9, 155.3, 154.9, 132.4, 132.3, 132.0, 131.9, 129.1, 127.8, 79.2, 59.2, 55.7, 52.1, 48.7, 32.7, 32.6, 30.2, 29.0, 28.2, 28.1, 22.8, 22.6. ESI-MS n/z 340 [M−H]−

This intermediate (366 mg; 1.07 mmol) was stirred for 3 h with 15 mL dichloromethane and 1.5 mL trifluoroacetic acid. Rotary evaporation at 60° C. was followed by chromatography on silica with dichloromethane gave the product 3.24, as the TFA-salt.

3.25: This compound was prepared as according to general procedure G. ¹H-NMR (CDCl₃) δ 8.58 (m, 2H), 7.60 (m, 4H), 7.4-6.9 (m, 4H), 5.29 (m, 1H), 4.46 (m, 1H), 3.72 (q, J=8.7, 1H), 2.55-2.25 (m, 3H), 2.15-1.85 (m, 2H), 1.85-1.75 (m, 1H). Signals of the minor isomer were observed at 8.45, 5.45, 4.6 and 4.15.

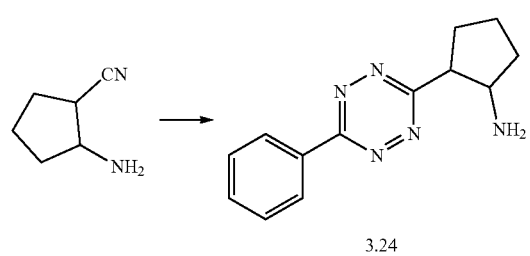

3.24

3.26

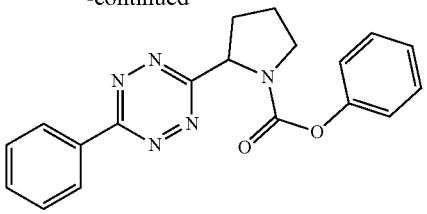

3.27

3.26: This compound was prepared from benzonitrile and 2-cyano-1-pyrrolidinecarboxylic acid tbutyl ester that were reacted in a molar ratio of 8:1 according to general procedure A, affording Boc-protected 3.26 (2.23 mmol, 21%) after silica chromatography with dichloromethane and toluene/ethylacetate. $^1$H-NMR (CDCl$_3$) δ 8.65 (m, 2H), 7.65 (m, 3H), 5.45 and 5.35 (2m, 1/1 ratio, 1H), 3.85-3.55 (m, 2H), 2.6 (m, 1H), 2.3-1.95 (m, 3H), 1.4 and 1.15 (2s, 1/1 ratio, 9H). $^{13}$C-NMR (CDCl$_3$) δ 171.3, 170.8, 164.6, 154.3, 153.3, 132.6, 132.4, 131.7, 131.5, 129.2, 129.0, 127.9, 79.9, 60.2, 60.1, 47.2, 47.0, 33.9, 33.0, 28.4, 28.2, 24.1, 23.6. Boc-deprotection according to general procedure E afforded 3.26, which was used as such in the next step.

3.27: This compound was prepared as according to general procedure G, followed by silica chromatography with dichloromethane, yielded 60 mg (0.173 mmol, 40% over two steps). $^1$H-NMR (CDCl$_3$) δ 8.6 (m, 2H), 7.6 (m, 3H), 7.4-6.8 (m, 5H), 5.7 and 5.6 (2dd, ca. 3/5 ratio, 1H; J=4.2, 6.0; J=3.8, 5.9). $^{13}$C-NMR (CDCl$_3$) δ 170.4 170.2, 151.1, 150.9, 133.0, 132.8, 131.7, 131.5, 129.5, 129.4, 128.1, 125.4, 121.6, 121.3, 60.8, 60.5, 47.8, 47.7, 33.9, 33.0, 22.2, 21.2.

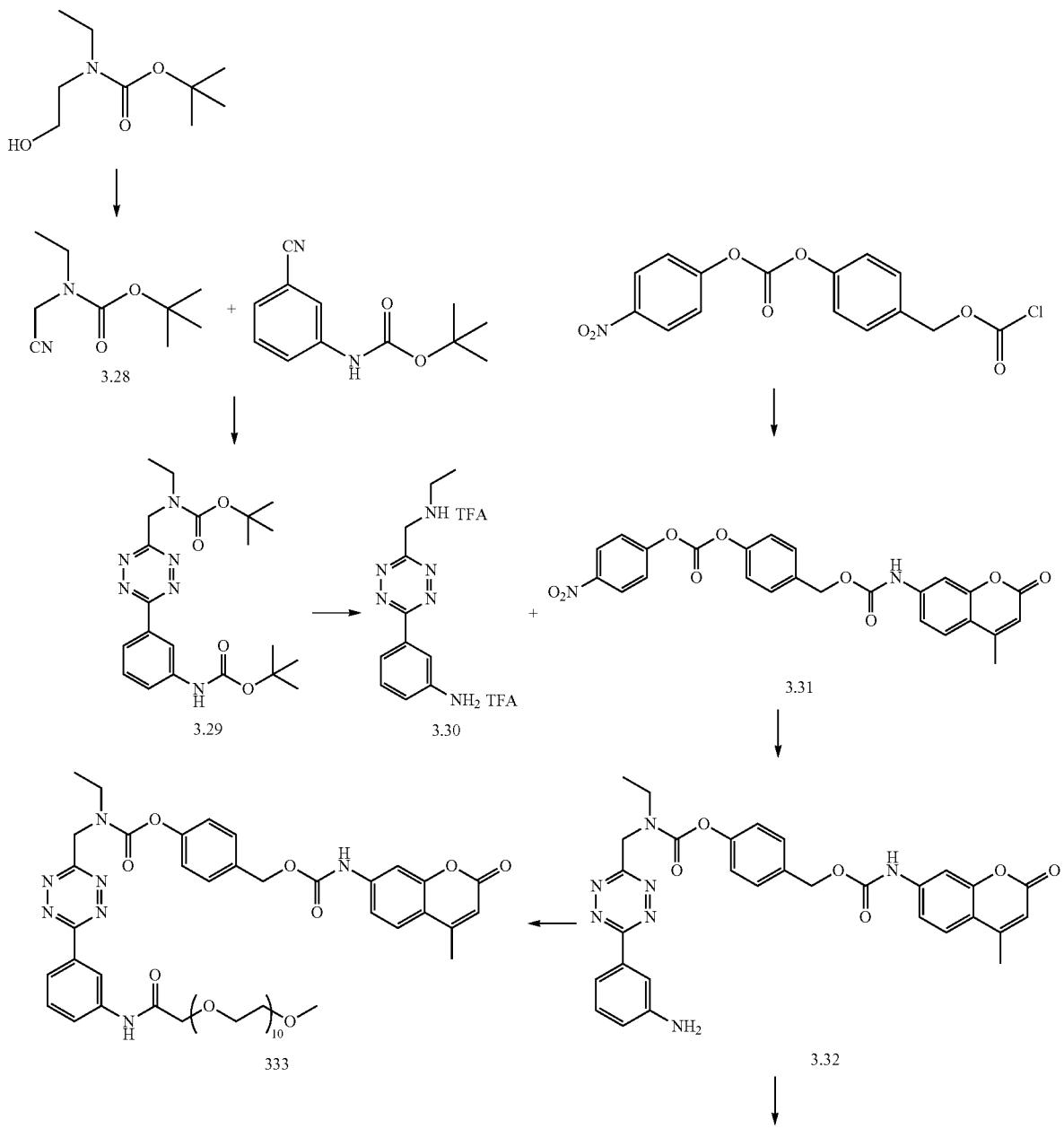

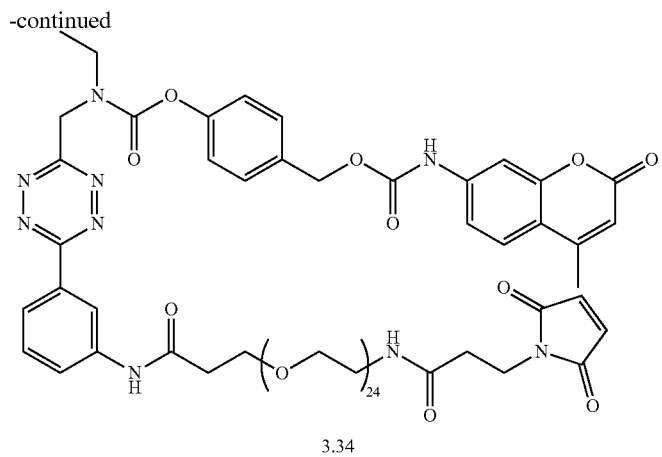

3.34

3.28: This compound was synthesized from t-butyl N-ethyl-N-(2-hydroxyethyl)carbamate following a general literature procedure (Ref. 7). Column chromatography (flash $SiO_2$) using an elution gradient of 0% to 5% EtOAc in $CHCl_3$ yielded pure 3.28 (0.37 g, 2.00 mmol, 76%) as a colorless oil. $^1$H-NMR ($CDCl_3$): δ=4.14 (br s, 2H, $CH_2CN$), 3.39 (q, 2H, $CH_2CH_3$), 1.49 (s, 9H, $C(CH_3)_3$), 1.19 (t, 3H, $CH_2CH_3$). GC-MS: m/z Calc. for $C_9H_{16}N_2O_2$ 184.12; Obs. $[M]^+$ 184.

3.29: This compound was prepared from t-butyl N-(3-cyanophenyl)carbamate and 3.28 that were reacted in a 8:1 molar ratio according to general procedure A. EtOH was used as reaction solvent in the preparation of the [2H]-TZ precursor. Directly after oxidation and work-up the volatiles were removed in vacuo and the mixture was stirred at 50° C. in EtOAc/$CHCl_3$ 1:1 (150 mL). Most of the relatively insoluble diphenyltetrazine derivative byproduct was removed by hot filtration over Celite. Column chromatography (flash $SiO_2$) using an elution gradient of 0% to 10% EtOAc in $CHCl_3$ and, in a second chromatography step, an elution gradient of 5% to 10% acetone in heptane yielded pure 3.29 (220 mg, 0.51 mmol, 38%) as a red solid. $^1$H-NMR ($CDCl_3$): δ=8.50 (d, 1H, ArH), 8.27 (s, 1H, ArH), 7.78 (d, 1H, ArH), 7.53 (t, 1H, ArH), 6.69 (br s, 1H, NH), 5.06 and 4.99 (2s, 2H, $TZCH_2$), 3.56 and 3.50 (2m, 2H, $CH_2CH_3$), 1.59-1.18 (m, 21H, $CH_2CH_3$, $C(CH_3)_3$). ESI-MS: m/z Calc. for $C_{21}H_{30}N_6O_4$ 430.23; Obs. $[M-tboc+2H]^+$ 331.33, $[M-tbutyl+2H]^+$ 375.00, $[M+Na]^+$ 453.25, $[2M+Na]^+$ 883.33.

3.30: This compound was prepared from 3.29 according to general procedure E. Pure 3.30 (119 mg, 0.26 mmol, 100%) was obtained as a red oil. $^1$H-NMR ($CD_3OD$): δ=8.33-8.29 (m, 2H, ArH), 7.60 (t, 1H, ArH), 7.37 (m, 1H, ArH), 4.99 (s, 2H, $TZCH_2$), 3.38 (q, 2H, $CH_2CH_3$), 1.46 (t, 3H, $CH_3$).

3.31: 7-Amino-4-methylcoumarin (50 mg, 0.28 mmol) was suspended with N,N-diisopropylethylamine (100 µL, 0.57 mmol, 2 eq) in dry THF (2 mL). A solution of the chloroformate derivative as shown in the above synthetic scheme (Ref. 8) (0.28 mmol, 1 eq) in dry THF (1 mL) was added and the mixture was stirred at r.t. for 72 h. The resulting white (fine) precipitate was isolated by filtration. The filtrate still contained precipitate, and was centrifuged to collect a second crop of product. The combined residues were washed with $CHCl_3$ and dried in vacuo yielding pure 3.31 (130 mg, 0.26 mmol, 94%) as a white solid. $^1$H-NMR (DMSO-d6): δ=10.31 (s, 1H, NH), 8.37 (m, 2H, ArH), 7.71 (m, 3H, ArH), 7.57 (m, 3H, ArH), 7.46 (m, 2H, ArH), 7.41 (m, 1H, ArH), 6.24 (s, 1H, CH), 5.22 (s, 2H, $CH_2$), 2.39 (s, 3H, $CH_3$).

3.32: Compound 3.30 (130 mg, 0.26 mmol) was dissolved in dry DMSO (2 mL), a solution of 3.31 (128 mg, 0.26 mmol, 1 eq) and N,N-diisopropylethylamine (0.3 mL, 1.7 mmol, 6.5 eq) in dry DMSO (2 mL) was added and the mixture was stirred at 35° C. for 17 h. $CHCl_3$ (120 mL) was added and the organic layer was sequentially washed with saturated $NaHCO_3$ (3×50 mL) and brine (50 mL). The organic layer was dried with $Na_2SO_4$, filtrated and the filtrate was concentrated in vacuo. Column chromatography (flash $SiO_2$) using an elution gradient of 0% to 30% EtOAc in $CHCl_3$ to 2% MeOH in $CHCl_3$ yielded pure 3.32 (80 mg, 0.14 mmol, 53%) as a red solid. $^1$H-NMR ($CDCl_3$): δ=7.97 (t, 1H, ArH), 7.90 (d, 1H, ArH), 7.48 (d, 1H, ArH), 7.42-7.30 (m, 6H, ArH), 7.16 (d, 1H, ArH), 7.06 (d, 1H, ArH), 6.92 (br, 1H, NH), 6.16 (s, 1H, CH), 5.24 and 5.13 (2s, 2H, $TZCH_2$), 5.16 (s, 2H, $ArCH_2$), 3.93 (br s, 2H, $NH_2$), 3.74 and 3.64 (2q, 2H, $CH_2CH_3$), 2.38 (s, 3H, $CCH_3$), 1.37 and 1.27 (2t, 3H, $CH_2CH_3$). ESI-MS: m/z Calc. for $C_{30}H_{27}N_7O_6$ 581.20; Obs. $[M+H]^+$ 582.17, $[2M+H]^+$ 1163.17, $[2M+Na]^+$ 1184.67.

3.33: Compound 3.32 (5.1 mg, 8.8 µmol) and 3,6,9,12,15,18,21,24,27,30,33-undecaoxatetratriacontanoic acid (6.2 mg, 12 µmol, 1.3 eq) were dissolved in dry DMF (65 µL). N,N-Diisopropylethylamine (6 µL, 34 µmol, 4 eq) and PyBOP (6.0 mg, 11 µmol, 1.3 eq), partly as a solid and as a solution in dry DMF (35 µL), were added and the mixture was stirred at r.t. for 22 h. $CHCl_3$ (50 mL) was added and the organic layer was sequentially washed with $H_2O$, 0.1 M HCl, sat. $NaHCO_3$ and brine (all 20 mL). The organic solution was dried with $Na_2SO_4$, filtrated, and the filtrate was concentrated in vacuo. Column chromatography (flash $SiO_2$) using an elution gradient of 0.5% to 4% MeOH in $CHCl_3$ yielded pure 3.33 (6.0 mg, 5.5 µmol, 63%) as a pink oil. $^1$H-NMR ($CDCl_3$): δ=9.16 and 9.12 (2 br, 1H, NH), 8.67 (d, 1H, ArH), 8.36 (t, 1H, ArH), 8.12 (d, 1H, ArH), 7.62-7.32 (m, 7H, ArH, NH), 7.17 (d, 1H, ArH), 7.06 (d, 1H, ArH), 6.17 (s, 1H, CH), 5.26 and 5.16 (2s, 2H, $TZCH_2$), 5.19 and 5.18 (2s, 2H, $ArCH_2$), 4.16 (s, 2H, $COCH_2$), 3.82-3.51 (m, 42H, PEG $OCH_2$, $CH_2CH_3$), 3.37 (s, 3H, $OCH_3$), 2.39 (s, 3H, $CCH_3$), 1.39 and 1.29 (2t, 3H, $CH_2CH_3$). ESI-MS: m/z Calc. for $C_{53}H_{71}N_7O_{18}$ 1093.49; Obs. $[M+2H]2^+$ 547.75, $[M+H]^+$ 1094.33, $[M+Na]^+$ 1116.42.

3.34: Compound 3.32 (17.5 mg, 30 µmol) and maleimide-PEG24-acid (49.5 mg, 38 µmol, 1.3 eq) were dissolved in $CH_2Cl_2$/DMF 1:1 (150 µL). N,N-Diisopropylethylamine (22

μL, 0.13 mmol, 4 eq) and PyBOP (25.8 mg, 48 μmol, 1.6 eq) were added and the mixture was stirred at r.t. for 17 h. CHCl₃ (50 mL) was added and the organic layer was washed with 0.1 M HCl, sat. NaHCO₃ and brine (all 20 mL). The solvent was removed in vacuo and the compound was purified with preparative RP-HPLC using an elution gradient of 51% to 52% MeCN in H₂O (both containing 0.1% formic acid). After extraction from the aqueous layer with CHCl₃ (2×10 mL) the combined organic fractions were washed with brine (10 mL), dried with Na₂SO₄, filtrated and the solvent was removed in vacuo. Flushing with CHCl₃ (2×) yielded pure 3.34 (30 mg, 16 μmol, 86%) as a pink oil. ¹H-NMR (CDCl₃): δ=9.15 and 9.11 (2 br, 1H, NH), 8.68 (d, 1H, ArH), 8.30 (t, 1H, ArH), 8.06 (d, 1H, ArH), 7.58-7.30 (m, 7H, ArH, NH), 7.17 (d, 1H, ArH), 7.05 (d, 1H, ArH), 6.69 (s, 2H, CH=CH), 6.35 (br, 1H, NH), 6.16 (s, 1H, C=CH), 5.25 and 5.15 (2s, 2H, TZCH₂), 5.18 and 5.17 (2s, 2H, ArCH₂), 3.89-3.37 (m, 102H, PEG OCH₂, CH₂NH, COCH₂CH₂N, CH₂CH₃), 2.71 (t, 2H, COCH₂CH₂N), 2.51 (t, 2H, COCH₂CH₂O), 2.39 (s, 3H, CCH₃), 1.39 and 1.30 (2t, 3H, CH₂CH₃). ESI-MS: m/z Calc. for C₈₈H₁₃₃N₉O₃₄ 1860.90; Obs. [M+3H]³⁺ 621.08, [M+2H]²⁺ 931.25, [M+H]⁺ 1861.50.

Example 4: Synthesis of Trans-Cyclooctene (TCO)-Based Activators

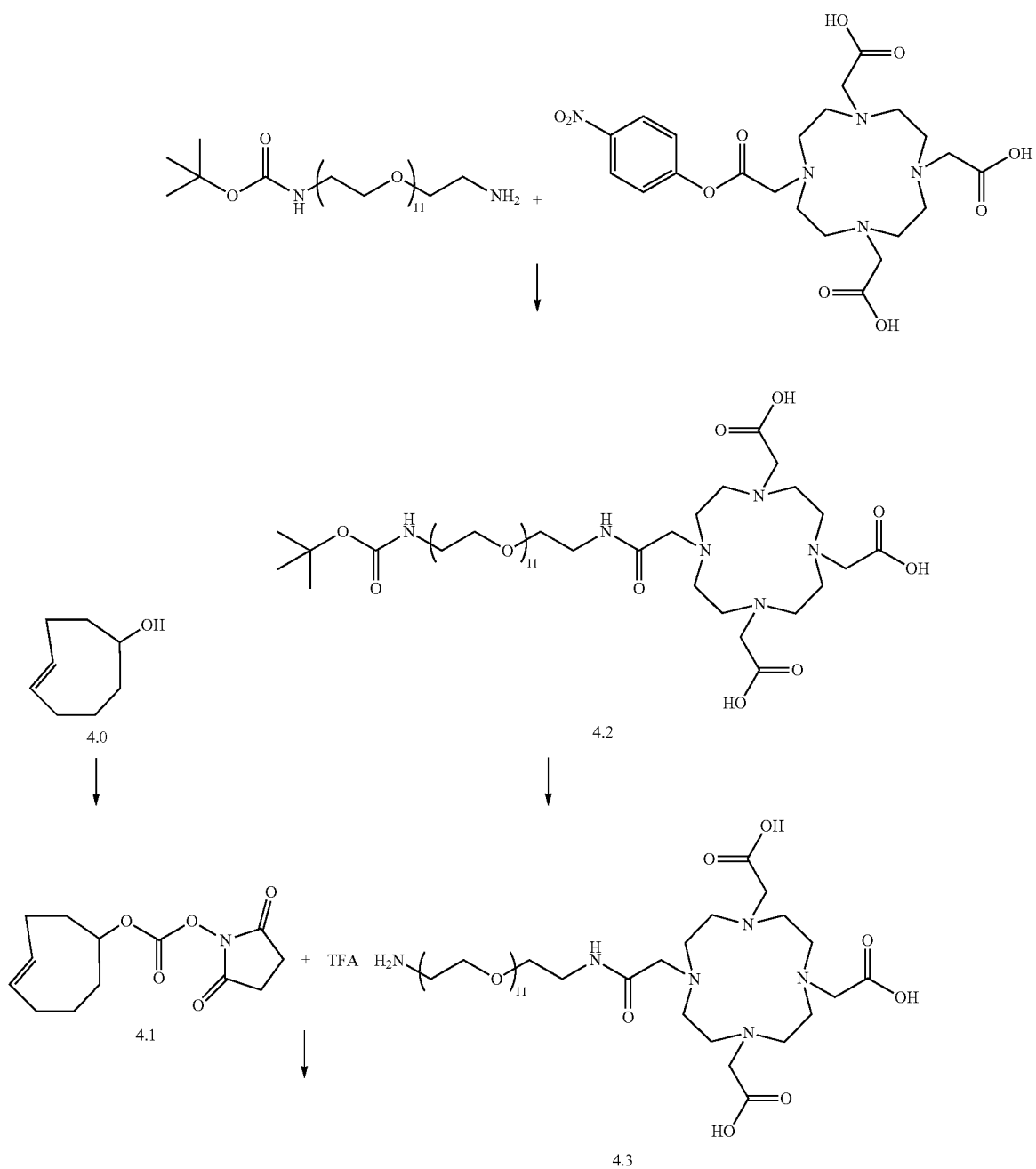

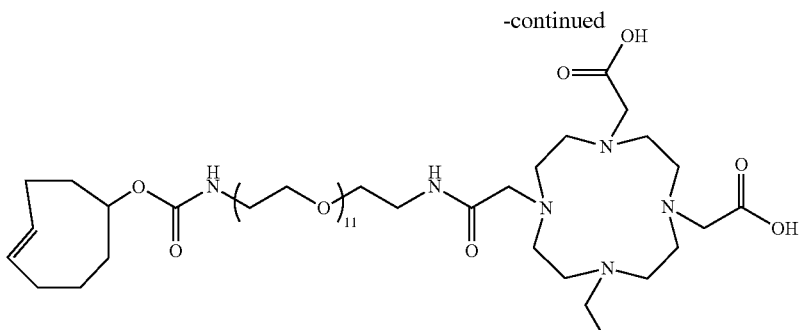

4.4

4.1: The axial isomer was prepared according to a published literature procedure (Ref. 12).

4.2: 37-Amino-5,8,11,14,17,20,23,26,29,32,35-undecaoxa-2-azaheptatriacontanoic acid t-butyl ester (103 mg, 0.16 mmol) and N,N-diisopropylethylamine (140 μL, 0.80 mmol, 5 eq) were dissolved in dry DMF (1 mL). 1,4,7,10-Tetraazacyclododecane-1,4,7,10-tetraacetic acid mono(4-nitrophenyl) ester (Ref. 9) (120 mg, 0.16 mmol, 1 eq) was added as a solid and the mixture was stirred at room temperature for 2 h. The reaction mixture was added dropwise to a stirring solution of diethylether (35 mL), centrifuged (5 min at 4000 rpm) and decanted. The resulting solid was washed with diethylether (20 mL) after which centrifugation and decantation were repeated. Drying of the solid in vacuo yielded pure 4.2 (165 mg, 0.16 mmol, 100%) as a white solid. ESI-MS: m/z Calc. for $C_{45}H_{86}N_6O_{20}$ 1030.59; Obs. $[M+2H]^{2+}$ 516.33, $[M+H]^+$ 1031.67, $[M+Na]^+$ 1053.50.

4.3: Compound 4.2 (165 mg, 0.16 mmol) was dissolved in DMF/TFA 1:2 (1.5 mL) and the solution was stirred at room temperature for 2 h. The reaction mixture was added dropwise to a stirring solution of diisopropylether (35 mL), centrifuged (5 min at 4000 rpm) and decanted. Precipitation (1.5 mL MeCN→35 mL diethylether), centrifugation and decantation were repeated and drying of the solid in vacuo and lyophilization yielded pure 4.3 (167 mg, 0.16 mmol, 100%) as a white solid. ESI-MS: m/z Calc. for $C_{42}H_{79}F_3N_6O_{20}$ 1044.53; Obs. $[M-TFA+2H]^{2+}$ 466.58, $[M-TFA+H]^+$ 931.58.

4.4: Compound 4.3 (88 mg, 84 μmol) and N,N-diisopropylethylamine (120 μL, 0.68 mmol, 8 eq) were dissolved in DMF (1 mL). 4.1 (32 mg, 0.12 mmol, 1.4 eq) was added and the mixture was stirred at room temperature in the dark for 1 h. The reaction mixture was added dropwise to a stirring solution of diethylether (30 mL), centrifuged (5 min at 4000 rpm) and decanted. The resulting solid was washed with diethylether (20 mL) after which centrifugation and decantation were repeated. The solid was dried in vacuo and lyophilized followed by purification with preparative RP-HPLC using an elution gradient of 28% to 30% MeCN in $H_2O$ (both containing 0.1% formic acid). After lyophilization in the dark this yielded pure TCO-derivative 4.4 (49 mg, 45 μmol, 54%; axial isomer) as a white solid. ESI-MS: m/z Calc. for $C_{49}H_{90}N_6O_{20}$ 1082.62; Obs. $[M+2H]^{2+}$ 542.33, $[M+H]^+$ 1083.92, $[M+Na]^+$ 1105.75.

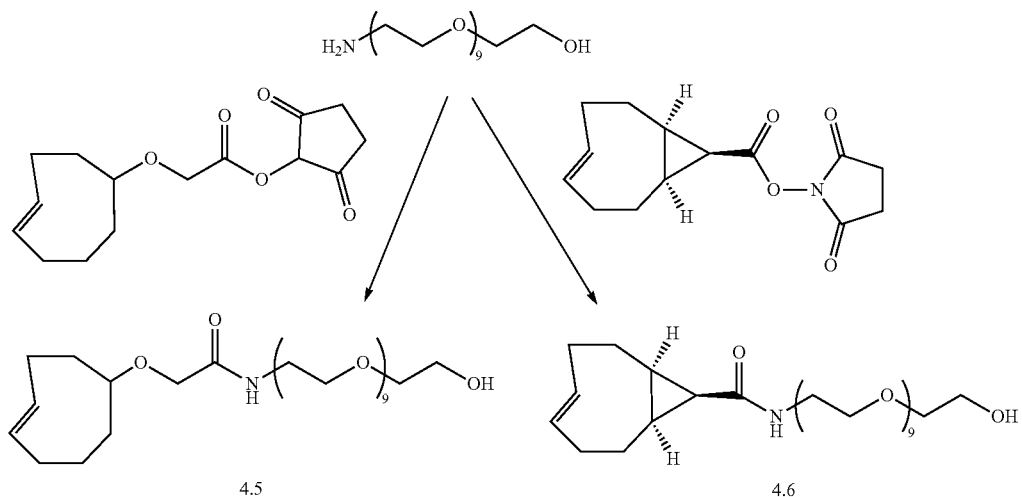

4.5: 29-Amino-3,6,9,12,15,18,21,24,27-nonaoxanonacosan-1-ol (103 mg, 0.22 mmol) and N,N-diisopropylethylamine (116 μL, 0.66 mmol, 3 eq) were dissolved in dry DMF (500 μL). Axial-(E)-2,5-dioxopyrrolidin-1-yl 2-(cyclooct-4-en-1-yloxy)acetate (Ref. 10) (62 mg, 0.22 mmol, 1 eq) was added, partly as a solid and as a solution in dry DMF (200

µL). After stirring at room temperature in the dark for 1 h, the solvent was removed in vacuo and the compound was purified with preparative RP-HPLC using an elution gradient of 38% to 41% MeCN in $H_2O$ (both containing 0.1% formic acid). After extraction from the aqueous layer with $CHCl_3$ (4×10 mL) the organic layer was washed with brine (20 mL), dried with $Na_2SO_4$, filtrated and the solvent was removed in vacuo. Flushing with $CHCl_3$ (2×) yielded 4.5 (96 mg, 0.15 mmol, 70%; axial isomer) as a colorless oil, containing about 5% cis isomer. $^1$H-NMR ($CDCl_3$): δ=7.06 (br, 1H, NH), 5.61-5.45 (2m, 2H, CH=CH), 3.91 (2d, 2H, $CH_2CO$), 3.75-3.45 (m, 41H, PEG $OCH_2$, $NHCH_2$, OCH), 2.74 (br, 1H, OH), 2.37-1.66 (m, 8H, TCO H), 1.54 (m, 1H, TCO H), 1.22 (m, 1H, TCO H). ESI-MS: m/z Calc. for $C_{30}H_{57}NO_{12}$ 623.39; Obs. $[M+H]^+$ 624.50, $[M+Na]^+$ 646.58.

4.6: 29-Amino-3,6,9,12,15,18,21,24,27-nonaoxanonacosan-1-ol (41 mg, 90 µmol) and N,N-diisopropylethylamine (47 µL, 0.27 mmol, 3 eq) were dissolved in dry $CH_2Cl_2$ (300 µL). (E-endo)-2,5-Dioxopyrrolidin-1-yl bicyclo[6.1.0]non-4-ene-9-carboxylate (Ref. 11) (24 mg, 90 µmol, 1 eq) was added as a solid and the mixture was stirred at room temperature in the dark for 1 h. $CHCl_3$ (50 mL) was added and the organic layer was sequentially washed with 0.5 M citric acid, sat. $Na_2CO_3$ and brine (all 20 mL). The chloroform layer was dried with $Na_2SO_4$, filtered, and the solvent in the filtrate was removed in vacuo. Pure 4.6 (48 mg, 79 µmol, 92%; endo isomer) was obtained as a colorless oil. $^1$H-NMR ($CDCl_3$): δ=6.24 (br t, 1H, NH), 5.79 (m, 1H, CH=CH), 5.29 (m, 1H, CH=CH), 3.75-3.50 (m, 38H, PEG $OCH_2$), 3.40 (q, 2H, $NHCH_2$), 2.71 (t, 1H, OH), 2.41-2.27 (m, 2H, TCO H), 2.01-1.77 (m, 5H, TCO H), 1.64-1.51 (m, 2H, TCO H), 1.03 (m, 1H, TCO CH), 0.91 (m, 1H, TCO CH). ESI-MS: m/z Calc. for $C_{30}H_{55}NO_{11}$ 605.38; Obs. $[M+H]^+$ 606.50, $[M+Na]^+$ 628.58.

4.7

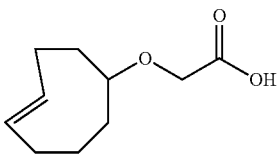 [SMILES: O=C(O)COC1CC/C=C/CCC1]

This compound was prepared according to a literature procedure (Ref. 10).

4.8

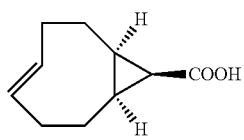

This endo sTCO material (E-endo)-bicyclo[6.1.0]non-4-ene-9-carboxylic acid was prepared according to a literature procedure (Ref. 11).

4.9

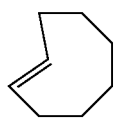

This compound was prepared according to a published literature procedure (Ref. 13).

Example 5: Determining the Stability of Tetrazine (TZ) Triggers in a MeCN/PBS Mixture 10 µL of a 25 mM TZ stock solution in DMSO (2.5×10−7 mol TZ) was diluted with MeCN and PBS to a total volume of 1 mL. The aqueous solution was incubated at 20° C. or at 37° C. At selected time points, the TZ solution was analyzed by HPLC-PDA/MS. The decrease in time of the characteristic TZ absorption at λ=540 nm is a measure for the stability of the TZ, where $t_{1/2}$ is defined as the time at which the TZ absorption has decreased by 50% relative to the TZ absorption at t=0. Depending on the used Method, different temperatures and/or different MeCN/PBS mixtures have been used, see Examples 8 and 9.

Example 6: Determining the Reactivity Between Tetrazine (TZ) Triggers and Trans-Cyclooctene (TCO) Activator 4.9 in MeCN at 20° C.

The second order rate constant of the reaction ($k_2$) between a TZ and TCO 4.9 was determined under pseudo first order conditions in MeCN at 20° C. using UV spectroscopic monitoring. A cuvette was filled with 3 mL of a 3.33 mM TCO solution in MeCN (1.0×10−5 mol TCO) and this solution was equilibrated at 20° C. Subsequently, 10 µL of a 25 mM TZ stock solution in DMSO (2.5×10−7 mol TZ) was added and the decrease of the characteristic TZ absorption at λ=540 nm was measured at regular intervals. From the decrease of this absorption, the half-life of the pseudo first order reaction between TZ and TCO was determined. The second order rate constant $k_2$ was obtained by calculation from this half-life and the concentration of TCO Example 7: Determining the Rate of Release of Constructs from IEDDA Adducts that are Formed by Activation of a Tetrazine (TZ) Trigger with Trans-Cyclooctene (TCO) Activator 4.9

10 µL of a 25 mM TZ stock solution in DMSO (2.5×10−7 mol TZ) was diluted with MeCN. Then, 10 µL of a 50 mM TCO 4.9 stock solution in DMSO (5.0×10−7 mol TCO) was added. After the complete disappearance of the pink color (this takes typically between 5 and 30 min, and is due to the IEDDA reaction between TZ and TCO thereby forming IEDDA adducts), the sample was diluted with PBS to a total volume of 1 mL (t=0). The aqueous solution was incubated at 20° C. or at 37° C. At selected time points, this solution was analyzed by HPLC-PDA/MS. The decrease of the IEDDA adduct absorption(s) and/or the rise of the leaving group absorption indicated the conversion of the release reaction. The rate of the release reaction can be indicated by the $t_{1/2}$-value that is defined as the time at which the IEDDA adduct absorptions have decreased by 50% relative to their absorptions at t=0. Alternatively, the rate of the release reaction can be indicated by the conversion (in %) after a certain reaction time (in hours). Depending on the used Method, different temperatures and/or different MeCN/PBS mixtures have been used, see Examples 8 and 9.

It shall be understood that the Constructs A that are released in Examples 8, 9, 12, 13: benzylamine and aniline derivatives, phenol, benzylalcohol, benzoic acid, also represent other types of Constructs A, such as small molecule drugs, protein drugs, biomolecules, Masking Moieties, polymers, resins, and the like, as defined herein. In addition, these Constructs can also be viewed as models for self-immolative linkers. The chemical moieties being released in these examples is identical or very similar to those moieties comprised in other Constructs $C^A$ and in self-immolative linkers $L^C$. The PABC-coumarin that is released in example 9 is a dye linked via a self-immolative linker. The coumarin can also be viewed a model for a small molecule drug.

Likewise, the stability and reactivity reported for the Trigger-Construct conjugates in Examples 8, 9, and 12, are representative of conjugates with other Constructs $C^A$ and/or linkers $L^C$, optionally additionally comprising a Construct B.

Example 8: Stability and Reactivity for a Series of Tetrazine Triggers (TZs), and their IEDDA Induced Release Believed to Occur Via the Cascade Mechanism IEDDA induced Construct release via the Cascade mechanism as illustrated for asymmetric TZ 2.42. N-isopropyl-N-benzylamine is the released Construct in this reaction between 2.42 and TCO.

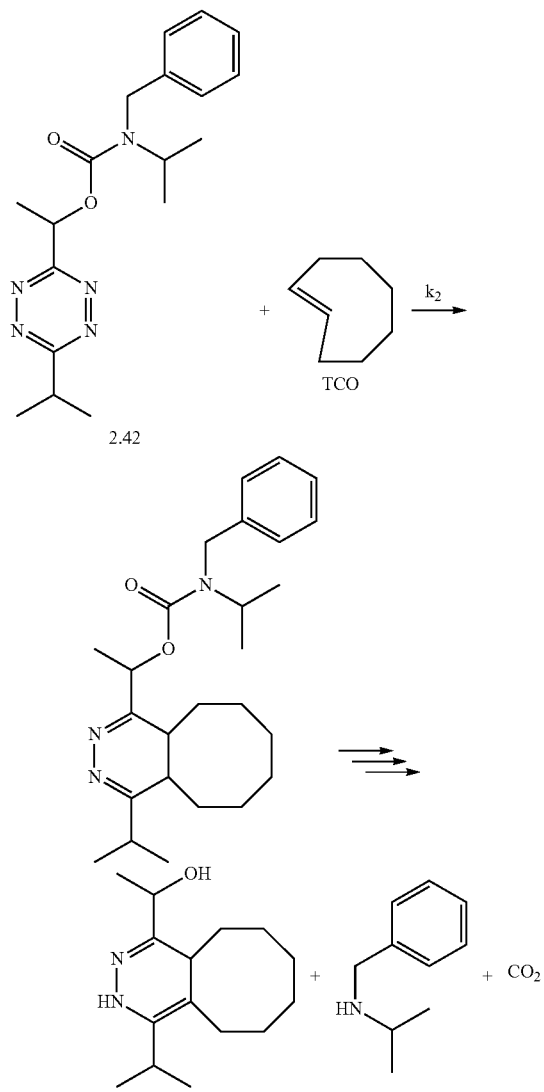

| Code | Stability [1] $t_{1/2}$ (h) | Reactivity [2] $k_2$ ($M^{-1} s^{-1}$) | Release [3] % (h) or $t_{1/2}$ (h) | Method [4] |
|---|---|---|---|---|
| 2.4 | | 24 | 95 h | A |
| 2.5 | | 1.5 | 9.5 h | A |
| 2.6 | | n.d. | 20 h | A |
| 2.7 | 18 | n.d. | 96% (16h) | A |
| 2.8 | 6.5 | n.d. | 100% (16h) | A |
| 2.16 | 47 | n.d. | | A |
| 2.17 | 312 | 4.5 | | A |
| 2.18 | n.d. | n.d. | 10% (23h) | F |
| | <4 | | n.d. | C |
| 2.19 | 850 | 0.79 | 10 h | C |
| 2.20 | 70 | 0.19 | 45% (1.3h), 100% (16h) | C |
| 2.21 | >4800 | 2.54 | 30 h | B |
| 2.22 | 3600 | 2.51 | 11 h | B |
| 2.23 | 65 | n.d. | 1.9 h | D |
| 2.24 | 350 | 4.6 | 20 h | C |
| | 300 | | n.d. | E |
| 2.36 | 7 | n.d. | 100% (16h) | C |
| 2.37 | 12 | n.d. | 2.5 h | C |
| 2.38 | 20 | n.d. | 3 h | C |
| 2.39 | 0.5 | n.d. | 0.83 h | C |
| 2.40 | 5 | 1.22 | 100% (22h) | C |
| 2.41 | 300 | 0.15 | 45% (2.5h), 100% (16h) | C |
| 2.42 | 650 | 0.21 | 100% (16h) | C |
| 2.43 | 35 | 0.15 | 100% (16h) | C |
| 2.44 | 230 | 0.25 | 100% (19h) | C |
| 2.45 | >4800 | 0.97 | 29 h | B |
| 2.46 | >4800 | 1.13 | 35 h | B |
| 2.47 | 400 | 0.96 | 55% (2.5h), 100% (16h) | C |
| | 140 | | n.d. | E |
| 2.48 | >4800 | 1.46 | 30 h | B |
| 2.49 | >4800 | 0.44 | 25 h | B |
| 2.53 | >400 | n.d. | | C |
| 2.57 | >400 | 0.33 | | C |

[1] The stability of the TZ is indicated by a $t_{1/2}$ (in hours), determined as according to Example 5.
[2] The reactivity $k_2$ of the TZ with TCO in MeCN at 20° C., determined as according to Example 6.
[3] The rate of release is indicated by a $t_{1/2}$ (in hours), or by a conversion (in %) at a certain time point (in hours), both determined as according to Example 7. Released Constructs: benzylamine and aniline derivatives, except for 2.18 (phenol), 2.8 (benzylalcohol), 2.7 (benzoic acid).
[4] Conditions used in the stability and release experiments: (A) 33% MeCN in PBS at 20° C., (B) 33% MeCN in PBS at 37° C., (C) 20% MeCN in PBS at 37° C., (D) 10% MeCN in PBS at 37° C., (E) 5% MeCN in PBS at 37° C., (F) MeCN at 37° C.
n.d. = not determined

Example 9: Stability and Reactivity for a Series of Tetrazines Triggers (TZs), and their IEDDA Induced Release Believed to Occur Via the Cyclization Mechanism IEDDA induced release via the Cyclization mechanism as illustrated for asymmetric TZ 3.22. Phenol is the released Construct in this reaction between 3.22 and TCO.

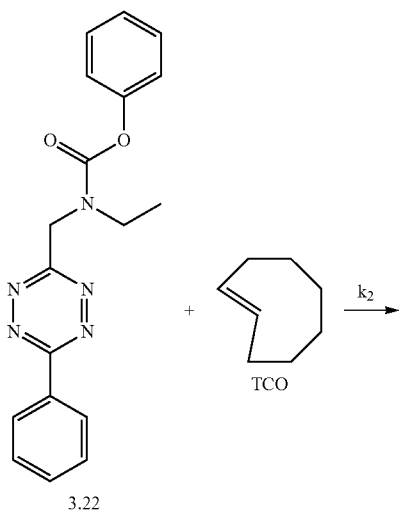
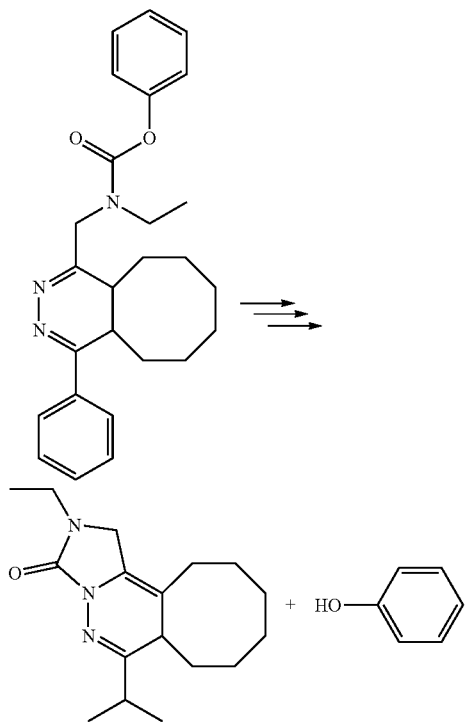
| Code | Stability [1] $t_{1/2}$ (h) | Reactivity [2] $k_2$ (M$^{-1}$ s$^{-1}$) | Release [3] % (h) | Method [4] |
|---|---|---|---|---|
| 3.2 | n.d. | n.d. | 25% (19 h) | B |
| 3.17 | 95 | n.d. | 11% (19h), 57% (168h) | A |
|  |  | 5 | 24% (2h), 80% (19h), 96% (96h) | E |
| 3.18 | 125 | n.d. | 17% (22h), 80% (144h) | A |
|  |  | 4 | 25% (1h), 98% (19h) | E |
| 3.19 | n.d. | 1.9 | 17% (19h), 32% (168h) | A |
|  |  | 20 | 35% (1h), 68% (19h), 99% (96h) | E |
| 3.20 | 400 | n.d. | 7% (20h), 30% (168h) | A |
|  |  | 16 | 5% (1h), 50% (20h) | E |
| 3.21 | n.d. | 3.7 | 20% (22h), 61% (168h) | A |
|  |  | 250 | 39% (1h), 90% (12h), 94% (28h) | E |
| 3.22 | 360 |  | 30% (1h), 75% (5h), 95% (72h) | E |
| 3.23 | 300 | 19 | 6% (22h), 32% (168h) | A |
|  |  | 25 | 20% (2h), 64% (26h), 80% (168h) | E |

-continued

| | | | | |
|---|---|---|---|---|
| 3.25 | >140 | n.d. | 57% (16h) | G |
| 3.27 | >>150 | n.d. | 49% (24h), 72% (48h) | C |
| 3.33 | 200 | 4.7 | 50% (1h), 80% (4h), 90% (72h) | E |
| | | 520([5]) | 20% (1h), 80% (8h) [6] | E [6] |

[1] The stability of the TZ is indicated by a $t_{1/2}$ (in hours), determined as according to Example 5.
[2] The reactivity $k_2$ of the TZ with TCO in MeCN at 20° C., determined as according to Example 6.
[3] The rate of release (of phenol, except for 3.33 that releases PABC and coumarin) is indicated by conversions (in %) at certain time points (in hours), determined as according to Example 7.
[4] Methods used in the stability and release experiments: (A) 33% MeCN in PBS at 20° C., (B) 33% MeCN in PBS at 37° C., (C) 20% MeCN in PBS at 37° C., (D) 10% MeCN in PBS at 37° C., (E) 5% MeCN in PBS at 37° C., (G) 50% MeCN in PBS at 37° C.
[5] Reactivity determined as according to Example 6, but assessed with sTCO 4.8 and not TCO 4.9.
[6] Release data determined as according to Example 7, but assessed after reaction with sTCO 4.8 and not TCO 4.9.
n.d. = not determined

Example 10: Determining the Stability of Tetrazine (TZ) Triggers in 50% Mouse Serum/PBS 10 µL of a 25 mM TZ stock solution in DMSO ($2.5 \times 10^{-7}$ mol TZ) was diluted with MeCN (50 µL), PBS (475 µL), and mouse serum (475 µL). The mixture was incubated at 37° C. At selected time points, aliquots (250 µL) were taken, diluted with cold MeCN (500 µL), stored at 4° C. for 30 min, and then centrifuged at 13400 rpm for 5 min. Part of the clear supernatant (250 µL) was diluted with water (500 µL) and the sample was analyzed by HPLC-PDA/MS. The stability was determined as outlined in Example 5.

Example 11: Determining the Rate of Release of a Construct from the IEDDA Adduct Formed by Activation of Tetrazine Triggers (TZ) with a Trans-Cyclooctene Activator in 50% Mouse Serum/PBS 10 µL of a 25 mM TZ stock solution in DMSO ($2.5 \times 10^{-7}$ mol TZ) was diluted with MeCN (50 µL), PBS (475 µL), and mouse serum (475 µL). Then, a stock solution of the appropriate TCO (20 µL 50 mM in DMSO; $1.0 \times 10^{-6}$ mol) was added, and the mixture was incubated at 37° C. At selected time points, aliquots (250 µL) were taken, diluted with cold MeCN (500 µL), stored at 4° C. for 30 min, and then centrifuged at 13400 rpm for 5 min. Part of the clear supernatant (250 µL) was diluted with water (500 µL) and the sample was analyzed by HPLC-PDA/MS. The release was determined as outlined in Example 7.

Example 12: Stability of Tetrazine Triggers (TZs), and their IEDDA Induced Construct Release by Trans-Cyclooctene Activators, in 50% Mouse Serum/PBS, 37° C.

| Code | Stability [1] $t_{1/2}$ (h) | Dienophile | Release [2] % (h |
|---|---|---|---|
| 2.19 | 32 | 4.0; axial isomer | 61% (21 h) |
| 2.24 | 16 | 4.0; axial isomer | 51% (21 h) |
| 2.41 | 45 | 4.0; axial isomer | 59% (21 h) |
| 2.42 | 55 | 4.8; endo isomer | 77% (21 h) |
| 2.47 | 24 | 4.9 | 81% (21 h) |
| 3.19 | 42 | 4.9 | 42% (19 h) |
| 3.21 | 43 | 4.9 | 37% (21 h) |

[1] The stability of the TZ is indicated by a $t_{1/2}$ (in hours), determined as according to Example 10.
[2] The rate of release is indicated by a conversion (in %) at certain time point (in hours), determined as according to Example 11.

Example 13: Demonstrating the Rate of Release of the Construct Phenol from the IEDDA Adduct Formed by Activation of Tetrazine Trigger 3.21 with 2-Norbornene

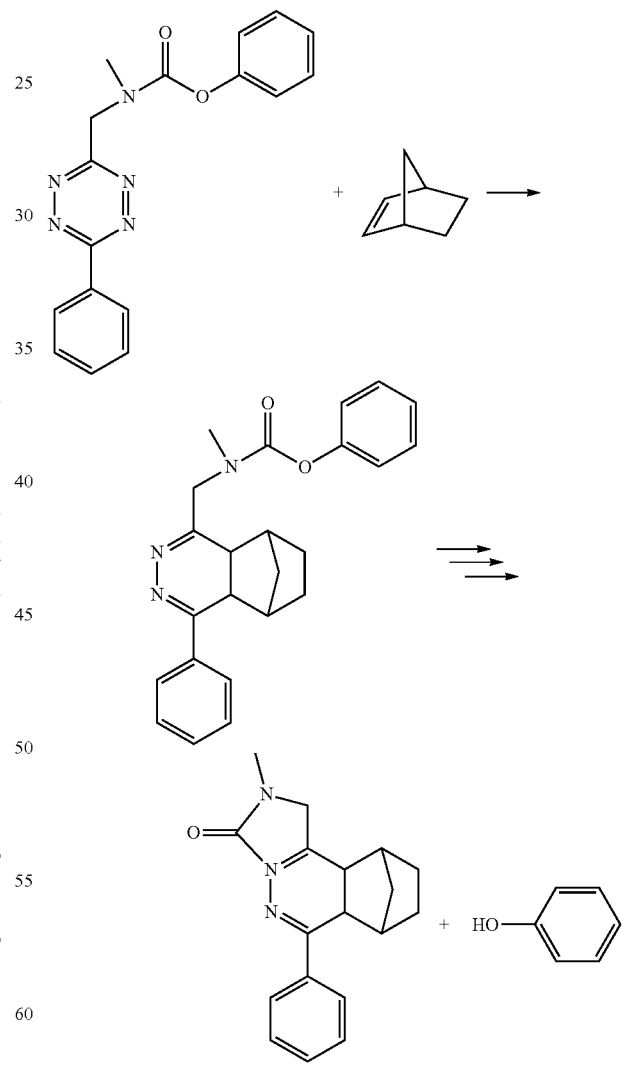

10 µL of a 25 mM stock solution of tetrazine 3.21 in DMSO ($2.5 \times 10^{-7}$ mol) was diluted with MeCN (300 µL), and 2-norbornene (2.35 mg; $2.5 \times 10^5$ mol) and PBS (900 µL) were added. The mixture was incubated at 37° C. overnight.

Subsequently, the sample was analyzed by HPLC-PDA/MS, which showed the formation of the cyclized product (m/z=294 Da) and phenol ($\lambda_{max}$=270 nm).

Example 14: Synthesis of Tetrazine Conjugates 14.1

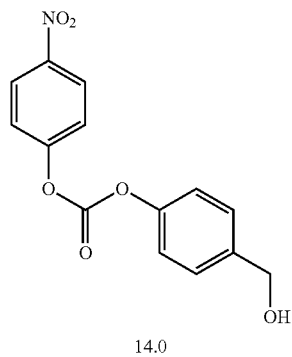

14.0

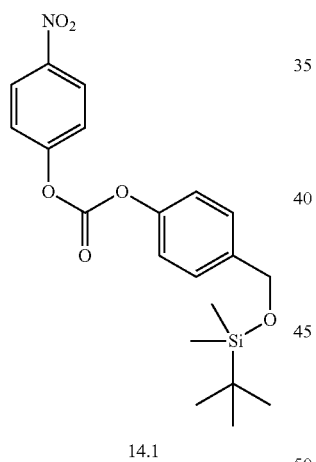

14.1

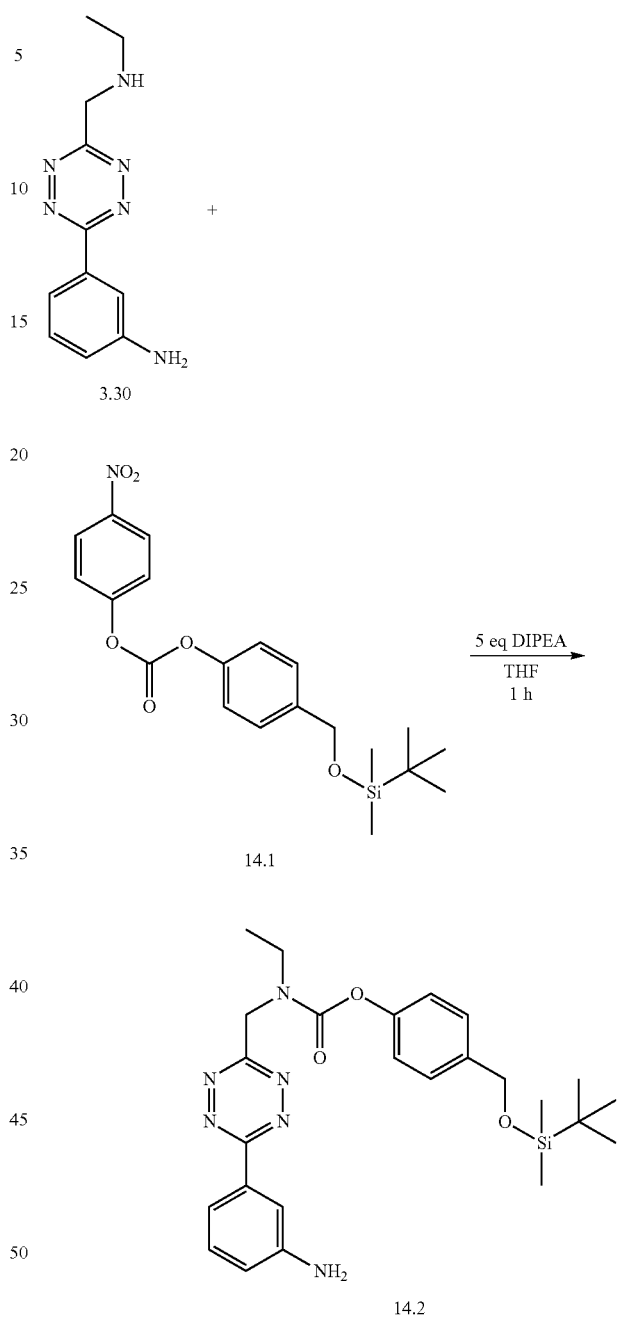

25 mg (86.4 µmol, 1 eq) of 14.0 was dissolved in dry DMF and cooled on ice batch to 0° C. Tert-butyldimethyl-silyl chloride (15.5 mg, 1.2 eq, 103 µmol) and 7.01 mg (1.2 eq, 103 µmol) imidazole were added and the reaction solution was warmed to room temperature and allowed to react for 2 h while stirring. The solution was concentrated in vacuo and residue was taken up in ether/water after which the organic fraction was washed with NH$_4$Cl (sat, aq) and brine after which the clear organic fraction was concentrated in vacuo. The crude was applied on isocratic automated column chromatography purification (SiO$_2$, CHCl$_3$), yielding 29 mg (71.9 µmol, 83%) of 14.1. R$_f$ on SiO$_2$ TLC: 0.37; $^1$H-NMR CDCl$_3$: 8.31 (d, 2H), 7.48 (d, 2H), 7.39 (d, 2H), 7.24 (d, 2H), 4.75 (s, 2H), 0.94 (s, 9H), 0.11 (s, 6H).

14.2

41 mg (0.102 mmol, 1 eq) of 14.1 and 26.7 mg (0.116 mmol, 1.14 eq) of 3.30 were dissolved in 1 mL tetrahydrofuran and 89 µL (5 eq) of DIPEA was added. The reaction solution was stirred for 4 h, concentrated in vacuo and dissolved again in CHCl$_3$, for washing with Na$_2$CO$_3$ (sat, aq) and brine, dried with Na$_2$SO$_4$ and concentrated. The crude was applied on MeOH/CHCl$_3$ automated column chromatography purification (SiO$_2$, 0→5%), yielding 36.1 mg (73.0 µmol, 71%) of 14.2. R$_f$ on SiO$_2$ 5% MeOH/CHCl$_3$ TLC: 0.55; LC-MS analysis: calc [M+H]$^+$=495.25, observed=495.08, calc [M+Na]$^+$=517.24, observed=517.25, calc [2M+H]$^+$=989.5, observed=989.0, calc [2M+Na]$^+$=1011.49, observed=1011.25.

14.3

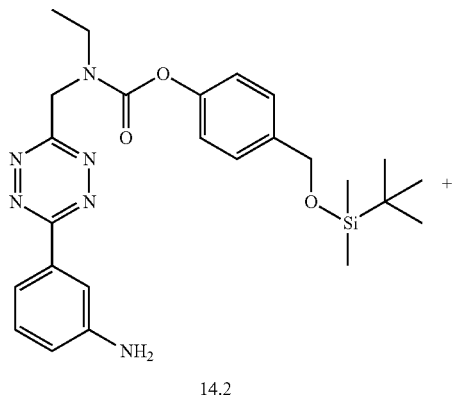

14.2

14.4

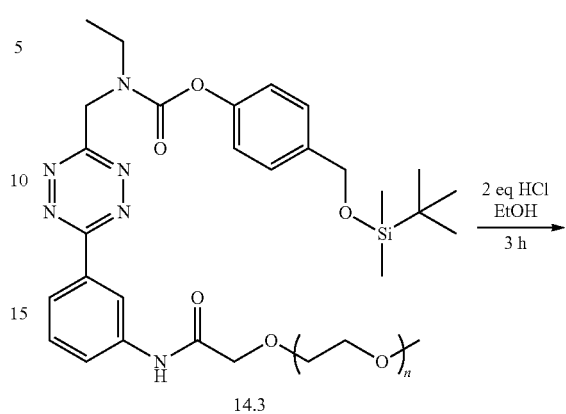

14.3

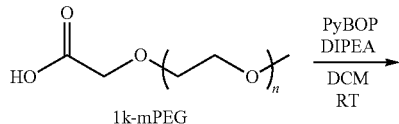

1k-mPEG

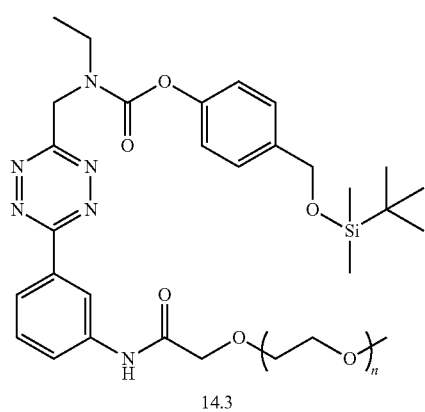

14.3

Combined 24.3 mg (49.1 μmol, 1 eq) of 14.2, 59.8 mg (58.9 μmol, 1.2 eq) carboxylic-acid-PEG and 40.9 mg (78.6 μmol, 1.6 eq) PyBOP in 200 μL dichloromethane, followed by the addition of 34 μL (4 eq) DIPEA. After 4 hours stirring, another 24 mg (46 μmol, 1 eq) of PyBOP was added and solution was incubated for 14 hours, concentrated in vacuo, yielding a pink wax. The wax was dissolved in CHCl$_3$ and washed with 0.1 M HCl (aq), brine, dried over Na$_2$SO$_4$ and concentrated in vacuo. A fraction was applied on acetone/heptane automated column chromatography purification (SiO$_2$, 50→100%), yielding 16.0 mg (10.7 μmol, 55%) of 14.3. $^1$H-NMR CDCl$_3$: 9.15 (d, 1H), 8.69 (d, 1H), 8.35 (t, 1H), 8.09 (d, 1H), 7.57 (s, 1H), 7.30 and 7.24 (2d, 2H), 7.10 and 7.00 (2d, 2H), 5.25 and 5.17 (2s, 2H), 4.68 (d, 2H), 4.16 (s, 2H), 3.75-3.5 (m, 101H), 3.36 (s, 3H), 1.36 and 1.27 (2t, 3H), 1.24 (s, 1H), 0.91 (s, 9H), 0.06 (6H). MALDI-ToF: calc [M+Na]$^+$=1513.81, observed=1513.80.

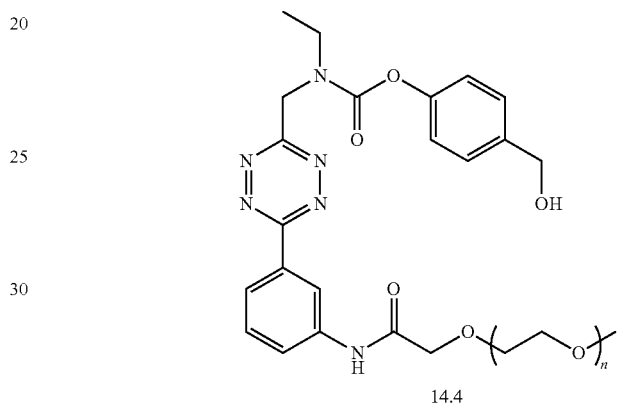

14.4

Dissolved 16.0 mg (10.7 μmol, 1 eq) of 14.3 in a small amount of ethanol and prepared a 1 v % HCl in ethanol solution from concentrated hydrochloric acid (37.2%), of which 160 μL was drop wise added to predissolved 14.3. The solution was stirred for 3 hours and concentrated in vacuo, affording 14.4 quantitatively as a pink wax. $^1$H-NMR CDCl$_3$: 9.14 (d, 1H), 8.67 (d, 1H), 8.35 (t, 1H), 8.11 (d, 1H), 7.58 (s, 1H), 7.35-7.30 (2d, 2H), 7.13 and 7.02 (2d, 2H), 5.25 and 5.17 (2s, 2H), 4.63 (d, 2H), 4.15 (s, 2H), 3.80-3.5 (m, 101H), 3.37 (s, 3H), 1.38 and 1.28 (2t, 3H), 1.24 (s, 1H). MALDI-ToF: calc [M+Na]$^+$=1399.72, observed=1399.75.

14.5

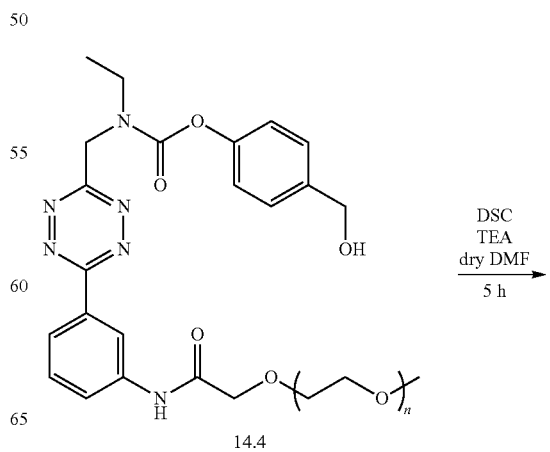

14.4

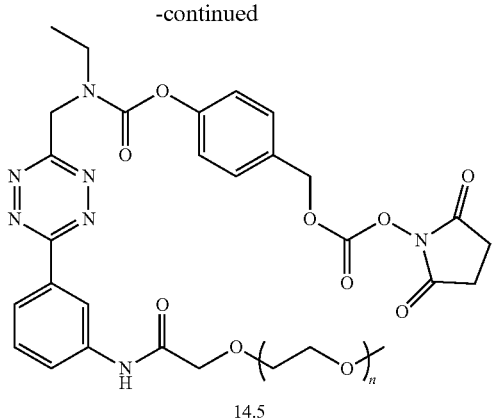

14.5

Dissolved 15.5 mg of 14.4 (11.3 μmol, 1 eq) in 100 μL dry DMF and 9.2 μL (66.1 μmol, 6 eq) triethylamine was added. N,N'-Disuccinimidyl carbonate was dissolved in a small amount of dry DMF and 14 mg (54.7 μmol, 5 eq) was added to the solution, followed by incubation at room temperature for 5 hours. Solution was concentrated in vacuo, taken up in $CHCl_3$, washed several times with 0.1 M HCl (aq) and brine, affording 13.9 mg (9.15 μmol) of compound 14.5 in 81%. $^1$H-NMR $CDCl_3$: 9.15 (d, 1H), 8.68 (d, 1H), 8.36 (t, 1H), 8.10 (d, 1H), 7.57 (s, 1H), 7.41-7.35 (2d, 2H), 7.19 and 7.10 (2d, 2H), 5.28 and 5.18 (2s, 2H), 4.16 (s, 2H), 3.80-3.5 (m, 101H), 3.37 (s, 3H), 2.85 (s, 4H) 1.38 and 1.28 (2t, 3H), 1.24 (s, 1H).

Ethanolamine-TZ-PEG 14.6

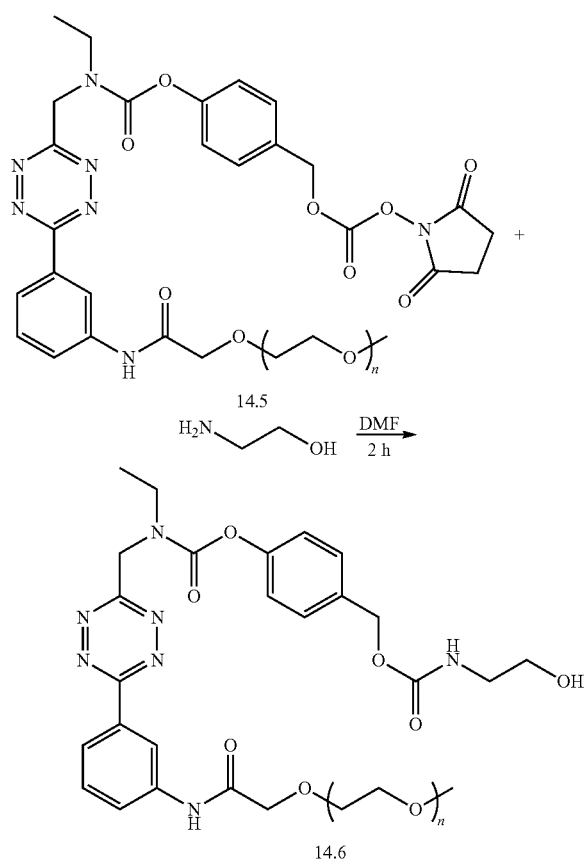

Compound 14.5 was prepared as described vide supra and during synthesis, a small amount of crude reaction mixture containing 2.7 mg (1.77 μmol, 1 eq) 14.5 was combined with 0.22 μL (3.64 μmol, 2 eq) of ethanolamine and incubated for 2 hours. LC-MS analysis revealed full conversion from 14.5 to 14.6. LC-MS analysis: calc $[M+H]^+=1463.76$, observed=1463.67, calc $[M+Na]^+=1486.75$, observed=1487.08.

Dipeptide-TZ-PEG 14.7

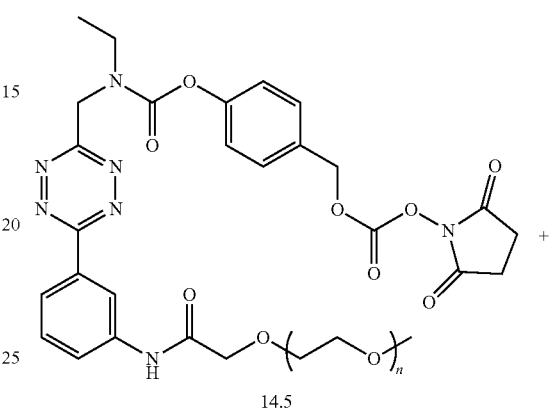

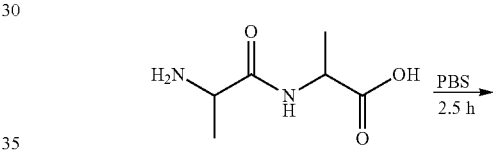

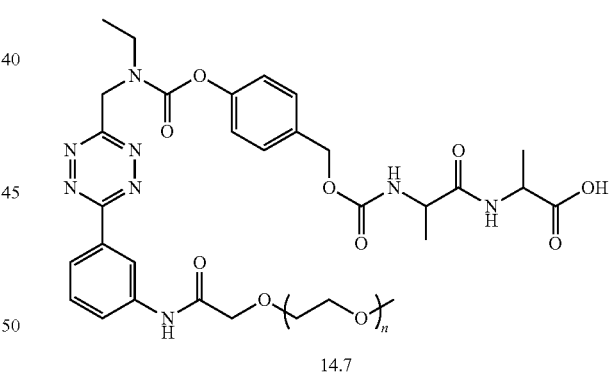

14.7

0.063 mg (0.40 μmol, 2 eq) of the dipeptide Ala-Ala was dissolved in PBS, of which the pH was adjusted to 8.3 with concentrated NaOH (aq) and subsequently, 0.3 mg (0.20 μmol, 1 eq) of 14.5 was added and solution was incubated for 2.5 hours. LC-MS analysis revealed full conversion from 14.5 to 14.7. LC-MS analysis: calc $[M+Na]^+=1585.79$, observed=1585.56, calc $[M+2H]^{2+}=782.40$, observed=782.68.

Example 15: Synthesis of Linker-Drug Maleimide-PEG24-TZ-MMAE

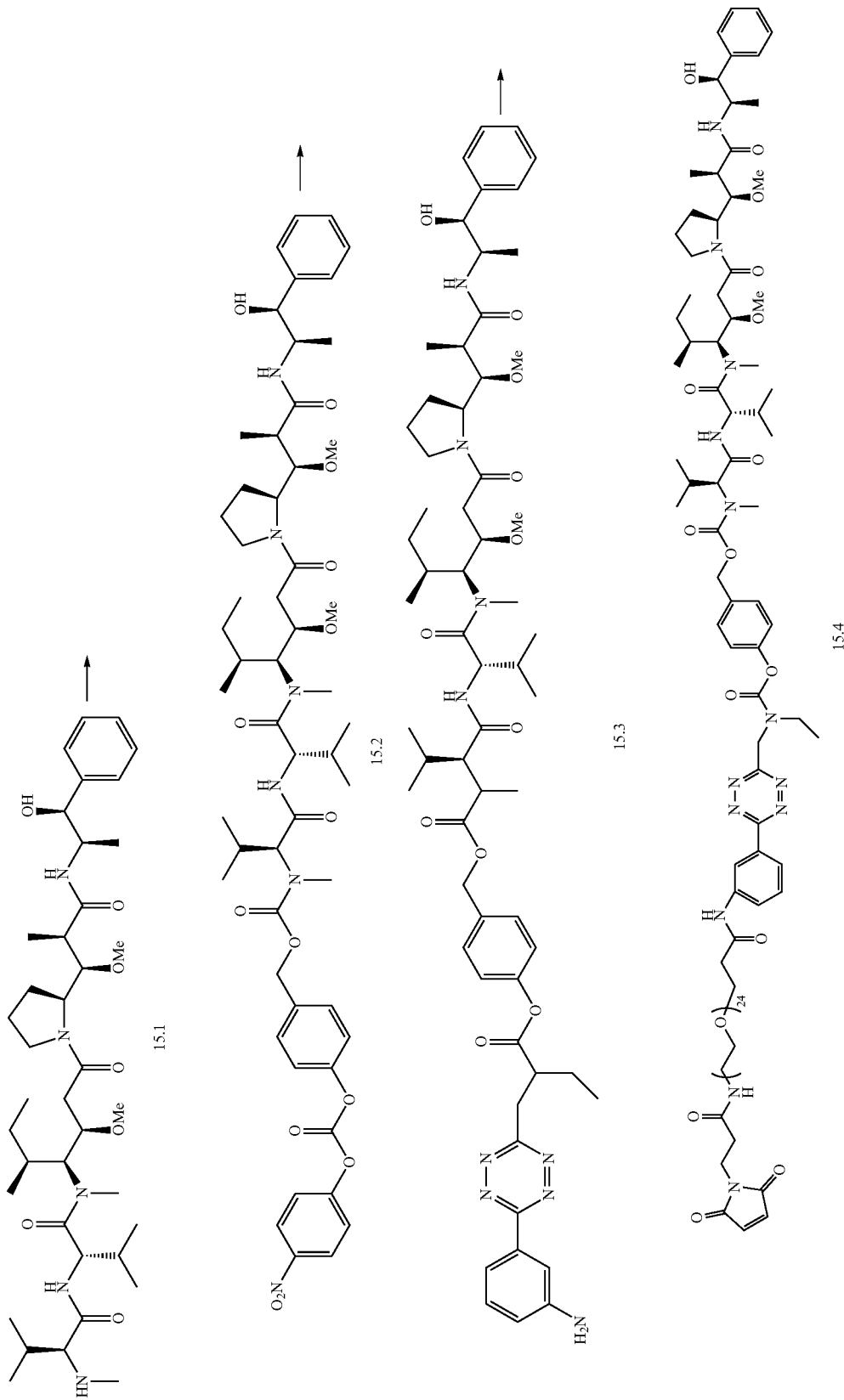

MMAE (15.1, 287 mg, 0.4 mmol) was added to the PNP-PABC-chloroformate derivative (0.4 mmol; Ref. 8; used previously for the synthesis of 3.31) in THF (5 mL), followed by DIPEA (0.21 mL, 1.2 mmol). The reaction was stirred at room temperature for 10 min and then diluted with EtOAc (100 mL) and the mixture was washed with 1N hydrochloric acid (30 mL) and water (30 mL). The organic layer was dried (over anhydrous $Na_2SO_4$, 1 h) and concentrated to dryness. The crude compound 15.2 was dissolved in anhydrous DMF (5 mL). Compound 3.30 (0.37 mmol) was added, followed by DIPEA (0.28 mL, 1.6 mmol). The mixture was stirred at room temperature for 16 h. and purified directly by reverse phase preparative HPLC to give compound 15.3 as a red solid after lyophilization (224 mg, 0.18 mmol). MS m/z: 1124.8 $(M+H)^+$ To a solution of compound 15.3 (224 mg, 0.18 mmol) in anhydrous DMF (4 mL) was added Mal-PEG24-COOH (246 mg, 0.19 mmol), followed by PyAOP (105 mg, 0.2 mmol) and DIPEA (0.1 mL, 0.57 mmol). The reaction was stirred at room temperature for 24 h and purified by reverse phase preparative HPLC to give compound 15.4 as a red gum after lyophilization (397 mg, 0.165 mmol). MS m/z: 1203.1 $(M+2H^+)/2$.

Example 16: Preparation of ADC with Maleimide-PEG24-Tz-MMAE 15.4 incubated at 4° C. overnight. The conjugation mixture was purified by gel filtration on AKTA with a Superdex column eluted with EDTA-PBS buffer. The purified fractions were combined and mixed with 5% DMSO. The solution with the pure ADC AVP0450-15.4 was then concentrated using Amicon Ultra-15 centrifugal filters (10K). ESI-TOF MS: Expected for drug-antibody ratio of 4: MW 30353 (for monomer), found: 30353.

A stock solution of ADC conjugate AVP0450-15.4 in 5% DMSO/PBS was stored at 4° C. The stability of this stock solution was determined by HPLC-QTOF-HRMS, by monitoring the peak with MW of 30353 Da. No degradation was observed within 3 months storage at 4° C.

Example 17: Preparation of Model ADCs with Bromoacetamide-PEG24-Tz-Benzylamine Derivatives 2.29 and 2.30

With reference to Example 7, this example uses benzylamine as a model compound to represent a drug comprised in an ADC. It shall be understood that benzylamine is Construct A and a such represents small molecule drugs as well as other types of Constructs A, such as protein drugs, biomolecules, Masking Moieties, polymers, resins, and the like, as defined herein. In addition, these Constructs can also be viewed as models for self-immolative linkers. The chemical moieties being released in these examples are identical or

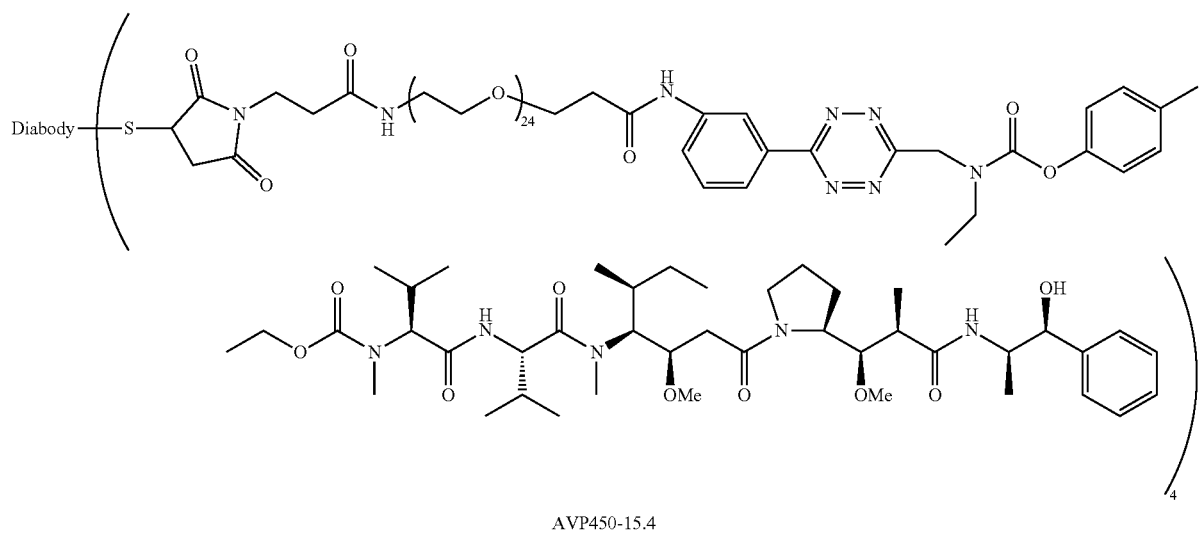

AVP450-15.4

MMAE is widely used a drug in antibody-drug conjugates, in many cases linked via the self immolative linker ($L^C$) PABC, as is the case in this example. EDTA-PBS solution (55 mM $Na_2HPO_4$, 45 mM $NaH_2PO_4H2O$, 2 mM EDTA, pH 6.8) was freshly deoxygenated by bubbling with N2 over 30 min to 1 h. Anti-TAG72 diabody AVP0450, comprising 4 cysteines for conjugation (Li et al. *Bioconjug Chem* 2011, 22, 709-716), was diluted with EDTA-PBS (eg 1 ml AVP0450 diluted with 0.6 ml buffer). To a solution of the diabody was added a freshly prepared solution of DTT (100 mM in EDTA-PBS buffer the final DTT concentration was around 6 mM). The reaction was incubated at rt 1 h and then desalted on a PD 10 column with EDTA-PBS buffer. The freshly reduced AVP0450(SH)$_4$ was treated with a solution of Mal-PEG-Tz-MMAE 15.4 (~7.5 eq/SH) in DMSO (final DMSO v/v % 9%~20%). The reaction was very similar to those moieties comprised in other Constructs $C^A$ and in self-immolative linkers $L^C$. Therefore, the stability, reactivity and release reported for the model ADC of this example, in Examples 21, 24, 25, are representative of conjugates with other Constructs $C^A$ and/or linkers $L^C$, optionally additionally comprising a Construct B.

4 mg of AVP-0450 diabody, in 1.93 mL PBS was combined with 1.16 mL EDTA-PBS buffer. The EDTA-PBS consisted of 55 mM $Na_2HPO_4$, 45 mM $NaH_2PO_4H_2O$, 2 mM EDTA in water at pH 6.8 and was degassed before use. A 100 mM dithiothreitol (DTT) was prepared in EDTA-PBS buffer and 185 µL was added to the diabody solution. After 1 hour incubation, size-exclusion-spin column (zeba) was used to remove the DTT and rebuffer the diabody to PBS of which the pH was set to 8.3 using concentrated NaOH (aq). The obtained solution was split in two, to which 20 equivalents/SH of 2.29 or 2.30 was added (78 μL, originating from a 40 mM DMSO stock solution). Both solutions were incubated for 14 hours at 4° C. Excess of linker was removed by centrifugation filtration (amicon, 30 kDa cut-off), using 5% DMSO/PBS for washing. Two light pink solutions were obtained with a volume of 1 mL and concentration of $C_{2.29}$=1.79±0.02 mg/mL and $C_{2.30}$=1.70-0.01 mg/mL. The linker to diabody ratio was determined to be $DAR_{2.29}$=2.3±0.2 and $DAR_{2.30}$=2.6±0.3, by a radiochemical titration experiment. Q-ToF analysis revealed the presence predominantly one linker per monomer of diabody: calc $[M2.29+H]^+$=27061.22, observed=27061.2296, calc $[M_{2.30}+H]^+$=27076.2001, observed=27076.2501.

Example 18: pH-Dependent TCO-Triggered Release of Ethanolamine from Tetrazine 14.6

Figure 4:
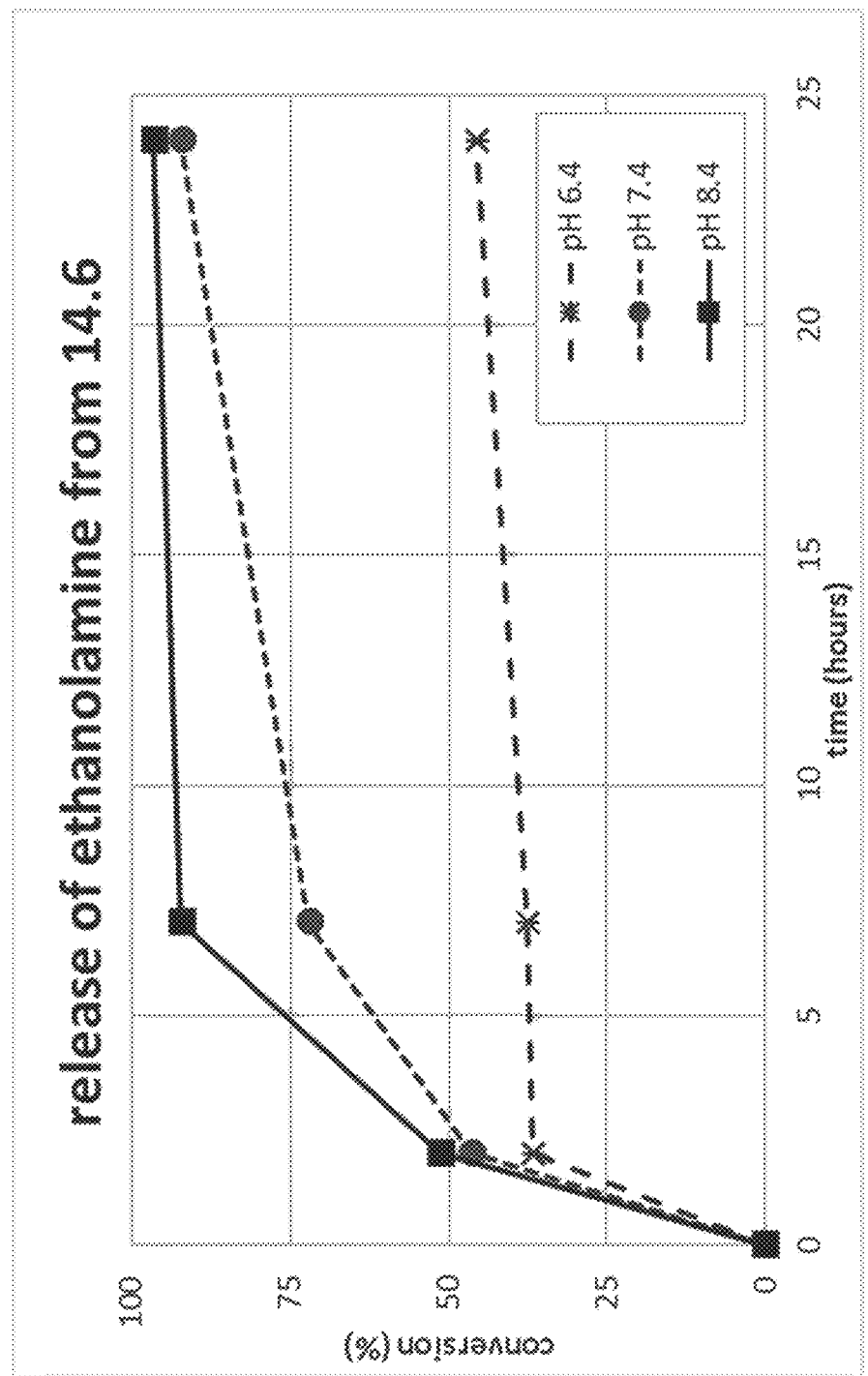
FIG. 4 depicts pH dependent release of ethanolamine from model prodrug 14.6

With reference to Example 7 and 17, ethanolamine is Construct A and as such represents a range of constructs, such as peptides, proteins, drugs, polymers, resins, as defined herein. Compound 14.6 (6.7 μL, 24.5 mg/mL stock, DMF) was combined with 10 μL of 4.8 (25 mM, DMSO) and 33.3 μL of acetonitrile and incubated for few seconds to let the solution become colourless. Next 950 μL of PBS at various pH values was added and ethanolamine release was monitored overtime by the UV trace on LC-MS, see FIG. 4.

Example 19: TCO-Triggered Release of Peptide from Dipeptide-TZ-PEG 14.7

Combined 3 μL of 14.7 (3.66 mg/mL, PBS) with 2 μL of 4.8 (80.7 mM, $H_2O$) and added 95 μL of TRIS-buffer at pH 8.3 at 37° C. Release was monitored overtime by the MS and UV trace on LC-MS, demonstrating a release of 70% within 20 hours.

Example 20: In Vitro Stability and Triggered Drug Release of AVP0450-15.4

AVP0450-15.4 (1 μg/μL in PBS/serum (1/1)) was incubated at 37° C. for 1, 5, and 24 h. After incubation, 2 parts of cold ACN was added and the turbid mixture was vortexed, stored at 4° C. for 30 min, and centrifuged for 5 min. The supernatant was diluted with 2 parts of water and measured with LC-QTOF-MS, demonstrating that the ADC was stable as MMAE release (free MMAE) was not observed.

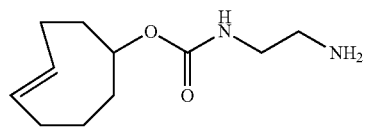

20.1

AVP0450-15.4 (1 μg/μL in PBS) was incubated with 10 molar eq of TCO-amine 20.1 (Kerafast) at 37° C. for 3 h. ESI-TOF MS showed full conversion of AVP04-15.4 into the clicked product with 4×20.1, giving mass of 30768 Da, followed by MMAE release, demonstrated by masses 29900 Da and 29011 Da (masses for the monomer).

Example 21: In Vitro Stability and Triggered Release of AVP0450-2.30 in PBS

AVP0450-2.30 (0.15 μg/μl) in PBS was incubated with and without 25 eq TCO 4.8 at 37° C. LC-QTOF-MS demonstrated that the model ADC was fully stable for 48 h. Also, the ADC fully converted to the clicked product with 4.8 (MS: 27230.3) followed by 32% release of benzylamine within 5 h.

Example 22: In Vivo Evaluation of ADC AVP0450-15.4 in a Colon Carcinoma Mouse Model (LS174T)

Figure 5:
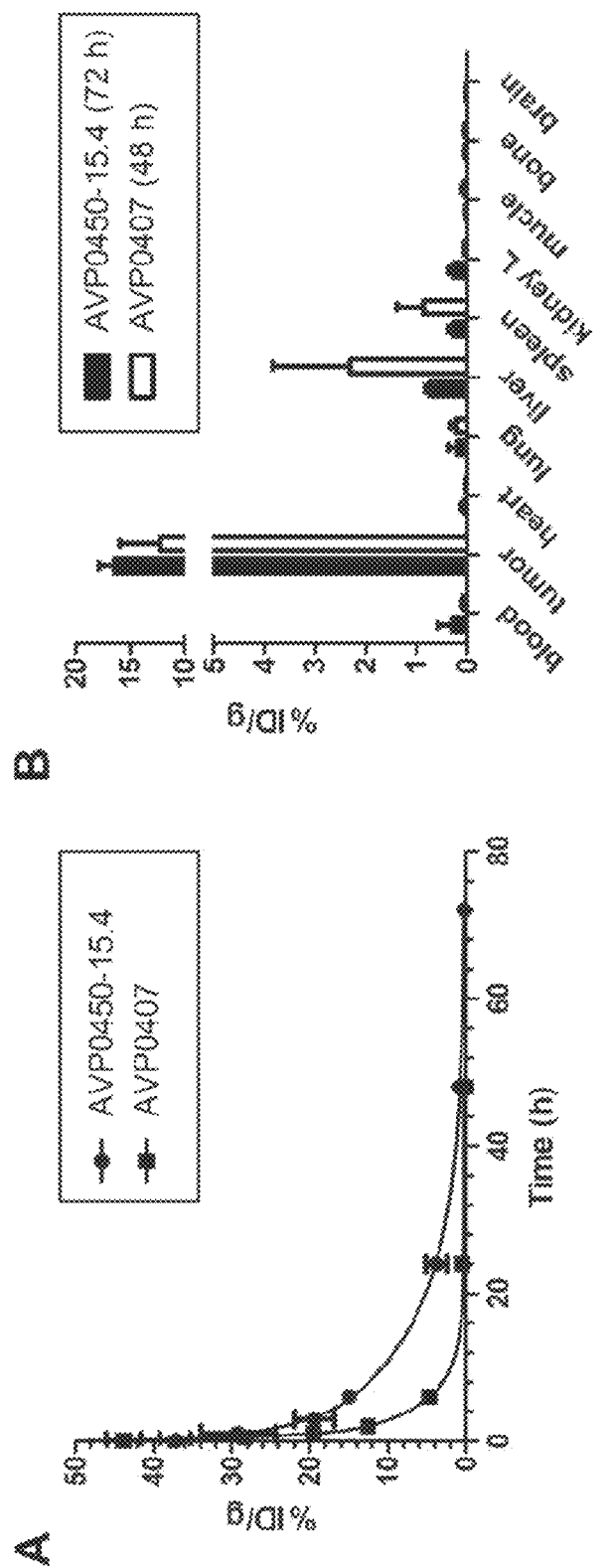
FIG. 5 depicts (A) blood clearance and (B) biodistribution of ADC $^{125}$I-AVP0450-15.4 and $^{125}$I-AVP0407 in tumor-bearing mice.

All animal experiments were performed according to the principles of laboratory animal care (NIH publication 85-23, revised 1985) and the Dutch national law "Wet op de Dierproeven" (Stb 1985, 336). The in vivo experiments were performed in nude female Balb/C mice (20-25 g body weight, Janvier). The AVP0450-15.4 ADC was labeled with iodine-125 using the Bolton-Hunter procedure, as previously described (Ref. 14). Eleven days after subcutaneous inoculation of $3×10^6$ LS174T cells (0.8±0.3 $cm^3$ tumor size), a group of 4 mice was injected $^{125}$I-ADC (2 mg/kg, 0.4 MBq/mouse in 100 μL) and the mice were serially bled (ca. 20 μL samples) via the vena saphena at selected times (1, 3, 6, 24, and 48 h post-injection). Three days post injection the mice were euthanized, blood was obtained via heart puncture, organs and tissues were dissected, blotted dry, weighed and the organ radioactivity was measured with a gamma-counter. The blood data was fitted to a two-phase decay (GraphPad Prism) and pharmacokinetic parameters and tissue distribution were compared to that of parent AVP0407 diabody without the 4 cysteines (Ref 14) (FIG. 5A).

The radioiodinated AVP0450-15.4 showed sustained circulation in blood ($T_{1/2,\alpha}$=1.03 h (42%); $T_{1/2,\beta}$=9.32 h), significantly longer than that of native diabody AVP0407 ($T_{1/2,\alpha}$=0.36 h (60%); $T_{1/2,\beta}$=2.83 h) (FIG. 5A). As a result, the ADC uptake in tumor 3 days post-injection was also slightly higher than that of native diabody (16.48±1.38 and 12.26±3.63% ID/g, respectively; p=0.081). However, despite the sustained blood circulation, the ADC cleared effectively from the system and 3 days post-injections the radioactivity in all organs and tissues (beside tumor) was less than 1% ID/g (FIG. 5B). Low levels of activity in thyroids and stomachs (1.17±0.53 and 0.03±0.01% ID, respectively) indicated no dehalogenation of $^{125}$I-AVP0450-15.4 in vivo.

Example 23: In Vivo On-Tumor Reaction Between AVP450-15.4 ADC and TCO Activators DOTA-$PEG_{11}$-TCO probe 4.4 was labeled with indium-111 in 0.2 M ammonium acetate buffer (pH 6.0) for 10 min at 60° C. followed by a DTPA-challenge to complex any unreacted radiometal. The radiolabeling yield (>95%) and radiochemical purity (>95%) of the obtained $^{111}$In-TCO probe was assessed by radio-ITLC and radio-RP-HPLC, respectively. The on-tumor reactivity between AVP0450-15.4 ADC and two different activators, sTCO-COOH (4.8) and sTCO-$PEG_{11}$-OH (4.6) in two different doses (100 and 1000 eq with respect to ADC) was evaluated with an in vivo competition assay (tumor blocking), as previously described for a CC49-TCO-Dox conjugate and tetrazine-activators (R. Rossin et al., *Bioconjug Chem* 2016, 27, 1697-1706). Briefly, mice bearing subcutaneous LS174T colon carcinoma xenografts (n=4 per group) were administered the ADC (2 mg/kg) followed after 48 h by the activator and, one hour later, by the $^{111}$In-TCO probe (1 eq with respect to ADC). The probe uptake in tumors was then compared with mice that received the ADC followed only by the $^{111}$In-TCO probe (no blocking) and with mice that received the $^{111}$In- TCO probe alone (complete blocking). All mice were euthanized 4 h after probe injection. Blood samples were obtained from heart puncture, tumors and other tissues of interest were dissected, blotted dry, weighed and counted in a gamma-counter. The table below shows the $^{111}$In uptake in tumors in the various groups of mice. A marked decrease in probe uptake in tumor was observed in all mice that received the ADC followed by an activator, down to the level of the non-specific tumor uptake of the $^{111}$In-TCO probe alone (no ADC group). This decrease demonstrates complete on-tumor reaction between the tetrazine-linker in AVP0450-15.4 and both TCO activators at both doses.

TABLE

Tumor uptake of $^{111}$In-TCO probe in mice pre-treated with AVP0458-15.4 (no activator), with AVP0450-15.4 followed by an activator, or in mice not pre-treated (no ADC). Data presented as mean percent injected dose per gram of tumor (% ID/g) with one SD (n = 4).

| activator | $^{111}$In-uptake in tumor (% ID/g) |
| --- | --- |
| no activator | 0.26 ± 0.07 |
| 100 eq 4.8 | 0.03 ± 0.13 |
| 1000 eq 4.8 | 0.10 ± 0.03 |
| 100 eq 4.6 | 0.15 ± 0.05 |
| 1000 eq 4.6 | 0.14 ± 0.52 |
| no ADC | 0.12 ± 0.04 |

Example 24: Blood Clearance and In Vivo TZ-Linker Stability of AVP0450-2.29 and AVP0450-2.30

Model ADCs AVP0450-2.29 and AVP0450-2.30 were labeled with iodine-125 using the Bolton-Hunter procedure, as previously described (Ref. 14) and were then injected in two groups of 4 mice (nude female Balb/C mice, 20-25 g body weight, Janvier) at a 5 mg/kg dose (0.4 MBq/mouse in 100 µL). The mice were serially bled (ca. 50 µL samples) via the vena saphena at 1, 3 and 6 h post-injection. The blood samples were weighed, counted in a gamma-counter (together with standards to determine the percent injected dose per gram (% ID/g)) and immediately frozen at −80° C. Twenty-four hours post-injection the mice were euthanized, one more blood sample was obtained via heart puncture, stomachs and thyroids were dissected, blotted dry and counted in a gamma-counter. The in vivo stability of the tetrazine-linkers in AVP0450-2.29 and AVP0450-2.30 was determined as previously reported (R. Rossin et al., Bioconjug Chem 2013, 24(7), 1210-1217), with minor modifications. Briefly, the blood samples obtained at 1, 3 and 6 h post-injection were diluted to 100 µL with PBS, added with a known excess of $^{111}$In-labeled 4.4 and incubated at 37° C. for 3 h. The mixtures were then passed twice over Zeba desalting spin cartridges (40 MW cut-off) and the amount of $^{125}$I and $^{111}$In in the eluate was measured in a gamma-counter using a dual-isotope protocol with cross-contamination correction. The in vivo stability of the linkers was then determined based on the $^{111}$In/$^{125}$I counts ratio.

Figure 6:
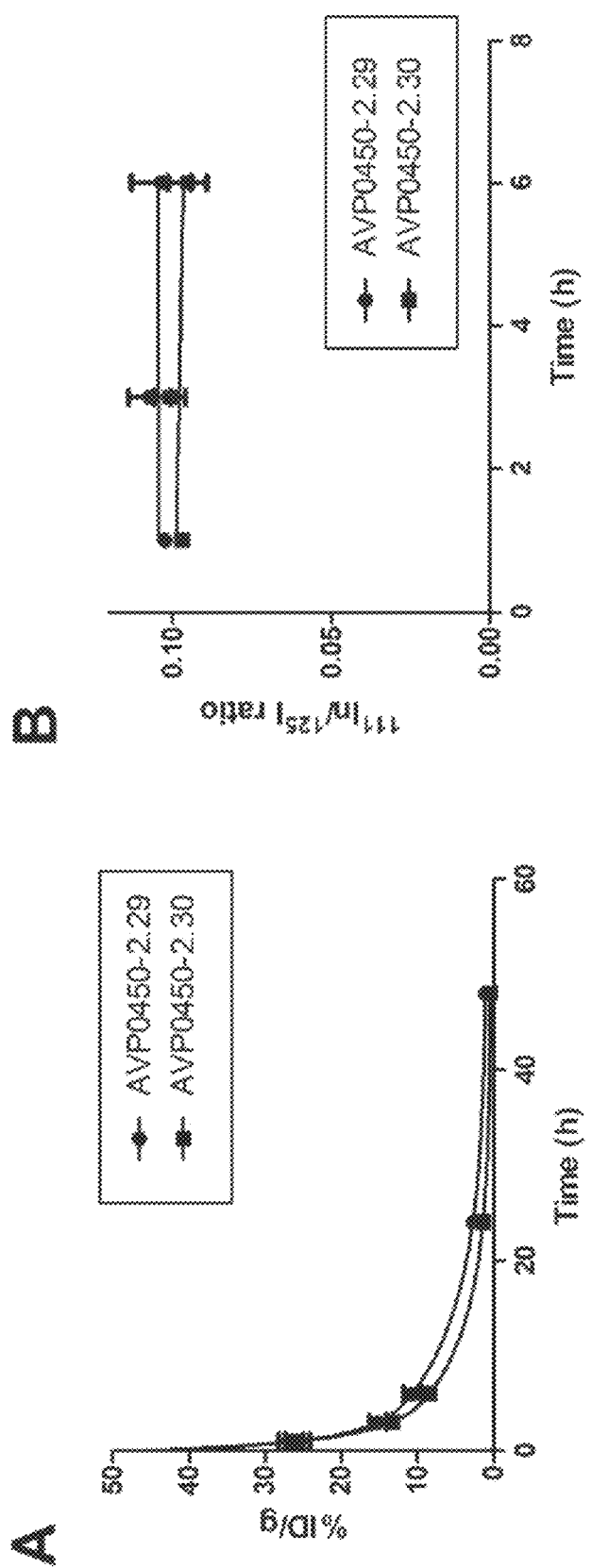
FIG. 6 depicts (A) blood clearance of model ADCs $^{125}$I-AVP0450-2.29 and $^{125}$I-AVP0450-2.30 in mice, and (B) stability of the tetrazine linkers in blood in mice up to 6 h post-injection. The data represent the mean with SD (n=4).

The radioiodinated AVP0450-2.29 and AVP0450-2.30 showed similar circulation in blood (AVP0450-2.29: $T_{1/2,\alpha}$=0.74 h (60%), $T_{1/2,\beta}$=7.56 h; AVP0450-2.30: $T_{1/2,\alpha}$=0.75 h (66%), $T_{1/2,\beta}$=6.21 h; GraphPad Prism; FIG. 6A), significantly longer than that of native diabody AVP0407 ($T_{1/2,\alpha}$=0.36 h (60%); $T_{1/2,\beta}$=2.83 h) (S. M. J. van Duijnhoven, J Nucl Med 2015, 56(9), 1422-1428). Up to 6 h post injection the tetrazine linker in both constructs showed no loss of reactivity towards $^{111}$In-labeled 4.4 (FIG. 6B), indicating prolonged in vivo stability. Low levels of activity in thyroids and stomachs (<0.5% ID) indicated no dehalogenation of $^{125}$I-AVP0450-2.29 and $^{125}$I-AVP0450-2.30 in vivo.

Example 25. Biodistribution of AVP0450-2.29 and AVP0450-2.30 in Tumor Bearing Mice and On-Tumor Reaction with Probe 4.4

Model ADCs AVP0450-2.29 and AVP0450-2.30 were radiolabeled with iodine-125 and probe 4.4 was labeled as described in Example 23. Seven days after subcutaneous inoculation of 3×10⁶ LS174T cells (0.3±0.1 cm³ tumor size), two groups of mice were injected $^{125}$I-AVP0450-2.29 and $^{125}$I-AVP0450-2.30 (2 mg/kg, 0.4 MBq/mouse in 100 µL sterile saline; n=3-4) followed, 48 h post-injection, by $^{111}$In-labeled probe 4.4 (1 eq with respect to ADC; 1.1 MBq/mouse in 100 µL sterile saline). A third group of tumor-bearing mice was injected the probe without pre-treatment. Four hours post-probe injection the mice were euthanized, blood was obtained via heart puncture, organs and tissues were dissected, blotted dry, weighed and the organ radioactivity was measured with a gamma-counter using a dual-isotope protocol with cross-contamination correction.

Figure 7:
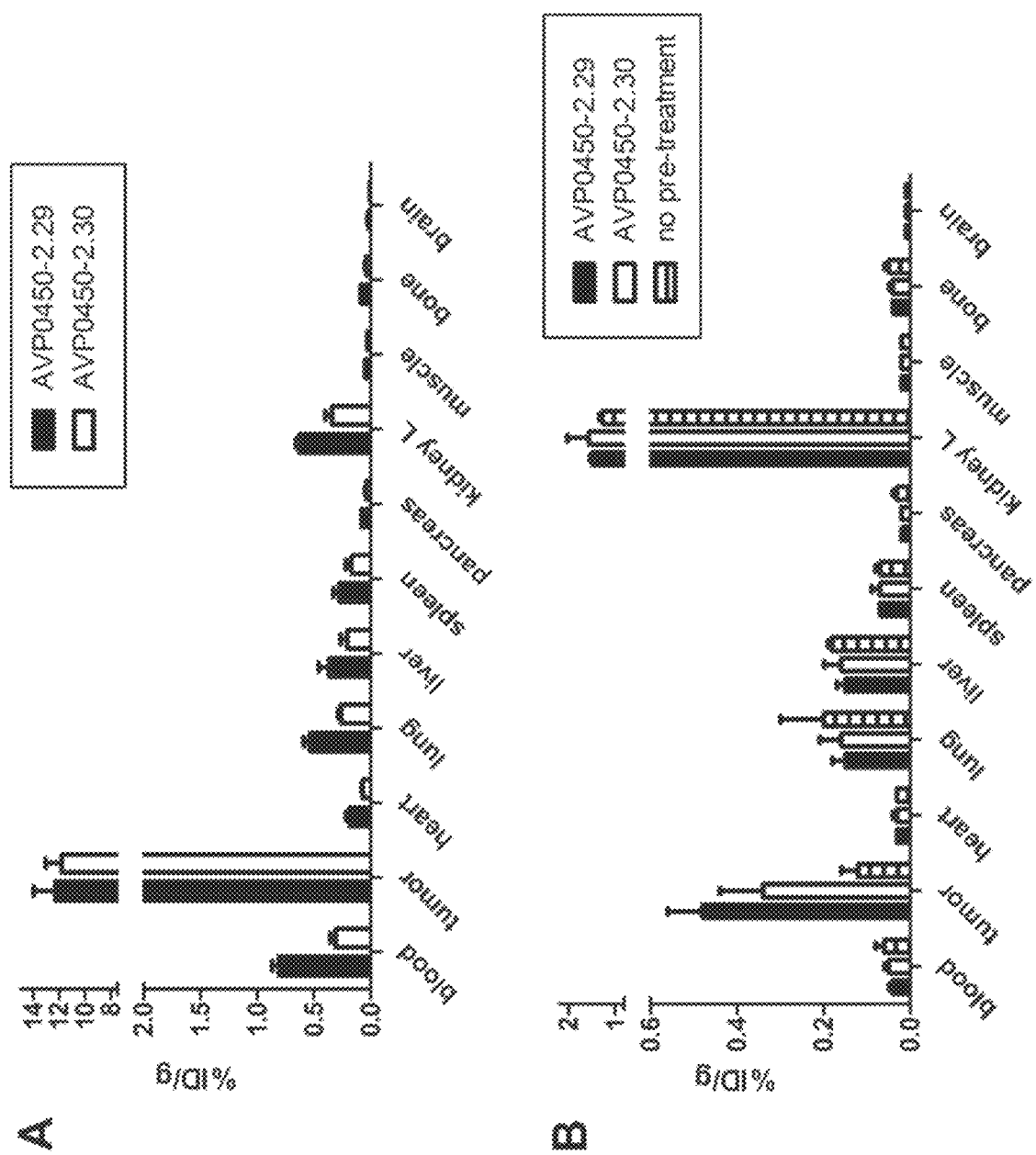
FIG. 7 depicts (A) biodistribution of ADCs $^{125}$I-AVP0450-2.29 and $^{125}$I-AVP0450-2.30 in mice bearing LS174T xenografts, and (B) biodistribution of $^{111}$In-labeled TCO probe 4.4 in LS174T-bearing mice pre-treated with $^{125}$I-AVP0450-2.29, $^{125}$I-AVP0450-2.30, and not pre-treated. The data represent the mean percent injected dose per gram (% ID/g) with SD (n=3-4).

Both ADCs showed high uptake (12.26±1.69 and 11.79±1.25% ID/g, respectively) in the TAG72 overexpressing LS174T xenografts and low nonspecific retention in non-target tissues (<1% ID/g) 52 h post injection (FIG. 7A). Furthermore, the [111]In-4.4 uptake in the tumors of the mice pre-treated with the ADCs was higher than that in tumors of non-pre-treated mice, while all non-target organs and tissues the $^{111}$In uptake was similar (FIG. 7B). This finding demonstrates efficient on-tumor reaction between the tetrazine-linker in AVP0450-2.29 and AVP0450-2.30 and the TCO.

Example 26: Trigger Activation with Other TCO Activators

The following TCO activators were prepared and shown to afford Construct release in a release assay with tetrazines 2.47 and 3.19 in serum/PBS (1/1) at 37° C. following the method of Example 11. TCOs 1 and 3 were prepared according to WO2012153254A1. TCOs 2 and 4 were prepared according to WO2012156920A1. TCO 5 was prepared according to WO2014081303A1. TCO 6 was prepared according to WO2012156919A1. TCO 7 was prepared according to Darko et al. Chem. Sci., 2014, 5, 3770-3776.

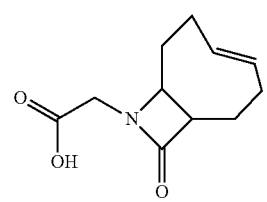

1

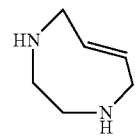

2

309
-continued

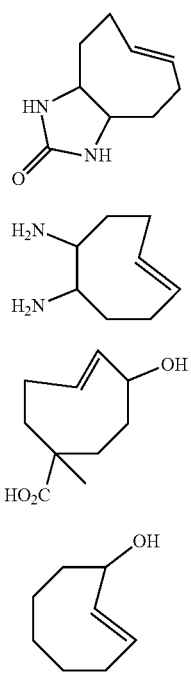

310
-continued

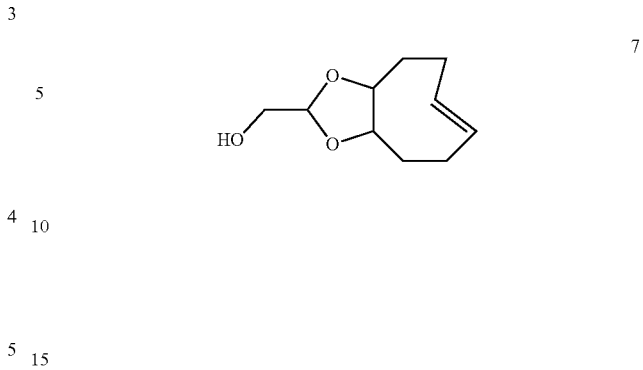

Example 27. Alternative Cascade Release Mechanism

Without wishing to be bound by theory, the inventors believe that below depicted mechanism may afford the release of Construct A, through an electron cascade that is initiated by the H-4 proton instead of an N—H proton. In this mechanism, shift of the H-4 electron pair into the ring of the 4,5-dihydropyridazine tautomer 2, leads to an electron cascade through the pyridazine affording release of amine 4 and non aromatic pyridazine 3 which may oxidize to pyridazine 7 or react with water to compounds 5, 6, and 8.

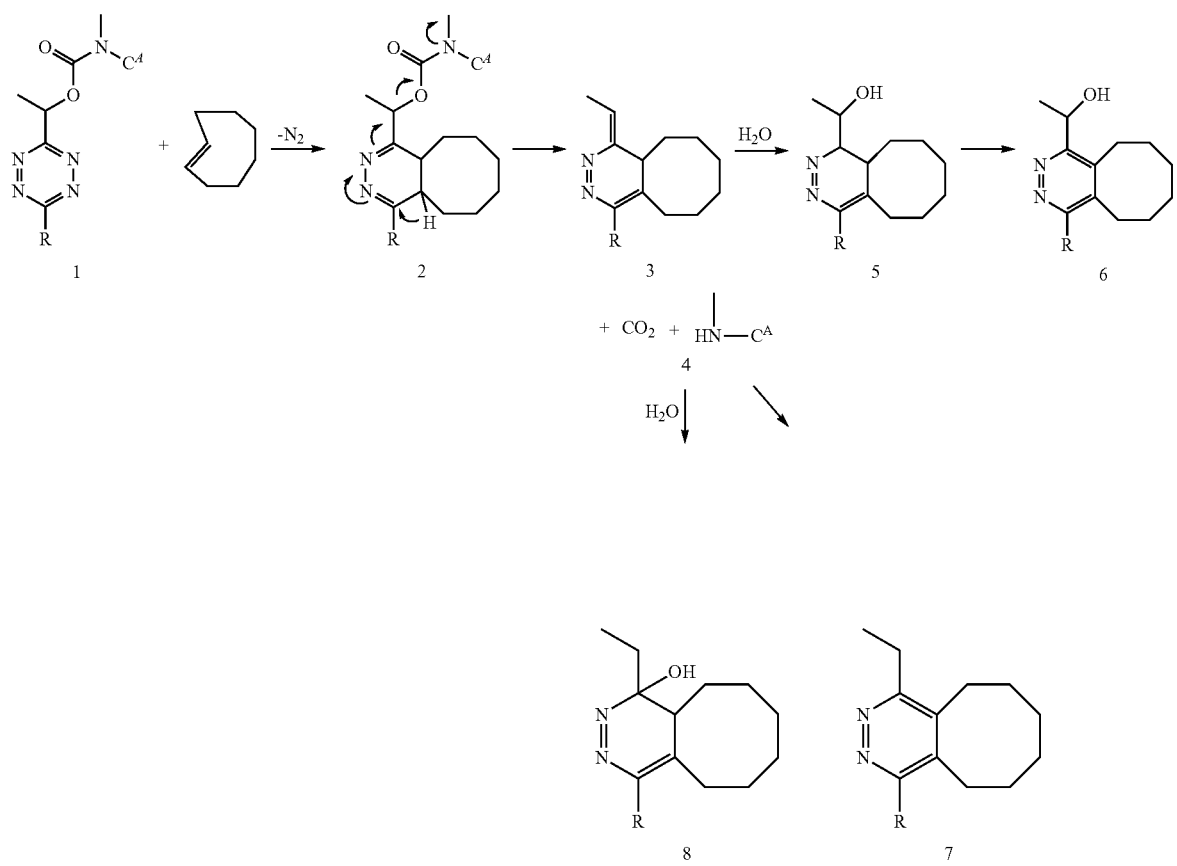

Example 28. Alternative Cyclization Release Mechanism

Without wishing to be bound by theory, the inventors believe that below depicted mechanism may afford the release of Construct A, through a cyclization that is initiated by the H-5 proton instead of an N—H proton. In this mechanism, shift of the H-5 electron pair into the ring of the 4,5-dihydropyridazine tautomer 2 and/or from the 2,5-tautomer 5, leads to an intramolecular cyclization affording free $C^A$—OH and cyclized pyridazines 3 and/or 6 which may interconvert.

Second, the dienes of the invention react fast with dienophiles, in organic solvents but also in aqueous environments such as for example in serum or blood. And third, the IEDDA adducts of the invention, formed after reaction of the diene of the invention and a dienophile, display a spontaneous release of Construct-A. These features allow for a diene that is relatively stable, a fast reaction of the diene with the dienophile and subsequent release of Construct-A. These events can also take place organic solvents, but also in aqueous environments such as in serum or blood, and thus may also take place in living organisms. Hereunder these

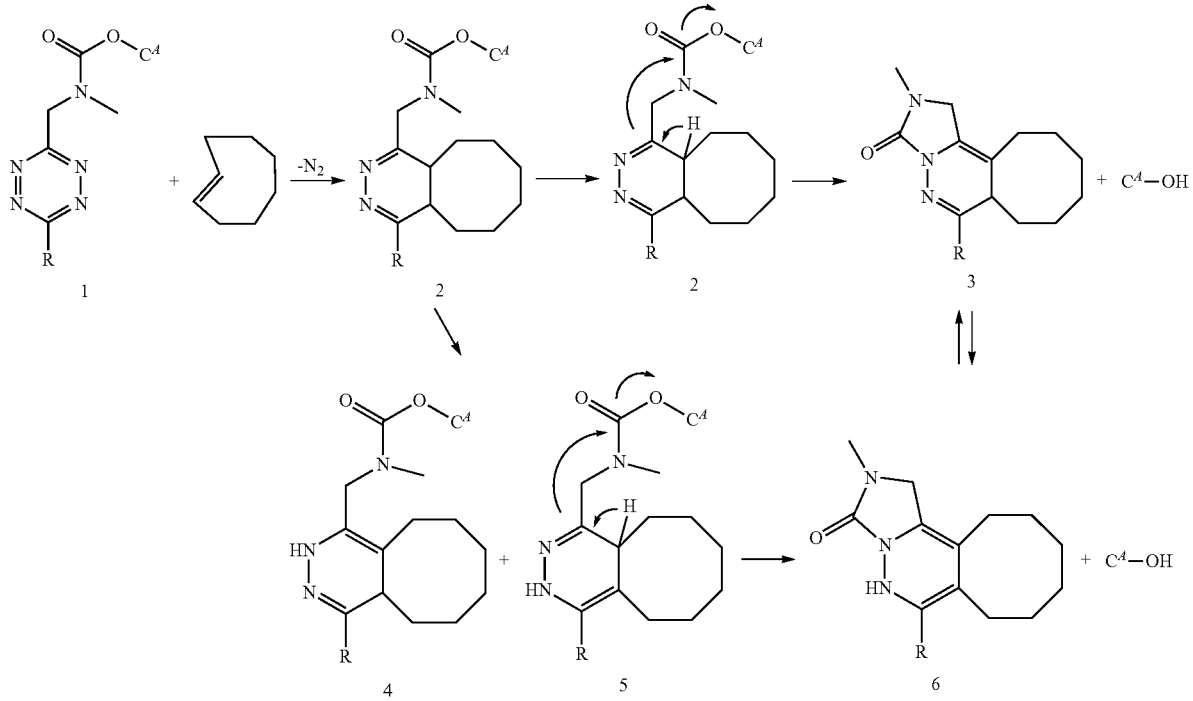

Example 29: Considerations Regarding the Diene, Dienophile and their Combination, Based on Model Compounds The performance of dienes of this invention can be compared to one another by studying model compounds in vitro in standard assays. These model compounds comprise the Trigger (i.e. diene, or tetrazine) bound to a molecule that serves as a model for Construct-A or Linker $L^C$. Typical Construct-A models include but are not limited to phenol, phenol derivatives, aniline or aniline derivatives, or small molecules comprising a primary or secondary amine, alcohol or thiol. For the avoidance of doubt, these compounds typically do not include a $S^P$, or Construct-B.

The dienes and corresponding IEDDA adducts of the invention have certain beneficial physical and chemical properties. First, the dienes of the invention are sufficiently stable in organic solvents, such as but not limited to dichloromethane, acetonitrile (MeCN), dimethylformamide (DMF), dimethylsulfoxide (DMSO). In preferred embodiments the dienes of the invention are sufficiently stable for use in aqueous environments, such as for example in cell culture medium, serum or blood. In some embodiments this stability is sufficient to allow for use in living organisms.

three specific beneficial physical and chemical properties of the dienes and IEDDA adducts of the invention are detailed.

Stability: the dienes (e.g. tetrazine) of the invention preferably have a half-life that is longer than 10 minutes at 20° C. as measured in MeCN/PBS ½ (v/v). More preferably, this half life is longer than 60 minutes, even more preferably it is longer than 10 hours, even more preferably it is longer 50 hours. Most preferably, this half life is longer than 150 hours. The dienes (e.g. tetrazine) of the invention preferably have a half-life that is longer than 10 minutes at 37° C. as measured in MeCN/PBS 5/95 (v/v). More preferably, this half life is longer than 60 minutes, even more preferably it is longer than 10 hours, even more preferably it is longer 50 hours. Most preferably, this half life is longer than 150 hours.

Reactivity: the dienes (e.g. tetrazines) of the invention preferably have a reactivity towards unsubstituted TCO as measured at 20° C. in MeCN (or in DMSO), as given by the second order rate constant $k_2$, that is higher than 0.01 L*mol$^{-1}$*s$^{-1}$. More preferably, this $k_2$ is higher than 0.1, even more preferably it is higher than about 1. Even more preferred are $k_2$ values higher than about 10, and most preferred are $k_2$ rates higher than about 100 L*mol$^{-1}$*s$^{-1}$.

Release: the IEDDA adducts, formed after reaction of dienes of the invention with unsubstituted TCO, preferably show release half-lives at 20° C. in MeCN/PBS=½ (v/v) that are shorter than 250 hours. More preferably, these IEDDA adducts show half-lives that are shorter than 125 hours. Even more preferably, this half life is shorter than 25 hours, and most preferably, this half life is shorter than 10 hours. At 37° C. in MeCN/PBS=½ (v/v) (or in MeCN/PBS mixtures with even less MeCN) the release half life is preferably shorter than 125 hours. More preferably, these IEDDA adducts show half-lives that are shorter than 50 hours. Even more preferably, this half life is shorter than 10 hours, and most preferably, this half life is shorter than 5 hours.

Alternatively, the IEDDA adducts, formed after reaction of dienes of the invention with unsubstituted TCO show a release at 20° C. in MeCN/PBS=½ (v/v), that is higher than 10% of the maximally achievable release, preferably this release is higher than 25%, more preferably this release is higher than 50%, and most preferably this release is higher than 85%. Here, the time point of measurement is shorter than 500 hours, preferably it is shorter than 100 hours, more preferably it is shorter than 24 hours, and most preferably it is shorter than 10 hours.

In some embodiments it is preferred that the half life of the release of Construct-A from the IEDDA adduct is at least the same or shorter than the half life of the stability of the corresponding diene-Construct-A conjugate in the same conditions; more preferably the half life of the release of Construct-A from the IEDDA adduct is at least 2-fold shorter than the half life of the stability of the corresponding diene-Construct-A conjugate in the same conditions; most preferably the half life of the release of Construct-A from the IEDDA adduct is at least 10-fold shorter than the half life of the stability of the corresponding diene-Construct-A conjugate in the same conditions.

In sum, the invention presents an advancement in provoked chemical cleavage. Thereby the invention provides the use of a diene as a chemically cleavable group attached to a Construct, and the use of a dienophile to provoke the release of the Construct by allowing the diene to react with a dienophile capable of undergoing an inverse electron demand Diels Alder reaction with the diene. The invention includes a kit for releasing a Construct $C^A$ bound to a Trigger $T^R$, the kit comprising a tetrazine and a dienophile, wherein the Trigger is the tetrazine. The invention also includes the use of the formation of a pyridazine by reacting a tetrazine comprising a Construct $C^A$ bound thereto and a dienophile, as a chemical tool for the release, in a chemical, biological or physiological environment, of said Construct.

REFERENCES

1. G. A. Showell, T. L. Gibbons, C. O. Kneen, A. M. MacLeod, K. Merchant, J. Saunders, S. B. Freedman, S. Patel, and R. Baker, *J. Med. Chem.* 1991, 34, 1086-1094.
2. J. R. Anderson, R. L. Edwards, and A. J. S. Whalley, *J. Chem. Soc., Perkin Trans.* 1, 1982, 1, 215-221.
3. L. Veum, M. Kuster, S. Telalovic, U. Hanefeld, and T. Maschmeyer, *Eur. J. Org. Chem.* 2002, 1516-1522.
4. Y. Feng, P. Lo-Grasso, T. Schroeter, and Y. Yin, WO 2010/036316 A1, p. 76.
5. J. Yang, M. R. Karver, W. Li, S. Sahu, and N. K. Devaraj, *Angew. Chem. Int. Ed.* 2012, 124, 5312-5315.
6. R. Rossin, S. M. J. van Duijnhoven, W. ten Hoeve, H. M. Janssen, L. H. J. Kleijn, F. J. M. Hoeben, R. M. Versteegen, and M. S. Robillard, *Bioconjugate Chem.* 2016, 27, 1697-1706.
7. J-M. Vatele, *Synlett* 2014, 25, 1275-1278.
8. M. S. Robillard, W. ten Hoeve, R. M. Versteegen, R. Rossin, and F. J. M. Hoeben, WO 2012/156920 A1, p. 74.
9. W. Mier, J. Hoffend, S. Krämer, J. Schuhmacher, W. E. Hull, M. Eisenhut, and U. Haberkorn, *Bioconjugate Chem.* 2005, 16, 237-240.
10. R. Rossin, S. M. van den Bosch, W. ten Hoeve, M. Carvelli, R. M. Versteegen, J. Lub, and M. S. Robillard, *Bioconjugate Chem.* 2013, 24, 1210-1217.
11. M. S. Robillard, J. Lub, R. Rossin, S. M. van den Bosch, and R. M. Versteegen, WO 2012/153254 A1, p. 36.
12. Devaraj et al., *Angewandte Chemie Int. Ed.* 2009, 48 (38) 7013-7016.
13. K. J. Shea, J. S. Kim, *J. Am. Chem. Soc.* 1992, 144, 3044-3051
14. S. M. J. van Duijnhoven, *J Nucl Med* 2015, 56, 1422-1428

The invention claimed is:
1. A kit for releasing a Construct $C^A$ bound to a Trigger $T^R$, the kit comprising a tetrazine; and a dienophile; wherein the Trigger is the tetrazine, said tetrazine with said Construct bound thereto satisfying formula (1);

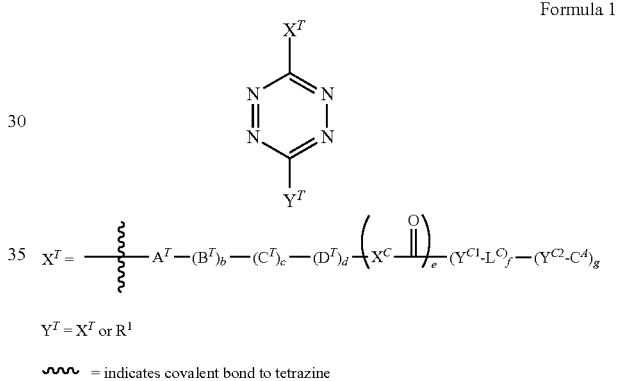

$Y^T = X^T$ or $R^1$

∿∿∿ = indicates covalent bond to tetrazine $A^T$, $B^T$, $C^T$, $D^T$ each independently are selected from the group consisting of $CR^2_2$, C=O, C=$CR^3_2$, C=$NR^6$, $NR^4$, O, S, S(=O), or S(=O)$_2$, provided that no sets consisting of adjacent atoms are present selected from the group consisting of —O—O—, —S—N($R^4$)—, —O—S—, —O—S(=O)—, —O—S(=O)$_2$—, and —S—S—, and wherein one $R^2$ or $R^4$ group from $B^T$ and one $R^2$ or $R^4$ group from $A^T$ or $C^T$ can together be a bond, so as to form a double bond, and wherein two or more groups selected from $R^2$, $R^3$, $R^4$, $R^5$, $R^6$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; $X^C$ is O, S, $CR^5_2$ or $NR^6$; $L^C$ is a self-immolative linker with f being 0 or 1; $C^A$ is Construct A; $Y^{C1}$ is O, S or a secondary amine or a tertiary amine, wherein these moieties are part of $L^C$; $Y^{C2}$ is O, S or a secondary amine or a tertiary amine, wherein these moieties are part of $C^A$; wherein f is 0 and g is 1, or wherein f is 1 and g is an integer from 1 to 9; wherein b, c, d and e are independently 0 or 1, provided that if b is 0 then c and d are 0, and if c is 0 then d is 0, and provided that if d is 1 then b and c are 1, and that if c is 1 then b is 1, and provided that if c is 0 then e is 1; wherein when f is 1 then $Y^{C1}$ is referred to as $Y^C$, and when f is 0, then $Y^{C2}$ is referred to as $Y^C$;

wherein each $R^1$, $R^2$, $R^3$ and $R^5$ is independently selected from the group consisting of H, (hetero)alkyl, aryl, heterocycle, carbocycle, F, Cl, Br, I, $CF_3$, $CF_2$—R', $NO_2$, $N_3$, OR', SR', CN, C(=O)R', S(=O)R', S(=O)$_2$R'', S(=O)$_2$OR', OS(=O)$_2$R'', $PO_3R'_2$, Si—R''$_3$, Si—O—R''$_3$, B(OR')$_2$, S(=O)$_2$NR'$_2$, NR'S(=O)$_2$R'', C(=O)NR'$_2$, C(=S)NR'$_2$, C(=NR')NR'$_2$, NR'$_2$, NR ions-NR'C(=O)R', NR'C(=S)R', NR'C(=O)NR'$_2$, NR'C(=S)NR'$_2$ wherein each R' is independently selected from the group consisting of H, (hetero)alkyl, aryl, carbocycle, heterocycle, and each R'' is independently selected from the group consisting of (hetero)alkyl, aryl, carbocycle, heterocycle, wherein all (hetero)alkyl, aryl, carbocycle, heterocycle moieties comprised in $R^1$, $R^2$, $R^3$ and $R^5$ can be unsubstituted or substituted, and wherein two R' or R'' groups can together form a ring;

each $R^4$ and $R^6$ is independently selected from the group consisting of H, (hetero)alkyl, aryl, heterocycle, carbocycle, OR', C(=O)R', C(=O)NR'$_2$, C(=S)NR'$_2$, C(=NR')NR'$_2$, NR'$_2$, such that no sets consisting of adjacent atoms are present selected from the group consisting of —N—N—, —N—O—, —N—S—, —N—Si— and —N—P—, and wherein each R' is independently selected from the group consisting of (hetero)alkyl, aryl, carbocycle, heterocycle, wherein all (hetero)alkyl, aryl, carbocycle, heterocycle moieties comprised in $R^4$ and $R^6$ can be unsubstituted or substituted, and wherein two R' groups can together form a ring;

wherein, in all of the above embodiments, one or more of $R^1$, $R^2$, $R^3$, $R^4$, $R^5$, $R^6$ and the self-immolative linker $L^C$, may be bound to an $S^P$, $C^B$, and/or $S^P$—$C^B$;

wherein $S^P$ is a spacer;

wherein $C^B$ is Construct B;

wherein Construct A and Construct B are each independently selected from the group consisting of small molecules, organic molecules, metal coordination compounds, inorganic molecules, organometallic molecules, biomolecules, drugs, polymers, resins, particles, gels, surfaces, cells, biological tissues, pathogens, solid supports, and combinations thereof; and wherein Construct B may additionally be a radioisotope.

2. A kit according to claim 1, wherein the dienophile has a structure according to formula (4)

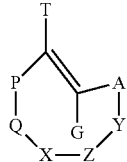

Formula 4 wherein A,Y,Z,X,Q,P each independently are selected from the group consisting of $CR^a_2$, C=$CR^a_2$, C=O, S, S=O, $SO_2$, O, $NR^b$, and $SiR^c_2$, provided that A and P are not O or S and that $NR^b$, if present in A or P, is part of an amide moiety, with at most three of A,Y,Z,X,Q and P being selected from the group consisting of C=$CR^a_2$ and C=O, wherein two or more $R^a$, $R^b$, and/or $R^c$ moieties together may form a ring or rings, and with the proviso that no sets consisting of adjacent atoms are present selected from the group consisting of O—O, O—$NR^b$, S—$NR^b$, O—S, O—S(O), O—S(O)$_2$, and S—S, and such that Si is only adjacent to $CR^a_2$ or O;

T, G each independently denotes H, or a substituent selected from the group consisting of alkyl, OR', NR'R', F, Cl, Br, or I, with R' being alkyl or aryl;

each $R^a$ as above-indicated can independently be selected from the group consisting of H, (hetero)alkyl, aryl, heterocycle, carbocycle, F, Cl, Br, I, $CF_3$, $CF_2$—R', $NO_2$, OR', SR', CN, C(=O)R', S(=O)R', S(=O)$_2$R'', S(=O)$_2$OR', OS(=O)$_2$R'', $PO_3R'_2$, Si—R''$_3$, Si—O—R''$_3$, B(OR')$_2$, S(=O)$_2$NR'$_2$, NR'S(=O)$_2$R'', C(=O)NR'$_2$, C(=S)NR'$_2$, C(=NR')NR'$_2$, NR'$_2$, NR'C(=O)R', NR'C(=S)R', NR'C(=O)OR', NR'C(=S)OR', NR'C(=O)SR', NR'C(=S)SR', NR'C(=O)NR'$_2$, NR'C(=S)NR'$_2$, wherein each R' is independently selected from the group consisting of H, (hetero)alkyl, aryl, carbocycle, heterocycle, and each R'' is independently selected from the group consisting of (hetero)alkyl, aryl, carbocycle, heterocycle, wherein all (hetero)alkyl, aryl, carbocycle, heterocycle moieties comprised in $R^a$ can be unsubstituted or substituted, and wherein two R' or R'' groups can together form a ring;

each $R^b$ is independently selected from the group consisting of H, (hetero)alkyl, aryl, heterocycle, carbocycle, OR', C(=O)R', C(=O)O—R', C(=O)S—R', C(=S)O—R', C(=S)S—R', C(=O)NR'$_2$, C(=S)NR'$_2$, C(=NR')NR'$_2$, NR'$_2$ such that no sets consisting of adjacent atoms are present selected from the group consisting of —N—N—, —N—O—, —N—S—, —N—Si— and —N—P—, and wherein each R' is independently selected from the group consisting of H, (hetero)alkyl, aryl, carbocycle, heterocycle, wherein all (hetero)alkyl, aryl, carbocycle, heterocycle moieties comprised in $R^b$ can be unsubstituted or substituted, and wherein two R' groups can together form a ring;

each $R^c$ as above indicated is independently selected from the group consisting of H, alkyl, aryl, O-alkyl, O-aryl, OH;

wherein one or more $R^{a,b,c}$ moieties may be bound to one or more of the group consisting of Targeting agent $T^T$, Spacer $S^P$, chelator, albumin-binding moiety, polymersome, micelle, particle, resin, gel, surface, bead, membrane translocation moiety, radioisotope, and fluorescent moiety; and wherein said Targeting agent $T^T$, Spacer $S^P$, chelator, albumin-binding moiety, polymersome, micelle, particle, resin, gel, surface, bead, membrane translocation moiety, radioisotope, and fluorescent moiety, may be bound to more than one dienophile moiety.

3. A kit according to claim 1, wherein $Y^T$ is $R^1$, $A^T$ is $CHR^2$, $B^T$ is $CR^2_2$, $X^C$ is $NR^6$, $Y^C$ is O or S attached to an aromatic carbon atom of $L^C$ or $C^A$, satisfying at least one of the following requirements:

a) c is 0, b and e is 1, $R^6$ is H;
b) c is 0, b and e is 1, $R^6$ is (hetero)alkyl, aryl, heterocycle, or carbocycle;
c) b is 0, e is 1, $R^6$ is H, (hetero)alkyl, aryl, heterocycle, or carbocycle; and
d) b is 0, e is 1, $R^6$ is $C_1$-$C_3$ alkyl.

4. A kit according to claim 1, wherein $Y^T$ is $R^1$, $X^C$ is O, $Y^C$ is secondary or tertiary amine, b is 0, e is 1, satisfying at least one of the following requirements:

a) $Y^C$ is a secondary amine, $A^T$ is $CHR^2$ with $R^2$ being H, (hetero)alkyl, aryl, heterocycle, or carbocycle;

b) $Y^C$ is a secondary amine, $A^T$ is $CHR^2$ with $R^2$ being $C_1$-$C_3$ alkyl;
c) $Y^C$ is a tertiary amine, $A^T$ is $CHR^2$ with $R^2$ being H, (hetero)alkyl, aryl, heterocycle, or carbocycle; and
d) $Y^C$ is a tertiary amine, $A^T$ is $CHR^2$ with $R^2$ being $C_1$-$C_3$ alkyl.

5. A kit according to claim 1, wherein the $X^T$ satisfies one of the following structures, wherein $Y^C$ is O or S, wherein the O or S may be attached to an aromatic carbon atom of $L^C$ or $C^A$

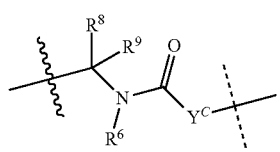

X$^T$-1

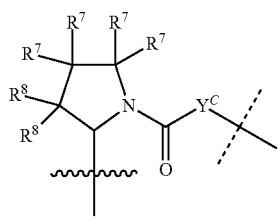

X$^T$-2

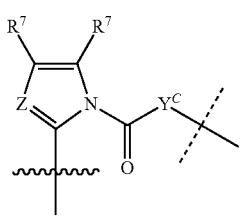

X$^T$-3

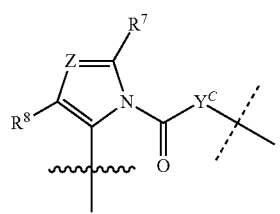

X$^T$-4

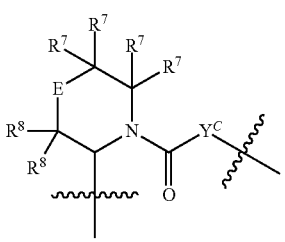

X$^T$-5

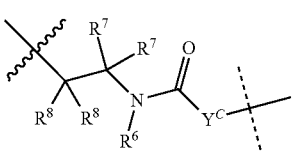

X$^T$-6

-continued

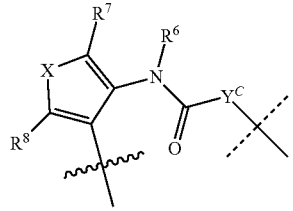

X$^T$-7

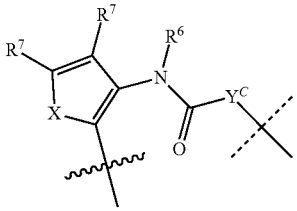

X$^T$-8

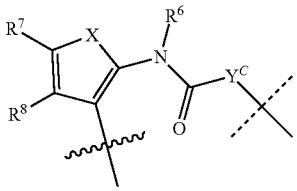

X$^T$-9

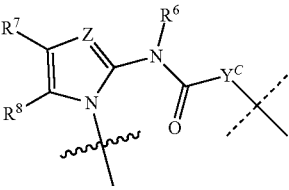

X$^T$-10

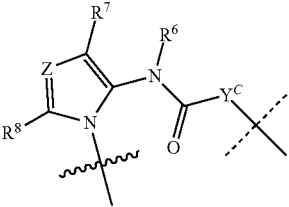

X$^T$-11

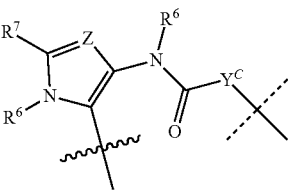

X$^T$-12

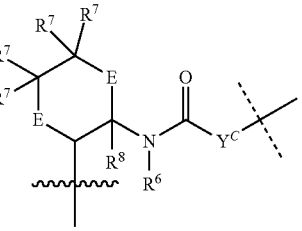

X$^T$-13

-continued

X^T-14
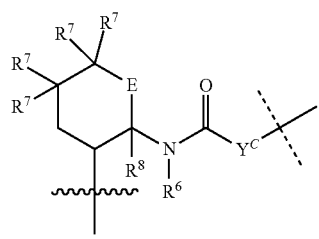

X^T-15
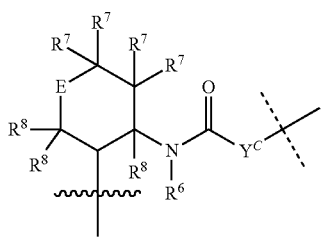

X^T-16
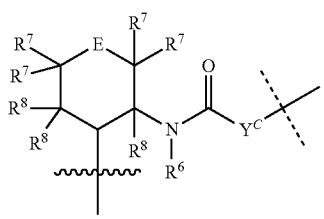

X^T-17
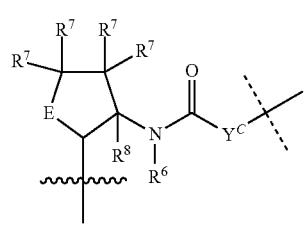

X^T-18
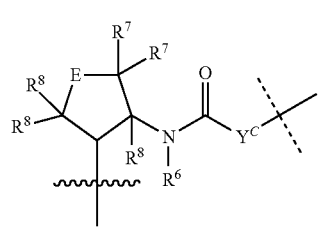

X^T-19
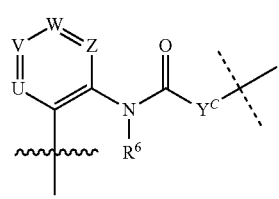

-continued

X^T-20
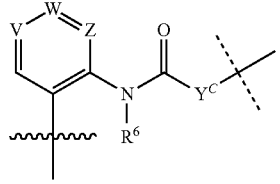

∿∿ indicates covalent bond to tetrazine
---- indicates covalent bond to (remainder of) $L^C$ or $C^A$ U, V, W, Z = N or $CR^7$
X = O or S or $NR^6$
E = O, S, $NR^6$, $CR^7_2$ wherein U, V, W, Z are each independently chosen from the group consisting of N and $CR^7$; X is independently chosen from the group consisting of O, S and $NR^6$; E is independently chosen from the group consisting of O, S, $NR^6$ and $CR^7_2$; with $R^7$, $R^8$ and $R^9$ each independently being selected from the group defined in claim 1 for $R^1$, $R^2$, $R^3$, $R^5$, wherein two $R^6$, $R^7$, $R^8$ and/or $R^9$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; and wherein one or more of $R^6$, $R^7$, $R^8$, $R^9$, and $L^C$ may be bound to a Spacer $S^P$, $C^B$, and/or $S^P$—$C^B$.

6. A kit according to claim 1, wherein the $X^T$ satisfies one of the following structures, wherein $Y^C$ is secondary or tertiary amine X^T-60
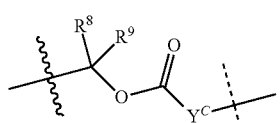

X^T-35
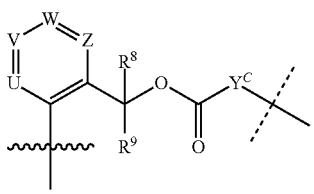

X^T-61
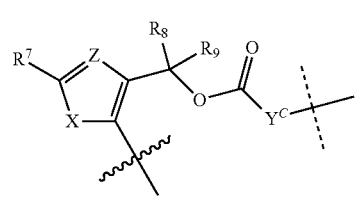

X^T-33
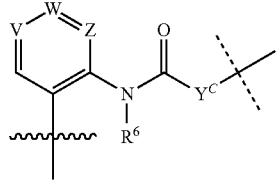

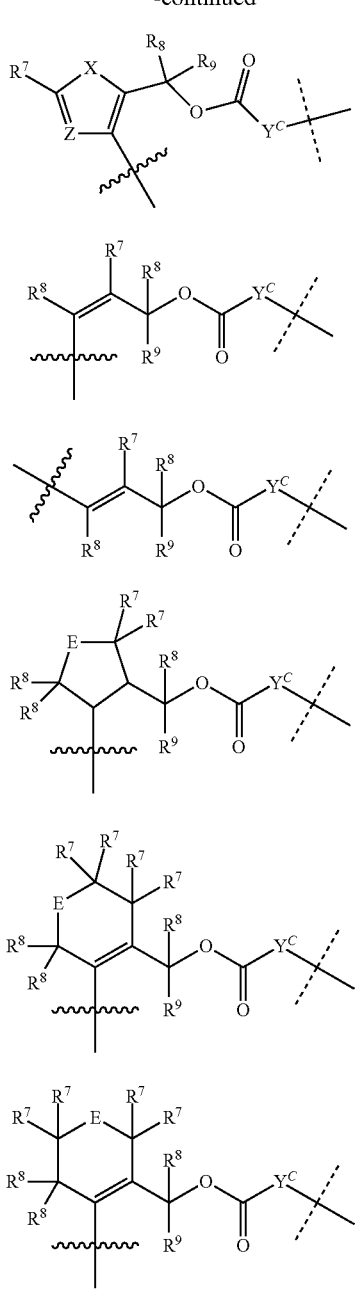

indicates covalent bond to tetrazine
----- indicates covalent bond to (remainder of) $L^C$ or $C^A$ U, V, W, Z = N or $CR^7$
X = O or S or $NR^6$
E = O, S, $NR^6$, $CR^7_2$ wherein U, V, W, Z are each independently chosen from the group consisting of N and $CR^7$; X is independently chosen from the group consisting of O, S and $NR^6$; E is independently chosen from the group consisting of O, S, $NR^6$ and $CR^7_2$; with $R^7$, $R^8$ and $R^9$ each independently being selected from the group defined in claim 1 for $R^1$, $R^2$, $R^3$, $R^5$, wherein two $R^6$, $R^7$, $R^8$ and/or $R^9$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; and wherein one or more of $R^6$, $R^7$, $R^8$, $R^9$, and $L^C$ may be bound to a Spacer $S^P$, $C^B$, and/or $S^P$—$C^B$.

7. A kit according to claim 1, wherein $R^1$ is (hetero)alkyl, aryl, heterocycle or carbocycle.

8. A kit according to claim 2, wherein the dienophile according to Formula (4) satisfies at least one of the following
   a) T and G are H, and all the ring members of the dienophile are carbon atoms;
   b) T and G are H, and A,Y,Z,X,Q and P are $CR^a_2$, such that at most three $R^a$ moieties are not hydrogen;
   c) T and G are H, and A,Y,Z,X,Q and P are $CR^a_2$, such that at most one $R^a$ moiety is not hydrogen;
   d) T and G are H, and one or two of Y,Z,X,Q each independently are selected from the group consisting of S, O, $NR^b$, such that no sets consisting of adjacent atoms are present selected from the group consisting of O—O, O—$NR^b$, S—$NR^b$, O—S, and S—S; the remaining groups (A,Y,Z,X,Q, P) being $CR^a_2$, such that at most three $R^a$ moieties are not hydrogen;
   e) T and G are H, and one of the bonds PQ, QX, XZ, ZY, YA is an amide, the remaining groups (A,Y,Z,X,Q, P) being $CR^a_2$, such that at most three $R^a$ moieties are not hydrogen;
   f) T and G are H, and one of the bonds PQ, QX, XZ, ZY, YA is part of a fused ring, such that two exocyclic bonds are fixed in the same plane; the remaining groups (A,Y,Z,X,Q, P) being $CR^a_2$;
   g) T and G are H, and one of the bonds PQ, QX, XZ, ZY, YA is part of a fused aliphatic 3-membered ring, 4-membered ring, or 5-membered ring, such that two exocyclic bonds are fixed in the same plane; the remaining groups (A,Y,Z,X,Q, P) being $CR^a_2$.

9. A kit according to claim 8, wherein A and P are $CH_2$.

10. A kit according to according to claim 1, wherein one $C^A$ is bound to more than one $T^R$ or $L^C$-$T^R$ moieties, wherein the $T^R$ and/or $L^C$ moieties may be bound to one or more $S^P$, $C^B$ and/or $S^P$—$C^B$ moieties, wherein $C^A$ is $D^D$, $C^B$ is $T^T$, $M^M$ or a Binding Partner for $M^M$; wherein $D^D$ is a drug, $T^T$ is a targeting agent, and $M^M$ is a masking moiety.

11. A kit according to claim 1, wherein the release occurs in a chemical or biological environment in vitro.

12. A kit according to claim 11, wherein either or both of the Constructs $C^A$ and $C^B$ is a biomolecule.

13. A kit according to claim 11, wherein the Construct $C^A$ or $C^B$ is a polymer, resin, particle, solid support, gel, or surface.

14. A kit according to claim 11, wherein $C^A$ is or is comprised in a binding to a polymer, resin, particle, solid support, gel, surface, and wherein $C^B$ comprises a radioisotope.

15. A kit according to claim 11, wherein the Construct A comprises one or more chemical reactants, the reactivity of which is masked by being linked to the diene.

16. A tetrazine according to formula (1):

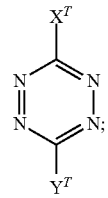

Formula (1)

323

-continued

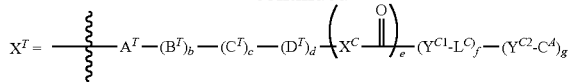

$Y^T = X^T$ or $R^1$

∿∿ = indicates covalent bond to tetrazine wherein:
$A^T$, $B^T$ $C^T$, $D^T$ each independently are selected from the group consisting of $CR^2{}_2$, C=O, C=$CR^3{}_2$, C=$NR^6$, $NR^4$, O, S, S(=O), or S(=O)$_2$, provided that no sets consisting of adjacent atoms are present selected from the group consisting of —O—O—, —S—N($R^4$)—, —O—S—, —O—S(=O)—, —O—S(=O)$_2$—, and —S—S—, and wherein one $R^2$ or $R^4$ group from $B^T$ and one $R^2$ or $R^4$ group from $A^T$ or $C^T$ can together be a bond, so as to form a double bond, and wherein two or more groups selected from $R^2$, $R^3$, $R^4$, $R^5$, $R^6$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; $X^C$ is O, S, $CR^5{}_2$ or $NR^6$; $L^C$ is a self-immolative linker with f being 0 or 1; $C^A$ is Construct A; $Y^{C1}$ is O, S or a secondary amine or a tertiary amine, wherein these moieties are part of $L^C$; $Y^{C2}$ is O, S or a secondary amine or a tertiary amine, wherein these moieties are part of $C^A$; wherein f is 0 and g is 1, or wherein f is 1 and g is an integer from 1 to 9; wherein b, c, d and e are independently 0 or 1, provided that if b is 0 then c and d are 0, and if c is 0 then d is 0, and provided that if d is 1 then b and c are 1, and that if c is 1 then b is 1, and provided that if c is 0 then e is 1; wherein when f is 1 then $Y^{C1}$ is referred to as $Y^C$, and when f is 0, then $Y^{C2}$ is referred to as $Y^C$;
wherein each $R^1$, $R^2$, $R^3$ and $R^5$ is independently selected from the group consisting of H, (hetero)alkyl, aryl, heterocycle, carbocycle, F, Cl, Br, I, $CF_3$, $CF_2$—R', $NO_2$, N3, OR', SR', CN, C(=O)R', S(=O)R', S(=O)$_2$R", S(=O)$_2$OR', OS(=O)$_2$R", $PO_3$R'$_2$, Si—R"$_3$, Si—O—R"$_3$, B(OR')$_2$, S(=O)$_2$NR'$_2$, NR'S(=O)$_2$R", C(=O)NR'$_2$, C(=S)NR'$_2$, C(=NR')NR'$_2$, NR'$_2$, NR'C(=O)R', NR'C(=S)R', NR'C(=O)NR'$_2$, NR'C(=S)NR'$_2$ wherein each R' is independently selected from the group consisting of H, (hetero)alkyl, aryl, carbocycle, heterocycle, and each R" is independently selected from the group consisting of (hetero)alkyl, aryl, carbocycle, heterocycle, wherein all (hetero)alkyl, aryl, carbocycle, heterocycle moieties comprised in $R^1$, $R^2$, $R^3$ and $R^5$ can be unsubstituted or substituted, and wherein two R' or R" groups can together form a ring;
each $R^4$ and $R^6$ is independently selected from the group consisting of H, (hetero)alkyl, aryl, heterocycle, carbocycle, OR', C(=O)R', C(=O)NR'$_2$, C(=S)NR'$_2$, C(=NR')NR'$_2$, NR'$_2$, such that no sets consisting of adjacent atoms are present selected from the group consisting of —N—N—, —N—O—, —N—S—, —N—Si— and —N—P—, and wherein each R' is independently selected from the group consisting of (hetero)alkyl, aryl, carbocycle, heterocycle, wherein all (hetero)alkyl, aryl, carbocycle, heterocycle moieties comprised in $R^4$ and $R^6$ can be unsubstituted or substituted, and wherein two R' groups can together form a ring;

324 wherein in all of the above embodiments, one or more of $R^1$, $R^2$, $R^3$, $R^4$, $R^5$, $R^6$ and the self-immolative linker $L^C$, may be bound to an $S^P$, $C^B$, and/or $S^P$—$C^B$;
wherein $S^P$ is a spacer;
wherein $C^B$ is Construct B;
wherein Construct B is selected from the group consisting of small molecules, organic molecules, metal coordination compounds, inorganic molecules, organometallic molecules, biomolecules, drugs, polymers, resins, particles, gels, surfaces, cells, biological tissues, pathogens, and combinations thereof,
wherein $C^A$ is selected from the group consisting of Drug $D^D$, Masking Moiety MM, biomolecule, polymer, resin, particle, solid support, gel, surface, Conjugation Moiety $M^C$.

17. A method for the formation of a pyridazine, comprising reacting a tetrazine comprising a Construct $C^A$ bound thereto and a dienophile; said tetrazine with said Construct bound thereto satisfying formula (1):

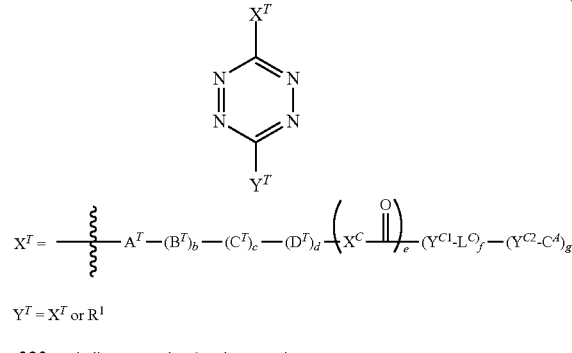

Formula (1)

$Y^T = X^T$ or $R^1$

∿∿ = indicates covalent bond to tetrazine wherein:
$A^T$, $B^T$ $C^T$, $D^T$ each independently are selected from the group consisting of $CR^2{}_2$, C=O, C=$CR^3{}_2$, C=$NR^6$, $NR^4$, O, S, S(=O), or S(=O)$_2$, provided that no sets consisting of adjacent atoms are present selected from the group consisting of —O—O—, —S—N($R^4$)—, —O—S—, —O—S(=O)—, —O—S(=O)$_2$—, and —S—S—, and wherein one $R^2$ or $R^4$ group from $B^T$ and one $R^2$ or $R^4$ group from $A^T$ or $C^T$ can together be a bond, so as to form a double bond, and wherein two or more groups selected from $R^2$, $R^3$, $R^4$, $R^5$, $R^6$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; $X^C$ is O, S, $CR^5{}_2$ or $NR^6$; $L^C$ is a self-immolative linker with f being 0 or 1; $C^A$ is Construct A; $Y^{C1}$ is O, S or a secondary amine or a tertiary amine, wherein these moieties are part of $L^C$; $Y^{C2}$ is O, S or a secondary amine or a tertiary amine, wherein these moieties are part of $C^A$; wherein f is 0 and g is 1, or wherein f is 1 and g is an integer from 1 to 9; wherein b, c, d and e are independently 0 or 1, provided that if b is 0 then c and d are 0, and if c is 0 then d is 0, and provided that if d is 1 then b and c are 1, and that if c is 1 then b is 1, and provided that if c is 0 then e is 1; wherein when f is 1 then $Y^{C1}$ is referred to as $Y^C$, and when f is 0, then $Y^{C2}$ is referred to as $Y^C$;
wherein each $R^1$, $R^2$, $R^3$ and $R^5$ is independently selected from the group consisting of H, (hetero)alkyl, aryl, heterocycle, carbocycle, F, Cl, Br, I, $CF_3$, $CF_2$—R', $NO_2$, $N_3$, OR', SR', CN, C(=O)R', S(=O)R', $S(=O)_2R''$, $S(=O)_2OR'$, $OS(=O)_2R''$, $PO_3R'_2$, Si—$R''_3$, Si—O—$R''_3$, $B(OR')_2$, $S(=O)_2NR'_2$, NR'S$(=O)_2R''$, $C(=O)NR'_2$, $C(=S)NR'_2$, $C(=NR')NR'_2$, $NR'_2$, NR'C(=O)R', NR'C(=S)R', $NR'C(=O)NR'_2$, $NR'C(=S)NR'_2$ wherein each R' is independently selected from the group consisting of H, (hetero)alkyl, aryl, carbocycle, heterocycle, and each R" is independently selected from the group consisting of (hetero)alkyl, aryl, carbocycle, heterocycle, wherein all (hetero)alkyl, aryl, carbocycle, heterocycle moieties comprised in $R^1$, $R^2$, $R^3$ and $R^5$ can be unsubstituted or substituted, and wherein two R' or R" groups can together form a ring;

each $R^4$ and $R^6$ is independently selected from the group consisting of H, (hetero)alkyl, aryl, heterocycle, carbocycle, OR', C(=O)R', $C(=O)NR'_2$, $C(=S)NR'_2$, $C(=NR')NR'_2$, $NR'_2$, such that no sets consisting of adjacent atoms are present selected from the group consisting of —N—N—, —N—O—, —N—S—, —N—Si— and —N—P—, and wherein each R' is independently selected from the group consisting of (hetero)alkyl, aryl, carbocycle, heterocycle, wherein all (hetero)alkyl, aryl, carbocycle, heterocycle moieties comprised in $R^4$ and $R^6$ can be unsubstituted or substituted, and wherein two R' groups can together form a ring;

wherein in all of the above embodiments, one or more of $R^1$, $R^2$, $R^3$, $R^4$, $R^5$, $R^6$ and the self-immolative linker $L^C$, may be bound to an $S^P$, $C^B$, and/or $S^P$—$C^B$;

wherein $S^P$ is a spacer;

wherein $C^B$ is Construct B;

wherein Construct A and Construct B are each independently selected from the group consisting of small molecules, organic molecules, metal coordination compounds, inorganic molecules, organometallic molecules, biomolecules, drugs, polymers, resins, particles, gels, surfaces, cells, biological tissues, pathogens, and combinations thereof.

18. A method of modifying a Drug $D^D$ compound into a Prodrug; wherein the Prodrug can be triggered by an abiotic, bio-orthogonal reaction, the method comprising the steps of chemically linking the Drug to a tetrazine moiety satisfying Formula (1);

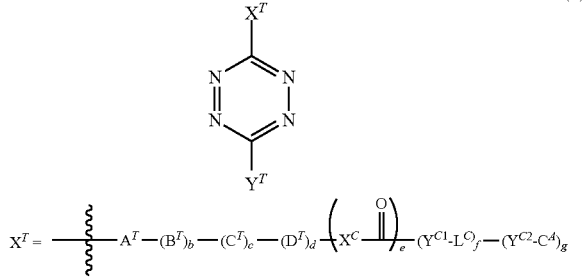

wherein:

$A^T$, $B^T$ $C^T$, $D^T$ each independently are selected from the group consisting of $CR^2_2$, C=O, $C=CR^3_2$, $C=NR^6$, $NR^4$, O, S, S(=O), or $S(=O)_2$, provided that no sets consisting of adjacent atoms are present selected from the group consisting of —O—O—, —S—N($R^4$)—, —O—S—, —O—S(=O)—, —O—S(=O)$_2$—, and —S—S—, and wherein one $R^2$ or $R^4$ group from $B^T$ and one $R^2$ or $R^4$ group from $A^T$ or $C^T$ can together be a bond, so as to form a double bond, and wherein two or more groups selected from $R^2$, $R^3$, $R^4$, $R^5$, $R^6$ can together form a $C_6$-$C_{12}$ aryl, or a 3- to 8-membered heterocycle, a 3- to 8-membered annelated hetero(alkyl), a 3- to 8-membered spiro carbocycle or a 3- to 8-membered spiro heterocycle; $X^C$ is O, S, $CR^5_2$ or $NR^6$; $L^C$ is a self-immolative linker with f being 0 or 1; $C^A$ is the Drug $D^D$; $Y^{C1}$ is O, S or a secondary amine or a tertiary amine, wherein these moieties are part of $L^C$; $Y^{C2}$ is O, S or a secondary amine or a tertiary amine, wherein these moieties are part of $C^A$; wherein f is 0 and g is 1, or wherein f is 1 and g is an integer from 1 to 9; wherein b, c, d and e are independently 0 or 1, provided that if b is 0 then c and d are 0, and if c is 0 then d is 0, and provided that if d is 1 then b and c are 1, and that if c is 1 then b is 1, and provided that if c is 0 then e is 1; wherein when f is 1 then $Y^{C1}$ is referred to as $Y^C$, and when f is 0, then $Y^{C2}$ is referred to as $Y^C$;

wherein each $R^1$, $R^2$, $R^3$ and $R^5$ is independently selected from the group consisting of H, (hetero)alkyl, aryl, heterocycle, carbocycle, F, Cl, Br, I, $CF_3$, $CF_2$—R', $NO_2$, $N_3$, OR', SR', CN, C(=O)R', S(=O)R', $S(=O)_2R''$, $S(=O)_2OR'$, $OS(=O)_2R''$, $PO_3R'_2$, Si—$R''_3$, Si—O—$R''_3$, $B(OR')_2$, $S(=O)_2NR'_2$, NR'S$(=O)_2R''$, $C(=O)NR'_2$, $C(=S)NR'_2$, $C(=NR')NR'_2$, $NR'_2$, NR'C(=O)R', NR'C(=S)R', $NR'C(=O)NR'_2$, $NR'C(=S)NR'_2$ wherein each R' is independently selected from the group consisting of H, (hetero)alkyl, aryl, carbocycle, heterocycle, and each R" is independently selected from the group consisting of (hetero)alkyl, aryl, carbocycle, heterocycle, wherein all (hetero)alkyl, aryl, carbocycle, heterocycle moieties comprised in $R^1$, $R^2$, $R^3$ and $R^5$ can be unsubstituted or substituted, and wherein two R' or R" groups can together form a ring;

each $R^4$ and $R^6$ is independently selected from the group consisting of H, (hetero)alkyl, aryl, heterocycle, carbocycle, OR', C(=O)R', $C(=O)NR'_2$, $C(=S)NR'_2$, $C(=NR')NR'_2$, $NR'_2$, such that no sets consisting of adjacent atoms are present selected from the group consisting of —N—N—, —N—O—, —N—S—, —N—Si— and —N—P—, and wherein each R' is independently selected from the group consisting of (hetero)alkyl, aryl, carbocycle, heterocycle, wherein all (hetero)alkyl, aryl, carbocycle, heterocycle moieties comprised in $R^4$ and $R^6$ can be unsubstituted or substituted, and wherein two R' groups can together form a ring;

wherein in all of the above embodiments, one or more of $R^1$, $R^2$, $R^3$, $R^4$, $R^5$, $R^6$ and the self-immolative linker $L^C$, may be bound to an $S^P$, $C^B$, and/or $S^P$—$C^B$;

wherein $S^P$ is a spacer;

wherein $C^B$ is Construct B;

wherein Construct B is selected from the group consisting of small molecules, organic molecules, metal coordination compounds, inorganic molecules, organometallic molecules, biomolecules, drugs, polymers, resins, particles, gels, surfaces, cells, biological tissues, pathogens, and combinations thereof.

19. The method according to claim 17, wherein the dienophile has a structure according to formula (4)

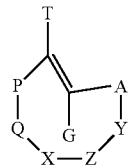

Formula 4 wherein A,Y,Z,X,Q,P each independently are selected from the group consisting of $CR^a_2$, $C=CR^a_2$, $C=O$, S, $S=O$, $SO_2$, O, $NR^b$, and $SiR'_2$, provided that A and P are not O or S and that $NR^b$, if present in A or P, is part of an amide moiety, with at most three of A,Y,Z,X,Q and P being selected from the group consisting of $C=CR^a_2$ and $C=O$, wherein two or more $R^a$, $R^b$, and/or $R^c$ moieties together may form a ring or rings, and with the proviso that no sets consisting of adjacent atoms are present selected from the group consisting of O—O, O—$NR^b$, S—$NR^b$, O—S, O—S(O), O—$S(O)_2$, and S—S, and such that Si is only adjacent to $CR^a_2$ or O;

T, G each independently denotes H, or a substituent selected from the group consisting of alkyl, OR', NR'R', F, Cl, Br, or I, with R' being alkyl or aryl;

each $R^a$ as above-indicated can independently be selected from the group consisting of H, (hetero)alkyl, aryl, heterocycle, carbocycle, F, Cl, Br, I, $CF_3$, $CF_2$—R', $NO_2$, OR', SR', CN, C(=O)R', S(=O)R', $S(=O)_2R''$, $S(=O)_2OR'$, $OS(=O)_2R''$, $PO_3R'_2$, Si—$R''_3$, Si—O—$R''_3$, $B(OR')_2$, $S(=O)_2NR'_2$, $NR'S(=O)_2R''$, C(=O)$NR'_2$, C(=S)$NR'_2$, C(=NR')$NR'_2$, $NR'_2$, NR'C(=O)R', NR'C(=S)R', NR'C(=O)OR', NR'C(=S)OR', NR'C(=O)SR', NR'C(=S)SR', NR'C(=O)$NR'_2$, NR'C(=S)$NR'_2$, wherein each R' is independently selected from the group consisting of H, (hetero)alkyl, aryl, carbocycle, heterocycle, and each R'' is independently selected from the group consisting of (hetero)alkyl, aryl, carbocycle, heterocycle, wherein all (hetero)alkyl, aryl, carbocycle, heterocycle moieties comprised in $R^a$ can be unsubstituted or substituted, and wherein two R' or R'' groups can together form a ring;

each $R^b$ is independently selected from the group consisting of H, (hetero)alkyl, aryl, heterocycle, carbocycle, OR', C(=O)R', C(=O)O—R', C(=O)S—R', C(=S)O—R', C(=S)S—R', C(=O)$NR'_2$, C(=S)$NR'_2$, C(=NR')$NR'_2$, $NR'_2$ such that no sets consisting of adjacent atoms are present selected from the group consisting of —N—N—, —N—O—, —N—S—, —N—Si— and —N—P—, and wherein each R' is independently selected from the group consisting of H, (hetero)alkyl, aryl, carbocycle, heterocycle, wherein all (hetero)alkyl, aryl, carbocycle, heterocycle moieties comprised in $R^b$ can be unsubstituted or substituted, and wherein two R' groups can together form a ring;

each $R^c$ as above indicated is independently selected from the group consisting of H, alkyl, aryl, O-alkyl, O-aryl, OH;

wherein one or more $R^{a,b,c}$ moieties may be bound to one or more of the group consisting of Targeting agent $T^T$, Spacer $S^P$, chelator, albumin-binding moiety, polymersome, micelle, particle, resin, gel, surface, bead, membrane translocation moiety, radioisotope, and fluorescent moiety; and wherein said Targeting agent $T^T$, Spacer $S^P$, chelator, albumin-binding moiety, polymersome, micelle, particle, resin, gel, surface, bead, membrane translocation moiety, radioisotope, and fluorescent moiety, may be bound to more than one dienophile moiety.

20. A kit according to claim 1, wherein g is an integer from 1 to 3.

21. A kit according to claim 1, wherein g is 1.

22. A kit according to claim 1, wherein one or more of $R^1$, $R^2$, $R^3$, $R^4$, $R^5$, $R^6$ and the self-immolative linker $L^C$, is bound to an $S^P$, $C^B$, and/or $S^P$—$C^B$.

23. A kit according to claim 2, wherein one or more $R^{a,b,c}$ moieties is bound to one or more of the group consisting of Targeting agent $T^T$, Spacer $S^P$, chelator, albumin-binding moiety, polymersome, micelle, particle, resin, gel, surface, bead, membrane translocation moiety, radioisotope, and fluorescent moiety.

24. A kit according to claim 2, wherein said Targeting agent $T^T$, Spacer $S^P$, chelator, albumin-binding moiety, polymersome, micelle, particle, resin, gel, surface, bead, membrane translocation moiety, radioisotope, and/or fluorescent moiety, is bound to more than one dienophile moiety.

25. A kit according to claim 5, wherein the O or S is attached to an aromatic carbon atom of $L^C$ or $C^A$.

26. A kit according to claim 5, wherein one or more of $R^6$, $R^7$, $R^8$, $R^9$, and $L^C$ is bound to a Spacer $S^P$, $C^B$, and/or $S^P$—$C^B$.

27. A kit according to claim 6, wherein one or more of $R^6$, $R^7$, $R^8$, $R^9$, and $L^C$ is bound to a Spacer $S^P$, $C^B$, and/or $S^P$—$C^B$.

28. A kit according to claim 8, wherein for c) and/or d) the $R^a$ moiety not being hydrogen is in the axial position.

29. A kit according to claim 10, wherein the $T^R$ and/or $L^C$ moieties are bound to one or more $S^P$, $C^B$ and/or $S^P$—$C^B$ moieties.

30. A tetrazine according to claim 16, wherein g is an integer from 1 to 3.

31. A tetrazine according to claim 16, wherein g is 1.

32. A tetrazine according to claim 16, wherein one or more of $R^1$, $R^2$, $R^3$, $R^4$, $R^5$, $R^6$ and the self-immolative linker $L^C$, is bound to an $S^P$, $C^B$, and/or $S^P$—$C^B$.

33. A method according to claim 17, wherein g is an integer from 1 to 3.

34. A method according to claim 17, wherein g is 1.

35. A method according to claim 17, wherein one or more of $R^1$, $R^2$, $R^3$, $R^4$, $R^5$, $R^6$ and the self-immolative linker $L^C$, is bound to an $S^P$, $C^B$, and/or $S^P$—$C^B$.

36. A method according to claim 18, wherein g is an integer from 1 to 3.

37. A method according to claim 18, wherein g is 1.

38. A method according to claim 18, wherein one or more of $R^1$, $R^2$, $R^3$, $R^4$, $R^5$, $R^6$ and the self-immolative linker $L^C$, is bound to an $S^P$, $C^B$, and/or $S^P$—$C^B$.

39. A method according to claim 19, wherein T and G are H.

40. A method according to claim 19, wherein one or more $R^{a,b,c}$ moieties is bound to one or more of the group consisting of Targeting agent $T^T$, Spacer $S^P$, chelator, albumin-binding moiety, polymersome, micelle, particle, resin, gel, surface, bead, membrane translocation moiety, radioisotope, and fluorescent moiety.

41. A method according to claim 19, wherein said Targeting agent $T^T$, Spacer $S^P$, chelator, albumin-binding moiety, polymersome, micelle, particle, resin, gel, surface, bead, membrane translocation moiety, radioisotope, and/or fluorescent moiety, is bound to more than one dienophile moiety.

* * * * *

UNITED STATES PATENT AND TRADEMARK OFFICE
CERTIFICATE OF CORRECTION

| | |
|---|---|
| PATENT NO. | : 11,617,799 B2 |
| APPLICATION NO. | : 16/312569 |
| DATED | : April 4, 2023 |
| INVENTOR(S) | : Marc Stefan Robillard et al. |

It is certified that error appears in the above-identified patent and that said Letters Patent is hereby corrected as shown below:

On the Title Page

Item (72) the fifth inventor's name should read:
--Henricus Marie Janssen, Eindhoven (NL)--

Signed and Sealed this
Second Day of April, 2024

*Katherine Kelly Vidal*

Katherine Kelly Vidal
*Director of the United States Patent and Trademark Office*